US012767953B2

(12) United States Patent
Huang et al.

(10) Patent No.: US 12,767,953 B2
(45) Date of Patent: Oct. 20, 2026

(54) MOGROSIDE COMPOSITIONS AND METHODS OF PRODUCING SAME

(71) Applicant: Elo Life Systems, Durham, NC (US)

(72) Inventors: Tengfang Huang, Cary, NC (US); Jack Q. Wilkinson, Cary, NC (US); Anna Matthiadis, Durham, NC (US); Devarshi Selote, Apex, NC (US); Matthew Kilgore, Cary, NC (US); Matthew DiLeo, Durham, NC (US); Fayaz Khazi, Chapel Hill, NC (US); Kevin Potter, Cary, NC (US); Daniel Stauffer, Raleigh, NC (US); Todd Rands, Naples, FL (US)

(73) Assignee: Elo Life Systems, Durham, NC (US)

( * ) Notice: Subject to any disclaimer, the term of this patent is extended or adjusted under 35 U.S.C. 154(b) by 0 days.

(21) Appl. No.: 18/470,037

(22) Filed: Sep. 19, 2023

(65) Prior Publication Data

US 2024/0132902 A1 Apr. 25, 2024
US 2024/0229055 A9 Jul. 11, 2024

Related U.S. Application Data

(60) Provisional application No. 63/491,721, filed on Mar. 22, 2023, provisional application No. 63/376,194, filed on Sep. 19, 2022.

(51) Int. Cl.
*C12N 15/82* (2006.01)
*A23L 27/30* (2016.01)
(Continued)

(52) U.S. Cl.
CPC .......... *C12N 15/8243* (2013.01); *A23L 27/36* (2016.08); *C12N 9/0004* (2013.01); (Continued)

(58) Field of Classification Search
None
See application file for complete search history.

(56) References Cited

U.S. PATENT DOCUMENTS 9,642,381 B2 5/2017 Ley et al.
9,932,619 B2 4/2018 Liu et al.
(Continued)

FOREIGN PATENT DOCUMENTS

WO 2014122227 8/2014
WO 2016038617 A1 3/2016
(Continued)

OTHER PUBLICATIONS

Soliman, Z. N., Atwa, M. A., & Assous, M. T. M. (2008). Production and evaluation of low-calorie juices prepared from mandarin concentrates. Egyptian Journal of Nutrition, 23(3), 69-92. (Year: 2008).*
(Continued)

*Primary Examiner* — Amjad Abraham
*Assistant Examiner* — Dequantarius Javon Speed
(74) *Attorney, Agent, or Firm* — Dentons US LLP

(57) ABSTRACT

The present disclosure provides compositions and methods for producing transgenic plants and other organisms that exhibit increased production of mogroside compounds, in particular mogroside V, and the mogroside compounds, plants and plant parts so produced.

15 Claims, 50 Drawing Sheets

Specification includes a Sequence Listing.

(51) Int. Cl.

| | |
|---|---|
| ***C12N 9/02*** | (2006.01) |
| ***C12N 9/04*** | (2006.01) |
| ***C12N 9/10*** | (2006.01) |
| ***C12N 9/90*** | (2006.01) |
| ***C12N 15/52*** | (2006.01) |

(52) U.S. Cl.

CPC ......... *C12N 9/0006* (2013.01); *C12N 9/0042* (2013.01); *C12N 9/0071* (2013.01); *C12N 9/1051* (2013.01); *C12N 9/90* (2013.01); *C12N 15/52* (2013.01); *C12Y 101/01088* (2013.01); *C12Y 106/02004* (2013.01); *C12Y 504/99003* (2013.01)

(56) References Cited

U.S. PATENT DOCUMENTS

| | | | |
|---|---|---|---|
| 10,011,859 | B2 | 7/2018 | Liu et al. |
| 10,465,222 | B2 | 11/2019 | Liu et al. |
| 10,633,685 | B2 | 4/2020 | Houghton-Larsen et al. |
| 11,008,600 | B2 | 5/2021 | Ochiai et al. |
| 11,060,124 | B2 | 7/2021 | Patron et al. |
| 11,180,789 | B2 | 11/2021 | Lo et al. |
| 11,419,351 | B2 | 8/2022 | Markosyan |
| 2009/0320160 | A1 | 12/2009 | Li |
| 2020/0154738 | A1 | 5/2020 | Prakash et al. |
| 2020/0165652 | A1 | 5/2020 | Houghton-Larsen |
| 2020/0325517 | A1 | 10/2020 | Houghton-Larsen et al. |
| 2021/0084950 | A1 | 3/2021 | Ohkuri et al. |
| 2021/0100272 | A1 | 4/2021 | O'Hara et al. |
| 2021/0324439 | A1 | 10/2021 | Patron et al. |
| 2021/0403921 | A1 | 12/2021 | Anderson et al. |
| 2022/0017564 | A1 | 1/2022 | Gan et al. |
| 2022/0170063 | A1 | 6/2022 | Itkin et al. |
| 2022/0205010 | A1 | 6/2022 | Prakash et al. |
| 2023/0174993 | A1 | 6/2023 | Boucher et al. |
| 2025/0290110 | A1 | 9/2025 | Huang et al. |

FOREIGN PATENT DOCUMENTS

| | | | | |
|---|---|---|---|---|
| WO | WO-2021126960 A1 * | 6/2021 | ........... C07K 14/415 |
| WO | 2021188703 A1 | 9/2021 | |

OTHER PUBLICATIONS

Itkin, et al., "The biosynthetic pathway of the nonsugar, high-intensity sweetener mogroside V from Siraitia grosvenorii". Proc Nat Acad Sci USA 113:E7619-E7628, (2016).

Seki, et al., "Plant-derived isoprenoid sweeteners: recent progress in biosynthetic gene discovery and perspectives on microbial production". Biosci. Biotechnol. Biochem. 82:927-934, (2018).

Chronis, et al., "Potato transformation". Bio protocol, vol. 4, (2014).

Rodriquez. Invitation to Pay Additional Search Fees. PCT/US23/74602, mailed Jan. 1, 2024.

Liu, et al., "Structural Insights into the Catalytic Mechanism of a Plant Diterpene Glycosyltransferase SrUGT76G1", Plant Commun. 1, 100004, 2020.

Yu, et al., "Mutation of Stevia glycosyltransferase UGT76G1 for efficient biotransformation of rebaudioside E into rebaudioside M". J. Funct. Foods 92, 105033, 2022.

Wang, et al., "Heterologous expression of EUGT11 from *Oryza sativa* in Pichia pastoris for highly efficient one-pot production of rebaudioside D from rebaudioside A". Int. J. Biol. Macromol. 163: 1669-1676, 2020.

U.S. Appl. No. 18/608,621, filed Mar. 8, 2024, Huang, et al.

Rodriquez. International Search Report and Written Opinion regarding International App. No. PCT/US23/74602, mailed Apr. 24, 2024.

International Search Report and Written Opinion for International Application No. PCT/US2025/018956, dated Jul. 9, 2025.

USPTO: Restriction Requirement regarding U.S. Appl. No. 18/608,621, mailed Oct. 27, 2025.

Rodriquez, Invitation to Pay Additional Search Fees regarding International App. No. PCT/US2025/018956, mailed Apr. 28, 2025.

USPTO: Response to Restriction Requirement regarding U.S. Appl. No. 18/608,621, filed Dec. 1, 2025.

Anonymous, Risk and Technical Assessment Report—Application A1129—Monk Fruit Extract as a Food Additive, available at www.foodstandards.gov.au/sites/default/files/food-standards-code/applications/Documents/A1129%20SD1%20at%20approval.pdf, 2018.

Extended European Search Report regarding EP App. No. 23869110.9, dated Jun. 2, 2026.

Liao et al. Plant Metabolic Engineering by Multigene Stacking: Synthesis of Diverse Mogrosides, Int J Mol Sci. 23 (18):10422, 2022.

Liao et al., Heterologous mogrosides biosynthesis in cucumber and tomato by genetic manipulation, Commun Biol. 6:191, 2023.

* cited by examiner

| | 0336CG25 | 14638-J39 | 1463BL203-140 | 1463CG100-1 | 1463CG115-2 | 1463J200-80 | 1908-L204-38 | 3488BY8-A | 3190CG103-1 |
|---|---|---|---|---|---|---|---|---|---|
| Mog IIs | 0.3 | 0.0 | 270.7 | 583.1 | 9.1 | 574.5 | 0.0 | 6.0 | 11.9 |
| Mog IIIs | 0.9 | 89.7 | 216.2 | 251.2 | 16.0 | 1382.9 | 15.7 | 21.1 | 278.2 |
| Mog IVs | 0.6 | 106.8 | 124.8 | 179.1 | 16.3 | 139.1 | 0.0 | 10.0 | 2.7 |
| Mog Vs | 0.4 | 265.6 | 1575.5 | 788.1 | 293.4 | 3317.3 | 204.5 | 193.9 | 337.5 |
| 11-oxo Mog II | 1.7 | 0.0 | 0.0 | 0.0 | 0.0 | 0.0 | 0.0 | 0.7 | 0.0 |
| 11-oxo Mog V | 0.8 | 33.9 | 314.5 | 252.4 | 47.0 | 427.6 | 60.2 | 160.9 | 138.0 |

| Sampling Date | Mogroside V | Mogroside II-A | Mogroside II-A1 | 11-Oxomogroside II-E | 11-Oxomogroside V | Isomogroside V | Siamenoside | Mogroside IV-A | Mogroside IV | Mogroside III | Mogroside III-E |
|---|---|---|---|---|---|---|---|---|---|---|---|
| 3/30/2023 | 77.2 | 13.4 | 27 | 0.815 | 8.34 | 2.38 | 2.09 | 1.92 | 5.51 | 1.08 | 0.731 |
| 3/30/2023 | 77.6 | 12.7 | 25.7 | | 8.62 | 2.17 | 2.01 | 1.9 | 5.51 | 0.949 | 0.571 |
| 4/27/2023 | 11.1 | 1.42 | 2.46 | 1.95 | 2.88 | | 0.418 | 0.29 | 0.78 | 0.38 | 1.02 |
| 4/27/2023 | 13.1 | 1.51 | 2.76 | 2.03 | 3.31 | | 0.545 | 0.415 | 1.56 | 0.43 | 1.16 |
| 6/22/2023 | 5.68 | 0.16 | 0.435 | | 2.53 | | 0.126 | 0.235 | | 0.16 | |

| Mogroside III-A1 | Mogroside II-E | 11-oxomogroside IV | 11-Oxomogroside III | 11-oxomogroside III-A1 | 11-Oxomogroside II-A2 | 11-Oxomogroside II-A | 11-Oxomogroside II-A1 | Mogroside III-A2 | Mogroside II-A2 | Total sweet mogrosides | Total mogrosides |
|---|---|---|---|---|---|---|---|---|---|---|---|
| 180 | 0.705 | 0.922 | 0.622 | 24.4 | 90.1 | 1.92 | 17.3 | | 71.3 | 280 | 528 |
| 176 | 0.759 | 0.803 | 0.711 | 23.9 | 87.7 | 1.95 | 17.1 | 2.74 | 70.1 | 279 | 520 |
| 9.18 | 0.734 | 0.422 | 0.491 | 3.12 | 29.2 | 0.591 | 3.8 | 2.24 | 14.1 | 28.3 | 86.5 |
| 10 | 0.713 | 0.438 | 0.543 | 3.49 | 33.5 | 0.463 | 4.19 | 2.53 | 16.1 | 33 | 98.7 |
| 1.31 | | 0.128 | 0.29 | 0.678 | 21.3 | 0.132 | 0.83 | | 6.98 | 10.1 | 41 |

FIG. 19

MOGROSIDE COMPOSITIONS AND METHODS OF PRODUCING SAME

CROSS-REFERENCE TO RELATED APPLICATIONS

This application claims the benefit under 35 U.S.C. § 119 (e) of U.S. provisional application Ser. No. 63/376,194, filed on Sep. 19, 2022, and 63/491,721, filed on Mar. 22, 2023, each of which is herein incorporated by reference in its entirety.

INCORPORATION OF SEQUENCE LISTING

A sequence listing containing the file named "ELSS002US_ST26.xml" which is 540 kilobytes (measured in MS-Windows®) and created on Sep. 14, 2023, and comprises 305 sequences, is incorporated herein by reference in its entirety.

FIELD OF THE INVENTION

The present disclosure relates to the field of genetically engineering plants and other organisms, and more specifically to methods and compositions for producing plants and other organisms exhibiting increased production of mogroside compounds, in particular mogroside V. The present disclosure also relates to the use of such plants and other organisms to produce novel ingredients (e.g., plant extracts, purified and partially purified fractions containing mogrosides) for foods and beverages, and novel foods and beverages (and other compositions of matter) resulting therefrom.

BACKGROUND OF THE INVENTION

Low or non-caloric sweeteners, in particular natural low or non-caloric sweeteners, as an alternative to traditional high calorie sweeteners and artificial sweeteners are becoming increasingly important to the food and beverage industry, in addition to other industries. These alternative sweeteners are used as a substitute for artificial sweeteners or high calorie sweeteners comprising sucrose, fructose, and glucose. Like some artificial sweeteners, some of these alternative sweeteners provide a greater sweetening effect than comparable amounts of caloric sweeteners, and therefore smaller amounts of these alternative sweeteners are required to achieve sweetness comparable to that of sugar. However, some low calorie sweeteners can be expensive to produce and/or possess unfavorable taste characteristics and/or off-tastes, including but not limited to sweetness linger, delayed sweetness onset, negative mouth feel, and bitter, metallic, cooling, astringent, and licorice-like tastes.

A few natural plants produce low or non-calorie sweeteners. For example, mogrosides, an important class of natural sweeteners, are chemically a class of triterpene glycosides or mogrol glycosides naturally produced by monkfruit (also known as luohan guo; scientific name: *Siraitia grosvenorii*). Mogrosides contain "zero" calories (less than 5 calories per 8 oz. serving), and are 100-400 times sweeter than sucrose. Mogrosides have also been reported to have a variety of important pharmacological effects. However, although plants like *Siraitia grosvenorii* make mogrosides, production of mogrosides from these plants is limited and expensive due to the limited natural or agricultural production of these plants. Also, *Siraitia grosvenorii* prefers to grow in subtropical mountainous regions and requires laborious pollination to set fruits. In addition, production of mogrosides in vitro or in microorganisms has been attempted, but due to extensive processing and other issues has not proven to be economically feasible.

Therefore there is a need for new compositions and methods for the efficient production of mogrosides.

SUMMARY

The present disclosure solves these and other problems in the art by providing novel compositions and methods for the efficient and cost-effective production of mogrosides in plants and other organisms, in particular sweet mogrosides, such as those including more than three glucose residues in the molecule, including, but not limited to, mogroside V, isomogroside V, siamenoside I, α-siamenoside I, mogroside IV, mogroside IV A, mogroside III, mogroside III E, mogroside III A1 and 11-oxo-mogroside V.

The present disclosure provides a transgenic plant, plant part or seed, comprising: a) a first polynucleotide sequence that encodes a cytochrome P450 polypeptide having at least 91% sequence identity to SEQ ID NO:2 or at least 95% sequence identity to SEQ ID NO:86; b) a second polynucleotide sequence that encodes a cucurbitadienol synthase polypeptide having at least 90% sequence identity to SEQ ID NO:5; c) a third polynucleotide sequence that encodes a cytochrome P450 polypeptide having at least 90% sequence identity to SEQ ID NO:7, SEQ ID NO:25, SEQ ID NO: 27, SEQ ID NO:29, SEQ ID NO:31 or SEQ ID NO:33; d) a fourth polynucleotide sequence that encodes a uridine phosphorylase dependent glycosyltransferase polypeptide having at least 90% sequence identity to SEQ ID NO:9; e) a fifth polynucleotide sequence that encodes a uridine phosphorylase dependent glycosyltransferase polypeptide having at least 90% sequence identity to SEQ ID NO:11; f) a sixth polynucleotide sequence that encodes a squalene epoxidase polypeptide having at least 90% sequence identity to SEQ ID NO:13; g) a seventh polynucleotide sequence that encodes an epoxy hydrolase polypeptide having at least 90% sequence identity to SEQ ID NO:15; or h) an eighth polynucleotide sequence that encodes a truncated 3-hydroxy-3-methylglutaryl-CoA reductase polypeptide having at least 90% sequence identity to SEQ ID NO: 17, SEQ ID NO:274, SEQ ID NO:276 or SEQ ID NO:278; wherein the first, second, third, fourth, fifth, sixth, seventh or eighth polynucleotide sequence is operably linked to a heterologous promoter, and wherein the transgenic plant, plant part or seed produces at least a first mogroside compound. In certain embodiments the first, second, third, fourth, fifth, sixth, seventh or eighth polynucleotide sequences are operably linked to different heterologous promoters. In some embodiments at least two of the first, second, third, fourth, fifth, sixth, seventh or eighth polynucleotide sequences are operably linked to a single heterologous promoter. In other embodiments one or more of the first, second, third, fourth, fifth, sixth, seventh or eighth polynucleotide sequences are present in multiple copies, and are operably linked to the same or different endogenous or heterologous promoters.

In various embodiments the plant is a Cucurbitaceae, Solanaceae or Asteraceae plant. In some embodiments the plant is a *Cucurbita, Citrullus, Cucumis, Momordica, Solanum* or *Lactuca* plant. In further embodiments the plant is a watermelon, cantaloupe, honeydew, winter melon, casaba melon, Persian melon, citron melon, muskmelon, bailan melon, crenshaw melon, Christmas melon, sprite melon, caravelle melon, hami melon, rocky melon, golden Langkawi melon, Korean melon, saticoy melon, galia melon, jade dew melon, golden prize melon, ten me melon, new century melon, banana melon, yubari king melon, sugar melon, tiger melon, vert grimpant melon, horned melon, cucamelon, casabanana melon, pepino melon, *ananas* melon, camouflage melon, canary melon, bitter melon, charentais melon, crane melon, SkyRocket melon, honey globe melon, gac melon, autumn sweet melon, snap melon, lettuce, spinach, rice, oat, maize, sorghum, wheat, alfalfa, bitter apple (*Citrullus colocynthis*), pumpkin, chard, tobacco, switch grass, tomato, cucumber, potato, amaranth, sunflower, canola, dry bean, field pea, flax, safflower, buckwheat, cotton, soybean, sugar beet or *Nicotiana benthamiana* plant. In particular embodiments the plant is a watermelon, tomato, lettuce or cucumber plant, or other leafy bulky biomass green plant or other food crop plant that can be used as foundational ingredients for processed foods. In certain embodiments the plant is a monocot plant or a dicot plant. In some embodiments the plant part is a fruit, leaf, root, flower, shoot, cell, endosperm, ovule, or pollen. In other embodiments the plant is a species useful for producing mogrosides for processing into foods where the mogrosides can replace or partially replace the need for added sugars.

In certain embodiments the heterologous promoter is an inducible, plant, bacterial, viral, synthetic, constitutive, tissue specific, developmentally regulated, cell cycle regulated, temporally regulated, spatially regulated, and/or spatio-temporally regulated promoter. In other embodiments the heterologous promoter is a FSgt/PFLt (SEQ ID NO:62), FMVSgt (SEQ ID NO: 69), CsVMV (SEQ ID NO:68), dMMV (SEQ ID NO:63), HLVH12 (SEQ ID NO:60), NOS (SEQ ID NO:66), ScBV (SEQ ID NO:67), DCMV (SEQ ID NO:61), CmYLCV (SEQ ID NO:64), FS1_1 (SEQ ID NO:70), FE_3 (SEQ ID NO:71), e35S (SEQ ID NO:65), AtUBQ10 (SEQ ID NO: 259), PCLSV (SEQ ID NO:260), FS4 (SEQ ID NO:261), AtACT2 (SEQ ID NO:262), enhanced AtEf-1A (SEQ ID NO:263), FuasFScp (SEQ ID NO:264), FE4 (SEQ ID NO:269), cucumisin (SEQ ID NO:270) or SgCDS (SEQ ID NO:271) promoter. In further embodiments the first, second, third, fourth, fifth, sixth, seventh or eighth polynucleotide sequence is operably linked to a heterologous terminator. In yet further embodiments the first, second, third, fourth, fifth, sixth, seventh or eighth heterologous terminator sequence is a GmaxMYB2 (SEQ ID NO:74), 35S T (SEQ ID NO:), ATHSP18.2 (SEQ ID NO:77), AtRBCS2b (SEQ ID NO:75), AtUBQ3 (SEQ ID NO: 73), Pea E9 (SEQ ID NO:76), Pea3A (SEQ ID NO:72), potato Ubi3 (SEQ ID NO:78), AtTubB9 (SEQ ID NO:79), AtFAD2 (SEQ ID NO:265), AtNDUFA8 (SEQ ID NO:266), CsHSP17.3 (SEQ ID NO:267) or CsHSP22 (SEQ ID NO:268) terminator sequence. In additional embodiments the transgenic plant, plant part or seed further comprises a selectable marker sequence. In some embodiments the selectable marker sequence is a β-glucuronidase, green fluorescent protein, or antibiotic resistance sequence. In particular embodiments the selectable marker sequence is a hygromycin B phosphotransferase (HygR) or neomycin phosphotransferase II (nptII) selectable marker sequence.

In some embodiments the transgenic plant, plant part or cell further comprises i) a ninth polynucleotide sequence that encodes an NADPH:cytochrome P450 reductase polypeptide having at least 90% sequence identity to SEQ ID NO:19; or j) a tenth polynucleotide sequence that encodes a uridine phosphorylase dependent glycosyltransferase polypeptide having at least 90% sequence identity to SEQ ID NO:21, SEQ ID NO:23, SEQ ID NO:120 or SEQ ID NO:126; k) an eleventh polynucleotide sequence that encodes a 3-hydroxy-3-methylglutaryl-CoA synthase polypeptide having at least 90% sequence identity to SEQ ID NO:227; or l) a twelfth polynucleotide sequence that encodes a geranyl diphosphate synthase polypeptide having at least 90% sequence identity to SEQ ID NO:256; wherein the ninth, tenth, eleventh or twelfth polynucleotide sequence is operably linked to a heterologous promoter. In other embodiments the transgenic plant, plant part or cell further comprises a 2A linker, insulator, selectable marker or stuffer sequence.

In certain embodiments the at least a first mogroside compound is a non-native mogrol precursor, mogrol, mogroside, or a metabolite or derivative thereof. In various embodiments the mogroside is mogroside II A, mogroside II A1, mogroside II A2, mogroside II E, 11-oxo-mogroside II, mogroside III, mogroside III A1, mogroside III A2, mogroside III E 11-oxo-mogroside III, mogroside IV, mogroside IV A, 11-oxo-mogroside IV, siamenoside I, mogroside V, 11-oxo-mogroside V or mogroside VI, or an isomer thereof. In additional embodiments the transgenic plant, plant part or seed produces at least 10 ng/g to 30 mg/g dry weight of the at least a first mogroside compound. In some embodiments the transgenic plant, plant part or seed produces at least 10 ng/g, at least 25 ng/g, at least 50 ng/g, at least 75 ng/g, at least 100 ng/g, at least 250 ng/g, at least 500 ng/g, at least 750 ng/g, at least 1 mg/g, at least 2.5 mg/g, at least 5 mg/g, at least 7.5 mg/g, at least 10 mg/g, at least 12.5 mg/g, at least 15 mg/g, at least 17.5 mg/g, at least 20 mg/g, at least 22.5 mg/g, at least 25 mg/g, at least 27.5 mg/g, or at least 30 mg/g of the at least a first mogroside compound. In further embodiments the amount of at least a first mogroside compound is greater than the level in a non-transgenic plant, plant part or seed of the same species. In other embodiments the ratio of individual mogroside compounds is different from the ratio of mogroside compounds in native plant tissues or fruit or other plants or organisms that produce mogroside compounds. For example, the ratio of a mogroside compound produced by the plants or organisms of the present disclosure to a mogroside compound produced by a native plant tissues or fruit or other plants or organisms can be 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 7.5:1, 8:1, 9:1, 10:1, 12.5:1, 15:1, 20:1, 25:1, 30:1, 40:1, 50:1, 60:1, 70:1, 75:1, 80:1, 90:1, 100:1, 250:1, 500:1, 750:1, 1000:1, or more, or 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:7.5, 1:8, 1:9, 1:10, 1:12.5, 1:15, 1:20, 1:25, 1:30, 1:40, 1:50, 1:60, 1:70, 1:75, 1:80, 1:90, 1:100, 1:250, 1:500, 1:750, 1:1000, or lower. These ratios can apply to one or more of the following mogroside compounds: mogroside II A, mogroside II A1, mogroside II A2, mogroside II E, 11-oxo-mogroside II, mogroside III, mogroside III A1, mogroside III A2, mogroside III E 11-oxo-mogroside III, mogroside IV, mogroside IV A, 11-oxo-mogroside IV, siamenoside I, mogroside V, 11-oxo-mogroside V or mogroside VI, or an isomer thereof. Generally higher ratios of sweet mogroside compounds, such as those including more than three glucose residues in the molecule, including, but not limited to, mogroside V, isomogroside V, siamenoside I, α-siamenoside I, mogroside IV, mogroside IV A, mogroside III, mogroside III E, mogroside III A1 and 11-oxo-mogroside V, to other mogroside compound(s) are used. In other words this applies to the ratio of one or more mogroside compound, for example mogroside V, to one or more other mogroside compound.

The present disclosure additionally provides a recombinant host cell comprising: a) a first polynucleotide sequence that encodes a cytochrome P450 polypeptide having at least 91% sequence identity to SEQ ID NO:2 or at least 95% sequence identity to SEQ ID NO:86; b) a second polynucleotide sequence that encodes a cucurbitadienol synthase polypeptide having at least 90% sequence identity to SEQ ID NO:5; c) a third polynucleotide sequence that encodes a cytochrome P450 polypeptide having at least 90% sequence identity to SEQ ID NO:7, SEQ ID NO:25, SEQ ID NO: 27, SEQ ID NO:29, SEQ ID NO:31 or SEQ ID NO:33; d) a fourth polynucleotide sequence that encodes a uridine phosphorylase dependent glycosyltransferase polypeptide having at least 90% sequence identity to SEQ ID NO:9; e) a fifth polynucleotide sequence that encodes a uridine phosphorylase dependent glycosyltransferase polypeptide having at least 90% sequence identity to SEQ ID NO:11; f) a sixth polynucleotide sequence that encodes a squalene epoxidase polypeptide having at least 90% sequence identity to SEQ ID NO:13; g) a seventh polynucleotide sequence that encodes an epoxy hydrolase polypeptide having at least 90% sequence identity to SEQ ID NO:15; or h) an eighth polynucleotide sequence that encodes a truncated 3-hydroxy-3-methylglutaryl-CoA reductase polypeptide having at least 90% sequence identity to SEQ ID NO: 17, SEQ ID NO:274, SEQ ID NO:276 or SEQ ID NO:278; wherein the first, second, third, fourth, fifth, sixth, seventh or eighth polynucleotide sequence is operably linked to a heterologous promoter. In certain embodiments the recombinant host cell produces at least a first mogroside compound.

The present disclosure also provides a processed lower calorie food or beverage product produced from a transgenic plant, plant part or seed comprising: a) a first polynucleotide sequence that encodes a cytochrome P450 polypeptide having at least 91% sequence identity to SEQ ID NO:2 or at least 95% sequence identity to SEQ ID NO:86; b) a second polynucleotide sequence that encodes a cucurbitadienol synthase polypeptide having at least 90% sequence identity to SEQ ID NO:5; c) a third polynucleotide sequence that encodes a cytochrome P450 polypeptide having at least 90% sequence identity to SEQ ID NO:7, SEQ ID NO:25, SEQ ID NO: 27, SEQ ID NO:29, SEQ ID NO:31 or SEQ ID NO:33; d) a fourth polynucleotide sequence that encodes a uridine phosphorylase dependent glycosyltransferase polypeptide having at least 90% sequence identity to SEQ ID NO:9; e) a fifth polynucleotide sequence that encodes a uridine phosphorylase dependent glycosyltransferase polypeptide having at least 90% sequence identity to SEQ ID NO:11; f) a sixth polynucleotide sequence that encodes a squalene epoxidase polypeptide having at least 90% sequence identity to SEQ ID NO:13; g) a seventh polynucleotide sequence that encodes an epoxy hydrolase polypeptide having at least 90% sequence identity to SEQ ID NO:15; or h) an eighth polynucleotide sequence that encodes a truncated 3-hydroxy-3-methylglutaryl-CoA reductase polypeptide having at least 90% sequence identity to SEQ ID NO: 17, SEQ ID NO:274, SEQ ID NO:276 or SEQ ID NO:278; wherein the first, second, third, fourth, fifth, sixth, seventh or eighth polynucleotide sequence is operably linked to a heterologous promoter, and wherein the transgenic plant, plant part or seed produces at least a first mogroside compound. In certain embodiments the product is produced from a juice, extract, powder, fruit or rind of a fruit, vegetable, legume, tuber or grain of the transgenic plant, plant part or seed.

The present disclosure additionally provides a juice, powder or extract produced from a transgenic plant, plant part or seed comprising: a) a first polynucleotide sequence that encodes a cytochrome P450 polypeptide having at least 91% sequence identity to SEQ ID NO:2 or at least 95% sequence identity to SEQ ID NO:86; b) a second polynucleotide sequence that encodes a cucurbitadienol synthase polypeptide having at least 90% sequence identity to SEQ ID NO:5; c) a third polynucleotide sequence that encodes a cytochrome P450 polypeptide having at least 90% sequence identity to SEQ ID NO:7, SEQ ID NO:25, SEQ ID NO:27, SEQ ID NO:29, SEQ ID NO: 31 or SEQ ID NO:33; d) a fourth polynucleotide sequence that encodes a uridine phosphorylase dependent glycosyltransferase polypeptide having at least 90% sequence identity to SEQ ID NO:9; e) a fifth polynucleotide sequence that encodes a uridine phosphorylase dependent glycosyltransferase polypeptide having at least 90% sequence identity to SEQ ID NO: 11; f) a sixth polynucleotide sequence that encodes a squalene epoxidase polypeptide having at least 90% sequence identity to SEQ ID NO:13; g) a seventh polynucleotide sequence that encodes an epoxy hydrolase polypeptide having at least 90% sequence identity to SEQ ID NO:15; or h) an eighth polynucleotide sequence that encodes a truncated 3-hydroxy-3-methylglutaryl-CoA reductase polypeptide having at least 90% sequence identity to SEQ ID NO:17, SEQ ID NO:274, SEQ ID NO:276 or SEQ ID NO:278; wherein the first, second, third, fourth, fifth, sixth, seventh or eighth polynucleotide sequence is operably linked to a heterologous promoter, and wherein the transgenic plant, plant part or seed produces at least a first mogroside compound.

The present disclosure further provides a recombinant DNA molecule comprising: a) a first polynucleotide sequence that encodes a cytochrome P450 polypeptide having at least 91% sequence identity to SEQ ID NO:2 or at least 95% sequence identity to SEQ ID NO:86; b) a second polynucleotide sequence that encodes a cucurbitadienol synthase polypeptide having at least 90% sequence identity to SEQ ID NO:5; c) a third polynucleotide sequence that encodes a cytochrome P450 polypeptide having at least 90% sequence identity to SEQ ID NO:7, SEQ ID NO:25, SEQ ID NO: 27, SEQ ID NO:29, SEQ ID NO:31 or SEQ ID NO:33; d) a fourth polynucleotide sequence that encodes a uridine phosphorylase dependent glycosyltransferase polypeptide having at least 90% sequence identity to SEQ ID NO:9; e) a fifth polynucleotide sequence that encodes a uridine phosphorylase dependent glycosyltransferase polypeptide having at least 90% sequence identity to SEQ ID NO:11; f) a sixth polynucleotide sequence that encodes a squalene epoxidase polypeptide having at least 90% sequence identity to SEQ ID NO:13; g) a seventh polynucleotide sequence that encodes an epoxy hydrolase polypeptide having at least 90% sequence identity to SEQ ID NO:15 or h) an eighth polynucleotide sequence that encodes a truncated 3-hydroxy-3-methylglutaryl-CoA reductase polypeptide having at least 90% sequence identity to SEQ ID NO: 17, SEQ ID NO:274, SEQ ID NO:276 or SEQ ID NO:278; wherein the first, second, third, fourth, fifth, sixth, seventh or eighth polynucleotide sequence is operably linked to a heterologous promoter. In certain embodiments the first, second, third, fourth, fifth, sixth, seventh or eighth polynucleotide sequences are operably linked to different heterologous promoters. In other embodiments at least two of the first, second, third, fourth, fifth, sixth, seventh or eighth polynucleotide sequences are operably linked to a single heterologous promoter. In some embodiments one or more of the first, second, third, fourth, fifth, sixth, seventh or eighth polynucleotide sequences are present in multiple copies, and are operably linked to the same or different endogenous or heterologous promoters.

The present disclosure also provides a DNA molecule comprising polynucleotide sequence that encodes a cytochrome P450 polypeptide having at least 91% sequence identity to SEQ ID NO:2 or at least 95% sequence identity to SEQ ID NO:86. In certain embodiments the DNA molecule is operably linked to a heterologous promoter. The present disclosure additionally provides a DNA molecule exhibiting a gene regulatory functional activity comprising a polynucleotide sequence selected from the group consisting of: a) a sequence with at least 90 or 95 percent sequence identity to SEQ ID NOs: 70 or 71 and exhibiting promoter activity; b) a sequence comprising SEQ ID NOs: 70 or 71; and c) a fragment of SEQ ID NOs: 70 or 71, wherein said fragment exhibits promoter activity; wherein said DNA molecule is operably linked to a heterologous transcribable polynucleotide molecule. In certain embodiments SEQ ID NO:70 and SEQ ID NO:71 can lead to increased expression in the fruit of a plant.

The present disclosure further provides a method of producing at least a first mogroside compound, comprising growing a transgenic plant or organism comprising: a) a first polynucleotide sequence that encodes a cytochrome P450 polypeptide having at least 91% sequence identity to SEQ ID NO:2 or at least 95% sequence identity to SEQ ID NO:86; b) a second polynucleotide sequence that encodes a cucurbitadienol synthase polypeptide having at least 90% sequence identity to SEQ ID NO:5; c) a third polynucleotide sequence that encodes a cytochrome P450 polypeptide having at least 90% sequence identity to SEQ ID NO:7, SEQ ID NO:25, SEQ ID NO: 27, SEQ ID NO:29, SEQ ID NO:31 or SEQ ID NO:33; d) a fourth polynucleotide sequence that encodes a uridine phosphorylase dependent glycosyltransferase polypeptide having at least 90% sequence identity to SEQ ID NO:9; e) a fifth polynucleotide sequence that encodes a uridine phosphorylase dependent glycosyltransferase polypeptide having at least 90% sequence identity to SEQ ID NO:11; f) a sixth polynucleotide sequence that encodes a squalene epoxidase polypeptide having at least 90% sequence identity to SEQ ID NO:13; g) a seventh polynucleotide sequence that encodes an epoxy hydrolase polypeptide having at least 90% sequence identity to SEQ ID NO:15; or h) an eighth polynucleotide sequence that encodes a truncated 3-hydroxy-3-methylglutaryl-CoA reductase polypeptide having at least 90% sequence identity to SEQ ID NO: 17, SEQ ID NO:274, SEQ ID NO:276 or SEQ ID NO:278; wherein the first, second, third, fourth, fifth, sixth, seventh or eighth polynucleotide sequence is operably linked to a heterologous promoter, and wherein the transgenic plant, plant part or seed produces at least a first mogroside compound. In certain embodiments the transgenic plant produces the at least a first mogroside compound in a plant part or seed of the plant. In some embodiments the transgenic plant produces the at least a first mogroside compound in a fruit or leaf of the plant. In additional embodiments the method further comprises the step of isolating the at least a first mogroside compound from the transgenic plant. In other embodiments the at least a first mogroside compound is isolated, purified or partially purified from a plant part or seed of the transgenic plant. In yet other embodiments the at least a first mogroside compound is isolated from a fruit, leaf, vegetable, legume, tuber or grain of the transgenic plant. In further embodiments a combination of mogroside compounds are purified or partially purified from the transgenic plant, plant part or seed.

The present disclosure also provides a composition comprising: a) about 80% mogroside V, about 15% 11-oxo-mogroside V and about 5% mogroside III-A1; or b) about 40% siamenoside I, about 40% mogroside V and about 20% 11-oxo-mogroside V. In certain embodiments the composition comprises about 75%, about 76%, about 77%, about 78%, about 79%, about 80%, about 81%, about 82%, about 83%, about 84% or about 85% of mogroside V, about 10%, about 11%, about 12%, about 13%, about 14%, about 15%, about 16%, about 17%, about 18%, about 19% or about 20% of 11-oxo-mogroside V, and about 1%, about 2%, about 3%, about 4%, about 5%, about 6%, about 7%, about 8%, about 9% or about 10% of mogroside III A1. In some embodiments, the composition comprises about 35%, about 36%, about 37%, about 38%, about 39%, about 40%, about 41%, about 42%, about 43%, about 44% or about 45% of siamenoside I, about 35%, about 36%, about 37%, about 38%, about 39%, about 40%, about 41%, about 42%, about 43%, about 44% or about 45% of mogroside V, and about 15%, about 16%, about 17%, about 18%, about 19%, about 20%, about 21%, about 22%, about 23%, about 24% or about 25% of 11-oxo-mogroside V. In other embodiments the composition is a liquid. In yet other embodiments the composition is a dry powder.

BRIEF DESCRIPTION OF THE DRAWINGS

The following drawings form part of the present specification and are included to further demonstrate certain aspects of the present disclosure. The present disclosure may be better understood by reference to one or more of these drawings in combination with the detailed description of specific embodiments presented herein.

FIG. 19. Production of mogrosides and siamenoside in transgenic watermelon cell suspension.

BRIEF DESCRIPTION OF THE SEQUENCES

Figure 1:
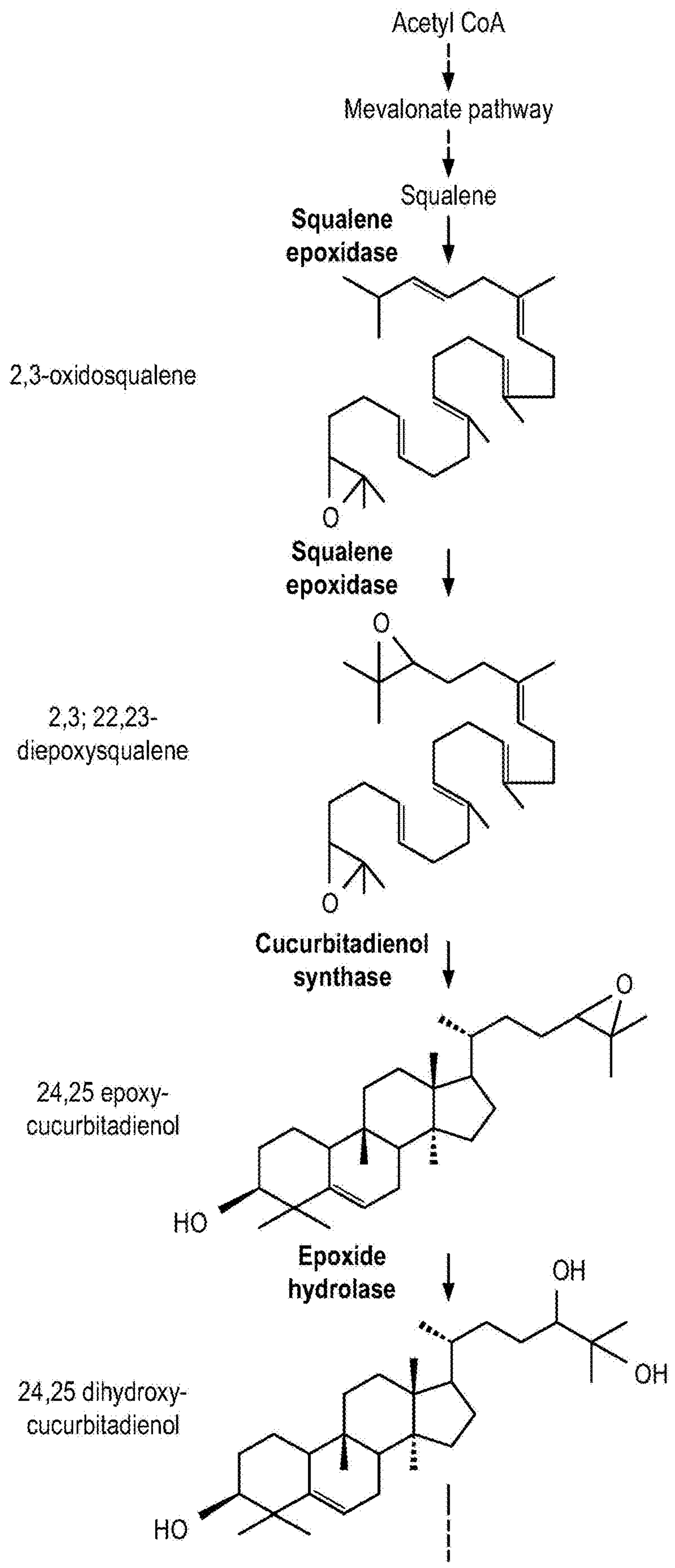
FIG. 1. A mogroside biosynthetic pathway from *Siraitia grosvenorii.*
Figure 1:
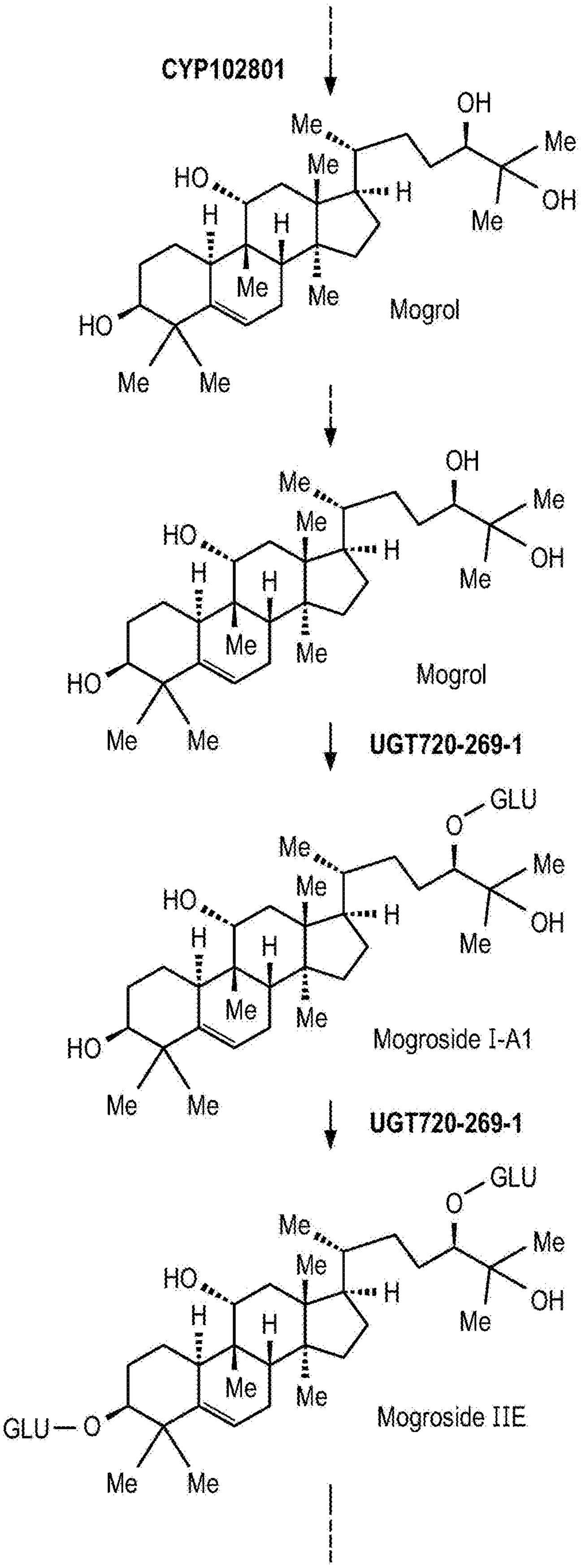
Figure 1:
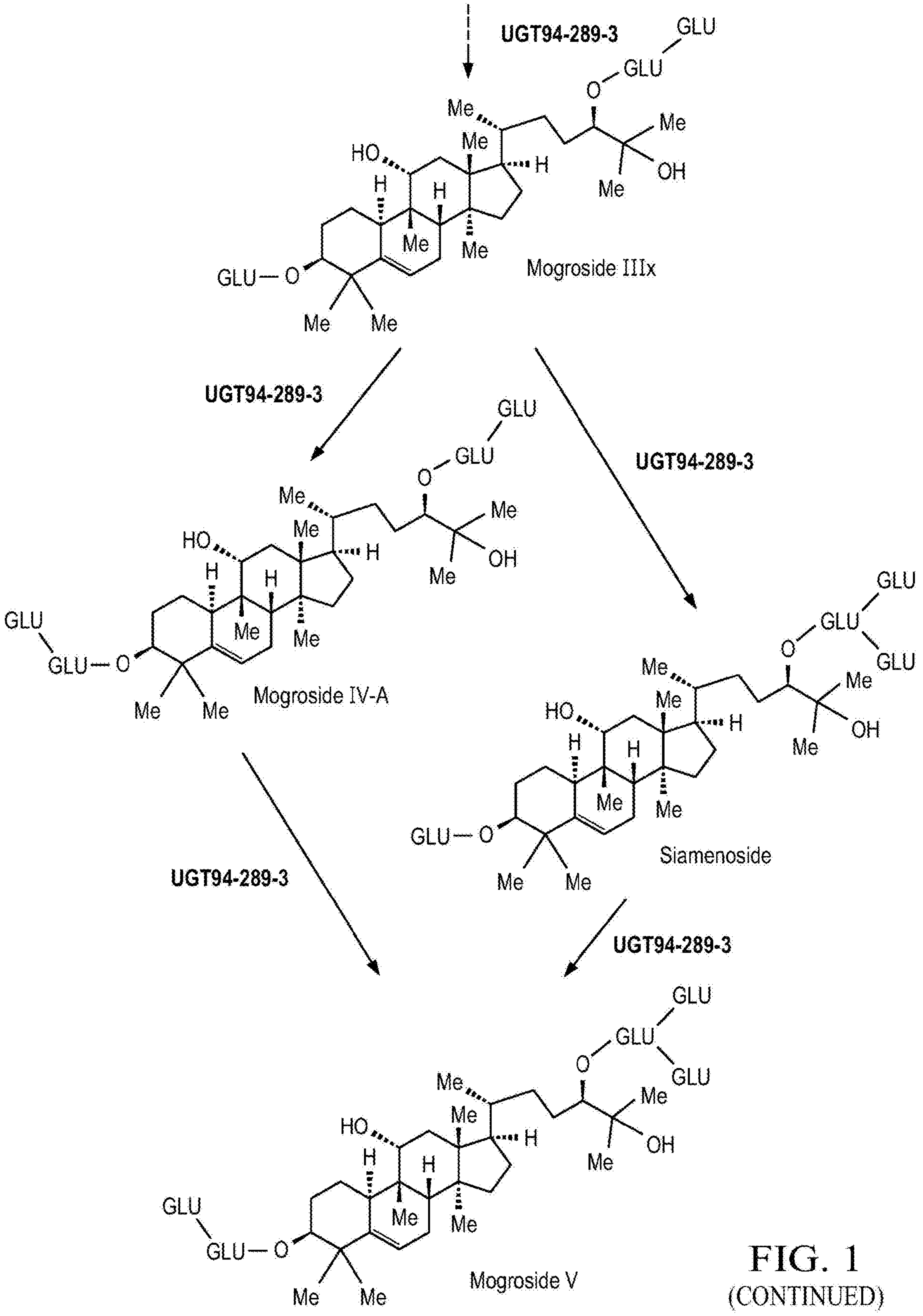

SEQ ID NO:1: cytochrome P450-72 (CYP72 Zm) nucleic acid sequence based on *Zea mays* codon usage.

SEQ ID NO:2: cytochrome P450-72 (CYP72) amino acid sequence.

SEQ ID NO:3: cytochrome P450-72 (CYP72 GC) nucleic acid sequence with higher GC content than SEQ ID NO:1.

SEQ ID NO:4: cucurbitadienol synthase (CDS) nucleic acid sequence.

SEQ ID NO:5: cucurbitadienol synthase (CDS) amino acid sequence.

SEQ ID NO:6: cytochrome P450-87 (CYP87) nucleic acid sequence.

SEQ ID NO:7: cytochrome P450-87 (CYP87) amino acid sequence.

SEQ ID NO:8: uridine phosphorylase dependent glycosyltransferase-720 (UGT720) nucleic acid sequence.

SEQ ID NO:9: uridine phosphorylase dependent glycosyltransferase-720 (UGT720) amino acid sequence.

SEQ ID NO:10: uridine phosphorylase dependent glycosyltransferase-94 (UGT94) nucleic acid sequence.

SEQ ID NO:11: uridine phosphorylase dependent glycosyltransferase-94 (UGT94) amino acid sequence.

SEQ ID NO:12: squalene epoxidase (SQE) nucleic acid sequence.

SEQ ID NO:13: squalene epoxidase (SQE) amino acid sequence.

SEQ ID NO:14: epoxy hydrolase (EPH) nucleic acid sequence.

SEQ ID NO:15: epoxy hydrolase (EPH) amino acid sequence.

SEQ ID NO:16: truncated 3-hydroxy-3-methylglutaryl-CoA reductase (tHMGR) nucleic acid sequence.

SEQ ID NO:17: truncated 3-hydroxy-3-methylglutaryl-CoA reductase (tHMGR) amino acid sequence.

SEQ ID NO:18: NADPH:cytochrome P450 reductase (SgCPR2) nucleic acid sequence.

SEQ ID NO:19: NADPH:cytochrome P450 reductase (SgCPR2) amino acid sequence.

SEQ ID NO:20: uridine phosphorylase dependent glycosyltransferase 74 (UGT74_3) nucleic acid sequence.

SEQ ID NO:21: uridine phosphorylase dependent glycosyltransferase 74 (UGT74_3) amino acid sequence.

SEQ ID NO:22: uridine phosphorylase dependent glycosyltransferase 74 (UGT74_4) nucleic acid sequence.

SEQ ID NO:23: uridine phosphorylase dependent glycosyltransferase 74 (UGT74_4) amino acid sequence.

SEQ ID NO:24: cytochrome P450-87 (ClCYP87D18_B m3) nucleic acid sequence from *Citrullus lanatus.*

SEQ ID NO:25: cytochrome P450-87 (ClCYP87D18_B m3) amino acid sequence from *Citrullus lanatus.*

SEQ ID NO:26: mutated cytochrome P450-87 (CYP87D17 m2) nucleic acid sequence.

SEQ ID NO:27: mutated cytochrome P450-87 (CYP87D17 m2) amino acid sequence.

SEQ ID NO:28: mutated cytochrome P450-87 (CYP87D17 m3) nucleic acid sequence.

SEQ ID NO:29: mutated cytochrome P450-87 (CYP87D17 m3) amino acid sequence.

SEQ ID NO:30: mutated cytochrome P450-87 (CYP87D20 m2) nucleic acid sequence.

SEQ ID NO:31: mutated cytochrome P450-87 (CYP87D20 m2) amino acid sequence.

SEQ ID NO:32: mutated cytochrome P450-87 (CYP87D20 m3) nucleic acid sequence.

SEQ ID NO:33: mutated cytochrome P450-87 (CYP87D20 m3) amino acid sequence.

SEQ ID NO:34: cytochrome P450-72 (CYP72)-2A-cytochrome P450-72 (CYP72) bicistronic nucleic acid sequence.

SEQ ID NO:35: first CYP72 amino acid sequence that can be produced from cytochrome P450-72 (CYP72)-2A-cytochrome P450-72 (CYP72) bicistronic nucleic acid sequence after cleavage.

SEQ ID NO:36: second CYP72 amino acid sequence that can be produced from cytochrome P450-72 (CYP72)-2A-cytochrome P450-72 (CYP72) bicistronic nucleic acid sequence after cleavage.

SEQ ID NO:37: full length CYP72-2A-CYP72 amino acid sequence from cytochrome P450-72 (CYP72)-2A-cytochrome P450-72 (CYP72) bicistronic nucleic acid sequence.

SEQ ID NO:38: uridine phosphorylase dependent glycosyltransferase-720 (UGT720)-2A-uridine phosphorylase dependent glycosyltransferase-720 (UGT720) bicistronic nucleic acid sequence.

SEQ ID NO:39: first UGT720 amino acid sequence that can be produced from uridine phosphorylase dependent glycosyltransferase-720 (UGT720)-2A-uridine phosphorylase dependent glycosyltransferase-720 (UGT720) bicistronic nucleic acid sequence after cleavage.

SEQ ID NO:40: second UGT720 amino acid sequence that can be produced from uridine phosphorylase dependent glycosyltransferase-720 (UGT720)-2A-uridine phosphorylase dependent glycosyltransferase-720 (UGT720) bicistronic nucleic acid sequence after cleavage.

SEQ ID NO:41: full length UGT720 amino acid sequence from uridine phosphorylase dependent glycosyltransferase-720 (UGT720)-2A-uridine phosphorylase dependent glycosyltransferase-720 (UGT720) bicistronic nucleic acid sequence.

SEQ ID NO:42: uridine phosphorylase dependent glycosyltransferase-94 (UGT94)-2A-uridine phosphorylase dependent glycosyltransferase-94 (UGT94) bicistronic nucleic acid sequence.

SEQ ID NO:43: first UGT94 amino acid sequence that can be produced from uridine phosphorylase dependent glycosyltransferase-94 (UGT94)-2A-uridine phosphorylase dependent glycosyltransferase-94 (UGT94) bicistronic nucleic acid sequence after cleavage.

SEQ ID NO:44: second UGT94 amino acid sequence that can be produced from uridine phosphorylase dependent glycosyltransferase-94 (UGT94)-2A-uridine phosphorylase dependent glycosyltransferase-94 (UGT94) bicistronic nucleic acid sequence after cleavage.

SEQ ID NO:45: full length UGT94-2A-UGT94 amino acid sequence that can be produced from uridine phosphorylase dependent glycosyltransferase-94 (UGT94)-2A-uridine phosphorylase dependent glycosyltransferase-94 (UGT94) bicistronic nucleic acid sequence after cleavage.

SEQ ID NO:46: truncated 3-hydroxy-3-methylglutaryl-CoA reductase (tHMGR)-2A-truncated 3-hydroxy-3-methylglutaryl-CoA reductase (tHMGR) bicistronic nucleic acid sequence.

SEQ ID NO:47: first tHMGR amino acid sequence that can be produced from truncated 3-hydroxy-3-methylglutaryl-CoA reductase (tHMGR)-2A-truncated 3-hydroxy-3-methylglutaryl-CoA reductase (tHMGR) bicistronic nucleic acid sequence after cleavage.

SEQ ID NO:48: second tHMGR amino acid sequence that can be produced from truncated 3-hydroxy-3-methylglutaryl-CoA reductase (tHMGR)-2A-truncated 3-hydroxy-3-methylglutaryl-CoA reductase (tHMGR) bicistronic nucleic acid sequence after cleavage.

SEQ ID NO:49: full length tHMGR-2A-tHMGR amino acid sequence that can be produced from truncated 3-hydroxy-3-methylglutaryl-CoA reductase (tHMGR)-2A-truncated 3-hydroxy-3-methylglutaryl-CoA reductase (tHMGR) bicistronic nucleic acid sequence after cleavage.

SEQ ID NO:50: uridine phosphorylase dependent glycosyltransferase-720 (UGT720)-2A-cytochrome P450-72 (CYP72) bicistronic nucleic acid sequence.

SEQ ID NO:51: UGT720 amino acid sequence that can be produced from uridine phosphorylase dependent glycosyltransferase-720 (UGT720)-2A-cytochrome P450-72 (CYP72) bicistronic nucleic acid sequence after cleavage.

SEQ ID NO:52: CYP72 amino acid sequence that can be produced from uridine phosphorylase dependent glycosyltransferase-720 (UGT720)-2A-cytochrome P450-72 (CYP72) bicistronic nucleic acid sequence after cleavage.

SEQ ID NO:53: full length UGT720-2A-CYP72 amino acid sequence from uridine phosphorylase dependent glycosyltransferase-720 (UGT720)-2A-cytochrome P450-72 (CYP72) bicistronic nucleic acid sequence.

SEQ ID NO:54: uridine phosphorylase dependent glycosyltransferase-94 (UGT94)-2A-truncated 3-hydroxy-3-methylglutaryl-CoA reductase (tHMGR) bicistronic nucleic acid sequence.

SEQ ID NO:55: UGT94 amino acid sequence that can be produced from uridine phosphorylase dependent glycosyltransferase-94 (UGT94)-2A-truncated 3-hydroxy-3-methylglutaryl-CoA reductase (tHMGR) bicistronic nucleic acid sequence after cleavage.

SEQ ID NO:56: tHMGR amino acid sequence that can be produced from uridine phosphorylase dependent glycosyltransferase-94 (UGT94)-2A-truncated 3-hydroxy-3-methylglutaryl-CoA reductase (tHMGR) bicistronic nucleic acid sequence after cleavage.

SEQ ID NO:57: UGT94-2A-tHMGR amino acid sequence from uridine phosphorylase dependent glycosyltransferase-94 (UGT94)-2A-truncated 3-hydroxy-3-methylglutaryl-CoA reductase (tHMGR) bicistronic nucleic acid sequence.

SEQ ID NO:58: Hygromycin resistance (HygR) gene nucleic acid sequence.

SEQ ID NO:59: Hygromycin resistance (HygR) gene amino acid sequence.

SEQ ID NO:60: HLVH12 promoter nucleic acid sequence.

SEQ ID NO:61: DCMV promoter nucleic acid sequence.

SEQ ID NO:62: FMVSgt: PCLSVFlt (also referred to as FSgt/PFLt) chimeric promoter nucleic acid sequence.

SEQ ID NO:63: Duplicated MMV (dMMV) promoter nucleic acid sequence.

SEQ ID NO:64: CmYLCV promoter nucleic acid sequence.

SEQ ID NO:65: CaMV e35S (e35S) promoter nucleic acid sequence.

SEQ ID NO:66: NOS promoter nucleic acid sequence.

SEQ ID NO:67: ScBV promoter nucleic acid sequence.

SEQ ID NO:68: CsVMV promoter nucleic acid sequence.

SEQ ID NO:69: FMVSgt promoter nucleic acid sequence.

SEQ ID NO:70: FS1_1 promoter nucleic acid sequence.

SEQ ID NO:71: FE_3 promoter nucleic acid sequence.

SEQ ID NO:72: Pea3A terminator nucleic acid sequence.

SEQ ID NO:73: At UBQ3 terminator nucleic acid sequence.

SEQ ID NO:74: Gmax MYB2 terminator nucleic acid sequence.

SEQ ID NO:75: AtRBCS2B terminator nucleic acid sequence.

SEQ ID NO:76: Pea E9 terminator nucleic acid sequence.

SEQ ID NO:77: AtHSP18.2 terminator nucleic acid sequence.

SEQ ID NO:78: Potato Ubi3 terminator nucleic acid sequence.

SEQ ID NO:79: At Tubulin B9 (AtTub) terminator nucleic acid sequence.

SEQ ID NO:80: 35S terminator nucleic acid sequence.

SEQ ID NO:81: SynJ 5UTR nucleic acid sequence.

SEQ ID NO:82: TM6 MAR insulator nucleic acid sequence.

SEQ ID NO:83: 2A self-cleaving peptide nucleic acid sequence.

SEQ ID NO:84: 2A self-cleaving peptide amino acid sequence.

SEQ ID NO:85: cytochrome P450-72 (CYP72 V1) nucleic acid sequence.

SEQ ID NO:86: cytochrome P450-72 (CYP72 V1) amino acid sequence.

SEQ ID NO:87: alternative squalene epoxidase (SQE) nucleic acid sequence.

SEQ ID NO:88: alternative cytochrome P450-87 (CYP87) nucleic acid sequence.

SEQ ID NO:89: alternative cucurbitadienol synthase (CDS) nucleic acid sequence.

SEQ ID NO:90: alternative epoxy hydrolase (EPH) nucleic acid sequence.

SEQ ID NO:91: alternative uridine phosphorylase dependent glycosyltransferase-720 (UGT720) nucleic acid sequence.

SEQ ID NO:92: alternative uridine phosphorylase dependent glycosyltransferase-94 (UGT94) nucleic acid sequence.

SEQ ID NO:93: upstream terpenoid biosynthetic enzyme (FPS; SP0231), *Citrullus lanatus* cDNA, nucleic acid sequence.

SEQ ID NO:94: upstream terpenoid biosynthetic enzyme (FPS; SP0231), *Citrullus lanatus*, amino acid sequence.

SEQ ID NO:95: cytochrome P450 biosynthetic enzyme, high GC version (CYP87D20 m2 (V2-146L-A49L-C343Y) GC63; SP0577), *Siraitia grosvenorii* cDNA, nucleic acid sequence.

SEQ ID NO:96: cytochrome P450 biosynthetic enzyme, high GC version (CYP87D20 m2 (V2-146L-A49L-C343Y) GC63; SP0577), *Siraitia grosvenorii*, nucleic acid sequence.

SEQ ID NO:97: upstream squalene biosynthetic enzyme (SQS; SP0951), *Citrullus lanatus* cDNA, nucleic acid sequence.

SEQ ID NO:98: upstream squalene biosynthetic enzyme (SQS; SP0951), *Citrullus lanatus*, amino acid sequence.

SEQ ID NO:99: cytochrome P450 biosynthetic enzyme, mutant, high GC version (CYP87D17 m3 GC63; SP1333), *Siraitia grosvenorii* cDNA, nucleic acid sequence.

SEQ ID NO:100: cytochrome P450 biosynthetic enzyme, mutant, high GC version (CYP87D17 m3 GC63; SP1333), *Siraitia grosvenorii*, amino acid sequence.

SEQ ID NO:101: cytochrome P450 biosynthetic enzyme, mutant, high GC version (CYP87D17 m2 GC63; SP2503), *Siraitia grosvenorii* cDNA, nucleic acid sequence.

SEQ ID NO:102: cytochrome P450 biosynthetic enzyme, mutant high GC version (CYP87D17 m2 GC63; SP2503), *Siraitia grosvenorii*, protein.

SEQ ID NO:103: cytochrome p450 reductase biosynthetic enzyme, high GC version (SgCPR2 GC66; SP2571), *Siraitia grosvenorii* cDNA, nucleic acid sequence.

SEQ ID NO:104: cytochrome p450 reductase biosynthetic enzyme, high GC version (SgCPR2 GC66; SP2571), *Siraitia grosvenorii*, amino acid sequence.

SEQ ID NO:105: uridine phosphorylase dependent glycosyltransferase 74, high GC version (SgUGT74_406_2 GC64; SP2666), *Siraitia grosvenorii* cDNA, nucleic acid sequence.

SEQ ID NO:106: uridine phosphorylase dependent glycosyltransferase 74, high GC version (SgUGT74_406_2 GC64; SP2666), *Siraitia grosvenorii*, amino acid sequence.

SEQ ID NO:107: uridine phosphorylase dependent glycosyltransferase 74, high GC version (SgUGT74_345_2 GC65; SP3201), *Siraitia grosvenorii* cDNA, nucleic acid sequence.

SEQ ID NO:108: uridine phosphorylase dependent glycosyltransferase 74, high GC version (SgUGT74_345_2 GC65; SP3201), *Siraitia grosvenorii*, amino acid sequence.

SEQ ID NO:109: cytochrome P450 biosynthetic enzyme, mutant, high GC version (ClCYP87D18_B m3 GC62; SP4900), *Citrullus lanatus* cDNA, nucleic acid sequence.

SEQ ID NO:110: cytochrome P450 biosynthetic enzyme, mutant, high GC version (ClCYP87D18_B m3 GC62; SP4900), *Citrullus lanatus*, amino acid sequence.

SEQ ID NO:111: cytochrome P450 biosynthetic enzyme (CYP87D20 m3 (V2-146L-A49L-C343Y L193KO) GC63; SP4910), *Siraitia grosvenorii* cDNA, nucleic acid sequence.

SEQ ID NO:112: cytochrome P450 biosynthetic enzyme (CYP87D20 m3 (V2-146L-A49L-C343Y L193KO) GC63; SP4910), *Siraitia grosvenorii*, amino acid sequence.

SEQ ID NO:113: uridine phosphorylase dependent glycosyltransferase (Solyc01g107825.1 UGT, SP5024), *Solanum lycopersicum* cDNA, nucleic acid sequence.

SEQ ID NO:114: uridine phosphorylase dependent glycosyltransferase (Solyc01g107825.1 UGT, SP5024), *Solanum lycopersicum*, amino acid sequence.

SEQ ID NO:115: uridine phosphorylase dependent glycosyltransferase (Solyc02g070020.1 UGT; SP5025), *Solanum lycopersicum* cDNA, nucleic acid sequence.

SEQ ID NO:116: uridine phosphorylase dependent glycosyltransferase (Solyc02g070020.1 UGT; SP5025), *Solanum lycopersicum*, amino acid sequence.

SEQ ID NO:117: uridine phosphorylase dependent glycosyltransferase (Solyc09g092500.1 UGT; SP5026), *Solanum lycopersicum* cDNA, nucleic acid sequence.

SEQ ID NO:118: uridine phosphorylase dependent glycosyltransferase (Solyc09g092500.1 UGT; SP5026), *Solanum lycopersicum*, amino acid sequence.

SEQ ID NO:119: uridine phosphorylase dependent glycosyltransferase (Solyc10g085230.2 UGT; SP5027), *Solanum lycopersicum* cDNA, nucleic acid sequence.

SEQ ID NO:120: uridine phosphorylase dependent glycosyltransferase (Solyc10g085230.2 UGT; SP5027), *Solanum lycopersicum*, amino acid sequence.

SEQ ID NO:121: uridine phosphorylase dependent glycosyltransferase (Solyc10g085880.1 UGT; SP5028), *Solanum lycopersicum* cDNA, nucleic acid sequence.

SEQ ID NO:122: uridine phosphorylase dependent glycosyltransferase (Solyc10g085880.1 UGT; SP5028), *Solanum lycopersicum*, amino acid sequence.

SEQ ID NO:123: uridine phosphorylase dependent glycosyltransferase 94 (Sg UGT94-289-3-MS1; SP5034), *Siraitia grosvenorii* cDNA, nucleic acid sequence.

SEQ ID NO:124: -uridine phosphorylase dependent glycosyltransferase 94 (Sg UGT94-289-3-MS1; SP5034), *Siraitia grosvenorii*, amino acid sequence.

SEQ ID NO:125: upstream terpenoid biosynthetic enzyme (GPS1; SP5035), *Citrullus lanatus* cDNA, nucleic acid sequence.

SEQ ID NO:126: upstream terpenoid biosynthetic enzyme (GPS1; SP5035), *Citrullus lanatus*, amino acid sequence.

SEQ ID NO:127: uridine phosphorylase dependent glycosyltransferase, high GC version (SgUGT75-281-2 GC65; SP5036), *Siraitia grosvenorii* cDNA, nucleic acid sequence.

SEQ ID NO:128: uridine phosphorylase dependent glycosyltransferase, high GC version (SgUGT75-281-2 GC65; SP5036), *Siraitia grosvenorii*, amino acid sequence.

SEQ ID NO:129: uridine phosphorylase dependent glycosyltransferase 74 (SgUGT74AC1 (no stop); SP5037), *Siraitia grosvenorii* cDNA, nucleic acid sequence.

SEQ ID NO:130: uridine phosphorylase dependent glycosyltransferase 74 (SgUGT74AC1 (no stop); SP5037), *Siraitia grosvenorii*, amino acid sequence.

SEQ ID NO:131: uridine phosphorylase dependent glycosyltransferase (Sg MG1 GC63; SP5038), *Siraitia grosvenorii* cDNA, nucleic acid sequence.

SEQ ID NO:132: uridine phosphorylase dependent glycosyltransferase (Sg MG1 GC63; SP5038), *Siraitia grosvenorii*, amino acid sequence.

SEQ ID NO:133: uridine phosphorylase dependent glycosyltransferase (t134248; SP5039), *Stevia rebaudiana* cDNA, nucleic acid sequence.

SEQ ID NO:134: uridine phosphorylase dependent glycosyltransferase (t134248; SP5039), *Stevia rebaudiana*, amino acid sequence.

SEQ ID NO:135: uridine phosphorylase dependent glycosyltransferase (t72140; SP5040), *Stevia rebaudiana* cDNA, nucleic acid sequence.

SEQ ID NO:136: uridine phosphorylase dependent glycosyltransferase (t72140; SP5040), *Stevia rebaudiana*, amino acid sequence.

SEQ ID NO:137: uridine phosphorylase dependent glycosyltransferase (t72143; SP5041), *Stevia rebaudiana* cDNA, nucleic acid sequence.

SEQ ID NO:138: uridine phosphorylase dependent glycosyltransferase (t72143; SP5041), *Stevia rebaudiana*, amino acid sequence.

SEQ ID NO:139: uridine phosphorylase dependent glycosyltransferase (t74692; SP5042), *Stevia rebaudiana* cDNA, nucleic acid sequence.

SEQ ID NO:140: uridine phosphorylase dependent glycosyltransferase (t74692; SP5042), *Stevia rebaudiana*, amino acid sequence.

SEQ ID NO:141: uridine phosphorylase dependent glycosyltransferase (t85004; SP5043), *Stevia rebaudiana* cDNA, nucleic acid sequence.

SEQ ID NO:142: uridine phosphorylase dependent glycosyltransferase (t85004; SP5043), *Stevia rebaudiana*, amino acid sequence.

SEQ ID NO:143: upstream terpenoid biosynthetic enzyme (Sg 00000109.2_FPS1; SP5044), *Siraitia grosvenorii* cDNA, nucleic acid sequence.

SEQ ID NO:144: upstream terpenoid biosynthetic enzyme (Sg 00000109.2_FPS1; SP5044), *Siraitia grosvenorii*, amino acid sequence.

SEQ ID NO:145: upstream squalene biosynthetic enzyme (Sg 00000892.729_SQS1; SP5045), *Siraitia grosvenorii* cDNA, nucleic acid sequence.

SEQ ID NO:146: upstream squalene biosynthetic enzyme (Sg 00000892.729_SQS1; SP5045), *Siraitia grosvenorii*, amino acid sequence.

SEQ ID NO:147: upstream terpenoid biosynthetic enzyme (Bj HMGS mutant; SP5046), *Brassica* junea cDNA, nucleic acid sequence.

SEQ ID NO:148: upstream terpenoid biosynthetic enzyme (Bj HMGS mutant; SP5046), *Brassica* junea, amino acid sequence.

SEQ ID NO:149: UDPG pyrophosphorylase (Ta UDP-Glucose Pyrophosphorylase; SP5047), Thermocrispum agreste cDNA, nucleic acid sequence.

SEQ ID NO:150: UDPG pyrophosphorylase (Ta UDP-Glucose Pyrophosphorylase; SP5047), Thermocrispum agreste, amino acid sequence.

SEQ ID NO:151: upstream terpenoid biosynthetic enzyme (CIGPS_2; SP5048), *Citrullus lanatus* cDNA, nucleic acid sequence.

SEQ ID NO:152: upstream terpenoid biosynthetic enzyme (CIGPS_2; SP5048), *Citrullus lanatus*, amino acid sequence.

SEQ ID NO:153: upstream terpenoid biosynthetic enzyme (MpGPS-SSU; SP5049), Peppermint (*Mentha* x *piperita*) cDNA, nucleic acid sequence.

SEQ ID NO:154: upstream terpenoid biosynthetic enzyme (MpGPS-SSU; SP5049), Peppermint (*Mentha* x *piperita*), amino acid sequence.

SEQ ID NO:155: upstream terpenoid biosynthetic enzyme (LcGPS-SSU; SP5050), *Litsea cubeba* cDNA, nucleic acid sequence.

SEQ ID NO:156: upstream terpenoid biosynthetic enzyme (LcGPS-SSU; SP5050), *Litsea cubeba*, amino acid sequence.

SEQ ID NO:157: hydrolase biosynthetic enzyme (DbExg1; SP5051), Dekkera bruxellensis cDNA, nucleic acid sequence.

SEQ ID NO:158: hydrolase biosynthetic enzyme (DbExg1; SP5051), Dekkera bruxellensis, amino acid sequence.

SEQ ID NO:159: upstream terpenoid biosynthetic enzyme (CICG09G011560.1_PMK; SP5072), *Citrullus lanatus* cDNA, nucleic acid sequence.

SEQ ID NO:160: upstream terpenoid biosynthetic enzyme (CICG09G011560.1_PMK; SP5072), *Citrullus lanatus*, amino acid sequence.

SEQ ID NO:161: upstream terpenoid biosynthetic enzyme (CICG10G001230.1_PMK; SP5073), *Citrullus lanatus* cDNA, nucleic acid sequence.

SEQ ID NO:162: upstream terpenoid biosynthetic enzyme (CICG10G001230.1_PMK; SP5073), *Citrullus lanatus*, amino acid sequence.

SEQ ID NO:163: upstream terpenoid biosynthetic enzyme (CICG09G022040.1_IPK; SP5074), *Citrullus lanatus* cDNA, nucleic acid sequence.

SEQ ID NO:164: upstream terpenoid biosynthetic enzyme (CICG09G022040.1_IPK; SP5074), *Citrullus lanatus*, amino acid sequence.

SEQ ID NO:165: upstream terpenoid biosynthetic enzyme (CICG05G021710.1_MVD; SP5075), *Citrullus lanatus* cDNA, nucleic acid sequence.

SEQ ID NO:166: upstream terpenoid biosynthetic enzyme (CICG05G021710.1_MVD; SP5075), *Citrullus lanatus*, amino acid sequence.

SEQ ID NO:167: upstream terpenoid biosynthetic enzyme (Sg 00153574.101_FPS1; SP5076), *Siraitia grosvenorii* cDNA, nucleic acid sequence.

SEQ ID NO:168: upstream terpenoid biosynthetic enzyme (Sg 00153574.101_FPS1; SP5076), *Siraitia grosvenorii*, amino acid sequence.

SEQ ID NO:169: upstream terpenoid biosynthetic enzyme (Sg 00010190.2_SQS1; SP5077), *Siraitia grosvenorii* cDNA, nucleic acid sequence.

SEQ ID NO:170: upstream terpenoid biosynthetic enzyme (Sg 00010190.2_SQS1; SP5077), *Siraitia grosvenorii*, amino acid sequence.

SEQ ID NO:171: upstream terpenoid biosynthetic enzyme (Sg 00153449.125_PMK; SP5078), *Siraitia grosvenorii* cDNA, nucleic acid sequence.

SEQ ID NO:172: upstream terpenoid biosynthetic enzyme (Sg 00153449.125_PMK; SP5078), *Siraitia grosvenorii*, amino acid sequence.

SEQ ID NO:173: upstream terpenoid biosynthetic enzyme, high GC version (tHMGR GC69; SP5079), *Avena* strigose cDNA, nucleic acid sequence.

SEQ ID NO:174: upstream terpenoid biosynthetic enzyme, high GC version (tHMGR GC69; SP5079), *Avena* strigose, amino acid sequence.

SEQ ID NO:175: uridine phosphorylase dependent glycosyltransferase, high GC version (Sg UGT720-269-1 Itkin GC65; SP5080), *Siraitia grosvenorii* cDNA, nucleic acid sequence.

SEQ ID NO:176: uridine phosphorylase dependent glycosyltransferase, high GC version (Sg UGT720-269-1 Itkin GC65; SP5080), *Siraitia grosvenorii*, amino acid sequence.

SEQ ID NO:177: uridine phosphorylase dependent glycosyltransferase, high GC version (Sg UGT720-269-4 Itkin GC65; SP5081), *Siraitia grosvenorii* cDNA, nucleic acid sequence.

SEQ ID NO:178: uridine phosphorylase dependent glycosyltransferase, high GC version (Sg UGT720-269-4 Itkin GC65; SP5081), *Siraitia grosvenorii*, amino acid sequence.

SEQ ID NO:179: uridine phosphorylase dependent glycosyltransferase (Sg UGT94-289-2; SP5082), *Siraitia grosvenorii* cDNA, nucleic acid sequence.

SEQ ID NO:180: uridine phosphorylase dependent glycosyltransferase (Sg UGT94-289-2; SP5082), *Siraitia grosvenorii*, amino acid sequence.

SEQ ID NO:181: uridine phosphorylase dependent glycosyltransferase (Sg UGT94-289-2 Itkin; SP5083), *Siraitia grosvenorii* cDNA, nucleic acid sequence.

SEQ ID NO:182: uridine phosphorylase dependent glycosyltransferase (Sg UGT94-289-2 Itkin; SP5083), *Siraitia grosvenorii*, amino acid sequence.

SEQ ID NO:183: uridine phosphorylase dependent glycosyltransferase (Sg UGT94-289-3 Itkin; SP5084), *Siraitia grosvenorii* cDNA, nucleic acid sequence.

SEQ ID NO:184: uridine phosphorylase dependent glycosyltransferase (Sg UGT94-289-3 Itkin; SP5084), *Siraitia grosvenorii*, amino acid sequence.

SEQ ID NO:185: uridine phosphorylase dependent glycosyltransferase (t134583; SP5085), *Siraitia grosvenorii* cDNA, nucleic acid sequence.

SEQ ID NO:186: uridine phosphorylase dependent glycosyltransferase (t134583; SP5085), *Siraitia grosvenorii*, amino acid sequence.

SEQ ID NO:187: uridine phosphorylase dependent glycosyltransferase (t74645; SP5086), *Siraitia grosvenorii* cDNA, nucleic acid sequence.

SEQ ID NO:188: uridine phosphorylase dependent glycosyltransferase (t74645; SP5086), *Siraitia grosvenorii*, amino acid sequence.

SEQ ID NO:189: uridine phosphorylase dependent glycosyltransferase (t74693; SP5087), *Siraitia grosvenorii* cDNA, nucleic acid sequence.

SEQ ID NO:190: uridine phosphorylase dependent glycosyltransferase (t74693; SP5087), *Siraitia grosvenorii*, amino acid sequence.

SEQ ID NO:191: upstream terpenoid biosynthetic enzyme (Sg 00001291.26_PMK; SP5088), *Siraitia grosvenorii* cDNA, nucleic acid sequence.

SEQ ID NO:192: upstream terpenoid biosynthetic enzyme (Sg 00001291.26_PMK; SP5088), *Siraitia grosvenorii*, amino acid sequence.

SEQ ID NO:193: upstream terpenoid biosynthetic enzyme (Sg 00154122.1_IPK; SP5089), *Siraitia grosvenorii* cDNA, nucleic acid sequence.

SEQ ID NO:194: upstream terpenoid biosynthetic enzyme (Sg 00154122.1_IPK; SP5089), *Siraitia grosvenorii*, amino acid sequence.

SEQ ID NO:195: upstream terpenoid biosynthetic enzyme (Sg 27366_MVD; SP5090), *Siraitia grosvenorii* cDNA, nucleic acid sequence.

SEQ ID NO:196: upstream terpenoid biosynthetic enzyme (Sg 27366_MVD; SP5090), *Siraitia grosvenorii*, amino acid sequence.

SEQ ID NO:197: hydrolase biosynthetic enzyme (E142A-RRK67; SP5091), *Aspergillus oryzae* cDNA, nucleic acid sequence.

SEQ ID NO:198: hydrolase biosynthetic enzyme (E142A-RRK67; SP5091), *Aspergillus oryzae*, amino acid sequence.

SEQ ID NO:199: upstream terpenoid biosynthetic enzyme (Mc CDS; SP5092), *Momordica charantia* cDNA, nucleic acid sequence.

SEQ ID NO:200: upstream terpenoid biosynthetic enzyme (Mc CDS; SP5092), *Momordica charantia*, amino acid sequence.

SEQ ID NO: 201: upstream terpenoid biosynthetic enzyme (Cp CDS; SP5093), *Cucurbita pepo* cDNA, nucleic acid sequence.

SEQ ID NO:202: upstream terpenoid biosynthetic enzyme (Cp CDS; SP5093), *Cucurbita pepo*, amino acid sequence.

SEQ ID NO:203: upstream terpenoid biosynthetic enzyme (Tc CDS; SP5094), *Trichosanthes cucumerina* cDNA, nucleic acid sequence.

SEQ ID NO:204: upstream terpenoid biosynthetic enzyme (Tc CDS; SP5094), *Trichosanthes cucumerina*, amino acid sequence.

SEQ ID NO:205: upstream terpenoid biosynthetic enzyme (Cc CDS; SP5095), *Citrullus colocynthis* cDNA, nucleic acid sequence.

SEQ ID NO:206: upstream terpenoid biosynthetic enzyme (Cc CDS; SP5095), *Citrullus colocynthis*, amino acid sequence.

SEQ ID NO:207: upstream terpenoid biosynthetic enzyme (Ac SQS with intron 6; SP5096), *Amaranthus cruentus* cDNA, nucleic acid sequence.

SEQ ID NO:208: upstream terpenoid biosynthetic enzyme (Ac SQS with intron 6; SP5096), *Amaranthus cruentus*, amino acid sequence.

SEQ ID NO:209: upstream terpenoid biosynthetic enzyme (Oe SQS; SP5097), *Olea europaea* cDNA, nucleic acid sequence.

SEQ ID NO:210: upstream terpenoid biosynthetic enzyme (Oe SQS; SP5097), *Olea europaea*, amino acid sequence.

SEQ ID NO:211: upstream terpenoid biosynthetic enzyme (Cr SQS; SP5098), *Chlamydomonas reinhardtii* cDNA, nucleic acid sequence.

SEQ ID NO:212: upstream terpenoid biosynthetic enzyme (Cr SQS; SP5098), *Chlamydomonas reinhardtii*, amino acid sequence.

SEQ ID NO:213: epoxidase biosynthetic enzyme (Cp SQE1; SP5099), *Cucurbita pepo* cDNA, nucleic acid sequence.

SEQ ID NO:214: epoxidase biosynthetic enzyme (Cp SQE1; SP5099), *Cucurbita pepo*, amino acid sequence.

SEQ ID NO:215: epoxidase biosynthetic enzyme (Mc SQE1; SP5100), *Momordica charantia* cDNA, nucleic acid sequence.

SEQ ID NO:216: epoxidase biosynthetic enzyme (Mc SQE1; SP5100), *Momordica charantia*, amino acid sequence.

SEQ ID NO:217: epoxidase biosynthetic enzyme (Pg SQE1; SP5101), *Panax ginseng* cDNA, nucleic acid sequence.

SEQ ID NO:218: epoxidase biosynthetic enzyme (Pg SQE1; SP5101), *Panax ginseng*, amino acid sequence.

SEQ ID NO:219: upstream terpenoid biosynthetic enzyme (Ab tHMGR; SP5102), Achyranthes *bidentata* cDNA, nucleic acid sequence.

SEQ ID NO:220: upstream terpenoid biosynthetic enzyme (Ab tHMGR; SP5102), Achyranthes *bidentata*, amino acid sequence.

SEQ ID NO:221: upstream terpenoid biosynthetic enzyme (Hb tHMGR; SP5103), Hevea *brasiliensis* cDNA, nucleic acid sequence.

SEQ ID NO:222: upstream terpenoid biosynthetic enzyme (Hb tHMGR; SP5103), Hevea *brasiliensis*, amino acid sequence.

SEQ ID NO:223: upstream terpenoid biosynthetic enzyme (Pg tHMGR; SP5104), *Panax ginseng* cDNA, nucleic acid sequence.

SEQ ID NO:224: upstream terpenoid biosynthetic enzyme (Pg tHMGR; SP5104), *Panax ginseng*, amino acid sequence.

SEQ ID NO:225: transcription factor (At MYC2D105N mutant; SP5105), *Arabidopsis thaliana* cDNA, nucleic acid sequence.

SEQ ID NO:226: transcription factor (At MYC2D105N mutant; SP5105), *Arabidopsis thaliana*, amino acid sequence.

SEQ ID NO:227: transcription Factor (Cs bHLH; SP5106), *Cucumis sativus* cDNA, nucleic acid sequence.

SEQ ID NO:228: transcription Factor (Cs bHLH; SP5106), *Cucumis sativus*, amino acid sequence.

SEQ ID NO:229: transcription Factor (Bh bHLH; Sp5107), Benincasa *hispida* cDNA, nucleic acid sequence.

SEQ ID NO:230: transcription Factor (Bh bHLH; Sp5107), Benincasa *hispida*, amino acid sequence.

SEQ ID NO:231: transcription Factor 2 (Cs bHLH; SP5108), *Cucumis sativus* cDNA, nucleic acid sequence.

SEQ ID NO:232: transcription Factor 2 (Cs bHLH; SP5108), *Cucumis sativus*, amino acid sequence.

SEQ ID NO:233: transcription Factor 2 (Bh bHLH; SP5109), Benincasa *hispida* cDNA, nucleic acid sequence.

SEQ ID NO:234: transcription Factor 2 (Bh bHLH; SP5109), Benincasa *hispida*, amino acid sequence.

SEQ ID NO:235: poplar sucrose synthase (SP5110) *Populus alba* cDNA, nucleic acid sequence.

SEQ ID NO:236: poplar sucrose synthase (SP5110) *Populus alba*, amino acid sequence.

SEQ ID NO:237: UDPG pyrophosphorylase (Lg UDP-Glucose Pyrophosphorylase; SP5111), *Larix gmelinii* cDNA, nucleic acid sequence.

SEQ ID NO:238: UDPG pyrophosphorylase (Lg UDP-Glucose Pyrophosphorylase; SP5111), *Larix gmelinii*, amino acid sequence.

SEQ ID NO:239: transcription factor (At PAP2; SP5112), *Arabidopsis thaliana* cDNA, nucleic acid sequence.

SEQ ID NO:240: transcription factor (At PAP2; SP5112), *Arabidopsis thaliana*, amino acid sequence.

SEQ ID NO:241: heat shock protein (Ms HSP17.6; SP5113), *Medicago sativa* cDNA, nucleic acid sequence.

SEQ ID NO:242: heat shock protein (Ms HSP17.6; SP5113), *Medicago sativa*, amino acid sequence.

SEQ ID NO:243: transcription factor (At JUNGB-RUNNEN1 Nac factor; SP5114), *Arabidopsis thaliana* cDNA, nucleic acid sequence.

SEQ ID NO:244: transcription factor (At JUNGB-RUNNEN1 Nac factor; SP5114), *Arabidopsis thaliana*, amino acid sequence.

SEQ ID NO:245: upstream terpenoid biosynthetic enzyme (AmGPS-SSU (no stop); SP5115), *Antirrhinum majus* cDNA, nucleic acid sequence.

SEQ ID NO:246: upstream terpenoid biosynthetic enzyme (AmGPS-SSU (no stop); SP5115), *Antirrhinum majus*, amino acid sequence.

SEQ ID NO:247: upstream terpenoid biosynthetic enzyme (PgFPS; SP5116), *Panax ginseng* cDNA, nucleic acid sequence.

SEQ ID NO:248: upstream terpenoid biosynthetic enzyme (PgFPS; SP5116), *Panax ginseng*, amino acid sequence.

SEQ ID NO:249: upstream terpenoid biosynthetic enzyme (PgSQS; SP5117), *Panax ginseng* cDNA, nucleic acid sequence.

SEQ ID NO:250: upstream terpenoid biosynthetic enzyme (PgSQS; SP5117), *Panax ginseng*, amino acid sequence.

SEQ ID NO:251: upstream terpenoid biosynthetic enzyme (gbHMGS1; SP5118), *Ginkgo biloba* cDNA, nucleic acid sequence.

SEQ ID NO:252: upstream terpenoid biosynthetic enzyme (gbHMGS1; SP5118), *Ginkgo biloba*, amino acid sequence.

SEQ ID NO:253: uridine phosphorylase dependent glycosyltransferase (UGT73AM3; SP5263), *Cucumis sativus* cDNA, nucleic acid sequence.

SEQ ID NO:254: uridine phosphorylase dependent glycosyltransferase (UGT73AM3; SP5263), *Cucumis sativus*, amino acid sequence.

SEQ ID NO:255: uridine phosphorylase dependent glycosyltransferase, high GC version (Solyc10g085230.2 UGT GC61; SP5265), *Solanum lycopersicum* cDNA, nucleic acid sequence.

SEQ ID NO:256: uridine phosphorylase dependent glycosyltransferase, high GC version (Solyc10g085230.2 UGT GC61; SP5265), *Solanum lycopersicum*, amino acid sequence.

SEQ ID NO:257: uridine phosphorylase dependent glycosyltransferase, high GC version (UGT73AM3 GC64; SP5350), *Cucumis sativus* cDNA, nucleic acid sequence.

SEQ ID NO:258: uridine phosphorylase dependent glycosyltransferase, high GC version (UGT73AM3 GC64; SP5350), *Cucumis sativus*, amino acid sequence.

SEQ ID NO:259: AtUBQ10 promoter, *Arabidopsis thaliana*, nucleic acid sequence.

SEQ ID NO:260: PCLSV promoter, Peanut chlorotic streak virus, nucleic acid sequence.

SEQ ID NO:261: FS4 promoter, *Citrullus lanatus*, nucleic acid sequence.

SEQ ID NO:262: AtACT2 promoter, *Arabidopsis thaliana*, nucleic acid sequence.

SEQ ID NO:263: Enhanced AtEf-1A promoter, Cauliflower mosaic virus/*Arabidopsis thaliana*, nucleic acid sequence.

SEQ ID NO:264: FuasFScp promoter, Figwort mosaic virus hybrid P, nucleic acid sequence.

SEQ ID NO:265: AtFAD2 terminator, *Arabidopsis thaliana*, nucleic acid sequence.

SEQ ID NO:266: AtNDUFA8 terminator, *Arabidopsis thaliana*, nucleic acid sequence.

SEQ ID NO:267: CsHSP17.3 terminator, *Cucumis sativus*, nucleic acid sequence.

SEQ ID NO:268: CsHSP22 terminator, *Cucumis sativus*, nucleic acid sequence.

SEQ ID NO:269: FE4 promoter, *Citrullus lanatus*, nucleic acid sequence.

SEQ ID NO:270: Cucumisin promoter, *Cucumis melo* L., nucleic acid sequence.

SEQ ID NO:271: SgCDS promoter, *Siraitia grosvenorii*, nucleic acid sequence.

SEQ ID NO:272: upstream terpenoid biosynthetic enzyme, high GC version (CITHMGR GC; SP2040), *Citrullus lanatus* cDNA, nucleic acid sequence.

SEQ ID NO:273: upstream terpenoid biosynthetic enzyme, high GC version (CltHMGR GC 2A; SP2040), *Citrullus lanatus*, amino acid sequence.\

SEQ ID NO:274: upstream terpenoid biosynthetic enzyme (CltHMGR GC 2A; SP3351), *Citrullus lanatus* cDNA, nucleic acid sequence.

SEQ ID NO:275: upstream terpenoid biosynthetic enzyme (CltHMGR GC 2A; SP3351), *Citrullus lanatus*, amino acid sequence.

SEQ ID NO:276: upstream terpenoid biosynthetic enzyme (CltHMGR Zm (for 2A); SP4989), *Citrullus lanatus* cDNA, nucleic acid sequence.

SEQ ID NO:277: upstream terpenoid biosynthetic enzyme (CltHMGR Zm (for 2A); SP4989), *Citrullus lanatus*, amino acid sequence.

SEQ ID NO:278: cytochrome P450 biosynthetic enzyme, optimized to corn (mf CYP72A459v1a Zm (GC48); SP2015), *Siraitia grosvenorii* cDNA, nucleic acid sequence.

SEQ ID NO:279: cytochrome P450 biosynthetic enzyme, optimized to corn (mf CYP72A459v1a Zm (GC48); SP2015), *Siraitia grosvenorii*, amino acid sequence.

SEQ ID NO:280: uridine phosphorylase dependent glycosyltransferase (mf UGT720; SP4263), *Siraitia grosvenorii* cDNA, nucleic acid sequence.

SEQ ID NO:281: uridine phosphorylase dependent glycosyltransferase (mf UGT720; SP4263), *Siraitia grosvenorii*, amino acid sequence.

SEQ ID NO:282: uridine phosphorylase dependent glycosyltransferase, high GC version (Sg UGT94-289-1 GC65; SP4332), *Siraitia grosvenorii* cDNA, nucleic acid sequence.

SEQ ID NO:283: uridine phosphorylase dependent glycosyltransferase, high GC version (Sg UGT94-289-1 GC65; SP4332), *Siraitia grosvenorii*, amino acid sequence.

SEQ ID NO:284: upstream terpenoid biosynthetic enzyme, optimized for corn (Sg CDS *Z mays* GC51; SP5029), *Siraitia grosvenorii* cDNA, nucleic acid sequence.

SEQ ID NO:285: upstream terpenoid biosynthetic enzyme, optimized for corn (Sg CDS *Z mays* GC51; SP5029), *Siraitia grosvenorii*, amino acid sequence.

SEQ ID NO:286: uridine phosphorylase dependent glycosyltransferase, high GC version (mf UGT720 GC; SP5030), *Siraitia grosvenorii* cDNA, nucleic acid sequence.

SEQ ID NO:287: uridine phosphorylase dependent glycosyltransferase, high GC version (mf UGT720 GC; SP5030), *Siraitia grosvenorii*, amino acid sequence.

SEQ ID NO:288: cytochrome P450 biosynthetic enzyme, high GC version (Sg CYP87D18 GC62; SP5031), *Siraitia grosvenorii* cDNA, nucleic acid sequence.

SEQ ID NO:289: cytochrome P450 biosynthetic enzyme, high GC version (Sg CYP87D18 GC62; SP5031), *Siraitia grosvenorii*, amino acid sequence.

SEQ ID NO:290: upstream squalene biosynthetic enzyme, high GC version (Sg SQE1 GC66; SP5032), *Siraitia grosvenorii* cDNA, nucleic acid sequence.

SEQ ID NO:291: upstream squalene biosynthetic enzyme, high GC version (Sg SQE1 GC66; SP5032), *Siraitia grosvenorii*, amino acid sequence.

SEQ ID NO:292: epoxide hydrolase biosynthetic enzyme, high GC version (Sg EPH3 GC64; SP5033), *Siraitia grosvenorii* cDNA, nucleic acid sequence.

SEQ ID NO:293: epoxide hydrolase biosynthetic enzyme, high GC version (Sg EPH3 GC64; SP5033), *Siraitia grosvenorii*, amino acid sequence.

SEQ ID NO:294: uridine phosphorylase dependent glycosyltransferase, high GC version (SgUGT720 GC 2A; SP3186), *Siraitia grosvenorii* cDNA, nucleic acid sequence.

SEQ ID NO:295: uridine phosphorylase dependent glycosyltransferase, high GC version (SgUGT720 GC 2A; SP3186), *Siraitia grosvenorii*, amino acid sequence.

SEQ ID NO:296: cytochrome P450 biosynthetic enzyme (Sg SgCYP72v1a Zm (for 2A, GC47); SP3204), *Siraitia grosvenorii* cDNA, nucleic acid sequence.

SEQ ID NO:297: cytochrome P450 biosynthetic enzyme (Sg SgCYP72v1a Zm (for 2A, GC47); SP3204), *Siraitia grosvenorii*, amino acid sequence.

SEQ ID NO:298: uridine phosphorylase dependent glycosyltransferase (SgUGT94-1 GC 2A; SP3807), *Siraitia grosvenorii* cDNA, nucleic acid sequence.

SEQ ID NO:299: uridine phosphorylase dependent glycosyltransferase (SgUGT94-1 GC 2A; SP3807), *Siraitia grosvenorii*, amino acid sequence.

SEQ ID NO:300: uridine phosphorylase dependent glycosyltransferase (SgUGT720 Zm (for 2A); SP3897), *Siraitia grosvenorii* cDNA, nucleic acid sequence.

SEQ ID NO:301: uridine phosphorylase dependent glycosyltransferase (SgUGT720 Zm (for 2A); SP3897), *Siraitia grosvenorii*, amino acid sequence.

SEQ ID NO:302: uridine phosphorylase dependent glycosyltransferase (mf UGT720; SP4263), *Siraitia grosvenorii* cDNA, nucleic acid sequence.

SEQ ID NO:303: uridine phosphorylase dependent glycosyltransferase (mf UGT720; SP4263), *Siraitia grosvenorii*, amino acid sequence.

SEQ ID NO:304: uridine phosphorylase dependent glycosyltransferase, high GC version (Sg UGT94-289-1 GC65; SP4332), *Siraitia grosvenorii* cDNA, nucleic acid sequence.

SEQ ID NO:305: uridine phosphorylase dependent glycosyltransferase, high GC version (Sg UGT94-289-1 GC65; SP4332), *Siraitia grosvenorii*, amino acid sequence.

DETAILED DESCRIPTION

The present disclosure generally describes transgenic plants and biosynthetic systems thereof for making mogrol/mogroside pathway enzymes and mogrosides, and methods for making such transgenic plants. The following sections provide embodiments that describe the subject matter in greater detail.

I. Mogroside Pathway Enzymes and Mogrosides

Mogrosides are highly stable molecules based on a triterpene skeleton, formed of varying numbers of glucose units, from 1 to 6 attached to the triterpene backbone. Mogrosides may also comprise a non-glucose moiety, such as grosmomoside I. FIG. 1 shows a mogroside biosynthetic pathway from *Siraitia grosvenorii* (Itkin et al., *Proc Nat Acad Sci USA* 113: E7619-E7628, 2016; Seki et al., Biosci. Biotechnol. Biochem. 82:927-934, 2018), and certain enzymes capable of catalyzing the reactions in the pathway. Importantly, the enzymatic pathway used for production of mogrosides according to the present disclosure is not limited by the mechanisms shown in FIG. 1. Other terpene structures, mogrol precursors, enzyme-catalyzed reactions or conversion mechanisms are also possible. Additionally, certain enzyme may catalyze more than one type of reaction, and one or more additional genes can be used to produce any of the mogrol intermediates, mogrol, or any of the mogroside compounds.

Provided herein are exemplary nucleic acid and protein sequences for certain mogroside pathway (also referred to as mogroside biosynthetic pathway) enzymes for conversion of mogrol precursors, such as squalene, to mogrol and eventually various mogroside compounds, including, but not limited to, mogroside V. The enzymes of the mogroside pathway include, but are not limited to, squalene epoxidase (SQE), cucurbitadienol synthase (CDS), epoxy or epoxide hydrolase (EPH), various cytochrome P450 enzymes (CYP), including, but not limited to, CYP72 and CYP87, uridine phosphorylase dependent glycosyltransferase enzymes (UGT), including, but not limited to, UGT720, UGT94 and UGT74, and can additionally include 3 hydroxy-3-methylglutaryl-CoA reductase (HMGR), or truncated versions thereof, and NADPH:cytochrome P450 reductase (CPR2).

SQE, CDS, CYP and EPH are involved in the successive steps of producing and converting mogrol precursors, such as squalene, into mogrol. Intermediate products of the enzymatic pathway include, but are not limited to, 2,3-oxidosqualene, 2,3;22.23-dioxidosqualene, 24,25 epoxycucurbitadienol, and 24,25-dihydroxycucurbitadienol. CDS, which is an oxidosqualene cyclase, uses 2,3;22,23-diepoxysqualene as its substrate to produce 24,25-epoxycucurbitadienol. Genomic analysis has revealed that *S. grosvenorii* has five genes that may encode SQEs. Of these, two are strongly expressed during the initial stages of fruit development, as are CDS, CYP enzymes, and EPHs, which catalyze subsequent steps. The *S. grosvenorii* genome contains eight genes encoding EPHs, which catalyze conversion of 24,25-epoxycucurbitadienol to 24,25-dihydroxycucurbitadienol. Certain enzyme may catalyze more than one type of reaction.

After the formation of mogrol, a series of glycosylations occurs to add glucose molecules, at position C-3 and position C-24, to produce Mogrosides I-VI with various degrees of glycosylation. The Roman numeral I, II, III, IV, V, and VI respectively stand for the number of glucose unit(s) in the corresponding glycosylated mogroside, isomogroside, or oxomogroside. Two UGTs contribute to these steps. One is UGT720, which is strongly expressed in the initial stages of fruit development and transfers one glucose molecule each to the hydroxyl groups at positions C-24 and C 3 of mogrol. The second is UGT94, which is strongly expressed in the latter stages of fruit development and adds sugars to the other sugars already present on the acceptor molecule.

Although the mogroside pathway was initially described in *S. grosvenorii* (monkfruit), certain non-monkfruit plants can make tetracyclic triterpenoid compounds similar to mogrol, because at least one of the intermediates, such as triterpenes, exist in the cellular pathway. Moreover, given that the related pathways for modifying tetracyclic triterpenoid compounds require associated enzymes such as reductases, these plants already express certain associated network enzymes. Although such non-monkfruit plants may express enzymes that produce mogrol precursors, these plants do not naturally produce all enzymes in a coordinated fashion required to produce mogrosides. For instance, plants such as cucumber, melon, and watermelon naturally express cucurbitadienol synthases, which are capable of producing cucurbitadienol. However, other enzymes like the CYP enzymes, which are capable of altering the cucurbitadienol scaffold, redirect this intermediate to other terpene derivatives. Therefore, changes to the genomes of these non-monkfruit plants, either by recombinant, gene editing, or other modern plant breeding technologies, may allow for these non-monkfruit plants to produce mogrol and mogrosides. Therefore, in certain embodiments one or more additional genes could be introduced into non-monkfruit plants, or enzymes native to such non-monkfruit plants could be upregulated, to allow for intermediate metabolite production in order to yield mogrol, mogrosides, and mogroside-based sweeteners.

The term "mogrol precursor" broadly encompasses all possible terpene derivatives and intermediate products towards the production of mogrol and mogroside compounds, including, but not limited to, 2,3-oxidosqualene, 2,3;22.23-dioxidosqualene, 24,25-epoxycucurbitadienol, and 24,25-dihydroxycucurbitadienol, cucurbitadienol, 11-hydroxy-cucurbitadienol, and 11-oxo-cucurbitadienol. Mogrosides refer to any possible glycosylation products of mogrol, including, but not limited to, Siamenoside I, Siratose (a stereoisomer of Siamenoside I), Mogroside VI, Mogroside V, Isomogroside V, Mogroside IV, Mogroside III, Mogroside IIIE, Mogroside IIE, Mogroside IIA, Mogroside IE, and Mogroside IA. Other examples of mogrosides include, but are not limited to, Mogroside IIB, 7-Oxomogroside IIE, 11 Oxomogroside Al, Mogroside III A2, 11-Deoxymogroside III, 11-Oxomogroside IVA, 7 Oxomogroside V, and 11-Oxo-mogroside V. Metabolites and derivatives of mogrosides refer to any close variation of mogrosides through a metabolic reaction, naturally occurring reaction, or non-naturally occurring reaction. Derivatives of mogrosides may comprise deletions, alterations, or additions of atom(s) or functional groups compared with standard mogrosides. However, metabolites and derivatives of mogrosides retain substantially the same function and characteristics of standard mogrosides. In certain instances the mogroside compounds produced by the presently disclosed transgenic plants and organisms can also undergo non-enzymatic (spontaneous) conversion to other mogroside compounds.

One or more of these mogroside compounds can be isolated, purified or partially purified from the disclosed transgenic plants, or transgenic organisms grown via fermentation techniques. For example the one or more mogroside compounds can be harvested via wet extraction or an aqueous layer containing the mogroside compounds in bulk processing steps that do not necessarily result in the isolation of a single mogroside compound. Alternatively, the whole transgenic plant (or part thereof) or transgenic organism producing the mogroside compounds may be dried and pulverized into powder or extracted, or the whole transgenic plant (or part thereof) or transgenic organism producing the mogroside compounds can be minimally processed and used as a food ingredient.

In certain embodiments the presently disclosed transgenic plants and organisms will produce a unique ratio of mogroside compounds. In some embodiments the presently disclosed transgenic plants and organisms can produce more of one or more of the mogroside compounds and less of other mogroside compounds, for example higher amounts of mogroside V compared to other mogroside compounds.

In further embodiments the complete mogroside biosynthetic pathway can be established in a selected plant or organism using a combination approach, for example by endogenously activating one or more mogroside biosynthetic pathway nucleic acid sequences that are naturally present in the plant or organism and providing any mogroside biosynthetic pathway nucleic acid sequences that are not naturally present in the plant or organism via one or more expression vector(s) comprising the non-endogenous mogroside biosynthetic pathway nucleic acid sequences.

In further embodiments the transgenic plant or organism can also be engineered to express one or more nucleic acids involved in the biosynthesis of other sweeteners, for example genes involved in the production of siamenoside I, α-siamenoside, steviol glycosides (*stevia*), Rebaudioside M or glycyrrhizin. Additionally, the transgenic plants or organisms can be engineered to produce mogrosides and other sweeteners together in the same plant or organism, for example to produce mogrosides and Rebaudioside M.

II. Recombinant Host Cells and Species

Although transgenic plants are generally described throughout the present disclosure, other host cells and organisms are also envisioned for use in certain embodiments of the present disclosure.

As used herein, the term “recombinant host cell” is intended to refer to any host cell whose genome has been engineered to include at least one of the presently disclosed mogroside biosynthetic pathway nucleic acid sequences, which in certain embodiments encode one or more polypeptides. These sequences include, but are not limited to, nucleic acid or amino acid sequences that are not naturally present in the host cell or organism, DNA sequences that are not normally transcribed into RNA or translated into a protein (“expressed”), and other sequences that have been altered from those normally present in the host cell, for example by increasing the copy number of the DNA sequence or altering the expression patterns or expression levels.

In addition to the plants species disclosed herein, a number of prokaryotes and additional eukaryotes are suitable for use as recombinant hosts in different aspects of the present disclosure. In addition to any plant species, the recombinant host cells may be a bacteria, yeast or fungi. A host cell or species selected for mogroside compound production can be analyzed to determine if any mogroside biosynthetic pathway genes are endogenous to the host cell or species, and which mogroside biosynthetic pathway genes are not present. Genes for which an endogenous counterpart is not present in the host cell or organism are generally assembled in one or more recombinant constructs, which are then transformed into the host cell or organism in order to supply the missing function(s).

Exemplary prokaryotic and eukaryotic species useful in certain aspects of the present disclosure include, but are not limited to, *Agaricus, Aspergillus, Bacillus, Candida, corynebacterium, Escherichia, Fusarium/Gibberella, Kluyveromyces, Laetiporus, Lentinus, Phaffia, Phanerochaete, Pichia, Physcomitrella, Rhodoturula, Saccharomyces, Sphaceloma, Schizosaccharomyces, Xanthophyllomyces and Yarrowia*. In some embodiments, a recombinant host may be a microorganism, for example *Pichia pastoris, Schizosaccharomyces pombe, Aspergillus niger*, or *Saccharomyces cerevisiae*. In some embodiments, a recombinant host may be a microorganism such as *Escherichia coli* or *Agrobacterium tumefaciens*. It will be appreciated that certain microorganisms can be used to screen and test genes of interest in a high throughput manner, while other microorganisms with desired productivity or growth characteristics can be used for large-scale production of mogroside compounds. In certain embodiments food grade microorganisms may be useful for large-scale production purposes.

III. Nucleic Acid and Polypeptide Sequences

Certain embodiments of the current disclosure concern nucleic acid sequences (polynucleotides) and the corresponding amino acid sequences (proteins or polypeptides) for mogroside biosynthesis pathway genes. Complements to any nucleic acid or protein sequences described herein are also provided.

“Identity,” as is well understood in the art, is a relationship between two or more polypeptide sequences or two or more polynucleotide sequences, as determined by comparing the sequences. In the art, “identity” also means the degree of sequence relatedness between polypeptide or polynucleotide sequences, as determined by the match between strings of such sequences. Methods to determine “identity” are designed to give the largest match between the sequences tested. Moreover, methods to determine identity are codified in publicly available programs. “Identity” can be readily calculated by any of the many methods known to those of skill in the art. Computer programs can be used to determine “identity” between two sequences these programs include but are not limited to, GCG; suite of five BLAST programs, three designed for nucleotide sequences queries (BLASTN, BLASTX, and TBLASTX) and two designed for protein sequence queries (BLASTP and TBLASTN). The BLASTX program is publicly available from NCBI and other sources (BLAST Manual, NCBI NLM NIH, Bethesda, Md. 20894). The well-known Smith Waterman algorithm can also be used to determine identity.

In accordance with the present disclosure, a polynucleotide or polypeptide sequence as described herein may exhibit at least from about 34%, 40%, 50%, 60%, 62% or 70% to about 100% sequence identity to at least one of the sequences set forth herein. For example, in one embodiment, a mogroside biosynthesis pathway gene as described herein may comprise, for example, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a sequence selected from SEQ ID NOs: 1, 3, 4, 6, 8, 10, 12, 14, 16, 18, 20, 22, 24, 26, 28, 30, 32, 34, 38, 42, 46, 50, 54, 85 or 87-92, or a complement thereof. In other embodiments, a mogroside biosynthesis pathway protein as described herein may comprise for example, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a sequence selected from SEQ ID NOs: 2, 5, 7, 9, 11, 13, 15, 17, 19, 21, 23, 25, 27, 29, 31, 33, 35-37, 39-41, 43-45, 47-49, 51-53, 55-57 or 86.

Parameters for polypeptide sequence comparison include the following: Algorithm: Needleman and Wunsch (*J. Mol. Biol.* 48:443-453, 1970); Comparison matrix: BLOSUM62 from Hentikoff and Hentikoff, (*Proc. Natl. Acad. Sci. USA* 89:10915-10919, 1992); Gap Penalty: 12; and Gap Length Penalty: 4. A program that can be used with these parameters is publicly available as the “gap” program from Genetics Computer Group, Madison WI. The above parameters along with no penalty for end gap may serve as default parameters for peptide comparisons.

Parameters for nucleic acid sequence comparison include the following: Algorithm: Needleman and Wunsch (supra); Comparison matrix: matches=+10; mismatches=0; Gap Penalty: 50; and Gap Length Penalty: 3. A program that can be used with these parameters is publicly available as the “gap” program from Genetics Computer Group, Madison Wis. The above parameters may serve as the default parameters for nucleic acid comparisons.

As used herein, “hybridization,” “hybridizes,” or “capable of hybridizing” is understood to mean the forming of a double- or triple-stranded molecule or a molecule with partial double- or triple-stranded nature. Such hybridization may take place under relatively high-stringency conditions, including low salt and/or high temperature conditions, such as provided by a wash in about 0.02 M to about 0.15 M NaCl at temperatures of about 50° C. to about 70° C. for 10 min. In one embodiment of the present disclosure, the conditions are 0.15 M NaCl and 70° C. Stringent conditions tolerate little mismatch between a nucleic acid and a target strand. Such conditions are well-known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like. Also included may be a protein or polypeptide, or fragment thereof, such as any of those set forth herein.

“Fragment”, with respect to the nucleic acid sequences disclosed herein, refers to any part of a polynucleotide molecule that retains a usable, functional characteristic. Useful fragments include oligonucleotides and polynucleotides that may be used as probes or primers in hybridization or amplification technologies or in the regulation of replication, transcription or translation. A polynucleotide fragment refers to any subsequence of a polynucleotide, typically, of at least about 15 consecutive nucleotides, at least about 16 consecutive nucleotides, at least about 17 consecutive nucleotides, at least about 18 consecutive nucleotides, at least about 19 consecutive nucleotides, at least about 20 consecutive nucleotides, at least about 21 consecutive nucleotides, at least about 22 consecutive nucleotides, at least about 23 consecutive nucleotides, at least about 24 consecutive nucleotides, at least about 25 consecutive nucleotides, at least about 30 consecutive nucleotides, at least about 35 nucleotides, at least about 40 consecutive nucleotides, at least about 45 consecutive nucleotides, or at least about 50 nucleotides or more, of any of the nucleic acid sequences provided herein.

Fragments may also include subsequences of polypeptides and protein molecules, or a subsequence of the polypeptide, as disclosed herein. Fragments may have antigenic potential, or may be a subsequence of the polypeptide that performs at least one biological function of the intact polypeptide in substantially the same manner, or to a similar extent, as does the intact polypeptide. Fragments can vary in size from as few as 5 amino acids to the full length of the intact polypeptide, but are preferably at least about 10 amino acids in length, at least about 15 amino acids in length, at least about 20 amino acids in length, at least about 25 amino acids in length, at least about 30 amino acids in length, at least about 35 amino acids in length, at least about 40 amino acids in length, at least about 45 amino acids in length, at least about 50 amino acids in length, at least about 55 amino acids in length, or at least about 60 amino acids in length or more, of any of the amino acid sequences provided herein.

The nucleic acids provided herein as SEQ ID NOs: 1, 3, 4, 6, 8, 10, 12, 14, 16, 18, 20, 22, 24, 26, 28, 30, 32, 34, 38, 42, 46, 50, 54, 58, 85 or 87-92, and amino acids provided herein as SEQ ID NOs: 2, 5, 7, 9, 11, 13, 15, 17, 19, 21, 23, 25, 27, 29, 31, 33, 35-37, 39-41, 43-45, 47-49, 51-53, 55-57, 59 or 86, may be from any source, e.g., identified as naturally occurring in a plant, or synthesized, e.g., by mutagenesis of SEQ ID NOs: 1, 3, 4, 6, 8, 10, 12, 14, 16, 18, 20, 22, 24, 26, 28, 30, 32, 34, 38, 42, 46, 50, 54, 58, 85 or 87-92, for example to create a coding sequence with a G/C content more like the G/C content of naturally occurring genes from a particular plant. The naturally occurring sequence may be from any plant or algal species, as described herein.

IV. Transformation Constructs

Vectors used for plant transformation, or transformation of other host cells or organisms, may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the present disclosure, this could be used to introduce genes corresponding to an entire biosynthetic pathway into a plant. Introduction of such sequences may be facilitated by use of bacterial or yeast artificial chromosomes (BACs or YACs, respectively), or even plant artificial chromosomes. For example, the use of BACs for *Agrobacterium*-mediated transformation was disclosed by Hamilton et al. (*Proc. Natl. Acad. Sci. USA* 93:9975-9979, 1996).

Particularly useful for transformation are expression cassettes that have been isolated from such vectors. DNA segments used for transforming plant cells will, of course, generally comprise the cDNA, gene or genes that one desires to introduce into and have expressed in the host cells. These DNA segments can further include structures such as promoters, enhancers, polylinkers, terminators or even regulatory genes as desired. The DNA segment or gene chosen for cellular introduction will often encode a protein that will be expressed in the resultant recombinant cells resulting in a screenable or selectable trait and/or that will impart an improved phenotype to the resulting transgenic plant. However, this may not always be the case, and the present disclosure also encompasses transgenic plants incorporating non-expressed transgenes. As previously discussed, in addition to plant cells the host cells in certain aspects of the present disclosure may be a bacterial cell, such as *Escherichia* colt or *Agrobacterium tumefaciens*, yeast cells, fungal, algal or cyanobacterial cells. The skilled artisan is aware of the genetic elements that must be present on a vector in order to successfully transform, select and propagate host cells containing a sequence of interest. Components that may be included with vectors used in the current disclosure are as follows.

A. Promoters and Other Regulatory Elements

In certain embodiments, the presently disclosed expression cassettes further comprise one or more promoters, for example one or more of the nucleotide sequences set forth in SEQ ID NOs: 60-71, or a nucleotide sequence having a sequence identity of at least 70%, at least 75%, at least 80%, at least 85%, at least 90%, at least 95%, at least 96%, at least 97%, at least 98%, or at least 99% to one or more of the nucleotide sequences set forth in SEQ ID NOs: 60-71.

In addition to the promoter sequences disclosed in the Sequence Listing, other exemplary promoters for expression of a nucleic acid sequence include a plant promoter such as the CaMV 35S promoter (Odell et al., *Nature* 313:810-812, 1985), or others such as CaMV 19S (Lawton et al., *Plant Mol. Biol.* 9:315-324, 1987), nos (Ebert et al., *Proc. Natl. Acad. Sci. USA* 84:5745-5749, 1987), Adh (Walker et al., *Proc. Natl. Acad. Sci. USA* 84:6624-6628, 1987), sucrose synthase (Yang and Russell, *Proc. Natl. Acad. Sci. USA* 87:4144-4148, 1990), α-tubulin, actin (Wang et al., *Mol. Cell Biol.* 12:3399-3406, 1992), cab (Sullivan et al., *Mol. Gen. Genet.* 215:431-440, 1989), PEPCase (Hudspeth and Grula, *Plant Mol. Biol.* 12:579-589, 1989) or those associated with the R gene complex (Chandler et al., *Plant Cell* 1:1175-1183, 1989). Tissue specific promoters such as root cell promoters (Conkling et al., *Plant Physiol.* 93:1203-1211, 1990) and tissue specific enhancers are also contemplated to be useful, as are inducible promoters such as ABA- and turgor-inducible promoters. The PAL2 promoter may in particular be useful with the disclosure (U.S. Patent Application Publication No. 2004/0049802, the entire disclosure of which is specifically incorporated herein by reference). In one embodiment of the present disclosure, the native promoter of one or more of the mogroside pathway genes is used. In some embodiments, the promoter is a strong promoter or a weak promoter.

The DNA sequence between the transcription initiation site and the start of the coding sequence, i.e., the untranslated leader sequence, can also influence gene expression. One may thus wish to employ a particular leader sequence with a transformation construct of the present disclosure. Leader sequences are contemplated to include those that comprise sequences predicted to direct optimum expression of the attached gene, i.e., to include a consensus leader sequence that may increase or maintain mRNA stability and prevent inappropriate initiation of translation. The choice of such sequences will be known to those of skill in the art in light of the present disclosure. Sequences that are derived from genes that are highly expressed in plants may be desirable.

It is contemplated that vectors for use in accordance with the present disclosure may be constructed to include an ocs enhancer element. This element was first identified as a 16 bp palindromic enhancer from the octopine synthase (ocs) gene of *Agrobacterium* (Ellis et al., *EMBO J.* 6:3203-3208, 1987), and is present in at least 10 other promoters (Bouchez et al., *EMBO J.* 8:4197-4204, 1989). The use of an enhancer element, such as the ocs element and particularly multiple copies of the element, may act to increase the level of transcription from adjacent promoters when applied in the context of plant transformation.

It is envisioned that mogroside biosynthesis pathway coding sequences may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters that direct specific or enhanced expression in certain plant tissues will be known to those of skill in the art in light of the present disclosure. These include, for example, the rbcS promoter, specific for green tissue; the ocs, nos and mas promoters that have higher activity in roots or wounded leaf tissue.

B. Terminators

In certain embodiments, the presently disclosed expression cassettes further comprise one or more terminators, for example one or more of the nucleotide sequences set forth in SEQ ID NOs: 72-80, or a nucleotide sequence having a sequence identity of at least 70%, at least 75%, at least 80%, at least 85%, at least 90%, at least 95%, at least 96%, at least 97%, at least 98%, or at least 99% to one or more of the nucleotide sequences set forth in SEQ ID NOs: 72-80.

Transformation constructs prepared in accordance with the present disclosure will typically include a 3' end DNA sequence that acts as a signal to terminate transcription and allow for the polyadenylation of the mRNA produced by coding sequences operably linked to a promoter. In one embodiment of the present disclosure, the native terminator of a mogroside biosynthesis pathway coding sequence is used. Alternatively, a heterologous 3' end may enhance the expression of sense or antisense mogroside biosynthesis pathway coding sequences. In addition to the terminator sequences disclosed in the Sequence Listing, further examples of terminators that are deemed to be useful in this context include those from the nopaline synthase gene of

*Agrobacterium tumefaciens* (nos 3' end) (Bevan et al., *Nucl. Acids Res.* 11:369-385, 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., *Genes Dev.* 1:1183-1200, 1987), sucrose synthase intron (Vasil et al., *Plant Physiol.* 91:1575-1579, 1989) or TMV omega element (Gallie and Kado, *Proc. Natl. Acad. Sci. USA* 86:129-132, 1989), may further be included where desired.

C. Transit or Signal Peptides

In certain embodiments of the present disclosure transit or signal sequences may be incorporated into the mogroside biosynthesis pathway coding sequences. Sequences that are joined to the coding sequence of an expressed gene, which are removed post-translationally from the initial translation product and that facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait that one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). In addition to the marker genes disclosed in the Sequence Listing, many additional examples of suitable marker proteins are known to the art and can be employed in the practice of the present disclosure.

Included within the terms "selectable" or "screenable" markers also are genes that encode a "secretable marker" whose secretion can be detected as a means of identifying or selecting for transformed cells. Examples include markers that are secretable antigens that can be identified by antibody interaction, or even secretable enzymes that can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR S).

Many selectable marker coding regions are known and could be used with the present disclosure including, but not limited to, neo (Potrykus et al., *Mol. Gen. Genet.* 199:169-177, 1985), which provides kanamycin resistance and can be selected for using kanamycin, G418, paromomycin, etc.; bar, which confers bialaphos or phosphinothricin resistance; a mutant EPSP synthase protein conferring glyphosate resistance; a nitrilase such as bxn from *Klebsiella ozaenae*, which confers resistance to bromoxynil (Stalker et al., *J. Biol. Chem.* 263:6310-6314, 1988); a mutant acetolactate synthase (ALS), which confers resistance to imidazolinone, sulfonylurea or other ALS inhibiting chemicals (European Patent Application 154,204, 1985); a methotrexate resistant DHFR (Thillet et al., *J. Biol. Chem.* 263:12500-12508, 1988), a dalapon dehalogenase that confers resistance to the herbicide dalapon; or a mutated anthranilate synthase that confers resistance to 5-methyl tryptophan, or sequences that confer resistance to dicamba.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, causing rapid accumulation of ammonia and cell death.

Screenable markers that may be employed include a β glucuronidase (GUS) or uidA gene, which encodes an enzyme for which various chromogenic substrates are known; an R-locus gene, which encodes a product that regulates the production of anthocyanin pigments (red color) in plant tissues; a β lactamase gene (Sutcliffe, *Proc. Natl. Acad. Sci. USA* 75:3737-3741, 1978), which encodes an enzyme for which various chromogenic substrates are known (e.g., PADAC, a chromogenic cephalosporin); a xylE gene (Zukowsky et al., *Proc. Natl. Acad. Sci. USA* 80:1101-1105, 1983), which encodes a catechol dioxygenase that can convert chromogenic catechols; an α-amylase gene (Ikuta et al., *Biotechnology* 8:241-242, 1990); a tyrosinase gene (Katz et al., *J. Gen. Microbiol.* 129:2703-2714, 1983), which encodes an enzyme capable of oxidizing tyrosine to DOPA and dopaquinone, which in turn condenses to form the easily-detectable compound melanin; a β galactosidase gene, which encodes an enzyme for which there are chromogenic substrates; a luciferase (lux) gene (Ow et al., *Science* 234:856-859, 1986), which allows for bioluminescence detection; an aequorin gene (Prasher et al., *Biochem. Biophys. Res. Commun.* 126:1259-1268, 1985), which may be employed in calcium-sensitive bioluminescence detection; or a gene encoding for green fluorescent protein (GFP; Sheen et al., *Plant J.* 8:777-784, 1995; Haseloff et al., *Proc. Natl. Acad. Sci. USA* 94:2122-2127, 1997; Reichel et al.,

*Proc. Natl. Acad. Sci. USA* 93:5888-5893, 1996; WO 97/41228) is also contemplated as a useful reporter gene. Expression of green fluorescent protein may be visualized in a cell or plant as fluorescence following illumination by particular wavelengths of light.

E. Additional Agronomic Traits

In certain embodiments one or more additional agronomically beneficial trait(s) are engineered into the presently disclosed transgenic plants or organisms. A "trait" refers to a physiological, morphological, biochemical, or physical characteristic of a plant or organism or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g., by measuring uptake of carbon dioxide, or by the observation of the expression level of a gene or genes, e.g., by employing northern analysis, RT-PCR, microarray gene expression assays, or reporter gene expression systems, or by agricultural observations such as stress tolerance, yield, or pathogen tolerance. Any technique can be used to measure the amount of, comparative level of, or difference in any selected chemical compound or macromolecule in the transgenic plants, however.

"Trait modification" refers to a detectable difference in a characteristic in a plant or organism expressing or ectopically expressing a polynucleotide or polypeptide relative to a plant or organism not doing so, such as a wild-type or other control plant or organism. In some cases, the trait modification can be evaluated quantitatively. For example, the trait modification can entail at least about a 2% increase or decrease in an observed trait (difference), at least a 5% difference, at least about a 10% difference, at least about a 20% difference, at least about a 30%, at least about a 50%, at least about a 70%, or at least about a 100%, or an even greater difference compared with a wild-type or other control plant or organism. It is known that there can be a natural variation in the modified trait. Therefore, the trait modification observed entails a change of the normal distribution of the trait in the plant or organism compared with the distribution observed in wild-type plant or organism.

Trait modifications of particular interest in the presently disclosed plants include those to seed (such as embryo or endosperm), fruit, root, flower, leaf, stem, shoot, seedling or the like, including: enhanced tolerance to environmental conditions, including freezing, chilling, heat, drought, water saturation, radiation and ozone; improved tolerance to microbial, fungal or viral diseases; improved tolerance to pest infestations, including insects, nematodes, mollicutes, parasitic higher plants or the like; decreased herbicide sensitivity or increased herbicide tolerance, for example increased glyphosate or dicamba tolerance; improved tolerance of heavy metals or enhanced ability to take up heavy metals; improved growth under poor photoconditions (e.g., low light and/or short day length), or changes in expression levels of genes of interest. Other phenotypes that can be modified relate to the production of plant metabolites, such as variations in the production of taxol, tocopherol, tocotrienol, sterols, phytosterols, vitamins, wax monomers, antioxidants, amino acids, lignins, cellulose, tannins, prenyllipids (such as chlorophylls and carotenoids), glucosinolates, and terpenoids, enhanced or compositionally altered protein or oil production (especially in seeds), or modified sugar (insoluble or soluble) and/or starch composition. Physical plant characteristics that can be modified include cell development (such as the number of trichomes), fruit and seed size and number, yields of plant parts such as stems, leaves, inflorescences, and roots, the stability of the seeds during storage, characteristics of the seed pod (e.g., susceptibility to shattering), root hair length and quantity, internode distances, or the quality of seed coat. Plant growth characteristics that can be modified include growth rate, germination rate of seeds, vigor of plants and seedlings, leaf and flower senescence, male sterility, apomixis, flowering time, flower abscission, rate of nitrogen uptake, osmotic sensitivity to soluble sugar concentrations, biomass or transpiration characteristics, as well as plant architecture characteristics such as apical dominance, branching patterns, number of organs, organ identity, organ shape or size. Additionally, the amount of natural sugar(s) can be reduced, and color can be reduced or removed.

V. Gene Editing

One method for producing the transgenic plants of the present disclosure is through genome modification using site-specific integration or genome editing. Targeted modification of plant genomes through the use of genome editing methods can be used to create improved plant lines through modification of plant genomic DNA. As used herein "site-directed integration" refers to genome editing methods that enable targeted insertion of one or more nucleic acids of interest into a plant genome. Suitable methods for altering a wild-type DNA sequence or a preexisting transgenic sequence or for inserting DNA into a plant genome at a pre-determined chromosomal site include any method known in the art. Exemplary methods include the use of sequence specific nucleases, such as zinc-finger nucleases, engineered or native meganucleases, TALE-endonucleases, or an RNA-guided endonucleases (for example, a Clustered Regularly Interspersed Short Palindromic Repeat (CRISPR)/Cas9 system, a CRISPR/Cpf1 system, a CRISPR/CasX system, a CRISPR/CasY system, or a CRISPR/Cascade system). Several embodiments relate to methods of genome editing by using single-stranded oligonucleotides to introduce precise base pair modifications in a plant genome. Methods of genome editing to modify, delete, or insert nucleic acid sequences into genomic DNA are known in the art.

In certain embodiments, the present disclosure provides modification or replacement of an existing coding sequence, such as an existing transgenic insert, within a plant genome with a sequence encoding a different protein, or an expression cassette comprising such a protein. Several embodiments relate to the use of a known genome editing methods, such as zinc-finger nucleases, engineered or native meganucleases, TALE-endonucleases, or an RNA-guided endonucleases (for example, a Clustered Regularly Interspersed Short Palindromic Repeat (CRISPR)/Cas9 system, a CRISPR/Cpf1 system, a CRISPR/CasX system, a CRISPR/CasY system, or a CRISPR/Cascade system).

Several embodiments may therefore relate to a recombinant DNA construct comprising an expression cassette(s) encoding a site-specific nuclease and, optionally, any associated protein(s) to carry out genome modification. These nuclease-expressing cassette(s) may be present in the same molecule or vector as a donor template for templated editing. Several methods for site-directed integration are known in the art involving different sequence-specific nucleases (or complexes of proteins or guide RNA or both) that cut the genomic DNA to produce a double strand break (DSB) or nick at a desired genomic site or locus. As understood in the art, during the process of repairing the DSB or nick introduced by the nuclease enzyme, the donor template DNA, transgene, or expression cassette may become integrated into the genome at the site of the DSB or nick. The presence of the homology arm(s) in the DNA to be integrated may promote the adoption and targeting of the insertion sequence into the plant genome during the repair process through homologous recombination, although an insertion event may occur through non-homologous end joining (NHEJ). As used herein, the term "double-strand break inducing agent" refers to any agent that can induce a double-strand break (DSB) in a DNA molecule. In some embodiments, the double-strand break inducing agent is a site-specific genome modification enzyme.

As used herein, the term "site-specific genome modification enzyme" refers to any enzyme that can modify a nucleotide sequence in a sequence-specific manner. In some embodiments, a site-specific genome modification enzyme modifies the genome by inducing a single-strand break. In some embodiments, a site-specific genome modification enzyme modifies the genome by inducing a double-strand break. In some embodiments, a site-specific genome modification enzyme comprises a cytidine deaminase. In some embodiments, a site specific genome modification enzyme comprises an adenine deaminase. Site-specific genome modification enzymes include endonucleases, recombinases, transposases, deaminases, helicases and any combination thereof. In some embodiments, the site-specific genome modification enzyme is a sequence-specific nuclease.

In one aspect, the endonuclease is selected from a meganuclease, a zinc-finger nuclease (ZFN), a transcription activator-like effector nucleases (TALEN), an Argonaute (non-limiting examples of Argonaute proteins include *Thermus thermophilus* Argonaute (TtAgo), *Pyrococcus furiosus* Argonaute (PfAgo), and Natronobacterium gregoryi Argonaute (NgAgo)), an RNA-guided nuclease, such as a CRISPR associated nuclease (non-limiting examples of CRISPR associated nucleases include, but are not limited to, Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, homologs thereof, or modified versions thereof).

In some embodiments, the site-specific genome modification enzyme is a recombinase. Non-limiting examples of recombinases include a tyrosine recombinase attached to a DNA recognition motif and is selected from the group consisting of a Cre recombinase, a Gin recombinase, a Flp recombinase, and a Tnp1 recombinase. In one aspect, a Cre recombinase or a Gin recombinase is tethered to a zinc-finger DNA-binding domain, or a TALE DNA binding domain, or a Cas9 nuclease. In another aspect, a serine recombinase attached to a DNA recognition motif is selected from the group consisting of a PhiC31 integrase, an R4 integrase, and a TP-901 integrase. In another aspect, a DNA transposase attached to a DNA binding domain provided herein is selected from the group consisting of a TALE-piggyBac and TALE-Mutator.

Any DNA of interest as provided herein can be integrated into a target site of a chromosome sequence by introducing the DNA of interest and the disclosed site-specific genome modification enzymes. Any method provided herein can utilize any site-specific genome modification enzyme disclosed herein.

VI. Antisense and RNAi Constructs

Antisense and RNAi treatments represent one way of altering mogroside biosynthesis pathway gene activity in accordance with the present disclosure (e.g., by down regulation of genes or transcription factors that inhibit expression of mogroside biosynthesis pathway genes).

Techniques for RNAi are well known in the art and are described in, for example, Lehner et al., (*Brief Funct. Genomic Proteomic* 3:68-83, 2004) and Downward (BMJ 328:1245-1248, 2004). The technique is based on the fact that double stranded RNA is capable of directing the degradation of messenger RNA with sequence complementary to one or the other strand (Fire et al., *Nature* 391:806-811, 1998). Therefore, by expression of a particular coding sequence in sense and antisense orientation, either as a fragment or longer portion of the corresponding coding sequence, the expression of that coding sequence can be down-regulated.

Antisense, and in some aspects RNAi, methodology takes advantage of the fact that nucleic acids tend to pair with "complementary" sequences. By complementary, it is meant that polynucleotides are those that are capable of base-pairing according to the standard Watson-Crick complementarity rules. That is, the larger purines will base pair with the smaller pyrimidines to form combinations of guanine paired with cytosine (G: C) and adenine paired with either thymine (A: T) in the case of DNA, or adenine paired with uracil (A: U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense oligonucleotides, when introduced into a target cell, specifically bind to their target polynucleotide and interfere with transcription, RNA processing, transport, translation and/or stability. Antisense and RNAi constructs, or DNA encoding such RNA's, may be employed to inhibit gene transcription or translation or both within a host cell, either in vitro or in vivo, such as within a host plant cell. In certain embodiments of the present disclosure, such an oligonucleotide may comprise any unique portion of a nucleic acid sequence provided herein. In certain embodiments of the present disclosure, such a sequence comprises at least 18, 20, 25, 30, 50, 75 or 100 or more contiguous nucleic acids of a nucleic acid sequence of interest, and/or complements thereof, which may be in sense and/or antisense orientation. By including sequences in both sense and antisense orientation, increased suppression of the corresponding coding sequence may be achieved.

Constructs may be designed that are complementary to all or part of the promoter and other control regions, exons, introns or even exon-intron boundaries of a gene. It is contemplated that the most effective constructs may include regions complementary to intron/exon splice junctions. Thus, it is proposed that one embodiment includes a construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences that are completely complementary will be sequences that are entirely complementary throughout their entire length and have no base mismatches. Other sequences with lower degrees of homology also are contemplated. For example, an RNAi or antisense construct that has limited regions of high homology, but also contains a non-homologous region (e.g., ribozyme; see above) could be designed. Methods for selection and design of sequences that generate RNAi are well known in the art (e.g., Reynolds et al., *Nat. Biotechnol.* 22:326-330, 2004). These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone may be used. The cDNA or a synthesized polynucleotide may provide more convenient restriction sites for the remaining portion of the construct and, therefore, would be used for the rest of the sequence. Constructs useful for generating RNAi may also comprise concatemers of sub-sequences that display gene regulating activity.

VII. Transformation

In some embodiments, transgenic plants of the present disclosure are created by transforming the selected natural plants with one or more of the expression cassettes disclosed herein. The natural plants prior to transformation do not naturally produce all mogrol/mogroside pathway enzymes, and do not produce non-native mogrol and mogroside compounds. Although the natural plants may produce one or more enzymes capable of producing mogrol precursors or mogrol, these plants do not produce non-native mogrosides naturally. In certain embodiments, the selected natural plants for transformation include wild-type, or untransformed, or non-transformed watermelons, which do not naturally produce detectable amounts of mogrol or mogroside compounds. Other plants that can be transformed with one or more of the expression cassettes disclosed herein include, but are not limited to, cantaloupe, honeydew, winter melon, casaba melon, Persian melon, citron melon, muskmelon, bailan melon, crenshaw melon, Christmas melon, sprite melon, caravelle melon, hami melon, rocky melon, golden Langkawi melon, Korean melon, saticoy melon, galia melon, jade dew melon, golden prize melon, ten me melon, new century melon, banana melon, yubari king melon, sugar melon, tiger melon, vert grimpant melon, horned melon, cucamelon, casabanana melon, pepino melon, *ananas* melon, camouflage melon, canary melon, bitter melon, charentais melon, crane melon, SkyRocket melon, honey globe melon, gac melon, autumn sweet melon, snap melon, cucumber, tomato, lettuce, spinach, rice, oat, maize, sorghum, bitter apple (*Citrullus colocynthis*), pumpkin, chard, tobacco, switch grass, bush cherry, peach, nectarine, apricot, radish, plum, sour cherry, apple, pear, sweet cherry, citrus, zucchini, pea, turnip or *Nicotiana benthamiana* plants. Mogroside compounds can be isolated from any part of the transformed plant, including, but not limited to, the fruit (juice or rind), leaves, roots, seeds or flowers.

Suitable methods for transformation of plant or other cells for use with the current disclosure are believed to include virtually any method by which DNA can be introduced into a cell, such as by direct delivery of DNA such as by PEG-mediated transformation of protoplasts (Omirulleh et al., *Plant. Mol. Biol.* 21:414-428, 1993), by desiccation/inhibition-mediated DNA uptake (Potrykus et al., *Mol. Gen. Genet.* 199:169-177, 1985), by electroporation (U.S. Pat. No. 5,384,253, specifically incorporated herein by reference in its entirety), by agitation with silicon carbide fibers (U.S. Pat. Nos. 5,302,523 and 5,464,765, specifically incorporated herein by reference in their entirety), by *Agrobacterium*-mediated transformation (U.S. Pat. Nos. 5,591,616 and 5,563,055; both specifically incorporated herein by reference in their entirety) and by acceleration of DNA coated particles (U.S. Pat. Nos. 5,550,318; 5,538,877; and 5,538,880; each specifically incorporated herein by reference in their entirety), etc. Through the application of techniques such as these, the cells of virtually any plant species may be transiently transformed, or stably transformed, and these cells developed into transgenic plants.

A. *Agrobacterium*-mediated Transformation

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (*Proc. Natl. Acad. Sci. USA* 80:4803-4807, 1985), and U.S. Pat. No. 5,563,055, specifically incorporated herein by reference in its entirety.

*Agrobacterium*-mediated transformation is most efficient in dicotyledonous plants and is an efficient method for transformation of dicots, including *Arabidopsis*, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., *Plant Mol. Biol.* 35:205-218, 1997; U.S. Pat. No. 5,591,616, specifically incorporated herein by reference in its entirety), wheat and barley (McCormac et al., *Mol. Biotechnol.* 9:155-159, 1998), alfalfa and maize (Ishida et al., *Nat. Biotechnol.* 14:745-750, 1996). Similarly, *Agrobacterium*-mediated transformation has also proven to be effective in switchgrass.

Modern *Agrobacterium* transformation vectors are capable of replication in *E. coli* as well as *Agrobacterium*, allowing for convenient manipulations. Moreover, recent technological advances in vectors for *Agrobacterium*-mediated gene transfer have improved the arrangement of genes and restriction sites in the vectors to facilitate the construction of vectors capable of expressing various polypeptide coding genes. The vectors have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agro-*

*bacterium*-mediated transformation is efficient, it is the method of choice because of the facile and defined nature of the gene transfer.

B. Electroporation

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species that have been transformed by electroporation of intact cells include maize (U.S. Pat. No. 5,384,253, incorporated herein by reference in its entirety; Rhodes et al., *Methods Mol. Biol.* 55:121-131, 1995; D'Halluin et al., *Plant Cell* 4:1495-1505, 1992), wheat (Zhou et al., *Plant Cell Rep.* 12:612-616, 1993), tomato (Tsukada et al., *Plant Cell Physiol.* 30:599-603, 1989), soybean (Christou et al., *Proc. Natl. Acad. Sci. USA* 84:3962-3966, 1987) and tobacco (Riggs and Bates, *Proc. Natl. Acad. Sci. USA* 83:5602-5606, 1986).

One also may employ protoplasts for electroporation transformation of plants (Bates, *Mol. Biotechnol.* 2:135-145, 1994; *Lazzeri, Methods Mol. Biol.* 49:95-106, 1995). For example, the generation of transgenic soybean plants by electroporation of cotyledon-derived protoplasts is described in WO 9217598 (specifically incorporated herein by reference). Other examples of species for which protoplast transformation has been described include barley (Lazzeri, supra), sorghum (Battraw et al., *Theor. Appl. Genet.* 82:161-168, 1991), maize (Rhodes et al., *Science* 240:204-207, 1988), wheat (He et al., *Plant Cell Rep.* 14:192-196, 1994) and tomato (Tsukada, supra).

C. Microprojectile Bombardment

Another method for delivering transforming DNA segments to plant cells in accordance with the present disclosure is microprojectile bombardment (U.S. Pat. Nos. 5,550,318; 5,538,880; 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and often, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species that have been transformed by microprojectile bombardment include monocot species such as maize (PCT Application WO 95/06128), barley (Ritala et al., *Plant Mol. Biol.* 24:317-325, 1994; Hensgens et al., *Plant Mol. Biol.* 22:1101-1127, 1993), wheat (U.S. Pat. No. 5,563,055, specifically incorporated herein by reference in its entirety), rice (Hensgens et al., supra), oat (Torbet et al., *Crop Science* 38:226-231, 1998), rye (Hensgens et al., supra), sugarcane (Bower et al., *Plant J.* 2:409-416, 1992), and sorghum (Casas et al., *Proc. Natl. Acad. Sci. USA* 90:11212-11216, 1993; Hagio et al., *Plant Cell Rep.* 10:260-264, 1991); as well as a number of dicots including tobacco (Tomes et al., *Plant Mol. Biol.* 14:261-268, 1990), soybean (U.S. Pat. No. 5,322,783, specifically incorporated herein by reference in its entirety), sunflower (Knittel et al., *Plant Cell Rep.* 14:81-86, 1994), peanut (Singsit et al., *Transgenic Res.* 6:169-176, 1997), cotton (McCabe and Martinell, *Nat. Biotechnol.* 11:596-598, 1993), tomato (VanEck et al., *Plant Cell. Rep.* 14:299-304, 1995), switchgrass (Richards et al., *Plant Cell Rep.* 20:48-54, 2001) and legumes in general (U.S. Pat. No. 5,563,055, specifically incorporated herein by reference in its entirety).

D. Other Transformation Methods

Transformation of protoplasts can be achieved using methods based on calcium phosphate precipitation, polyethylene glycol treatment, electroporation, and combinations of these treatments (see, e.g., Potrykus et al., supra; Omirulleh et al., supra). Application of these systems to different plant strains depends upon the ability to regenerate that particular plant strain from protoplasts. Illustrative methods for the regeneration of cereals from protoplasts have been described (Toriyama et al., *Nat. Biotechnol.* 6:1072-1074, 1988; Abdullah et al., *Nat. Biotechnol.* 4:1087-1090, 1986; Omirulleh et al., supra, and U.S. Pat. No. 5,508,184; each specifically incorporated herein by reference in its entirety). Examples of the use of direct uptake transformation of cereal protoplasts include transformation of rice (Ghosh-Biswas et al., *J. Biotechnol.* 32:1-10, 1994), sorghum (Battraw et al., supra), barley (Lazzeri, supra), oat, and maize (Omirulleh et al., supra).

To transform plant strains that cannot be successfully regenerated from protoplasts, other ways to introduce DNA into intact cells or tissues can be utilized. For example, regeneration of cereals from immature embryos or explants can be effected as described (Vasil, supra). Also, silicon carbide fiber-mediated transformation may be used with or without protoplasting (Kaeppler et al., *Theor. Appl. Genet.* 84:560-566, 1992; U.S. Pat. No. 5,563,055, specifically incorporated herein by reference in its entirety). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128, specifically incorporated herein by reference in its entirety) and rice (Nagatani et al., *Biotechnol. Tech.* 11:471-473, 1997).

E. Tissue Cultures

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. BACTO® AGAR, GELRITE®, and GELGRO® are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Tissue that can be grown in a culture includes meristem cells, Type I, Type II, and Type III callus, immature embryos and gametic cells such as microspores, pollen, sperm and egg cells. Type I, Type II, and Type III callus may be initiated from tissue sources including, but not limited to, immature embryos, seedling apical meristems, root, leaf, microspores and the like. Those cells that are capable of proliferating as callus also are recipient cells for genetic transformation.

Somatic cells are of various types. Embryogenic cells are one example of somatic cells that may be induced to regenerate a plant through embryo formation. Non-embryogenic cells are those that typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques that can be employed to select target cells may include, e.g., assessing cell morphology and differentiation, or may use various physical or biological means. Cryopreservation also is a possible method of selecting for recipient cells.

Manual selection of recipient cells, e.g., by selecting embryogenic cells from the surface of a Type II callus, is one means that may be used in an attempt to enrich for particular cells prior to culturing (whether cultured on solid media or in suspension).

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the present disclosure will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al., (*Sci. Sin*. [Peking] 18:659-668, 1975) and MS media (Murashige and Skoog, *Physiol. Plant* 15:473-479, 1962).

VIII. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the present disclosure. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce into the host cell, a marker gene that confers resistance to some normally inhibitory agent, such as an antibiotic or herbicide. Examples of antibiotics that may be used include the aminoglycoside antibiotics neomycin, kanamycin and paromomycin, or the antibiotic hygromycin. Resistance to the aminoglycoside antibiotics is conferred by aminoglycoside phosphotransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide that constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., *Sci. Rep. Meiji Seika* 13:42-48, 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT), which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., *EMBO J.* 6:2519-2523, 1987). The bar gene has been cloned (Thompson et al., supra) and expressed in transgenic tobacco, tomato, potato (De Block et al., *EMBO J.* 6:2513-2518, 1987) *Brassica* (De Block et al., *Plant Physiol.* 91:694-701, 1989) and maize (U.S. Pat. No. 5,550,318, incorporated herein by reference in its entirety).

Another example of a herbicide that is useful for selection of transformed cell lines in the practice of the present disclosure is the broad spectrum herbicide glyphosate. Glyphosate inhibits the action of the enzyme EPSPS, which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 (incorporated herein by reference in its entirety) describes the isolation of EPSPS mutations that confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103.

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate may be beneficial, it is proposed that ranges of 0.1-50 mg/l bialaphos or 0.1-50 mM glyphosate will find utility.

An example of a screenable marker trait is the enzyme luciferase. In the presence of the substrate luciferin, cells expressing luciferase emit light that can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells that are expressing luciferase and manipulate those in real time. Another screenable marker that may be used in a similar fashion is the gene coding for green fluorescent protein.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 weeks, then transferred to media conducive to maturation of embryoids. Cultures are transferred every 2 weeks on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm CO2, and 25-250 microeinsteins m 2 s−1 of light. Plants may be matured in a growth chamber or greenhouse. Plants can be regenerated from about 6 weeks to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 week on media containing the above ingredients along with 105M abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this disclosure may be determined, for example, by polymerase chain reaction (PCR™). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization, which are modifications of Southern hybridization techniques, one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

E. Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}C$-acetyl COA or for anthranilate synthase activity by following loss of fluorescence of anthranilate, to name two.

Very frequently the expression of a gene product is determined by evaluating the phenotypic results of its expression. These assays also may take many forms including, but not limited to, analyzing changes in the chemical composition, morphology, or physiological properties of the plant. Chemical composition may be altered by expression of genes encoding enzymes or storage proteins that change amino acid composition and may be detected by amino acid analysis, or by enzymes that change starch quantity, which may be analyzed by near infrared reflectance spectrometry. Morphological changes may include greater stature or thicker stalks. Most often changes in response of plants or plant parts to imposed treatments are evaluated under carefully controlled conditions termed bioassays.

IX. Mogroside Containing Sweeteners and Consumables

In some embodiments, the present disclosure relates generally to a sweetener or sweetening composition comprising mogroside and/or metabolites or derivatives thereof, wherein the sweetener or sweetening composition is derived from a transgenic plant producing and comprising non-native mogrol/mogrosides. The term "sweetener", as used herein, refers to a consumable product, which produces a sweet taste when consumed alone. In certain embodiments, the sweetener or sweetening composition is derived from the mogrol/mogroside pathway transgenic plants made according to the present disclosure. In some embodiments the sweeteners are high intensity or low intensity sweeteners. Mogroside-containing sweeteners can be derived from the mogrol/mogroside pathway transgenic plants of the present disclosure upon appropriate processing. The resulting sweeteners could be used to provide low or non-caloric sweetness for many purposes. Examples of such uses to provide sweetness are in beverages, such as tea, coffee, fruit juice, and fruit beverages, foods, such as jams and jellies, peanut butter, pies, puddings, cereals, candies, ice creams, yogurts, bakery products; health care products, such as toothpastes, mouthwashes, cough drops, cough syrups; chewing gums; and sugar substitutes.

In certain embodiments, the sweetener is in a juice of the fruit from a transgenic plant according to the present disclosure. Applications for juice, for example, watermelon juice, containing one or more mogroside compound include, but are not limited to, as a beverage, including, for example, premixed cocktails and dairy alternatives, as an ingredient, for example to be sprayed onto bars or cereal, or used to sweeten ketchup or other common products. In such embodiments the juice can be devitalized, have the protein removed or concentrated. Additionally concentrated fruit or vegetable syrup, for example watermelon syrup produced from the presently disclosed watermelons, can be used to substitute for high fructose corn syrup in various foods and beverages. In some embodiments of the present disclosure the mogroside compounds are produced in transgenic tomatoes, which can then be used, for example, to produce lower calorie ketchup or other tomato-based sauces or soups.

In some embodiments, the present disclosure also relates to methods of making a sweetener derived from the presently disclosed transgenic plants producing non-native mogrol/mogrosides. The methods generally encompasses steps that can include, but are not limited to, pre-treatment cleaning and crushing of the transgenic plant or the parts thereof, extraction of the transgenic plant or the parts thereof, sedimentation and/or centrifuge, adsorption and/or separation, concentration and recovery to produce the crude sweetener, further purification, optional concentration/drying, and formulation. Means of extraction encompasses water-extraction at room temperatures, or heated temperature, or refrigerated temperature; extraction via organic solvent such as alcohol, etc. Means of separation and purification encompasses centrifuge, steeping, gravity sedimentation, filtration, micro-filtration, nano filtration, ultra-filtration, reverse osmosis, chromatography, absorption chromatogram, exchanged resin purification, etc.

In further embodiments the presently disclosed transgenic plants can be processed to produce mogroside-containing ingredients, for example by whole plant extracts, tissue extraction, fruit processing, aqueous separation of small molecules having a mogroside fraction, removal of residual proteins to yield an aqueous fraction free from any genetically engineered components. The resulting mogroside containing ingredient(s) can be in any form, including, but not limited to, a powder, liquid, syrup, concentrate or extract. Additionally in some embodiments a whole mogroside containing fruit or vegetable is the consumable.

In certain embodiments, the sweetener is obtained from the leaves of the transgenic plant made according to the present disclosure. In other embodiments, the sweetener is obtained from the fruit, a part of a fruit (e.g., the rind), or other part of an organ or tissue of the transgenic plant made according to the present disclosure.

Additionally the mogroside compounds produced by the presently disclosed transgenic plants and organisms can be blended with one or more other naturally occurring or artificial sweeteners, such as steviol glycosides, siamenoside I, α-siamenoside I, sucrose, glucose, fructose, lactose, maltose, sorbitol, galactose, thaumtin, sucrooctate, bernadame, sucrononic acid, carrelame, lugduname, high fructose corn syrup, RealSweet™ Sugarcane RebM, erythritol, xylitol, yacon syrup, allulose, saccharin, aspartame, acesulfame potassium, sucralose, neotame, advantame, cyclamates or glycyrrhizin. The ratio of the mogroside compound(s) to the other sweetener in the final formulation can be, for example, 10/90, 20/80, 30/70, 40/60/50/50, 60/40, 70/30, 80/20 or 90/10, or any other desired ratio. In one embodiment, the ratio is about 80% mogroside V, about 15% 11-oxo-mogroside V and about 5% mogroside III A1. In another embodiment, the ratio is about 40% siamenoside I, about 40% mogroside V and about 20% 11-oxo-mogroside V.

In certain embodiments, the one or more additional sweeteners may be a carbohydrate sweetener. Non-limiting examples of suitable carbohydrate sweeteners include sucrose, fructose, glucose, erythritol, maltitol, lactitol, sorbitol, mannitol, xylitol, tagatose, trehalose, galactose, rhamnose, cyclodextrin (e.g., α-cyclodextrin, β-cyclodextrin, and γ-cyclodextrin), ribulose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, glucosamine, mannosamine, fucose, fuculose, glucuronic acid, gluconic acid, glucono-lactone, abequose, galactosamine, xylo-oligosaccharides (xylotriose, xylobiose and the like), gentio-oligoscaccharides (gentiobiose, gentiotriose, gentiotetraose and the like), galacto-oligosaccharides, sorbose, ketotriose (dehydroxyacetone), aldotriose (glyceraldehyde), nigero-oligosaccharides, fructooligosaccharides (kestose, nystose and the like), maltotetraose, maltotriol, tetrasaccharides, mannan-oligosaccharides, malto-oligosaccharides (maltotriose, maltotetraose, maltopentaose, maltohexaose, maltoheptaose and the like), dextrins, lactulose, melibiose, raffinose, rhamnose, ribose, isomerized liquid sugars such as high fructose corn/starch syrup (HFCS/HFSS) (e.g., HFCS55, HFCS42, or HFCS90), coupling sugars, soybean oligosaccharides, glucose syrup and combinations thereof. D- or L-configurations can be used when applicable. In other embodiments, the additional sweetener is a carbohydrate sweetener selected from the group consisting of glucose, fructose, sucrose and combinations thereof. In another embodiment, the additional sweetener is a carbohydrate sweetener selected from D-allose, D-psicose, L-ribose, D-tagatose, L-glucose, L-fucose, L-Arabinose, Turanose and combinations thereof.

In yet other embodiments, the one or more additional sweeteners is not directly derived from a natural extraction. Such a sweetener characteristically has a sweetness potency greater than sucrose, fructose, or glucose, yet has less calories. Non-limiting examples of such sweeteners suitable for embodiments of this disclosure include sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, glucosylated steviol glycosides (GSGs) and combinations thereof. The at least one sweetener not directly derived from natural extraction is present in the sweetener composition in an amount effective to provide a concentration from about 0.3 ppm to about 3,500 ppm when present in a sweetened composition, such as, for example, a food, other consumable or beverage. In one embodiment, the at least one sweetener not directly derived from natural extraction is present in the sweetener composition in an amount effective to provide a concentration from about 0.5 ppm to about 3,000 ppm, from about 1.0 ppm to about 2,500 ppm, from about 5.0 ppm to about 2,000 ppm, from about 10 ppm to about 1,500 ppm, from about 50 ppm to about 1000 ppm, from about 100 ppm to about 800 ppm, or from about 400 ppm to about 600 ppm when present in a sweetened beverage. In another embodiment, the at least one embodiment, the at least one sweetener not directly derived from natural extraction is present in the sweetener composition in an amount effective to provide a concentration greater than about 0.3 ppm, greater than about 0.5 ppm, greater than about 1.0 ppm, greater than about 5.0 ppm, greater than about 10 ppm, greater than about 20 ppm, greater than about 50 ppm, greater than about 100 ppm, greater than about 250 ppm, greater than about 500 ppm or greater than about 1000 ppm when present in a sweetened composition, such as, for example, a food, other consumable or beverage.

In still other embodiments, the additional sweetener can be a natural high potency sweetener. Suitable natural high potency sweeteners include, but are not limited to, rebaudioside A, rebaudioside B, rebaudioside C, rebaudioside D, rebaudioside E, rebaudioside F, rebaudioside I, rebaudioside H, rebaudioside L, rebaudioside K, rebaudioside J, rebaudioside M, rebaudioside N, rebaudioside O, dulcoside A, dulcoside B, rubusoside, *Stevia*, stevioside, mogroside IV, mogroside V, Luo Han Guo, miraculin, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, steviolbioside and cyclocarioside I. The natural high potency sweetener can be provided as a pure compound or, alternatively, as part of an extract. For example, rebaudioside A can be provided as a sole compound or as part of a *Stevia* extract. The natural high potency sweetener is present in the sweetener composition in an amount effective to provide a concentration from about 0.1 ppm to about 3,000 ppm when present in a sweetened composition, such as, for example, a food, other consumable or beverage. In one embodiment, the natural high potency sweetener is present in the sweetener composition in an amount effective to provide a concentration from about 0.5 ppm to about 2500 ppm, from about 1.0 ppm to about 2000 ppm, from about 5 ppm to about 1500 ppm, from about 10 ppm to about 1000 ppm, or about 25 ppm to about 500 ppm when present in a sweetened composition, such as, for example, a food, other consumable or beverage. In one embodiment, the natural high potency sweetener is present in the sweetener composition in an amount effective to provide a concentration of greater than about 0.1 ppm, about 0.5 ppm, about 1.0 ppm, about 2.5 ppm, about 5.0 ppm, about 10 ppm, about 20 ppm, about 25 ppm, about 50 ppm, about 75 ppm, about 100 ppm, about 200 ppm, about 500 ppm, about 1000 ppm, about 2000 ppm, or about 300 ppm when present in a sweetened composition, such as, for example, a food, other consumable or beverage.

In still other embodiments, the additional sweetener can be chemically or enzymatically modified natural high potency sweetener. Modified natural high potency sweeteners include glycosylated natural high potency sweetener such as glucosyl-, galactosyl-, or fructosyl-derivatives containing 1-50 glycosidic residues. Glycosylated natural high potency sweeteners may be prepared by an enzymatic transglycosylation reaction catalyzed by various enzymes possessing transglycosylating activity.

When the sweetener composition contains more than one sweetener, the sweeteners may exhibit synergy when combined and have improved flavor and temporal profiles compared to each sweetener alone. As used herein, the term "temporal profile" of a composition means the intensity of sweetness perceived over time in tasting of a composition by a human. The term "flavor profile" or "taste profile," as generally used herein, refers to the intensity of various flavor/taste attributes of a sweetener or sweetened composition. Exemplary flavor/taste attributes are sweetness intensity, bitterness intensity, salty intensity, licorice intensity, cooling intensity, and licorice intensity. Methods of determining the flavor profile of a given sweetener or sweetened composition are known in the art. The term "synergistic" or "synergistic effect" refers to an effect (e.g., flavor, temporal profile) achieved with the combination of two or more sweeteners which is greater than the sum of the effects that effect from using the particular sweeteners alone or separately. Advantageously, such synergy between the two or more sweeteners allows for the use of smaller doses of one or both sweeteners or provides greater effect at the same amounts. The amount or degree of synergism may vary.

The amount of sucrose in a reference solution may be described in degrees Brix (° Bx). One degree Brix is 1 gram of sucrose in 100 grams of solution and represents the strength of the solution as percentage by weight (% w/w) (strictly speaking, by mass). In one embodiment, a sweetener composition contains one or more of the presently disclosed sweetener compounds in an amount effective to provide sweetness equivalent from of at least about 5 degrees Brix of sugar when present in a sweetened composition, such as, for example, from at least about 5, at least about 6, at least about 7, at least about 8, at least about 9, at least about 10, at least about 11, at least about 12, at least about 13, at least about 14 or at least about 15 or more degrees Brix.

The sweetness of a non-sucrose sweetener can also be measured against a sucrose reference by determining the non-sucrose sweetener's sucrose equivalence. Typically, taste panelists are trained to detect sweetness of reference sucrose solutions containing between 1-15% sucrose (w/v). Other non-sucrose sweeteners are then tasted at a series of dilutions to determine the concentration of the non-sucrose sweetener that is as sweet as a given percent sucrose reference. For example, if a 1% solution of a sweetener is as sweet as a 10% sucrose solution, then the sweetener is said to be 10 times as potent as sucrose.

The sweetener compositions can be customized to provide the desired calorie content. For example, sweetener compositions can be "full-calorie", such that they impart the desired sweetness when added to a sweetenable composition (such as, for example, a food, other consumable or beverage) and have about 120 calories per 8 oz. serving. Alternatively, sweetener compositions can be "mid-calorie", such that they impart the desired sweetness when added to a sweetenable composition and have less than about 60 calories per 8 oz. serving. In other embodiments, sweetener compositions can be "low-calorie", such that they impart the desired sweetness when added to a sweetenable composition and have less than 40 calories per 8 oz. serving. In still other embodiments, the sweetener compositions can be "zero-calorie", such that they impart the desired sweetness when added to a sweetenable composition and have less than 5 calories per 8 oz. serving.

The presently disclosed the sweetener compositions can optionally include one or more additional additives. In some embodiments, the sweetener composition contains additives including, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, weighing agents, gums, antioxidants, colorants, flavonoids, alcohols, polymers and combinations thereof. In some embodiments, the additives act to improve the temporal and flavor profile of the sweetener to provide a sweetener composition with a taste similar to sucrose. The sweetened compositions can contain one or more functional ingredients, as detailed above. Functional ingredients include, but are not limited to, vitamins, minerals, antioxidants, preservatives, glucosamine, polyphenols and combinations thereof. Any suitable functional ingredient described herein can be used.

There is a beneficial environmental impact of the presently disclosed mogroside sweeteners compared to existing monkfruit production. The presently disclosed mogroside sweeteners enables local production, resulting in less transportation and fewer food miles as a result, compared to for example harvesting and processing only in China and shipping across the globe to food companies. The presently disclosed mogroside sweeteners also require minimal processing because of the ease of access to the mogroside sweeteners in the presently disclosed transgenic plants or organisms compared to, for example, factory processing of monkfruit sweetener in China.

X. Sweetened Compositions

The presently disclosed sweetener compositions can be incorporated in any known edible material (referred to herein as a "sweetenable composition"), such as, for example, pharmaceutical compositions, edible gel mixes and compositions, dental compositions, foodstuffs (confections, condiments, chewing gum, cereal compositions baked goods dairy products, and tabletop sweetener compositions) beverages and beverage products.

The sweetened compositions disclosed here include beverages, i.e., ready to drink liquid formulations, beverage concentrates and the like. In certain embodiments, beverage concentrates are prepared with an initial volume of liquid (e.g., water) to which the additional ingredients are added. Full strength beverage compositions can be formed from the beverage concentrate by adding further volumes of liquid (e.g., water) to the concentrate.

In embodiments of sweetenable compositions using mogroside-containing filler juice concentrate (about 80% mogroside V, about 15% 11-oxo-mogroside V and about 5% mogroside III A1), studies have shown the taste to be the sweetest and cleanest tasting natural sweetener. The presently disclosed mogroside-containing filler juice concentrate can be produced from consumer friendly fruits that can be locally grown with sustainable production, is the only sweetener for high sugar reduction while maintaining 100% juice labeling, and is an affordable drop in solution. The filler juice may be used as single strength or concentrated to deliver clean, sweet taste across various inclusion levels. The filler juice mogroside concentrations can deliver the equivalent of ~10 sucrose equivalent value (SEV) when used at various formula inclusions.

Besides concentration, other juice parameters are also readily changeable, resulting in different sweetener products. For example, the natural sugars in the fruit (for example watermelon) may be partially or fully removed, the juice color and/or flavor may be minimized or removed, the pulp may be removed as is typical, or remain fully or partially as in purees, and the acidity may be reduced, or combinations of one or more of these parameters can be changed.

Filler juice applications include, but are not limited to, juices, nectars, fruit/flavored still drinks, energy and sports drinks, carbonated soft drinks, flavored waters, nutritional drinks, vitamins and dietary supplements or oral rehydration in the form of liquids or chews/gummies, snacks such as snack bars or fruit snacks, sugar and gum confectionary in the form of jellies and chews, dairy products such as spoonable yogurt, drinking yogurt and flavored drinks, desserts, ice cream, frozen yogurt, water-based ice pops and sorbets, breakfast cereals and other cold cereals, tabletop sweeteners, sweet spreads such as syrups and fruit spreads, sauces and seasonings such as table sauces and cooking sauces, and processed and packaged fruit and vegetables.

In embodiments of sweetenable compositions using mogroside-containing dry powder (about 40% siamenoside I, about 40% mogroside V, and about 20% 11-oxo-mogroside V), studies have shown the taste to be clean, with high levels of sweetness with no off-tastes in demanding applications. The presently disclosed mogroside-containing dry powder can be produced from consumer friendly vegetables that can be locally grown with sustainable production, results in sugar and calorie reduction with strong positive associations to health benefits, and is a fraction of monk fruit/parity with sucrose. The dry powder may be used across a wide range of food and drink applications to deliver the cleanest, sweetest taste at low inclusion levels. The dry powder concentrations can deliver the equivalent of ~10 SEV when used at various purity levels.

Dry powder application include, but are not limited to: wellness and functional drinks, such as energy and sports drinks, carbonated soft drinks, flavored waters, juices, nectars, fruit/flavored still drinks, protein and meal replacement drinks, drink mixes, drink concentrates, ready-to-drink tea and ready-to-drink coffee; dietary supplements and over-the-counter products, such as vitamins and dietary supplements, oral hydration, cold relief, digestive treatments, sleep aids, pain relief in capsule, tablet, liquid, powder, chew/gummy, lozenge and other formats; snacks such as snack bars, fruit snacks, nuts, trail mixes, corn rice, potato and wheat snacks; bakery products such as cookies, cakes and sweet goods, baking mixes and ingredients and breads; dairy and desserts such as spoonable and drinking yogurt, flavored drinks, creamers, ice cream and frozen yogurt, water-based ice pops and sorbets, shelf-stable desserts and dessert toppings; hot and cold breakfast cereals; artificial and other natural sweeteners (tabletop sweeteners); sugar and chocolate confectionary such as jellies and chews, mints, gum, toffee and caramels, marshmallows and various chocolate formats; sweet spreads such as syrups, fruit, nut and chocolate spreads; sauces and seasonings such as table, cooking and pasta sauces, vinegar and dressings and pickled condiments; meals and processed meats such as prepared meals, meal kits, sandwiches and wraps and poultry and meat products; and processed and packaged fruit and vegetables.

A. Beverage and Beverage Products

In one embodiment, the sweetened composition is a beverage or beverage product. "Beverage product", as used herein, is a ready-to-drink beverage, a beverage concentrate, a beverage syrup, or a powdered beverage. Suitable ready-to-drink beverages include carbonated and non-carbonated beverages. Carbonated beverages include, but are not limited to, frozen carbonated beverages, enhanced sparkling beverages, cola, fruit-flavored sparkling beverages (e.g., lemon-lime, orange, grape, strawberry and pineapple), ginger-ale, soft drinks and root beer. Non-carbonated beverages include, but are not limited to, fruit juice, fruit-flavored juice or water, juice drinks, nectars, fruit/flavored still drinks, energy and sports drinks, vegetable juice, vegetable-flavored juice, sports drinks, energy drinks, nutritional drinks, enhanced water drinks, enhanced water with vitamins, near water drinks (e.g., water with natural or synthetic flavorants), coconut water, tea type drinks (e.g., black tea, green tea, red tea, oolong tea), coffee, cocoa drink, beverage containing milk components (e.g., milk beverages, coffee containing milk components, cafe au lait, milk tea, fruit milk beverages), beverages containing cereal extracts and smoothies.

In certain embodiments, the beverage is a juice beverage that has been modified to remove at least some sucrose. In certain embodiments, such juice may be modified to remove at least 10%, at least 20%, at least 30%, at least 40%, at least 50% or more of the sucrose in the non-modified juice. In certain embodiments, the modification occurs through filtration of such juice to remove sucrose. In certain embodiments, sucrose in the juice is broken down to fructose and glucose, prior to adding the sweetening composition described herein.

Beverages comprise a matrix, i.e., the basic ingredient in which the ingredients—including the compositions of the present disclosure—are dissolved. In one embodiment, a beverage comprises water of beverage quality as the matrix, such as, for example deionized water, distilled water, reverse osmosis water, carbon-treated water, purified water, demineralized water and combinations thereof, can be used. Additional suitable matrices include, but are not limited to phosphoric acid, phosphate buffer, citric acid, citrate buffer and carbon-treated water. Beverage concentrates and beverage syrups are prepared with an initial volume of liquid matrix (e.g., water) and the desired beverage ingredients. Full strength beverages are then prepared by adding further volumes of water. Powdered beverages are prepared by dry-mixing all of the beverage ingredients in the absence of a liquid matrix. Full strength beverages are then prepared by adding the full volume of water.

It is contemplated that the pH of the beverage does not materially or adversely affect the taste of the sweetener. A non-limiting example of the pH range of the beverage may be from about 1.8 to about 10. In one embodiment, the pH of the beverage is about 4. In another embodiment, the pH of the beverage is less than about 4. In a particular embodiment, the pH of the beverage is less than about 3.8, less than about 3.6, less than about 3.4, less than about 3.2, less than about 3.0, less than about 2.8, less than about 2.6, less than about 2.4 or less than about 2.2. In another embodiment, the pH of the beverage is about 3.8, about 3.6, about 3.4, about 3.2, about 3.0, about 2.8, about 2.6, about 2.4 or about 2.2 or less.

B. Edible Gel Mixes and Edible Gel Compositions

In one embodiment, the sweetened composition is an edible gel or edible gel mix. Edible gels are gels that can be eaten. Non-limiting examples of edible gel compositions for use in particular embodiments include gel desserts, puddings, jellies, pastes, trifles, aspics, marshmallows, gummy candies/chews, or the like. Edible gel mixes generally are powdered or granular solids to which a fluid may be added to form an edible gel composition. Non-limiting examples of fluids for use in particular embodiments include water, dairy fluids, dairy analogue fluids, juices, alcohol, alcoholic beverages, and combinations thereof. Non-limiting examples of dairy fluids which may be used in particular embodiments include milk, cultured milk, cream, fluid whey, and mixtures thereof. Non-limiting examples of dairy analogue fluids which may be used in particular embodiments include, for example, soy milk and non-dairy coffee whitener.

C. Confections

In one embodiment, the sweetened composition is a confection. As referred to herein, "confection" can mean a sweet, a lollie, a confectionery, or similar term. The confection generally contains a base composition component and a sweetener component. According to particular embodiments of the present disclosure, the confections may be desserts such as yogurt, jellies, drinkable jellies, puddings, Bavarian cream, blancmange, cakes, brownies, mousse and the like, sweetened food products eaten at tea time or following meals; frozen foods; cold confections, e.g., types of ice cream such as ice cream, ice milk, lacto-ice and the like, and ice confections such as sherbets, dessert ices and the like; general confections, e.g., baked confections or steamed confections such as crackers, biscuits, buns with bean-jam filling, halvah, alfajor, and the like; rice cakes and snacks; table top products; general sugar confections such as chewing gum, hard candy, soft candy, mints, nougat candy, jelly beans, fudge, toffee, taffy, Swiss milk tablet, licorice candy, chocolates, gelatin candies, marshmallow, marzipan, divinity, cotton candy, and the like; sauces including fruit flavored sauces, chocolate sauces and the like; edible gels; cremes including butter cremes, flour pastes, whipped cream and the like; jams including strawberry jam, marmalade and the like; and breads including sweet breads and the like or other starch products, and combinations thereof.

D. Condiment Compositions

In one embodiment, the sweetened composition is a condiment composition. Condiments, as used herein, are compositions used to enhance or improve the flavor of a food or beverage. Non-limiting examples of condiments include ketchup; mustard; barbecue sauce; butter; chili sauce; chutney; cocktail sauce; curry; dips; fish sauce; horseradish; hot sauce; jellies, jams, marmalades, or preserves; mayonnaise; peanut butter; relish; remoulade; salad dressings, salsa; sauerkraut; soy sauce; steak sauce; syrups; tartar sauce; and Worcestershire sauce. Condiment bases generally comprise a mixture of different ingredients, non-limiting examples of which include vehicles (e.g., water and vinegar); spices or seasonings (e.g., salt, pepper, garlic, mustard seed, onion, paprika, turmeric, and combinations thereof); fruits, vegetables, or their products (e.g., tomatoes or tomato-based products (paste, puree), fruit juices, fruit juice peels, and combinations thereof); oils or oil emulsions, particularly vegetable oils; thickeners (e.g., xanthan gum, food starch, other hydrocolloids, and combinations thereof); and emulsifying agents (e.g., egg yolk solids, protein, gum arabic, carob bean gum, guar gum, gum karaya, gum tragacanth, carageenan, pectin, propylene glycol esters of alginic acid, sodium carboxymethyl-cellulose, polysorbates, and combinations thereof). Recipes for condiment bases and methods of making condiment bases are well known to those of ordinary skill in the art.

E. Chewing Gum Compositions

In one embodiment, the sweetened composition is a chewing gum composition. Chewing gum compositions generally comprise a water-soluble portion and a water-insoluble chewable gum base portion. The water soluble portion dissipates with a portion of the flavoring agent over a period of time during chewing while the insoluble gum base portion is retained in the mouth. The insoluble gum base generally determines whether a gum is considered chewing gum, bubble gum, or a functional gum.

Flavoring agents may be used in either the insoluble gum base or soluble portion of the chewing gum composition. Such flavoring agents may be natural or artificial flavors. In a particular embodiment, the flavoring agent comprises an essential oil, such as an oil derived from a plant or a fruit, peppermint oil, spearmint oil, other mint oils, clove oil, cinnamon oil, oil of wintergreen, bay, thyme, cedar leaf, nutmeg, allspice, sage, mace, and almonds. In another particular embodiment, the flavoring agent comprises a plant extract or a fruit essence such as apple, banana, watermelon, pear, peach, grape, strawberry, raspberry, cherry, plum, pineapple, apricot, and mixtures thereof. In still another particular embodiment, the flavoring agent comprises a citrus flavor, such as an extract, essence, or oil of lemon, lime, orange, tangerine, grapefruit, citron, or kumquat.

F. Cereal Compositions

In one embodiment, the sweetened composition is a cereal composition. Cereal compositions typically are eaten either as staple foods or as snacks. Non-limiting examples of cereal compositions for use in particular embodiments include ready-to-eat cereals as well as hot cereals. Ready-to-eat cereals are cereals which may be eaten without further processing (i.e., cooking) by the consumer. Examples of ready-to-eat cereals include breakfast cereals and snack bars. Breakfast cereals typically are processed to produce a shredded, flaky, puffy, or extruded form. Breakfast cereals generally are eaten cold and are often mixed with milk and/or fruit. Snack bars include, for example, energy bars, rice cakes, granola bars, and nutritional bars. Hot cereals generally are cooked, usually in either milk or water, before being eaten. Non-limiting examples of hot cereals include grits, porridge, polenta, rice, and rolled oats.

Cereal compositions generally comprise at least one cereal ingredient. As used herein, the term "cereal ingredient" denotes materials such as whole or part grains, whole or part seeds, and whole or part grass. Non-limiting examples of cereal ingredients for use in particular embodiments include maize, wheat, rice, barley, bran, bran endosperm, bulgur, sorghums, millets, oats, rye, triticale, buckwheat, fonio, quinoa, bean, soybean, amaranth, teff, spelt, and kaniwa.

G. Baked Goods

In one embodiment, the sweetened composition is a baked good. "Baked goods," as used herein, include ready to eat and all ready to bake products, flours, and mixes requiring preparation before serving. Non-limiting examples of baked goods include cakes, crackers, cookies, brownies, muffins, rolls, bagels, donuts, strudels, pastries, croissants, biscuits, bread, bread products, and buns.

Baked goods in accordance with particular embodiments of this disclosure generally comprise a combination of sweetener, water, fat and leavening agent. Baked goods made in accordance with many embodiments of this disclosure also contain flour in order to make a dough or a batter.

According to particular embodiments of this disclosure, leavening agents may comprise chemical leavening agents or yeast leavening agents. Non-limiting examples of chemical leavening agents suitable for use in particular embodiments of this disclosure include baking soda (e.g., sodium, potassium, or aluminum bicarbonate), baking acid (e.g., sodium aluminum phosphate, monocalcium phosphate, or dicalcium phosphate), and combinations thereof.

H. Dairy Products

In one embodiment, the sweetened composition is a dairy product. Dairy products and processes for making dairy products suitable for use in this disclosure are well known to those of ordinary skill in the art. Dairy products, as used herein, comprise milk or foodstuffs produced from milk. Non-limiting examples of dairy products suitable for use in embodiments of this disclosure include milk, milk cream, sour cream, creme fraiche, buttermilk, cultured buttermilk, milk powder, condensed milk, evaporated milk, butter, cheese, cottage cheese, cream cheese, yogurt, ice cream, frozen custard, frozen yogurt, gelato, v1a, piima, filmjolk, kajmak, kephir, viili, kumiss, airag, ice milk, casein, ayran, lassi, khoa, or combinations thereof. The dairy products can be produced through conventional means or can be filtered or further modified to adjust the taste properties. In certain embodiments, the dairy products can be liquid dairy products from which one or more of the carbohydrate sugars (lactose or its breakdown products galactose or glucose) are reduced as compared to milk prior to such processing, or are substantially removed and which are supplemented with the sweetening composition described herein. The reduction of carbohydrates can be about 5% or about 10% or about 20% or about 50% or about 70% or more as compared to unprocessed milk.

According to particular embodiments of this disclosure, the dairy compositions also may comprise other additives. Non-limiting examples of suitable additives include sweeteners as disclosed herein and flavorants such as chocolate, strawberry, and banana. Particular embodiments of the dairy compositions provided herein also may comprise additional nutritional supplements such as vitamins (e.g., vitamin D) and minerals (e.g., calcium) to improve the nutritional composition of the milk.

I. Tabletop Sweetener Compositions

In one embodiment, the sweetened composition is a tabletop sweetener. The tabletop sweetener can further include at least one bulking agent, additive, anti-caking agent, functional ingredient or combination thereof.

Suitable "bulking agents" include, but are not limited to, maltodextrin (10 DE, 18 DE, or 5 DE), corn syrup solids (20 or 36 DE), sucrose, fructose, glucose, invert sugar, sorbitol, xylose, ribulose, mannose, xylitol, mannitol, galactitol, erythritol, maltitol, lactitol, isomalt, maltose, tagatose, lactose, inulin, glycerol, propylene glycol, polyols, polydextrose, fructooligosaccharides, cellulose and cellulose derivatives, and the like, and mixtures thereof. Additionally, in accordance with still other embodiments of the present disclosure, granulated sugar (sucrose) or other caloric sweeteners such as crystalline fructose, other carbohydrates, or sugar alcohol can be used as a bulking agent due to their provision of good content uniformity without the addition of significant calories.

As used herein, the phrase "anti-caking agent" and "flow agent" refer to any composition which assists in content uniformity and uniform dissolution. In accordance with particular embodiments, non-limiting examples of anti-caking agents include cream of tartar, calcium silicate, silicon dioxide, microcrystalline cellulose (Avicel, FMC BioPolymer, Philadelphia, PA), and tricalcium phosphate. In one embodiment, the anti-caking agents are present in the tabletop sweetener composition in an amount from about 0.001 to about 3% by weight of the tabletop sweetener composition.

The tabletop sweetener compositions can be packaged in any form known in the art. Non-limiting forms include, but are not limited to, powder form, granular form, packets, tablets, sachets, pellets, cubes, solids, and liquids.

In one embodiment, the tabletop sweetener composition is a single-serving (portion control) packet comprising a dry-blend. Dry-blend formulations generally may comprise powder or granules. Although the tabletop sweetener composition may be in a packet of any size, an illustrative non-limiting example of conventional portion control tabletop sweetener packets are approximately 2.5 by 1.5 inches and hold approximately 1 gram of a sweetener composition having a sweetness equivalent to 2 teaspoons of granulated sugar (.about 0.8 g). In a particular embodiment, a dry-blend tabletop sweetener formulation may contain a sweetener an amount from about 1% (w/w) to about 10% (w/w).

A tabletop sweetener composition also may be embodied in the form of a liquid, wherein a composition of the present disclosure is combined with a liquid carrier. Suitable non-limiting examples of carrier agents for liquid tabletop sweeteners include water, alcohol, polyol, glycerin base or citric acid base dissolved in water, and mixtures thereof. The sweetness equivalent of a tabletop sweetener composition for any of the forms described herein or known in the art may be varied to obtain a desired sweetness profile. For example, a tabletop sweetener composition may comprise a sweetness comparable to that of an equivalent amount of standard sugar. In another embodiment, the tabletop sweetener composition may comprise a sweetness of up to 100 times that of an equivalent amount of sugar. In another embodiment, the tabletop sweetener composition may comprise a sweetness of up to 90 times, 80 times, 70 times, 60 times, 50 times, 40 times, 30 times, 20 times, 10 times, 9 times, 8 times, 7 times, 6 times, 5 times, 4 times, 3 times, and 2 times that of an equivalent amount of sugar.

J. Delivery Systems

The presently disclosed sweetener compositions can also be formulated into various delivery systems having improved ease of handling and rate of dissolution. Non-limiting examples of suitable delivery systems comprise sweetener compositions co-crystallized with a sugar or a polyol, agglomerated sweetener compositions, compacted sweetener compositions, dried sweetener compositions, particle sweetener compositions, spheronized sweetener compositions, granular sweetener compositions, and liquid sweetener compositions.

XI. Breeding Plants

In addition to direct transformation of a particular plant genotype with a construct prepared according to the current disclosure, transgenic plants may be made by crossing a plant having a selected DNA of the present disclosure to a second plant lacking the construct. For example, a selected mogroside biosynthesis pathway coding sequence can be introduced into a particular plant variety by crossing, without the need for ever directly transforming a plant of that given variety. Therefore, the current disclosure not only encompasses a plant directly transformed or regenerated from cells that have been transformed in accordance with the current disclosure, but also the progeny of such plants.

As used herein the term "progeny" denotes the offspring of any generation of a parent plant prepared in accordance with the instant disclosure, wherein the progeny comprises a selected DNA construct. "Crossing" a plant to provide a plant line having one or more added transgenes relative to a starting plant line, as disclosed herein, is defined as the techniques that result in a transgene of the present disclosure being introduced into a plant line by crossing a starting line with a donor plant line that comprises a transgene of the present disclosure. To achieve this one could, for example, perform the following steps:

(a) plant seeds of the first (starting line) and second (donor plant line that comprises a transgene of the present disclosure) parent plants;
(b) grow the seeds of the first and second parent plants into plants that bear flowers;
(c) pollinate a flower from the first parent plant with pollen from the second parent plant; and
(d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;
(b) selecting one or more progeny plant containing the desired gene, DNA sequence or element;
(c) crossing the progeny plant to a plant of the second genotype; and
(d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

XII. Additional Definitions

The following definitions or interpretations of technical terms will be used throughout the present disclosure. The technical terms used herein are generally to be given the meaning commonly applied to them in the pertinent art of plant biology, molecular biology, bioinformatics, and plant breeding. All of the following term definitions apply to the complete content of this application.

To facilitate the understanding of this disclosure, a number of terms are defined below. Terms defined herein have meanings as commonly understood by a person of ordinary skill in the areas relevant to the present disclosure. The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of." As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about," "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

The terms "peptides," "oligopeptides," "polypeptide," "protein", or "enzyme" are used interchangeably herein and refer to amino acids in a polymeric form of any length, linked together by peptide bonds, unless mentioned herein otherwise. The terms "gene sequence(s)," "polynucleotide (s)," "nucleic acid sequence(s)," "nucleotide sequence(s)," "nucleic acid(s)," "nucleic acid molecule" are used interchangeably herein and refer to nucleotides, either ribonucleotides or deoxyribonucleotides or a combination of both, in a polymeric unbranched form of any length.

Endogenous. An "endogenous" or "native" nucleic acid and/or protein refers to a nucleic acid and/or protein as found in a plant or other organism in its natural form (i.e., without there being any human intervention, such as recombinant DNA engineering technology), Exogenous. The term "exogenous" (in contrast to "endogenous") means a nucleic acid or protein that has been introduced in a plant or other organism by means of recombinant DNA technology. An "exogenous" nucleic acid or protein can either not occur in a plant in its natural form, be different from the nucleic acid or protein as found in a plant in its natural form, be present at a higher or lower level than the nucleic acid or protein naturally present in a plant, or in the case of a nucleic acid can be identical to a nucleic acid found in a plant in its natural form, but integrated at a location different that its natural genetic environment.

Expression: The combination of intracellular processes, including transcription and translation undergone by a coding DNA molecule such as a structural gene to produce a polypeptide.

Expression Cassette. A nucleic acid sequence of interest operably linked to one or more control sequences (at least to a promoter) as described herein. An expression cassette can also include additional transcriptional and/or translational enhancers. An expression cassette can also include terminator, silencer and enhancer sequences, intron sequences added to the 5' untranslated region (UTR) or in the coding sequence of the nucleic acid sequence, and/or other control sequences such as protein and/or RNA stabilizing elements. An expression cassette may be integrated into the genome of a host cell and replicated together with the genome of said host cell, or transiently present in a host cell.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence that is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Modulation. The term modulation refers to when the expression level is changed in comparison to the expression seen in a control plant. Modulation refers to an expression level that is either increased or decreased.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an RO transgenic plant or may be from a progeny of any generation thereof that inherits a given transgenic sequence from a starting transgenic parent plant.

Operably Linked. The term "operably linked" or "functionally linked" is used interchangeably and, as used herein, refers to a functional linkage between, for example, a promoter sequence and a nucleic acid sequence of interest, such that the promoter sequence is able to direct transcription of the nucleic acid sequence of interest, or a functional linkage between a terminator sequence and a nucleic acid sequence of interest, such that the terminator sequence is able to stop or terminate transcription of the nucleic acid sequence of interest.

Plant. The term "plant" as used herein encompasses whole plants, ancestors and progeny of the plants and plant parts, including fruits, seeds, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Ploidy. Ploidy or chromosomal ploidy refers the number of complete sets of chromosomes occurring in the nucleus of a cell. Somatic cells, tissues, and individual organisms can be described according to the number of sets of chromosomes present (the "ploidy level"): monoploid (1 set), diploid (2 sets), triploid (3 sets), tetraploid (4 sets), pentaploid (5 sets), hexaploid (6 sets), heptaploid or septaploid (7 sets), etc. The generic term polyploidy is used herein to describe cells with three or more chromosome sets.

Promoter: A recognition site on a DNA sequence or group of DNA sequences that provides an expression control element for a structural gene and to which RNA polymerase specifically binds and initiates RNA synthesis (transcription) of that gene.

RO transgenic plant: A plant that has been genetically transformed or has been regenerated from a plant cell or cells that have been genetically transformed.

Recombinant. A nucleic acid sequence, expression cassette, genetic construct, or vector comprising a nucleic acid sequence as disclosed herein, or an organism transformed with such nucleic acid sequences, expression cassettes or vectors, created by genetic engineering techniques in which either (a) the sequences of the nucleic acids or a part thereof, or (b) genetic control sequence(s) that is operably linked with the nucleic acid sequence, for example a promoter or terminator, or (c) combinations of (a) and (b), are not located in their natural genetic environment or have been modified and/or inserted artificially by genetic engineering methods.

Regeneration: The process of growing a plant from a plant cell (e.g., plant protoplast, callus or explant).

Selected DNA: A DNA segment that one desires to introduce or has introduced into a plant genome by genetic transformation.

Terminator. A DNA control sequence at the end of a transcriptional unit that signals 3' processing and polyadenylation of a primary transcript and termination of transcription.

Transformation construct: A chimeric DNA molecule that is designed for introduction into a host genome by genetic transformation. Transformation constructs will often comprise all of the genetic elements necessary to direct the expression of one or more exogenous genes. In particular embodiments of the instant disclosure, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA that has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation that was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences that are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

EXAMPLES

The following examples are included to demonstrate illustrative embodiments of the present disclosure. It should be appreciated by those of skill in the art that the techniques disclosed in the examples that follow represent techniques discovered by the inventor to function well in the practice of the present disclosure, and thus can be considered to constitute one embodiment of modes for its practice. However, those of skill in the art should, in light of the present disclosure, appreciate that many changes can be made in the specific embodiments that are disclosed and still obtain a like or similar result without departing from the spirit and scope of the present disclosure.

Example 1

Construction of Expression Cassettes

Various expression cassettes having different combinations of nucleotide sequences encoding the mogroside pathway enzymes and regulatory elements were constructed. Construction of these expression cassettes was carried out following standard genetic engineering methods. The following expression cassettes were constructed.

SP1463: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, an e35S promoter operably linked to a CYP72:2A:CYP72 bicistronic nucleic acid sequence, which is operably linked to an AtRBCS2B terminator, an e35S promoter operably linked to a UGT720:2A:UGT720 bicistronic nucleic acid sequence, which is operably linked to an E9 terminator, a CmYLCV promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP3139: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72 Zm nucleic acid sequence, which is operably linked to an AtRBCS2B terminator, a CmYLCV promoter operably linked to a UGT720 nucleic acid sequence, which is operably linked to an E9 terminator, an e35S promoter operably linked to a UGT94 nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR nucleic acid sequence, which is operably linked to an AtTub89 terminator, a e35S promoter operably linked to a HygR nucleic acid sequence, which is operably linked to a 35S terminator, followed by a TM6 MAR insulator sequence.

SP1908: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72 Zm nucleic acid sequence, which is operably linked to an AtRBCS2B terminator, a CmYLCV promoter operably linked to a UGT720 nucleic acid sequence, which is operably linked to an E9 terminator, an e35S promoter operably linked to a UGT94 nucleic acid sequence, which is operably linked to an ATHSP18.2 terminator, a NOS promoter operably linked to an EPH nucleic acid sequence, which is operably linked to an Ubi3 terminator, a e35S promoter operably linked to a HygR nucleic acid sequence, which is operably linked to a 35S terminator, followed by a TM6 MAR insulator sequence.

SP3488: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, an e35S promoter operably linked to a CYP72:2A:CYP72 bicistronic nucleic acid sequence, which is operably linked to an AtRBCS2B terminator, an CmYLCV promoter operably linked to a UGT720:2A:UGT720 bicistronic nucleic acid sequence, which is operably linked to an E9 terminator, a dMMV promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP3015: This expression cassette was assembled using a TM6 MAR insulator sequence, followed by a dMMV promoter operably linked to a CYP72 nucleic acid sequence, which is operably linked to an AtRBCS2B terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, an e35S promoter operably linked to a UGT720 nucleic acid sequence, which is operably linked to an E9 terminator, a CmYLCV promoter operably linked to a UGT94 nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP3432: This expression cassette was assembled using a TM6 MAR insulator sequence, followed by a CmYLCV promoter operably linked to a SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, an e35S promoter operably linked to a CYP72:2A:CYP72 bicistronic nucleic acid sequence, which is operably linked to an AtRBCS2B terminator, an e35S promoter operably linked to a UGT720:2A:UGT720 bicistronic nucleic acid sequence, which is operably linked to an E9 terminator, a dMMV promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, an e35S promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP1160: This expression cassette was assembled using a TM6 MAR insulator sequence, followed by an e35S promoter operably linked to a CYP72:2A:CYP72 bicistronic nucleic acid sequence, which is operably linked to a AtRBCS2B terminator, a CmYLCV promoter operably linked to a UGT720:2A:UGT720 bicistronic nucleic acid sequence, which is operably linked to an E9 terminator, a FSgt/PFLt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a dMMV promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP2916: This expression cassette was assembled using a TM6 MAR insulator sequence, followed by an e35S promoter operably linked to a CYP72:2A:CYP72 bicistronic nucleic acid sequence, which is operably linked to a AtRBCS2B terminator (all in reverse orientation), a CmYLCV promoter operably linked to a UGT720:2A:UGT720 bicistronic nucleic acid sequence, which is operably linked to an E9 terminator, a FSgt/PFLt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a dMMV promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP4643: This expression cassette was assembled using a TM6 MAR insulator sequence, followed by an e35S promoter operably linked to a CYP72:2A:CYP72 bicistronic nucleic acid sequence, which is operably linked to a AtRBCS2B terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a CmYLCV promoter operably linked to a UGT720:2A:UGT720 bicistronic nucleic acid sequence, which is operably linked to an E9 terminator, a dMMV promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP4870: This expression cassette was assembled using a TM6 MAR insulator sequence, followed by an e35S promoter operably linked to a CYP72:2A:CYP72 bicistronic nucleic acid sequence, which is operably linked to a AtRBCS2B terminator, a CmYLCV promoter operably linked to a UGT720:2A:UGT720 bicistronic nucleic acid sequence, which is operably linked to an E9 terminator, a FMVSgt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a dMMV promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP1603: This expression cassette was assembled using a TM6 MAR insulator sequence, followed by an e35S promoter operably linked to a CYP72:2A:CYP72 bicistronic nucleic acid sequence, which is operably linked to a AtRBCS2B terminator (all in reverse orientation), a CmYLCV promoter operably linked to a UGT720:2A:UGT720 bicistronic nucleic acid sequence, which is operably linked to an E9 terminator, a FMVSgt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a dMMV promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP3095: This expression cassette was assembled using a TM6 MAR insulator sequence, followed by an e35S promoter operably linked to a CYP72:2A:CYP72 bicistronic nucleic acid sequence, which is operably linked to a AtRBCS2B terminator (all in reverse orientation), a CmYLCV promoter operably linked to a UGT720:2A:UGT720 bicistronic nucleic acid sequence, which is operably linked to an E9 terminator, a FMVSgt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a dMMV promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a FE3 promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP0265: This expression cassette was assembled using a TM6 MAR insulator sequence, followed by a CmYLCV promoter operably linked to a SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, an e35S promoter operably linked to a UGT720:2A:CYP72 bicistronic nucleic acid sequence, which is operably linked to an E9 terminator, a dMMV promoter operably linked to a UGT94:2A:tHMGR bicistronic nucleic acid sequence, which is operably linked to an ATHSP18.2 terminator, a NOS promoter operably linked to an EPH nucleic acid sequence, which is operably linked to an Ubi3 terminator, a CsVMV promoter operably linked to a HygR nucleic acid sequence, which is operably linked to a 35S terminator, followed by a TM6 MAR insulator sequence.

SP4406: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, an e35S promoter operably linked to a CYP72:2A:CYP72 bicistronic nucleic acid sequence, which is operably linked to a AtRBCS2B terminator, a CmYLCV promoter operably linked to a UGT720:2A:UGT720 bicistronic nucleic acid sequence, which is operably linked to an E9 terminator, a dMMV promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP2152: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, an e35S promoter operably linked to a CYP72:2A:CYP72 bicistronic nucleic acid sequence, which is operably linked to a AtRBCS2B terminator, a CmYLCV promoter operably linked to a UGT720:2A:UGT720 bicistronic nucleic acid sequence, which is operably linked to an E9 terminator, a dMMV promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a FE3 promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP4311: This expression cassette was assembled using a TM6 MAR insulator sequence, followed by an e35S promoter operably linked to a CYP72:2A:CYP72 bicistronic nucleic acid sequence, which is operably linked to a AtRBCS2B terminator, a CmYLCV promoter operably linked to a UGT720:2A:UGT720 bicistronic nucleic acid sequence, which is operably linked to an E9 terminator, a FSgt/PFLt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a dMMV promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP4378: This expression cassette was assembled using a TM6 MAR insulator sequence, followed by an e35S promoter operably linked to a CYP72:2A:CYP72 bicistronic nucleic acid sequence, which is operably linked to a AtRBCS2B terminator (all in reverse orientation), a CmYLCV promoter operably linked to a UGT720:2A:UGT720 bicistronic nucleic acid sequence, which is operably linked to an E9 terminator, a FSgt/PFLt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a dMMV promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP3132: This expression cassette was assembled using a TM6 MAR insulator sequence, followed by an e35S promoter operably linked to a CYP72:2A:CYP72 bicistronic nucleic acid sequence, which is operably linked to a AtRBCS2B terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a CmYLCV promoter operably linked to a UGT720:2A:UGT720 bicistronic nucleic acid sequence, which is operably linked to an E9 terminator, a dMMV promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP2355: This expression cassette was assembled using a TM6 MAR insulator sequence, followed by an e35S promoter operably linked to a CYP72:2A:CYP72 bicistronic nucleic acid sequence, which is operably linked to a AtRBCS2B terminator, a CmYLCV promoter operably linked to a UGT720:2A:UGT720 bicistronic nucleic acid sequence, which is operably linked to an E9 terminator, a FMVSgt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a dMMV promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP4762: This expression cassette was assembled using a TM6 MAR insulator sequence, followed by an e35S promoter operably linked to a CYP72:2A:CYP72 bicistronic nucleic acid sequence, which is operably linked to a AtRBCS2B terminator (all in reverse orientation), a CmYLCV promoter operably linked to a UGT720:2A:UGT720 bicistronic nucleic acid sequence, which is operably linked to an E9 terminator, a FMVSgt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a dMMV promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP0892: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72 nucleic acid sequence, which is operably linked to an AtRBCS2B terminator, a CmYLCV promoter operably linked to a UGT720 nucleic acid sequence, which is operably linked to an E9 terminator, an e35S promoter operably linked to a UGT94 nucleic acid sequence, which is operably linked to a ATHSP18.2 terminator, a NOS promoter operably linked to an EPH nucleic acid sequence, which is operably linked to an Ubi3 terminator, a ScBV promoter operably linked to a tHMGR nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP2249: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72 nucleic acid sequence, which is operably linked to an AtRBCS2B terminator, an e35S promoter operably linked to a UGT720 nucleic acid sequence, which is operably linked to an E9 terminator, a CmYLCV promoter operably linked to a UGT94 nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP0796: This expression cassette was assembled using a TM6 MAR insulator sequence, followed by a dMMV promoter operably linked to a CYP72 nucleic acid sequence, which is operably linked to an AtRBCS2B terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a CmYLCV promoter operably linked to a UGT720 nucleic acid sequence, which is operably linked to an E9 terminator, an e35S promoter operably linked to a UGT94 nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP2057: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72 nucleic acid sequence, which is operably linked to an AtRBCS2B terminator, a NOS promoter operably linked to an EPH nucleic acid sequence, which is operably linked to an Ubi3 terminator, an e35S promoter operably linked to a UGT94 nucleic acid sequence, which is operably linked to an ATHSP18.2 terminator, a CmYLCV promoter operably linked to a UGT720 nucleic acid sequence, which is operably linked to an E9 terminator, a ScBV promoter operably linked to a tHMGR nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP3308: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, an e35S promoter operably linked to a CYP72 nucleic acid sequence, which is operably linked to an AtRBCS2B terminator, a CmYLCV promoter operably linked to a UGT720 nucleic acid sequence, which is operably linked to an E9 terminator, a dMMV promoter operably linked to a UGT94 nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP1379: This expression cassette was assembled using a TM6 MAR insulator sequence, followed by a dMMV promoter operably linked to a CYP72 nucleic acid sequence, which is operably linked to an AtRBCS2B terminator, a CmYLCV promoter operably linked to a UGT720 nucleic acid sequence, which is operably linked to an E9 terminator, a FSgt/PFLt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, an e35S promoter operably linked to a UGT94 nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP3494: This expression cassette was assembled using a TM6 MAR insulator sequence, followed by a dMMV promoter operably linked to a CYP72 nucleic acid sequence, which is operably linked to an AtRBCS2B terminator (all in reverse orientation), a CmYLCV promoter operably linked to a UGT720 nucleic acid sequence, which is operably linked to an E9 terminator, a FSgt/PFLt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, an e35S promoter operably linked to a UGT94 nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP2585: This expression cassette was assembled using a TM6 MAR insulator sequence, followed by a CmYLCV promoter operably linked to a SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72 nucleic acid sequence, which is operably linked to an AtRBCS2B terminator, an e35S promoter operably linked to a UGT720 nucleic acid sequence, which is operably linked to an E9 terminator, an e35S promoter operably linked to a UGT94 nucleic acid sequence, which is operably linked to an ATHSP18.2 terminator, a NOS promoter operably linked to an EPH nucleic acid sequence, which is operably linked to an Ubi3 terminator, an e35S promoter operably linked to a tHMGR nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP3635: This expression cassette was assembled using a TM6 MAR insulator sequence, followed by a CmYLCV promoter operably linked to a SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, an e35S promoter operably linked to a UGT720:2A:CYP72 bicistronic nucleic acid sequence, which is operably linked to an E9 terminator, an e35S promoter operably linked to a UGT94:2A:tHMGR bicistronic nucleic acid sequence, which is operably linked to an ATHSP18.2 terminator, a NOS promoter operably linked to an EPH nucleic acid sequence, which is operably linked to an Ubi3 terminator, a CsVMV promoter operably linked to a HygR nucleic acid sequence, which is operably linked to a 35S terminator, followed by a TM6 MAR insulator sequence.

SP3800: This expression cassette was assembled using a TM6 MAR insulator sequence, followed by a CmYLCV promoter operably linked to a SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, an e35S promoter operably linked to a CYP72:2A:CYP72 bicistronic nucleic acid sequence, which is operably linked to an AtRBCS2B terminator, an e35S promoter operably linked to a UGT720:2A:UGT720 bicistronic nucleic acid sequence, which is operably linked to an E9 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, an e35S promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP0981: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72:2A:CYP72 bicistronic nucleic acid sequence, which is operably linked to an AtRBCS2B terminator, a CmYLCV promoter operably linked to a UGT720:2A:UGT720 bicistronic nucleic acid sequence, which is operably linked to an E9 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP0137: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72:2A:CYP72 bicistronic nucleic acid sequence, which is operably linked to an AtRBCS2B terminator, a CmYLCV promoter operably linked to a UGT720:2A:UGT720 bicistronic nucleic acid sequence, which is operably linked to an E9 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a FE3 promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP2154: This expression cassette was assembled using a TM6 MAR insulator sequence, followed by a dMMV promoter operably linked to a CYP72:2A:CYP72 bicistronic nucleic acid sequence, which is operably linked to an AtRBCS2B terminator, a CmYLCV promoter operably linked to a UGT720:2A:UGT720 bicistronic nucleic acid sequence, which is operably linked to an E9 terminator, a FSgt/PFLt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP1727: This expression cassette was assembled using a TM6 MAR insulator sequence, followed by a dMMV promoter operably linked to a CYP72:2A:CYP72 bicistronic nucleic acid sequence, which is operably linked to an AtRBCS2B terminator (all in reverse orientation), a CmYLCV promoter operably linked to a UGT720:2A:UGT720 bicistronic nucleic acid sequence, which is operably linked to an E9 terminator, a FSgt/PFLt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP0075: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72:2A:CYP72 bicistronic nucleic acid sequence, which is operably linked to an AtRBCS2B terminator, an e35S promoter operably linked to a UGT720:2A:UGT720 bicistronic nucleic acid sequence, which is operably linked to an E9 terminator, a CmYLCV promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP4305: This expression cassette was assembled using a TM6 MAR insulator sequence, followed by a dMMV promoter operably linked to a CYP72:2A:CYP72 bicistronic nucleic acid sequence, which is operably linked to an AtRBCS2B terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a CmYLCV promoter operably linked to a UGT720:2A:UGT720 bicistronic nucleic acid sequence, which is operably linked to an E9 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP4221: This expression cassette was assembled using a TM6 MAR insulator sequence, followed by a dMMV promoter operably linked to a CYP72:2A:CYP72 bicistronic nucleic acid sequence, which is operably linked to an AtRBCS2B terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, an e35S promoter operably linked to a UGT720:2A:UGT720 bicistronic nucleic acid sequence, which is operably linked to an E9 terminator, a CmYLCV promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP3488: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, an e35S promoter operably linked to a CYP72:2A:CYP72 bicistronic nucleic acid sequence, which is operably linked to an AtRBCS2B terminator, an CmYLCV promoter operably linked to a UGT720:2A:UGT720 bicistronic nucleic acid sequence, which is operably linked to an E9 terminator, a dMMV promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP4094: This expression cassette was assembled using a TM6 MAR insulator sequence, followed by a dMMV promoter operably linked to a CYP72:2A:CYP72 bicistronic nucleic acid sequence, which is operably linked to an AtRBCS2B terminator, a CmYLCV promoter operably linked to a UGT720:2A:UGT720 bicistronic nucleic acid sequence, which is operably linked to an E9 terminator, a FMVSgt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP2971: This expression cassette was assembled using a TM6 MAR insulator sequence, followed by a dMMV promoter operably linked to a CYP72:2A:CYP72 bicistronic nucleic acid sequence, which is operably linked to an AtRBCS2B terminator (all in reverse orientation), a CmYLCV promoter operably linked to a UGT720:2A:UGT720 bicistronic nucleic acid sequence, which is operably linked to an E9 terminator, a FMVSgt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP2049: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FMVSgt promoter operably linked to a CDS nucleic acid sequence, which is operably linked to a GmaxMYB2 terminator, a dMMV promoter operably linked to a CYP72:2A:CYP72 bicistronic nucleic acid sequence, which is operably linked to an AtRBCS2B terminator, an e35S promoter operably linked to a UGT720:2A:UGT720 bicistronic nucleic acid sequence, which is operably linked to an E9 terminator, a CmYLCV promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP4063: This expression cassette was assembled using a TM6 MAR insulator sequence, followed by a dMMV promoter operably linked to a CYP72:2A:CYP72 bicistronic nucleic acid sequence, which is operably linked to an AtRBCS2B terminator (all in reverse orientation), a CmYLCV promoter operably linked to a UGT720:2A:UGT720 bicistronic nucleic acid sequence, which is operably linked to an E9 terminator, a FMVSgt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a FE3 promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP0121: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FMVSgt promoter operably linked to a CDS nucleic acid sequence, which is operably linked to a GmaxMYB2 terminator, a dMMV promoter operably linked to a CYP72:2A:CYP72 bicistronic nucleic acid sequence, which is operably linked to an AtRBCS2B terminator, an e35S promoter operably linked to a UGT720:2A:UGT720 bicistronic nucleic acid sequence, which is operably linked to an E9 terminator, a CmYLCV promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a FE3 promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP3358: This expression cassette was assembled using a TM6 MAR insulator sequence, followed by a CmYLCV promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, an e35S promoter operably linked to a CYP72:2A:CYP72 bicistronic nucleic acid sequence, which is operably linked to an AtRBCS2B terminator, an e35S promoter operably linked to a UGT720:2A:UGT720 bicistronic nucleic acid sequence, which is operably linked to an E9 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, an e35S promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP4513: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72:2A:CYP72 bicistronic nucleic acid sequence, which is operably linked to an AtRBCS2B terminator, a CmYLCV promoter operably linked to a UGT720:2A:UGT720 bicistronic nucleic acid sequence, which is operably linked to an E9 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR: 2A:HMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP2221: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72:2A:CYP72 bicistronic nucleic acid sequence, which is operably linked to an AtRBCS2B terminator, a CmYLCV promoter operably linked to a UGT720:2A:UGT720 bicistronic nucleic acid sequence, which is operably linked to an E9 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a FE3 promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP3925: This expression cassette was assembled using a TM6 MAR insulator sequence, followed by a dMMV promoter operably linked to a CYP72:2A:CYP72 bicistronic nucleic acid sequence, which is operably linked to an AtRBCS2B terminator, a CmYLCV promoter operably linked to a UGT720:2A:UGT720 bicistronic nucleic acid sequence, which is operably linked to an E9 terminator, a FSgt/PFLt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP3748: This expression cassette was assembled using a TM6 MAR insulator sequence, followed by a dMMV promoter operably linked to a CYP72:2A:CYP72 bicistronic nucleic acid sequence, which is operably linked to an AtRBCS2B terminator (all in reverse orientation), a CmYLCV promoter operably linked to a UGT720:2A:UGT720 bicistronic nucleic acid sequence, which is operably linked to an E9 terminator, a FSgt/PFLt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP4511: This expression cassette was assembled using a TM6 MAR insulator sequence, followed by a dMMV promoter operably linked to a CYP72:2A:CYP72 bicistronic nucleic acid sequence, which is operably linked to an AtRBCS2B terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a CmYLCV promoter operably linked to a UGT720:2A:UGT720 bicistronic nucleic acid sequence, which is operably linked to an E9 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP3547: This expression cassette was assembled using a TM6 MAR insulator sequence, followed by a dMMV promoter operably linked to a CYP72:2A:CYP72 bicistronic nucleic acid sequence, which is operably linked to an AtRBCS2B terminator, a CmYLCV promoter operably linked to a UGT720:2A:UGT720 bicistronic nucleic acid sequence, which is operably linked to an E9 terminator, a FMVSgt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP3481: This expression cassette was assembled using a TM6 MAR insulator sequence, followed by a dMMV promoter operably linked to a CYP72:2A:CYP72 bicistronic nucleic acid sequence, which is operably linked to an AtRBCS2B terminator (all in reverse orientation), a CmYLCV promoter operably linked to a UGT720:2A:UGT720 bicistronic nucleic acid sequence, which is operably linked to an E9 terminator, a FMVSgt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP2185: This expression cassette was assembled using a TM6 MAR insulator sequence, followed by a dMMV promoter operably linked to a CYP72:2A:CYP72 bicistronic nucleic acid sequence, which is operably linked to an AtRBCS2B terminator (all in reverse orientation), a CmYLCV promoter operably linked to a UGT720:2A:UGT720 bicistronic nucleic acid sequence, which is operably linked to an E9 terminator, a FMVSgt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a FE3 promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP2792: This expression cassette was assembled using a TM6 MAR insulator sequence, followed by a CmYLCV promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, an e35S promoter operably linked to a UGT720:2A:CYP72 bicistronic nucleic acid sequence, which is operably linked to an E9 terminator, an e35S promoter operably linked to a UGT94:2A:tHMGR bicistronic nucleic acid sequence, which is operably linked to an ATHSP18.2 terminator, a NOS promoter operably linked to an EPH nucleic acid sequence, which is operably linked to an Ubi3 terminator, a CsVMV promoter operably linked to a HygR nucleic acid sequence, which is operably linked to a 35S terminator, followed by a TM6 MAR insulator sequence.

SP1000: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, an e35S promoter operably linked to a CYP72:2A:CYP72 bicistronic nucleic acid sequence, which is operably linked to an AtRBCS2B terminator, a CmYLCV promoter operably linked to a UGT720:2A:UGT720 bicistronic nucleic acid sequence, which is operably linked to an E9 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP3766: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, an e35S promoter operably linked to a CYP72:2A:CYP72 bicistronic nucleic acid sequence, which is operably linked to an AtRBCS2B terminator, a CmYLCV promoter operably linked to a UGT720:2A:UGT720 bicistronic nucleic acid sequence, which is operably linked to an E9 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a FE3 promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP4353: This expression cassette was assembled using a TM6 MAR insulator sequence, followed by a dMMV promoter operably linked to a CYP72:2A:CYP72 bicistronic nucleic acid sequence, which is operably linked to an AtRBCS2B terminator, a CmYLCV promoter operably linked to a UGT720:2A:UGT720 bicistronic nucleic acid sequence, which is operably linked to an E9 terminator, a FSgt/PFLt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP0255: This expression cassette was assembled using a TM6 MAR insulator sequence, followed by a dMMV promoter operably linked to a CYP72:2A:CYP72 bicistronic nucleic acid sequence, which is operably linked to an AtRBCS2B terminator (all in reverse orientation), a CmYLCV promoter operably linked to a UGT720:2A:UGT720 bicistronic nucleic acid sequence, which is operably linked to an E9 terminator, a FSgt/PFLt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP4815: This expression cassette was assembled using a TM6 MAR insulator sequence, followed by a dMMV promoter operably linked to a CYP72:2A:CYP72 bicistronic nucleic acid sequence, which is operably linked to an AtRBCS2B terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a CmYLCV promoter operably linked to a UGT720:2A:UGT720 bicistronic nucleic acid sequence, which is operably linked to an E9 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP1073: This expression cassette was assembled using a TM6 MAR insulator sequence, followed by a dMMV promoter operably linked to a CYP72:2A:CYP72 bicistronic nucleic acid sequence, which is operably linked to an AtRBCS2B terminator, a CmYLCV promoter operably linked to a UGT720:2A:UGT720 bicistronic nucleic acid sequence, which is operably linked to an E9 terminator, a FMVSgt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP4402: This expression cassette was assembled using a TM6 MAR insulator sequence, followed by a dMMV promoter operably linked to a CYP72:2A:CYP72 bicistronic nucleic acid sequence, which is operably linked to an AtRBCS2B terminator (all in reverse orientation), a CmYLCV promoter operably linked to a UGT720:2A:UGT720 bicistronic nucleic acid sequence, which is operably linked to an E9 terminator, a FMVSgt promoter operably linked to a CDS nucleic acid sequence, which is operably linked to a GmaxMYB2 terminator, a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP1415: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, an e35S promoter operably linked to a CYP72:2A:CYP72 bicistronic nucleic acid sequence, which is operably linked to an AtRBCS2B terminator, a CmYLCV promoter operably linked to a UGT720:2A:UGT720 bicistronic nucleic acid sequence, which is operably linked to an E9 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP2353: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, an e35S promoter operably linked to a CYP72:2A:

CYP72 bicistronic nucleic acid sequence, which is operably linked to an AtRBCS2B terminator, a CmYLCV promoter operably linked to a UGT720:2A:UGT720 bicistronic nucleic acid sequence, which is operably linked to an E9 terminator, an e35S promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a FE3 promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP0565: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FMVSgt promoter operably linked to a CDS nucleic acid sequence, which is operably linked to a GmaxMYB2 terminator, an e35S promoter operably linked to a CYP72:2A:CYP72 bicistronic nucleic acid sequence, which is operably linked to an AtRBCS2B terminator, an e35S promoter operably linked to a UGT720:2A:UGT720 bicistronic nucleic acid sequence, which is operably linked to an E9 terminator, a CmYLCV promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP1202: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FMVSgt promoter operably linked to a CDS nucleic acid sequence, which is operably linked to a GmaxMYB2 terminator, an e35S promoter operably linked to a CYP72:2A:CYP72 bicistronic nucleic acid sequence, which is operably linked to an AtRBCS2B terminator, an e35S promoter operably linked to a UGT720:2A:UGT720 bicistronic nucleic acid sequence, which is operably linked to an E9 terminator, a CmYLCV promoter operably linked to a UGT94:2A:UGT94 bicistronic nucleic acid sequence, which is operably linked to an ATHSP18.2 terminator, a NOS promoter operably linked to an EPH nucleic acid sequence, which is operably linked to an Ubi3 terminator, a FE3 promoter operably linked to a tHMGR:2A:tHMGR bicistronic nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP2808: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72 Zm nucleic acid sequence, which is operably linked to an AtRBCS2B terminator, a CmYLCV promoter operably linked to a UGT720 nucleic acid sequence, which is operably linked to an E9 terminator, an e35S promoter operably linked to a UGT94 nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR nucleic acid sequence, which is operably linked to an AtTub89 terminator, a CsVMV promoter operably linked to a HygR nucleic acid sequence, which is operably linked to a 35S terminator, followed by a TM6 MAR insulator sequence.

SP3684: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72 Zm nucleic acid sequence, which is operably linked to an AtRBCS2B terminator, an e35S promoter operably linked to a UGT720 nucleic acid sequence, which is operably linked to an ATHSP18.2 terminator, an e35S promoter operably linked to a UGT94 nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR nucleic acid sequence, which is operably linked to a 35S terminator, a CsVMV promoter operably linked to a HygR nucleic acid sequence, which is operably linked to a 35S terminator, followed by a TM6 MAR insulator sequence.

SP4522: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, an e35S promoter operably linked to a CYP72 Zm nucleic acid sequence, which is operably linked to an ATHSP18.2 terminator, an e35S promoter operably linked to a UGT720 nucleic acid sequence, which is operably linked to an ATHSP18.2 terminator, an e35S promoter operably linked to a UGT94 nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR nucleic acid sequence, which is operably linked to a 35S terminator, a CsVMV promoter operably linked to a HygR nucleic acid sequence, which is operably linked to a 35S terminator, followed by a TM6 MAR insulator sequence.

SP3842: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/

PFLt promoter operably linked to a CDS nucleic acid sequence, which is operably linked to a GmaxMYB2 terminator, a dMMV promoter operably linked to a CYP72 Zm nucleic acid sequence, which is operably linked to an AtRBCS2B terminator, a CmYLCV promoter operably linked to a UGT720 nucleic acid sequence, which is operably linked to a 35S terminator, a CmYLCV promoter operably linked to a UGT94 nucleic acid sequence, which is operably linked to an 35S terminator, a NOS promoter operably linked to an EPH nucleic acid sequence, which is operably linked to an Ubi3 terminator, a e35S promoter operably linked to a tHMGR nucleic acid sequence, which is operably linked to an ATHSP18.2 terminator, a CsVMV promoter operably linked to a HygR nucleic acid sequence, which is operably linked to a 35S terminator, followed by a TM6 MAR insulator sequence.

SP3938: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72 Zm nucleic acid sequence, which is operably linked to an AtRBCS2B terminator, a CmYLCV promoter operably linked to a UGT720 nucleic acid sequence, which is operably linked to a 35S terminator, a CmYLCV promoter operably linked to a UGT94 nucleic acid sequence, which is operably linked to an 35S terminator, a NOS promoter operably linked to an EPH nucleic acid sequence, which is operably linked to an Ubi3 terminator, a e35S promoter operably linked to a tHMGR nucleic acid sequence, which is operably linked to an ATHSP18.2 terminator, a DCMV promoter operably linked to a SgCPR2 nucleic acid sequence, which is operably linked to an AtUBQ3 terminator, a CsVMV promoter operably linked to a HygR nucleic acid sequence, which is operably linked to a 35S terminator, followed by a TM6 MAR insulator sequence.

SP3318: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72 Zm nucleic acid sequence, which is operably linked to an AtRBCS2B terminator, a CmYLCV promoter operably linked to a UGT720 nucleic acid sequence, which is operably linked to a 35S terminator, a CmYLCV promoter operably linked to a UGT94 nucleic acid sequence, which is operably linked to an 35S terminator, a NOS promoter operably linked to an EPH nucleic acid sequence, which is operably linked to an Ubi3 terminator, a e35S promoter operably linked to a tHMGR nucleic acid sequence, which is operably linked to an ATHSP18.2 terminator, a DCMV promoter operably linked to a SgCPR2 nucleic acid sequence, which is operably linked to an AtUBQ3 terminator, a CmYLCV promoter operably linked to a UGT74_3 nucleic acid sequence, which is operably linked to a 35S terminator, a CsVMV promoter operably linked to a HygR nucleic acid sequence, which is operably linked to a 35S terminator, followed by a TM6 MAR insulator sequence.

SP3493: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72 Zm nucleic acid sequence, which is operably linked to an AtRBCS2B terminator, a CmYLCV promoter operably linked to a UGT720 nucleic acid sequence, which is operably linked to a 35S terminator, a CmYLCV promoter operably linked to a UGT94 nucleic acid sequence, which is operably linked to an 35S terminator, a NOS promoter operably linked to an EPH nucleic acid sequence, which is operably linked to an Ubi3 terminator, a e35S promoter operably linked to a tHMGR nucleic acid sequence, which is operably linked to an ATHSP18.2 terminator, a DCMV promoter operably linked to a SgCPR2 nucleic acid sequence, which is operably linked to an AtUBQ3 terminator, a CmYLCV promoter operably linked to a UGT74_4 nucleic acid sequence, which is operably linked to a 35S terminator, a CsVMV promoter operably linked to a HygR nucleic acid sequence, which is operably linked to a 35S terminator, followed by a TM6 MAR insulator sequence.

SP2476: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87D20 m2 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72 Zm nucleic acid sequence, which is operably linked to an AtRBCS2B terminator, a CmYLCV promoter operably linked to a UGT720 nucleic acid sequence, which is operably linked to a 35S terminator, a CmYLCV promoter operably linked to a UGT94 nucleic acid sequence, which is operably linked to an 35S terminator, a NOS promoter operably linked to an EPH nucleic acid sequence, which is operably linked to an Ubi3 terminator, a e35S promoter operably linked to a tHMGR nucleic acid sequence, which is operably linked to an ATHSP18.2 terminator, a DCMV promoter operably linked to a SgCPR2 nucleic acid sequence, which is operably linked to an AtUBQ3 terminator, a CsVMV promoter operably linked to a HygR nucleic acid sequence, which is operably linked to a 35S terminator, followed by a TM6 MAR insulator sequence.

SP4983: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87D20 m3 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72 Zm nucleic acid sequence, which is operably linked to an AtRBCS2B terminator, a CmYLCV promoter operably linked to a UGT720 nucleic acid sequence, which is operably linked to a 35S terminator, a CmYLCV promoter operably linked to a UGT94 nucleic acid sequence, which is operably linked to an 35S terminator, a NOS promoter operably linked to an EPH nucleic acid sequence, which is operably linked to an Ubi3 terminator, a e35S promoter operably linked to a tHMGR nucleic acid sequence, which is operably linked to an ATHSP18.2 terminator, a DCMV promoter operably linked to a SgCPR2 nucleic acid sequence, which is operably linked to an AtUBQ3 terminator, a CsVMV promoter operably linked to a HygR nucleic acid sequence, which is operably linked to a 35S terminator, followed by a TM6 MAR insulator sequence.

SP4003: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87D17 m2 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72 Zm nucleic acid sequence, which is operably linked to an AtRBCS2B terminator, a CmYLCV promoter operably linked to a UGT720 nucleic acid sequence, which is operably linked to a 35S terminator, a CmYLCV promoter operably linked to a UGT94 nucleic acid sequence, which is operably linked to an 35S terminator, a NOS promoter operably linked to an EPH nucleic acid sequence, which is operably linked to an Ubi3 terminator, a e35S promoter operably linked to a tHMGR nucleic acid sequence, which is operably linked to an ATHSP18.2 terminator, a DCMV promoter operably linked to a SgCPR2 nucleic acid sequence, which is operably linked to an AtUBQ3 terminator, a CsVMV promoter operably linked to a HygR nucleic acid sequence, which is operably linked to a 35S terminator, followed by a TM6 MAR insulator sequence.

SP4074: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87D17 m3 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72 Zm nucleic acid sequence, which is operably linked to an AtRBCS2B terminator, a CmYLCV promoter operably linked to a UGT720 nucleic acid sequence, which is operably linked to a 35S terminator, a CmYLCV promoter operably linked to a UGT94 nucleic acid sequence, which is operably linked to an 35S terminator, a NOS promoter operably linked to an EPH nucleic acid sequence, which is operably linked to an Ubi3 terminator, a e35S promoter operably linked to a tHMGR nucleic acid sequence, which is operably linked to an ATHSP18.2 terminator, a DCMV promoter operably linked to a SgCPR2 nucleic acid sequence, which is operably linked to an AtUBQ3 terminator, a CsVMV promoter operably linked to a HygR nucleic acid sequence, which is operably linked to a 35S terminator, followed by a TM6 MAR insulator sequence.

SP2649: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87D18_B m3 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72 Zm nucleic acid sequence, which is operably linked to an AtRBCS2B terminator, a CmYLCV promoter operably linked to a UGT720 nucleic acid sequence, which is operably linked to a 35S terminator, a CmYLCV promoter operably linked to a UGT94 nucleic acid sequence, which is operably linked to an 35S terminator, a NOS promoter operably linked to an EPH nucleic acid sequence, which is operably linked to an Ubi3 terminator, a e35S promoter operably linked to a tHMGR nucleic acid sequence, which is operably linked to an ATHSP18.2 terminator, a DCMV promoter operably linked to a SgCPR2 nucleic acid sequence, which is operably linked to an AtUBQ3 terminator, a CsVMV promoter operably linked to a HygR nucleic acid sequence, which is operably linked to a 35S terminator, followed by a TM6 MAR insulator sequence.

SP3397: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87D17 m2 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72 Zm nucleic acid sequence, which is operably linked to an AtRBCS2B terminator, a CmYLCV promoter operably linked to a UGT720 nucleic acid sequence, which is operably linked to a 35S terminator, a CmYLCV promoter operably linked to a UGT94 nucleic acid sequence, which is operably linked to an 35S terminator, a NOS promoter operably linked to an EPH nucleic acid sequence, which is operably linked to an Ubi3 terminator, a e35S promoter operably linked to a tHMGR nucleic acid sequence, which is operably linked to an ATHSP18.2 terminator, a DCMV promoter operably linked to a SgCPR2 nucleic acid sequence, which is operably linked to an AtUBQ3 terminator, a CmYLCV promoter operably linked to a UGT74_3 nucleic acid sequence, which is operably linked to a 35S terminator, a CsVMV promoter operably linked to a HygR nucleic acid sequence, which is operably linked to a 35S terminator, followed by a TM6 MAR insulator sequence.

SP2771: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87D17 m3 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72 Zm nucleic acid sequence, which is operably linked to an AtRBCS2B terminator, a CmYLCV promoter operably linked to a UGT720 nucleic acid sequence, which is operably linked to a 35S terminator, a CmYLCV promoter operably linked to a UGT94 nucleic acid sequence, which is operably linked to an 35S terminator, a NOS promoter operably linked to an EPH nucleic acid sequence, which is operably linked to an Ubi3 terminator, a e35S promoter operably linked to a tHMGR nucleic acid sequence, which is operably linked to an ATHSP18.2 terminator, a DCMV promoter operably linked to a SgCPR2 nucleic acid sequence, which is operably linked to an AtUBQ3 terminator, a CmYLCV promoter operably linked to a UGT74_3 nucleic acid sequence, which is operably linked to a 35S terminator, a CsVMV promoter operably linked to a HygR nucleic acid sequence, which is operably linked to a 35S terminator, followed by a TM6 MAR insulator sequence.

SP0847: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87D17 m3 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72 Zm nucleic acid sequence, which is operably linked to an AtRBCS2B terminator, a CmYLCV promoter operably linked to a UGT720 nucleic acid sequence, which is operably linked to a 35S terminator, a CmYLCV promoter operably linked to a UGT94 nucleic acid sequence, which is operably linked to an 35S terminator, a NOS promoter operably linked to an EPH nucleic acid sequence, which is operably linked to an Ubi3 terminator, a e35S promoter operably linked to a tHMGR nucleic acid sequence, which is operably linked to an ATHSP18.2 terminator, a DCMV promoter operably linked to a SgCPR2 nucleic acid sequence, which is operably linked to an AtUBQ3 terminator, a CmYLCV promoter operably linked to a UGT74_4 nucleic acid sequence, which is operably linked to a 35S terminator, a CsVMV promoter operably linked to a HygR nucleic acid sequence, which is operably linked to a 35S terminator, followed by a TM6 MAR insulator sequence.

SP3468: This expression cassette was assembled using a TM6 MAR insulator sequence, followed by a FE_3 promoter operably linked to a CYP87 nucleic acid sequence, which is operably linked to an ATHSP18.2 terminator, a FE_3 promoter operably linked to a CDS nucleic acid sequence, which is operably linked to a 35S terminator, a dMMV promoter operably linked to a CYP72 Zm nucleic acid sequence, which is operably linked to an AtRBCS2B terminator, a CmYLCV promoter operably linked to a UGT720 nucleic acid sequence, which is operably linked to a 35S terminator, a CmYLCV promoter operably linked to a UGT94 nucleic acid sequence, which is operably linked to an 35S terminator, a FS1_1 promoter operably linked to a tHMGR nucleic acid sequence, which is operably linked to an Ubi3 terminator, a CsVMV promoter operably linked to a HygR nucleic acid sequence, which is operably linked to a 35S terminator, followed by a TM6 MAR insulator sequence.

SP2177: This expression cassette was assembled using a TM6 MAR insulator sequence, followed by a FS1_1 promoter operably linked to an SQE nucleic acid sequence, which is operably linked to a 35S terminator, a FE_3 promoter operably linked to a CYP87 nucleic acid sequence, which is operably linked to a 35S terminator, a FE_3 promoter operably linked to a CDS nucleic acid sequence, which is operably linked to a 35S terminator, a FE_3 promoter operably linked to a CYP72 Zm nucleic acid sequence, which is operably linked to an 35S terminator, a FE_3 promoter operably linked to a UGT720 nucleic acid sequence, which is operably linked to a 35S terminator, a FE_3 promoter operably linked to a UGT94 nucleic acid sequence, which is operably linked to an 35S terminator, a FS1_1 promoter operably linked to an EPH nucleic acid sequence, which is operably linked to a 35S terminator, a FS1_1 promoter operably linked to a tHMGR nucleic acid sequence, which is operably linked to a 35S terminator, a CsVMV promoter operably linked to a HygR nucleic acid sequence, which is operably linked to a 35S terminator, followed by a TM6 MAR insulator sequence.

SP3804: This expression cassette was assembled using a TM6 MAR insulator sequence, followed by a HLVH12 promoter operably linked to an SQE nucleic acid sequence, which is operably linked to a Pea3A terminator, an e35S promoter operably linked to a CYP87 nucleic acid sequence, which is operably linked to an ATHSP18.2 terminator, a FSgt/PFLt promoter operably linked to a CDS nucleic acid sequence, which is operably linked to a ATHSP18.2 terminator, an e35S promoter operably linked to a CYP72 Zm nucleic acid sequence, which is operably linked to an ATHSP18.2 terminator, an e35S promoter operably linked to a UGT720 nucleic acid sequence, which is operably linked to an ATHSP18.2 terminator, an e35S promoter operably linked to a UGT94 nucleic acid sequence, which is operably linked to an ATHSP18.2 terminator, a NOS promoter operably linked to an EPH nucleic acid sequence, which is operably linked to an Ubi3 terminator, a e35S promoter operably linked to a tHMGR nucleic acid sequence, which is operably linked to an ATHSP18.2 terminator, a CsVMV promoter operably linked to a HygR nucleic acid sequence, which is operably linked to a 35S terminator, followed by a TM6 MAR insulator sequence.

SP3016: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72 Zm nucleic acid sequence, which is operably linked to an AtRBCS2B terminator, an e35S promoter operably linked to a UGT720 nucleic acid sequence, which is operably linked to an ATHSP18.2 terminator, an e35S promoter operably linked to a UGT94 nucleic acid sequence, which is operably linked to an ATHSP18.2 terminator, a NOS promoter operably linked to an EPH nucleic acid sequence, which is operably linked to an Ubi3 terminator, a CsVMV promoter operably linked to a HygR nucleic acid sequence, which is operably linked to a 35S terminator, followed by a TM6 MAR insulator sequence.

SP0036: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, an e35S promoter operably linked to a CDS nucleic acid sequence, which is operably linked to an ATHSP18.2 terminator, a dMMV promoter operably linked to a CYP72 Zm nucleic acid sequence, which is operably linked to an AtRBCS2B terminator, a CmYLCV promoter operably linked to a UGT720 nucleic acid sequence, which is operably linked to a 35S terminator, an e35S promoter operably linked to a UGT94 nucleic acid sequence, which is operably linked to an ATHSP18.2 terminator, a NOS promoter operably linked to an EPH nucleic acid sequence, which is operably linked to an Ubi3 terminator, a CsVMV promoter operably linked to a HygR nucleic acid sequence, which is operably linked to a 35S terminator, followed by a TM6 MAR insulator sequence.

SP1458: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, an e35S promoter operably linked to a CDS nucleic acid sequence, which is operably linked to a GmaxMYB2 terminator, a dMMV promoter operably linked to a CYP72 Zm nucleic acid sequence, which is operably linked to an AtRBCS2B terminator, a CmYLCV promoter operably linked to a UGT720 nucleic acid sequence, which is operably linked to a 35S terminator, an e35S promoter operably linked to a UGT94 nucleic acid sequence, which is operably linked to an ATHSP18.2 terminator, a NOS promoter operably linked to an EPH nucleic acid sequence, which is operably linked to an Ubi3 terminator, a CsVMV promoter operably linked to a HygR nucleic acid sequence, which is operably linked to a 35S terminator, followed by a TM6 MAR insulator sequence.

SP0336: This expression cassette was assembled using a TM6 MAR insulator sequence, followed by a dMMV promoter operably linked to an green fluorescent protein nucleic acid sequence, which is operably linked to a PBI terminator, a PCLSV promoter operably linked to an SQE-2 nucleic acid sequence, which is operably linked to a Pea3A terminator, a DCMV promoter operably linked to a CYP87-2 nucleic acid sequence, which is operably linked to an AtUBQ3 terminator, a Fsgt/PFLT promoter operably linked to a CDS-2 nucleic acid sequence, which is operably linked to a GmaxMYB2 terminator, a CsVMV promoter operably linked to an EPH-2 nucleic acid sequence, which is operably linked to an ATHSP18.2 terminator, a HLVH12 promoter operably linked to a UGT720-2 nucleic acid sequence, which is operably linked to an E9 terminator, a FMVSgt promoter operably linked to an EPH-2 nucleic acid sequence, which is operably linked to an Ubi3 terminator, an e35S promoter operably linked to a HygR nucleic acid sequence, which is operably linked to a 35S terminator, followed by a TM6 MAR insulator sequence.

SP0315: This expression cassette was assembled using a TM6 MAR insulator sequence, followed by a CmYLCV promoter operably linked to an SQE nucleic acid sequence, which is operably linked to a Pea3A terminator, a DCMV promoter operably linked to a CYP87 nucleic acid sequence, which is operably linked to an AtUBQ3 terminator, a Fgt/PFLt promoter operably linked to a CDS nucleic acid sequence, which is operably linked to a GmaxMYB2 terminator, a dMMV promoter operably linked to a CYP72 Zm nucleic acid sequence, which is operably linked to an AtRBCS2B terminator, a HLVH12 promoter operably linked to a UGT720 nucleic acid sequence, which is operably linked to an E9 terminator, a CsVMV promoter operably linked to a UGT94 nucleic acid sequence, which is operably linked to an ATHSP18.2 terminator, a NOS promoter operably linked to an EPH nucleic acid sequence, which is operably linked to an Ubi3 terminator, a 35S promoter operably linked to a HygR nucleic acid sequence, which is operably linked to a 35S terminator, followed by a TM6 MAR insulator sequence.

SP3190: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72 Zm nucleic acid sequence, which is operably linked to an AtRBCS2B terminator, a CmYLCV promoter operably linked to a UGT720 nucleic acid sequence, which is operably linked to an E9 terminator, an e35S promoter operably linked to a UGT94 nucleic acid sequence, which is operably linked to an ATHSP18.2 terminator, a NOS promoter operably linked to an EPH nucleic acid sequence, which is operably linked to an Ubi3 terminator, a CsVMV promoter operably linked to a HygR nucleic acid sequence, which is operably linked to a 35S terminator, followed by a TM6 MAR insulator sequence.

SP3029: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72 Zm nucleic acid sequence, which is operably linked to an AtRBCS2B terminator, a CmYLCV promoter operably linked to a UGT720 nucleic acid sequence, which is operably linked to an E9 terminator, an e35S promoter operably linked to a UGT94 nucleic acid sequence, which is operably linked to an ATHSP18.2 terminator, a NOS promoter operably linked to an EPH nucleic acid sequence, which is operably linked to an Ubi3 terminator, a ScBV promoter operably linked to a tHMGR nucleic acid sequence, which is operably linked to an AtTub terminator, a CsVMV promoter operably linked to a HygR nucleic acid sequence, which is operably linked to a 35S terminator, followed by a TM6 MAR insulator sequence.

SP0545: This expression cassette was assembled using a TM6 MAR insulator sequence, followed by a HLVH12 promoter operably linked to an SQE nucleic acid sequence, which is operably linked to a Pea3A terminator, a DCMV promoter operably linked to a CYP87 nucleic acid sequence, which is operably linked to an AtUBQ3 terminator, a FSgt/PFLt promoter operably linked to a CDS nucleic acid sequence, which is operably linked to a GmaxMYB2 terminator, a dMMV promoter operably linked to a CYP72 Zm nucleic acid sequence, which is operably linked to an AtRBCS2B terminator, a CmYLCV promoter operably linked to a UGT720 nucleic acid sequence, which is operably linked to an E9 terminator, an e35S promoter operably linked to a UGT94 nucleic acid sequence, which is operably linked to an ATHSP18.2 terminator, a NOS promoter operably linked to an EPH nucleic acid sequence, which is operably linked to an Ubi3 terminator, a FE_3 promoter operably linked to a tHMGR nucleic acid sequence, which is operably linked to an AtTub terminator, a CsVMV promoter operably linked to a HygR nucleic acid sequence, which is operably linked to a 35S terminator, followed by a TM6 MAR insulator sequence.

SP4156: This expression cassette was assembled using a TM6 MAR insulator sequence, followed by a CmYLCV promoter operably linked to an SQE nucleic acid sequence, which is operably linked to a Pea3A terminator, a DCMV promoter operably linked to a CYP87 nucleic acid sequence, which is operably linked to an AtUBQ3 terminator, a Fgt/PFLt promoter operably linked to a CDS nucleic acid sequence, which is operably linked to a GmaxMYB2 terminator, a dMMV promoter operably linked to a CYP72 Zm nucleic acid sequence, which is operably linked to an AtRBCS2B terminator, a HLVH12 promoter operably linked to a UGT720 nucleic acid sequence, which is operably linked to an E9 terminator, a CsVMV promoter operably linked to a UGT94 nucleic acid sequence, which is operably linked to an ATHSP18.2 terminator, a NOS promoter operably linked to an EPH nucleic acid sequence, which is operably linked to an Ubi3 terminator, a 35S promoter operably linked to a nptII nucleic acid sequence, which is operably linked to a 35S terminator, followed by a TM6 MAR insulator sequence.

Example 2

Initiation and Maintenance of Watermelon Anther-Derived Cell Suspension Cultures This example details how to initiate callus from male flowers of watermelon and how to establish and maintain watermelon cell suspension cultures. Watermelon cell suspension cultures can be used for the production of mogrosides or for gene/parts/vector testing in transient assays.

Materials

Sterile containers (e.g., magenta boxes, flip cap tubes, etc., pick a size that is appropriate for the volume of plant tissue and sterilization solution); scalpel (#10); scalpel handle; forceps; full-strength commercial bleach; sterile water; 70% ethanol; sterile paper towels; sterile filter paper (125 mm); 15 mL Falcon™ tubes; 50 mL Falcon™ tubes; sterile 60×15 mm petri plates; sterile 150×15 mm petri plates; 100% ethanol; sterile 10 mL wide-mouth pipettes; sterile 25 mL pipettes; Pipet-Aid®; sterile 125 mL Erlenmeyer flasks; sterile 250 mL Erlenmeyer flasks; 1000 μm pluriStrainer™ (Pluriselect: SKU 43-50750-03).

Media

Callus initiation from anther and maintenance (CIM): full strength MS salts and vitamins, sucrose: 30 g/L, pH: 5.8, agar: 6.0 g/L, autoclave 500 mL on liquid 25 cycle, after autoclaving and cooling add: 2,4-D: 0.5 mg/L, thidiazuron (TDZ): 0.5 mg/L, pour media into tall culture plates.

Cell suspension liquid media (initiation and maintenance): full strength MS salts and vitamins, sucrose: 30 g/L, pH 5.8, autoclave 500 mL on liquid 25 cycle, after autoclaving and cooling add: 2,4-D: 0.5 mg/L, TDZ: 0.5 mg/L, STABA vitamins: 10 mL per liter.

Method

All procedures are performed in a sterile laminar flow hood unless otherwise specified. It takes anywhere from 1 to 2 months for callus to develop from the male flowers. After callus forms, it takes another 1 to 2 months for callus proliferation.

Disinfection of male flowers and callus initiation: 1. Collect the immature male flowers from the vine. The flower should still be closed at time of collection and petals should be green in color. 2. Place the immature male flowers in a sterile tissue culture container big enough for the sampling. Sterile magenta boxes, flip-cap tubes, and one liter containers can be used. 3. Add 70% ethanol to the container. Use enough to cover the flowers. 4. Incubate the flowers in the ethanol for 1 minute while gently swirling the container. 5. Pour off and discard the ethanol solution. 6. Add a solution of 10% commercial bleach (v/v)+0.05% Tween 20 to the container. Use enough to cover the flowers. Place sterile paper towels on top of the solution so that the towels fully immerse the flowers in the bleach. 7. Place the cap or lid on the sterile container and then place the container on a rotary shaker. Incubate the flowers in the bleach solution for 15 minutes on the rotary shaker (~90 rpm). 8. In a sterile laminar flow hood, pour off and discard the bleach solution. 9. Rinse the tissue three times with sterile water containing 400 mg/L Timentin. 10. Transfer the flowers to a sterile 150 mm×15 mm petri plate containing sterile 125 mm filter paper. 11. Use the scalpel to gently remove the outer layer of petals. Once the outer layer is removed, carefully dissect out the anthers and place them in petri plates containing callus induction media (CIM). 12. Wrap the plates with cling wrap and place them in a chamber with growth conditions of 16/8 hour day/night cycle at 25° C./23° C.±2° C.

Callus selection and propagation: 1. After 1 month, the anther explants will exhibit signs of swelling and watery, pale, loose callus can be observed on the surface of the explants. 2. Remove and transfer the callus to fresh CIM medium (same as used for initiation). 3. Sub-culture the callus every 2 to 3 weeks for differentiation and proliferation.

Cell suspension establishment and subculture (performed weekly). A 1:4 ratio of old media to new media is maintained during the weekly subculture: 1. After 3 to 4 months, different types of calli will be observed on the plates. White/yellow friable callus that is similar in texture and appearance to cotton candy is the best type to use for initiation of the cell suspension. 2. Using a sterile 25 mL pipet, add 25 ml of liquid cell suspension medium to a sterile 125 ml Erlenmeyer flask. 3. Add approximately 2 to 3 grams of watermelon callus to the flask and swirl the contents. The callus pieces should start to break apart in the liquid culture media. 4. Place the flask on a rotary shaker and culture at 110 rpm under constant lighting (1500 Lux) at 24±1° C. 5. After 7 days, transfer the culture to a sterile 50 mL conical tube. Allow the cells to settle. 6. Remove and discard 20 mL of the old media. 7. Add 20 mL of fresh media to the tube and transfer the contents (including cells) to a new 125 mL Erlenmeyer flask. 8. After 7 days, place a 1000 μm nylon mesh cell strainer into a 50 ml conical tube and filter the culture through the cell strainer. This removes large cell aggregates and leads to a finer cell suspension. 9. Allow the cells to settle to the bottom of the tube and then transfer those cells to a 15 mL conical tube. 10. Repeat steps 8 and 9 either one or two more times. 11. After the small cell population has been collected in the 15 ml conical tube, transfer the cells along with 10 mL of old media to a 250 mL Erlenmeyer flask. 12. Add 40 mL of fresh media to the flask. Place the flask back on the shaker and culture at 110 rpm under constant lighting (1500 Lux) at 24±1° C. 13. Record the settled cell volume every 7 days after sub-culture and replace old media with fresh media weekly. The cell suspension should begin to increase in volume 3-4× after three weeks of routine sub-culture. Use approximately 3 to 5 mL of settled cell volume per sub-culture. More cells than this will result in an unhealthy cell suspension as resources are diminished more quickly. Use 1000 μm nylon mesh cell strainers to filter the cells every third or fourth sub-culture. This helps to maintain a population of smaller cell aggregates.

Example 3

Transient Expression in Plants

Various expression cassettes selected from Example 1 were used for transient expression in various tissues of different plants, such as the fruit of watermelon, tomato, zucchini, and cucumber; leaves of *Nicotiana bentamiana*, lettuce, and sugar beet; and taproot of sugar beet. *Agrobacterium tumefaciens* strain EHA105 was transformed with one or more expression cassette plasmids (selected from Example 1) using a free-thaw method (Weigel, CSH Protoc. 2006 Dec. 1; 2006 (7): pdb.ip29. doi: 10.1101/pdb.ip29). Briefly, chemically competent *Agrobacterium* was prepared. After addition of the expression cassette plasmids, the mixture was alternately frozen in liquid nitrogen and thawed to liquid in a 37° C. water bath. The cells were then allowed to recover in LB medium for about 1 hour and plated out on LB plates with kanamycin.

Briefly, transformed EHA105 *Agrobacterium* strains were grown overnight and diluted to combined $OD_{600}$ readings of 0.5-2.5. Cores of watermelon fruit; whole tomato, zucchini, or cucumber fruits; leaves of *Nicotiana benthamiana*, lettuce, or sugar beet; or thin slices of sugar beet taproot were used for transient expression by infiltration. The diluted transformed *Agrobacterium* culture was loaded to a 1 or 5 mL syringe with or without needle, and about 1 mL was injected to the targeted plant tissue such as the fruit or the leaves. Sugar beet taproot slices were infiltrated by incubating in diluted *Agrobacterium* for 30 minutes. One or more *Agrobacterium* strains with different expression cassettes can be mixed prior to injection. The plants and plant tissues infiltrated with the transformed *Agrobacterium* cultures were grown for another four to nine days before sampling.

Mogroside Detection

About 100 mg of plant tissue was extracted in 500 μl extraction buffer (80% methanol). After centrifugation, the supernatant was forced to pass through 0.22 μM filter in order to remove remaining particles. Waters Acquity UPLC coupled by Waters Xevo Quadrupole Time of Flight Tandem Mass Spectrometer was used for metabolite analysis. For UPLC separation, Waters Acquity BEH C18 1.7 μm, 2.1×50 mm column was used with water and acetonitrile as solvents (both with 1% formic acid). For each analysis, 1.5 μl of sample was injected. MS/MS under negative ESI was used for detection of mogroside compounds. The collision energy was set to 30 V for detection of mogroside compounds.

Preliminary studies in transient assays from *Nicotiana bentamiana* leaves showed production of mogrosides and oxo-mogrosides.

Figure 2:
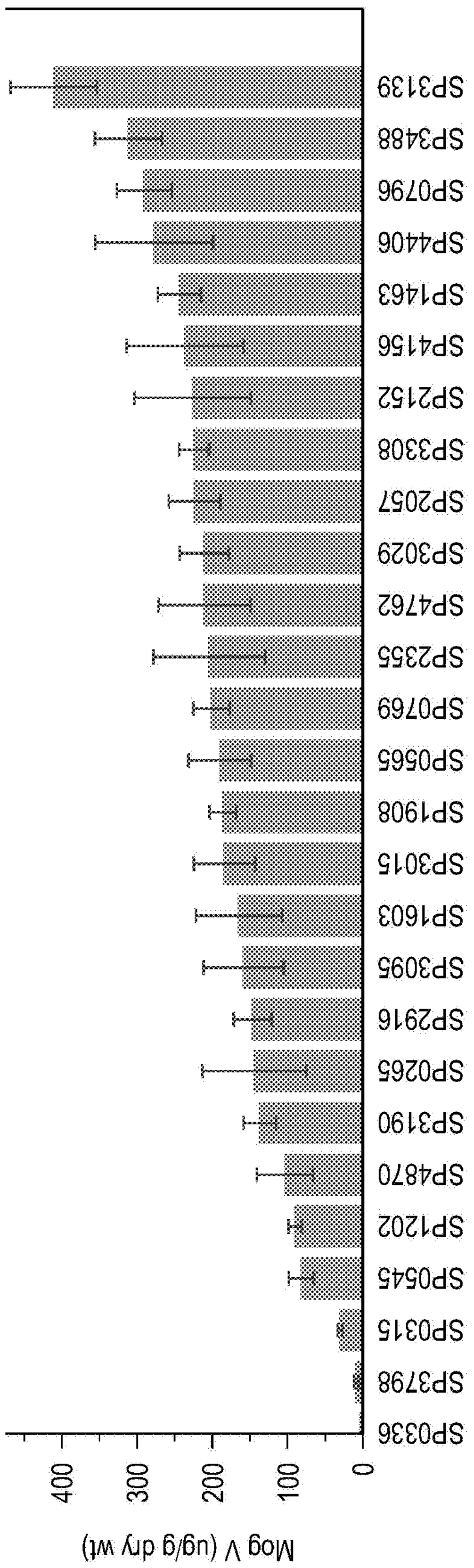
FIG. 2. Mogroside V production in transient expression of watermelon fruit with a number of different expression constructs.
Figure 3:
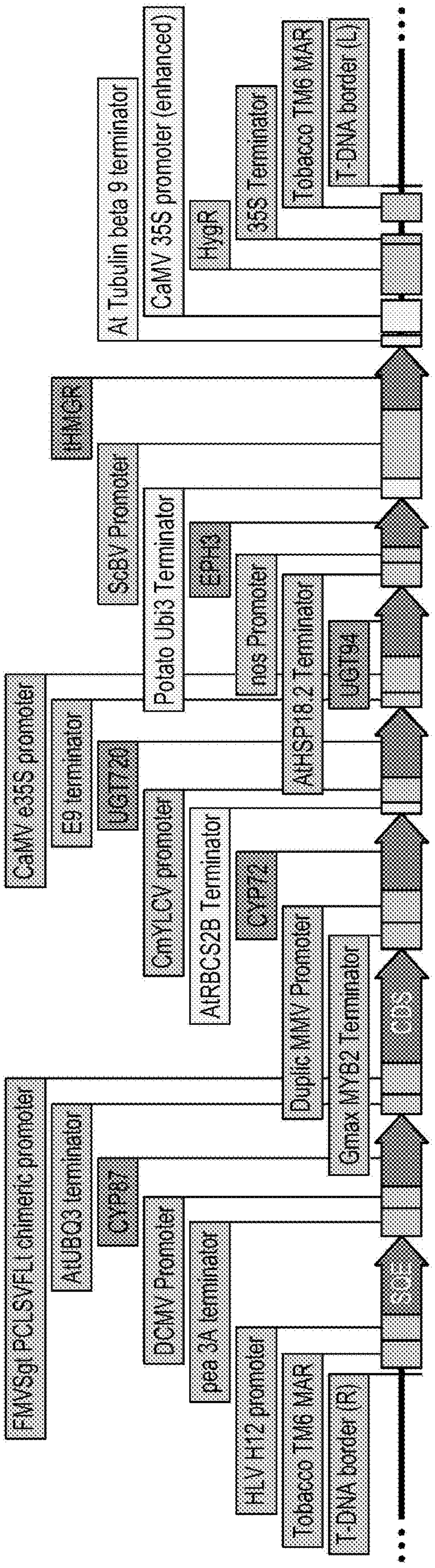
FIG. 3. Map of expression construct SP3139.

Mogroside V accumulation in transient assays from watermelon fruit infiltrated with a number of different expression constructs described in Example 1 is shown in FIG. 2. A number of the expression constructs produced high levels of mogroside V in these transient assays, but the SP3139 expression construct produced the highest levels of mogroside V. A map of the SP3139 expression construct is shown in FIG. 3.

Figure 4:
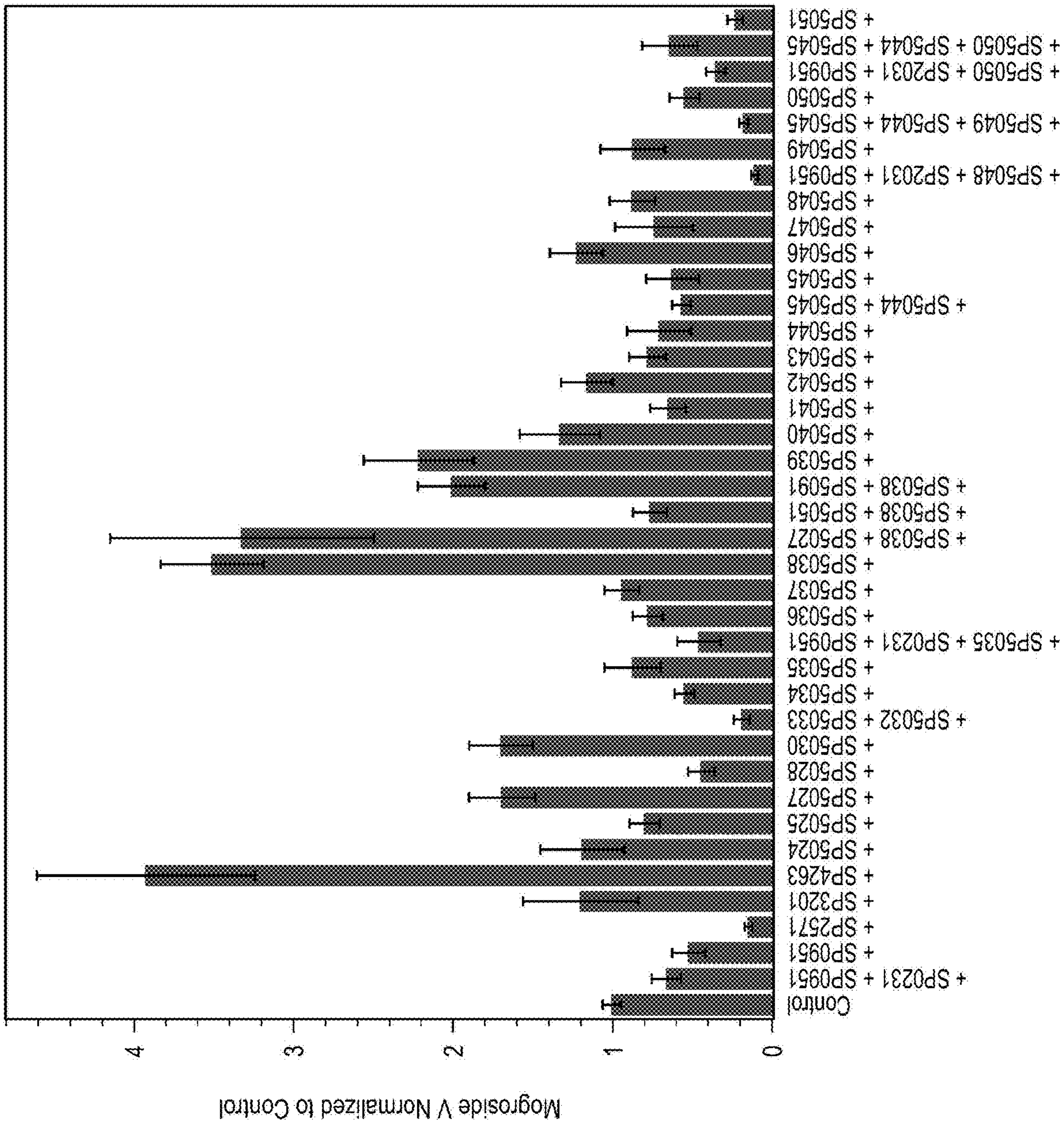
FIG. 4. Mogroside V production in transient expression in watermelon fruit using various constructs.
Figure 5:
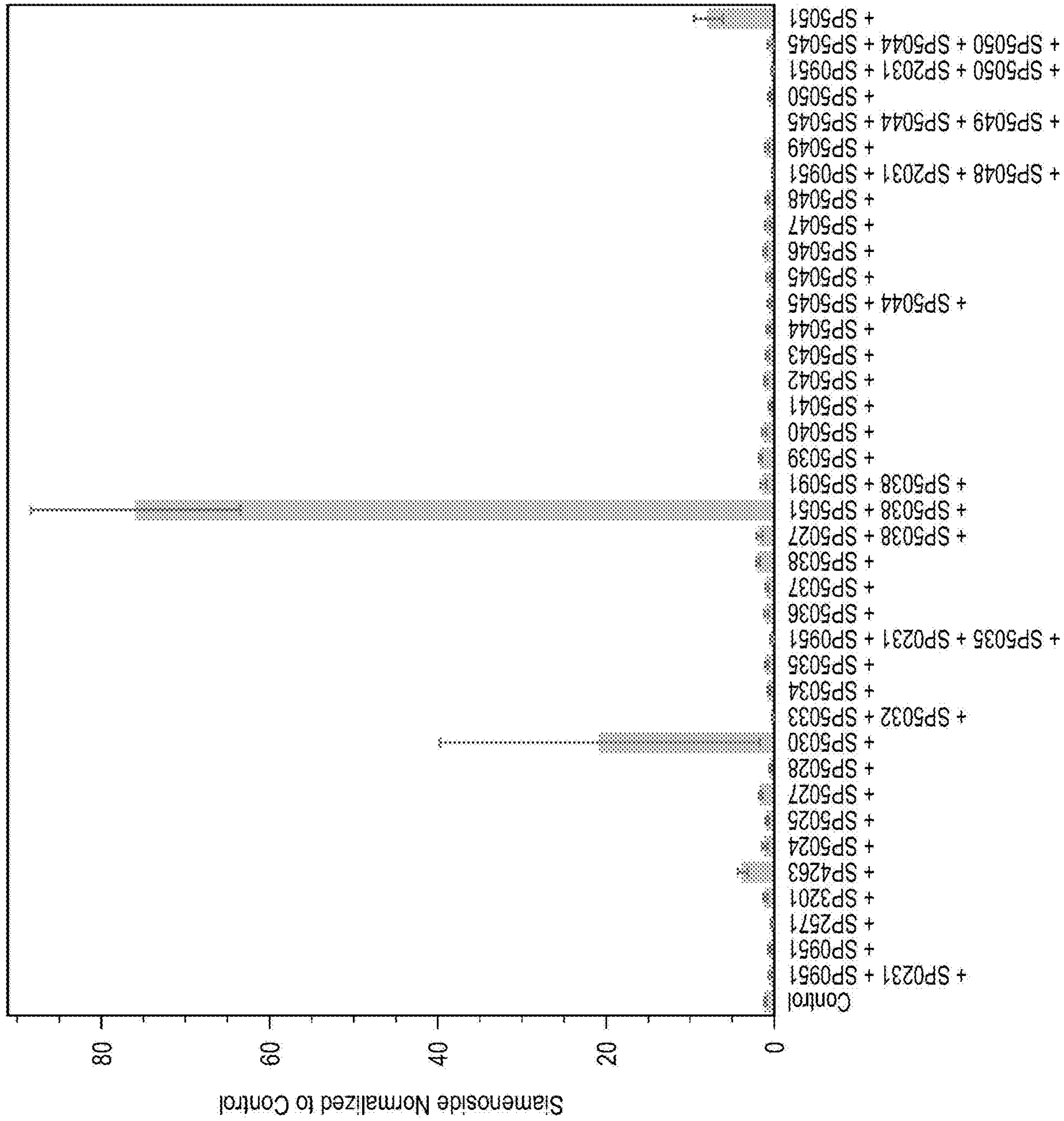
FIG. 5. Siamenoside production in transient expression in watermelon fruit using various constructs.

Additional studies in transient assays in watermelon fruit infiltrated with a number of different expression constructs described in Example 1, as well as certain combinations of these constructs, were performed. The production of various mogrosides and siamenoside was determined. The amount of mogroside V normalized to control is shown in FIG. 4. The SP4263 expression construct produced the highest levels of mogroside V, but the SP5038 construct and the combination of the SP5038 and SP5027 constructs also produced high levels of mogroside V. The amount of siamenoside normalized to control is shown in FIG. 5. The combination of SP5038 and SP5051 produced the highest levels of siamenoside.

Figure 6:
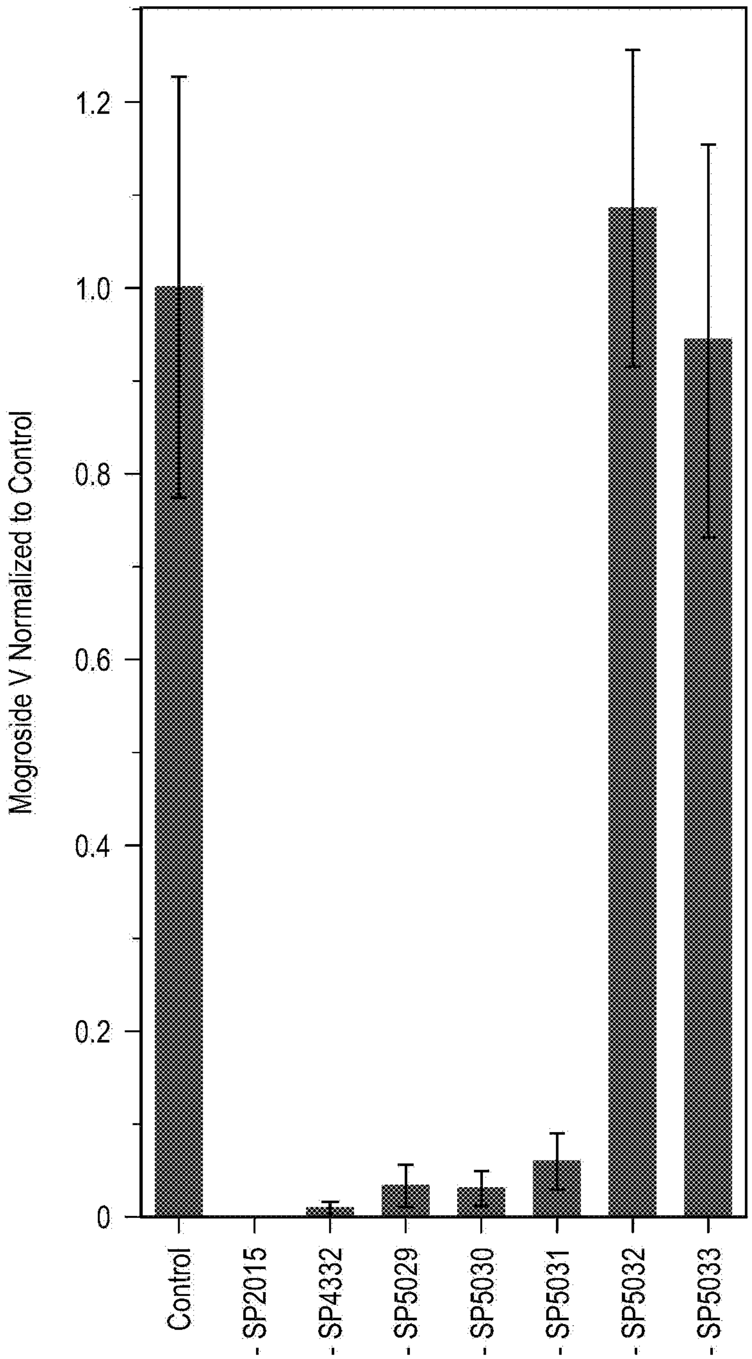
FIG. 6. Mogroside V production in transient expression in watermelon fruit using a combination of SP2015, SP4332, SP5029, SP5030, SP5031, SP5032, and SP5033 constructs (control), and the combination excluding one of the constructs.

Further studies in transient assays in watermelon fruit infiltrated with a combination of SP2015, SP4332, SP5029, SP5030, SP5031, SP5032, and SP5033 constructs (control), and the combination lacking a single construct, were performed. The production of various mogrosides and siamenoside was determined. The amount of mogroside V normalized to control is shown in FIG. 6. The amount of siamenoside produced by the various vectors was very low.

Figure 7:
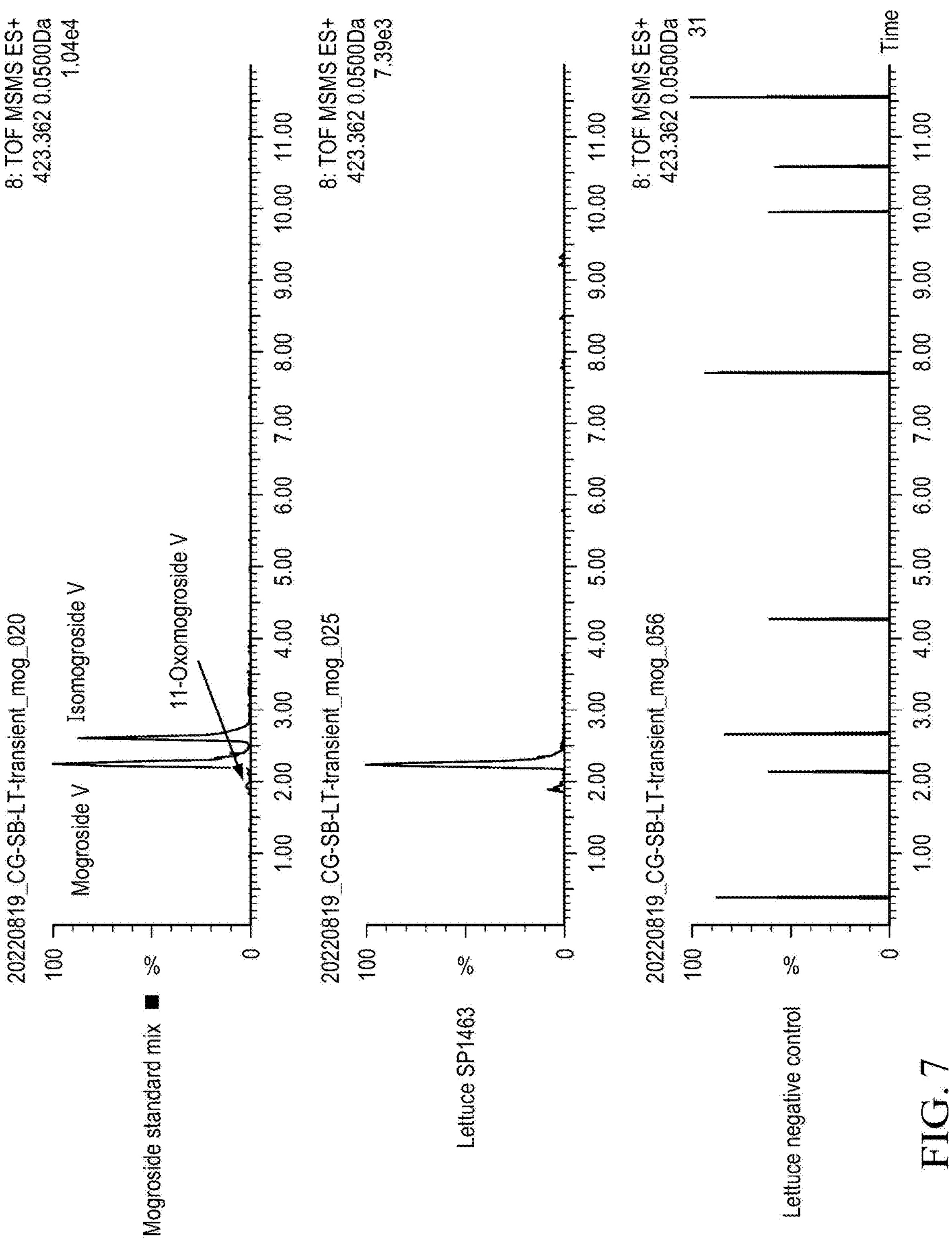
FIG. 7. Mogroside V production in transient expression in lettuce leaves infiltrated with the SP1463 construct compared to negative lettuce control and mogroside standard mix.
Figure 8:
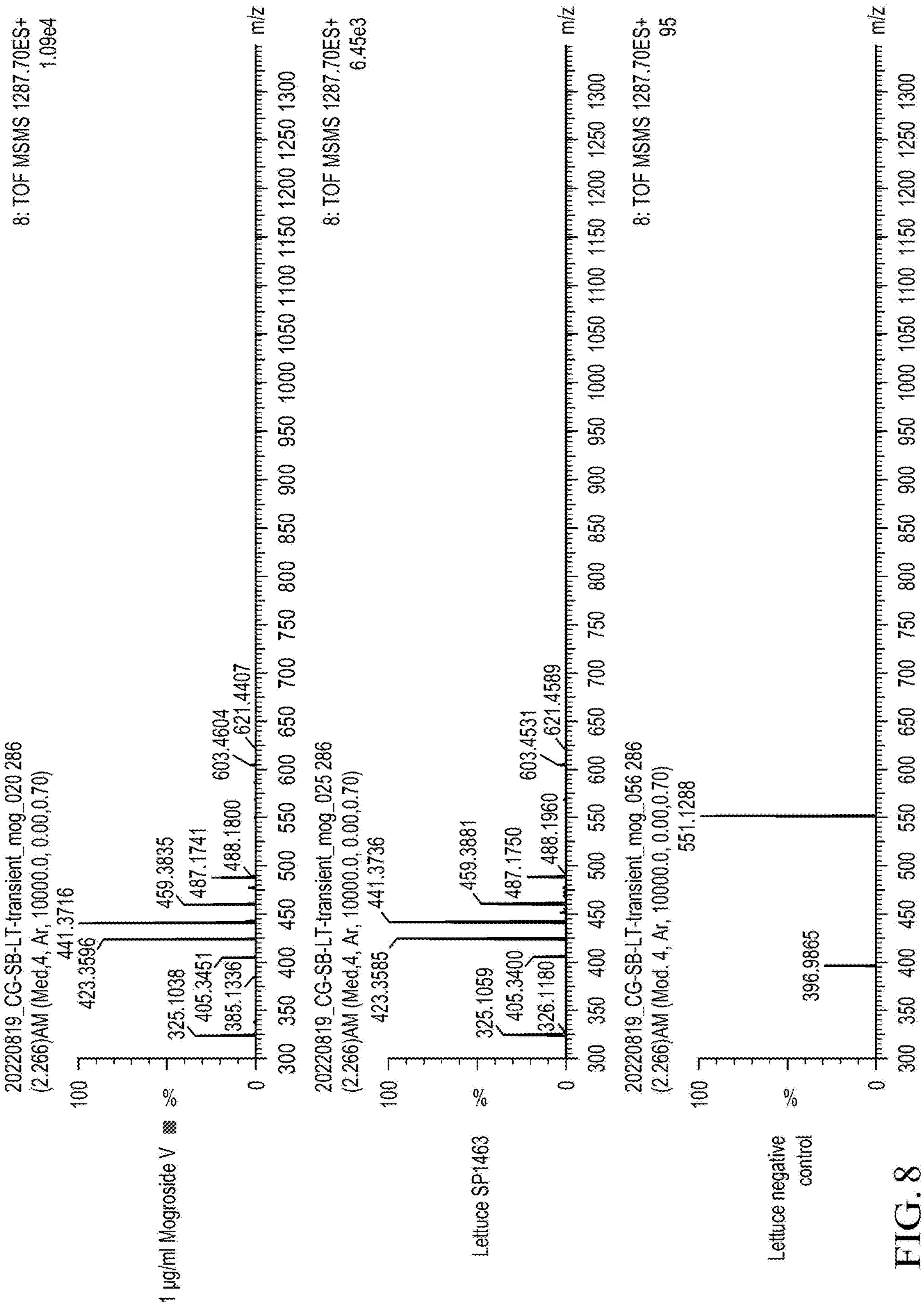
FIG. 8. Mass spectrum fingerprinting of mogroside V production in transient expression in lettuce leaves infiltrated with the SP1463 construct compared to negative lettuce control and mogroside V reference standard.
Figure 9:
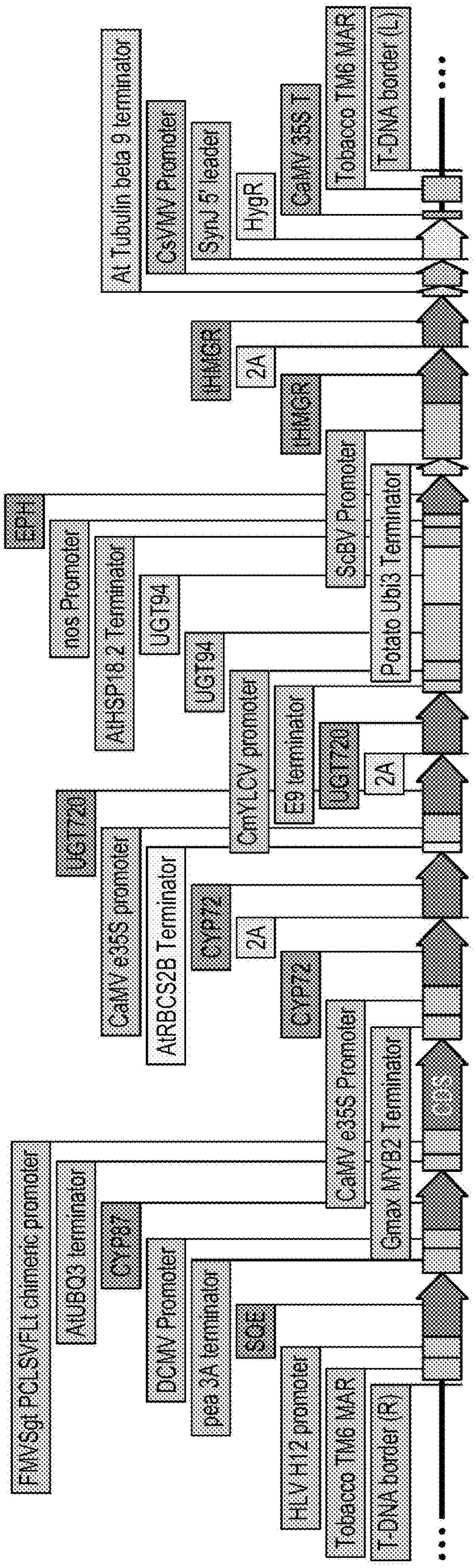
FIG. 9. Map of expression construct SP1463.
Figure 10:
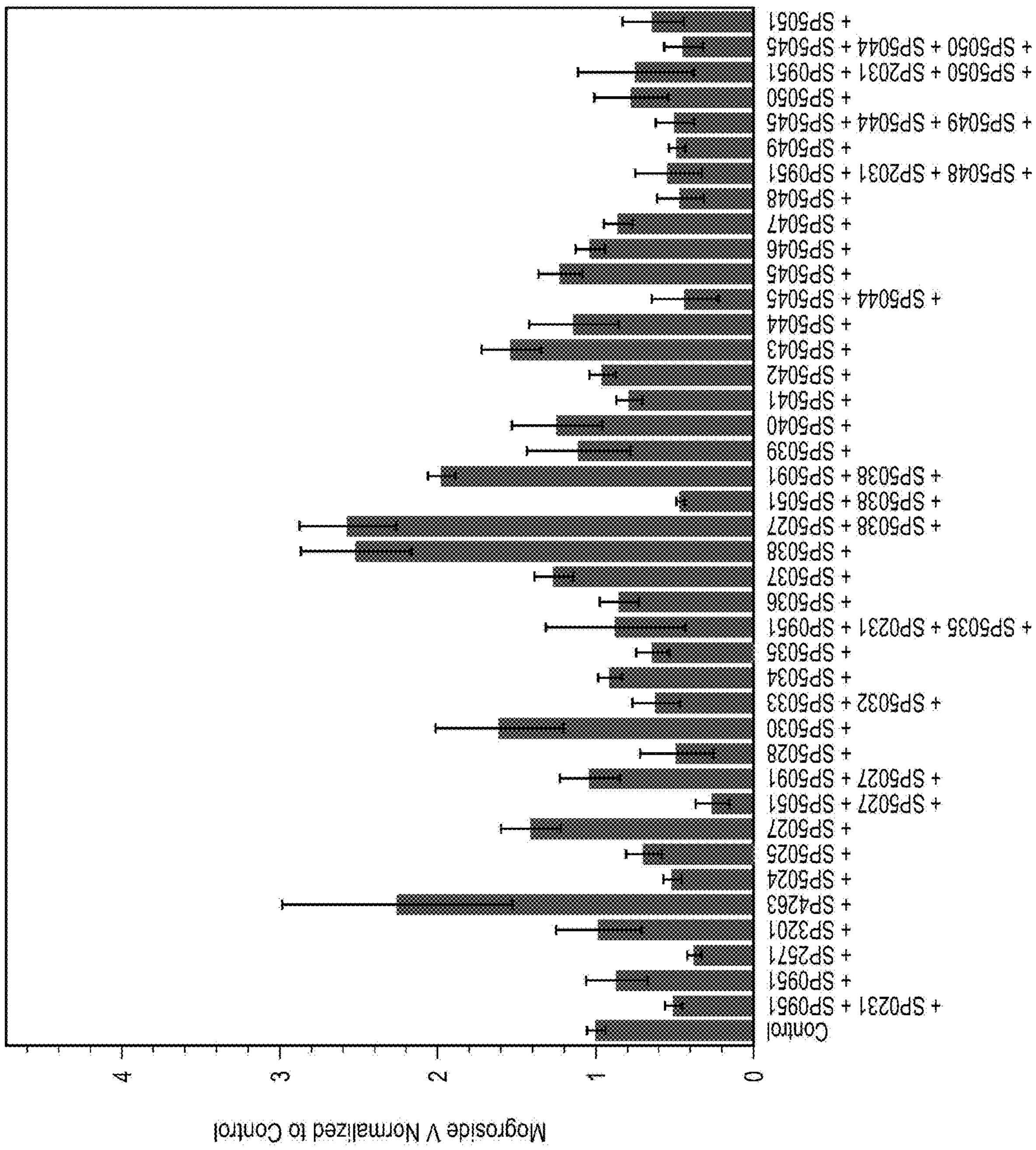
FIG. 10. Mogroside V production in transient expression in lettuce leaves using various constructs.

Mogroside V accumulation in transient assays from lettuce leaves infiltrated with the expression construct SP1463 is shown in FIG. 7 (middle panel). It can be seen that large amounts of mogroside V was produced, compared to the negative control (FIG. 7, bottom panel-note the difference in the scale of the middle panel and bottom panel of FIG. 7). The mogroside V eluted in the same location as mogroside V in a mogroside standard mix (FIG. 7, top panel). The mass spectrum fingerprinting of the mogroside V in transient assays from lettuce leaves infiltrated with the expression construct SP1463 is shown in FIG. 10. The mogroside V (FIG. 8, middle panel) matched the mass spectrum of the mogroside V reference standard (FIG. 8, top panel). The negative control showed no mogroside V (FIG. 8, bottom panel). A map of the SP1463 expression construct is shown in FIG. 9.

Figure 11:
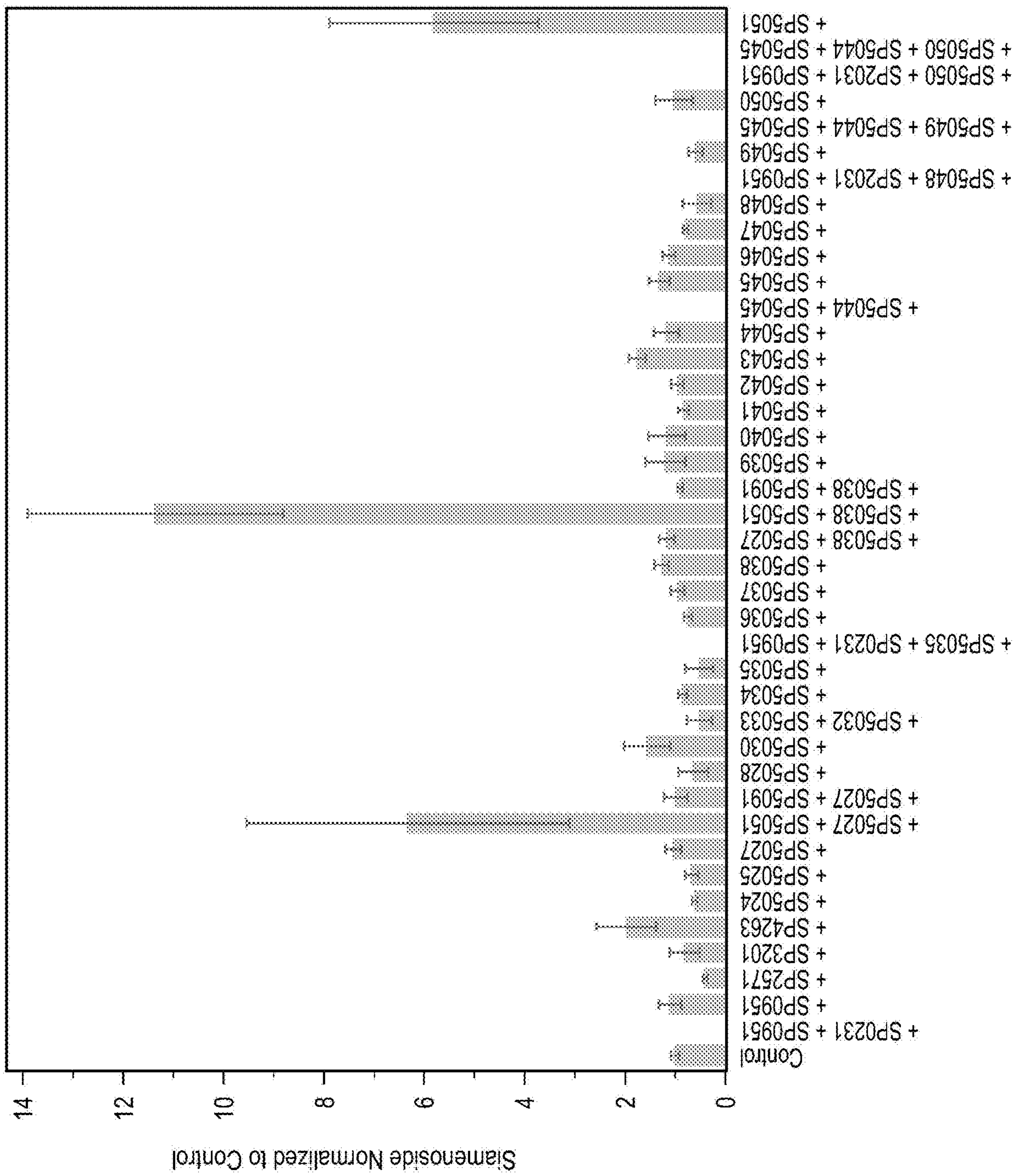
FIG. 11. Siamenoside production in transient expression in lettuce leaves using various constructs.

Additional studies in transient assays in lettuce leaves infiltrated with a number of different expression constructs described in Example 1, as well as certain combinations of these constructs, were performed. The production of various mogrosides and siamenoside was determined. The amount of mogroside V normalized to control is shown in FIG. 10, and the amount of siamenoside normalized to control is shown in FIG. 11.

Figure 12:
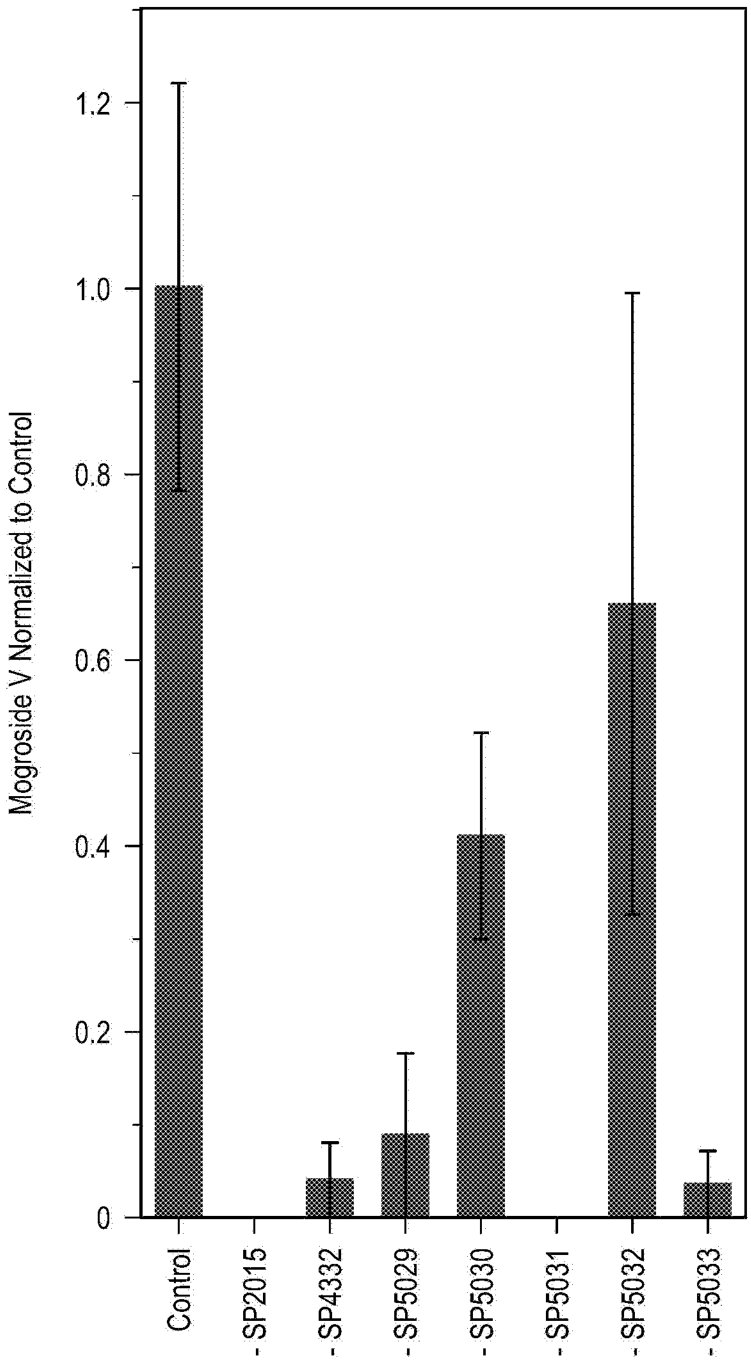
FIG. 12. Mogroside V production in transient expression in lettuce leaves using a combination of SP2015, SP4332, SP5029, SP5030, SP5031, SP5032, and SP5033 constructs (control), and the combination excluding one of the constructs.

Further studies in transient assays in lettuce leaves infiltrated with a combination of SP2015, SP4332, SP5029, SP5030, SP5031, SP5032, and SP5033 constructs (control), and the combination lacking a single construct, were performed. The production of various mogrosides and siamenoside was determined. The amount of mogroside V normalized to control is shown in FIG. 12. The amount of siamenoside produced by the various vectors was very low.

Example 4

Transgenic Watermelon Plants

Creation of Transformed Plants

Various expression cassettes selected from Example 1 were used for transforming *Citrullus lanatus. Agrobacterium tumefaciens* strain EHA105 was transformed with one or more expression cassette plasmids (selected from Example 1) using a free-thaw method (Weigel, CSH Protoc. 2006 Dec. 1; 2006 (7): pdb.ip29. doi: 10.1101/pdb.ip29). Briefly, chemically competent *Agrobacterium* was prepared. After addition of the expression cassette plasmids, the mixture was alternately frozen in liquid nitrogen and thawed to liquid in a 37° C. water bath. The cells were then allowed to recover in LB medium for about 1 hour and plated out on LB plates with kanamycin.

Briefly, the transformed EHA105 *Agrobacterium* was grown overnight and then diluted until the $OD_{600}$ reading reached 0.12. Two commercial varieties of watermelon, Charleston Gray and Sugar Baby, were used as hosts. Five-day-old watermelon seedlings were used for preparing explants for transformation. Cotyledons were cut off from hypocotyls and collected in petri plates filled with sterile water. Two attached cotyledons were split by cutting through remaining hypocotyl segment, and cotyledonary explants were cut into 2 mm pieces ready for transformation. For transformation, *Agrobacterium* culture was added to these explants and placed under vacuum for 5 minutes. After infection, explants were blotted on sterile paper towels and transferred to filter disks in petri plates with MS medium. The plates were sealed and placed at 25° C. for 3 days in the dark for co-cultivation.

Gene Expression Analysis of Target Genes in Transgenic Plants

To understand the difference in the ability to detect mogroside production in fruit, watermelons from various newly created plant lines were collected and dissected into the various fruit parts. RNA was then extracted from the various fruit part samples, and the RNA expression levels of the various newly integrated mogroside pathway genes were quantified using Q RT PCR using a standard protocol.

Mogroside Detection

About 100 mg of plant tissue was extracted in 500 μl extraction buffer (80% methanol). After centrifugation, the supernatant was forced to pass through 0.22 μM filter in order to remove remaining particles. Waters Acquity UPLC coupled by Waters Xevo Quadrupole Time of Flight Tandem Mass Spectrometer was used for metabolite analysis. The initial LC separation of the samples was done using a Waters Quaternary Solvent Manager ACQUITY UPLC H-Class PLUS connected to a Waters Sample Manager FTN-H ACQUITY UPLC and a PDA ex Detector ACQUITY UPLC. There were two different linear gradients, referred to as gradient A and gradient B, applied across different samples that use water 0.1% formic acid as mobile phase A (MPA) and acetonitrile 0.1% formic acid as mobile phase B (MPB) with a flow rate of 0.25 ml/minute and a column temperature of 35° C. Gradient A initializes at 10% MPB, at 1 minute it has increased to 20% MPB, 5 minutes 40% MPB, 8 minutes 70% MPB, 9 minutes 90% MPB, 12 minutes 95% MPB, 13 minutes 10% MPB, and 17 minutes 10% MPB. Gradient B initializes at 26% MPB, at 5 minutes it has increased to 35% MPB, 8.5 minutes 60% MPB, 9 minutes 90% MPB, 12 minutes 95% MPB, 13 minutes 26% MPB, and 17 minutes 26% MPB. The LC system was coupled to an Xevo G2-XS mass spectrometer in sensitivity positive mode using the MSMS scan mode with a scan range of 300-1350 m/z and collision energy of 30.

The following precursor and product ion pairs, expressed in m/z, were used to quantify the mogrosides with a 50 mDa window applied to the product ion: mogroside V (1287.7/423.3621), isomogroside V (1287.7/423.3621), mogroside IV (1125.6/423.3621), mogroside IV-A (1125.6/423.3621), siamenoside (1125.6/423.3621), mogroside III (963.6/423.3621), mogroside III-A (963.6/423.3621), mogroside III-A1 (963.6/423.3621), mogroside II-E (801.5/423.3621), mogroside II-A (801.5/423.3621), mogroside II-A1 (801.5/423.3621), 11-Oxo-mogroside V (1285.7/457.3680), and 11-Oxo-mogroside II-E (799.5/457.3680). For LockSpray mass correction, 200 μg/ml leucine-enkephalin monitoring for 556.2771 m/z was used. Data analysis was done using the Waters TargetLynx software, excel, and JMP. When creating figures, a 100 mDa or 50 mDa window was applied to the appropriate product listed above.

Figure 13:
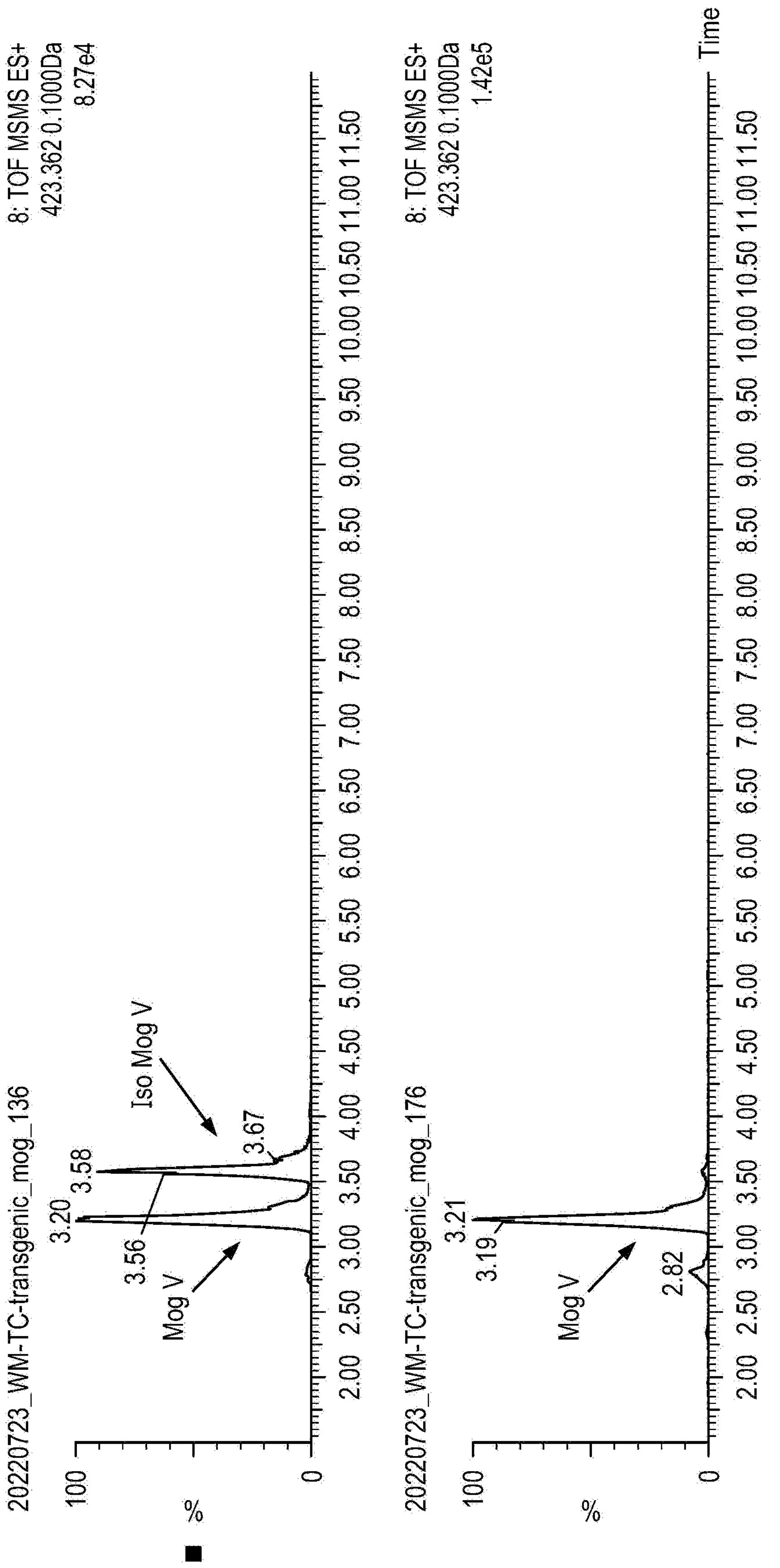
FIG. 13. Production of mogroside V in transgenic watermelon with expression construct SP1463 compared to mogroside V reference standard.

The levels of mogroside V were measured in the leaves of transgenic watermelon comprising expression cassette SP1463 The results are shown in FIG. 13 (bottom panel). The mogroside V eluted in the same location as mogroside V in a reference standard (FIG. 13, top panel). More than 3 mg/g (dry weight) of mogroside V was produced in transgenic watermelon. Interestingly, although the SP1463 construct did not produce the highest levels of mogroside V production in transient assays (see FIG. 2), extremely high levels of mogroside V was produced in transgenic watermelons comprising the SP1463 construct.

Figure 14:
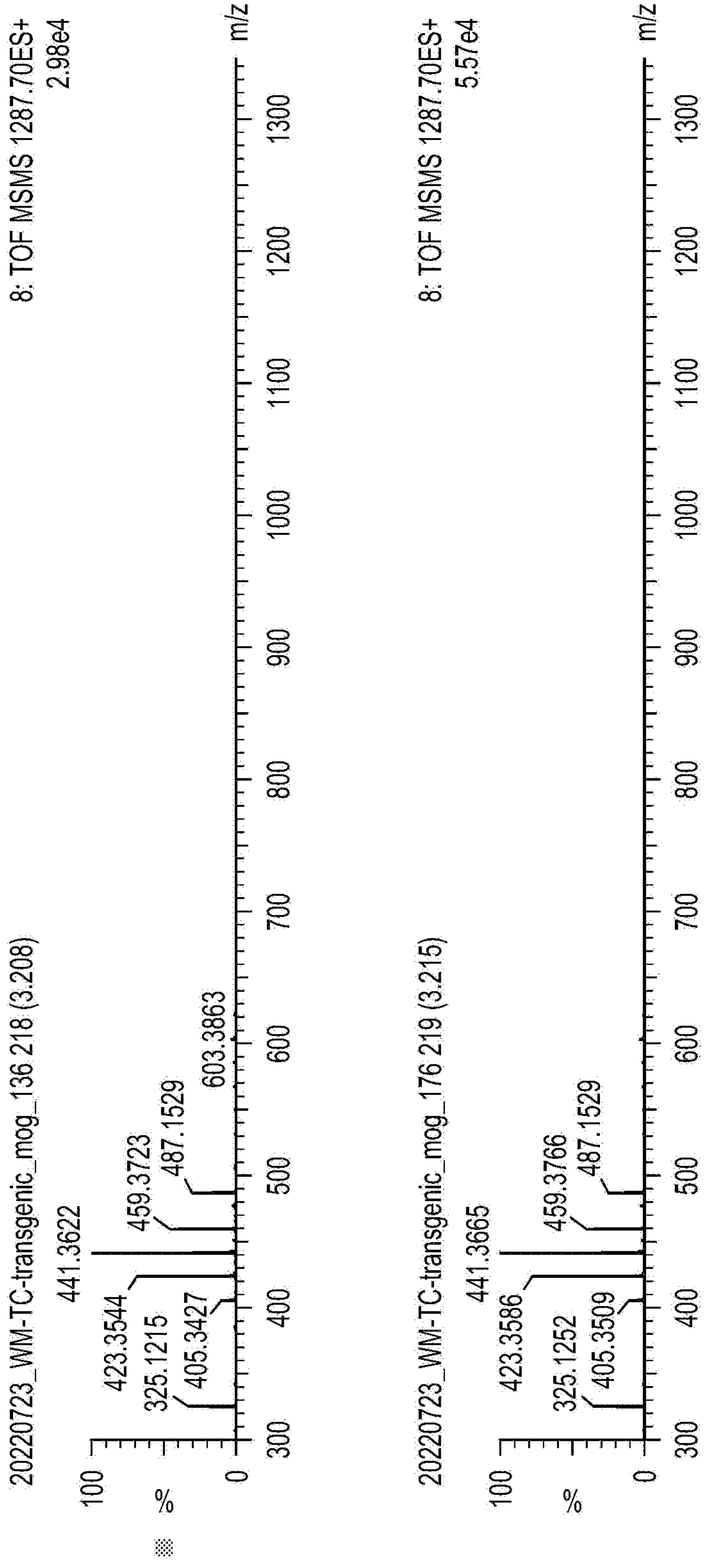
FIG. 14. Mass spectrum fingerprinting of mogroside V in transgenic watermelon with expression construct SP1463 compared to mogroside V reference standard.

The results of mass spectrum fingerprinting are shown in FIG. 14. The mass spectrum of the mogroside V from the transgenic watermelon comprising expression cassette SP1463 (FIG. 14, bottom panel) matched the mass spectrum of the mogroside V reference standard (FIG. 14, top panel).

Figure 15:
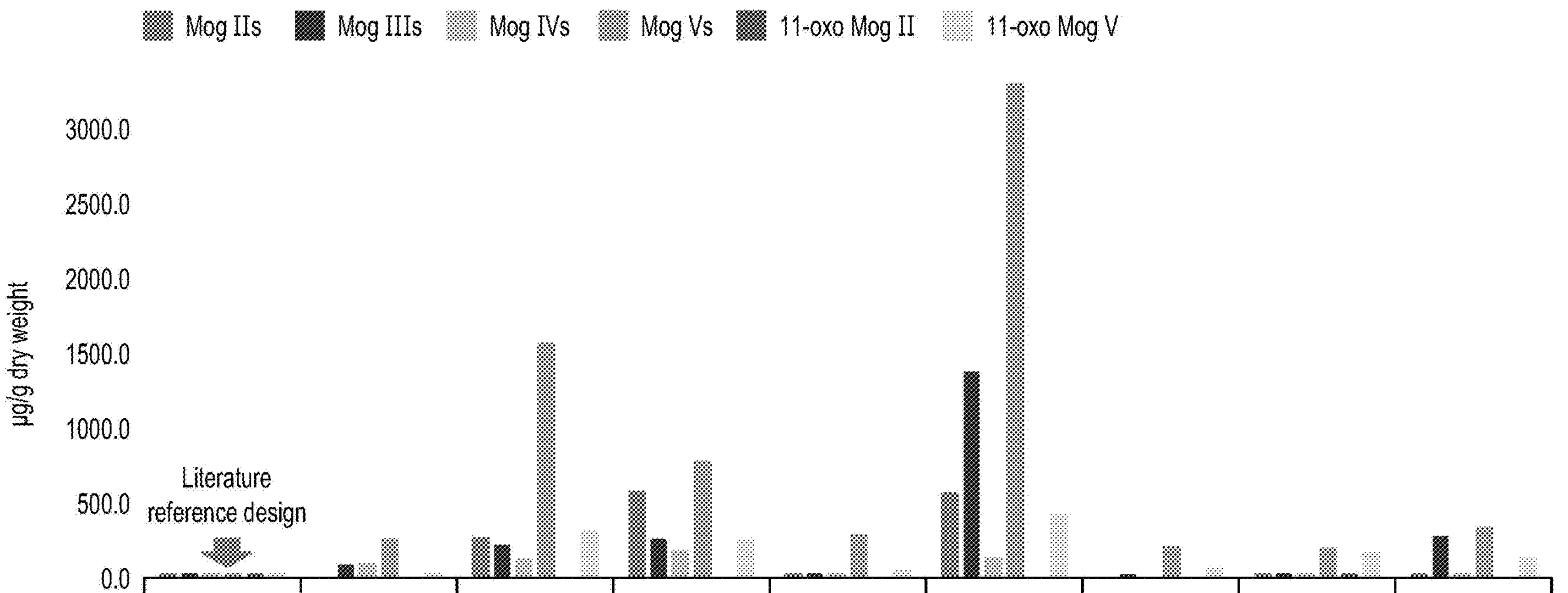
FIG. 15. Mogroside production in various transgenic watermelon lines with expression constructs SP0336, SP1463, SP1908, SP3488 and SP3190.
Figure 16:
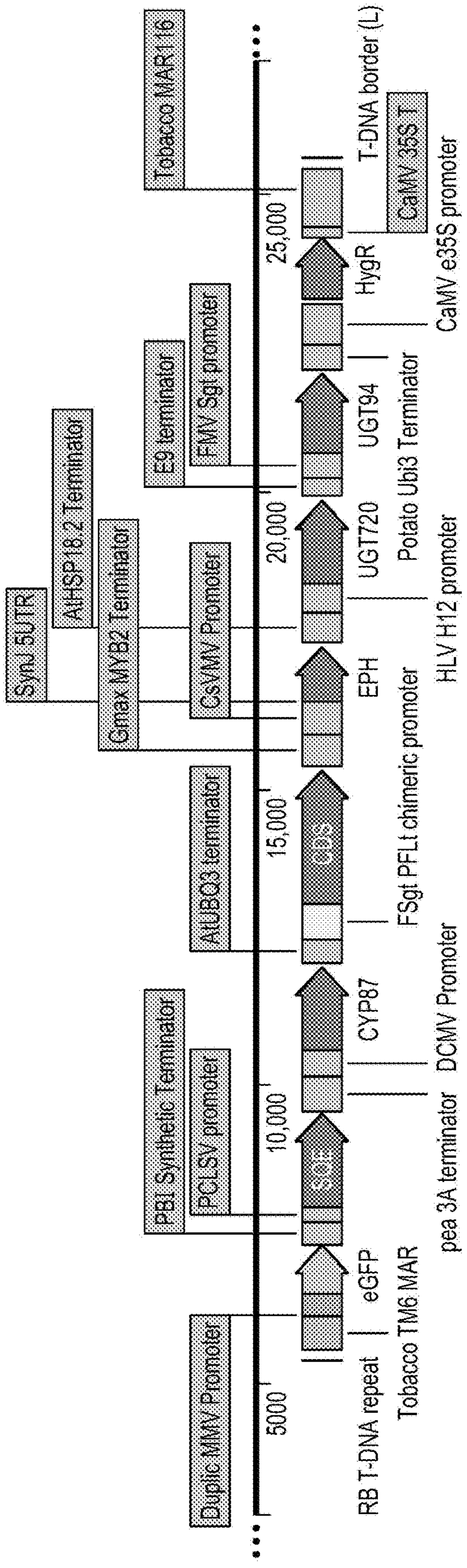
FIG. 16. Map of expression construct SP0336.
Figure 17:
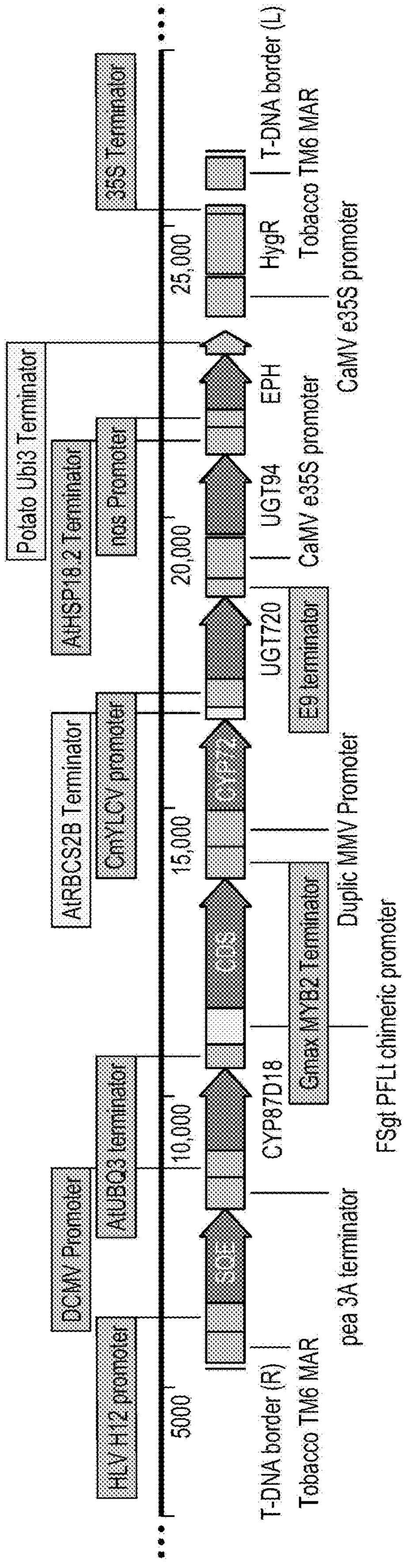
FIG. 17. Map of expression construct SP1908.

The levels of mogrosides, including mogroside V, were measured in the fruit of various transgenic watermelon lines comprising expression cassettes SP1463, SP1908, SP3190 and SP3488, and a construct (SP0336) based on the literature (Itkin et al., supra). The results are shown in FIG. 15. One of the SP1463 transgenic watermelon lines produced more than 3 mg/g (dry weight) of mogroside V. This was hundreds of thousands times more than was produced by the literature construct SP0336. A map of the SP0336 construct is shown in FIG. 16, and a map of the SP1908 construct is shown in FIG. 17.

Figure 18:
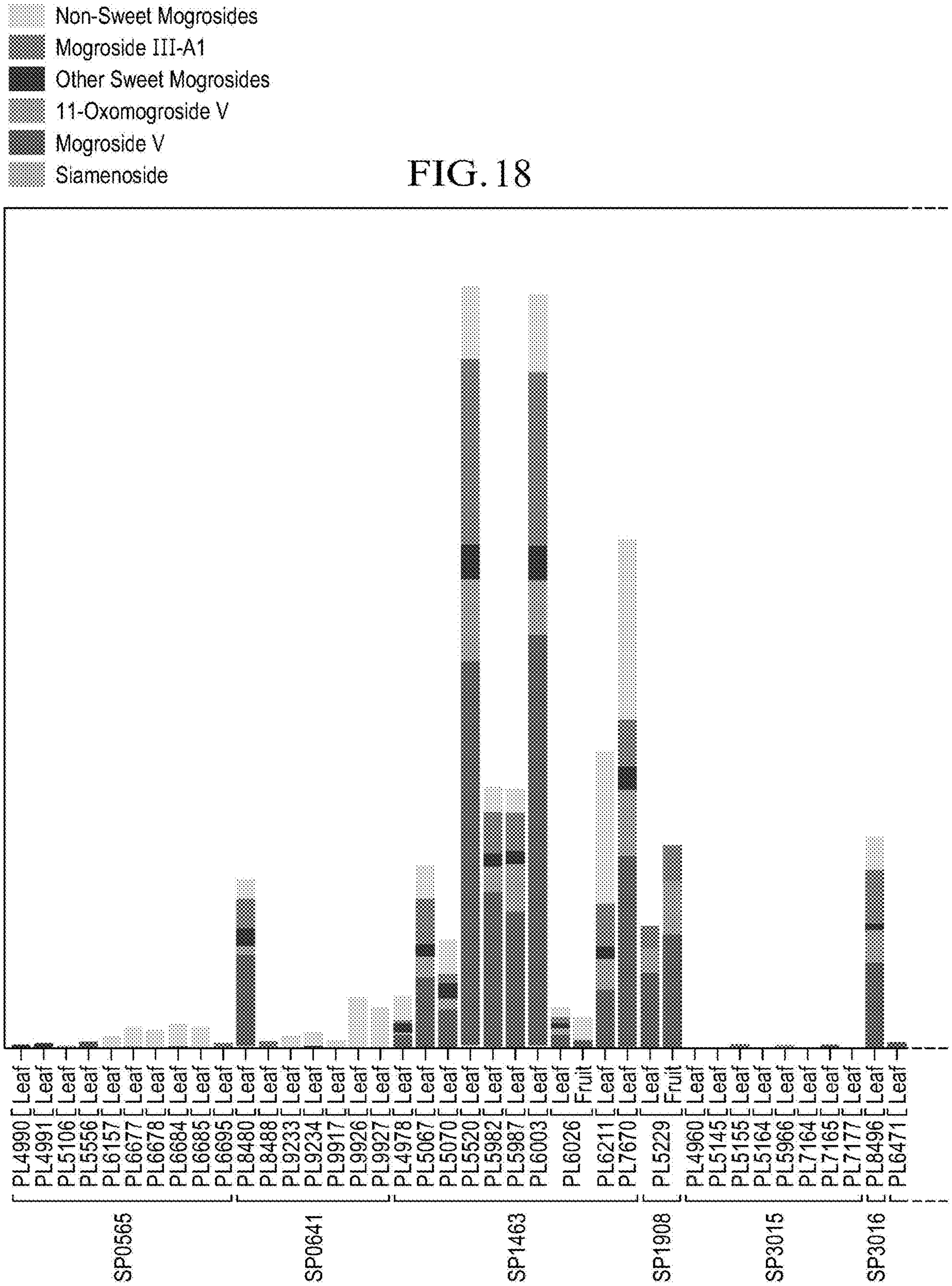
FIG. 18. Production of various mogrosides and siamenoside in transgenic watermelon with expression constructs SP0565, SP0641, SP1463, SP1908, SP3015, SP3016, SP3029, SP3190, SP3308 and SP3488.
Figure 18:
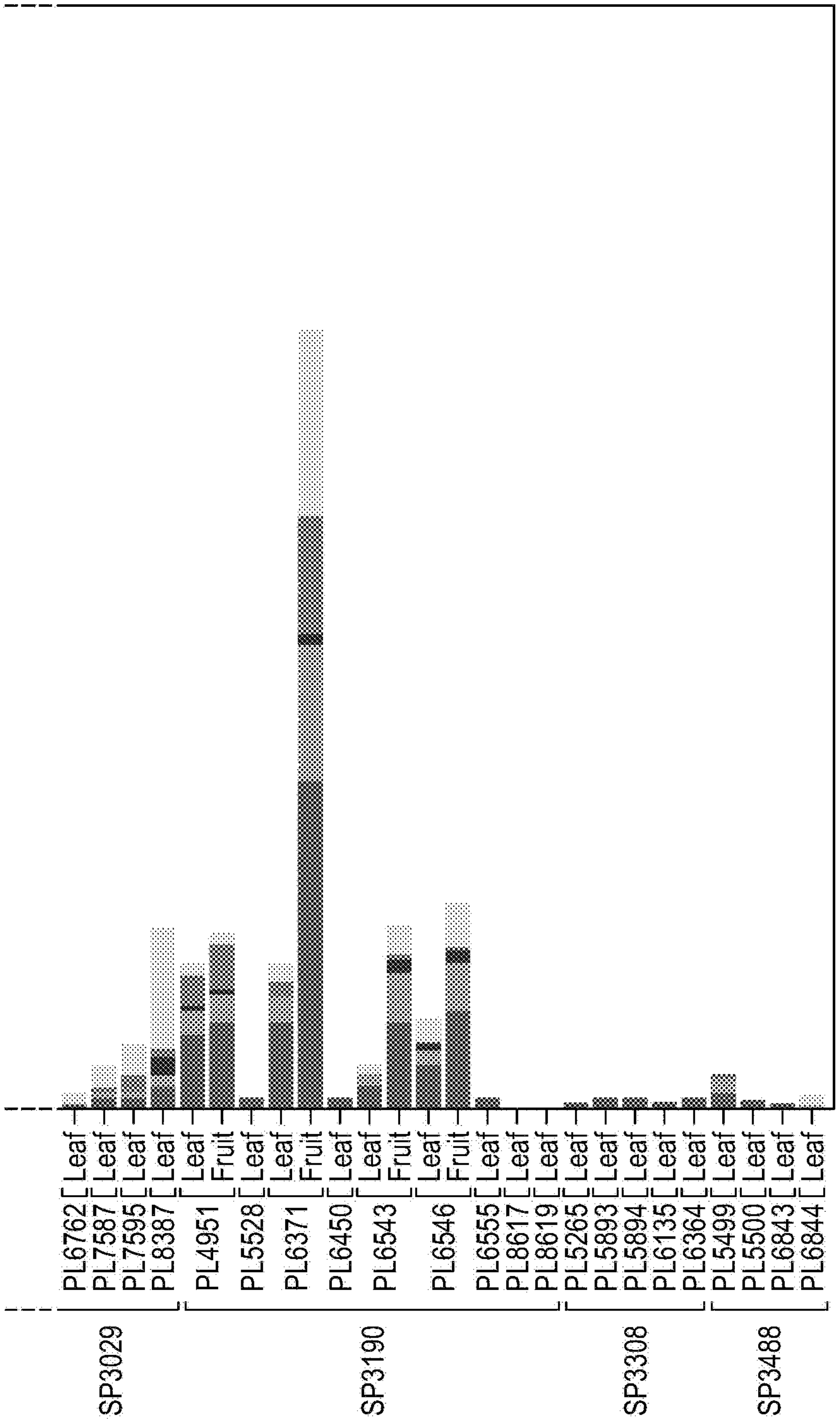

The levels of various mogrosides and siamenoside were measured in the fruit and leaves of various transgenic watermelon lines comprising expression cassettes SP0565, SP0641, SP1463, SP1908, SP3015, SP3016, SP3029, SP3190, SP3308 and SP3488. The results are shown in FIG. 18.

Example 5

Production of Mogrosides in a Transgenic Watermelon Cell Suspension

Figure 20:
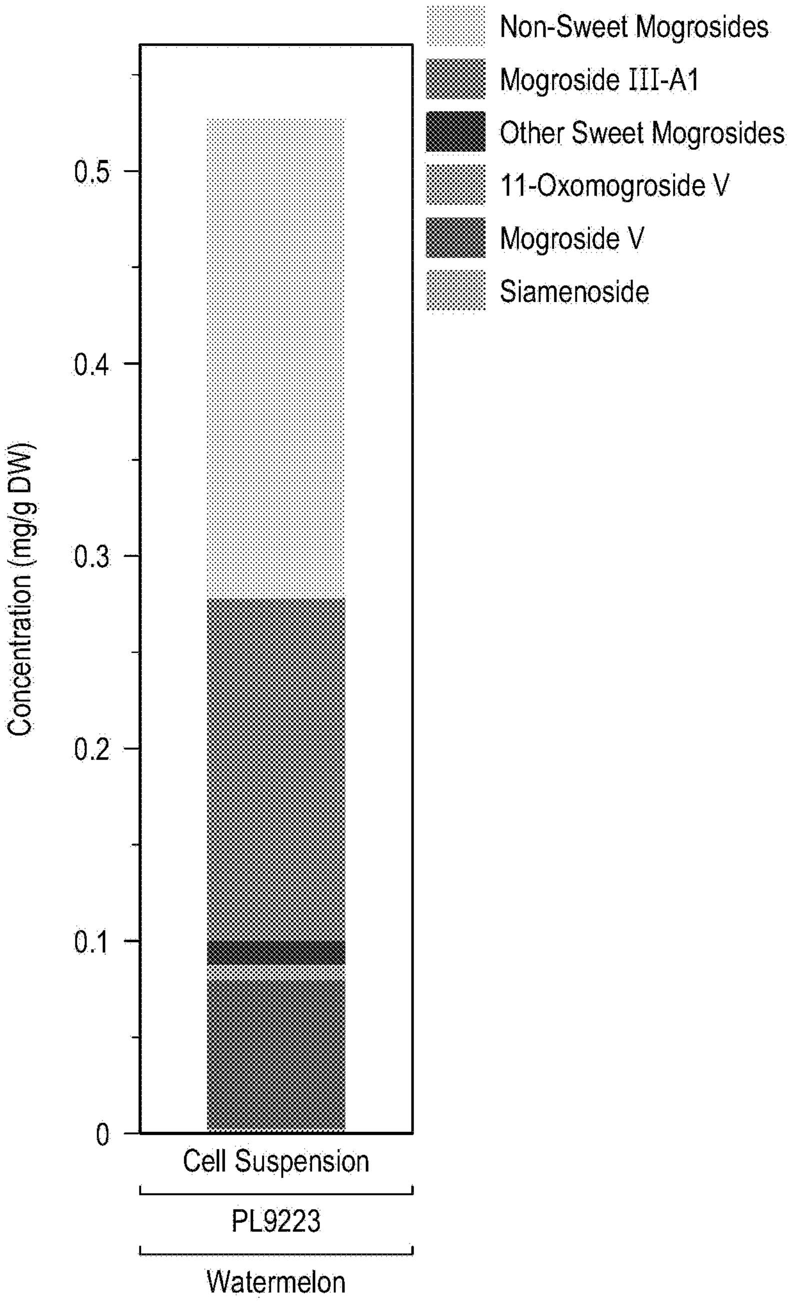
FIG. 20. Concentration of mogrosides and siamenoside in transgenic watermelon cell suspension.

A watermelon cell suspension was established that produces mogrosides. Cells originated from anther-derived callus induced from the immature flowers of a transgenic watermelon plant (transgenic construct=SP3190). After one month, the culture increased 4-5× in volume every 7 days. To determine amount and type of mogrosides in the cell suspension, approximately 1 mL of packed settled cell volume from a 7-day old culture was transferred to a 2 mL collection tube and the contents were centrifuged at 12,000×g for 10 minutes, the supernatant was removed and the samples were flash frozen in liquid nitrogen, and the samples were then analyzed for mogrosides and siamenoside. Mogroside measurements of the cell suspension by collection date are shown in FIG. 19 (samples with the same date are technical replicates). The concentration of mogrosides and siamenoside in transgenic watermelon cell suspension is shown in FIG. 20.

Example 6

Transgenic Tomato Plants

Various expression cassettes selected from Example 1 were used for transforming *Solanum lycopersicum. Agrobacterium tumefaciens* strain EHA105 was transformed with one or more expression cassette plasmids (selected from Example 1) using a free-thaw method (Weigel, CSH Protoc. 2006 Dec. 1; 2006 (7): pdb.ip29. doi: 10.1101/pdb.ip29). Briefly, chemically competent *Agrobacterium* was prepared. After addition of the expression cassette plasmids, the mixture was alternately frozen in liquid nitrogen and thawed to liquid in a 37° C. water bath. The cells were then allowed to recover in LB medium for about 1 hour and plated out on LB plates with kanamycin.

Briefly, the transformed EHA105 *Agrobacterium* was grown overnight and then diluted until the $OD_{600}$ reading reached 0.3. Two varieties of tomato, MicroTom and MoneyMaker, were used as hosts. Six-to-Seven-day-old tomato seedlings were used for preparing explants for transformation. Cotyledons and hypocotyles were cut off from seedlings and collected in petri plates filled with sterile water. Once all explants have been prepared, the water is removed from each plate by pipetting, being careful to not remove or excessively damage the explants. The cotyledons are immersed in 20-30 mL of *Agrobacterium* suspension, the plates are sealed and gently shaken at 50 rpm for 15 minutes. These explants, without excess bacteriual, are then placed on tomato co-cultivation media (Table 1).

TABLE 1

| Ingredient or Action | Amount |
|---|---|
| MS Media + Gamborg Vitamins (M404) | 1× |
| Sucrose (3%) | 30 g/L |
| Glucose (0.2%) | 2 g/L |
| pH to 5.6 | |
| 500 mL + 1.5 g Gelzan (G215) | 3 g/L Gelzan |
| BAP | 1 mg/L |
| NAA | 0.1 mg/L |
| Acetosyringone | 200 μM |

After 2 days of co-culture, transfer explants to Tomato Selection Media (TSM; Table 2), abaxial side up, 14-18 explants per plate depending on their size. Growth conditions are 16 hour photoperiod (provided by 20 watt cool-white fluorescent tubes yielding a light intensity of 30 μmol/m2/sec) at 25° C.

TABLE 2

| Ingredient or Action | Amount |
|---|---|
| MS Media + Gamborg Vitamins (M404) | 1× |
| Sucrose | 30 g/L |
| pH to 5.6 | |
| 500 mL + 1.5 g Gelzan (G215) | 3 g/L Gelzan |
| Autoclave 25 minutes | |
| IAA | 0.1 mg/L |
| Zeatin | 2 mg/L |
| Hygromycin | 25 mg/L |
| Timentin | 400 mg/L |

Subculture regularly every 2 weeks transferring to new TSM media. Transgenic events are then selected based on gene expression and mogroside accumulation.

The levels of various mogrosides and siamenoside were measured in the fruit and leaves of various transgenic tomato lines comprising expression cassettes SP0641, SP1463, SP1908, SP3016, SP3029, SP3190 and SP3684. Higher amounts of mogrosides were produced compared to siamenoside.

Example 7

Transgenic Potato Plants

Various expression cassettes selected from Example 1 were used for transforming potato. *Agrobacterium tumefaciens* strain EHA105 was transformed with one or more expression cassette plasmids (selected from Example 1) using a free-thaw method (Weigel, CSH Protoc. 2006 Dec. 1; 2006 (7): pdb.ip29. doi: 10.1101/pdb.ip29). Briefly, chemically competent *Agrobacterium* was prepared. After addition of the expression cassette plasmids, the mixture was alternately frozen in liquid nitrogen and thawed to liquid in a 37° C. water bath. The cells were then allowed to recover in LB medium for about 1 hour and plated out on LB plates with kanamycin.

Transformation to potato was performed based on a published protocol (Chronis, Bio protocol, 2014 DOI: 10.21769/BioProtoc.1017).

The levels of various mogrosides and siamenoside were measured in the fruit and leaves of various transgenic potato lines comprising expression cassettes SP0641, SP1463, SP3016, SP3029, SP3190 and SP3684. Higher amounts of mogrosides were produced compared to siamenoside.

Figure 52:
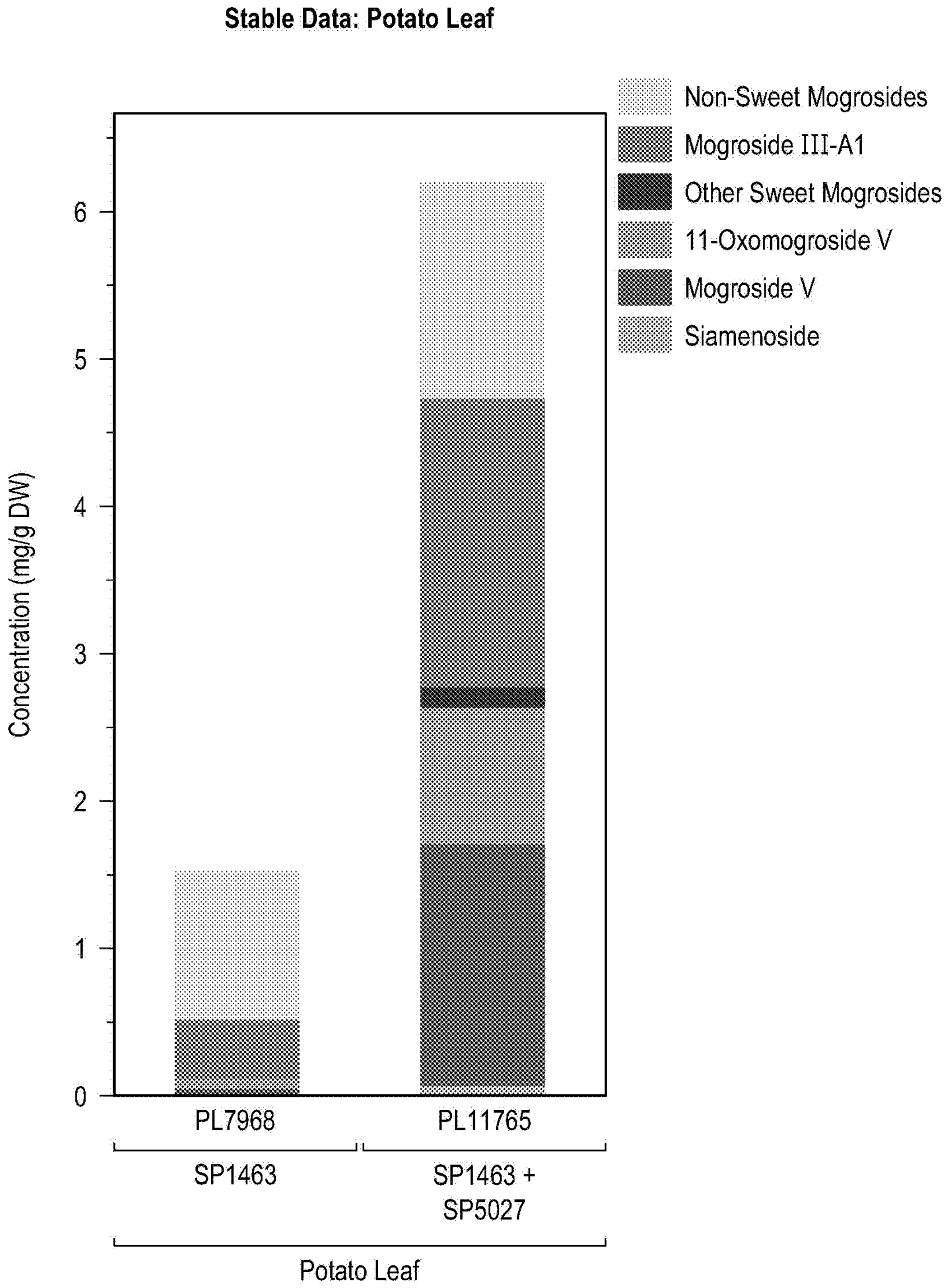
FIG. 52. Concentration of mogrosides and siamenoside in transgenic potato transformed with vector SP1463 and then re-transformed that transgenic event with SIUGT (SP5027).

Additional studies were performed by transforming potato with vector SP1463 and then re-transforming that transgenic event with SIUGT (SP5027). The results are shown in FIG. 52. The results show that transgenic potatoes were produced with up to 6 mg/g total mogrosides and almost 5 mg/g sweet mogrosides.

Example 8

Transgenic Lettuce Plants

Various expression cassettes selected from Example 1 were used for transforming lettuce (*Lactuca sativa*). *Agrobacterium tumefaciens* strain EHA105 was transformed with one or more expression cassette plasmids (selected from Example 1) using a free-thaw method (Weigel, CSH Protoc. 2006 Dec. 1; 2006 (7): pdb.ip29. doi: 10.1101/pdb.ip29). Briefly, chemically competent *Agrobacterium* was prepared. After addition of the expression cassette plasmids, the mixture was alternately frozen in liquid nitrogen and thawed to liquid in a 37° C. water bath. The cells were then allowed to recover in LB medium for about 1 hour and plated out on LB plates with kanamycin.

Briefly, the transformed EHA105 *Agrobacterium* was grown overnight and then diluted until the $OD_{600}$ reading reached 0.3. Five-day-old lettuce seedlings were used for preparing explants for transformation. Cotyledons were cut off from seedlings and collected in petri plates filled with sterile water. Once all explants have been prepared, the water is removed from each plate by pipetting, being careful to not remove or excessively damage the explants. The cotyledons are immersed in 20-30 mL of *Agrobacterium* suspension, the plates are sealed and gently shaken at 50 rpm for 10 minutes. These explants, without excess bacteriual, are then placed on tomato co-cultivation media (Table 3).

TABLE 3

| Ingredient or Action | Amount |
|---|---|
| MS Media + Vitamins (M519) | 1× |
| Sucrose (3%) | 30 g/L |
| pH to 5.7 | |
| 500 mL + 1.5 g Gelzan | 3 g/L Gelzan |
| Autoclave 25 minutes | |
| BAP | 0.5 mg/L |
| NAA | 0.1 mg/L |
| Acetosyringone | 50 μM |

After 3 days of co-culture, transfer explants to Lettuce Selection Media (LSM; Table 4), abaxial side up, 10 explants per plate depending on their size.

TABLE 4

| Ingredient or Action | Amount |
|---|---|
| MS Media + Vitamins (M519) | 1× |
| Sucrose | 30 g/L |
| pH to 5.7 | |
| 500 mL + 1.5 g Gelzan | 3 g/L Gelzan |
| Autoclave 25 minutes | |
| NAA | 0.1 mg/L |
| BAP | 0.5 mg/L |
| Hygromycin | 12.5 mg/L |
| Timentin | 400 mg/L |

Subculture regularly every 2 weeks transferring to new LSM media. Transgenic events are then selected based on gene expression and mogroside accumulation.

Example 9

Transgenic Sugar Beet Plants

Various expression cassettes selected from Example 1 were used for transforming sugar beet. *Agrobacterium tumefaciens* strain EHA105 was transformed with one or more expression cassette plasmids (selected from Example 1) using a free-thaw method (Weigel, CSH Protoc. 2006 Dec. 1; 2006 (7): pdb.ip29. doi: 10.1101/pdb.ip29). Briefly, chemically competent *Agrobacterium* was prepared. After addition of the expression cassette plasmids, the mixture was alternately frozen in liquid nitrogen and thawed to liquid in a 37° C. water bath. The cells were then allowed to recover in LB medium for about 1 hour and plated out on LB plates with kanamycin.

Briefly, the transformed EHA105 *Agrobacterium* was grown overnight and then diluted until the $OD_{600}$ reading reached 0.6. Sugar beet calli were used as explants for transformation. The materials were immersed in 20-30 mL of *Agrobacterium* suspension, the plates are sealed and gently shaken at 50 rpm for 15 minutes. These explants, without excess bacteria, are then placed on sugar beet co-cultivation media (Table 5).

TABLE 5

| Ingredient or Action | Amount |
|---|---|
| MS Media + Vitamins | 1× |
| Sucrose (3%) | 30 g/L |
| Glucose (0.2%) | 6 g/L |
| pH to 5.7 | |
| BAP | 1 mg/L |
| Acetosyringone | 200 µM |

After 3 days of co-culture, transfer explants to Sugar Beet Selection Media (SBSM; Table 6). Growth in dark at 25° C.

TABLE 6

| Ingredient or Action | Amount |
|---|---|
| MS Media + MS Vitamins | 1× |
| Sucrose | 30 g/L |
| pH to 5.7 | |
| Agar | 6 g/L |
| BAP | 1 mg/L |
| Hygromycin | 10 mg/L |
| Timentin | 400 mg/L |

Subculture regularly every 4 weeks transferring to new TSM media. Transgenic events are then selected based on gene expression and mogroside accumulation.

Studies were performed by transforming sugar beet with vector SP3684 and measuring mogrosides in callus. Higher amounts of mogrosides were produced compared to siamenoside.

The results show that transgenic sugar beet callus transformed with vector SP3684 produced 0.4 mg/g total mogrosides.

Example 10

Production of Mogrosides in Yeast

Production of mogrosides in yeast has been described previously (see, e.g., U.S. Pat. Nos. 10,465,222, 10,633,685 and 11,060,124, each of which is incorporated herein by reference in its entirety). By replacing one or more of the enzymes previously used to produce mogrosides with one or more of the enzymes disclosed herein, or by adding one of the CYP72 enzymes disclosed herein to the enzymes previously used to produce mogrosides, the present disclosure also provides methods for producing mogrosides in yeast, using control elements for expression of the nucleic acid sequences in yeast that are well-known to those of skill in the art or control elements previously described.

Example 11

Production of Siamenoside I

Using the presently disclosed methods for the production of mogrosides in plants and other organisms, siamenoside I can be produced by a number of different methods. First, starting with a plant or organism that produces mogroside V (such as plants and organisms disclosed herein), the plant or organism can be engineered to express enzymes such as glucan 1,3-beta-glucosidase I/II (ExgI) or DbExgI (see U.S. Pat. No. 11,180,789, incorporated herein by reference in its entirety) to convert mogroside V to siamenoside I and various mogroside II compounds, such as mogroside III E. Second, starting with a plant or organism that produces mogroside III E (such as plants and organisms disclosed above or elsewhere herein), the plant or organism can be engineered to express enzymes such as UGT-M2 (Xu, et al., *J. Agric. Food Chem.* 70:1601-1609, 2022) to convert mogroside III E to siamenoside I. Third, starting with a plant or organism that produces mogroside III A1 (such as plants and organisms disclosed herein), the plant or organism can be engineered to express enzymes such as UGT-74_345_2 or UGT74_406_2 (Itkin et al., *Proc Nat Acad Sci USA* 113: E7619-E7628, 2016) to convert mogroside III E to siamenoside I.

Example 12

Production of α-Siamenoside I

Starting with a plant or organism that produces mogrosides (such as plants and organisms disclosed herein), the plant or organism can be engineered to express enzymes such as those disclosed in U.S. Pat. No. 11,060,124 (incorporated herein by reference in its entirety) to convert mogrosides to compound 1 (α-siamenoside I). Alternatively, starting with a plant or organism that produces mogrosides (such as plants and organisms disclosed herein), the plant or organism can be engineered to express cyclodextrin glycosyltransferases (CGTases; Xu et al., *Food Chem.* 359:October 2021, doi.org/10.1016/j.foodchem.2021.129938) to convert mogrosides to α-siamenoside I.

Example 13

Co-Production of Mogrosides and Rebaudioside M

Biosynthesis of Rebaudioside M (RebM) in recombinant host cells has previously been described (PCT Patent Application Publication No. WO 2014/122227, incorporated herein by reference in its entirety). Starting with a plant or organism that produces mogrosides (such as plants and organisms disclosed herein), the plant or organism can be engineered to express the enzymes to produce Reb M to produce plants or organisms that produce mogrosides and Reb M, in the same cells. Alternatively, plants or organisms that are transformed to express Reb M pathway genes can be crossed with plants or organisms that express mogroside pathway genes (as disclosed herein), to produce plants or organisms that contain both pathways at the same time and produce a mixture of mogrosides and Reb M.

In addition, the following UGT enzymes can be used with rebaudioside biosynthesis genes to further improve the efficiency for biosynthesis of certain rebaudiosides in plants or other organisms: UGT76G1 T284S mutant (Liu et al., *Plant Commun.* 1:Jan. 13, 2020, doi.org/10.1016/j.xplc.2019.100004); UGT76G1 S195Q mutant (Yu et al., *J. Funct. Foods* 92: May 2022, doi.org/10.1016/j.jff.2022.105033); or *Oryza sativa* EUGT11 (Wang et al., *Int. J. Biol. Macromol.* 163:1669-1676, 2020).

Example 14

Detection of Non-Canonical Mogroside Isomers

Several non-canonical mogroside isomers are observed to a varying degree when vectors like SP3684 are transformed into many species, with some like tomato yielding prominent quantities of these isomers, and others like watermelon yielding minor quantities of these isomers. Because these non-canonical mogroside isomers show up at the same mass as mogrosides with two to five glucose groups and their 11-oxo forms, they likely have a glucose group added at a different position than the mogroside standards. Various mogrosides and non-canonical mogroside isomers were detected in transient watermelon fruit co-infiltrations with the construct SP3684 enhanced in t72143 (uridine phosphorylase dependent glycosyltransferase; SEQ ID NO: 138; SP5041) relative to green fluorescent protein (GFP).

Figure 21:
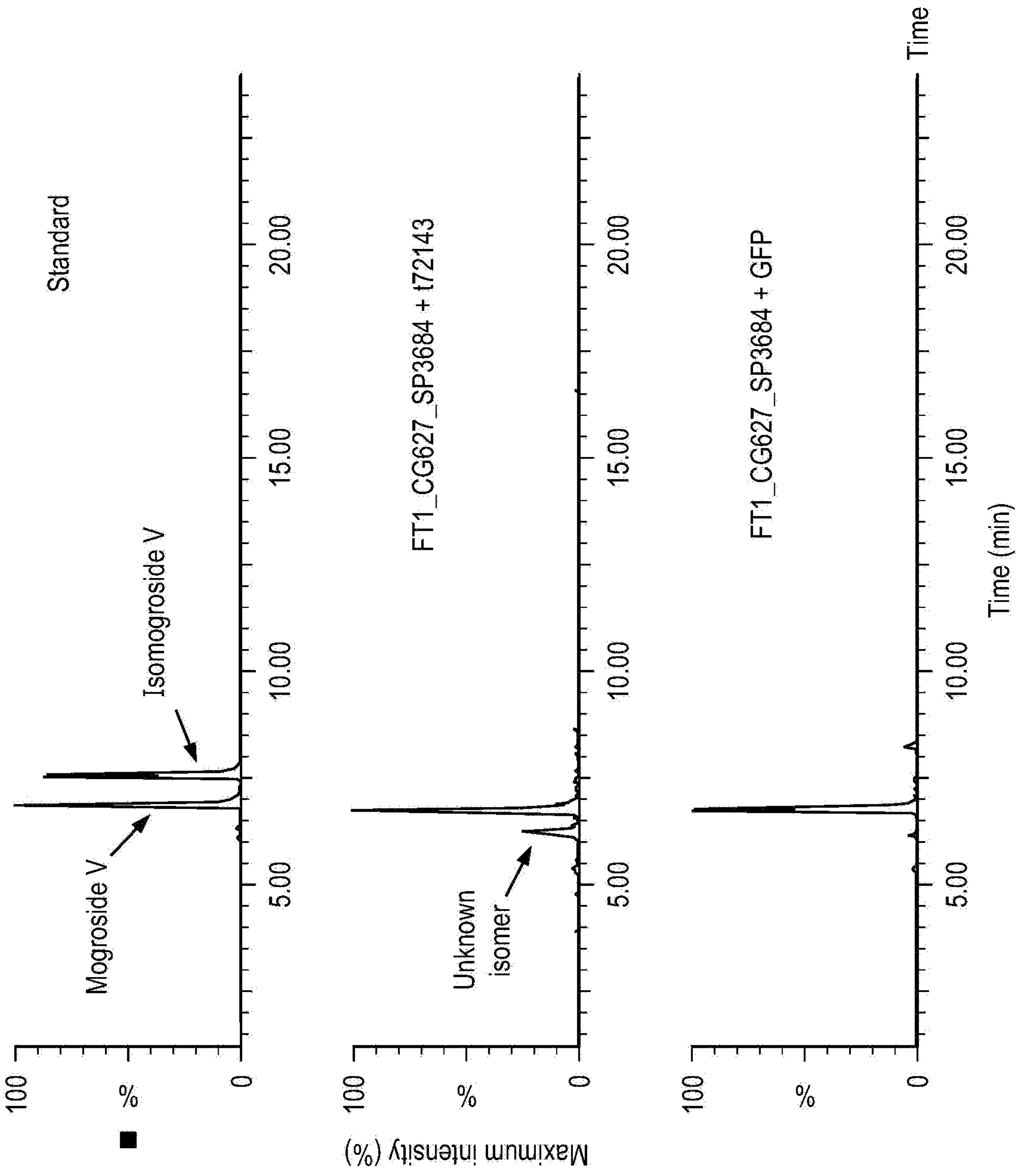
FIG. 21. Production of mogroside V and unknown mogroside V isomer in transient watermelon fruit co-infiltrated with the construct SP3684 and either t72143 or green fluorescent protein (GFP).
Figure 22:
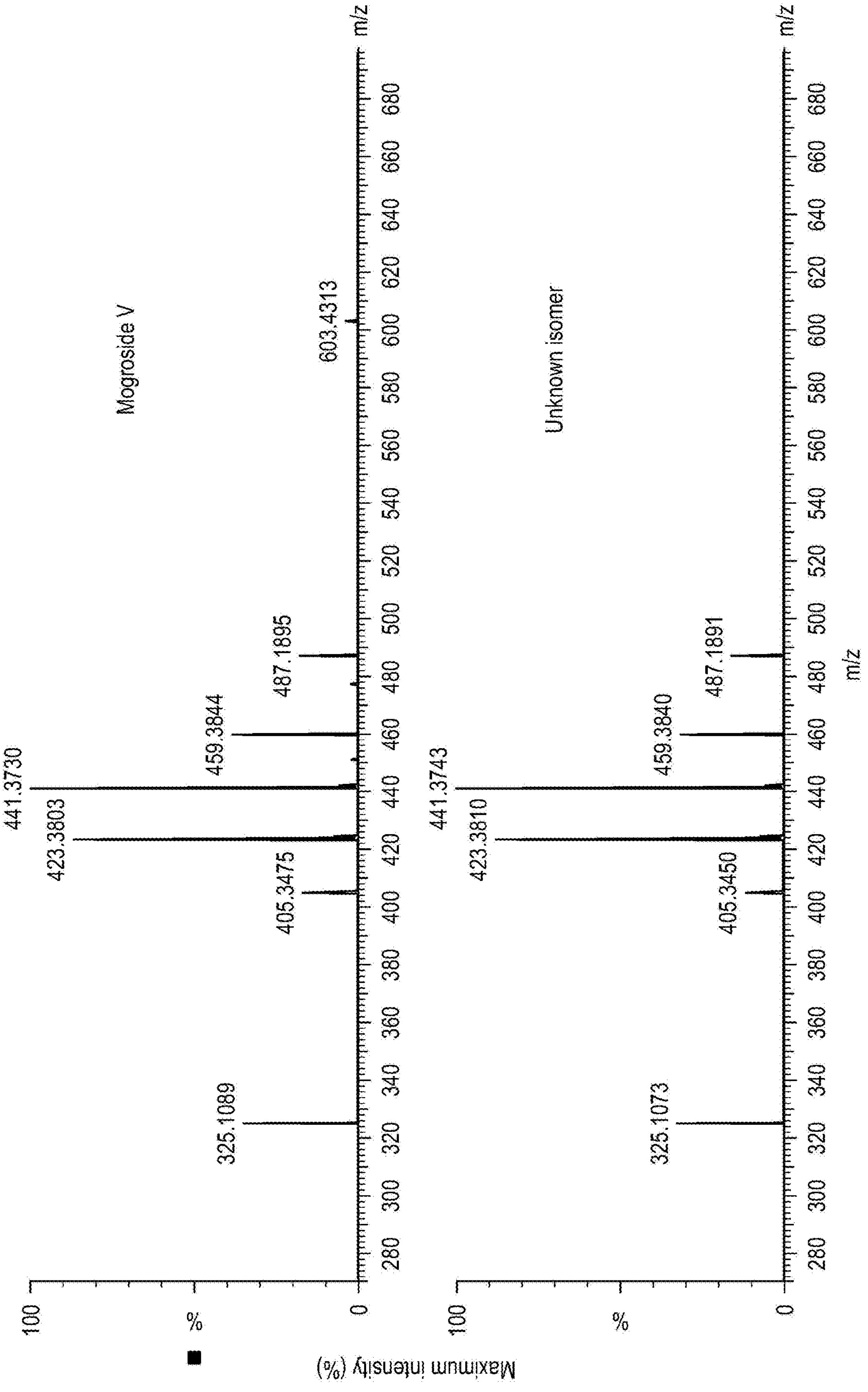
FIG. 22. Mass spectrum fingerprinting of mogroside V and the unknown mogroside V isomer.

Mogroside V and isomers accumulation in transient assays is shown in FIG. 21. For mogroside V, acquire data in TofMSMS ESI positive mode, selecting for mogroside V plus a proton (1287.6580 m/z), using the collision energy 30 V, and collecting a full high-resolution mass scan (270-1350 m/z) for resulting fragments. The chromatograms shown are selected for the fragment mass 423.3621 m/z with a 0.02 Da mass window. Mogroside V fragment mass 423.3603 m/z is 4.3 ppm error compared to the theoretical 423.3621 m/z. Unknown peak is 423.3610 m/z is 2.7 ppm error compared to the theoretical 423.3621 m/z. 5 ppm is considered an acceptable cutoff for high resolution mass error. Mogroside V and isomers accumulation in transient assays is shown in FIG. 21. The production of mogroside V and isomogroside V in transient watermelon fruit infiltrated with the construct SP3684 is shown in FIG. 21, top panel. It can be seen that an unknown mogroside V isomer was produced when SP3684 was co-infiltrated with t72143 (FIG. 21, middle panel), compared to SP3684 co-infiltrated with GFP (FIG. 21, bottom panel). FIG. 22 shows the mass spectrum fingerprinting of mogroside V (top panel) and the unknown mogroside V isomer (bottom panel).

Figure 23:
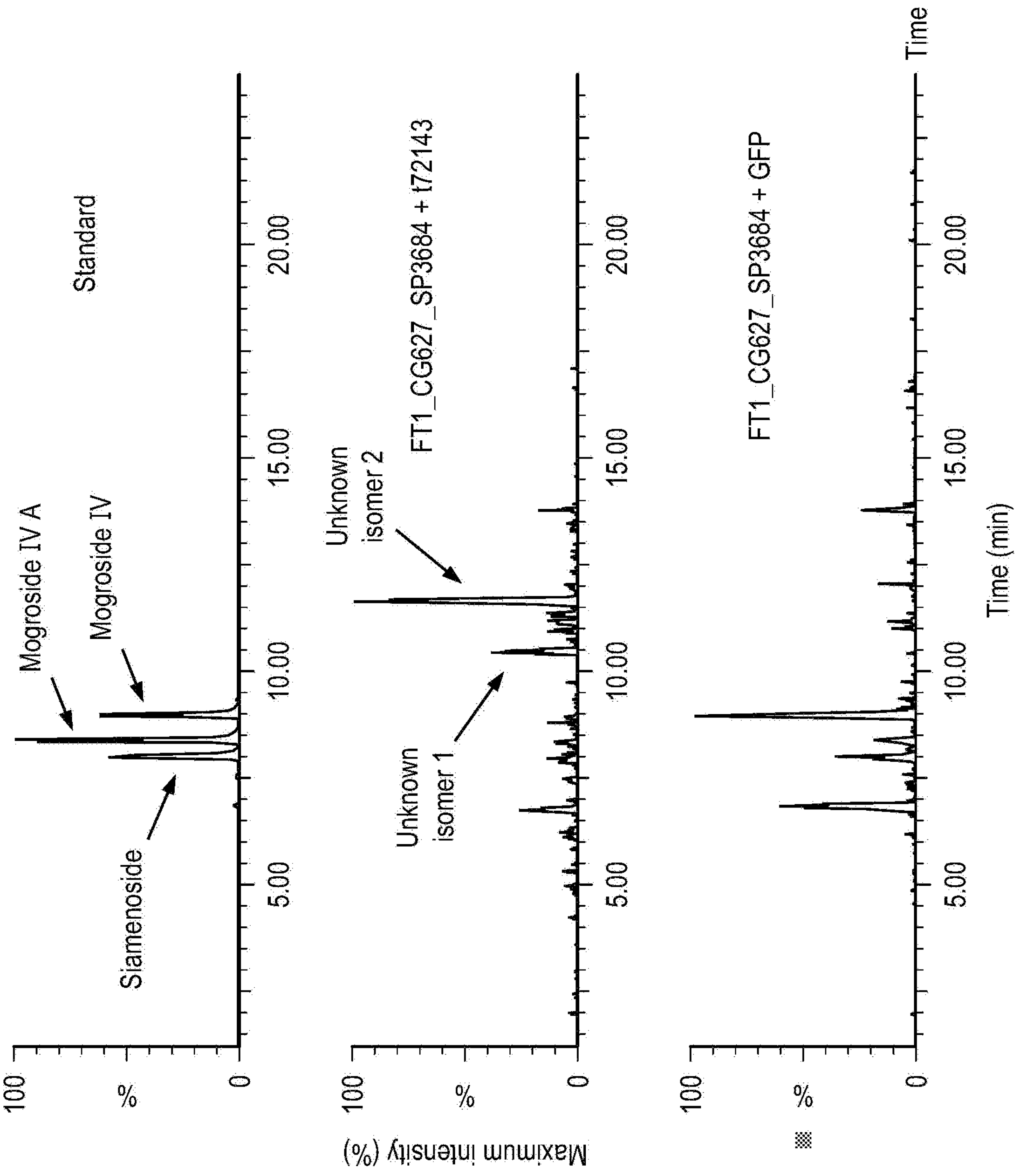
FIG. 23. Production of mogroside IV and unknown mogroside IV isomers in transient watermelon fruit co-infiltrated with the construct SP3684 and either t72143 or green fluorescent protein (GFP).
Figure 24:
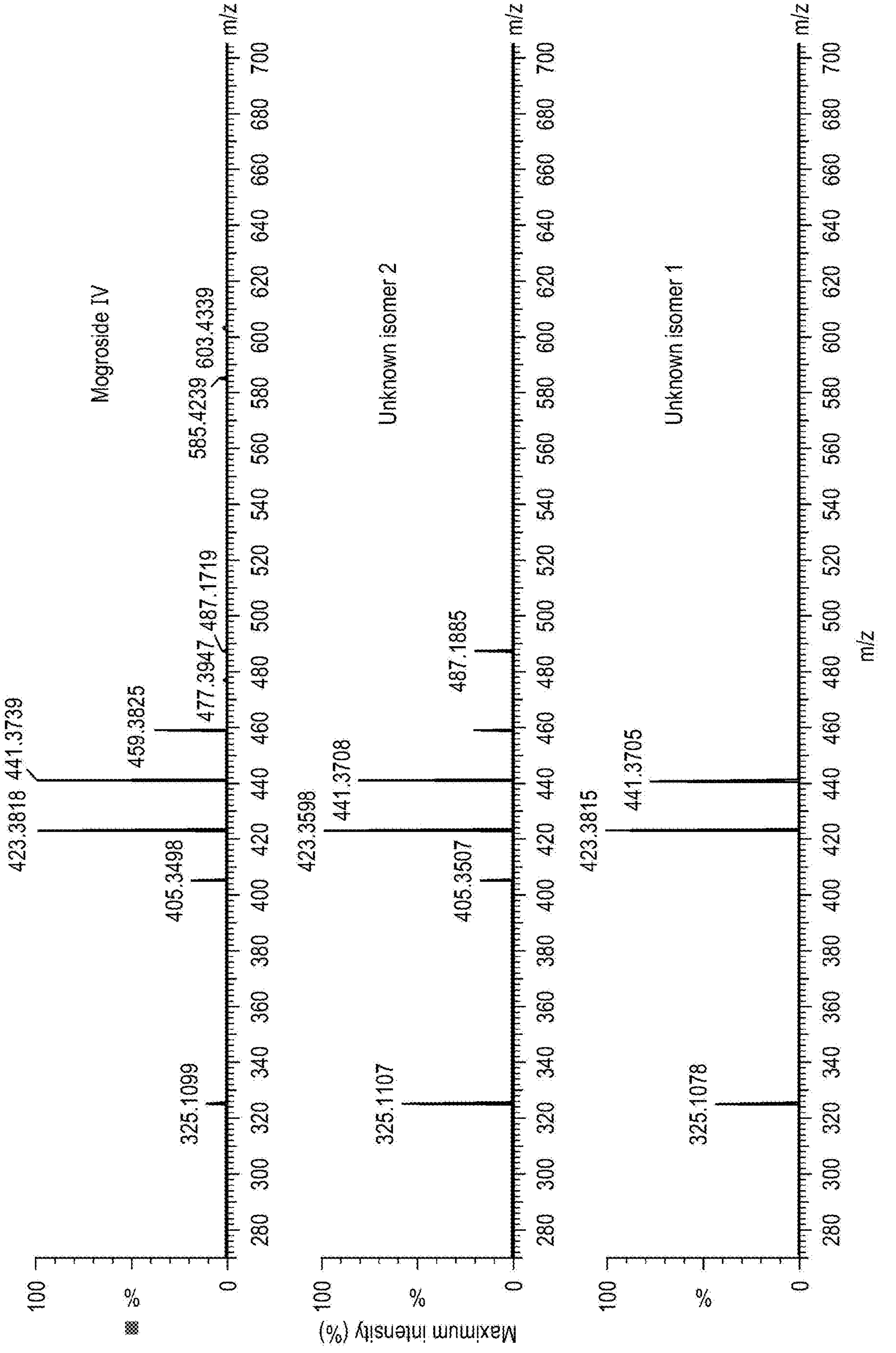
FIG. 24. Mass spectrum fingerprinting of mogroside IV and the unknown mogroside IV isomers.

Mogroside IV and isomers accumulation in transient assays is shown in FIG. 23. For mogroside IV, acquire data in TofMSMS ESI positive mode, selecting for the mogroside IV plus a proton (1125.6051 m/z), using the collision energy 30 V, and collecting a full high-resolution mass scan (270-1350 m/z) for resulting fragments. The chromatograms shown are selected for the fragment mass 423.3621 m/z with a 0.02 Da mass window. Mogroside IV fragment mass 423.3616 m/z is 1.3 ppm error compared to the theoretical 423.3621 m/z. Unknown peak 2 is 423.3596 m/z is 6.0 ppm error compared to the theoretical 423.3621 m/z. Unknown peak 1 is 423.3615 m/z is 1.5 ppm error compared to the theoretical 423.3621 m/z. Missing peaks are likely due to the low intensity of this peak. 5 ppm is considered an acceptable cutoff for high resolution mass error. The production of mogroside IV, mogroside IV-A and siamenoside in transient watermelon fruit infiltrated with the construct SP3684 is shown in FIG. 23, top panel. It can be seen that two unknown mogroside IV isomers were produced when SP3684 was co-infiltrated with t72143 (FIG. 23, middle panel), compared to SP3684 co-infiltrated with GFP (FIG. 23, bottom panel). FIG. 24 shows the mass spectrum fingerprinting of mogroside IV (top panel) and the unknown mogroside IV isomers (middle and bottom panels).

Figure 25:
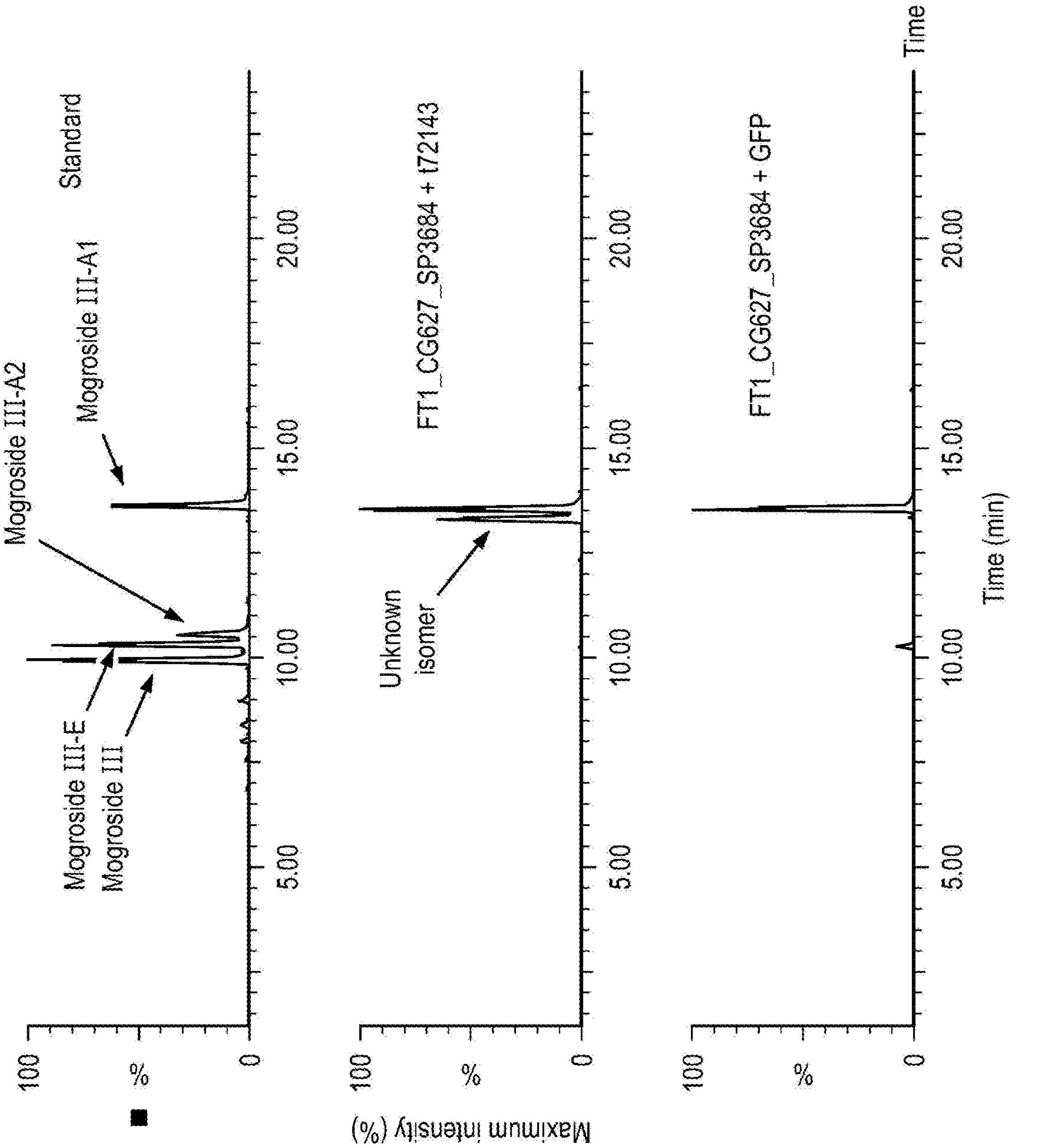
FIG. 25. Production of mogroside III and unknown mogroside III isomer in transient watermelon fruit co-infiltrated with the construct SP3684 and either t72143 or green fluorescent protein (GFP).
Figure 26:
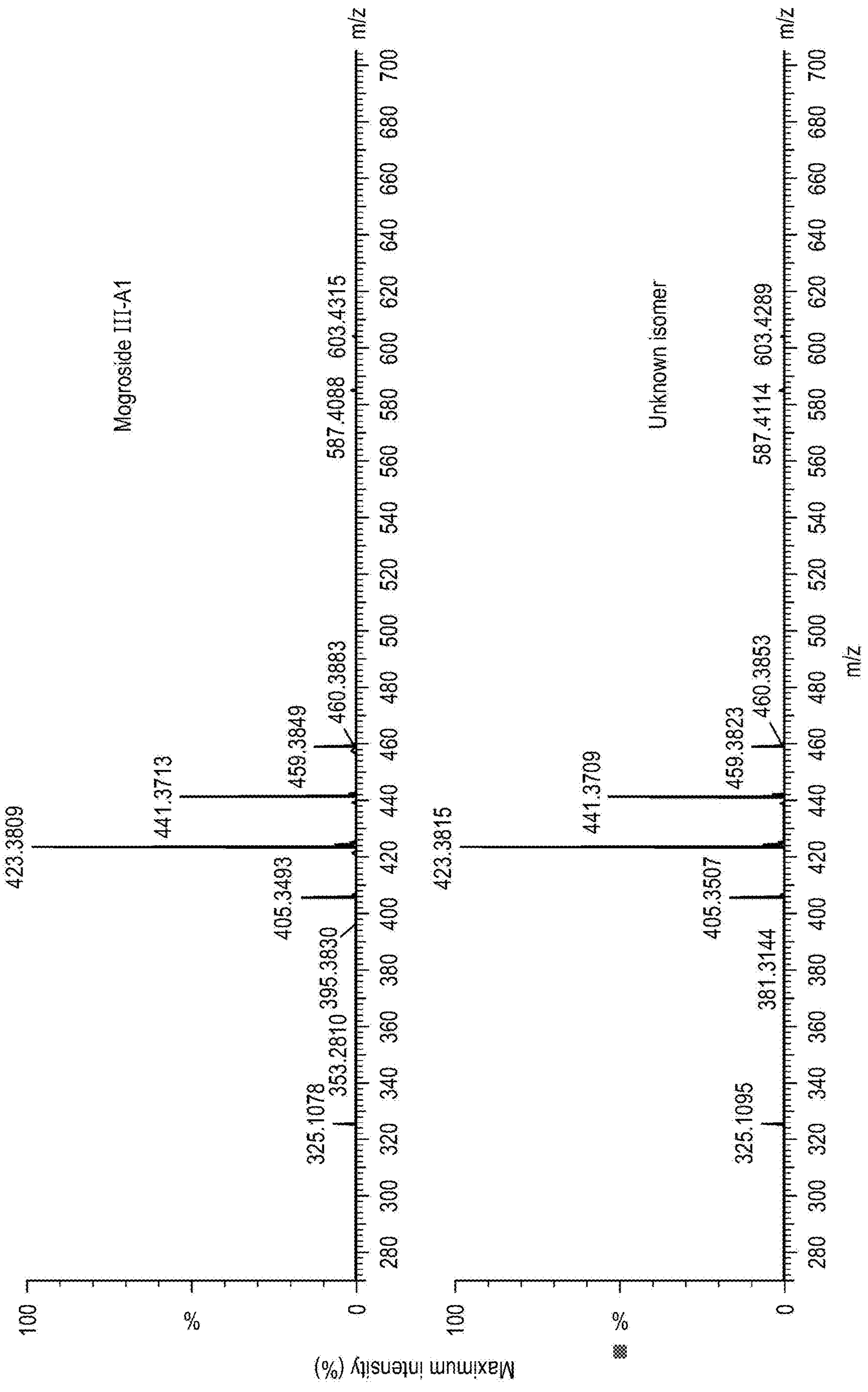
FIG. 26. Mass spectrum fingerprinting of mogroside III and the unknown mogroside III isomer.

Mogroside III and isomers accumulation in transient assays is shown in FIG. 25. For mogroside III, acquire data in TofMSMS ESI positive mode, selecting for the mogroside III plus a proton (963.5523 m/z), using the collision energy 30 V, and collecting a full high-resolution mass scan (270-1350 m/z) for resulting fragments. The chromatograms shown are selected for the fragment mass 423.3621 m/z with a 0.02 Da mass window. Mogroside III-A1 fragment mass 423.3609 m/z is 2.9 ppm error compared to the theoretical 423.3621 m/z. Unknown peak is 423.3615 m/z is 1.5 ppm error compared to the theoretical 423.3621 m/z. 5 ppm is considered an acceptable cutoff for high resolution mass error. The production of mogroside III, mogroside III-E, mogroside III-A1 and mogroside III-A2 in transient watermelon fruit infiltrated with the construct SP3684 is shown in FIG. 25, top panel. It can be seen that an unknown mogroside V isomer was produced when SP3684 was co-infiltrated with t72143 (FIG. 25, middle panel), compared to SP3684 co-infiltrated with GFP (FIG. 25, bottom panel). FIG. 26 shows the mass spectrum fingerprinting of mogroside III-A1 (top panel) and the unknown mogroside III isomer (bottom panel).

Figure 27:
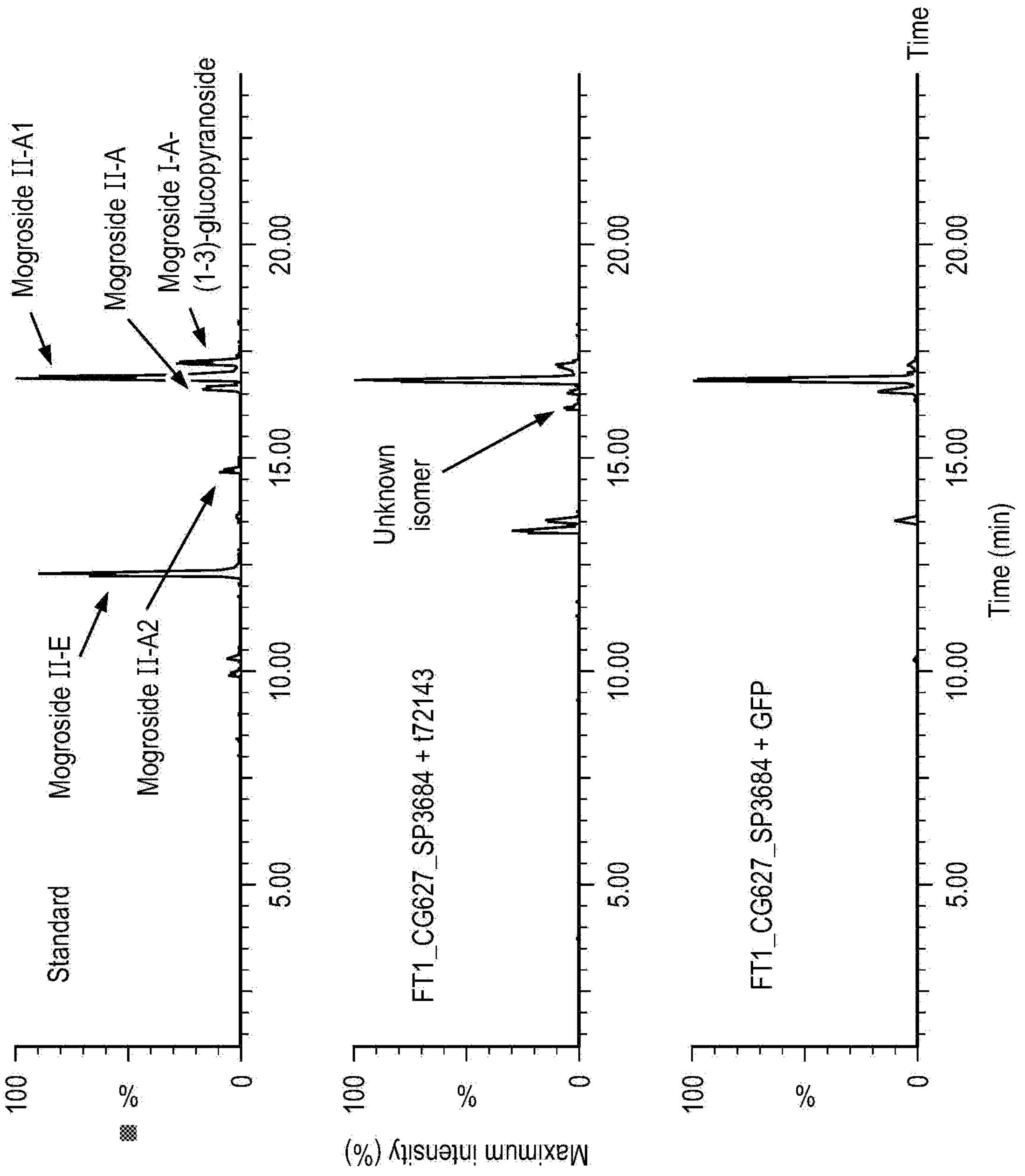
FIG. 27. Production of mogroside II and unknown mogroside II isomer in transient watermelon fruit co-infiltrated with the construct SP3684 and either t72143 or green fluorescent protein (GFP).
Figure 28:
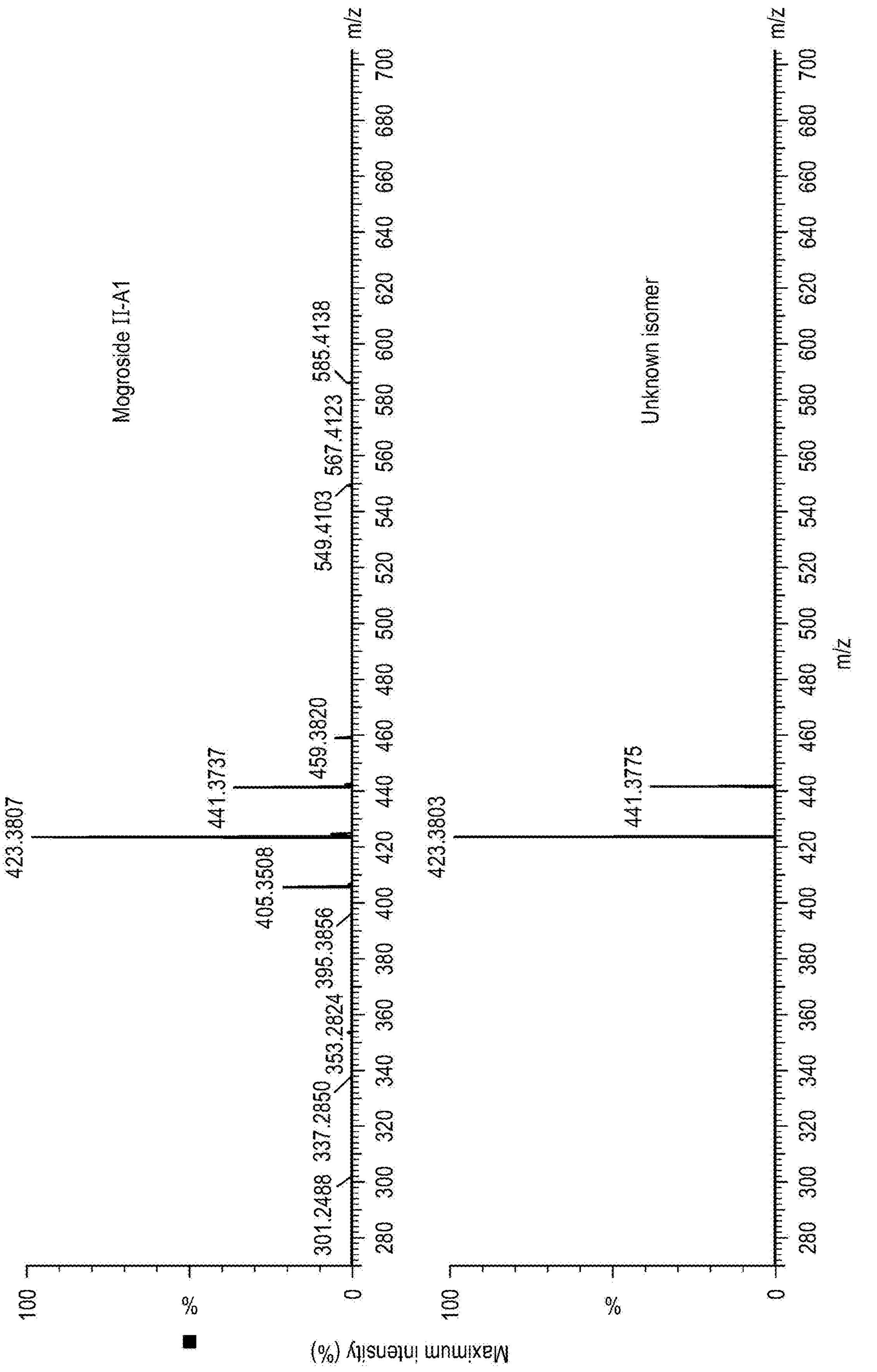
FIG. 28. Mass spectrum fingerprinting of mogroside II and the unknown mogroside II isomer.

Mogroside II and isomers accumulation in transient assays is shown in FIG. 27. For mogroside II, acquire data in TofMSMS ESI positive mode, selecting for the mogroside II plus a proton (801.4995 m/z), using the collision energy 30 V, and collecting a full high-resolution mass scan (270-1350 m/z) for resulting fragments. The chromatograms shown are selected for the fragment mass 423.3621 m/z with a 0.02 Da mass window. Mogroside II-A1 fragment mass 423.3607 m/z is 3.4 ppm error compared to the theoretical 423.3621 m/z. Unknown peak is 423.3603 m/z is 4.3 ppm error compared to the theoretical 423.3621 m/z. Missing peaks are likely due to the low intensity of this peak. 5 ppm is considered an acceptable cutoff for high resolution mass error. The production of mogroside II-A, mogroside II-A1, mogroside II A2, mogroside II-E and mogroside 1-A (1-3)-glucopyranoside in transient watermelon fruit infiltrated with the construct SP3684 is shown in FIG. 27, top panel. It can be seen that an unknown mogroside II isomer was produced when SP3684 was co-infiltrated with t72143 (FIG. 27, middle panel), compared to SP3684 co-infiltrated with GFP (FIG. 27, bottom panel). FIG. 28 shows the mass spectrum fingerprinting of mogroside II-A1 (top panel) and the unknown mogroside II isomer (bottom panel).

Figure 29:
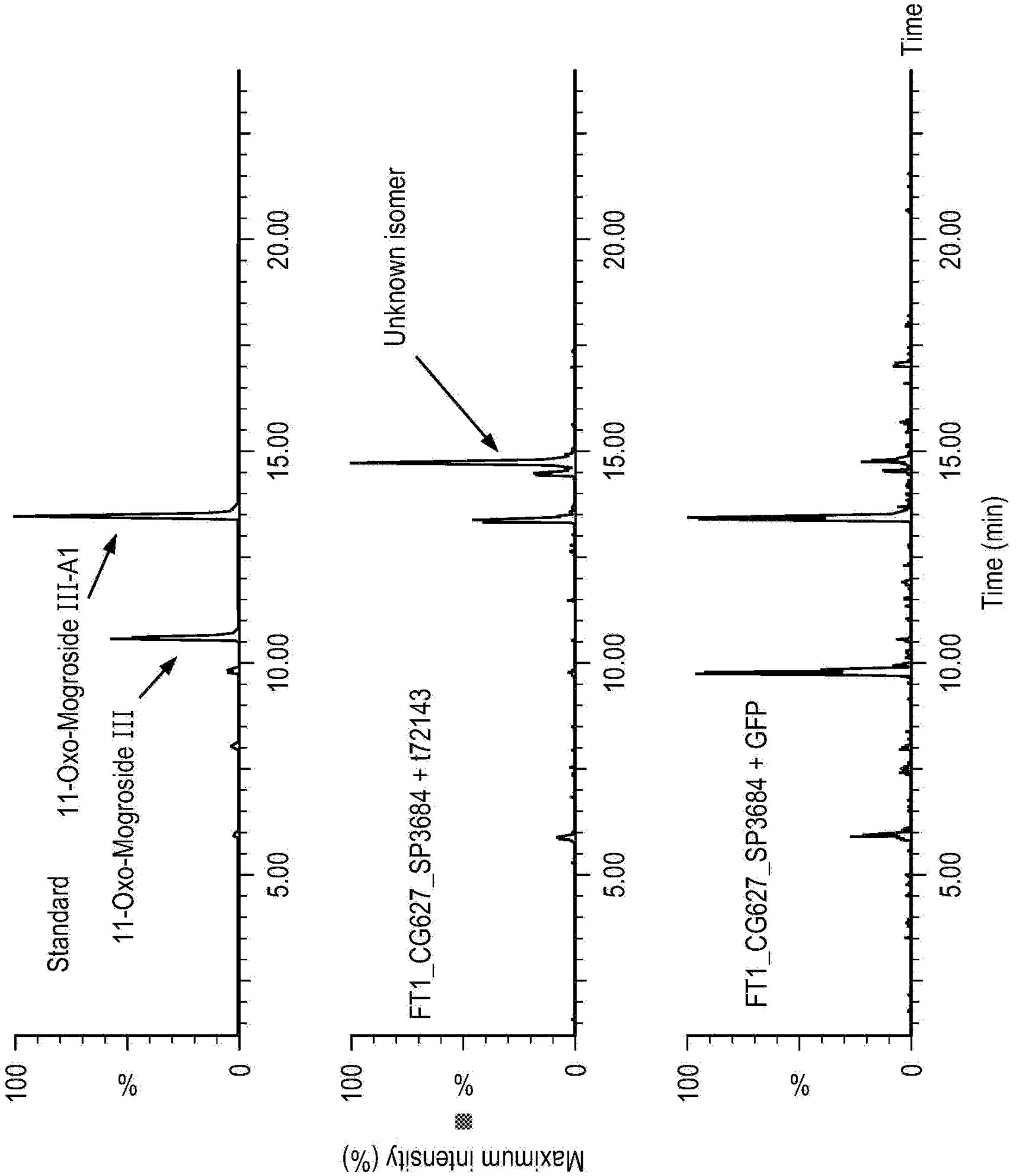
FIG. 29. Production of 11-oxo-mogroside III and unknown 11-oxo-mogroside III isomer in transient watermelon fruit co-infiltrated with the construct SP3684 and either t72143 or green fluorescent protein (GFP).
Figure 30:
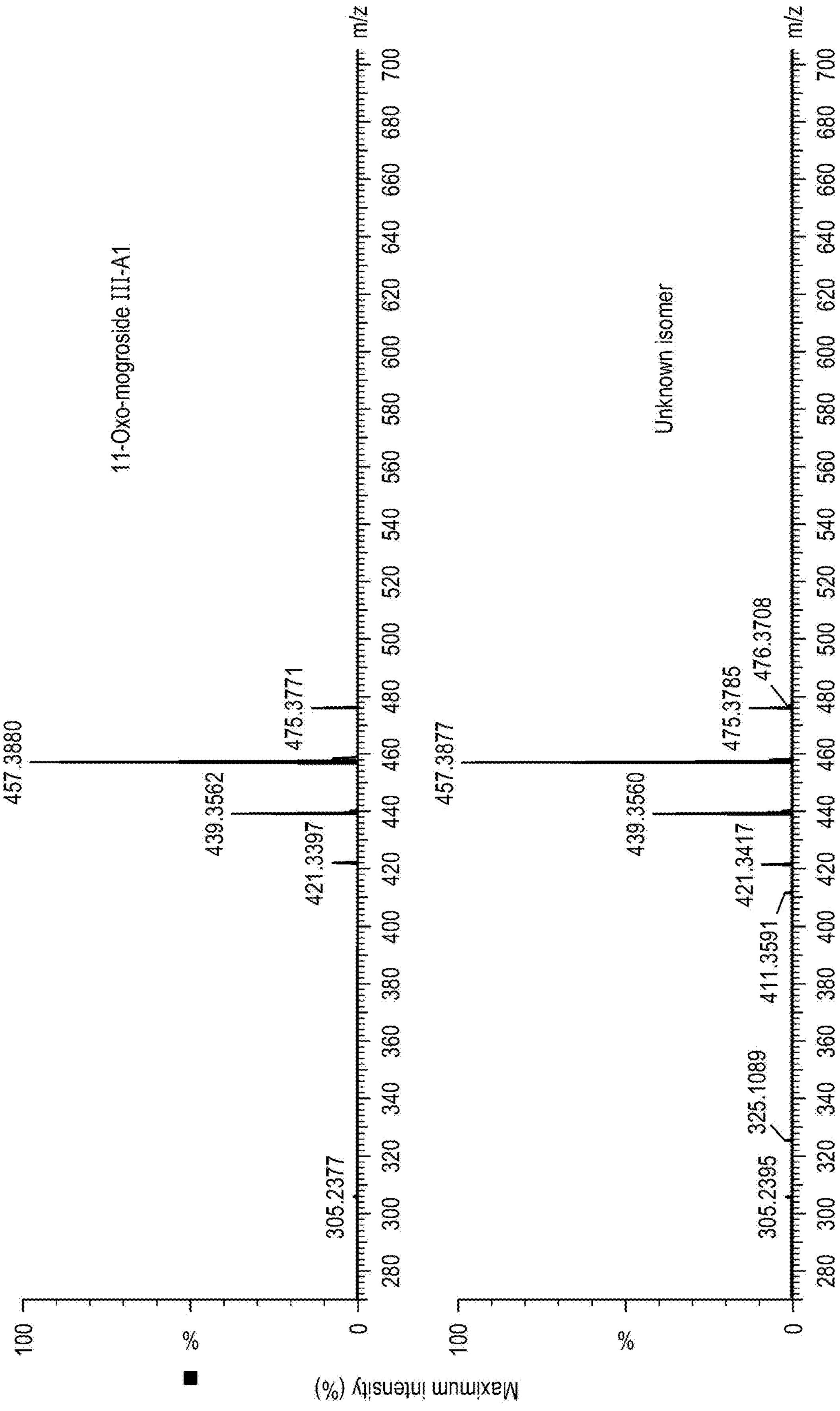
FIG. 30. Mass spectrum fingerprinting of 11-oxo-mogroside III and the unknown 11-oxo-mogroside III isomer.

11-oxo-mogroside III and isomers accumulation in transient assays is shown in FIG. 29. For 11-oxo-mogroside III, acquire data in TofMSMS ESI positive mode, selecting for the 11-Oxo-Mogroside III plus a proton (961.5367 m/z), using the collision energy 30 V, and collecting a full high-resolution mass scan (270-1350 m/z) for resulting fragments. The chromatograms shown are selected for the fragment mass 457.3677 m/z with a 0.02 Da mass window. 11-Oxo-Mogroside III-A1 fragment mass 457.3660 m/z is 3.7 ppm error compared to the theoretical 457.3677 m/z. Unknown peak is 457.3677 m/z is 0.0 ppm error compared to the theoretical 457.3677 m/z. 5 ppm is considered an acceptable cutoff for high resolution mass error. The production of 11-oxo-mogroside III and 11-oxo-mogroside III-A1 in transient watermelon fruit infiltrated with the construct SP3684 is shown in FIG. 29, top panel. It can be seen that an unknown 11-oxo-mogroside III isomer was produced when SP3684 was co-infiltrated with t72143 (FIG. 29, middle panel), compared to SP3684 co-infiltrated with GFP (FIG. 29, bottom panel). FIG. 30 shows the mass spectrum fingerprinting of 11-oxo-mogroside III (top panel) and the unknown 11-oxo-mogroside III isomer (bottom panel).

Figure 31:
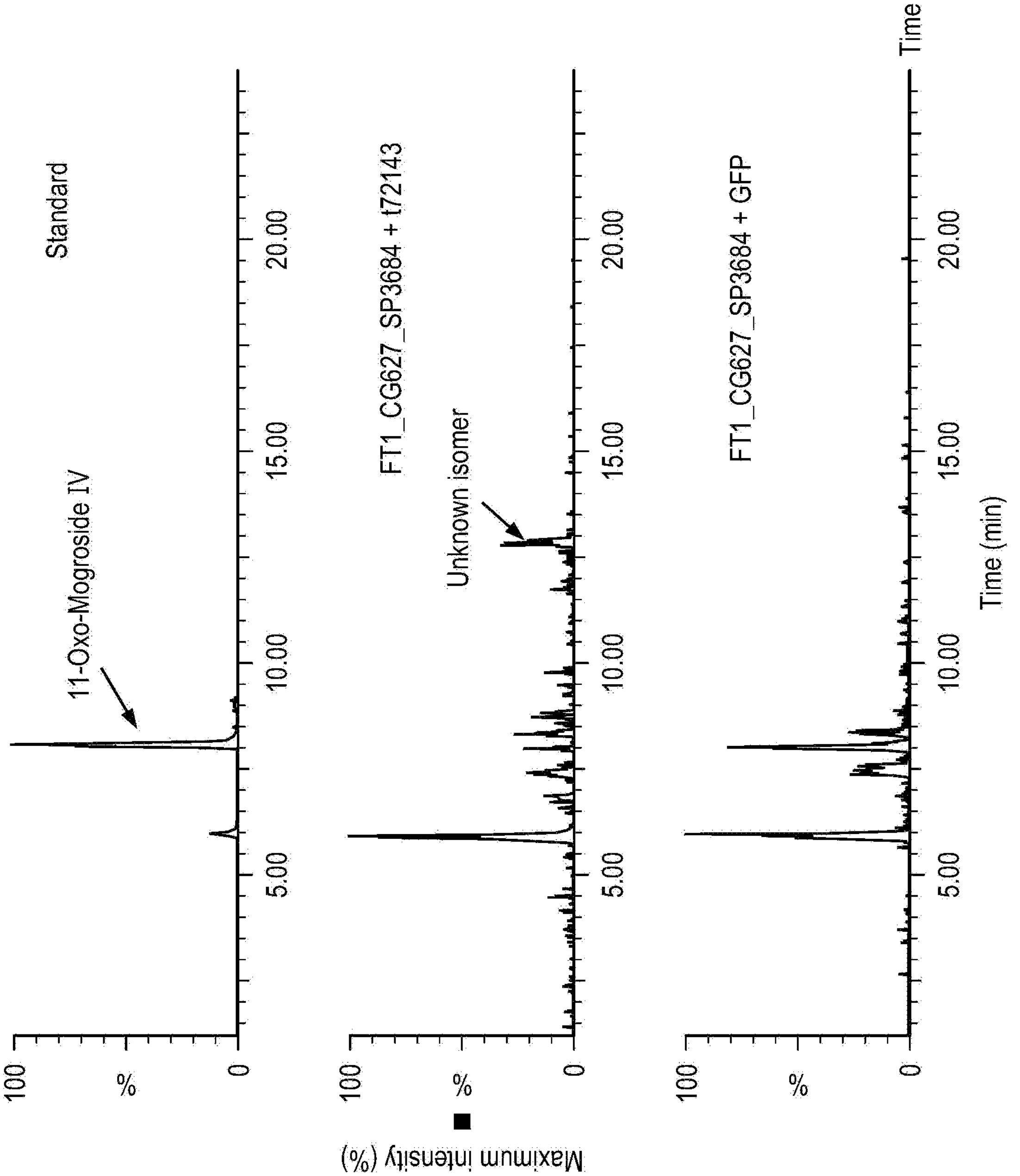
FIG. 31. Production of 11-oxo-mogroside IV and unknown 11-oxo-mogroside IV isomer in transient watermelon fruit co-infiltrated with the construct SP3684 and either t72143 or green fluorescent protein (GFP).
Figure 32:
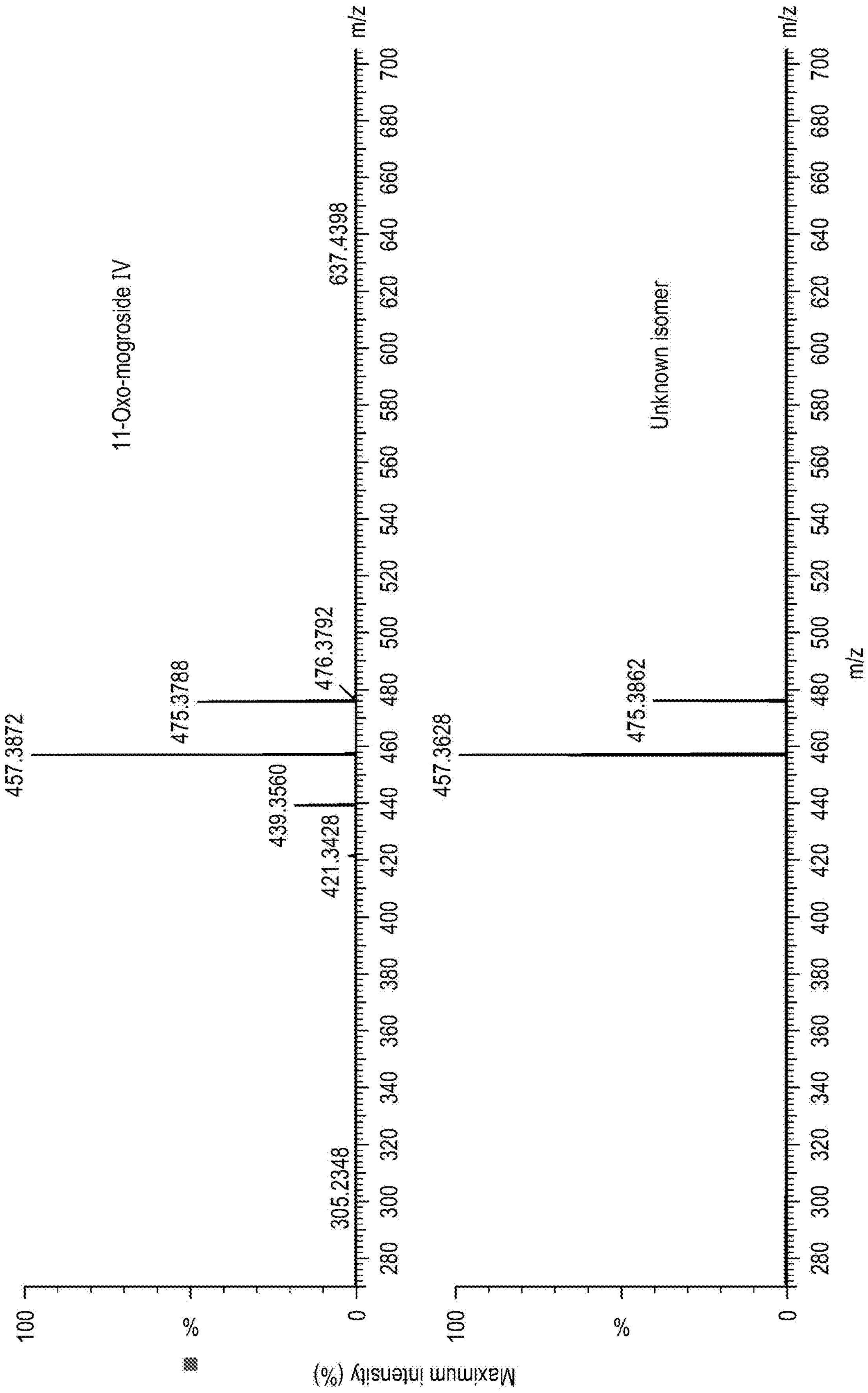
FIG. 32. Mass spectrum fingerprinting of 11-oxo-mogroside IV and the unknown 11-oxo-mogroside IV isomer.

11-oxo-mogroside IV and isomers accumulation in transient assays is shown in FIG. 31. For 11-oxo-mogroside IV, acquire data in TofMSMS ESI positive mode, selecting for the 11-Oxo-Mogroside IV plus a proton (1123.5895 m/z), using the collision energy 30 V, and collecting a full high-resolution mass scan (270-1350 m/z) for resulting fragments. The chromatograms shown are selected for the fragment mass 457.3677 m/z with a 0.02 Da mass window. 11-Oxo-Mogroside IV fragment mass 457.3672 m/z is 1.1 ppm error compared to the theoretical 457.3677 m/z. Unknown peak is 457.3626 m/z is 11.1 ppm error compared to the theoretical 457.3677 m/z. Missing peaks and the low mass accuracy are likely due to the low intensity of this peak. 5 ppm is considered an acceptable cutoff for high resolution mass error. The production of 11-oxo-mogroside IV in transient watermelon fruit infiltrated with the construct SP3684 is shown in FIG. 31, top panel. It can be seen that an unknown 11-oxo-mogroside IV isomer was produced when SP3684 was co-infiltrated with t72143 (FIG. 31, middle panel), compared to SP3684 co-infiltrated with GFP (FIG. 31, bottom panel). FIG. 32 shows the mass spectrum fingerprinting of 11-oxo-mogroside IV (top panel) and the unknown 11-oxo-mogroside IV isomer (bottom panel).

Figure 33:
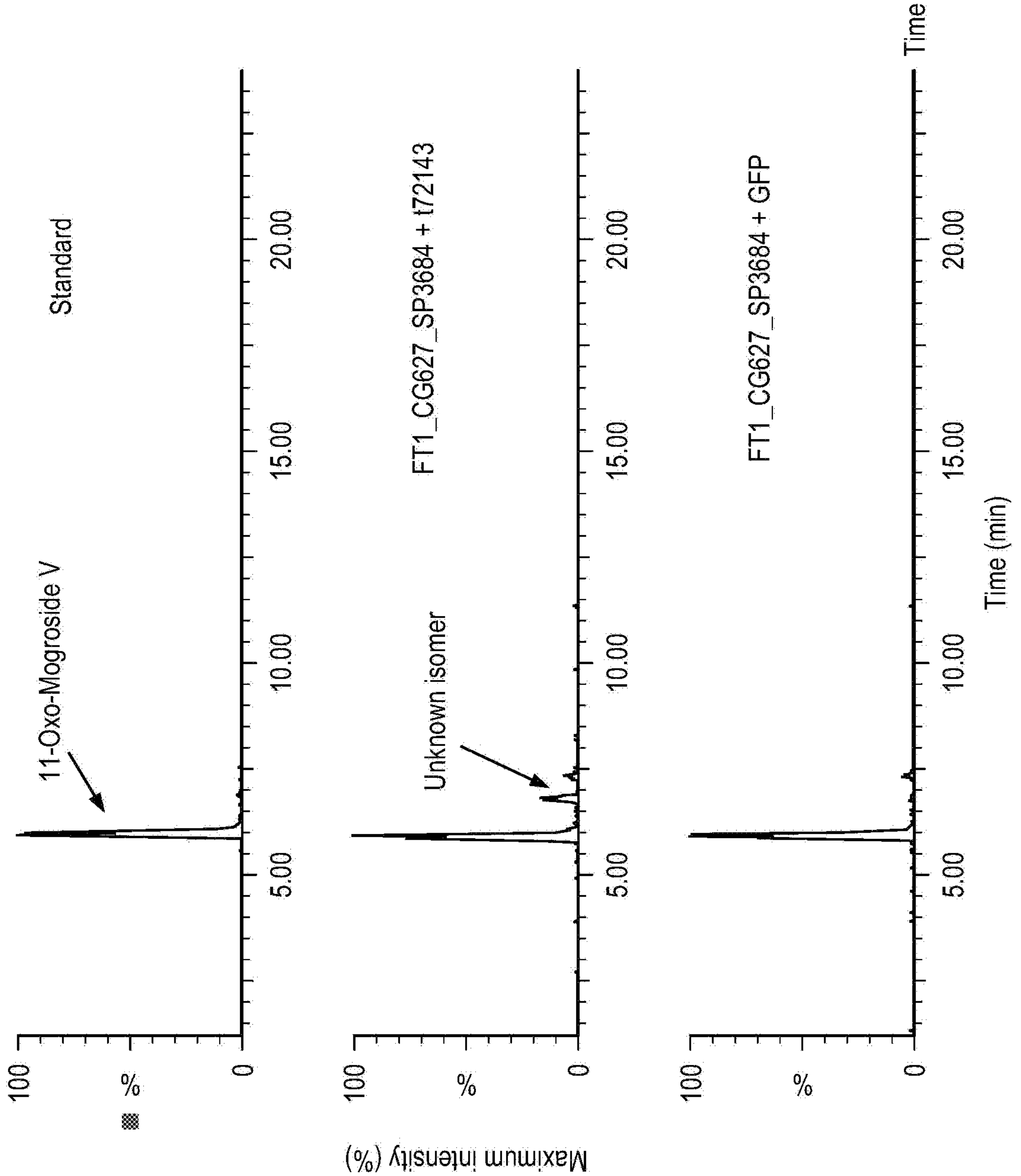
FIG. 33. Production of 11-oxo-mogroside V and unknown 11-oxo-mogroside V isomer in transient watermelon fruit co-infiltrated with the construct SP3684 and either t72143 or green fluorescent protein (GFP).
Figure 34:
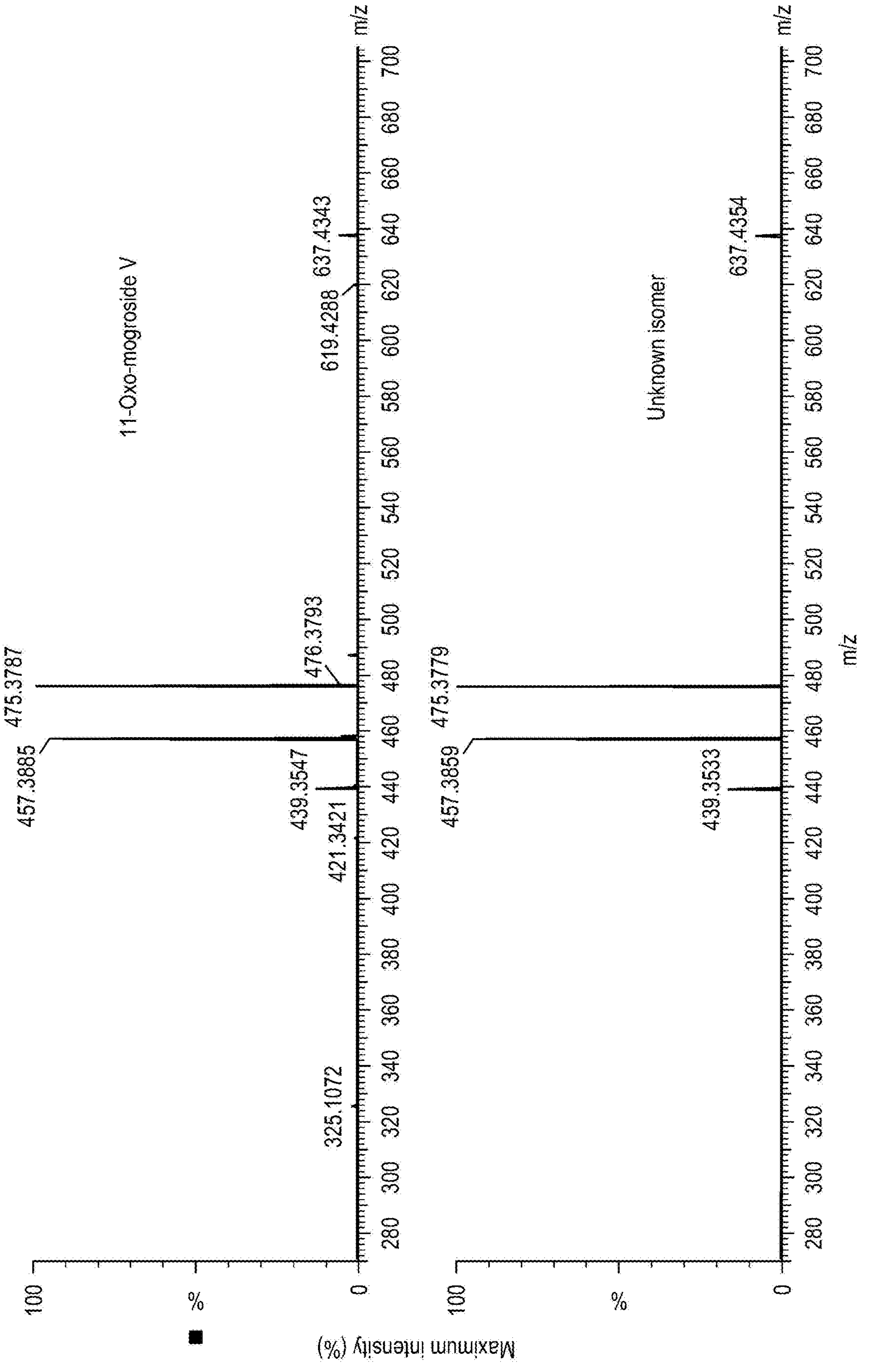
FIG. 34. Mass spectrum fingerprinting of 11-oxo-mogrosideV and the unknown 11 oxo-mogroside V isomer.

11-oxo-mogroside V and isomers accumulation in transient assays is shown in FIG. 33. For 11-oxo-mogroside V, Acquire data in TofMSMS ESI positive mode, selecting for the 11-Oxo-Mogroside V plus a proton (1285.6423 m/z), using the collision energy 30 V, and collecting a full high-resolution mass scan (270-1350 m/z) for resulting fragments. The chromatograms shown are selected for the fragment mass 457.3677 m/z with a 0.02 Da mass window. 11-Oxo-Mogroside V fragment mass 457.3665 m/z is 2.6 ppm error compared to the theoretical 457.3677 m/z. Unknown peak is 457.3659 m/z is 3.9 ppm error compared to the theoretical 457.3677 m/z. 5 ppm is considered an acceptable cutoff for high resolution mass error. The production of 11-oxo-mogroside V in transient watermelon fruit infiltrated with the construct SP3684 is shown in FIG. 33, top panel. It can be seen that an unknown 11-oxo-mogroside V isomer was produced when SP3684 was co-infiltrated with t72143 (FIG. 33, middle panel), compared to SP3684 co-infiltrated with GFP (FIG. 33, bottom panel). FIG. 34 shows the mass spectrum fingerprinting of 11-oxo-mogroside V (top panel) and the unknown 11-oxo-mogroside V isomer (bottom panel).

Example 15

Mogroside Blend Sensory Evaluation

This example evaluates a specific blend of mogrosides as well as some key individual mogrosides to identify their sensory attributes, and to help determine viable blends that are suitable for use as a commercial sweetener. A blend of 80% mogroside-V, 15% 11-oxo mogroside-V, and 5% mogroside IIIA-1 has a clean, sweet taste that is comparable to mogroside V. It is about 213 times as sweet as sucrose at 5 sucrose equivalent value (SEV) and reaches 10.5 SEV at 1,000 ppm. In comparison, mogroside V is 185 times as sweet as sucrose at 5 SEV and reaches 11.5 SEV at 1,000 ppm. V90 is a comparable sweetener to purified mogroside-V in taste and temporal attributes. It is slightly less potent (207× at 5 SEV) and reaches 8.9 SEV at 1,000 ppm. 11-oxo-mogroside-V exhibits slight bitterness and has a low potency (28 times as sweet as sucrose at 5 SEV) compared to mogroside-V. It does not produce high sweetness intensity and only reaches 4.2 SEV at 1,000 ppm. Mogroside IIIA-1 is strongly bitter with a strong lingering bitter aftertaste. It is only 71 times as sweet as sucrose at 5 SEV and plateaus at about 500 ppm. At 1,000 ppm, it only reaches about 5.3 SEV.

Materials and Methods

A blend composed of 80% purified mogroside-V (Chem Faces, CFS202202), 15% 11-oxo-mogroside-V (Chem Faces, CFS202201), and 5% mogroside IIIA-1 (Chem Faces, CFS202201) was diluted to six different concentrations (from 100 ppm to 650 ppm) in spring water (Ice Mountain, retail). For each solution, a set of five reference standards of sucrose dissolved in water in 0.5% (w/w) concentration increments was also prepared. Each concentration of the mogroside blend was evaluated by 6-8 trained judges. Samples were presented in 4-oz soufflé cups at room temperature, and the test sample was labeled with a random 3-digit code. Panelists tasted the blind-coded sample compared to the set of reference samples to determine the sweetness intensity score to the nearest 0.1 unit. Each concentration was evaluated in duplicate. The sweetness intensity scores were then plotted against the mogroside blend concentration to make a concentration response curve, and the best fitting Beidler equation was generated.

Mogroside Blend 80/15/5 Taste Quality: Temporal Properties

Equi-sweet solutions at about 6 SEV were made in spring water (Ice Mountain, retail) of the following sweeteners: purified mogroside-V (Chem Faces, CFS202202), rebaudioside M (95%, Tate & Lyle, lot #1802-2302-1), rebaudioside A (95%, Tate & Lyle, 210617-01), and monk fruit (50% mogroside V, Tate & Lyle, 45GF220305). Another solution was prepared at about 6 SEV of a blend composed of 80% purified mogroside-V (Chem Faces, CFS202202), 15% 11-oxo-mogroside-V (Chem Faces, CFS202201), and 5% mogroside IIIA-1 (Chem Faces, CFS202201). The concentration of each solution can be found in Table 7.

TABLE 7

| Sweetener | ppm |
|---|---|
| Mogroside V | 325 |
| Rebaudioside A | 330 |
| Rebaudioside M | 230 |
| Monk Fruit 50 | 525 |
| Mogroside Blend 80/15/5 | 315 |

A set of samples of each solution was evaluated by a panel of 7-9 trained judges. Panelists measured the time to onset of sweetness and time to reach maximum sweetness using a timer. Sweetness decay after expectorating was measured by rating sweetness intensity every 5 seconds on a 15-cm line scale graduated in evenly spaced 5-point increments and labeled low (0) to high (60). Samples were served at room temperature in 4-oz soufflé cups, labeled with random 3-digit codes. Water and saltine crackers were provided for rinsing between samples. Blind duplicates were evaluated in a second panel under the same conditions.

Mogroside Blend 80/15/5 Taste Quality: Descriptive Analysis

The same samples described above were presented to a panel of 6-9 experienced judges for descriptive analysis. Solutions were blind-coded with random 3-digit codes and served at room temperature for evaluation. Panelists individually scored attributes of each sample, such as sweetness intensity, bitterness, astringency, and the presence of side flavors such as licorice or fruitiness. Scores were based on a 15-cm line scale marked with evenly spaced 5-point increments from low (0) to high (60). Samples were evaluated in duplicate. Water and saltine crackers were provided for rinsing between samples.

V90 Characterization: Concentration Response Curve

V90 is a 90% pure mogroside V containing about 6% 11-oxo mogroside-V. Five different concentrations of V90 (Huacheng Bio, LHGE-230401), ranging from 100 ppm to 500 ppm, were diluted in spring water (Ice Mountain, retail). Each dilution was presented to a panel of 7-8 judges experienced in evaluating sweeteners and was accompanied by a range of five sucrose solution reference standards bracketing the sweetness intensity of the test sample in 0.5% (w/w) increments. Panelists assigned a sweetness intensity score to each test sample, including blind duplicates, to the nearest 0.1 unit. All samples were served at room temperature in 4-oz soufflé cups with the test samples labeled with random 3-digit codes. Water and saltine crackers were provided for rinsing between samples.

V90 Characterization: Temporal Dynamics and Descriptive Analysis

A solution of V90 was made at 410 ppm in spring water (Ice Mountain, retail) to be about 6 SEV. A second solution was made at about 6 SEV of purified mogroside-V (Chem Faces, CFS202202) at 325 ppm. A panel of 7-8 trained judges evaluated the temporal properties and taste attributes of each sample, including blind duplicates, in the same manner described previously in the Mogroside Blend 80/15/5 Taste Quality sections.

Individual Mogroside Taste Quality: Temporal Dynamics and Descriptive Analysis

Two individual mogroside components of the blend, 11-oxo mogroside-V (Chem Faces, CFS202202) and mogroside III-A1 (Chem Faces, 202301), were evaluated separately in spring water (Ice Mountain, retail) to determine the concentration needed to reach approximately 6 SEV. Solutions were then prepared at 3600 ppm of 11-oxo-mogroside-V and 600 ppm mogroside IIIA-1.

A panel of 6-7 trained judges evaluated the solutions by measuring the time to onset of sweetness and time to reach maximum sweetness using a timer. Decay of lingering aftertaste after expectorating was measured by rating sweetness intensity every 5 seconds on a 15-cm line scale graduated in evenly spaced 5-point increments and labeled low (0) to high (60). Samples were served at room temperature in 4-oz soufflé cups, labeled with random 3-digit codes, including blinded duplicates. Water and saltine crackers were provided for rinsing between samples.

The panel also evaluated the intensity of several sensory attributes such as bitterness, astringency, caramel flavor, and fruitiness. The same 15-cm line scale was used for scoring, labeled from low (0) to high (60) with evenly spaced 5-point increments. The samples were served in 4-oz soufflé cups that were labeled with random 3-digit codes. Samples were evaluated at room temperature and included blind duplicates. Water and saltine crackers were provided for rinsing between samples. A 400-ppm solution of V90 (Huacheng Bio, LHGE-230401) was tasted as a reference at the beginning of the descriptive analysis session for calibration verification among panelists.

Individual Mogroside Potency: Concentration Response Curve

Both individual mogrosides were also evaluated at five different concentrations in spring water (Ice Mountain, retail) for sweetness intensity. 11-oxo-mogroside was diluted to concentrations ranging from 200 ppm to 600 ppm and mogroside IIIA-1 was diluted to concentrations from 100 to 500 ppm. For each concentration, a set of five sucrose solution reference standards were prepared in 0.5% (w/w) increments to approximately bracket the sweetness intensity of the test sample. A panel of 6-8 trained judges evaluated each test sample in duplicate, accompanied by the corresponding reference standards, and assigned a sweetness intensity score to the sample to the nearest 0.1 unit. Samples were presented in 4-oz soufflé cups at room temperature, and the test sample was labeled with a random 3-digit code. The sweetness intensity scores were then plotted as a function of mogroside concentration to make a concentration response curve, and the best fitting Beidler equation was generated.

Results

Mogroside Blend 80/15/5 Potency: Concentration Response Curve

Figure 35:
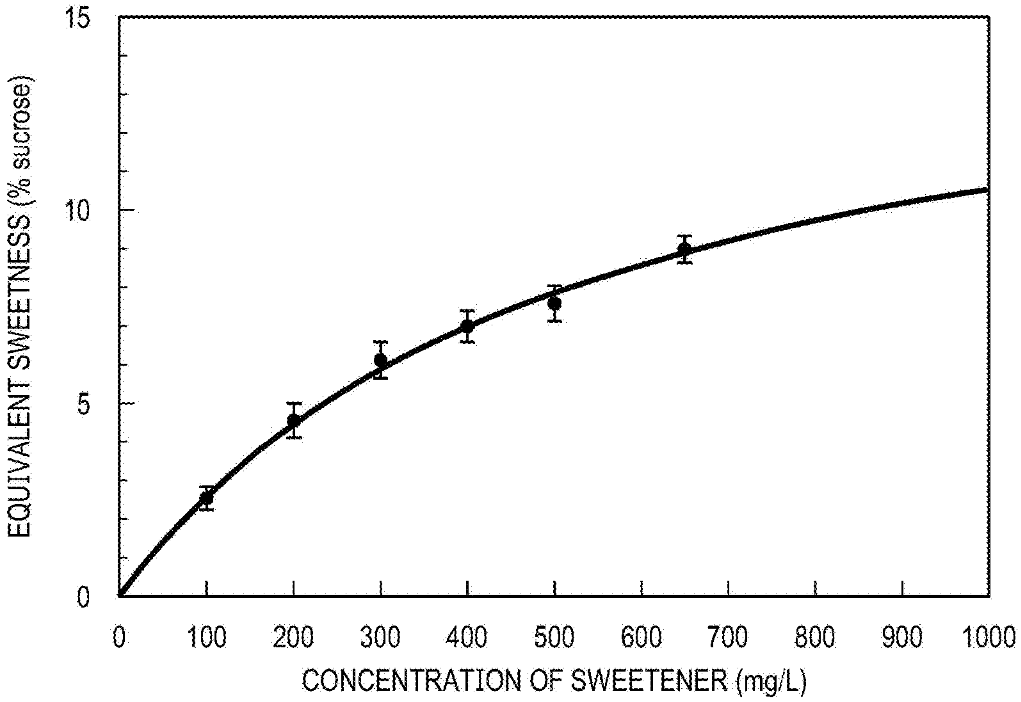
FIG. 35. Concentration response curve for Mogroside Blend 80/15/5.

The concentration response curve data for the mogroside blend are summarized in FIG. 35. The error bars around each point represent 1 standard deviation. The data fit a Beidler equation with an r2 value of 0.961. The equation for this line is:

$$SEV=16.08*C/(521.2+C)$$

where SEV is the % sucrose equivalent sweetness as determined by sensory panel and C is the concentration of mogroside blend in ppm or mg/L.

Figure 36:
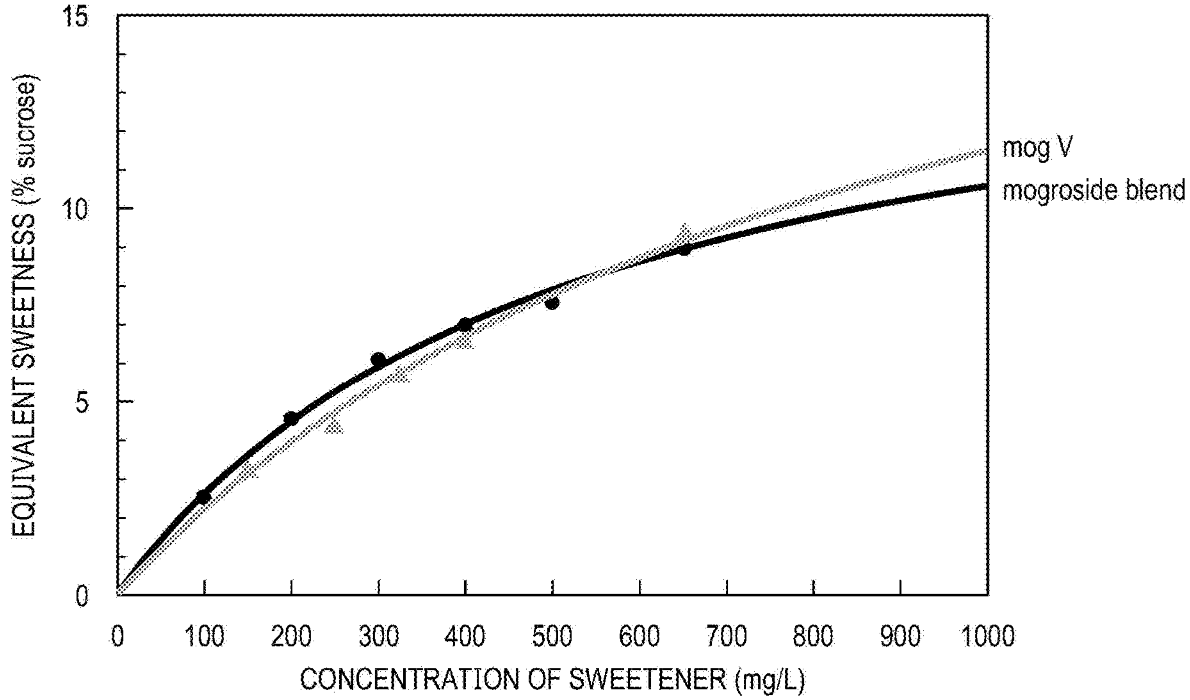
FIG. 36. Concentration response curves of Mogroside-V and Mogroside Blend 80/15/5.

The curve is similar to that of purified mogroside-V, as seen in FIG. 36. At lower concentrations, around 400 ppm or less, the mogroside blend has a slightly higher potency than purified mogroside-V. At 5 SEV, the blend is about 213 times as sweet as sugar, whereas mogroside-V is about 185 times as sweet as sugar. However, at higher concentrations, at about 700 ppm or more, the mogroside blend begins to plateau more rapidly than mogroside-V and is slightly less sweet in comparison. The blend reaches 10.5 SEV at 1,000 ppm compared to 11.5 SEV for mogroside-V. The previously reported equation for mogroside-V is: SEV=22.03*C/(920.8+C).

Both sweeteners exhibit typical curves of high potency sweeteners with steeper slopes at low concentrations that taper off at higher concentrations as potency declines. The potency at any given concentration can be determined by:

$$P=SEV*10,000/C$$

where C is the concentration of the mogroside blend in ppm or mg/L and SEV is the % sucrose equivalent sweetness determined by sensory panel.

Mogroside Blend 80/15/5 Taste Quality: Temporal Properties

Figure 37:
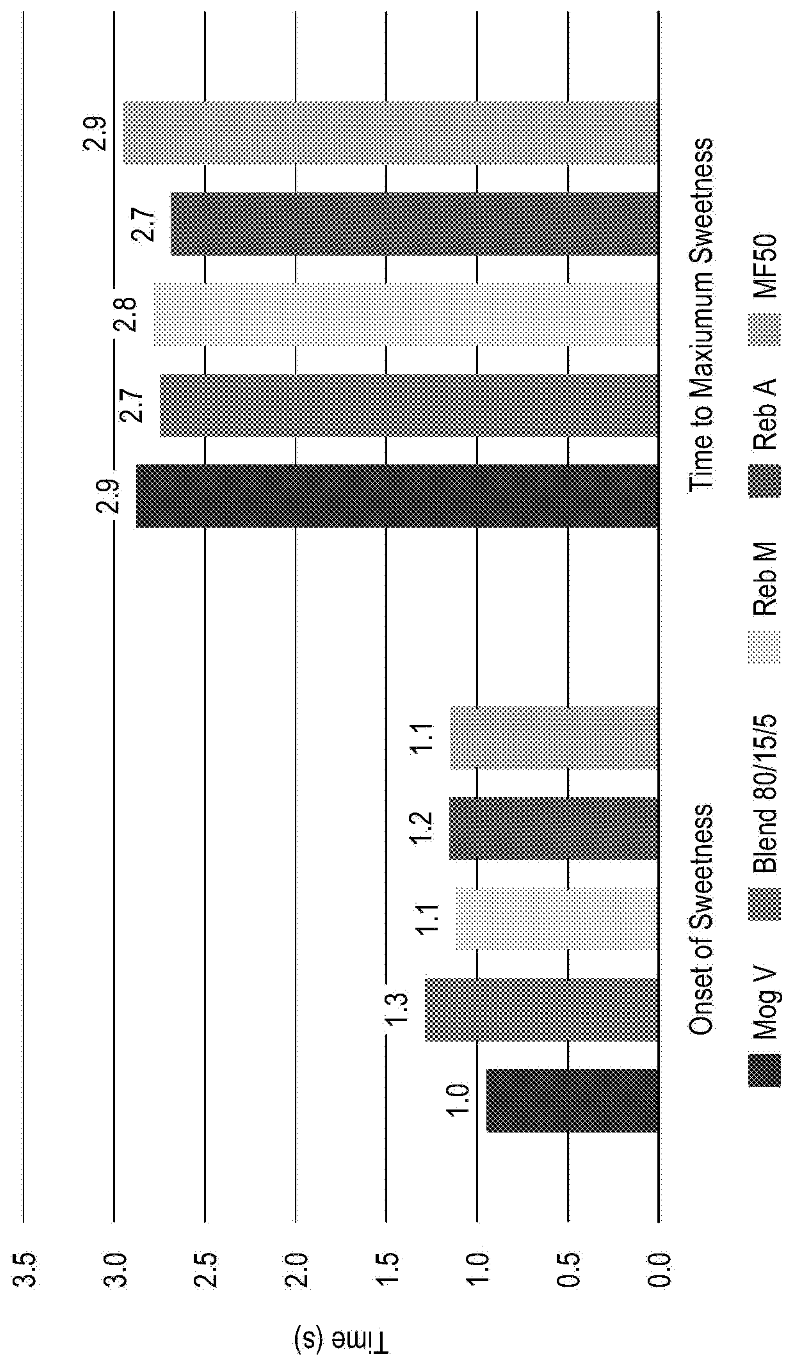
FIG. 37. Onset and time to reach maximum sweetness of Mogroside-V, Mogroside Blend 80/15/5, Rebaudioside M, Rebaudioside A and monk fruit 50 (MF50).

Temporal properties were evaluated for Mogroside-V, Mogroside Blend 80/15/5, Rebaudioside M, Rebaudioside A and monk fruit 50 (MF50). The onset of sweetness for all sweeteners tested was around 1 second, with maximum sweetness achieved at just under 3 seconds. This is a bit delayed compared to sucrose, which was not evaluated in this test but is considered the gold standard of sweetness, and generally has an onset of about 0.5 seconds, reaching maximum sweetness at about 1 second. The onset and time to reach maximum sweetness is shown in FIG. 37.

Figure 38:
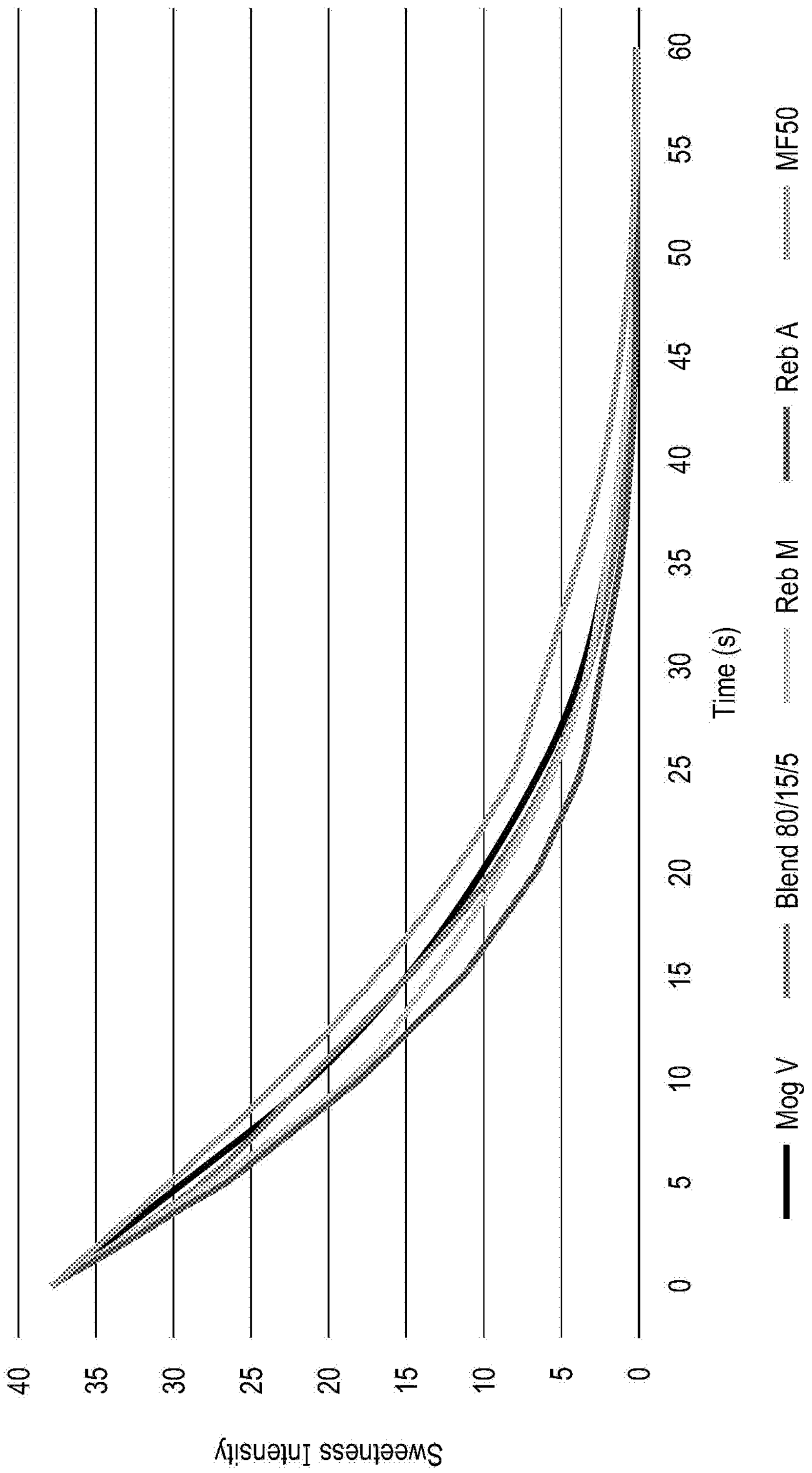
FIG. 38. Graph of sweetness decay over time of Mogroside-V, Mogroside Blend 80/15/5, Rebaudioside M, Rebaudioside A and MF50.

Sweetness from mogroside-V and the mogroside blend both lasted about 45 seconds after expectorating, with similar decay curves. Rebaudioside A had the least lingering sweetness, decaying in about 40 seconds, though a bitter taste continued to linger. Rebaudioside M and monk fruit 50 lingered the longest, lasting 50 and 55 seconds, respectively. Sweetness decay curves are shown in FIG. 38. All sweeteners evaluated had a longer sweet linger than is found in a 6 SEV solution of sucrose, which typically decays in about 20-25 seconds.

Mogroside Blend 80/15/5 Taste Quality: Descriptive Analysis

Figure 39:
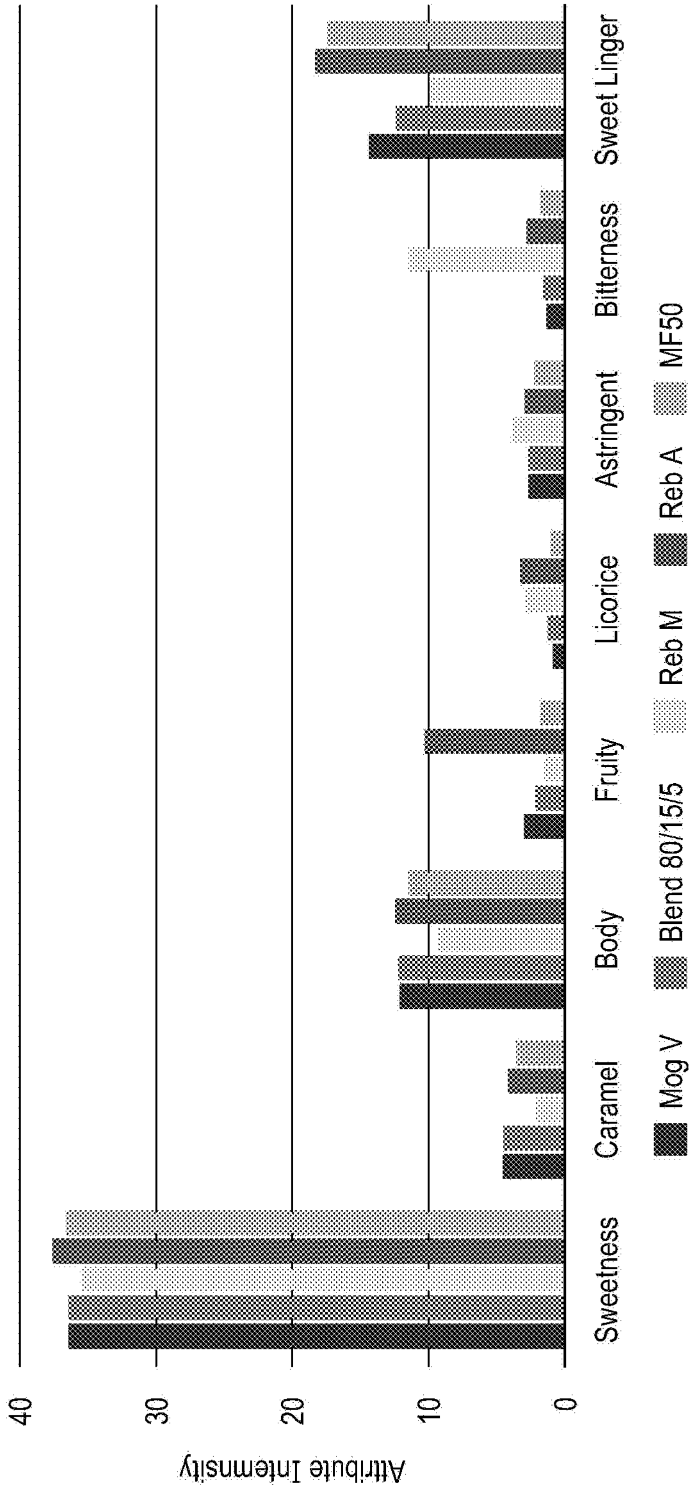
FIG. 39. Descriptive analysis scores of sweetener attributes for Mogroside-V, Mogroside Blend 80/15/5, Rebaudioside M, Rebaudioside A and MF50.
Figure 40:
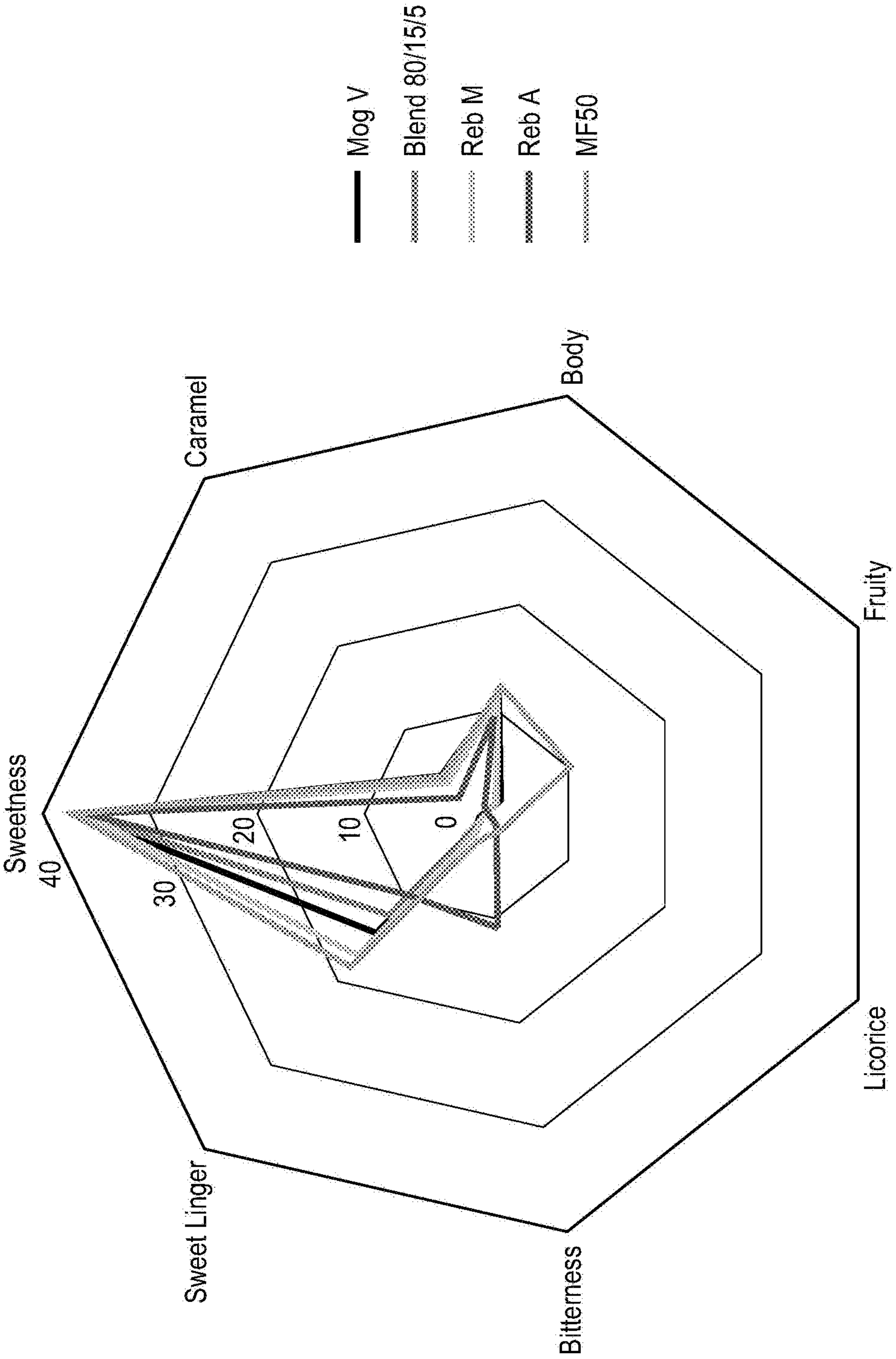
FIG. 40. Descriptive analysis of sweetener attributes for Mogroside-V, Mogroside Blend 80/15/5, Rebaudioside M, Rebaudioside A and MF50.

The mogroside blend was quite similar to purified mogroside-V. All sweeteners were characterized by slight caramel notes and body with low astringency. Rebaudioside A had notable bitterness compared to the other sweeteners, and monk fruit 50% had a stronger fruity side taste than the other sweeteners. Table 8 summarizes the average intensity scores for the attributes of each sweetener (0=low, 60=high). The results of the descriptive analysis are shown in FIG. 39 and FIG. 40.

TABLE 8

| | Mog-V | Blend-80/15/5 | Reb-M | Reb-A | MF50 |
|---|---|---|---|---|---|
| Sweetness | 36.3 | 36.3 | 36.4 | 35.1 | 37.3 |
| Caramel | 4.5 | 4.3 | 3.5 | 1.9 | 3.9 |
| Body | 12.1 | 12.1 | 11.2 | 9.1 | 12.1 |
| Fruity | 3.0 | 2.2 | 1.6 | 1.3 | 10.0 |
| Licorice | 0.7 | 1.1 | 1.0 | 2.7 | 3.1 |
| Astringent | 2.5 | 2.5 | 2.0 | 3.7 | 2.9 |
| Bitterness | 1.4 | 1.6 | 1.7 | 11.2 | 2.7 |
| Sweet-Linger | 14.3 | 12.3 | 17.3 | 9.6 | 18.1 |

V90 Characterization: Concentration Response Curve

Figure 41:
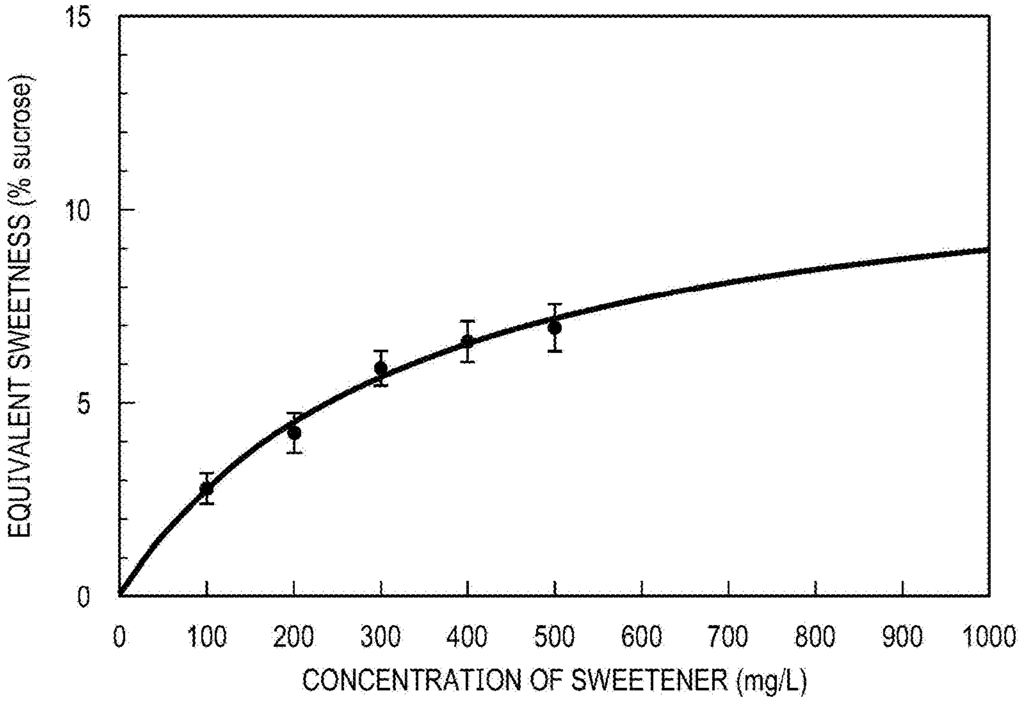
FIG. 41. Concentration response curve for V90.

The V90 sweetness intensity scores were plotted as a function of concentration (FIG. 41) using the Beidler equation. The error bars represent 1 standard deviation. The data fit the equation well with an r2 value of 0.938. The equation for this line is:

SEV=11.94*C/(335+C)

where SEV is the % sucrose equivalent sweetness as determined by sensory panel and C is the concentration of mogroside blend in ppm or mg/L. At 5 SEV, V90 is approximately 207 times as sweet as sucrose and it reaches a sweetness of about 8.9 SEV at 1,000 ppm.

Figure 42:
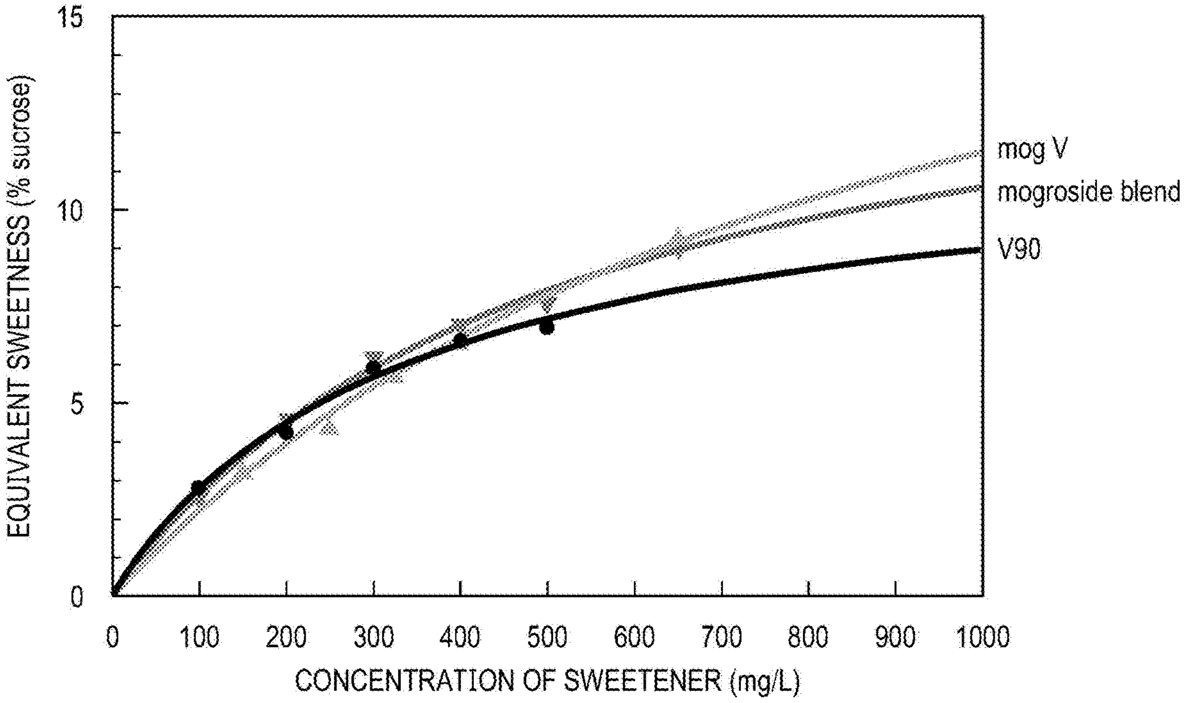
FIG. 42. Concentration response curves of Mogroside V, Blend 80/15/5, and V90.

Compared to the concentration response curves of mogroside-V and the 80/15/5 mogroside blend, the curve for V90 plateaus more quickly and reaches a lower sweetness at 1,000 ppm, as seen in FIG. 42.

The sweetness intensity results are lower than expected for assuming 90% mogroside-V in V90. The supplier later reported that V90 is 90% mogroside-V dry basis, not as-is, and analytical testing showed a value closer to 84.5% mogroside-V dry weight. When accounting for these differences, the results for V90 are likely more in line with mogroside-V and the blend values.

V90 remains steeper in slope at low concentrations than Mog-V, similar to the mogroside 80/15/5 blend. Both V90 and the mogroside blend contain 11-oxo mogroside-V, which may be affecting the shape of their curves.

V90 Characterization: Temporal Dynamics and Descriptive Analysis

Figure 43:
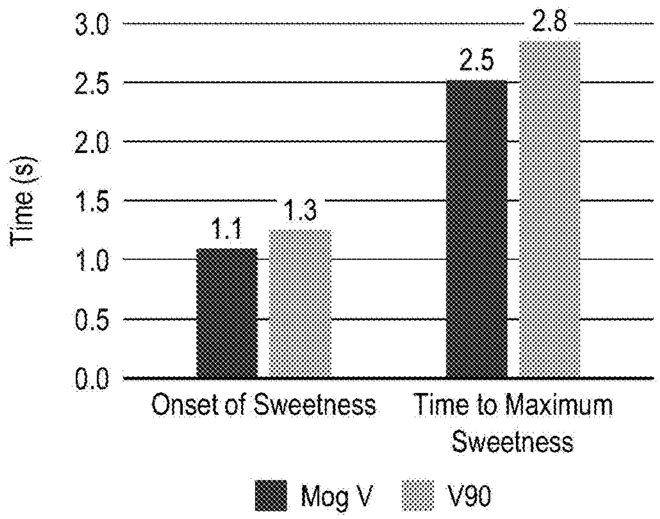
FIG. 43. Onset and time to maximum sweetness for Mogroside V and V90.
Figure 44:
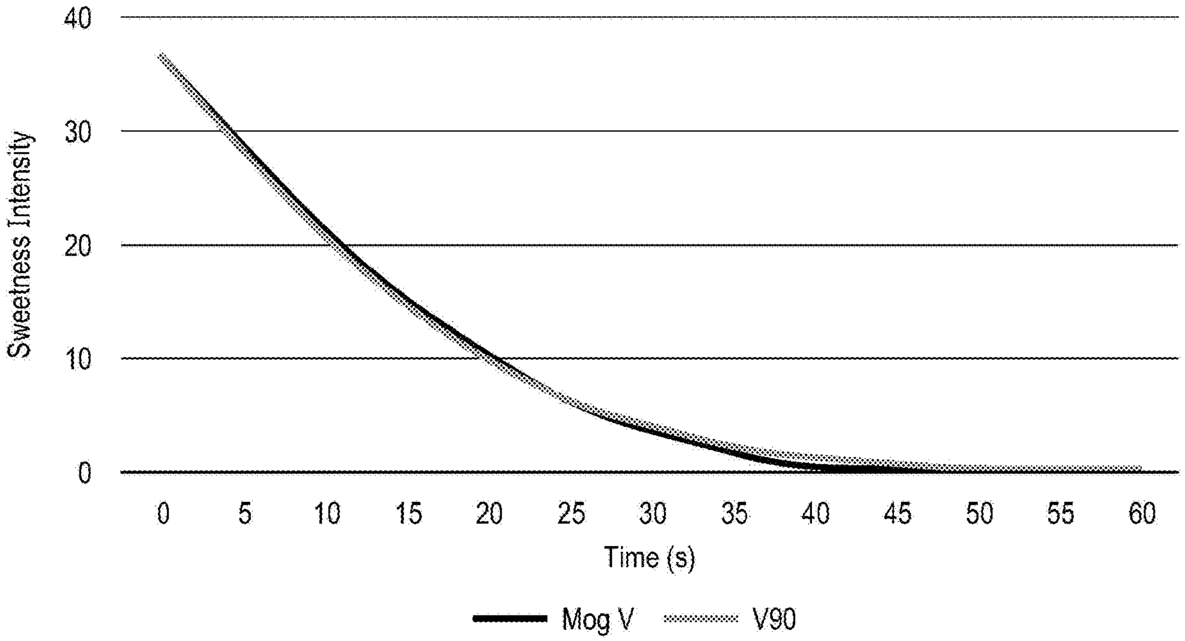
FIG. 44. Sweetness decay of Mogroside V and V90.

The temporal properties of mogroside-V and V90 were similar. Onset of sweetness occurred at 1.1 and 1.3 seconds, respectively, with maximum sweetness occurring at 2.5 seconds and 2.8 seconds, respectively. The onset and time to maximum sweetness for Mog V and V90 is shown in FIG. 43. The lingering sweet aftertaste of both sweeteners followed a nearly identical decay curve, with mogroside-V sweetness decaying in 40 seconds and V90 decaying in 45 seconds (FIG. 44).

Figure 45:
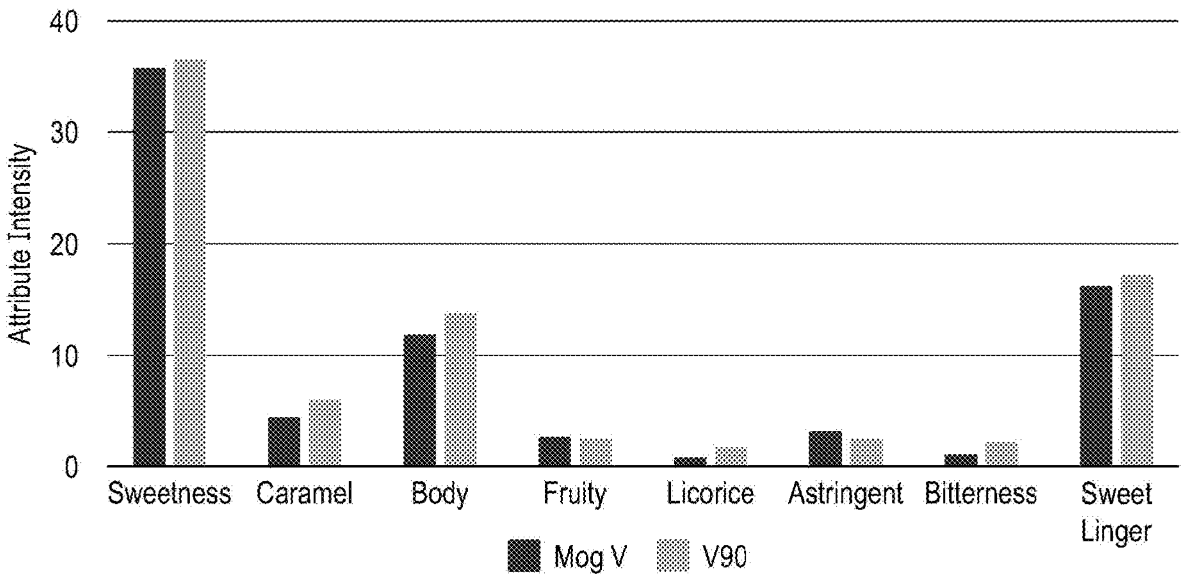
FIG. 45. Descriptive analysis scores of Mogroside V and V90.

Average intensity scores for sensory attributes of the sweeteners can be found in Table 9 (0=low, 60=high). Both sweeteners had a clean, sweet profile with slight caramel note and some body/mouthfeel, which are sugar-like attributes. Both sweeteners had some lingering sweet aftertaste, which is common among high potency sweeteners. Licorice, bitterness, and astringency, which are common rebaudioside A attributes, were very low. The descriptive analysis scores are shown in FIG. 45.

TABLE 9

| Attribute | Mogroside V | V90 |
|---|---|---|
| Sweetness | 35.9 | 36.5 |
| Caramel | 4.2 | 5.9 |
| Body | 11.9 | 13.8 |
| Fruity | 2.6 | 2.3 |
| Licorice | 0.8 | 1.6 |
| Astringent | 2.9 | 2.4 |
| Bitterness | 1.1 | 2.0 |
| Sweet Linger | 16.2 | 17.1 |

Individual Mogroside Potency: Concentration Response Curve

Figure 46:
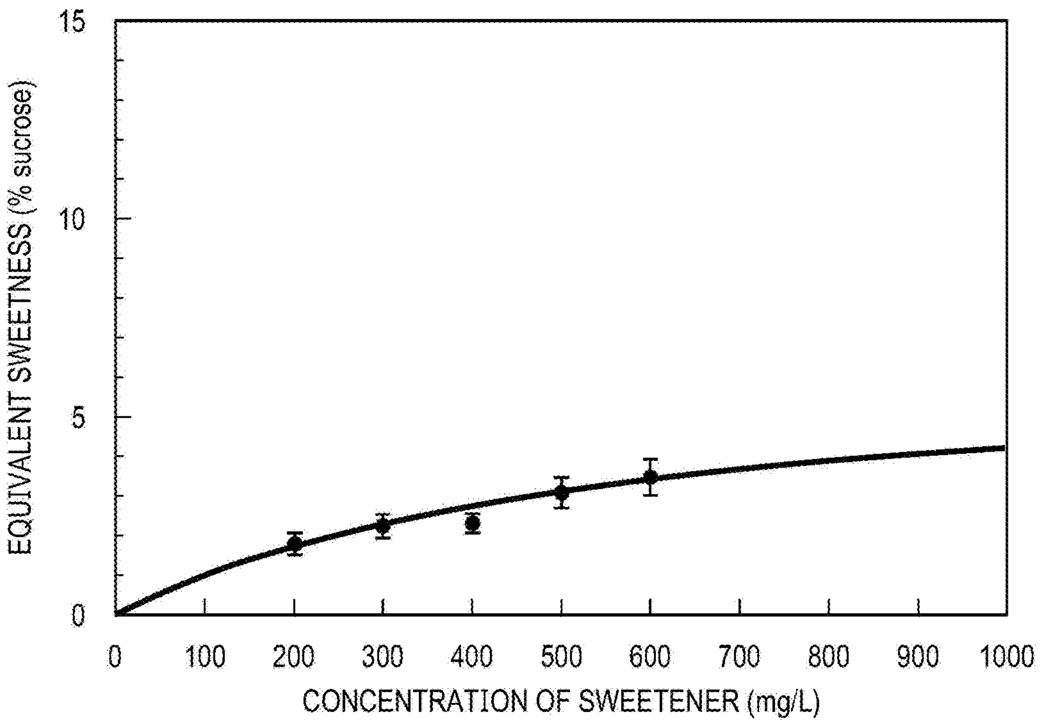
FIG. 46. Concentration response curve for 11-oxo Mogroside-V.
Figure 47:
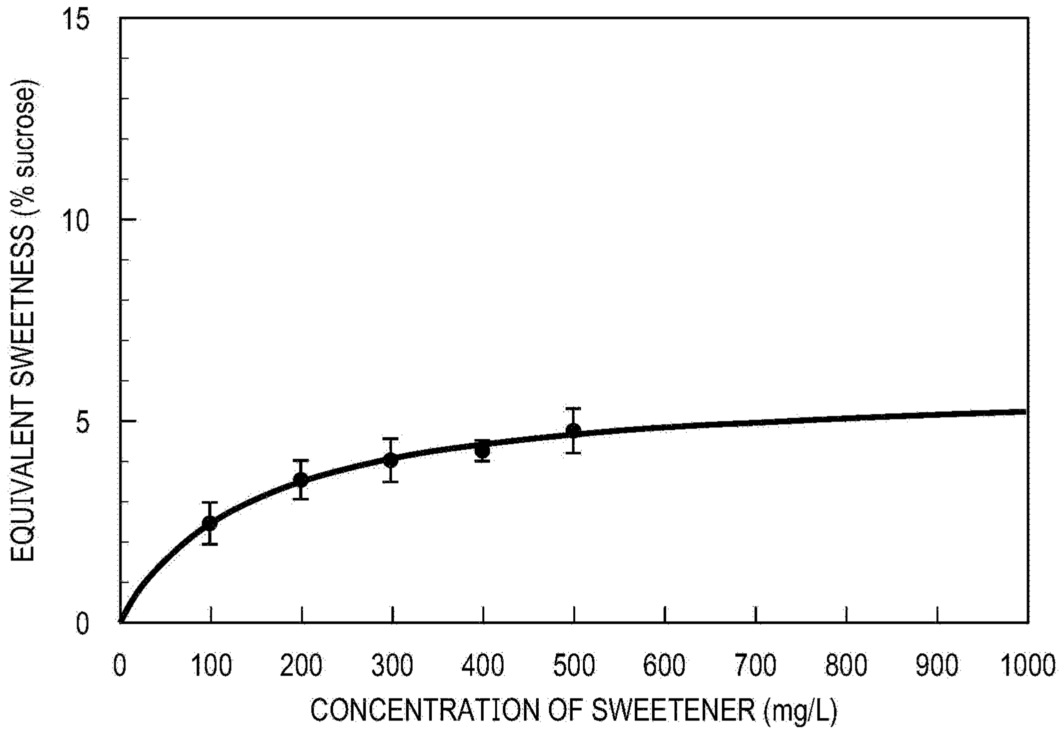
FIG. 47. Concentration response curve for Mogroside IIIA-1.

The sweetness intensity scores for both 11-oxo-mogroside-V and mogroside IIIA-1 were plotted against their concentrations to generate concentration response curves according to the Beidler equation. In FIG. 46 and FIG. 47, the error bars represent 1 standard deviation.

The curve for 11-oxo-mogroside-V omitted the data point at 400 ppm, as it appeared to be an outlier. The resultant equation fit well with the remaining data, with an r2 value of 0.946. The equation for this line is:

SEV=6.56*C/(546.3+C)

where SEV is the % sucrose equivalent sweetness as determined by sensory panel and C is the concentration of mogroside blend in ppm or mg/L. At 5 SEV, 11-oxo mogroside-V is approximately 28 times as sweet as sucrose. This potency is much lower than the potency previously seen in purified Mog-V, the mogroside blend, or V90, all of which were closer to 200 times as sweet as sucrose at 5 SEV.

The concentration response curve for mogroside IIIA-1 has a steep slope at very low concentrations (less than 100 ppm) and plateaus rapidly at a low SEV (around 4-5 SEV). This curve is typical of sweeteners that exhibit bitterness, which inhibits sweetness at higher concentrations. The data fit the equation very well with an r2 value of 0.983. The equation for this line is:

SEV=6.00*C/(139.9+C)

where SEV is the % sucrose equivalent sweetness as determined by sensory panel and C is the concentration of mogroside blend in ppm or mg/L. Mogroside IIIA-1 is approximately 71 times as sweet as sugar at 5 SEV and reaches about 5.3 SEV at 1,000 ppm.

A summary of potency and sweetness at 1,000 ppm for the mogroside sweeteners and blends in this study is shown in Table 10 below.

TABLE 10

| | Mogroside V | Blend 80/15/5 | V90 | 11-oxo-mogroside V | Mogroside IIIA-1 |
|---|---|---|---|---|---|
| Potency at 5 SEV | 185× | 213× | 207× | 28× | 71× |
| Potency at 10 SEV | 131× | 117× | 58× | n/a | n/a |
| SEV at 1,000 ppm | 11.5 | 10.5 | 8.9 | 4.2 | 5.3 (very bitter) |

Individual Mogroside Taste Quality: Temporal Dynamics and Descriptive Analysis

Figure 48:
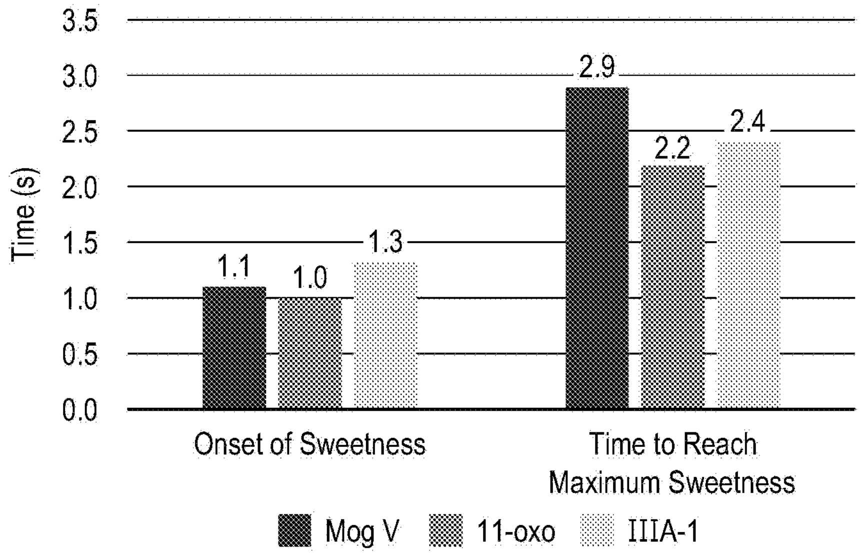
FIG. 48. Onset and time to maximum sweetness of Mogroside V, 11-oxo Mogroside-V and Mogroside IIIA-1.
Figure 49:
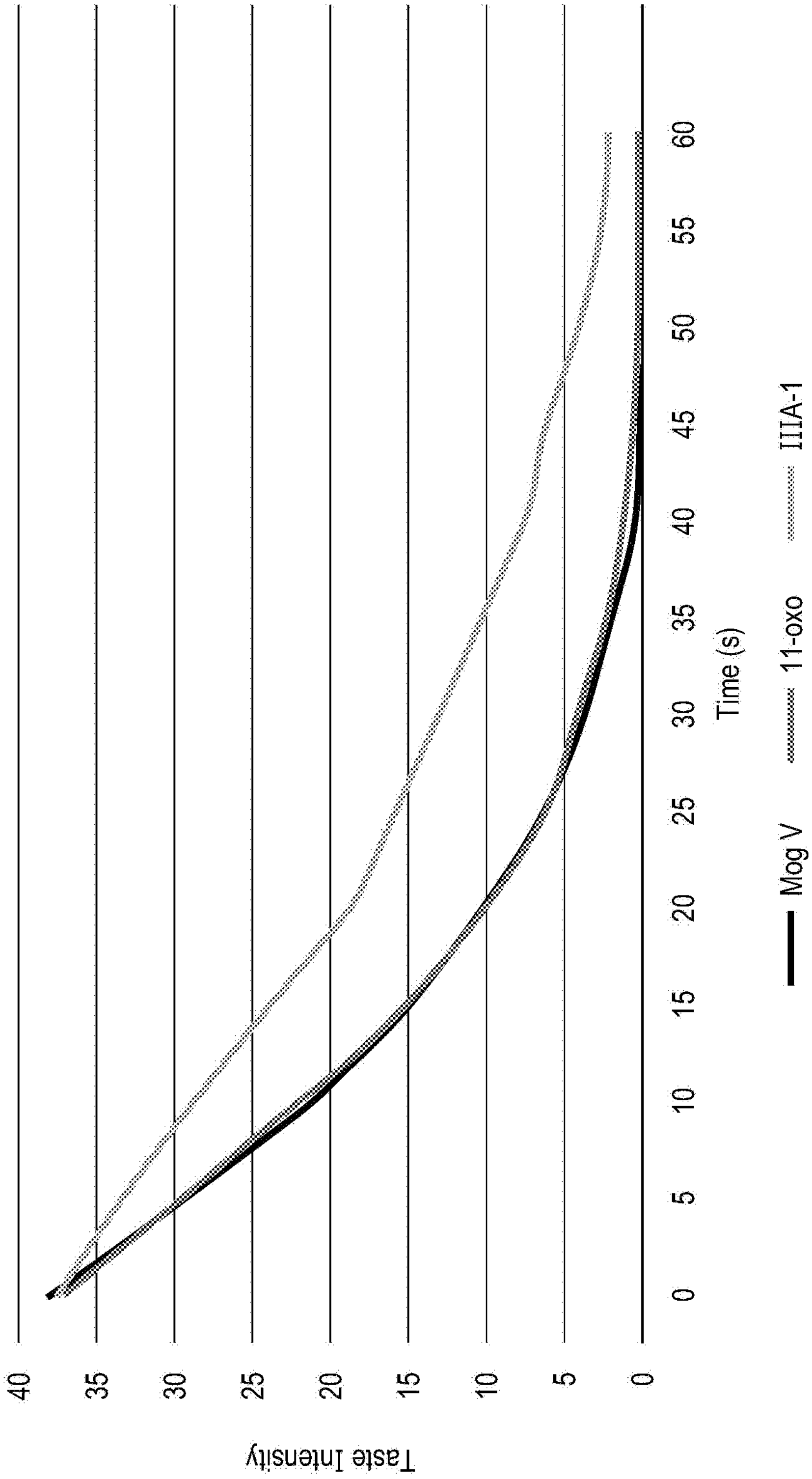
FIG. 49. Lingering aftertaste decay over time of Mogroside V, 11-oxo Mogroside-V and Mogroside IIIA-1.

The results of the temporal profiling of 11-oxo mogroside-V and mogroside IIIA-1 can be seen in FIG. 48 and FIG. 49, compared to previous data generated by the panel for mogroside-V. Mogroside V took slightly longer to reach peak sweetness compared to the other mogrosides, but onset of sweetness was comparable across all three samples.

When evaluating the solutions of mogroside IIIA-1, the panelists noted a strong bitter aftertaste that almost immediately overwhelmed any lingering sweet sensation. In FIG. 49, intensity of bitter aftertaste is plotted for mogroside IIIA-1 in comparison to intensity of sweet aftertaste for 11-oxo mogroside-V and previously generated data for mogroside-V. Sweetness from 11-oxo mogroside-V decayed in about 45 seconds, which is on par with the length of sweet aftertaste from mogroside-V. The strong bitter taste from mogroside IIIA-1 was much more lingering and still present more than 60 seconds after expectorating. The strong bitterness of mogroside IIIA-1 was also noted in the descriptive analysis attribute scores. Average intensity scores for all attributes can be found in Table 11, shown compared to mogroside-V data generated from a previous descriptive analysis sensory panel.

TABLE 11

| Attribute | 11-oxo-mogroside V | Mogroside IIIa-1 | Mogroside V |
|---|---|---|---|
| Sweetness | 37.1 | 34.5 | 36.3 |
| Caramel | 4.8 | 1.9 | 4.5 |
| Body | 12.7 | 12.1 | 12.1 |
| Fruity | 2.1 | 0.7 | 3.0 |
| Licorice | 2.1 | 2.2 | 0.7 |
| Astringent | 4.3 | 5.1 | 2.5 |
| Bitterness | 7.7 | 37.3 | 1.4 |
| Sweet Linger | 17.1 | 5.7 | 14.3 |
| Bitter Linger | 0.7 | 37.3 | 0.0 |

Figure 50:
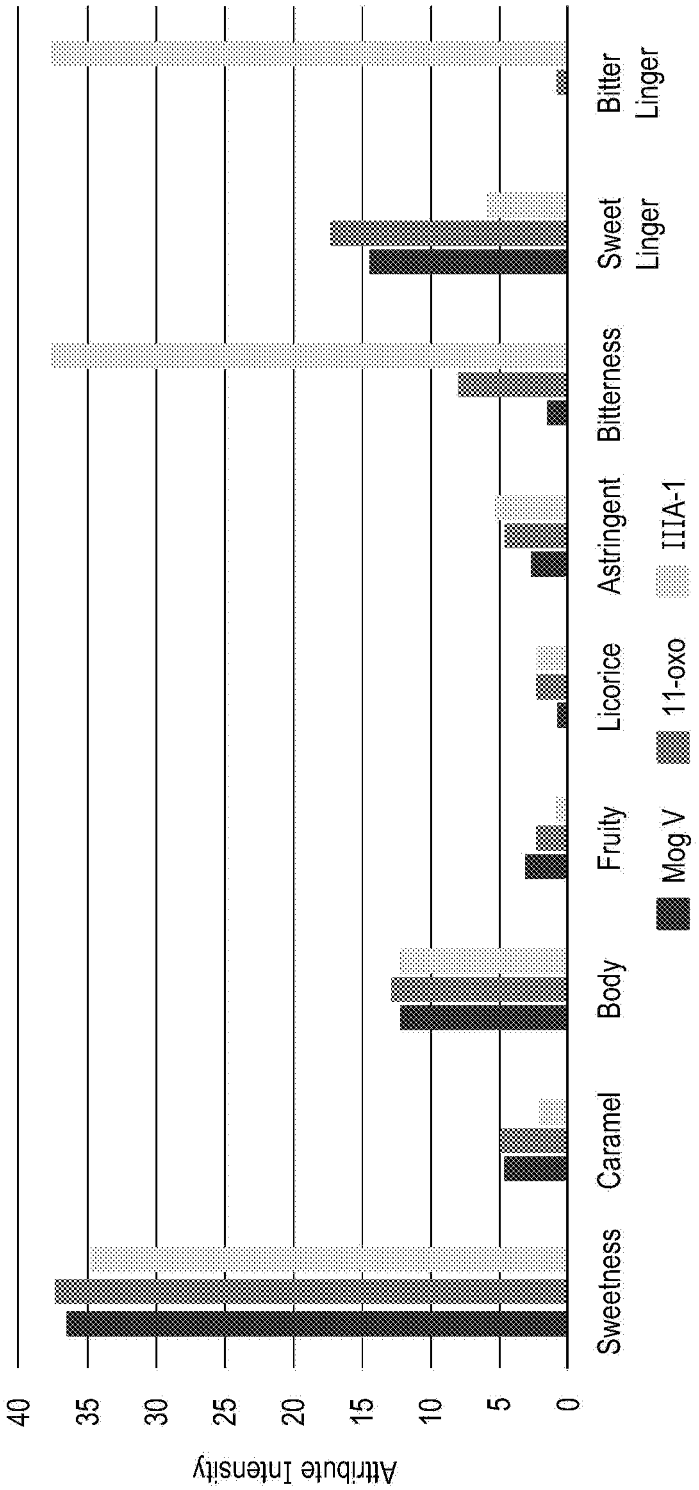
FIG. 50. Descriptive analysis scores of sweetener attributes for Mogroside-V, 11-oxo-mogroside V and mogroside IIIA-1.
Figure 51:
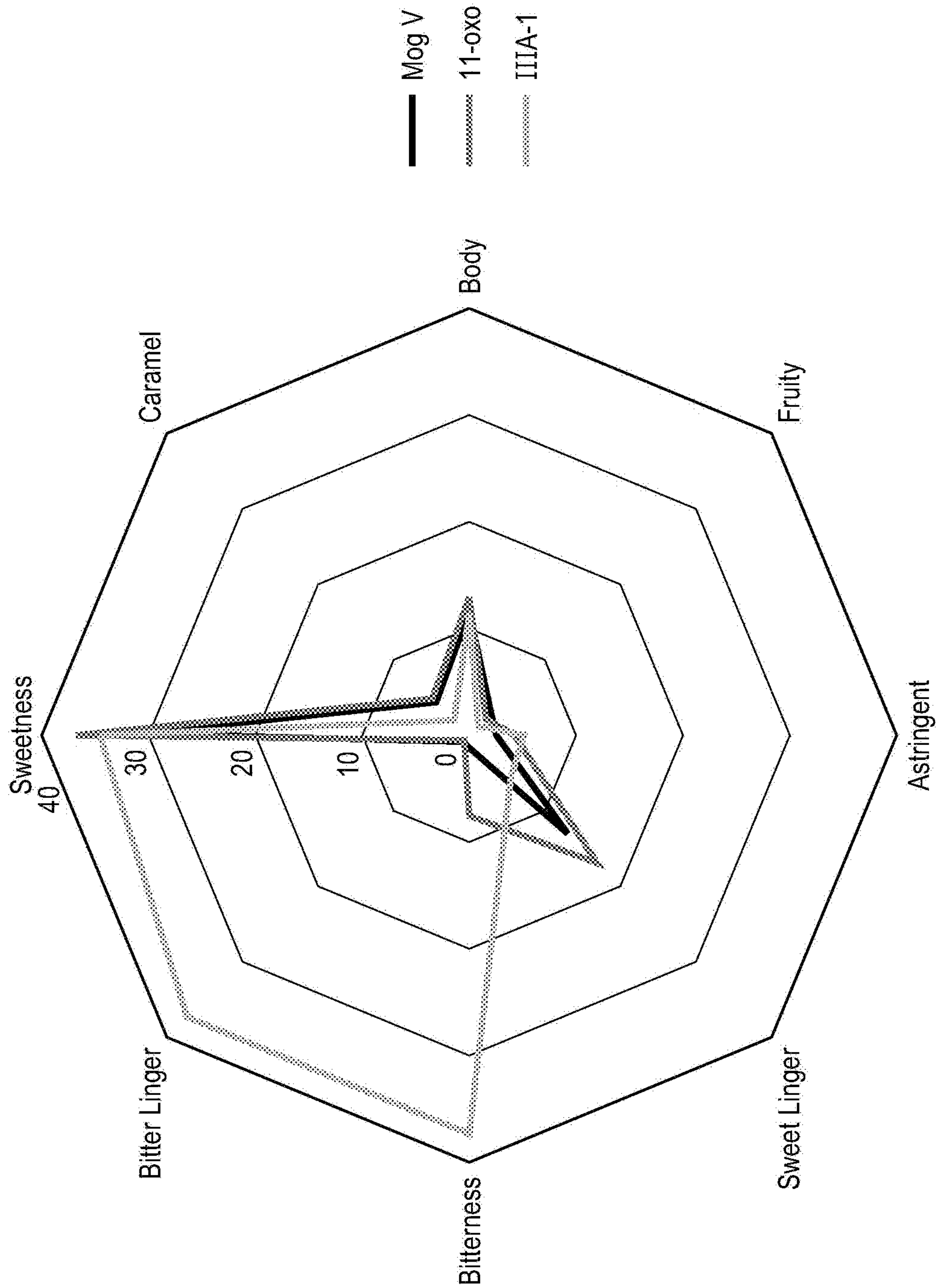
FIG. 51. Descriptive analysis of sweetener attributes for Mogroside-V, 11-oxo-mogroside V and mogroside IIIA-1.

The descriptive analysis scores of sweetener attributes for Mogroside-V, 11-oxo-mogroside V and mogroside IIIA-1 are shown in FIG. 50, and the descriptive analysis of sweetener attributes for Mogroside-V, 11-oxo-mogroside V and mogroside IIIA-1 are shown in FIG. 51.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. For example, all of the disclosed components of the preferred and alternative embodiments are interchangeable providing disclosure herein of many systems having combinations of all the preferred and alternative embodiment components. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims. All such similar substitutes and modifications apparent to those skilled in the art are deemed to be within the spirit, scope and concept of the disclosure as defined by the appended claims.

The invention claimed is:

1. A recombinant DNA molecule comprising:

a) a first polynucleotide sequence that encodes a cytochrome P450 polypeptide having at least 91% sequence identity to SEQ ID NO:2 or at least 95% sequence identity to SEQ ID NO: 86;

b) a second polynucleotide sequence that encodes a cucurbitadienol synthase polypeptide having at least 90% sequence identity to SEQ ID NO:5;

c) a third polynucleotide sequence that encodes a cytochrome P450 polypeptide having at least 90% sequence identity to SEQ ID NO:7, SEQ ID NO:25, SEQ ID NO:27, SEQ ID NO:29, SEQ ID NO:31 or SEQ ID NO:33;

d) a fourth polynucleotide sequence that encodes a uridine phosphorylase-dependent glycosyltransferase polypeptide having at least 90% sequence identity to SEQ ID NO:9;

e) a fifth polynucleotide sequence that encodes a uridine phosphorylase-dependent glycosyltransferase polypeptide having at least 90% sequence identity to SEQ ID NO:11;

f) a sixth polynucleotide sequence that encodes a squalene epoxidase polypeptide having at least 90% sequence identity to SEQ ID NO:13;

g) a seventh polynucleotide sequence that encodes an epoxy hydrolase polypeptide having at least 90% sequence identity to SEQ ID NO:15; and h) an eighth polynucleotide sequence that encodes a truncated 3-hydroxy-3-methylglutaryl-CoA reductase polypeptide having at least 95% sequence identity to SEQ ID NO: 273;

wherein the first, second, third, fourth, fifth, sixth, seventh and/or eighth polynucleotide sequence is operably linked to a heterologous promoter.

2. The recombinant DNA molecule of claim 1, wherein the heterologous promoter is a FSgt/PFLt promoter having the sequence of SEQ ID NO:62, FMVSgt promoter having the sequence of SEQ ID NO:69, CsVMV promoter having the sequence of SEQ ID NO: 68, dMMV promoter having the sequence of SEQ ID NO:63, HLVH12 promoter having the sequence of SEQ ID NO:60, NOS promoter having the sequence of SEQ ID NO:66, ScBV promoter having the sequence of SEQ ID NO:67, DCMV promoter having the sequence of SEQ ID NO: 61, Cm YLCV promoter having the sequence of SEQ ID NO:64, FS1_1 promoter having the sequence of SEQ ID NO:70, FE_3 promoter having the sequence of SEQ ID NO:71, e35S promoter having the sequence of SEQ ID NO:65, AtUBQ10 promoter having the sequence of SEQ ID NO: 259, PCLSV promoter having the sequence of SEQ ID NO:260, FS4 promoter having the sequence of SEQ ID NO:261, AtACT2 promoter having the sequence of SEQ ID NO:262, enhanced AtEf-1A promoter having the sequence of SEQ ID NO:263, FuasFScp promoter having the sequence of SEQ ID NO:264, FE4 promoter having the sequence of SEQ ID NO:269, cucumisin promoter having the sequence of SEQ ID NO:270 or SgCDS promoter having the sequence of SEQ ID NO:271.

3. The recombinant DNA molecule of claim 1, wherein the first, second, third, fourth, fifth, sixth, seventh and/or eighth polynucleotide sequence is operably linked to a heterologous terminator.

4. The recombinant DNA molecule of claim 3, wherein the first, second, third, fourth, fifth, sixth, seventh and/or eighth heterologous terminator sequence is a GmaxMYB2 terminator having the sequence of SEQ ID NO:74, 35S T terminator having the sequence of SEQ ID NO:80, ATHSP18.2 terminator having the sequence of SEQ ID NO:77, AtRBCS2b terminator having the sequence of SEQ ID NO:75, AtUBQ3 terminator having the sequence of SEQ ID NO:73, Pea E9 terminator having the sequence of SEQ ID NO:76, Pea3A terminator having the sequence of SEQ ID NO:72, potato Ubi3 terminator having the sequence of SEQ ID NO:78, AtTubB9 terminator having the sequence of SEQ ID NO:79, AtFAD2 terminator having the sequence of SEQ ID NO:265, AtNDUFA8 terminator having the sequence of SEQ ID NO:266, CsHSP 17.3 terminator having the sequence of SEQ ID NO:267 or CsHSP22 terminator having the sequence of (SEQ ID NO:268).

5. The recombinant DNA molecule of claim 1, further comprising:

i) a ninth polynucleotide sequence that encodes an NADPH:cytochrome P450 reductase polypeptide having at least 90% sequence identity to SEQ ID NO:19;

j) a tenth polynucleotide sequence that encodes a uridine phosphorylase-dependent glycosyltransferase polypeptide having at least 90% sequence identity to SEQ ID NO:21, SEQ ID NO: 23, SEQ ID NO: 120 or SEQ ID NO:122;

k) an eleventh polynucleotide sequence that encodes a 3-hydroxy-3-methylglutaryl-CoA synthase polypeptide having at least 90% sequence identity to SEQ ID NO:148;

l) a twelfth polynucleotide sequence that encodes a geranyl diphosphate synthase polypeptide having at least 90% sequence identity to SEQ ID NO:126;

m) a thirteenth polynucleotide sequence that encodes a hydrolase biosynthetic enzyme having at least 90% sequence identity to SEQ ID NO:158; and/or n) a fourteenth polynucleotide sequence that encodes a uridine phosphorylase-dependent glycosyltransferase enzyme having at least 90% sequence identity to SEQ ID NO:132;

wherein the ninth, tenth, eleventh, twelfth, thirteenth, and/or fourteenth polynucleotide sequence is operably linked to a heterologous promoter.

6. A recombinant host cell comprising the recombinant DNA molecule of claim 1.

7. A transgenic plant, plant part or seed comprising the recombinant DNA molecule of claim 1, wherein the transgenic plant, plant part or seed produces at least a first mogroside compound.

8. The transgenic plant, plant part or seed of claim 7, wherein the plant is a Cucurbitaceae, Solanaceae or Asteraceae plant.

9. The transgenic plant, plant part or seed of claim 8, wherein the plant is a watermelon, tomato, lettuce or cucumber plant.

10. The transgenic plant, plant part or seed of claim 7, wherein:

a) the plant produces at least 10 ng/g to 30 mg/g dry weight of the at least a first mogroside compound; or b) the plant produces an amount of the at least a first mogroside compound that is greater than the level in a non-transgenic plant, plant part or seed of the same species.

11. A method of producing a first mogroside compound comprising growing the transgenic plant of claim 7, wherein the transgenic plant produces the at least a first mogroside compound.

12. The method of claim 11, further comprising the step of isolating the at least a first mogroside compound from the transgenic plant.

13. A method of producing a processed lower calorie food or beverage product comprising adding the at least a first mogroside compound isolated from the transgenic plant, plant part or seed of claim 1 to a processed food or beverage product, wherein the processed lower calorie food or beverage product has less than 60 calories per 8 ounce serving of said processed lower calorie food or beverage product.

14. The method of claim 13, wherein the product is produced from a juice or extract of the transgenic plant, plant part or seed.

15. A method of producing a juice or extract, comprising isolating the juice or extract from the transgenic plant, plant part or seed of claim 7.

* * * * *

SEQUENCE LISTING

```
Sequence total quantity: 305
SEQ ID NO: 1           moltype = DNA  length = 1557
FEATURE                Location/Qualifiers
source                 1..1557
                       mol_type = other DNA
                       organism = synthetic construct
SEQUENCE: 1
atgtcctcat cagttgcagc tactatcagc atatggatgg tggtggtgtg catcgttggt  60
gttggctggc gggtggtgaa ttgggtttgg ttgaggccaa aaaaattgga gaagcggctc  120
cgcgaacagg gcttggcggg caactcgtat aggttgcttt tcggtgactt gaaggagaga  180
gccgctatgg cggagcaagc gaactctaag cccataaatt tttcccacga catcggtcct  240
agagtcttcc cgtcaatgta caagacgatt cagaactatg gaaagaattc ttatatgtgg  300
ctgggtccct atcctcgcgt ccacatcatg gacccccagc aattgaaaac ggtttttacg  360
ctcgtgtacg acatccagaa acccaacctg aatccactca ttaaattctt gctcgacggg  420
attgtcacac acgagggtga gaagtgggca aaacatagga agataataaa tcccgctttt  480
catatggcta agcttaaaga catgataccc gctttttttc agtcgtgtaa cgaaatagtc  540
tccgagtggg agcggatgat cccgaaagaa ggtagctttg aacttgatgt tatgccctac  600
atgcagaacc tcgccgcaga cgcaatttcc cgcactgctt tcggttcctc ctacaaggaa  660
ggacagatga tctttcagct gctgaaagag ctgactgact tggtggttaa agccgcgttt  720
ggaatctata ttcccggctg gcggtttctt cccacgaagt cgaacaacaa aatgaaagaa  780
ataaacagga agataaaaac cttgttgttg ggcataatag ataaacggca gaaagcgatg  840
aaggagggcg aggtcgttca gaacgacctg ctgggtattc tcgtggaatc gaatcttaat  900
gaaatcagag gccacgaaaa taataaggat gcaggaatgt caattgagga tgtgattgaa  960
gagtgtaagg ttttttatat cgggggtcaa gaaactaccg ctggcctcct tatctggact  1020
atgattctgc tttccttcca tacagagtgg caagaaagag ctcggacaga agtgctcgaa  1080
gtcgtgggca acaagaagcc tgactttgat ggattgaata gattgaaaat agttactatg  1140
atcctctacg aagtgttgag actctatccg cctgcgtcaa tgctgacccg gatagtccag  1200
```

```
aaggaaaccc gcataggaaa gttgacattg ccagctgggg ttactctgat aatcccaacg  1260
gtcctcattc atagagatca cgaattgtgg ggcgaagacg ctaacgagtt caagccggag  1320
cggttttctg agggagtgtc caaagccgcc aaggtccagc cggctttttt tcccttcggg  1380
tgggggccgc gcttgtgcct cggacagaat tttgcaatga tcgaagctaa aatggctttt  1440
agcctcattc ttcagcggtt tagctttcac ctctcatcat cttacgcgca tgccccaact  1500
gttgtgatga ctacgcagcc gcagcacggc gcccacatag tcctgcgcaa actctaa     1557

SEQ ID NO: 2            moltype = AA  length = 518
FEATURE                 Location/Qualifiers
source                  1..518
                        mol_type = protein
                        organism = Siraitia grosvenorii
SEQUENCE: 2
MSSSVAATIS IWMVVVCIVG VGWRVVNWVW LRPKKLEKRL REQGLAGNSY RLLFGDLKER  60
AAMAEQANSK PINFSHDIGP RVFPSMYKTI QNYGKNSYMW LGPYPRVHIM DPQQLKTVFT  120
LVYDIQKPNL NPLIKFLLDG IVTHEGEKWA KHRKIINPAF HMAKLKDMIP AFFQSCNEIV  180
SEWERMIPKE GSFELDVMPY MQNLAADAIS RTAFGSSYKE GQMIFQLLKE LTDLVVKAAF  240
GIYIPGWRFL PTKSNNKMKE INRKIKTLLL GIIDKRQKAM KEGEVVQNDL LGILVESNLN  300
EIRGHENNKD AGMSIEDVIE ECKVFYIGGQ ETTAGLLIWT MILLSFHTEW QERARTEVLE  360
VVGNKKPDFD GLNRLKIVTM ILYEVLRLYP PASMLTRIVQ KETRIGKLTL PAGVTLIIPT  420
VLIHRDHELW GEDANEFKPE RFSEGVSKAA KVQPAFFPFG WGPRLCLGQN FAMIEAKMAF  480
SLILQRFSFH LSSSYAHAPT VVMTTQPQHG AHIVLRKL                          518

SEQ ID NO: 3            moltype = DNA  length = 1557
FEATURE                 Location/Qualifiers
source                  1..1557
                        mol_type = other DNA
                        organism = synthetic construct
SEQUENCE: 3
atgtcgtcca gcgtggcggc cacgatcagc atctggatgg tggtcgtctg catcgtcggg  60
gtggggtggc gcgtcgtcaa ctgggtctgg ctccggccga agaagctgga gaagcgcctc  120
cgggagcagg ggctcgcggg caacagctac aggctgctgt tcggggacct caaggagagg  180
gccgcgatgg cggagcaggc gaacagcaag ccgatcaact tcagccacga catcggccg   240
cgcgtgttcc cgagcatgta caagacgatc cagaactacg gcaagaactc ctacatgtgg  300
ctcgggccgt acccgcgcgt gcacatcatg gacccgcagc agctcaagac cgtgttcacc  360
ctggtctacg acatccagaa gccgaacctg aacccgctga tcaagttcct cctggacggc  420
atcgtgaccc acgagggga gaagtgggcg aagcaccgca agatcatcaa cccggcgttc  480
cacatggcca agctcaagga catgatcccg gccttcttcc agtcctgcaa cgagatcgtc  540
tccgagtggg agcgcatgat cccgaaggag ggctccttcg agctggacgt gatgccgtac  600
atgcagaacc tggccgccga cgccatctcc cgcaccgcct tcggctcctc ctacaaggag  660
ggccagatga tcttccagct gctgaaggag ctgaccgacc tggtggtgaa ggccgccttc  720
ggcatctaca tcccgggctg gcgcttcctg ccgaccaagt ccaacaacaa gatgaaggag  780
atcaacagga agatcaagac cctgctgctg ggcatcatcg acaagcgcca gaaggccatg  840
aaggaggggg aggtcgtgca gaacgacctg ctgggcatcc tggtggagag caacctgaat  900
gagatccgcg gccacgagaa caacaaggac gcgggcatgt ccatcgagga cgtgatcgag  960
gagtgcaagg tgttctacat cgggggccag gagacgacgg ccgggctgct gatctggacc  1020
atgatcctcc tgtccttcca cacggagtgg caggagaggg cccgcaccga ggtgctggag  1080
gtggtgggga acaagaagcc ggacttcgac ggcctgaacc gcctgaagat cgtgaccatg  1140
atcctgtacg aggtcctgcg cctgtacccg ccggcgtcca tgctgaccag gatcgtgcag  1200
aaagaaaccc gcatcggcaa gctgaccctg ccggccgggg tgaccctgat catcccgacc  1260
gtgctgatcc accgcgacca cgagctgtgg ggggaggacg cgaacgagtt caagccggag  1320
aggttctccg agggggtgtc caaggcggcc aaggtgcagc cggcgttctt cccgttcggc  1380
tggggcccgc gcctgtgcct gggccagaac ttcgccatga tcgaggccaa aatggccttc  1440
tccctgatcc tgcagcgctt ctccttccac ctgtcctcct cctacgccca cgccccgacg  1500
gtggtgatga ccacccagcc gcagcacggc gcccacatcg tgctgaggaa gctgtaa     1557

SEQ ID NO: 4            moltype = DNA  length = 2277
FEATURE                 Location/Qualifiers
source                  1..2277
                        mol_type = other DNA
                        organism = synthetic construct
SEQUENCE: 4
atgtggcgcc ttaaggttgg ggccgagtct gtcggcgaga acgatgaaaa gtggctcaaa  60
tcaatcagca atcatcttgg caggcaggtc tgggaatttt gtcccgatgc cggaactcaa  120
caacagttgt tgcaagtcca caaagcgaga aaggcgttcc atgacgatag atttcatcgg  180
aaacagtcgt cggatctttt cattactata caatacggga aggaagttga gaacggtggg  240
aagacggctg gcgtgaaact taaagagggc gaagaggtga gaaaggaagc cgttgagagc  300
tccttggagc gggccttgtc gttttattca agcatccaga cgtctgacgg taattgggca  360
tcggacctcg ggggccccat gttcctcctg cccgggctgg tcatcgcgct ctacgttacc  420
ggtgttttga attcggtcct gtcaaaacat cacaggcagg agatgtgtcg gtatgtctat  480
aatcatcaga atgaggatgg cggttggggc ctgcacatag aagggccgtc tactatgttc  540
ggttcagcat tgaactacgt ggctctgcgg cttctcggtg aggacgccaa tgcgggtgca  600
atgccaaaag cgcgcgcttg gattctggac cacggcgggg ccaccggaat tacttcttgg  660
ggaaagctct ggctctcagt tcttggcgtg tacgagtggt ctggcaacaa cccactcccc  720
ccagaatttt ggctctttcc gtatttcctt cccttccatc cgggcagaat gtggtgtcat  780
tgtcggatgg tgtatttgcc gatgtcctat ttgtacggga aaaggttcgt tgggccgata  840
acgccgatcg ttcttagcct tagaaaagag ctctatgcgg tcccttatca cgagatcgac  900
tggaacaaat ctcggaacac atgtgcaaaa gaggacttgt actaccccca ccccaagatg  960
caggacatct tgtggggatc attgcaccat gtttacgagc ccctgtttac tcggtggcca  1020
```

```
gcgaaaaggc ttagggaaaa ggcgctgcag acggctatgc aacatattca ctatgaagat  1080
gaaaacactc gctatatttg cctgggccca gttaataaag tgctgaatct gctttgttgt  1140
tgggtcgaag atccatactc tgatgctttt aaactgcatc ttcaacgcgt gcatgattac  1200
ctttgggtgg cagaggatgg catgaaaatg cagggatata acggttccca actttgggat  1260
accgctttca gcattcaagc aatagtctca acgaagttgg tcgataacta cggtcccact  1320
ttgcggaagg cgcacgattt cgtcaaatca tcgcaaatac aacaggactg ccctggcgat  1380
cccaacgtgt ggtacaggca tatccacaaa ggagcatggc cattttctac gagggaccat  1440
gggtggctga tatcggattg taccgccgaa ggactcaagg cagcccttat gctcagcaag  1500
ttgccgtccg agacagtggg tgagtcgctt gaacgcaatc ggctgtgcga cgctgttaac  1560
gtcttgctgt ctttgcagaa cgacaacggc gggttcgcat cgtatgagct tactagatcg  1620
tatccgtggc ttgaactcat taatcccgcc gaaacattcg gagatatcgt gattgactat  1680
ccctatgtgg aatgcacttc tgcaacaatg gaagcgctta cactttcaa aaaacttcac  1740
cctgggcaca ggactaagga aatcgacaca gcgatagtgc gcgccgcgaa cttcctggag  1800
aatatgcaga gaactgacgg ctcttggtat ggctgctggg gcgtttgctt cacatatgca  1860
ggctggtttg gaattaaagg cctcgttgcc gccgggcgca cgtacaataa ctgtcttgct  1920
atcaggaaag cttgtgattt tctgctttcc aaggagcttc cgggcggtgg gtggggcgag  1980
tcgtatttga gctgccaaaa taaagtctat acaaacctcg agggtaaccg gcctcacctt  2040
gtcaacacag cttgggtttt gatggcgttg atagaggctg gtcaagctga gcgggacccc  2100
acaccacttc atagggccgc aaggcttttg ataaattcac agctcgaaaa tggcgatttc  2160
ccgcaacagg aaatcatggg agtttttaac aaaaactgca tgataaccta cgccgcttat  2220
aggaatatat tcccgatctg ggccctgggt gaatactgcc atcgggtgtt gacctaa     2277

SEQ ID NO: 5           moltype = AA  length = 758
FEATURE                Location/Qualifiers
source                 1..758
                       mol_type = protein
                       organism = synthetic construct
SEQUENCE: 5
MWRLKVGAES VGENDEKWLK SISNHLGRQV WEFCPDAGTQ QQLLQVHKAR KAFHDDRFHR  60
KQSSDLFITI QYGKEVENGG KTAGVKLKEG EEVRKEAVES SLERALSFYS SIQTSDGNWA  120
SDLGGPMFLL PGLVIALYVT GVLNSVLSKH HRQEMCRYVY NHQNEDGGWG LHIEGPSTMF  180
GSALNYVALR LLGEDANAGA MPKARAWILD HGGATGITSW GKLWLSVLGV YEWSGNNPLP  240
PEFWLFPYFL PFHPGRMWCH CRMVYLPMSY LYGKRFVGPI TPIVLSLRKE LYAVPYHEID  300
WNKSRNTCAK EDLYYPHPKM QDILWGSLHH VYEPLFTRWP AKRLREKALQ TAMQHIHYED  360
ENTRYICLGP VNKVLNLLCC WVEDPYSDAF KLHLQRVHDY LWVAEDGMKM QGYNGSQLWD  420
TAFSIQAIVS TKLVDNYGPT LRKAHDFVKS SQIQQDCPGD PNVWYRHIHK GAWPFSTRDH  480
GWLISDCTAE GLKAALMLSK LPSETVGESL ERNRLCDAVN VLLSLQNDNG GFASYELTRS  540
YPWLELINPA ETFGDIVIDY PYVECTSATM EALTLFKKLH PGHRTKEIDT AIVRAANFLE  600
NMQRTDGSWY GCWGVCFTYA GWFGIKGLVA AGRTYNNCLA IRKACDFLLS KELPGGGWGE  660
SYLSCQNKVY TNLEGNRPHL VNTAWVLMAL IEAGQAERDP TPLHRAARLL INSQLENGDF  720
PQQEIMGVFN KNCMITYAAY RNIFPIWALG EYCHRVLT                          758

SEQ ID NO: 6           moltype = DNA  length = 1422
FEATURE                Location/Qualifiers
source                 1..1422
                       mol_type = other DNA
                       organism = synthetic construct
SEQUENCE: 6
atgtggaccg tcgtgttggg cctcgcgacc ctgttcgtcg cgtactatat ccactggatt  60
aacaagtggc gcgacagcaa gttcaacggc gtcctccccc ccggcactat ggggcttccg  120
ctcataggcg aaacaatcca gctctcccgg ccgtccgaca gcctggacgt gcacccgttc  180
atccagaaga aggtggagcg gtacgggccg atcttcaaga cctgcctggc cgggcgcccg  240
gtggtcgtct cggcggacgc ggagttcaac aactacatca tgctccagga gggccgcgcc  300
gtcgagatgt ggtatcttga caccctgtcc aaatttttcg gcctggacac cgagtggctg  360
aaggcgctgg gcctgatcca caagtacatc cgctccatca ccctgaacca cttcggcgcc  420
gaggcgctcc gcgagcgctt cctgccgttc atcgaggcgt cctccatgga ggcgctgcac  480
tcttggtcta ctcagccgtc ggtcgaggtg aagaacgcgt ccgcgctgat ggtgttccgc  540
accagcgtga acaagatgtt cggcgaggac gcgaagaagc tgtccgggaa catcccgggc  600
aagttcacga agctcctcgg gggcttcctc tcgctcccgc tcaacttccc ggggaccacc  660
taccacaagt gcctcaagga catgaaggag atccagaaga agctgcgcga ggtggtcgac  720
gaccgcctgg cgaacgtggg gccggacgtg gaggacttcc tcggccaggc gctgaaggac  780
aaggagagcg agaagttcat ctccgaggag ttcatcatcc agcttctttt cagcatcagc  840
ttcgcgagct tcgagtccat cagcaccacg ctcacgctga tcctcaagct gctggacgag  900
cacccggagg tcgtgaagga gctggaggcg gagcacgagg cgatccgcaa ggcccgcgcc  960
gacccagacg gcccgatcac ctgggaggag tacaagtcca tgaccttcac cctccaggtg  1020
atcaacgaga cgctgcgcct ggggtccgtg accccggccc tgctgaggaa gaccgtcaag  1080
gacctccagg tgaagggcta catcatcccc gagggctgga ccatcatgct ggtgacggcc  1140
tcccgccacc gcgacccgaa ggtgtacaag gacccgcaca tcttcaaccc gtggaggtgg  1200
aaggacctgg actccatcac catccagaag aacttcatgc cgttcggcgg cggcctgcgc  1260
cactgcgcgg gggccgagta ctccaaagtg tacctgtgca ccttcctgca catcctgtgc  1320
accaagtacc gctggaccaa gctgggcggg gggacgatcg cccgcgccca catcctgtcc  1380
ttcgaggacg gcctgcacgt gaagttcacc ccaaaggagt ga                     1422

SEQ ID NO: 7           moltype = AA  length = 473
FEATURE                Location/Qualifiers
source                 1..473
                       mol_type = protein
                       organism = Siraitia grosvenorii
SEQUENCE: 7
```

```
MWTVVLGLAT LFVAYYIHWI NKWRDSKFNG VLPPGTMGLP LIGETIQLSR PSDSLDVHPF  60
IQKKVERYGP IFKTCLAGRP VVVSADAEFN NYIMLQEGRA VEMWYLDTLS KFFGLDTEWL  120
KALGLIHKYI RSITLNHFGA EALRERFLPF IEASSMEALH SWSTQPSVEV KNASALMVFR  180
TSVNKMFGED AKKLSGNIPG KFTKLLGGFL SLPLNFPGTT YHKCLKDMKE IQKKLREVVD  240
DRLANVGPDV EDFLGQALKD KESEKFISEE FIIQLLFSIS FASFESISTT LTLILKLLDE  300
HPEVVKELEA EHEAIRKARA DPDGPITWEE YKSMTFTLQV INETLRLGSV TPALLRKTVK  360
DLQVKGYIIP EGWTIMLVTA SRHRDPKVYK DPHIFNPWRW KDLDSITIQK NFMPFGGGLR  420
HCAGAEYSKV YLCTFLHILC TKYRWTKLGG GTIARAHILS FEDGLHVKFT PKE         473

SEQ ID NO: 8           moltype = DNA  length = 1425
FEATURE                Location/Qualifiers
source                 1..1425
                       mol_type = other DNA
                       organism = synthetic construct
SEQUENCE: 8
atggtgcagc cccgggtgct gctgttccct ttccccgcgc tgggccacgt gaagcccttc  60
ctgtcgctgg cggagctcct gtccgacgcc ggcatcgacg tggtcttcct ctcgacggag  120
tataaccacc gccgcatctc caacaccgag gccctggcct cccgcttccc caccctgcac  180
ttcgaaacga taccggacgg cctgccccccc aacgagtcgc gcgccctcgc ggacggcccc  240
ctgtacttca gcatgaggga gggcaccaag ccgcgcttcc ggcagctgat ccagagcctt  300
aacgacggcc gttggcccat cacctgtatc atcacggaca tcatgctcag ttcgcccatc  360
gaggtggcgg aggagttcgg gatcccggtg atcgcgttct gcccgtgctc cgctcgctac  420
ctctcgatcc acttcttcat cccgaagctg gtggaggagg ggcagatccc gtacgcggac  480
gacgacccca ttggggagat ccaggggggtg cccctcttcg aggggcttct ccgacggaac  540
cacctcccgg gatcttggtc cgacaagtcc gcggacattt ccttctcgca cggcctcatc  600
aaccagacgc tcgcggccgg gcgggcctcg gccctgatcc tcaacacctt cgacgagctc  660
gaggcccctt tcctcaccca cctgagctcc atcttcaaca agatctacac catcggcccc  720
ctccacgccc tgtccaagag ccggctcggg gactcctcct cgtcggccag cgcgctctcg  780
gggttctgga aggaggaccg cgcgtgcatg tcctggctcg actgccagcc gccgcgctcg  840
gtcgtgttcg tctccttcgg gtcgaccatg aagatgaagg cggacgagct tcgggagttc  900
tggtacgggc tggtgagcag cgggaagccg ttcctctgcg tgttgcggtc cgacgtcgtc  960
agcggcggcg aggcggcgga gctcatcgag cagatggcgg aggaggaggg ggctgggggc  1020
aagctgggca tggtcgtcga gtgggcggcg caggagaagg tcctctccca ccctgccgtg  1080
gggggcttcc tgacgcactg cggctggaac tcgacggtgg agagcatcgc cgccggcgtc  1140
cccatgatgt gctggcccgat cctcggggac cagccctcca acgccacttg gatcgaccgg  1200
gtctggaaga tcggggtcga gcgaaacaac cgggagtggg accggttgac ggtggagaag  1260
atggtccgcg cattgatgga gggccagaag cgggtggaga tccagcggtc gatggagaag  1320
ctgtcgaagc tggcgaacga gaaggtcgtc cggggggggc tgtctttcga caacctcgag  1380
gtcctcgtgg aggacatcaa gaagctgaag ccgtacaagt tctag                 1425

SEQ ID NO: 9           moltype = AA  length = 474
FEATURE                Location/Qualifiers
source                 1..474
                       mol_type = protein
                       organism = Siraitia grosvenorii
SEQUENCE: 9
MVQPRVLLFP FPALGHVKPF LSLAELLSDA GIDVVFLSTE YNHRRISNTE ALASRFPTLH  60
FETIPDGLPP NESRALADGP LYFSMREGTK PRFRQLIQSL NDGRWPITCI ITDIMLSSPI  120
EVAEEFGIPV IAFCPCSARY LSIHFFIPKL VEEGQIPYAD DDPIGEIQGV PLFEGLLRRN  180
HLPGSWSDKS ADISFSHGLI NQTLAAGRAS ALILNTFDEL EAPFLTHLSS IFNKIYTIGP  240
LHALSKSRLG DSSSSASALS GFWKEDRACM SWLDCQPPRS VVFVSFGSTM KMKADELREF  300
WYGLVSSGKP FLCVLRSDVV SGGEAAELIE QMAEEEGAGG KLGMVVEWAA QEKVLSHPAV  360
GGFLTHCGWN STVESIAAGV PMMCWPILGD QPSNATWIDR VWKIGVERNN REWDRLTVEK  420
MVRALMEGQK RVEIQRSMEK LSKLANEKVV RGGLSFDNLE VLVEDIKKLK PYKF        474

SEQ ID NO: 10          moltype = DNA  length = 1362
FEATURE                Location/Qualifiers
source                 1..1362
                       mol_type = other DNA
                       organism = synthetic construct
SEQUENCE: 10
atggacgcgc agcggggcca cacgacgacg atcctgatgt tcccctggct cggctacggg  60
cacctcagcg ccttcctcga gctggcgaag agcctgtccc ggcgcaactt ccacatctac  120
ttctgctcga ccagcgtcaa cctggacgcg atcaagccca agctgccctc cagcagctcc  180
tccgacagca tccagctggt ggagctgtgc ctgccctcca gccccgacca gctcccccccg  240
cacctccaca ccaccaacgc gctcccgccc cacctcatgc ccaccctcca ccaggccttc  300
agcatggcgg cgcagcactt cgcggccatc ctgcacaccc tcgcgcccca cctcctgatc  360
tacgactcgt tccagccgtg ggcaccccag ctggcctcct cgctcaacat cccggccatc  420
aacttcaaca cgaccggggc gtccgtcctg acccggatgc tgcacgcgac ccactacccg  480
agcagcaagt tccccatcag cgagttcgtg ctccacgact actggaaggc catgtacagc  540
gcggccgggg gcgcggtgac gaagaaggac cacaagatcg gcgagacgct ggcgaactgc  600
ctccacgcca gctgctcggt catcctgatc aactccttcc gcgagctgga ggagaagtac  660
atggactacc tgtccgtgct cctgaacaag aaggtggtgc cggtggggcc gctggtgtac  720
gagccgaacc aggatggaga ggacgagggg tactccagca taaagaactg gctcgacaag  780
aaggagccga gctccacggt gttcgtgtcc ttcggcagcg agtacttccc gagcaaggag  840
gagatggagg agatcgccca cgggctcgag gcctctgaag ttcatttcat ctgggttgtg  900
cggttcccgc agggggacaa cacctccgcg atcgaggacg ccctgccgaa gggcttcctc  960
gagagggtgg gcgagagggg catggtggtg aagggctggg ccccgcaggc gaagatcctg  1020
aagcactggt ccaccggggg cttcgtgtcc cactgcggct ggaacagcgt gatggagagc  1080
```

```
atgatgttcg gggtgccgat catcggcgtg ccgatgcacc tggaccagcc gttcaacgcc  1140
ggcctggccg aggaggccgg cgtgggggtg gaggcgaagc gcgaccccga cgggaagatc  1200
cagcgcgacg aggtcgccaa gctgatcaag gaggtggtgg tggagaagac ccgggaggac  1260
gtgaggaaga aggcgcgcga gatgtccgag atcctccgca gcaaggggga ggagaagatg  1320
gacgagatgg tggccgcgat ctccctcttc ctcaagatct ga                     1362

SEQ ID NO: 11          moltype = AA  length = 453
FEATURE                Location/Qualifiers
source                 1..453
                       mol_type = protein
                       organism = Siraitia grosvenorii
SEQUENCE: 11
MDAQRGHTTT ILMFPWLGYG HLSAFLELAK SLSRRNFHIY FCSTSVNLDA IKPKLPSSSS  60
SDSIQLVELC LPSSPDQLPP HLHTTNALPP HLMPTLHQAF SMAAQHFAAI LHTLAPHLLI  120
YDSFQPWAPQ LASSLNIPAI NFNTTGASVL TRMLHATHYP SSKFPISEFV LHDYWKAMYS  180
AAGGAVTKKD HKIGETLANC LHASCSVILI NSFRELEEKY MDYLSVLLNK KVVPVGPLVY  240
EPNQDGEDEG YSSIKNWLDK KEPSSTVFVS FGSEYFPSKE EMEEIAHGLE ASEVHFIWVV  300
RFPQGDNTSA IEDALPKGFL ERVGERGMVV KGWAPQAKIL KHWSTGGFVS HCGWNSVMES  360
MMFGVPIIGV PMHLDQPFNA GLAEEAGVGV EAKRDPDGKI QRDEVAKLIK EVVVEKTRED  420
VRKKAREMSE ILRSKGEEKM DEMVAAISLF LKI                                453

SEQ ID NO: 12          moltype = DNA  length = 1587
FEATURE                Location/Qualifiers
source                 1..1587
                       mol_type = other DNA
                       organism = synthetic construct
SEQUENCE: 12
atggtggacc agtgcgcctt gggctggatc ttggcctccg cgctgggcct cgtgatcgcc  60
ctgtgcttct tcgtcgcccc ccggcggaac caccgggggg tcgactcgaa ggagagggac  120
gagtgcgtcc agagcgcggc caccacgaag gggggagtgcc ggttcaacga ccgcgacgtc  180
gacgtgatcg tcgttggcgc cggcgtcgcg ggcagcgccc tcgcccacac tctggggaag  240
gacgggcggc gcgtgcacgt cattgagcgc gacctgacgg agcccgaccg gatcgtgggg  300
gagctcctcc agcccggggg gtacctcaag ctcatcgagc tgggtctgca ggactgcgtc  360
gaggagatcg acgcgcagag ggtgtacggc tacgcgctgt tcaaggacgg gaagaacacc  420
cggctctctt acccgttgga gaatttccac tccgacgtgt cggggcggag cttccacaac  480
ggccgcttca tccagcgcat gagggagaag gccgcgtccc tgcccaacgt gcggttggag  540
cagggcacgg ttacctccct gctggaggag aagggcacga tcaagggcgt gcagtacaag  600
tccaagaacg gtgaggagaa gacggcctac gccccccctga ccatcgtctg cgacggctgc  660
ttctcgaacc tgcgccgctc cctgtgcaac cctatggtgg acgtgcccag ctacttcgtg  720
ggcctcgtcc tggagaactg cgagctaccc ttcgcgaacc acgggcacgt tatcctcggg  780
gatccctcgc ccatcctctt ctaccagatc agccgtaccg agatccgttg cctcgtggac  840
gtccccgggc agaaggtccc ctccatcgcg aacggggaga tggagaagta ccttaagacg  900
gtggtcgcgc cccaggtgcc cccgcagatc tacgactcct tcatcgcggc gatcgacaag  960
gggaacatcc ggacgatgcc gaaccgctcc atgcccgctg cgccccaccc cacgcccggc  1020
gccttgctca tgggcgacgc gttcaacatg cgccaccccc tgaccggggg cggcatgacc  1080
gtggccctca gtgacatcgt cgtactccgc aacctgctca agccgctgaa ggacctgtcg  1140
gacgcctcta ccctctgcaa gtacctcgag agcttctaca cattgcggaa gccagtggct  1200
tcgaccatca acacgctagc gggggcgctg tacaaggtct tctgcgccag ccccgaccag  1260
gcgcgaaagg agatgcggca ggcctgcttc gactacctca gcctgggcgg catcttctca  1320
aacggccccg tctccctgct tagcggcttg aacccgcgcc ccctgtctct ggttctccac  1380
ttcttcgcgg tcgcgatcta cggcgtcggc cgcctgctgc tgccgttccc ctcggtgaag  1440
ggcatctgga tcggcgccag gttgatctac agcgcctcgg gcatcatctt ccccatcatc  1500
cgggccgagg gcgtccggca gatgttcttc cccgccacgg tcccggccta ctaccgctcc  1560
ccccccgtgt tcaagcccat cgtctga                                      1587

SEQ ID NO: 13          moltype = AA  length = 528
FEATURE                Location/Qualifiers
source                 1..528
                       mol_type = protein
                       organism = Siraitia grosvenorii
SEQUENCE: 13
MVDQCALGWI LASALGLVIA LCFFVAPRRN HRGVDSKERD ECVQSAATTK GECRFNDRDV  60
DVIVVGAGVA GSALAHTLGK DGRRVHVIER DLTEPDRIVG ELLQPGGYLK LIELGLQDCV  120
EEIDAQRVYG YALFKDGKNT RLSYPLENFH SDVSGRSFHN GRFIQRMREK AASLPNVRLE  180
QGTVTSLLEE KGTIKGVQYK SKNGEEKTAY APLTIVCDGC FSNLRRSLCN PMVDVPSYFV  240
GLVLENCELP FANHGHVILG DPSPILFYQI SRTEIRCLVD VPGQKVPSIA NGEMEKYLKT  300
VVAPQVPPQI YDSFIAAIDK GNIRTMPNRS MPAAPHPTPG ALLMGDAFNM RHPLTGGGMT  360
VALSDIVVLR NLLKPLKDLS DASTLCKYLE SFYTLRKPVA STINTLAGAL YKVFCASPDQ  420
ARKEMRQACF DYLSLGGIFS NGPVSLLSGL NPRPLSLVLH FFAVAIYGVG RLLLPFPSVK  480
GIWIGARLIY SASGIIFPII RAEGVRQMFF PATVPAYYRS PPVFKPIV                528

SEQ ID NO: 14          moltype = DNA  length = 951
FEATURE                Location/Qualifiers
source                 1..951
                       mol_type = other DNA
                       organism = synthetic construct
SEQUENCE: 14
atggaccaga tcgagcacat caccatcaac accaacggca tcaagatgca catcgcctcc  60
gtgggcacgg gcccggtggt gctgctgctg cacggcttcc cggagctgtg gtactcctgg  120
```

```
cgccaccagc tgctctacct gtcctccgtg ggctacaggg ccatcgcccc ggacctgagg  180
ggctacggcg acaccgactc ccccggcctcc ccgaccagct acaccgccct gcacatcgtc  240
ggggacctgg tgggcgccct ggacgagctc ggcatcgaga aggtgtttct cgtgggccac  300
gactggggcg cgatcatcgc ctggtacttc tgcctgttcc gcccggaccg catcaaggcc  360
ctggtgaacc tgtccgtgca gttcatcccg aggaacccgg ccatcccgtt catcgagggc  420
ttcaggaccg ccttcggcga cgacttctac atgtgcaggt tccaggtgcc gggcgaggcc  480
gaggaggact tcgcctccat cgacaccgcc cagctgttca agacctccct gtgcaaccgc  540
tcctccgccc cgccgtgcct gccgaaggag atcgggttca gggccatccc gccgccggag  600
aatctgccgt cctggctgac ggaggaagac atcaactatt atgccgccaa gttcaagcag  660
accggcttca ccggcgccct gaactactac agggccttcg acctgacctg ggagctgacc  720
gccccgtgga ccggcgcgca gatccaggtg ccggtgaagt tcatcgtcgg cgactccgac  780
ctgacgtacc acttcccggg cgccaaggag tacatccaca acggcgggtt caagaaggac  840
gtgccgctgc tggaggaggt cgtggtggtg aaggacgcct gccacttcat caatcaggag  900
cgcccgcagg agatcaacgc ccacatccac gacttcatca acaagttctg a           951

SEQ ID NO: 15          moltype = AA  length = 316
FEATURE                Location/Qualifiers
source                 1..316
                       mol_type = protein
                       organism = Siraitia grosvenorii
SEQUENCE: 15
MDQIEHITIN TNGIKMHIAS VGTGPVVLLL HGFPELWYSW RHQLLYLSSV GYRAIAPDLR  60
GYGDTDSPAS PTSYTALHIV GDLVGALDEL GIEKVFLVGH DWGAIIAWYF CLFRPDRIKA  120
LVNLSVQFIP RNPAIPFIEG FRTAFGDDFY MCRFQVPGEA EEDFASIDTA QLFKTSLCNR  180
SSAPPCLPKE IGFRAIPPPE NLPSWLTEED INYYAAKFKQ TGFTGALNYY RAFDLTWELT  240
APWTGAQIQV PVKFIVGDSD LTYHFPGAKE YIHNGGFKKD VPLLEEVVVV KDACHFINQE  300
RPQEINAHIH DFINKF                                                  316

SEQ ID NO: 16          moltype = DNA  length = 1275
FEATURE                Location/Qualifiers
source                 1..1275
                       mol_type = other DNA
                       organism = synthetic construct
SEQUENCE: 16
atgaacacga ccccgctgcc ggaggaggac gaggaggtgg tgaagatggt ggtggacggg  60
tccgtgccgt cctactcgct cgagtccaag ctcggcgacc cgaagcgcgc ggcgtccatc  120
cggcgggagg cgctgcagcg catgacgggg cggagcatcc acgggctgcc gttcgagggc  180
ttcgactacg agagcatcct gggccagtgc tgcgagatgc cggtggggta cgtccagatc  240
ccggtgggca tcgcggggcc gctgctgctc gacgggttcg agtacaccgt gccgatggcc  300
accacggagg gctgcctggt ggcctccacc aacaggggct gcaaggccat ctacgcctcc  360
ggcggggcga cctcaatgct cctcaaagac ggcatgacga gggcccccggt ggtcaggttc  420
ggcagcgcga agagggcgag cgagctgaag ttcttcctgg aggacccgaa caacttcgac  480
accctggccg tggtgttcaa ccgctccagc cgcttcgccc gcctgcagag catcaggtgc  540
agcatcgcgg gcaagaacct gtacgtccgc ttctgctgct ccaccggcga cgccatgggc  600
atgaacatgg tgtccaaggg cgtgcagaac gtgctggagt tcctgcagca cgacttctcc  660
gacatggagg tgatcggcat ctccggcaac ttctgcgccg acaagaagcc ggccgccgtg  720
aactggatcg agggcagggg caagtccgtg gtgtgcgagg ccattatcaa ggacgaggtg  780
gtgcgcaagg tgctcaagac cagcgtggcg agcctggtgg agctgaacat gctgaagaac  840
ctgaccggct ccgccatggc cggggccctc ggcggcttca acgcgcacag cagcaacatc  900
gtgtccgcca tcttcctggc caccggccag gacccggccc agaacgtgga gtcctcccac  960
tgcatcacga tgatggagcc ggtcaacaac ggcaaggacc tccacatctc cgtgaccatg  1020
ccgtccatcg aggtcgggac cgtgggggc ggcacccagc tggcgtccca gagcgcgtgc  1080
ctgaacctgc tgggggtcaa gggcgcgtcc aaggagagcc cgggggccaa cagcaggctg  1140
ctggcgacca tcgtggccgg ctccgtgctg gccggcgagc tctccctgat gtccgccatc  1200
gcggcgggcc agctggtgag gtcccacatg aagtacaacc gctcctccag ggatgtgtcc  1260
aaggtggaga gctaa                                                   1275

SEQ ID NO: 17          moltype = AA  length = 424
FEATURE                Location/Qualifiers
source                 1..424
                       mol_type = protein
                       organism = synthetic construct
SEQUENCE: 17
MNTTPLPEED EEVVKMVVDG SVPSYSLESK LGDPKRAASI RREALQRMTG RSIHGLPFEG  60
FDYESILGQC CEMPVGYVQI PVGIAGPLLL DGFEYTVPMA TTEGCLVAST NRGCKAIYAS  120
GGATSMLLKD GMTRAPVVRF GSAKRASELK FFLEDPNNFD TLAVVFNRSS RFARLQSIRC  180
SIAGKNLYVR FCCSTGDAMG MNMVSKGVQN VLEFLQHDFS DMEVIGISGN FCADKKPAAV  240
NWIEGRGKSV VCEAIIKDEV VRKVLKTSVA SLVELNMLKN LTGSAMAGAL GGFNAHSSNI  300
VSAIFLATGQ DPAQNVESSH CITMMEPVNN GKDLHISVTM PSIEVGTVGG GTQLASQSAC  360
LNLLGVKGAS KESPGANSRL LATIVAGSVL AGELSLMSAI AAGQLVRSHM KYNRSSRDVS  420
KVES                                                               424

SEQ ID NO: 18          moltype = DNA  length = 2127
FEATURE                Location/Qualifiers
source                 1..2127
                       mol_type = other DNA
                       organism = synthetic construct
SEQUENCE: 18
atgcagtccg agtccaggtc catgaaggtg tccccgctgg agctgatgtc cgccatcatc  60
```

```
aggaaggcca tggacccgtc cagggagtcc tccgagtccg tgagggaggt ggccaccctg  120
atcctggaga acagggagtt cgtgatgatc ctgaccaccc tgctggccgt gctgatcggc  180
tgcgtggtgg tgctggtgtg gaagaggtcc tccggccaga aggccaagcc gttcgagccg  240
ccgaagcagc tgatcgtgaa ggagccggag ccggaggtgg acgacggcaa gaagaaggtg  300
accgtgttct tcggcaccca gaccggcacc gccgagggct tcgccaaggc cctggccgag  360
gaggccaagg ccaggtacga gaaggccacc ttcagggtgg tggacctgga cgactacgcc  420
gccgacgacg acgagtacga ggagaagctg aagaaggaaa ccctggccat cttcttcctg  480
gccacctacg gcgacggcga gccgaccgac aacgccgcca ggttctacaa gtggttctcc  540
gagggcaagg agaagggcga ctggatctcc aacctgcagt acgccgtgtt cggcctgggc  600
aacaggcagt acgagcactt caacaagatc gccaaggtgg tggacgagca gctggccgag  660
cagggcggca agaggctggt gccggtgggc ctgggcgacg acgaccagtg catcgaggac  720
gacttctccg cctggaggga ggccctgtgg ccggagctgg acaagctgct gagggacgac  780
gacgactcca ccaccgtggc caccccgtac accgccgccg tgctggagta cagggtggtg  840
ttctacgacg ccgccgacgt gtccgtggag gacaagaggt gggccttcgc caacggccac  900
gccgtgtacg acgcccagca cccgtgcagg gccaacgtgg ccatgaggaa ggagctgcac  960
accccggcct ccgacaggtc ctgcatccac ctggagttcg acatctccgg caccggcctg  1020
acctacgaaa ccggcgacca cgtgggcgtg ttctgcgaga acctggacga aaccgtggag  1080
gacgccatca ggctgatcgg cctgtccccg gaaacctact tctccatcca caccgacaag  1140
gacgacggca ccccgctggg cggctcctcc ctgccgccgc cgttcgcccc gtgcaccctg  1200
aggaccgccc tgacccagta cgccgacctg ctgtcctccc cgaagaagtc cgccctggtg  1260
gccctggccg cccacgcctc cgacccggcc gaggccgaca ggctgaggca cctgtcctcc  1320
ccggccggca aggacgagta cgcccagtgg atcatcgcct cccagaggtc cctgctggag  1380
gtgatggccg agttcccgtc cgccaagccg ccgctgggcg tgttcttcgc cgccgtggcc  1440
ccgaggctgc agccgaggta ctactccatc tcctcctccc cgaggatggc cccgtccagg  1500
atccacgtga cctgcgccct ggtgtacgac aagaccccga ccggcaggat ccacaagggc  1560
gtgtgctcca cctggatgaa gaacgccgtg ccgctggagg agtcccaggc ctgctcctgg  1620
gccccgatct acgtgaggca gtccaacttc aagctgccga ccgactccaa gctgccgatc  1680
atcatgatcg gcccgggcac cggcctggcc ccgttcaggg gcttcctgca ggagaggctg  1740
gccctgaagg aggccggcgt ggagctgggc cactccatcc tgttcttcgg ctgcaggaac  1800
aggaagatgg actacatcta cgaggacgag ctgtccaact tcgccgaaac cggcgccctg  1860
tccgagctga tcgtggcctt ctccagggag ggcccgacca aggagtacgt gcagcacaag  1920
atggtggaca aggcctccga catctggaac atcctgtccc agggcggcta catctacgtg  1980
tgcggcgacg ccaagggcat ggccagggac gtgcacagga ccctgcacaa catcgtgcag  2040
gagcagggct ccctggactc ctccaaggcc gagtccatgg tgaagaacct gcagatgtcc  2100
ggcaggtacc tgagggacgt gtggtga                                      2127

SEQ ID NO: 19          moltype = AA  length = 708
FEATURE                Location/Qualifiers
source                 1..708
                       mol_type = protein
                       organism = Siraitia grosvenorii
SEQUENCE: 19
MQSESRSMKV SPLELMSAII RKAMDPSRES SESVREVATL ILENREFVMI LTTLLAVLIG  60
CVVVLVWKRS SGQKAKPFEP PKQLIVKEPE PEVDDGKKKV TVFFGTQTGT AEGFAKALAE  120
EAKARYEKAT FRVVDLDDYA ADDDEYEEKL KKETLAIFFL ATYGDGEPTD NAARFYKWFS  180
EGKEKGDWIS NLQYAVFGLG NRQYEHFNKI AKVVDEQLAE QGGKRLVPVG LGDDDQCIED  240
DFSAWREALW PELDKLLRDD DDSTTVATPY TAAVLEYRVV FYDAADVSVE DKRWAFANGH  300
AVYDAQHPCR ANVAMRKELH TPASDRSCIH LEFDISGTGL TYETGDHVGV FCENLDETVE  360
DAIRLIGLSP ETYFSIHTDK DDGTPLGGSS LPPPFAPCTL RTALTQYADL LSSPKKSALV  420
ALAAHASDPA EADRLRHLSS PAGKDEYAQW IIASQRSLLE VMAEFPSAKP PLGVFFAAVA  480
PRLQPRYYSI SSSPRMAPSR IHVTCALVYD KTPTGRIHKG VCSTWMKNAV PLEESQACSW  540
APIYVRQSNF KLPTDSKLPI IMIGPGTGLA PFRGFLQERL ALKEAGVELG HSILFFGCRN  600
RKMDYIYEDE LSNFAETGAL SELIVAFSRE GPTKEYVQHK MVDKASDIWN ILSQGGYIYV  660
CGDAKGMARD VHRTLHNIVQ EQGSLDSSKA ESMVKNLQMS GRYLRDVW                708

SEQ ID NO: 20          moltype = DNA  length = 1383
FEATURE                Location/Qualifiers
source                 1..1383
                       mol_type = other DNA
                       organism = synthetic construct
SEQUENCE: 20
atggacgaaa ccaccgtgaa cggcggcagg agggcctccg acgtggtggt gttcgccttc  60
ccgaggcacg gccacatgtc cccgatgctg cagttctcca agaggctggt gtccaagggc  120
ctgagggtga ccttcctgat caccacctcc gccaccgagt ccctgaggct gaacctgccg  180
ccgtcctcct ccctggacct gcaagtgatc tccgacgtgc cggagtccaa cgacatcgcc  240
accctggagg gctacctgag gtccttcaag gccaccgtgt ccaagaccct ggccgacttc  300
atcgacggca tcggcaaccc gccgaagttc atcgtgtacg actccgtgat gccgtgggtg  360
caggaggtgg ccaggggcag gggcctggac gccgccccgt tcttcaccca gtcctccgcc  420
gtgaaccaca tcctgaacca cgtgtacggc ggctccctgt ccatcccggc cccggagaac  480
accgccgtgt ccctgccgtc catgccggtg ctgcaggccg aggacctgcc ggccttcccg  540
gacgacccgg aggtggtgat gaacttcatg acctcccagt tctccaactt ccaggacgcc  600
aagtggatct tcttcaacac cttcgaccag ctggagtgca agaagcagtc ccaggtggtg  660
aactggatgg ccgacaggtg gccgatcaag accgtgggcc cgaccatccc gtccgcctac  720
ctggacgacg gcaggctgga ggacgacagg gccttcggcc tgaacctgct gaagccggag  780
gacggcaaga acaccaggca gtggcagtgg ctggactcca aggacaccgc ctccgtgctg  840
tacatctcct tcggctccct ggccatcctg caggaggagc aagtgaagga gctggcctac  900
ttcctgaagg acaccaacct gtccttcctg tgggtgctga gggactccga gctgcagaag  960
ctgccgcaca acttcgtgca ggaaacctcc cacaggggcc tggtggtgaa ctggtgctcc  1020
cagctgcaag tgctgtccca cagggccgtg tcctgcttcg tgacccactg cggctggaac  1080
```

```
tccaccctgg aggccctgtc cctgggcgtg ccgatggtgg ccatcccgca gtgggtggac  1140
cagaccacca acgccaagtt cgtggccgac gtgtggaggg tgggcgtgag ggtgaagaag  1200
aaggacgaga ggatcgtgac caaggaggag ctggaggcct ccatcaggca agtggtgcag  1260
ggcgagggca ggaacgagtt caagcacaac gccatcaagt ggaagaagct ggccaaggag  1320
gccgtggacg agggcggctc ctccgacaag aacatcgagg agttcgtgaa gaccatcgcc  1380
tga                                                                1383

SEQ ID NO: 21          moltype = AA  length = 460
FEATURE                Location/Qualifiers
source                 1..460
                       mol_type = protein
                       organism = Siraitia grosvenorii
SEQUENCE: 21
MDETTVNGGR RASDVVVFAF PRHGHMSPML QFSKRLVSKG LRVTFLITTS ATESLRLNLP  60
PSSSLDLQVI SDVPESNDIA TLEGYLRSFK ATVSKTLADF IDGIGNPPKF IVYDSVMPWV  120
QEVARGRGLD AAPFFTQSSA VNHILNHVYG GSLSIPAPEN TAVSLPSMPV LQAEDLPAFP  180
DDPEVVMNFM TSQFSNFQDA KWIFFNTFDQ LECKKQSQVV NWMADRWPIK TVGPTIPSAY  240
LDDGRLEDDR AFGLNLLKPE DGKNTRQWQW LDSKDTASVL YISFGSLAIL QEEQVKELAY  300
FLKDTNLSFL WVLRDSELQK LPHNFVQETS HRGLVVNWCS QLQVLSHRAV SCFVTHCGWN  360
STLEALSLGV PMVAIPQWVD QTTNAKFVAD VWRVGVRVKK KDERIVTKEE LEASIRQVVQ  420
GEGRNEFKHN AIKWKKLAKE AVDEGGSSDK NIEEFVKTIA                        460

SEQ ID NO: 22          moltype = DNA  length = 1374
FEATURE                Location/Qualifiers
source                 1..1374
                       mol_type = other DNA
                       organism = synthetic construct
SEQUENCE: 22
atgggcggca gggagggcaa ggtgcacgtg ctggtggtgc tgttcccgga cggccagggc  60
cacatcaacc cgatcctgca gttctccaag aggctggcct tcaagggcct ggccgtgacc  120
ctgctgaacg tgttcaggtc ccaggagtcc cacaccctga acctgcaccc gtccatcaac  180
gtggagcaca ggccgaggct gccgtaccag ggcaccgagc cggagtccct ggagtcccac  240
atgcacaggc tgcagacctc catctgcttc cacatgacca agctgatctc ccaccaccag  300
tcctccggct ccccgatcgc ctgcgtggtg tacgactccg tgaccccgtg ggtgctggac  360
gtggccaagg gcttcggcgt gccgggcgcc ccgttcttca ccgagtcctc cgccgtgaac  420
gccatcttct accacgtgca caggggctgg ctgaagatcc cgatcgacga ctcctccgtg  480
tccctgccgg gcctgccgct gctgcagatc tccgacctgc cgtccatgat cccgaacccg  540
cagcagtacc cgatcttcct gaggctgatg atcgaccagt tctccaacaa gccggactgg  600
atgttcatca acaccttcaa ctccctggag ccggaggtgc tgcagtggat ccagacccac  660
accccgctga agaccgtggg cccgaccgtg ccgtccatca tcaccgacaa gaggctgaag  720
gacgaccagc actacggcat cgacctgttc aagtccaccg gcgacgagat caagaccatc  780
gagtggctgg actccaagga ctccggctcc gtgatctacg tgtccttcgg ctccgtgtcc  840
gacctgggcg aggagcagat ggaggagctg gcctggggcc tgaagtccac caacaagtcc  900
ttcctgtggg tggtgaggga aaccggcacc tccaagctgc cgtccaacct gctggaggag  960
atgaaggaaa ccggcatggt ggtgaactgg tgctcccagc tgcaagtgct ggcccacaag  1020
tccgtgggct gcttcatcac ccactgcggc tggaactccg tgctggaggc cctgtccctg  1080
ggcatcccga tggtggccat gccgcagtgg accgaccaga tgaccaacgc caagttcgtg  1140
gaggacgtgt ggaaggtggg cgtgagggtg tcctccaagg agaacgccat cgccggcagg  1200
gaggagatcg agctgtgcat caggcaagtg atggagggcg agaggtccgc cgagatgagg  1260
gagaacgcct ccaggtggat gaagctggcc aaggaggccg tggacgaggg cggctcctcc  1320
gacaagaaca tcgacgagtt cgtggcccag ctgaccaaca ggaacccgaa ctga        1374

SEQ ID NO: 23          moltype = AA  length = 457
FEATURE                Location/Qualifiers
source                 1..457
                       mol_type = protein
                       organism = Siraitia grosvenorii
SEQUENCE: 23
MGGREGKVHV LVVLFPDGQG HINPILQFSK RLAFKGLAVT LLNVFRSQES HTLNLHPSIN  60
VEHRPRLPYQ GTEPESLESH MHRLQTSICF HMTKLISHHQ SSGSPIACVV YDSVTPWVLD  120
VAKGFGVPGA PFFTESSAVN AIFYHVHRGW LKIPIDDSSV SLPGLPLLQI SDLPSMIPNP  180
QQYPIFLRLM IDQFSNKPDW MFINTFNSLE PEVLQWIQTH TPLKTVGPTV PSIITDKRLK  240
DDQHYGIDLF KSTGDEIKTI EWLDSKDSGS VIYVSFGSVS DLGEEQMEEL AWGLKSTNKS  300
FLWVVRETGT SKLPSNLLEE MKETGMVVNW CSQLQVLAHK SVGCFITHCG WNSVLEALSL  360
GIPMVAMPQW TDQMTNAKFV EDVWKVGVRV SSKENAIAGR EEIELCIRQV MEGERSAEMR  420
ENASRWMKLA KEAVDEGGSS DKNIDEFVAQ LTNRNPN                           457

SEQ ID NO: 24          moltype = DNA  length = 1425
FEATURE                Location/Qualifiers
source                 1..1425
                       mol_type = other DNA
                       organism = synthetic construct
SEQUENCE: 24
atgtggacca tcttcctggg cttcgtgacc ctgaccatcg tgtactacat ctactggacc  60
aacaagtgga aggactccaa gttcaaccgc gtgctgccgc cgggcaccat gggcctcccg  120
ctgatcggcg aaaccctgca gttcctgagg ccgtcctact ccctggacct gcacccgttc  180
ttccagacca aggtgaagag gtacggcccg atcttcaaga cctgcctggc cggcaggccg  240
gtggtggtgt ccaccgacgc cgagttcaac cactacatca tgctgcagga gggcaaggcc  300
gtggagatgt ggtacctgga cgccttctcc aagttcttcg gcctggacac cgagtggacc  360
```

```
aaggccctgg gcctgatcca caagtacatc aggtccatca ccctgaacca ctacggcgtg  420
gagtccctga gggagaggtt cctgccgagg atcgaggagt ccgtgaggga aaccctgcac  480
tactgggcca cccagccgtc cgtggaggtg aaggactccg ccgccgccat ggtgctgaag  540
acctccgtga tcaagctgtt ctccgaggac tccaacaagc tgctgtccgg cggcctgctg  600
aagaagttca ccaagctgct gggcggcttc ctgaccctgc cgctgaacct gccgggcacc  660
acctaccaca ggtgcatcaa ggacatgaag gagatccaga agaagctgaa ggagatcctg  720
gaggagaggc tggccagggg caacggctcc gacgaggact tcctgggcca ggtgatcaag  780
gacaaggagt cccagaagtt catctccgag gagttcatca tccagctgct gttctccatg  840
tccttcgcca ccttcgagtc catctccgcc tccctgaccc tgatcctgat cctgctggcc  900
gaccacccgg aggtggccaa ggagctggag gtggagcacg aggccatcag gaaggcgcgc  960
gtggacccgg acggcctgat cacctgggag gagtacaagt ccatgacctt cacccacaac  1020
gtgatctacg aaaccctgcg cctgggctcc gtgatcccgt ccctgccccg gaagaccacc  1080
aaggagatcc agatcaaggg ctacaccatc ccggagggct ggaccatcat gctggtgatc  1140
gcctcccggc accgaaaccc gaaggtgtac aaggacccgg acaccttcaa cccgtggcgg  1200
tggaaggagc tggactccat caccatccag aagaacttca tgccgttcgg cggcggcctg  1260
cgccactgcg ccggcgccga gtacaccaag gtgtacctgt gcaccttcct gcacatcctg  1320
ttcaccaagt accgctggac caagctgaag ggcggcaaga tcgcccgcgc cctgatcctc  1380
aagttcgtgg acggcctgca cgtcaacttc accccgaagg agtga                 1425
```

```
SEQ ID NO: 25          moltype = AA  length = 474
FEATURE                Location/Qualifiers
source                 1..474
                       mol_type = protein
                       organism = Citrullus lanatus
SEQUENCE: 25
MWTIFLGFVT LTIVYYIYWT NKWKDSKFNR VLPPGTMGLP LIGETLQFLR PSYSLDLHPF  60
FQTKVKRYGP IFKTCLAGRP VVVSTDAEFN HYIMLQEGKA VEMWYLDAFS KFFGLDTEWT  120
KALGLIHKYI RSITLNHYGV ESLRERFLPR IEESVRETLH YWATQPSVEV KDSAAAMVLK  180
TSVIKLFSED SNKLLSGGLL KKFTKLLGGF LTLPLNLPGT TYHRCIKDMK EIQKKLKEIL  240
EERLARGNGS DEDFLGQVIK DKESQKFISE EFIIQLLFSM SFATFESISA SLTLILILLA  300
DHPEVAKELE VEHEAIRKAR VDPDGLITWE EYKSMTFTHN VIYETLRLGS VIPSLPRKTT  360
KEIQIKGYTI PEGWTIMLVI ASRHRNPKVY KDPDTFNPWR WKELDSITIQ KNFMPFGGGL  420
RHCAGAEYTK VYLCTFLHIL FTKYRWTKLK GGKIARALIL KFVDGLHVNF TPKE        474
```

```
SEQ ID NO: 26          moltype = DNA  length = 1422
FEATURE                Location/Qualifiers
source                 1..1422
                       mol_type = other DNA
                       organism = synthetic construct
SEQUENCE: 26
atgtggaccg tggtgctggg cctggccacc ctgttcgtgg cctactacat ccactggatc  60
aacaagtgga gggactccaa gttcaacggc gtgctgccgc cgggcaccat gggcctgccg  120
ctgatcggcg aaaccctgca gttcctgagg ccgtccgact ccctggacgt gcacccgttc  180
ttccagaaga aggtggagag gtacggcccg atcttcaaga cctgcctggc cggcaggccg  240
gtggtggtgt ccgccgacgc cgagttcaac aactacatca tgctgcagga gggcagggcc  300
gtggagatgt ggtacctgga caccctgtcc aagttcttcg gcctggacac cgagtggacc  360
aaggccctgg gcctgatcca caagtacatc aggtccatca ccctgaacca cttcggcgcc  420
gaggccctga gggagaggtt cctgccgttc atcgaggcct cctccatgga ggccctgcac  480
tcctggtcca cccagccgtc cgtggaggtg aagaacgcct ccgccctgat ggtgttcagg  540
acctccgtga acaagatgtt cggcgaggac gccaagaagc tgtccggcaa catcccgggc  600
aagttcacca agctgctggg cggcttcctg tccctgccgc tgaacttccc gggcaccacc  660
taccacaagt gcctgaagga catgaaggag atccagaaga agctgaggga ggtggtggac  720
gacaggctgg ccaacgtggg cccggacgtg gaggacttcc tgggccaggc cctgaaggac  780
aaggagtccg agaagttcat ctccgaggag ttcatcatcc agctgctgtt ctccatctcc  840
ttcgcctcct tcgagtccat ctccaccacc ctgaccctga tcctgaagct gctggacgag  900
cacccggagg tggtgaagga gctggaggcc gagcacgagg ccatcaggaa ggccagggcc  960
gacccggacg gcccgatcac ctgggaggag tacaagtcca tgaccttcac cctgcaagtg  1020
atctacgaaa ccctgaggct gggctccgtg atcccggccc tgccgaggaa gaccgtgaag  1080
gacctgcaag tgaagggcta catcatcccg gagggctgga ccatcatgct ggtgaccgcc  1140
tccaggcaca gggacccgaa ggtgtacaag gacccgcaca tcttcaaccc gtggaggtgg  1200
aaggacctgg actccatcac catccagaag aacttcatgc cgttcggcgg cggcctgagg  1260
cactgcgccg gcgccgagta ctccaaggtg tacctgtgca ccttcctgca catcctgtgc  1320
accaagtaca ggtggaccaa gctgggcggc ggcaccatcg ccagggccca catcctgtcc  1380
ttcgaggacg gcctgcacgt gaagttcacc ccgaaggagt ga                    1422
```

```
SEQ ID NO: 27          moltype = AA  length = 473
FEATURE                Location/Qualifiers
source                 1..473
                       mol_type = protein
                       organism = synthetic construct
SEQUENCE: 27
MWTVVLGLAT LFVAYYIHWI NKWRDSKFNG VLPPGTMGLP LIGETLQFLR PSDSLDVHPF  60
FQKKVERYGP IFKTCLAGRP VVVSADAEFN NYIMLQEGRA VEMWYLDTLS KFFGLDTEWT  120
KALGLIHKYI RSITLNHFGA EALRERFLPF IEASSMEALH SWSTQPSVEV KNASALMVFR  180
TSVNKMFGED AKKLSGNIPG KFTKLLGGFL SLPLNFPGTT YHKCLKDMKE IQKKLREVVD  240
DRLANVGPDV EDFLGQALKD KESEKFISEE FIIQLLFSIS FASFESISTT LTLILKLLDE  300
HPEVVKELEA EHEAIRKARA DPDGPITWEE YKSMTFTLQV IYETLRLGSV IPALPRKTVK  360
DLQVKGYIIP EGWTIMLVTA SRHRDPKVYK DPHIFNPWRW KDLDSITIQK NFMPFGGGLR  420
HCAGAEYSKV YLCTFLHILC TKYRWTKLGG GTIARAHILS FEDGLHVKFT PKE         473
```

SEQ ID NO: 28 moltype = DNA length = 1425
FEATURE Location/Qualifiers
source 1..1425
mol_type = other DNA
organism = synthetic construct
SEQUENCE: 28
atgtggaccg tggtgctggg cctggccacc ctgttcgtgg cctactacat ccactggatc 60
aacaagtgga gggactccaa gttcaacggc gtgctgccgc cgggcaccat gggcctgccg 120
ctgatcggcg aaaccctgca gttcctgagg ccgtccgact ccctggacgt gcacccgttc 180
ttccagaaga aggtggagag gtacggcccg atcttcaaga cctgcctggc cggcaggccg 240
gtggtggtgt ccgccgacgc cgagttcaac aactacatca tgctgcagga gggcagggcc 300
gtggagatgt ggtacctgga caccctgtcc aagttcttcg gcctggacac cgagtggacc 360
aaggccctgg gcctgatcca caagtacatc aggtccatca ccctgaacca cttcggcgcc 420
gaggccctga gggagaggtt cctgccgttc atcgaggcct cctccatgga ggccctgcac 480
tcctggtcca cccagccgtc cgtggaggtg aagaacgcct ccgccctgat ggtgttcagg 540
acctccgtga acaagatgtt cggcgaggac gccaagaagc tgctgtccgg caacatcccg 600
ggcaagttca ccaagctgct gggcggcttc ctgtccctgc cgctgaactt cccgggcacc 660
acctaccaca agtgcctgaa ggacatgaag gagatccaga agaagctgag ggaggtggtg 720
gacgacaggc tggccaacgt gggcccggac gtggaggact tcctgggcca ggccctgaag 780
gacaaggagt ccgagaagtt catctccgag gagttcatca tccagctgct gttctccatc 840
tccttcgcct ccttcgagtc catctccacc accctgaccc tgatcctgaa gctgctggac 900
gagcacccgg aggtggtgaa ggagctggag gccgagcacg aggccatcag gaaggccagg 960
gccgacccgg acggcccgat cacctgggag gagtacaagt ccatgacctt caccctgcaa 1020
gtgatctacg aaaccctgag gctgggctcc gtgatcccgg ccctgccgag gaagaccgtg 1080
aaggacctgc aagtgaaggg ctacatcatc ccggagggct ggaccatcat gctggtgacc 1140
gcctccaggc acagggaccc gaaggtgtac aaggacccgc acatcttcaa cccgtggagg 1200
tggaaggacc tggactccat caccatccag aagaacttca tgccgttcgg cggcggcctg 1260
aggcactgcg ccggcgccga gtactccaag gtgtacctgt gcaccttcct gcacatcctg 1320
tgcaccaagt acaggtggac caagctgggc ggcggcacca tcgccagggc ccacatcctg 1380
tccttcgagg acggcctgca cgtgaagttc accccgaagg agtga 1425

SEQ ID NO: 29 moltype = AA length = 474
FEATURE Location/Qualifiers
source 1..474
mol_type = protein
organism = synthetic construct
SEQUENCE: 29
MWTVVLGLAT LFVAYYIHWI NKWRDSKFNG VLPPGTMGLP LIGETLQFLR PSDSLDVHPF 60
FQKKVERYGP IFKTCLAGRP VVVSADAEFN NYIMLQEGRA VEMWYLDTLS KFFGLDTEWT 120
KALGLIHKYI RSITLNHFGA EALRERFLPF IEASSMEALH SWSTQPSVEV KNASALMVFR 180
TSVNKMFGED AKKLLSGNIP GKFTKLLGGF LSLPLNFPGT TYHKCLKDMK EIQKKLREVV 240
DDRLANVGPD VEDFLGQALK DKESEKFISE EFIIQLLFSI SFASFESIST TLTLILKLLD 300
EHPEVVKELE AEHEAIRKAR ADPDGPITWE EYKSMTFTLQ VIYETLRLGS VIPALPRKTV 360
KDLQVKGYII PEGWTIMLVT ASRHRDPKVY KDPHIFNPWR WKDLDSITIQ KNFMPFGGGL 420
RHCAGAEYSK VYLCTFLHIL CTKYRWTKLG GGTIARAHIL SFEDGLHVKF TPKE 474

SEQ ID NO: 30 moltype = DNA length = 1425
FEATURE Location/Qualifiers
source 1..1425
mol_type = other DNA
organism = synthetic construct
SEQUENCE: 30
atgtggacca tcctgctggg cctggccacc ctggccatcg cctactacat ccactgggtg 60
aacaagtgga aggactccaa gttcaacggc gtgctgccgc cgggcaccat gggcctgccg 120
ctgatcggcg aaaccctgca gttcctgagg ccgtccgact ccctggacgt gcacccgttc 180
ttccagagga aggtgaagag gtacggcccg atcttcaaga cctgcctggc cggcaggccg 240
gtggtggtgt ccaccgacgc cgagttcaac cactacatca tgctgcagga gggcagggcc 300
gtggagatgt ggtacctgga caccctgtcc aagttcttcg gcctggacac cgagtggacc 360
aaggccctgg gcctgatcca caagtacatc aggtccatca ccctgaacca cttcggcgcc 420
gagtccctga gggagaggtt cctgccgagg atcgaggagt ccgccaggga aaccctgcac 480
tactggtcca cccagacctc cgtggaggtg aaggagtccg ccgccgccat ggtgttcagg 540
acctccatcg tgaagatgtt ctccgaggac tcctccaagc tgctgaccga gggcctgacc 600
aagaagttca ccggcctgct gggcggcttc ctgaccctgc cgctgaacct gccgggcacc 660
acctaccaca agtgcatcaa ggacatgaag cagatccaga agaagctgaa ggacatcctg 720
gaggagaggc tggccaaggg cgtgaagatc gacgaggact tcctgggcca ggccatcaag 780
gacaaggagt cccagcagtt catctccgag gagttcatca tccagctgct gttctccatc 840
tccttcgcct ccttcgagtc catctccacc accctgaccc tgatcctgaa cttcctggcc 900
gaccacccgg acgtggtgaa ggagctggag gccgagcacg aggccatcag gaaggccagg 960
gccgacccgg acggcccgat cacctgggag gagtacaagt ccatgaactt caccctgaac 1020
gtgatctacg aaaccctgag gctgggctcc gtgatcccgg ccctgccgag gaagaccacc 1080
aaggagatcc agatcaaggg ctacaccatc ccggagggct ggaccgtgat gctggtgacc 1140
gcctccaggc acagggaccc ggaggtgtac aaggacccgg acaccttcaa cccgtggagg 1200
tggaaggagc tggactccat caccatccag aagaacttca tgccgttcgg cggcggcctg 1260
aggcactgcg ccggcgccga gtactccaag gtgtacctgt gcaccttcct gcacatcctg 1320
ttcaccaagt acaggtggag gaagctgaag ggcggcaaga tcgccagggc ccacatcctg 1380
aggttcgagg acggcctgta cgtgaacttc accccgaagg agtga 1425

SEQ ID NO: 31 moltype = AA length = 474

```
FEATURE                 Location/Qualifiers
source                  1..474
                        mol_type = protein
                        organism = synthetic construct
SEQUENCE: 31
MWTILLGLAT LAIAYYIHWV NKWKDSKFNG VLPPGTMGLP LIGETLQFLR PSDSLDVHPF  60
FQRKVKRYGP IFKTCLAGRP VVVSTDAEFN HYIMLQEGRA VEMWYLDTLS KFFGLDTEWT  120
KALGLIHKYI RSITLNHFGA ESLRERFLPR IEESARETLH YWSTQTSVEV KESAAAMVFR  180
TSIVKMFSED SSKLLTEGLT KKFTGLLGGF LTLPLNLPGT TYHKCIKDMK QIQKKLKDIL  240
EERLAKGVKI DEDFLGQAIK DKESQQFISE EFIIQLLFSI SFASFESIST TLTLILNFLA  300
DHPDVVKELE AEHEAIRKAR ADPDGPITWE EYKSMNFTLN VIYETLRLGS VIPALPRKTT  360
KEIQIKGYTI PEGWTVMLVT ASRHRDPEVY KDPDTFNPWR WKELDSITIQ KNFMPFGGGL  420
RHCAGAEYSK VYLCTFLHIL FTKYRWRKLK GGKIARAHIL RFEDGLYVNF TPKE        474

SEQ ID NO: 32           moltype = DNA  length = 1422
FEATURE                 Location/Qualifiers
source                  1..1422
                        mol_type = other DNA
                        organism = synthetic construct
SEQUENCE: 32
atgtggacca tcctgctggg cctggccacc ctggccatcg cctactacat ccactgggtg  60
aacaagtgga aggactccaa gttcaacggc gtgctgccgc cgggcaccat gggcctgccg  120
ctgatcggcg aaaccctgca gttcctgagg ccgtccgact ccctggacgt gcacccgttc  180
ttccagagga aggtgaagag gtacggcccg atcttcaaga cctgcctggc cggcaggccg  240
gtggtggtgt ccaccgacgc cgagttcaac cactacatca tgctgcagga gggcagggcc  300
gtggagatgt ggtacctgga caccctgtcc aagttcttcg gcctggacac cgagtggacc  360
aaggccctgg gcctgatcca caagtacatc aggtccatca ccctgaacca cttcggcgcc  420
gagtccctga gggagaggtt cctgccgagg atcgaggagt ccgccaggga aaccctgcac  480
tactggtcca cccagacctc cgtggaggtg aaggagtccg ccgccgccat ggtgttcagg  540
acctccatcg tgaagatgtt ctccgaggac tcctccaagc tgaccgaggg cctgaccaag  600
aagttcaccg gcctgctggg cggcttcctg accctgccgc tgaacctgcc gggcaccacc  660
taccacaagt gcatcaagga catgaagcag atccagaaga agctgaagga catcctggag  720
gagaggctgg ccaagggcgt gaagatcgac gaggacttcc tgggccaggc catcaaggac  780
aaggagtccc agcagttcat ctccgaggag ttcatcatcc agctgctgtt ctccatctcc  840
ttcgcctcct tcgagtccat ctccaccacc ctgaccctga tcctgaactt cctggccgac  900
cacccggacg tggtgaagga gctggaggcc gagcacgagg ccatcaggaa ggccagggcc  960
gacccggacg gcccgatcac ctgggaggag tacaagtcca tgaacttcac cctgaacgtg  1020
atctacgaaa ccctgaggct gggctccgtg atcccggccc tgccgaggaa gaccaccaag  1080
gagatccaga tcaagggcta caccatcccg gagggctgga ccgtgatgct ggtgaccgcc  1140
tccaggcaca gggacccgga ggtgtacaag gacccggaca ccttcaaccc gtggaggtgg  1200
aaggagctgg actccatcac catccagaag aacttcatgc cgttcggcgg cggcctgagg  1260
cactgcgccg gcgccgagta ctccaaggtg tacctgtgca ccttcctgca catcctgttc  1320
accaagtaca ggtggaggaa gctgaagggc ggcaagatcg ccagggccca catcctgagg  1380
ttcgaggacg gcctgtacgt gaacttcacc ccgaaggagt ga                     1422

SEQ ID NO: 33           moltype = AA  length = 473
FEATURE                 Location/Qualifiers
source                  1..473
                        mol_type = protein
                        organism = synthetic construct
SEQUENCE: 33
MWTILLGLAT LAIAYYIHWV NKWKDSKFNG VLPPGTMGLP LIGETLQFLR PSDSLDVHPF  60
FQRKVKRYGP IFKTCLAGRP VVVSTDAEFN HYIMLQEGRA VEMWYLDTLS KFFGLDTEWT  120
KALGLIHKYI RSITLNHFGA ESLRERFLPR IEESARETLH YWSTQTSVEV KESAAAMVFR  180
TSIVKMFSED SSKLTEGLTK KFTGLLGGFL TLPLNLPGTT YHKCIKDMKQ IQKKLKDILE  240
ERLAKGVKID EDFLGQAIKD KESQQFISEE FIIQLLFSIS FASFESISTT LTLILNFLAD  300
HPDVVKELEA EHEAIRKARA DPDGPITWEE YKSMNFTLNV IYETLRLGSV IPALPRKTTK  360
EIQIKGYTIP EGWTVMLVTA SRHRDPEVYK DPDTFNPWRW KELDSITIQK NFMPFGGGLR  420
HCAGAEYSKV YLCTFLHILF TKYRWRKLKG GKIARAHILR FEDGLYVNFT PKE         473

SEQ ID NO: 34           moltype = DNA  length = 3177
FEATURE                 Location/Qualifiers
source                  1..3177
                        mol_type = other DNA
                        organism = synthetic construct
SEQUENCE: 34
atgtcgtcca gcgtggcggc cacgatcagc atctggatgg tggtcgtctg catcgtcggg  60
gtggggtggc gcgtcgtcaa ctgggtctgg ctccggccga agaagctgga gaagcgcctc  120
cgggagcagg ggctcgcggg caacagctac aggctgctgt tcggggacct caaggagagg  180
gccgcgatgg cggagcaggc gaacagcaag ccgatcaact tcagccacga catcgggccg  240
cgcgtgttcc cgagcatgta caagacgatc cagaactacg gcaagaactc ctacatgtgg  300
ctcgggccgt acccgcgcgt gcacatcatg gacccgcagc agctcaagac cgtgttcacc  360
ctggtctacg acatccagaa gccgaacctg aacccgctga tcaagttcct cctggacggc  420
atcgtgaccc acgaggggga gaagtgggcg aagcaccgca agatcatcaa cccggcgttc  480
cacatggcca agctcaagga catgatcccg gccttcttcc agtcctgcaa cgagatcgtc  540
tccgagtggg agcgcatgat cccgaaggag ggctccttcg agctggacgt gatgccgtac  600
atgcagaacc tggccgccga cgccatctcc cgcaccgcct tcggctcctc ctacaaggag  660
ggccagatga tcttccagct gctgaaggag ctgaccgacc tggtggtgaa ggccgccttc  720
ggcatctaca tcccgggctg gcgcttcctg ccgaccaagt ccaacaacaa gatgaaggag  780
```

```
atcaacagga agatcaagac cctgctgctg ggcatcatcg acaagcgcca gaaggccatg  840
aaggaggggg aggtcgtgca gaacgacctg ctgggcatcc tggtggagag caacctgaat  900
gagatccgcg gccacgagaa caacaaggac gcgggcatgt ccatcgagga cgtgatcgag  960
gagtgcaagg tgttctacat cgggggccag gagacgacgg ccgggctgct gatctggacc  1020
atgatcctcc tgtccttcca cacggagtgg caggagaggg cccgcaccga ggtgctggag  1080
gtggtgggga acaagaagcc ggacttcgac ggcctgaacc gcctgaagat cgtgaccatg  1140
atcctgtacg aggtcctgcg cctgtacccg ccggcgtcca tgctgaccag gatcgtgcag  1200
aaagaaaccc gcatcggcaa gctgaccctg ccggccgggg tgaccctgat catcccgacc  1260
gtgctgatcc accgcgacca cgagctgtgg ggggaggacg cgaacgagtt caagccggag  1320
aggttctccg agggggtgtc caaggcggcc aaggtgcagc cggcgttctt cccgttcggc  1380
tggggcccgc gcctgtgcct gggccagaac ttcgccatga tcgaggccaa aatggccttc  1440
tccctgatcc tgcagcgctt ctccttccac ctgtcctcct cctacgccca cgccccgacg  1500
gtggtgatga ccacccagcc gcagcacggc gcccacatcg tgctgaggaa gctgggaagc  1560
ggagctacta acttcagcct gctgaagcag gctggagacg tggaggagaa ccctggacct  1620
atgtccagct cagtcgcggc taccataagc atatggatgg tcgttgtctg tatagtgggt  1680
gtcgggtggc gggtggtcaa ctgggtttgg cttcgcccca aaaaacttga gaagcggctc  1740
cgggaacaag gtctggctgg aaattcgtat cggctccttt tcggggacct taaagaaaga  1800
gccgcgatgg ctgaacaggc aaattcaaag ccaattaact tttcgcatga tatagggcca  1860
cgggtttttc cgtcgatgta taaaactatt cagaactatg gtaagaactc ttacatgtgg  1920
ttgggacctt atccgagggt tcatatcatg gatcctcagc agctgaagac tgtgtttacg  1980
cttgtgtacg acatacagaa gcccaatctt aatcccttga ttaaattttt gttggatgga  2040
attgttacgc atgaagggga aaagtgggct aaacaccgca aaatcattaa ccccgcattc  2100
catatggcaa agttgaaaga tatgattcca gcttttttcc aatcctgtaa tgaaattgtc  2160
agcgaatggg agaggatgat cccgaaggag gggagcttcg aattggatgt gatgccctat  2220
atgcagaatc tggccgctga cgctattagc cggactgcct tcggaagcag ctataaggaa  2280
ggtcaaatga tttttcagtt gctcaaagag ttgaccgatc ttgtggtgaa agcagccttc  2340
ggcatttata tccccggatg gagattcctc cccacgaaaa gcaacaataa aatgaaggag  2400
ataaaccgga agattaaaac tcttttgctt ggtattatag ataagaggca gaaggcaatg  2460
aaagaaggcg aggtcgtcca gaatgacctt cttgggattt tggtcgagtc gaaccttaac  2520
gagataagag ggcatgagaa taataaagac gcggggatgt ccatcgaaga tgtgatagaa  2580
gagtgtaagg tgttctacat aggtggccag gagacaactg caggcctgtt gatatggacc  2640
atgatattgc tcagcttcca tacggaatgg caggaacgcg ctagaaccga agttctcgaa  2700
gtcgttggga acaaaaaacc tgatttcgac ggattgaatc ggctgaagat agttacaatg  2760
attctctatg aggtgctccg gttgtatcct cccgcctcta tgttgacccg cattgtccaa  2820
aaggaaacga gaatagggaa gcttactctt ccggctggag tcacactgat aatcccaacg  2880
gtgttgatac accgcgatca cgaattgtgg ggcgaggacg cgaatgaatt caagcccgaa  2940
cgcttcagcg agggagttag caaggccgct aaggtgcagc ctgcgttctt cccgttcgga  3000
tgggggccca gactttgtct cggcaaaac ttcgcaatga ttgaggccaa aatggcgttt  3060
tctctgattc tgcaaagatt ctctttccac ctctcatcat catatgcaca cgcgcctacc  3120
gtcgttatga caactcagcc tcagcatggc gctcatatag ttctcagaaa gctctaa     3177
```

```
SEQ ID NO: 35          moltype = AA  length = 539
FEATURE                Location/Qualifiers
source                 1..539
                       mol_type = protein
                       organism = synthetic construct
SEQUENCE: 35
MSSSVAATIS IWMVVVCIVG VGWRVVNWVW LRPKKLEKRL REQGLAGNSY RLLFGDLKER  60
AAMAEQANSK PINFSHDIGP RVFPSMYKTI QNYGKNSYMW LGPYPRVHIM DPQQLKTVFT  120
LVYDIQKPNL NPLIKFLLDG IVTHEGEKWA KHRKIINPAF HMAKLKDMIP AFFQSCNEIV  180
SEWERMIPKE GSFELDVMPY MQNLAADAIS RTAFGSSYKE GQMIFQLLKE LTDLVVKAAF  240
GIYIPGWRFL PTKSNNKMKE INRKIKTLLL GIIDKRQKAM KEGEVVQNDL LGILVESNLN  300
EIRGHENNKD AGMSIEDVIE ECKVFYIGGQ ETTAGLLIWT MILLSFHTEW QERARTEVLE  360
VVGNKKPDFD GLNRLKIVTM ILYEVLRLYP PASMLTRIVQ KETRIGKLTL PAGVTLIIPT  420
VLIHRDHELW GEDANEFKPE RFSEGVSKAA KVQPAFFPFG WGPRLCLGQN FAMIEAKMAF  480
SLILQRFSFH LSSSYAHAPT VVMTTQPQHG AHIVLRKLGS GATNFSLLKQ AGDVEENPG   539

SEQ ID NO: 36          moltype = AA  length = 519
FEATURE                Location/Qualifiers
source                 1..519
                       mol_type = protein
                       organism = synthetic construct
SEQUENCE: 36
PMSSSVAATI SIWMVVVCIV GVGWRVVNWV WLRPKKLEKR LREQGLAGNS YRLLFGDLKE  60
RAAMAEQANS KPINFSHDIG PRVFPSMYKT IQNYGKNSYM WLGPYPRVHI MDPQQLKTVF  120
TLVYDIQKPN LNPLIKFLLD GIVTHEGEKW AKHRKIINPA FHMAKLKDMI PAFFQSCNEI  180
VSEWERMIPK EGSFELDVMP YMQNLAADAI SRTAFGSSYK EGQMIFQLLK ELTDLVVKAA  240
FGIYIPGWRF LPTKSNNKMK EINRKIKTLL LGIIDKRQKA MKEGEVVQND LLGILVESNL  300
NEIRGHENNK DAGMSIEDVI EECKVFYIGG QETTAGLLIW TMILLSFHTE WQERARTEVL  360
EVVGNKKPDF DGLNRLKIVT MILYEVLRLY PPASMLTRIV QKETRIGKLT LPAGVTLIIP  420
TVLIHRDHEL WGEDANEFKP ERFSEGVSKA AKVQPAFFPF GWGPRLCLGQ NFAMIEAKMA  480
FSLILQRFSF HLSSSYAHAP TVVMTTQPQH GAHIVLRKL                        519

SEQ ID NO: 37          moltype = AA  length = 1058
FEATURE                Location/Qualifiers
source                 1..1058
                       mol_type = protein
                       organism = synthetic construct
SEQUENCE: 37
```

-continued

```
MSSSVAATIS IWMVVVCIVG VGWRVVNWVW LRPKKLEKRL REQGLAGNSY RLLFGDLKER  60
AAMAEQANSK PINFSHDIGP RVFPSMYKTI QNYGKNSYMW LGPYPRVHIM DPQQLKTVFT  120
LVYDIQKPNL NPLIKFLLDG IVTHEGEKWA KHRKIINPAF HMAKLKDMIP AFFQSCNEIV  180
SEWERMIPKE GSFELDVMPY MQNLAADAIS RTAFGSSYKE GQMIFQLLKE LTDLVVKAAF  240
GIYIPGWRFL PTKSNNKMKE INRKIKTLLL GIIDKRQKAM KEGEVVQNDL LGILVESNLN  300
EIRGHENNKD AGMSIEDVIE ECKVFYIGGQ ETTAGLLIWT MILLSFHTEW QERARTEVLE  360
VVGNKKPDFD GLNRLKIVTM ILYEVLRLYP PASMLTRIVQ KETRIGKLTL PAGVTLIIPT  420
VLIHRDHELW GEDANEFKPE RFSEGVSKAA KVQPAFFPFG WGPRLCLGQN FAMIEAKMAF  480
SLILQRFSFH LSSSYAHAPT VVMTTQPQHG AHIVLRKLGS GATNFSLLKQ AGDVEENPGP  540
MSSSVAATIS IWMVVVCIVG VGWRVVNWVW LRPKKLEKRL REQGLAGNSY RLLFGDLKER  600
AAMAEQANSK PINFSHDIGP RVFPSMYKTI QNYGKNSYMW LGPYPRVHIM DPQQLKTVFT  660
LVYDIQKPNL NPLIKFLLDG IVTHEGEKWA KHRKIINPAF HMAKLKDMIP AFFQSCNEIV  720
SEWERMIPKE GSFELDVMPY MQNLAADAIS RTAFGSSYKE GQMIFQLLKE LTDLVVKAAF  780
GIYIPGWRFL PTKSNNKMKE INRKIKTLLL GIIDKRQKAM KEGEVVQNDL LGILVESNLN  840
EIRGHENNKD AGMSIEDVIE ECKVFYIGGQ ETTAGLLIWT MILLSFHTEW QERARTEVLE  900
VVGNKKPDFD GLNRLKIVTM ILYEVLRLYP PASMLTRIVQ KETRIGKLTL PAGVTLIIPT  960
VLIHRDHELW GEDANEFKPE RFSEGVSKAA KVQPAFFPFG WGPRLCLGQN FAMIEAKMAF  1020
SLILQRFSFH LSSSYAHAPT VVMTTQPQHG AHIVLRKL                          1058

SEQ ID NO: 38          moltype = DNA  length = 2913
FEATURE                Location/Qualifiers
source                 1..2913
                       mol_type = other DNA
                       organism = synthetic construct
SEQUENCE: 38
atggtgcagc cccgggtgct gctgttccct ttccccgcgc tgggccacgt gaagcccttc  60
ctgtcgctgg cggagctcct gtccgacgcc ggcatcgacg tggtcttcct ctcgacggag  120
tataaccacc gccgcatctc caacaccgag gccctggcct cccgcttccc caccctgcac  180
ttcgaaacga taccggacgg cctgcccccc aacgagtcgc gcgccctcgc ggacggcccc  240
ctgtacttca gcatgaggga gggcaccaag ccgcgcttcc ggcagctgat ccagagcctt  300
aacgacggcc gttggcccat cacctgtatc atcacggaca tcatgctcag ttcgcccatc  360
gaggtggcgg aggagttcgg gatcccggtg atcgcgttct gcccgtgctc cgctcgctac  420
ctctcgatcc acttcttcat cccgaagctg gtggaggagg ggcagatccc gtacgcggac  480
gacgacccca ttggggagat ccagggggtg cccctcttcg aggggcttct ccgacggaac  540
cacctcccgg gatcttggtc cgacaagtcc gcggacattt ccttctcgca cggcctcatc  600
aaccagacgc tcgcggccgg gcgggcctcg gccctgatcc tcaacacctt cgacgagctc  660
gaggcccctt tcctcaccca cctgagctcc atcttcaaca agatctacac catcggcccc  720
ctccacgccc tgtccaagag ccggctcggg gactcctcct cgtcggccag cgcgctctcg  780
gggttctgga aggaggaccg cgcgtgcatg tcctggctcg actgccagcc gccgcgctcg  840
gtcgtgttcg tctccttcgg gtcgaccatg aagatgaagg cggacgagct tcgggagttc  900
tggtacgggc tggtgagcag cgggaagccg ttcctctgcg tgttgcggtc cgacgtcgtc  960
agcggcggcg aggcggcgga gctcatcgag cagatggcgg aggaggaggg ggctgggggc  1020
aagctgggca tggtcgtcga gtgggcggcg caggagaagg tcctctccca ccctgccgtg  1080
gggggcttcc tgacgcactg cggctggaac tcgacggtgg agagcatcgc cgccggcgtc  1140
cccatgatgt gctggccgat cctcggggac cagccctcca acgccacttg gatcgaccgg  1200
gtctggaaga tcggggtcga gcgaaacaac cgggagtggg accggttgac ggtggagaag  1260
atggtccgcg cattgatgga gggccagaag cgggtggaga tccagcggtc gatggagaag  1320
ctgtcgaagc tggcgaacga gaaggtcgtc cggggggggc tgtctttcga caacctcgag  1380
gtcctcgtgg aggacatcaa gaagctgaag ccgtacaagt tcggaagcgg agctactaac  1440
ttcagcctgc tgaagcaggc tggagacgtg gaggagaacc ctggacctat ggtccaaccc  1500
cgggtcctgc tctttccgtt tccggctctt ggccatgtta aaccattcct ttcccttgcc  1560
gagctcctgt cggacgcagg aatagatgtc gtctttttgt caacggagta taatcatcgg  1620
aggatctcaa atacagaggc acttgcaagc cggtttccca ctcttcactt cgaaaccatt  1680
ccagatgggc tgccgccaaa tgagagcagg gctttggccg acggccctct ttacttctcg  1740
atgagggagg ggacaaaacc gaggtttcgc cagcttatac agagcctgaa tgatggtcgg  1800
tggcccatta cttgtataat tacggatata atgctttcca gccccatcga agttgcggag  1860
gagtttggga taccggtgat agcattttgt ccttgctcgg ctcgctactt gtctatacac  1920
ttctttatcc cgaagctcgt cgaagaaggc cagataccat acgcggatga cgaccccatt  1980
ggagaaatac aaggagtgcc tctttttgag gggctcctgc gcagaaatca tctgcctggt  2040
tcttggagcg ataaatccgc tgacatctca ttcagccatg ggctgataaa tcagacgctt  2100
gcggccggtc gggcatcggc actgattctt aacacctttg atgaacttga ggccccattt  2160
cttactcacc tctcgtcgat ttttaacaag atttacacaa tcgggccact tcatgctctt  2220
tccaaatcac ggcttggaga ttcgagcagc agcgcatccg ctctgtcggg attctggaaa  2280
gaggacagag cgtgcatgtc ttggcttgat tgccaaccac cccggtcggt tgtttttgtt  2340
tcctttgggt cgacaatgaa gatgaaggcg gatgagttgc gggagttttg gtacgggctt  2400
gtctcttccg gaaagccctt cctctgtgtg ctgagatcag atgttgtctc gggcggtgag  2460
gcagccgagc tcatagagca aatggcggaa gaggaggggg ccgggggtaa actcggtatg  2520
gtggtcgagt gggcggctca ggagaaagtg ttgtcacatc ctgctgtcgg gggattcctg  2580
acacattgcg gatggaattc tactgtcgag tcaattgcgg cgggcgtgcc tatgatgtgc  2640
tggcccatac tgggcgacca gccctctaat gcgacttgga tagaccgggt ctggaaaatt  2700
ggcgttgaac ggaacaaccg cgaatgggac cgcctgacag ttgagaagat ggttagagca  2760
ctcatggaag ggcaaaagag agtcgaaatt caacgctcta tggaaaaatt gagcaaactt  2820
gcaaatgaaa aggtcgtgag aggtgggctg tcgtttgata atctggaggt tctggttgag  2880
gacataaaaa agcttaagcc ctacaaattt tga                                2913

SEQ ID NO: 39          moltype = AA  length = 495
FEATURE                Location/Qualifiers
source                 1..495
                       mol_type = protein
```

```
                       organism = synthetic construct
SEQUENCE: 39
MVQPRVLLFP FPALGHVKPF LSLAELLSDA GIDVVFLSTE YNHRRISNTE ALASRFPTLH  60
FETIPDGLPP NESRALADGP LYFSMREGTK PRFRQLIQSL NDGRWPITCI ITDIMLSSPI  120
EVAEEFGIPV IAFCPCSARY LSIHFFIPKL VEEGQIPYAD DDPIGEIQGV PLFEGLLRRN  180
HLPGSWSDKS ADISFSHGLI NQTLAAGRAS ALILNTFDEL EAPFLTHLSS IFNKIYTIGP  240
LHALSKSRLG DSSSSASALS GFWKEDRACM SWLDCQPPRS VVFVSFGSTM KMKADELREF  300
WYGLVSSGKP FLCVLRSDVV SGGEAAELIE QMAEEEGAGG KLGMVVEWAA QEKVLSHPAV  360
GGFLTHCGWN STVESIAAGV PMMCWPILGD QPSNATWIDR VWKIGVERNN REWDRLTVEK  420
MVRALMEGQK RVEIQRSMEK LSKLANEKVV RGGLSFDNLE VLVEDIKKLK PYKFGSGATN  480
FSLLKQAGDV EENPG                                                 495

SEQ ID NO: 40          moltype = AA  length = 475
FEATURE                Location/Qualifiers
source                 1..475
                       mol_type = protein
                       organism = synthetic construct
SEQUENCE: 40
PMVQPRVLLF PFPALGHVKP FLSLAELLSD AGIDVVFLST EYNHRRISNT EALASRFPTL  60
HFETIPDGLP PNESRALADG PLYFSMREGT KPRFRQLIQS LNDGRWPITC IITDIMLSSP  120
IEVAEEFGIP VIAFCPCSAR YLSIHFFIPK LVEEGQIPYA DDDPIGEIQG VPLFEGLLRR  180
NHLPGSWSDK SADISFSHGL INQTLAAGRA SALILNTFDE LEAPFLTHLS SIFNKIYTIG  240
PLHALSKSRL GDSSSSASAL SGFWKEDRAC MSWLDCQPPR SVVFVSFGST MKMKADELRE  300
FWYGLVSSGK PFLCVLRSDV VSGGEAAELI EQMAEEEGAG GKLGMVVEWA AQEKVLSHPA  360
VGGFLTHCGW NSTVESIAAG VPMMCWPILG DQPSNATWID RVWKIGVERN NREWDRLTVE  420
KMVRALMEGQ KRVEIQRSME KLSKLANEKV VRGGLSFDNL EVLVEDIKKL KPYKF       475

SEQ ID NO: 41          moltype = AA  length = 970
FEATURE                Location/Qualifiers
source                 1..970
                       mol_type = protein
                       organism = synthetic construct
SEQUENCE: 41
MVQPRVLLFP FPALGHVKPF LSLAELLSDA GIDVVFLSTE YNHRRISNTE ALASRFPTLH  60
FETIPDGLPP NESRALADGP LYFSMREGTK PRFRQLIQSL NDGRWPITCI ITDIMLSSPI  120
EVAEEFGIPV IAFCPCSARY LSIHFFIPKL VEEGQIPYAD DDPIGEIQGV PLFEGLLRRN  180
HLPGSWSDKS ADISFSHGLI NQTLAAGRAS ALILNTFDEL EAPFLTHLSS IFNKIYTIGP  240
LHALSKSRLG DSSSSASALS GFWKEDRACM SWLDCQPPRS VVFVSFGSTM KMKADELREF  300
WYGLVSSGKP FLCVLRSDVV SGGEAAELIE QMAEEEGAGG KLGMVVEWAA QEKVLSHPAV  360
GGFLTHCGWN STVESIAAGV PMMCWPILGD QPSNATWIDR VWKIGVERNN REWDRLTVEK  420
MVRALMEGQK RVEIQRSMEK LSKLANEKVV RGGLSFDNLE VLVEDIKKLK PYKFGSGATN  480
FSLLKQAGDV EENPGPMVQP RVLLFPFPAL GHVKPFLSLA ELLSDAGIDV VFLSTEYNHR  540
RISNTEALAS RFPTLHFETI PDGLPPNESR ALADGPLYFS MREGTKPRFR QLIQSLNDGR  600
WPITCIITDI MLSSPIEVAE EFGIPVIAFC PCSARYLSIH FFIPKLVEEG QIPYADDDPI  660
GEIQGVPLFE GLLRRNHLPG SWSDKSADIS FSHGLINQTL AAGRASALIL NTFDELEAPF  720
LTHLSSIFNK IYTIGPLHAL SKSRLGDSSS SASALSGFWK EDRACMSWLD CQPPRSVVFV  780
SFGSTMKMKA DELREFWYGL VSSGKPFLCV LRSDVVSGGE AAELIEQMAE EEGAGGKLGM  840
VVEWAAQEKV LSHPAVGGFL THCGWNSTVE SIAAGVPMMC WPILGDQPSN ATWIDRVWKI  900
GVERNNREWD RLTVEKMVRA LMEGQKRVEI QRSMEKLSKL ANEKVVRGGL SFDNLEVLVE  960
DIKKLKPYKF                                                       970

SEQ ID NO: 42          moltype = DNA  length = 2787
FEATURE                Location/Qualifiers
source                 1..2787
                       mol_type = other DNA
                       organism = synthetic construct
SEQUENCE: 42
atggacgcgc agcggggcca cacgacgacg atcctgatgt tcccctggct cggctacggg  60
cacctcagcg ccttcctcga gctggcgaag agcctgtccc ggcgcaactt ccacatctac  120
ttctgctcga ccagcgtcaa cctggacgcg atcaagccca agctgccctc cagcagctcc  180
tccgacagca tccagctggt ggagctgtgc ctgccctcca gccccgacca gctcccccg  240
cacctccaca ccaccaacgc gctcccgccc cacctcatgc ccaccctcca ccaggccttc  300
agcatggcgg cgcagcactt cgcggccatc ctgcacaccc tcgcgcccca cctcctgatc  360
tacgactcgt tccagccgtg ggcaccccag ctggcctcct cgctcaacat cccggccatc  420
aacttcaaca cgaccggggc gtccgtcctg acccggatgc tgcacgcgac ccactacccg  480
agcagcaagt tccccatcag cgagttcgtg ctccacgact actggaaggc catgtacagc  540
gcggccgggg gcgcggtgac gaagaaggac cacaagatcg gcgagacgct ggcgaactgc  600
ctccacgcca gctgctcggt catcctgatc aactccttcc gcgagctgga ggagaagtac  660
atggactacc tgtccgtgct cctgaacaag aaggtggtgc cggtggggcc gctggtgtac  720
gagccgaacc aggatggaga ggacgagggg tactccagca taaagaactg gctcgacaag  780
aaggagccga gctccacggt gttcgtgtcc ttcggcagcg agtacttccc gagcaaggag  840
gagatggagg agatcgccca cggctcgag gcctctgaag ttcatttcat ctgggttgtg  900
cggttcccgc agggggacaa cacctccgcg atcgaggacg ccctgccgaa gggcttcctc  960
gagagggtgg gcgagagggg catggtggtg aagggctggg ccccgcaggc gaagatcctg  1020
aagcactggt ccaccggggg cttcgtgtcc cactgcggct ggaacagcgt gatggagagc  1080
atgatgttcg gggtgccgat catcggcgtg ccgatgcacc tggaccagcc gttcaacgcc  1140
ggcctggccg aggaggccgg cgtgggggtg gaggcgaagc gcgaccccga cgggaagatc  1200
cagcgcgacg aggtcgccaa gctgatcaag gaggtggtgg tggagaagac ccgggaggac  1260
gtgaggaaga aggcgcgcga gatgtccgag atcctccgca gcaaggggga ggagaagatg  1320
```

-continued

```
gacgagatgg tggccgcgat ctccctcttc ctcaagatcg gaagcggagc tactaacttc  1380
agcctgctga agcaggctgg agacgtggag gagaaccctg gacctatgga tgcccagcgc  1440
ggtcatacga ctacgatcct catgtttcca tggctgggtt acggacactt gagcgcgttt  1500
ctggaactcg ccaagtcgct gtcaaggaga aactttcata tatatttttg ctcgacatct  1560
gtcaacctgg acgccatcaa accaaaactg ccttcttcgt ccagctcgga cagcattcag  1620
ctggttgaac tttgtctgcc atcatctccg gaccaactcc ctccccatct tcacacaacc  1680
aacgctttgc cgccgcacct gatgcccaca ctccaccaag cgttctcaat ggcggcgcag  1740
catttcgcag ctatactgca cacccttgct ccgcacctcc tgatttacga ttcatttcaa  1800
ccgtgggccc cccaactggc gtcgagcttg aatatccccg caatcaattt taacaccacc  1860
ggagcatccg tgcttaccag aatgttgcac gctacacatt atccgtcctc caagtttcct  1920
atatccgaat ttgtcctgca tgactattgg aaagctatgt actcagccgc tggaggagct  1980
gtgacaaaaa aggaccataa gataggagag acactcgcga actgcttgca cgcttcttgt  2040
tcagtcattc tcatcaatag cttcagagag ctcgaggaga agtatatgga ctacctctca  2100
gttcttctta ataaaaaggt ggtcccggtg ggaccgctcg tctatgaacc aaaccaggac  2160
ggtgaagacg aaggatattc cagcatcaag aactggctgg ataaaaagga accttcatcg  2220
actgttttcg tttccttcgg atcggagtat ttcccttcta aggaagaaat ggaagaaatc  2280
gcccacgggc ttgaagcgtc ggaagtccat tttatttggg tggtcagatt tccgcaagga  2340
gataacacaa gcgcaataga ggacgcattg ccaaagggat tccttgaacg cgtcggggaa  2400
aggggggatgg tcgtgaaagg atgggcgccg caggcgaaga tccttaagca ctggtcaaca  2460
ggcggatttg tcagccattg tgggtggaat tctgttatgg aatcaatgat gttcggggtg  2520
cccataatag gagtcccgat gcatttggat cagcccttta acgctgggct tgcagaggag  2580
gccggtgtgg gtgtcgaggc taagcgcgac cccgatggta aaatccagag ggatgaagtg  2640
gcaaaactta taaaagaagt ggtcgtggag aaaactcgcg aggacgtgcg gaagaaggcg  2700
cgggaaatgt cagagatatt gaggagcaag ggggaagaga aaatggacga gatggttgca  2760
gccatctccc tgttcttgaa gatctga                                      2787

SEQ ID NO: 43          moltype = AA  length = 474
FEATURE                Location/Qualifiers
source                 1..474
                       mol_type = protein
                       organism = synthetic construct
SEQUENCE: 43
MDAQRGHTTT ILMFPWLGYG HLSAFLELAK SLSRRNFHIY FCSTSVNLDA IKPKLPSSSS  60
SDSIQLVELC LPSSPDQLPP HLHTTNALPP HLMPTLHQAF SMAAQHFAAI LHTLAPHLLI  120
YDSFQPWAPQ LASSLNIPAI NFNTTGASVL TRMLHATHYP SSKFPISEFV LHDYWKAMYS  180
AAGGAVTKKD HKIGETLANC LHASCSVILI NSFRELEEKY MDYLSVLLNK KVVPVGPLVY  240
EPNQDGEDEG YSSIKNWLDK KEPSSTVFVS FGSEYFPSKE EMEEIAHGLE ASEVHFIWVV  300
RFPQGDNTSA IEDALPKGFL ERVGERGMVV KGWAPQAKIL KHWSTGGFVS HCGWNSVMES  360
MMFGVPIIGV PMHLDQPFNA GLAEEAGVGV EAKRDPDGKI QRDEVAKLIK EVVVEKTRED  420
VRKKAREMSE ILRSKGEEKM DEMVAAISLF LKIGSGATNF SLLKQAGDVE ENPG        474

SEQ ID NO: 44          moltype = AA  length = 454
FEATURE                Location/Qualifiers
source                 1..454
                       mol_type = protein
                       organism = synthetic construct
SEQUENCE: 44
PMDAQRGHTT TILMFPWLGY GHLSAFLELA KSLSRRNFHI YFCSTSVNLD AIKPKLPSSS  60
SSDSIQLVEL CLPSSPDQLP PHLHTTNALP PHLMPTLHQA FSMAAQHFAA ILHTLAPHLL  120
IYDSFQPWAP QLASSLNIPA INFNTTGASV LTRMLHATHY PSSKFPISEF VLHDYWKAMY  180
SAAGGAVTKK DHKIGETLAN CLHASCSVIL INSFRELEEK YMDYLSVLLN KKVVPVGPLV  240
YEPNQDGEDE GYSSIKNWLD KKEPSSTVFV SFGSEYFPSK EEMEEIAHGL EASEVHFIWV  300
VRFPQGDNTS AIEDALPKGF LERVGERGMV VKGWAPQAKI LKHWSTGGFV SHCGWNSVME  360
SMMFGVPIIG VPMHLDQPFN AGLAEEAGVG VEAKRDPDGK IQRDEVAKLI KEVVVEKTRE  420
DVRKKAREMS EILRSKGEEK MDEMVAAISL FLKI                               454

SEQ ID NO: 45          moltype = AA  length = 928
FEATURE                Location/Qualifiers
source                 1..928
                       mol_type = protein
                       organism = synthetic construct
SEQUENCE: 45
MDAQRGHTTT ILMFPWLGYG HLSAFLELAK SLSRRNFHIY FCSTSVNLDA IKPKLPSSSS  60
SDSIQLVELC LPSSPDQLPP HLHTTNALPP HLMPTLHQAF SMAAQHFAAI LHTLAPHLLI  120
YDSFQPWAPQ LASSLNIPAI NFNTTGASVL TRMLHATHYP SSKFPISEFV LHDYWKAMYS  180
AAGGAVTKKD HKIGETLANC LHASCSVILI NSFRELEEKY MDYLSVLLNK KVVPVGPLVY  240
EPNQDGEDEG YSSIKNWLDK KEPSSTVFVS FGSEYFPSKE EMEEIAHGLE ASEVHFIWVV  300
RFPQGDNTSA IEDALPKGFL ERVGERGMVV KGWAPQAKIL KHWSTGGFVS HCGWNSVMES  360
MMFGVPIIGV PMHLDQPFNA GLAEEAGVGV EAKRDPDGKI QRDEVAKLIK EVVVEKTRED  420
VRKKAREMSE ILRSKGEEKM DEMVAAISLF LKIGSGATNF SLLKQAGDVE ENPGPMDAQR  480
GHTTTILMFP WLGYGHLSAF LELAKSLSRR NFHIYFCSTS VNLDAIKPKL PSSSSSDSIQ  540
LVELCLPSSP DQLPPHLHTT NALPPHLMPT LHQAFSMAAQ HFAAILHTLA PHLLIYDSFQ  600
PWAPQLASSL NIPAINFNTT GASVLTRMLH ATHYPSSKFP ISEFVLHDYW KAMYSAAGGA  660
VTKKDHKIGE TLANCLHASC SVILINSFRE LEEKYMDYLS VLLNKKVVPV GPLVYEPNQD  720
GEDEGYSSIK NWLDKKEPSS TVFVSFGSEY FPSKEEMEEI AHGLEASEVH FIWVVRFPQG  780
DNTSAIEDAL PKGFLERVGE RGMVVKGWAP QAKILKHWST GGFVSHCGWN SVMESMMFGV  840
PIIGVPMHLD QPFNAGLAEE AGVGVEAKRD PDGKIQRDEV AKLIKEVVVE KTREDVRKKA  900
REMSEILRSK GEEKMDEMVA AISLFLKI                                      928
```

```
SEQ ID NO: 46          moltype = DNA  length = 2613
FEATURE                Location/Qualifiers
source                 1..2613
                       mol_type = other DNA
                       organism = synthetic construct
SEQUENCE: 46
atgaacacga ccccgctgcc ggaggaggac gaggaggtgg tgaagatggt ggtggacggg  60
tccgtgccgt cctactcgct cgagtccaag ctcggcgacc cgaagcgcgc ggcgtccatc  120
cggcgggagg cgctgcagcg catgacgggg cggagcatcc acgggctgcc gttcgagggc  180
ttcgactacg agagcatcct gggccagtgc tgcgagatgc cggtggggta cgtccagatc  240
ccggtgggca tcgcggggcc gctgctgctc gacgggttcg agtacaccgt gccgatggcc  300
accacggagg gctgcctggt ggcctccacc aacaggggct gcaaggccat ctacgcctcc  360
ggcggggcga cctcaatgct cctcaaagac ggcatgacga gggccccggt ggtcaggttc  420
ggcagcgcga agagggcgag cgagctgaag ttcttcctgg aggacccgaa caacttcgac  480
accctggccg tggtgttcaa ccgctccagc cgcttcgccc gcctgcagag catcaggtgc  540
agcatcgcgg gcaagaacct gtacgtccgc ttctgctgct ccaccggcga cgccatgggc  600
atgaacatgg tgtccaaggg cgtgcagaac gtgctggagt tcctgcagca cgacttctcc  660
gacatggagg tgatcggcat ctccggcaac ttctgcgccg acaagaagcc ggccgccgtg  720
aactggatcg agggcagggg caagtccgtg gtgtgcgagg ccattatcaa ggacgaggtg  780
gtgcgcaagg tgctcaagac cagcgtggcg agcctggtgg agctgaacat gctgaagaac  840
ctgaccggct ccgccatggc cggggccctc ggcggcttca acgcgcacag cagcaacatc  900
gtgtccgcca tcttcctggc caccggccag gacccggccc agaacgtgga gtcctcccac  960
tgcatcacga tgatggagcc ggtcaacaac ggcaaggacc tccacatctc cgtgaccatg  1020
ccgtccatcg aggtcgggac cgtgggggc ggcacccagc tggcgtccca gagcgcgtgc  1080
ctgaacctgc tgggggtcaa gggcgcgtcc aaggagagcc cgggggccaa cagcaggctg  1140
ctggcgacca tcgtggccgg ctccgtgctg gccggcgagc tctccctgat gtccgccatc  1200
gcggcgggcc agctggtgag gtcccacatg aagtacaacc gctcctccag ggatgtgtcc  1260
aaggtggaga gcggaagcgg agctactaac ttcagcctgc tgaagcaggc tggagacgtg  1320
gaggagaacc ctggacctat gaacacgacc cctttgccgg aggaggatga agaagttgtg  1380
aaaatggtgg ttgatggcag cgtgccatcg tactcgctcg agtcaaagct cggcgaccca  1440
aaacgggcag cctcaatccg gcgggaggca ttgcagcgga tgacaggtcg gagcatccac  1500
gggctgcctt ttgaaggctt tgactatgaa tctatacttg ggcaatgctg cgaaatgccc  1560
gtcggttatg tccagattcc ggttggcatc gctggacctc tgttgctcga tgggtttgaa  1620
tatacggtgc ccatggcaac tacggagggt tgccttgtgg cttctactaa tcgcggttgc  1680
aaagctatct acgcctcagg aggggcgacc tcaatgctcc tcaaagacgg tatgacgagg  1740
gcacctgttg tcagattcgg tagcgcgaag agagcgtcag agttgaaatt ctttcttgaa  1800
gacccgaata atttcgacac cttggctgtc gtgttcaatc ggtcttcgag atttgcgaga  1860
ttgcaatcga tcaggtgcag catcgcgggc aaaaatctct atgttagatt ctgttgctca  1920
acaggagatg caatgggtat gaacatggtt tccaaagggg tccaaaacgt gcttgaattt  1980
ctgcaacacg attttagcga tatggaagtt ataggcattt caggcaattt ctgcgccgat  2040
aagaagcccg ctgccgttaa ttggatcgag ggtcgcggaa aatctgttgt ctgtgaggca  2100
attatcaagg atgaggttgt gcgcaaagtt ctcaagacta gcgtcgcaag cttggtcgaa  2160
ttgaacatgc tgaagaacct gactggctcc gcgatggcag gggccttggg tggtttcaac  2220
gctcacagca gcaacatagt ttctgccata tttttggcga ccggacagga cccggcacaa  2280
aatgttgagt cttctcactg catcacgatg atggaaccag tcaacaatgg aaaagacctc  2340
catatttctg tcacgatgcc ttcaatcgaa gtcgggacag ttggtggagg aacacaattg  2400
gcttcacaga gcgcgtgcct taatttgctg ggtgtcaagg gtgcctccaa ggaatcgcct  2460
ggggcgaatt ctaggctttt ggcgaccatc gttgcaggaa gcgttttggc gggggagctc  2520
tcgctgatgt ccgccatcgc ggcgggtcag ttggtgagat cgcacatgaa atataacaga  2580
agctccagag atgtgtcaaa agttgaaagc taa                               2613

SEQ ID NO: 47          moltype = AA  length = 445
FEATURE                Location/Qualifiers
source                 1..445
                       mol_type = protein
                       organism = synthetic construct
SEQUENCE: 47
MNTTPLPEED EEVVKMVVDG SVPSYSLESK LGDPKRAASI RREALQRMTG RSIHGLPFEG  60
FDYESILGQC CEMPVGYVQI PVGIAGPLLL DGFEYTVPMA TTEGCLVAST NRGCKAIYAS  120
GGATSMLLKD GMTRAPVVRF GSAKRASELK FFLEDPNNFD TLAVVFNRSS RFARLQSIRC  180
SIAGKNLYVR FCCSTGDAMG MNMVSKGVQN VLEFLQHDFS DMEVIGISGN FCADKKPAAV  240
NWIEGRGKSV VCEAIIKDEV VRKVLKTSVA SLVELNMLKN LTGSAMAGAL GGFNAHSSNI  300
VSAIFLATGQ DPAQNVESSH CITMMEPVNN GKDLHISVTM PSIEVGTVGG GTQLASQSAC  360
LNLLGVKGAS KESPGANSRL LATIVAGSVL AGELSLMSAI AAGQLVRSHM KYNRSSRDVS  420
KVESGSGATN FSLLKQAGDV EENPG                                        445

SEQ ID NO: 48          moltype = AA  length = 425
FEATURE                Location/Qualifiers
source                 1..425
                       mol_type = protein
                       organism = synthetic construct
SEQUENCE: 48
PMNTTPLPEE DEEVVKMVVD GSVPSYSLES KLGDPKRAAS IRREALQRMT GRSIHGLPFE  60
GFDYESILGQ CCEMPVGYVQ IPVGIAGPLL LDGFEYTVPM ATTEGCLVAS TNRGCKAIYA  120
SGGATSMLLK DGMTRAPVVR FGSAKRASEL KFFLEDPNNF DTLAVVFNRS SRFARLQSIR  180
CSIAGKNLYV RFCCSTGDAM GMNMVSKGVQ NVLEFLQHDF SDMEVIGISG NFCADKKPAA  240
VNWIEGRGKS VVCEAIIKDE VVRKVLKTSV ASLVELNMLK NLTGSAMAGA LGGFNAHSSN  300
IVSAIFLATG QDPAQNVESS HCITMMEPVN NGKDLHISVT MPSIEVGTVG GGTQLASQSA  360
CLNLLGVKGA SKESPGANSR LLATIVAGSV LAGELSLMSA IAAGQLVRSH MKYNRSSRDV  420
```

```
SKVES                                                              425

SEQ ID NO: 49          moltype = AA  length = 870
FEATURE                Location/Qualifiers
source                 1..870
                       mol_type = protein
                       organism = synthetic construct
SEQUENCE: 49
MNTTPLPEED EEVVKMVVDG SVPSYSLESK LGDPKRAASI RREALQRMTG RSIHGLPFEG  60
FDYESILGQC CEMPVGYVQI PVGIAGPLLL DGFEYTVPMA TTEGCLVAST NRGCKAIYAS  120
GGATSMLLKD GMTRAPVVRF GSAKRASELK FFLEDPNNFD TLAVVFNRSS RFARLQSIRC  180
SIAGKNLYVR FCCSTGDAMG MNMVSKGVQN VLEFLQHDFS DMEVIGISGN FCADKKPAAV  240
NWIEGRGKSV VCEAIIKDEV VRKVLKTSVA SLVELNMLKN LTGSAMAGAL GGFNAHSSNI  300
VSAIFLATGQ DPAQNVESSH CITMMEPVNN GKDLHISVTM PSIEVGTVGG GTQLASQSAC  360
LNLLGVKGAS KESPGANSRL LATIVAGSVL AGELSLMSAI AAGQLVRSHM KYNRSSRDVS  420
KVESGSGATN FSLLKQAGDV EENPGPMNTT PLPEEDEEVV KMVVDGSVPS YSLESKLGDP  480
KRAASIRREA LQRMTGRSIH GLPFEGFDYE SILGQCCEMP VGYVQIPVGI AGPLLLDGFE  540
YTVPMATTEG CLVASTNRGC KAIYASGGAT SMLLKDGMTR APVVRFGSAK RASELKFFLE  600
DPNNFDTLAV VFNRSSRFAR LQSIRCSIAG KNLYVRFCCS TGDAMGMNMV SKGVQNVLEF  660
LQHDFSDMEV IGISGNFCAD KKPAAVNWIE GRGKSVVCEA IIKDEVVRKV LKTSVASLVE  720
LNMLKNLTGS AMAGALGGFN AHSSNIVSAI FLATGQDPAQ NVESSHCITM MEPVNNGKDL  780
HISVTMPSIE VGTVGGGTQL ASQSACLNLL GVKGASKESP GANSRLLATI VAGSVLAGEL  840
SLMSAIAAGQ LVRSHMKYNR SSRDVSKVES                                   870

SEQ ID NO: 50          moltype = DNA  length = 3045
FEATURE                Location/Qualifiers
source                 1..3045
                       mol_type = other DNA
                       organism = synthetic construct
SEQUENCE: 50
atggtgcagc cccgggtgct gctgttccct ttccccgcgc tgggccacgt gaagcccttc  60
ctgtcgctgg cggagctcct gtccgacgcc ggcatcgacg tggtcttcct ctcgacggag  120
tataaccacc gccgcatctc caacaccgag gccctggcct cccgcttccc caccctgcac  180
ttcgaaacga taccggacgg cctgcccccc aacgagtcgc gcgccctcgc ggacggcccc  240
ctgtacttca gcatgaggga gggcaccaag ccgcgcttcc ggcagctgat ccagagcctt  300
aacgacggcc gttggcccat cacctgtatc atcacggaca tcatgctcag ttcgcccatc  360
gaggtggcgg aggagttcgg gatcccggtg atcgcgttct gcccgtgctc cgctcgctac  420
ctctcgatcc acttcttcat cccgaagctg gtggaggagg ggcagatccc gtacgcggac  480
gacgacccca ttggggagat ccaggggggtg cccctcttcg aggggcttct ccgacggaac  540
cacctcccgg gatcttggtc cgacaagtcc gcggacattt ccttctcgca cggcctcatc  600
aaccagacgc tcgcggccgg gcgggcctcg gccctgatcc tcaacacctt cgacgagctc  660
gaggcccctt tcctcaccca cctgagctcc atcttcaaca agatctacac catcggcccc  720
ctccacgccc tgtccaagag ccggctcggg gactcctcct cgtcggccag cgcgctctcg  780
gggttctgga aggaggaccg cgcgtgcatg tcctggctcg actgccagcc gccgcgctcg  840
gtcgtgttcg tctccttcgg gtcgaccatg aagatgaagg cggacgagct tcgggagttc  900
tggtacgggc tggtgagcag cgggaagccg ttcctctgcg tgttgcggtc cgacgtcgtc  960
agcggcggcg aggcggcgga gctcatcgag cagatggcgg aggaggaggg ggctgggggc  1020
aagctgggca tggtcgtcga gtgggcggcg caggagaagg tcctctccca ccctgccgtg  1080
gggggcttcc tgacgcactg cggctggaac tcgacggtgg agagcatcgc cgccggcgtc  1140
cccatgatgt gctggccgat cctcggggac cagccctcca acgccacttg gatcgaccgg  1200
gtctggaaga tcggggtcga gcgaaacaac cgggagtggg accggttgac ggtggagaag  1260
atggtccgcg cattgatgga gggccagaag cgggtggaga tccagcggtc gatggagaag  1320
ctgtcgaagc tggcgaacga gaaggtcgtc cggggggggc tgtctttcga caacctcgag  1380
gtcctcgtgg aggacatcaa gaagctgaag ccgtacaagt tcggaagcgg agctactaac  1440
ttcagcctgc tgaagcaggc tggagacgtg gaggagaacc ctggacctat gtccagctca  1500
gtcgcggcta ccataagcat atggatggtc gttgtctgta tagtgggtgt cgggtggcgg  1560
gtggtcaact gggtttggct tcgccccaaa aaacttgaga agcggctccg ggaacaaggt  1620
ctggctggaa attcgtatcg gctccttttc ggggacctta aagaaagagc cgcgatggct  1680
gaacaggcaa attcaaagcc aattaacttt tcgcatgata tagggccacg ggtttttccg  1740
tcgatgtata aaactattca gaactatggt aagaactctt acatgtggtt gggaccttat  1800
ccgagggttc atatcatgga tcctcagcag ctgaagactg tgtttacgct tgtgtacgac  1860
atacagaagc ccaatcttaa tcccttgatt aaatttttgt tggatggaat tgttacgcat  1920
gaaggggaaa agtgggctaa acaccgcaaa atcattaacc ccgcattcca tatggcaaag  1980
ttgaaagata tgattccagc tttttttccaa tcctgtaatg aaattgtcag cgaatgggag  2040
aggatgatcc cgaaggaggg gagcttcgaa ttggatgtga tgccctatat gcagaatctg  2100
gccgctgacg ctattagccg gactgccttc ggaagcagct ataaggaagg tcaaatgatt  2160
tttcagttgc tcaaagagtt gaccgatctt gtggtgaaag cagccttcgg catttatatc  2220
cccggatgga gattcctccc cacgaaaagc aacaataaaa tgaaggagat aaaccggaag  2280
attaaaactc ttttgcttgg tattatagat aagaggcaga aggcaatgaa agaaggcgag  2340
gtcgtccaga atgaccttct tgggattttg gtcgagtcga accttaacga gataagaggg  2400
catgagaata ataaagacgc ggggatgtcc atcgaagatg tgatagaaga gtgtaaggtg  2460
ttctacatag gtggccagga gacaactgca ggcctgttga tatggaccat gatattgctc  2520
agcttccata cggaatggca ggaacgcgct agaaccgaag ttctcgaagt cgttgggaac  2580
aaaaaacctg atttcgacgg attgaatcgg ctgaagatag ttacaatgat tctctatgag  2640
gtgctccggt tgtatcctcc cgcctctatg ttgacccgca ttgtccaaaa ggaaacgaga  2700
atagggaagc ttactcttcc ggctggagtc acactgataa tcccaacggt gttgatacac  2760
cgcgatcacg aattgtgggg cgaggacgcg aatgaattca agcccgaacg cttcagcgag  2820
ggagttagca aggccgctaa ggtgcagcct gcgttcttcc cgttcggatg ggggcccaga  2880
ctttgtctcg ggcaaaactt cgcaatgatt gaggccaaaa tggcgttttc tctgattctg  2940
```

```
caaagattct ctttccacct ctcatcatca tatgcacacg cgcctaccgt cgttatgaca  3000
actcagcctc agcatggcgc tcatatagtt ctcagaaagc tctaa                  3045

SEQ ID NO: 51           moltype = AA  length = 495
FEATURE                 Location/Qualifiers
source                  1..495
                        mol_type = protein
                        organism = synthetic construct
SEQUENCE: 51
MVQPRVLLFP FPALGHVKPF LSLAELLSDA GIDVVFLSTE YNHRRISNTE ALASRFPTLH  60
FETIPDGLPP NESRALADGP LYFSMREGTK PRFRQLIQSL NDGRWPITCI ITDIMLSSPI  120
EVAEEFGIPV IAFCPCSARY LSIHFFIPKL VEEGQIPYAD DDPIGEIQGV PLFEGLLRRN  180
HLPGSWSDKS ADISFSHGLI NQTLAAGRAS ALILNTFDEL EAPFLTHLSS IFNKIYTIGP  240
LHALSKSRLG DSSSSASALS GFWKEDRACM SWLDCQPPRS VVFVSFGSTM KMKADELREF  300
WYGLVSSGKP FLCVLRSDVV SGGEAAELIE QMAEEEGAGG KLGMVVEWAA QEKVLSHPAV  360
GGFLTHCGWN STVESIAAGV PMMCWPILGD QPSNATWIDR VWKIGVERNN REWDRLTVEK  420
MVRALMEGQK RVEIQRSMEK LSKLANEKVV RGGLSFDNLE VLVEDIKKLK PYKFGSGATN  480
FSLLKQAGDV EENPG                                                   495

SEQ ID NO: 52           moltype = AA  length = 519
FEATURE                 Location/Qualifiers
source                  1..519
                        mol_type = protein
                        organism = synthetic construct
SEQUENCE: 52
PMSSSVAATI SIWMVVVCIV GVGWRVVNWV WLRPKKLEKR LREQGLAGNS YRLLFGDLKE  60
RAAMAEQANS KPINFSHDIG PRVFPSMYKT IQNYGKNSYM WLGPYPRVHI MDPQQLKTVF  120
TLVYDIQKPN LNPLIKFLLD GIVTHEGEKW AKHRKIINPA FHMAKLKDMI PAFFQSCNEI  180
VSEWERMIPK EGSFELDVMP YMQNLAADAI SRTAFGSSYK EGQMIFQLLK ELTDLVVKAA  240
FGIYIPGWRF LPTKSNNKMK EINRKIKTLL LGIIDKRQKA MKEGEVVQND LLGILVESNL  300
NEIRGHENNK DAGMSIEDVI EECKVFYIGG QETTAGLLIW TMILLSFHTE WQERARTEVL  360
EVVGNKKPDF DGLNRLKIVT MILYEVLRLY PPASMLTRIV QKETRIGKLT LPAGVTLIIP  420
TVLIHRDHEL WGEDANEFKP ERFSEGVSKA AKVQPAFFPF GWGPRLCLGQ NFAMIEAKMA  480
FSLILQRFSF HLSSSYAHAP TVVMTTQPQH GAHIVLRKL                         519

SEQ ID NO: 53           moltype = AA  length = 1014
FEATURE                 Location/Qualifiers
source                  1..1014
                        mol_type = protein
                        organism = synthetic construct
SEQUENCE: 53
MVQPRVLLFP FPALGHVKPF LSLAELLSDA GIDVVFLSTE YNHRRISNTE ALASRFPTLH  60
FETIPDGLPP NESRALADGP LYFSMREGTK PRFRQLIQSL NDGRWPITCI ITDIMLSSPI  120
EVAEEFGIPV IAFCPCSARY LSIHFFIPKL VEEGQIPYAD DDPIGEIQGV PLFEGLLRRN  180
HLPGSWSDKS ADISFSHGLI NQTLAAGRAS ALILNTFDEL EAPFLTHLSS IFNKIYTIGP  240
LHALSKSRLG DSSSSASALS GFWKEDRACM SWLDCQPPRS VVFVSFGSTM KMKADELREF  300
WYGLVSSGKP FLCVLRSDVV SGGEAAELIE QMAEEEGAGG KLGMVVEWAA QEKVLSHPAV  360
GGFLTHCGWN STVESIAAGV PMMCWPILGD QPSNATWIDR VWKIGVERNN REWDRLTVEK  420
MVRALMEGQK RVEIQRSMEK LSKLANEKVV RGGLSFDNLE VLVEDIKKLK PYKFGSGATN  480
FSLLKQAGDV EENPGPMSSS VAATISIWMV VVCIVGVGWR VVNWVWLRPK KLEKRLREQG  540
LAGNSYRLLF GDLKERAAMA EQANSKPINF SHDIGPRVFP SMYKTIQNYG KNSYMWLGPY  600
PRVHIMDPQQ LKTVFTLVYD IQKPNLNPLI KFLLDGIVTH EGEKWAKHRK IINPAFHMAK  660
LKDMIPAFFQ SCNEIVSEWE RMIPKEGSFE LDVMPYMQNL AADAISRTAF GSSYKEGQMI  720
FQLLKELTDL VVKAAFGIYI PGWRFLPTKS NNKMKEINRK IKTLLLGIID KRQKAMKEGE  780
VVQNDLLGIL VESNLNEIRG HENNKDAGMS IEDVIEECKV FYIGGQETTA GLLIWTMILL  840
SFHTEWQERA RTEVLEVVGN KKPDFDGLNR LKIVTMILYE VLRLYPPASM LTRIVQKETR  900
IGKLTLPAGV TLIIPTVLIH RDHELWGEDA NEFKPERFSE GVSKAAKVQP AFFPFGWGPR  960
LCLGQNFAMI EAKMAFSLIL QRFSFHLSSS YAHAPTVVMT TQPQHGAHIV LRKL        1014

SEQ ID NO: 54           moltype = DNA  length = 2700
FEATURE                 Location/Qualifiers
source                  1..2700
                        mol_type = other DNA
                        organism = synthetic construct
SEQUENCE: 54
atggacgcgc agcggggcca cacgacgacg atcctgatgt tcccctggct cggctacggg  60
cacctcagcg ccttcctcga gctggcgaag agcctgtccc ggcgcaactt ccacatctac  120
ttctgctcga ccagcgtcaa cctggacgcg atcaagccca agctgccctc cagcagctcc  180
tccgacagca tccagctggt ggagctgtgc ctgccctcca gccccgacca gctccccccg  240
cacctccaca ccaccaacgc gctcccgccc cacctcatgc ccaccctcca ccaggccttc  300
agcatggcgg cgcagcactt cgcggccatc ctgcacaccc tcgcgcccca cctcctgatc  360
tacgactcgt tccagccgtg ggcaccccag ctggcctcct cgctcaacat cccggccatc  420
aacttcaaca cgaccggggc gtccgtcctg acccggatgc tgcacgcgac ccactacccg  480
agcagcaagt tccccatcag cgagttcgtg ctccacgact actggaaggc catgtacagc  540
gcggccgggg gcgcggtgac gaagaaggac cacaagatcg gcgagacgct ggcgaactgc  600
ctccacgcca gctgctcggt catcctgatc aactccttcc gcgagctgga ggagaagtac  660
atggactacc tgtccgtgct cctgaacaag aaggtggtgc cggtggggcc gctggtgtac  720
gagccgaacc aggatggaga ggacgagggg tactccagca taaagaactg gctcgacaag  780
aaggagccga gctccacggt gttcgtgtcc ttcggcagcg agtacttccc gagcaaggag  840
```

```
gagatggagg agatcgccca cgggctcgag gcctctgaag ttcatttcat ctgggttgtg  900
cggttcccgc agggggacaa cacctccgcg atcgaggacg ccctgccgaa gggcttcctc  960
gagagggtgg gcgagagggg catggtggtg aagggctggg ccccgcaggc gaagatcctg  1020
aagcactggt ccaccggggg cttcgtgtcc cactgcggct ggaacagcgt gatggagagc  1080
atgatgttcg gggtgccgat catcggcgtg ccgatgcacc tggaccagcc gttcaacgcc  1140
ggcctggccg aggaggccgg cgtgggggtg gaggcgaagc gcgaccccga cgggaagatc  1200
cagcgcgacg aggtcgccaa gctgatcaag gaggtggtgg tggagaagac ccgggaggac  1260
gtgaggaaga aggcgcgcga gatgtccgag atcctccgca gcaaggggga ggagaagatg  1320
gacgagatgg tggccgcgat ctccctcttc ctcaagatcg gaagcggagc tactaacttc  1380
agcctgctga agcaggctgg agacgtggag gagaaccctg gacctatgaa cacgacccct  1440
ttgccggagg aggatgaaga agttgtgaaa atggtggttg atggcagcgt gccatcgtac  1500
tcgctcgagt caaagctcgg cgacccaaaa cgggcagcct caatccggcg ggaggcattg  1560
cagcggatga caggtcggag catccacggg ctgccttttg aaggctttga ctatgaatct  1620
atacttgggc aatgctgcga aatgcccgtc ggttatgtcc agattccggt tggcatcgct  1680
ggacctctgt tgctcgatgg gtttgaatat acggtgccca tggcaactac ggagggttgc  1740
cttgtggctt ctactaatcg cggttgcaaa gctatctacg cctcaggagg ggcgacctca  1800
atgctcctca aagacggtat gacgagggca cctgttgtca gattcggtag cgcgaagaga  1860
gcgtcagagt tgaaattctt tcttgaagac ccgaataatt tcgacacctt ggctgtcgtg  1920
ttcaatcggt cttcgagatt tgcgagattg caatcgatca ggtgcagcat cgcgggcaaa  1980
aatctctatg ttagattctg ttgctcaaca ggagatgcaa tgggtatgaa catggtttcc  2040
aaaggggtcc aaaacgtgct tgaatttctg caacacgatt ttagcgatat ggaagttata  2100
ggcatttcag gcaatttctg cgccgataag aagcccgctg ccgttaattg gatcgagggt  2160
cgcggaaaat ctgttgtctg tgaggcaatt atcaaggatg aggttgtgcg caaagttctc  2220
aagactagcg tcgcaagctt ggtcgaattg aacatgctga agaacctgac tggctccgcg  2280
atggcagggg ccttgggtgg tttcaacgct cacagcagca acatagtttc tgccatattt  2340
ttggcgaccg gacaggaccc ggcacaaaat gttgagtctt ctcactgcat cacgatgatg  2400
gaaccagtca acaatggaaa agacctccat atttctgtca cgatgccttc aatcgaagtc  2460
gggacagttg gtggaggaac acaattggct tcacagagcg cgtgccttaa tttgctgggt  2520
gtcaagggtg cctccaagga atcgcctggg gcgaattcta ggcttttggc gaccatcgtt  2580
gcaggaagcg ttttggcggg ggagctctcg ctgatgtccg ccatcgcggc gggtcagttg  2640
gtgagatcgc acatgaaata taacagaagc tccagagatg tgtcaaaagt tgaaagctaa  2700

SEQ ID NO: 55          moltype = AA  length = 474
FEATURE                Location/Qualifiers
source                 1..474
                       mol_type = protein
                       organism = synthetic construct
SEQUENCE: 55
MDAQRGHTTT ILMFPWLGYG HLSAFLELAK SLSRRNFHIY FCSTSVNLDA IKPKLPSSSS  60
SDSIQLVELC LPSSPDQLPP HLHTTNALPP HLMPTLHQAF SMAAQHFAAI LHTLAPHLLI  120
YDSFQPWAPQ LASSLNIPAI NFNTTGASVL TRMLHATHYP SSKFPISEFV LHDYWKAMYS  180
AAGGAVTKKD HKIGETLANC LHASCSVILI NSFRELEEKY MDYLSVLLNK KVVPVGPLVY  240
EPNQDGEDEG YSSIKNWLDK KEPSSTVFVS FGSEYFPSKE EMEEIAHGLE ASEVHFIWVV  300
RFPQGDNTSA IEDALPKGFL ERVGERGMVV KGWAPQAKIL KHWSTGGFVS HCGWNSVMES  360
MMFGVPIIGV PMHLDQPFNA GLAEEAGVGV EAKRDPDGKI QRDEVAKLIK EVVVEKTRED  420
VRKKAREMSE ILRSKGEEKM DEMVAAISLF LKIGSGATNF SLLKQAGDVE ENPG        474

SEQ ID NO: 56          moltype = AA  length = 425
FEATURE                Location/Qualifiers
source                 1..425
                       mol_type = protein
                       organism = synthetic construct
SEQUENCE: 56
PMNTTPLPEE DEEVVKMVVD GSVPSYSLES KLGDPKRAAS IRREALQRMT GRSIHGLPFE  60
GFDYESILGQ CCEMPVGYVQ IPVGIAGPLL LDGFEYTVPM ATTEGCLVAS TNRGCKAIYA  120
SGGATSMLLK DGMTRAPVVR FGSAKRASEL KFFLEDPNNF DTLAVVFNRS SRFARLQSIR  180
CSIAGKNLYV RFCCSTGDAM GMNMVSKGVQ NVLEFLQHDF SDMEVIGISG NFCADKKPAA  240
VNWIEGRGKS VVCEAIIKDE VVRKVLKTSV ASLVELNMLK NLTGSAMAGA LGGFNAHSSN  300
IVSAIFLATG QDPAQNVESS HCITMMEPVN NGKDLHISVT MPSIEVGTVG GGTQLASQSA  360
CLNLLGVKGA SKESPGANSR LLATIVAGSV LAGELSLMSA IAAGQLVRSH MKYNRSSRDV  420
SKVES                                                            425

SEQ ID NO: 57          moltype = AA  length = 899
FEATURE                Location/Qualifiers
source                 1..899
                       mol_type = protein
                       organism = synthetic construct
SEQUENCE: 57
MDAQRGHTTT ILMFPWLGYG HLSAFLELAK SLSRRNFHIY FCSTSVNLDA IKPKLPSSSS  60
SDSIQLVELC LPSSPDQLPP HLHTTNALPP HLMPTLHQAF SMAAQHFAAI LHTLAPHLLI  120
YDSFQPWAPQ LASSLNIPAI NFNTTGASVL TRMLHATHYP SSKFPISEFV LHDYWKAMYS  180
AAGGAVTKKD HKIGETLANC LHASCSVILI NSFRELEEKY MDYLSVLLNK KVVPVGPLVY  240
EPNQDGEDEG YSSIKNWLDK KEPSSTVFVS FGSEYFPSKE EMEEIAHGLE ASEVHFIWVV  300
RFPQGDNTSA IEDALPKGFL ERVGERGMVV KGWAPQAKIL KHWSTGGFVS HCGWNSVMES  360
MMFGVPIIGV PMHLDQPFNA GLAEEAGVGV EAKRDPDGKI QRDEVAKLIK EVVVEKTRED  420
VRKKAREMSE ILRSKGEEKM DEMVAAISLF LKIGSGATNF SLLKQAGDVE ENPGPMNTTP  480
LPEEDEEVVK MVVDGSVPSY SLESKLGDPK RAASIRREAL QRMTGRSIHG LPFEGFDYES  540
ILGQCCEMPV GYVQIPVGIA GPLLLDGFEY TVPMATTEGC LVASTNRGCK AIYASGGATS  600
MLLKDGMTRA PVVRFGSAKR ASELKFFLED PNNFDTLAVV FNRSSRFARL QSIRCSIAGK  660
```

```
NLYVRFCCST GDAMGMNMVS KGVQNVLEFL QHDFSDMEVI GISGNFCADK KPAAVNWIEG  720
RGKSVVCEAI IKDEVVRKVL KTSVASLVEL NMLKNLTGSA MAGALGGFNA HSSNIVSAIF  780
LATGQDPAQN VESSHCITMM EPVNNGKDLH ISVTMPSIEV GTVGGGTQLA SQSACLNLLG  840
VKGASKESPG ANSRLLATIV AGSVLAGELS LMSAIAAGQL VRSHMKYNRS SRDVSKVES   899

SEQ ID NO: 58          moltype = DNA  length = 1029
FEATURE                Location/Qualifiers
source                 1..1029
                       mol_type = other DNA
                       organism = synthetic construct
SEQUENCE: 58
atgtccaaaa agcctgaact caccgcgacg tctgtcgaga agtttctgat cgaaaagttc  60
gacagcgtct ccgacctgat gcagctctcg gagggcgaag aatctcgtgc tttcagcttc  120
gatgtaggag ggcgtggata tgtcctgcgg gtaaatagct gcgccgatgg tttctacaaa  180
gatcgttatg tttatcggca ctttgcatcg gccgcgctcc cgattccgga agtgcttgac  240
attggggagt ttagcgagag cctgacctat tgcatctccc gccgttcaca gggtgtcacg  300
ttgcaagacc tgcctgaaac cgaactgccc gctgttctac aaccggtcgc ggaggctatg  360
gatgcgatcg ctgcggccga tcttagccag acgagcgggt tcggcccatt cggaccgcaa  420
ggaatcggtc aatacactac atggcgtgat ttcatctgcg cgattgctga tccccatgtg  480
tatcactggc aaactgtgat ggacgacacc gtcagtgcgt ccgtcgcgca ggctctcgat  540
gagctgatgc tttgggccga ggactgcccc gaagtccggc acctcgtgca cgcggatttc  600
ggctccaaca atgtcctgac ggacaatggc cgcataacag cggtcattga ctggagcgag  660
gcgatgttcg gggattccca atacgaggtc gccaacatct tcttctggag gccgtggttg  720
gcttgtatgg agcagcagac gcgctacttc gagcggaggc atccggagct tgcaggatcg  780
ccacgactcc gggcgtatat gctccgcatt ggtcttgacc aactctatca gagcttggtt  840
gacggcaatt tcgatgatgc agcttgggcg cagggtcgat gcgacgcaat cgtccgatcc  900
ggagccggga ctgtcgggcg tacacaaatc gcccgcagaa gcgcggccgt ctggaccgat  960
ggctgtgtag aagtactcgc cgatagtgga aaccgacgcc ccagcactcg tccgagggca  1020
aagaaatag                                                          1029

SEQ ID NO: 59          moltype = AA  length = 342
FEATURE                Location/Qualifiers
source                 1..342
                       mol_type = protein
                       organism = Escherichia coli
SEQUENCE: 59
MSKKPELTAT SVEKFLIEKF DSVSDLMQLS EGEESRAFSF DVGGRGYVLR VNSCADGFYK  60
DRYVYRHFAS AALPIPEVLD IGEFSESLTY CISRRSQGVT LQDLPETELP AVLQPVAEAM  120
DAIAAADLSQ TSGFGPFGPQ GIGQYTTWRD FICAIADPHV YHWQTVMDDT VSASVAQALD  180
ELMLWAEDCP EVRHLVHADF GSNNVLTDNG RITAVIDWSE AMFGDSQYEV ANIFFWRPWL  240
ACMEQQTRYF ERRHPELAGS PRLRAYMLRI GLDQLYQSLV DGNFDDAAWA QGRCDAIVRS  300
GAGTVGRTQI ARRSAAVWTD GCVEVLADSG NRRPSTRPRA KK                     342

SEQ ID NO: 60          moltype = DNA  length = 500
FEATURE                Location/Qualifiers
source                 1..500
                       mol_type = genomic DNA
                       organism = Horseradish latent virus
SEQUENCE: 60
tggtagacta tgaaacacta gtctactcaa agaacttgaa gaagacgact caggaagaca  60
ggagcgtcat caacaagttt cagcaaaagc tgattagtgg aaaaatcctt ggattccact  120
ctccagcaat ctgccagcac ataaaggtga cagcagaaaa agaagattgt gactaccact  180
gcaatcagtg cgaatcttca aaaggaaagg ctatcgtttg cgataagcct gccgacagtg  240
gtccagccga caatggaggg ccccagacac gtgaagacgc gtctgccgac agtgggtcta  300
ggacaacaga caccacgcac tcagcaagtg gatgaaataa ttcatctgct gacgtaaggg  360
atgacgatca atcccactat cccaagaccc ttcacttcta tataagtgaa gttgcttcat  420
ttggagaagg catctcgaaa tctcaacaca actcgagctc tcccttctct cttctttatc  480
tctctaaatg tgtgagtaga                                              500

SEQ ID NO: 61          moltype = DNA  length = 439
FEATURE                Location/Qualifiers
source                 1..439
                       mol_type = genomic DNA
                       organism = Dahlia mosaic virus
SEQUENCE: 61
tcgacgggaa gacaaaaatc aagatcaatt acgcacagga aaaagtattg atcatgagtc  60
actacggagc accaatctcc agacaagatg tcgacatctt atcttccttt gaagaaagca  120
ttgcacatgc caaagttgat gtagggacat ctacaaaatt attgctttgc aaacagctga  180
agaaattatt ggccgacaac cataaatgct cagcatgtga aagtggggcc tccaccagca  240
ataatacaag ctttacagct tgcagtgact catcctccaa taatggagaa aaagacgtca  300
gcagtgacga acaagggtcg aaagacttgc ctatataaga gcattctccc ctcagttgaa  360
gatcatcgaa agttggagca ataaactctc tcttcaacaa atctatcttt tgtctagaat  420
catgtgtgag tagtaaccc                                               439

SEQ ID NO: 62          moltype = DNA  length = 585
FEATURE                Location/Qualifiers
source                 1..585
                       mol_type = other DNA
                       organism = synthetic construct
```

```
SEQUENCE: 62
gtaatcttgt caacatcgag cagctggctt gtggggacca gacaaaaaag gaatggtgca  60
gaattgttag gcgcacctac caaaagcatc tttgccttta ttgcaaagat aaagcagatt  120
cctctagtac aagtggggaa caaaataacg tggaaaagag ctgtcctgac agcccactca  180
ctaatgcgta tgacgaacgc agtgacgacc agagttttta cttcggacag tcaaaaatga  240
gtttaacttc tcagccgagg taaaacaaga aatatgctta cgtctacaga gggatttctc  300
tgaagatcat gtttgccagc tatgcgaaca atcatcggga gatcctgagc caatcaaaga  360
ggagtgatgt agacctaaag caataatgga gccatgacgt aagggcttac gccattacga  420
aataattaaa ggctgatgtg acctgtcggt ctatcagaac ctttactttt tatatttggc  480
gtgtattttt aaatttccac ggcaatgacg atgtgacctg tgcatccgct ttgcctataa  540
ataagtttta gtttgtattg atcgacacga tcgagaagac acggc                 585

SEQ ID NO: 63           moltype = DNA  length = 621
FEATURE                 Location/Qualifiers
source                  1..621
                        mol_type = other DNA
                        organism = synthetic construct
SEQUENCE: 63
tcgtccacag acatcaacat cttatcgtcc tttgaagata agataataat gttgaagata  60
agagtgggag ccaccactaa aacattgctt tgtcaaaagc taaaaaagat gatgcccgac  120
agccacttgt gtgaagcatg tgaagccggt ccctccacta agaaaattag tgaagcatct  180
tccagtggtc cctccactca cagctcaatc agtgagcaac aggacgaagg aaatgacgta  240
agccatgacg tctaggatct tcgtccacag acatcaacat cttatcgtcc tttgaagata  300
agataataat gttgaagata agagtgggag ccaccactaa aacattgctt tgtcaaaagc  360
taaaaaagat gatgcccgac agccacttgt gtgaagcatg tgaagccggt ccctccacta  420
agaaaattag tgaagcatct tccagtggtc cctccactca cagctcaatc agtgagcaac  480
aggacgaagg aaatgacgta agccatgacg tctaggatcc cacaagaatt tccttatata  540
aggaacacaa atcagaagga agagatcaat cgaaatcaaa atcggaatcg aaatcaaaat  600
cggaatcgaa atctctcatc t                                           621

SEQ ID NO: 64           moltype = DNA  length = 465
FEATURE                 Location/Qualifiers
source                  1..465
                        mol_type = genomic DNA
                        organism = Cestrum yellow leaf curling virus
SEQUENCE: 64
tggcagacat actgtcccac aaatgaagat ggaatctgta aaagaaaacg cgtgaaataa  60
tgcgtctgac aaaggttagg tcggctgcct ttaatcaata ccaaagtggt ccctaccacg  120
atggaaaaac tgtgcagtcg gtttggcttt ttctgacgaa caaataagat tcgtggccga  180
caggtggggg tccaccatgt gaaggcatct tcagactcca ataatggagc aatgacgtaa  240
gggcttacga aataagtaag ggtagtttgg gaaatgtcca ctcacccgtc agtctataaa  300
tacttagccc ctccctcatt gttaagggag caaaatctca gagagatagt cctagagaga  360
gaaagagagc aagtagccta gaagtagtca aggcggcgaa gtattcaggc acgtggccag  420
gaagaagaaa agccaagacg acgaaaacag gtaagagcta agctt                 465

SEQ ID NO: 65           moltype = DNA  length = 742
FEATURE                 Location/Qualifiers
source                  1..742
                        mol_type = genomic DNA
                        organism = Cauliflower mosaic virus
SEQUENCE: 65
tgagactttt caacaaaggg taatatcggg aaacctcctc ggattccatt gcccagctat  60
ctgtcacttc atcaaaagga cagtagaaaa ggaaggtggc acctacaaat gccatcattg  120
cgataaagga aaggctatcg ttcaagatgc ctctgccgac agtggtccca aagatggacc  180
cccacccacg aggagcatcg tggaaaaaga agacgttcca accacgtctt caaagcaagt  240
ggattgatgt gaacatggtg gagcacgaca ctctcgtcta ctccaagaat atcaaagata  300
cagtctcaga agaccaaagg gctattgaga cttttcaaca aagggtaata tcgggaaacc  360
tcctcggatt ccattgccca gctatctgtc acttcatcaa aaggacagta gaaaaggaag  420
gtggcaccta caaatgccat cattgcgata aaggaaaggc tatcgttcaa gatgcctctg  480
ccgacagtgg tcccaaagat ggacccccac ccacgaggag catcgtggaa aaagaagacg  540
ttccaaccac gtcttcaaag caagtggatt gatgtgatat ctccactgac gtaagggatg  600
acgcacaatc ccactatcct tcgcaagacc cttcctctat ataaggaagt tcatttcatt  660
tggagaggac acgctgaaat caccagtctc tctctacaaa tctatctctc tcgagctttc  720
gcagatctgt cgatcgacca ac                                          742

SEQ ID NO: 66           moltype = DNA  length = 299
FEATURE                 Location/Qualifiers
source                  1..299
                        mol_type = genomic DNA
                        organism = Agrobacterium tumefaciens
SEQUENCE: 66
gatcatgagc ggagaattaa gggagtcacg ttatgacccc cgccgatgac gcgggacaag  60
ccgttttacg tttggaactg acagaaccgc aacgttgaag gagccactca gccgcgggtt  120
tctggagttt aatgagctaa gcacatacgt cagaaaccat tattgcgcgt tcaaaagtcg  180
cctaaggtca ctatcagcta gcaaatattt cttgtcaaaa atgctccact gacgttccat  240
aaattcccct cggtatccaa ttagagtctc atattcactc tcaatccaaa taatctgca  299

SEQ ID NO: 67           moltype = DNA  length = 1369
FEATURE                 Location/Qualifiers
```

```
source                  1..1369
                        mol_type = genomic DNA
                        organism = Sugarcane bacilliform badnavirus
SEQUENCE: 67
atccattccc cacattcaag aaggacatgt tcgaaagaac agagcaagct tttatgctaa  60
cagaggaacc agttctactc tgtgcatgca ggaagcctgc aattcagtta gtgtccagaa  120
catctgccaa cccaggaagg aaattcttca agtgcgcaat gaacaaatgc cattgctggt  180
actgggcaga tctcattgaa gaacacattc aagacagaat tgatgaattt ctcaagaatc  240
ttgaagttct gaagaccggt ggcgtgcaaa caatggagga ggaacttatg aaggaagtca  300
ccaagctgaa gatagaagag caggagttcg aggaatacca ggccacacca agggctatgt  360
cgccagtagc cgcagaagat gtgctagatc tccaagacgt aagcaatgac gattgaggag  420
gcattgacgt cagggatgac cgcagcggag agtactgggc ccattcagtg gatgctccac  480
tgagttgtat tattgtgtgc ttttcggaca agtgtgctgt ccactttctt ttggcacctg  540
tgccacttta ttccttgtct gccacgatgc ctttgcttag cttgtaagca aggatcgcag  600
tgcgtgtgtg acaccacccc ccttccgacg ctctgcctat ataaggcacc gtctgtaagc  660
tcttacgatc atcggtagtt caccacatga tcatttgagc aagtttgctt gaataaaaga  720
actatcattc cgcatacctg atcctatagt cctagcttga gaacaagagc gaagtctata  780
gttgagatcc taagagaaac tcgaggtttt tcgggtttcc tgggcgcgtt ccctggtatc  840
agagcgaggt atgatttctg tatccgctat gttctaaatt tcttagataa ggggccaagg  900
gctctgctga tgagtttaag gacaactact tgtgcaagtt acatagcatg atacgtcgaa  960
aggctgaaaa tatccaaaat actgtctatt gtttggaaaa ctaggttgtt ctaggggaga  1020
acgttaatga ggggtaagct tagttcattc tgaaaatcaa ggtctgtgat tgtagttgag  1080
ctcagtaatt aagtgctgaa ggaagtaaga tctaggtagg acaaaagtac ccgtcaaggc  1140
aggaggccgc taaggggaaa agagccagac gatcaaagct ttttcagcac ggttgttgag  1200
tttagctatc aagaaatagc cttgagacta agattcatca ctaagaactg cctactcaag  1260
cctccctgaa tccgcctatt agtacaaacg agacaacagt ataaggagaa actatatgcc  1320
tgtaagactt aagtgcaaaa gtaacctctg gaactgggta gaagtctag             1369

SEQ ID NO: 68           moltype = DNA  length = 514
FEATURE                 Location/Qualifiers
source                  1..514
                        mol_type = genomic DNA
                        organism = Cassava vein mosaic virus
SEQUENCE: 68
cagaaggtaa ttatccaaga tgtagcatca agaatccaat gtttacggga aaaactatgg  60
aagtattatg tgaactcagc aagaagcaga tcaatatgcg gcacatattc aacctatgtt  120
caaaaatgaa gaatgtacag atacaagatc ctatactgcc agaatacgaa gaagaataca  180
tagaaattga aaaagaagaa ccaggcgaag aaaagaatct tgaagacgta agcactgacg  240
acaacaatga aaagaagaag ataaggtcgg tgattgtgaa agagacatag aggacacatg  300
taaggtggaa aatgtaaggg cggaaagtaa ccttatcaca aaggaatctt atccccccact  360
acttatcctt ttatattttt ccgtgtcatt tttgcccttg agttttccta tataaggaac  420
caagttcggc atttgtgaaa acaagaaaaa atttggtgta agctattttc tttgaagtac  480
tgaggataca acttcagaga aatttgtaag tttg                             514

SEQ ID NO: 69           moltype = DNA  length = 400
FEATURE                 Location/Qualifiers
source                  1..400
                        mol_type = genomic DNA
                        organism = Figwort mosaic virus
SEQUENCE: 69
ttcaaacaag cagaaaagaa ttatcacagc aatgataaag aattactagc agtcaagcaa  60
gtaatcacca agttttcagc ttacctaaca ccagtcaggt ttacagtaag aactgataac  120
aaaaatttta cttatttcct tagaattaat cttaaaggtg atagtaaaca aggacgatta  180
gtccgttggc aaaattggtt cagcaagtat caatttgatg tcgaacatct tgaaggtgta  240
aaaaacgttt tagcagattg cctcacgaga gattttaatg cttaaaaacg taagcgctga  300
cgtatgattt caaaaaacgc agctataaaa gaagccctcc agcttcaaag ttttcatcaa  360
cacaaattct aaaaacaaaa ttttttagag agggggagtg                       400

SEQ ID NO: 70           moltype = DNA  length = 1932
FEATURE                 Location/Qualifiers
source                  1..1932
                        mol_type = genomic DNA
                        organism = Citrullus lanatus
SEQUENCE: 70
tcaacataaa cgcattagtg attaatacat ttatttatgt tttttgaagt tagaaattta  60
aattcttaaa tgtacctttg taaaaaaaaa tatatatata tatatatatt gtgcccatgt  120
ttatatccta gagcgcattg taatcacaaa tcagataaat atatatcaga ttaaaataat  180
aataataata ataataataa tataatccct tataattatg catttctaac tttaaaaaat  240
aatccgtcca taaacaaccc attaatatta accaagttgt tgcaaatttt gaaaacatat  300
atatttgaaa gccgtgtgaa tgtaaaatac taaataaaat gatacatatt ttagtttttg  360
tttgaacata tttcatagcc taacaaattc aaaagaaaga aaaaataatt cttcccaaat  420
ttgaacaaag ttttttcttt attctttaga tggagaaaat agtgtgagta ggttaaaaat  480
tttgggagag tgatattatt attggggtcg ataagatatt tttgtggaat tgtaataatt  540
tttcacatgt tgaaattttt atggtctgta gttttctttt ttctgaagtt tttctatatt  600
aatgcttgtg tttctaattt tattgctttc tttcaatttc tttgttgttt ttcttctcat  660
tcatatagta gtaatgggag gtttttccca aaagtataca cattattttt taattttatt  720
ttctaatttt tcacataaca tttatatatt atttttgttt tcaatttttt tagatggtgt  780
aatatgtgtt tatactattt taatttttag tacacttgaa atcaatttta aaaaattaat  840
tctaatttta tttttctcac atatacatat gcatatacaa atatttttaa tttttagtaa  900
```

```
atgattttat gaaaattagt tgtataaaaa acttctattt tgaaatttag ataaatattt  960
caagcttcat tatttgccta tatattttgg aaaaattatc ttaaatgata aaactggtga  1020
aatatttaca attaatagca aaatacatag tctattgcaa taaacaataa aattttgcta  1080
tatttataaa tatttgggtt tcgtttgcta tatttgaaaa tagccttata ttttgccatg  1140
gataattgtg taaagggtta ttatgatttt aaaactaata tatgaatatt agattaaagt  1200
tgagttccta aatttctaaa tttatgtcta atagaatctc taaattttta attttgtgta  1260
taattaagtc ttttaaaaat gtctaataga tctataaact tttatctaat agtttcaaac  1320
atacttaatt tttttttatt taaaaaaaaa aaaagggatg aactgttata ttgggcataa  1380
aatttaattt taggtttaaa tgaccctcac attttaaatc ttctaactaa taaatatatt  1440
catttttaa aatgtaaccc gttagatacg taaagttaaa ttttatattt aatataacat  1500
ttaattttca ataattagat aaaaattgaa actatatgaa tctattaaat acaagattaa  1560
gaacttagag acacattgaa aattaatttt aaagtttatg gacaatatat atcaacagaa  1620
atttaaaact tcataataag ctaaacttgt aagctttata tggatttgtg tccctgtcat  1680
gaagttatgg attcgtcact caatgtctgg tctaattaaa aagatgaata tgaaaaacgt  1740
tttaacgatt agcaaacacc aaaaccctaa ttaattatct ctctctctcc tccttagatt  1800
tggctttttc cttagcgtga aaagcccaac ttgttgtagt gaaactcagt cctataaata  1860
caagaaagaa aaaaccctct tcaaaaccca aaccataaag aaaagaaaaa aaaaaaaaaa  1920
aaaaaaaaga ga                                                      1932

SEQ ID NO: 71          moltype = DNA  length = 2000
FEATURE                Location/Qualifiers
source                 1..2000
                       mol_type = genomic DNA
                       organism = Citrullus lanatus
SEQUENCE: 71
tctctgtgta aaaaaataaa aaataaaaaa ctattttttt aaatatttgt attaaaatac  60
attaaaatta tataagcttt ttactattat tgtcatacat tatttaatca aatagaagca  120
gggcaggcta gaagagtaga agaattttgg cgggaataag ttcttgattc ctcaaaataa  180
ttcgtgatcc gtgatccgtg aacatttaaa aatcaaattg aaataaaatt caaaacataa  240
agactaaaag tgtaatattt taaaatacaa tggttaaatt aaaacatgta tatatatatt  300
taatttttgg aggaaaatag aaaaagaaag gaaaggtgta acacacaaca aataataaga  360
atttgaagtc aagaaatgag aacacacttc cccgtttcgt gtgttttggt tgaacaactt  420
caacctcaat ctcccaagtc ccaacatgtg aaatctcagt tttacccccc accgcctttg  480
aattaaacgc cgcgttttct tctttccttc ttcaacccaa acgccaagct cctcctttct  540
tttttccttt caacagacga cagcccacaa acagacctat ggttttaaaa cttttacaca  600
tatgtatact tcattagatg tcatattaag caaatcaacg attaaaatta atgcatagag  660
gatttaattt ccaaagtaat tcttgactaa taacaaaggc taaaaattaa tacaacactc  720
ttaaacaaac atgaagtaat ttagctttaa ccatatcaat taaatttcaa ttttaacatc  780
ttttaagaac aaattttctt accgcgtgga gtctaacgct gtagacctta ttggtttgct  840
tagtttttaa gtagtttgaa cttactgaat tagatatttt tgttgtatcc accaaatgct  900
aaatactttt gtttctctct cagaaaggag aataaagttg cttactctgt tgcaactttc  960
acatcatctc ttaaggattc ttttaggtgg aaggataaat tttataattg tattatctct  1020
atcattaatg gagagttcgt gtcgtatttg gggttggatg ctctatttgt atctttgtgt  1080
cttttttttt tttcaatctc aatgttgtct agaacatgtc tctaattttt gttttttaa  1140
accataagat ttctaaacat tttgttctgt gtctaataga tttataactt ctttttaaaa  1200
aaatgtttaa caagtccttg taagttgttg ttaatttaat tttagacatt tatttgacac  1260
tataactatg atatatgatc tttaaacgca aaatgtcaat ttgagcacaa ttcaattgat  1320
taaaatatta ttcgtaacat taataaaaag attaaactac taaaaaatgt taattttagc  1380
gactgtatag agcgttgaat taagttctaa aattatgtga gaatcatagt attaattttc  1440
cgtcaacatc tctatatttt ttttgtttcc atagatttga tatcgacatt agaggtgaat  1500
cgaaatctcc attatatcgt agaaaaatcc acgaaacata aaagataatc acgaaatgtt  1560
actaatataa atataattta aataatagac atgtcaactt gttcaaaaaa tcataaaaca  1620
tttatttact aatttaaatt tattttttat tttttaattt tatcacttaa aataaaaaaa  1680
tttaaaaaaa aattcttcaa taaatatgtt aacttcaatt ttcaacggta ttgaaattga  1740
gaaaggaaaa aaaaaaaaaa cacaatttgc agcgaacaca aataatttaa ttagttttta  1800
gtttttttgt attccacgtg gccacaaatc tcacgcgact tttcaccacg caattggacg  1860
cctagtcccg gtggggtcca cacgccttcc ggccaccccta taaataagct ccgaatacaa  1920
cgctctcatt tcaccgactc acaatttcca gaattcacac acattccttt tcttctctta  1980
agtaatttct ttcactttca                                              2000

SEQ ID NO: 72          moltype = DNA  length = 561
FEATURE                Location/Qualifiers
source                 1..561
                       mol_type = genomic DNA
                       organism = Pisum sativum
SEQUENCE: 72
gtttcattgc ccacacacca gaatcctact aagtttgagt attatggcat tggaaaagct  60
gttttcttct atcatttgtt ctgcttgtaa tttactgtgt tctttcagtt tttgttttcg  120
gacatcaaaa tgcaaatgga tggataagag ttaataaatg atatggtcct tttgttcatt  180
ctcaaattat tattatctgt tgtttttact ttaatgggtt gaatttaagt aagaaaggaa  240
ctaacagtgt gatattaagg tgcaatgtta gacatataaa acagtctttc acctctcttt  300
ggttatgtct tgaattggtt tgtttcttca cttatctgtg taatcaagtt tactatgagt  360
ctatgatcaa gtaattatgc aatcaagtta agtacagtat aggctttttg tgtcaacatt  420
tattcacttt cctttctgca attttcaaat catgtttgta gtttttattg gacttgatga  480
atctctctta ccaccaaaat agaacatttt ttcttgatat accagaatct caatatttgt  540
ctgataatta ttctagctgc a                                            561

SEQ ID NO: 73          moltype = DNA  length = 405
FEATURE                Location/Qualifiers
```

```
source                 1..405
                       mol_type = genomic DNA
                       organism = Arabidopsis thaliana
SEQUENCE: 73
tttttgtgat ctgatgataa gtggttggtt cgtgtctcat gcacttggga ggtgatctat  60
ttcacctggt gtagtttgtg tttccgtcag ttggaaaaac ttatccctat cgatttcgtt  120
ttcattttct gcttttcttt tatgtacctt cgtttgggct tgtaacgggc ctttgtattt  180
caactctcaa taataatcca agtgcatgtt aaacaatttg tcatctgttt cggctttgat  240
atactactgg tgaagatggg ccgtactact gcatcacaac gaaaaataat aataagatga  300
aaaacttgaa gtggaaaaaa aaaaaaactt gaatgttcac tactactcat tgaccataat  360
gtttaacata catagctcaa tagtattttt gtgaatatgg ccaac                  405

SEQ ID NO: 74          moltype = DNA  length = 540
FEATURE                Location/Qualifiers
source                 1..540
                       mol_type = genomic DNA
                       organism = Glycine max
SEQUENCE: 74
acgggaatta aacctataaa cataaatata aataatatat ataaacctaa gtgtctaagt  60
tccataaatt aagctgtagt ctctggctta aaacatgtta ggtttgttta tacaagtagt  120
tggatgtttg gagtacttcg gtcttttgcg taccatcaat atttaagaac taagttagtt  180
atgttccgta acttatgggc tcttaattaa actatatctg cacaaaatta tatatatatc  240
aaatgtgatg gtatgtggac tataaaaaga tatggttgag aaccacaaac tttgaaactt  300
cgaataatat attgccagtg acagtcttgt tgatttgtta tagcaagtcc tattttctta  360
atcattgctt tgttttaacg tacctagatt tcataacttt tgtctttgtc tcaagctgaa  420
cctaatgatg atagtaatat taacttattg tataggggta tttcatagga taaaaaatga  480
tgtgcaatta cgtgtagacc aaatattact tgatgacaga tggataaata ttttaaaact  540

SEQ ID NO: 75          moltype = DNA  length = 210
FEATURE                Location/Qualifiers
source                 1..210
                       mol_type = genomic DNA
                       organism = Arabidopsis thaliana
SEQUENCE: 75
tccccttttct ggaatattca gcgttgatta ttctggaacc catttctatg tggtcaatgc  60
aaatttaaga aattatttgc cgacttaaca gttgaggaac tattgtttga aagtgaaaat  120
gttattccta tcagtttctc tataattata gttatcattt catttcattt ttgcccttaa  180
atctttgaaa tcttattttt cgtttagctc                                   210

SEQ ID NO: 76          moltype = DNA  length = 295
FEATURE                Location/Qualifiers
source                 1..295
                       mol_type = genomic DNA
                       organism = Pisum sativum
SEQUENCE: 76
attatggcat tgggaaaact gtttttcttg taccatttgt tgtgcttgta atttactgtg  60
tttttattc ggttttcgct atcgaactgt gaaatggaaa tggatggaga agagttaatg  120
aatgatatgg tccttttgtt cattctcaaa ttaatattat ttgtttttc tcttatttgt  180
tgtgtgttga atttgaaatt ataagagata tgcaaacatt ttgttttgag taaaaatgtg  240
tcaaatcgtg gcctctaatg accgaagtta atatgaggag taaaacatcc caaac       295

SEQ ID NO: 77          moltype = DNA  length = 486
FEATURE                Location/Qualifiers
source                 1..486
                       mol_type = genomic DNA
                       organism = Arabidopsis thaliana
SEQUENCE: 77
gaagatgaag atgaaatatt tggtgtgtca aataaaaagc ttgtgtgctt aagtttgtgt  60
ttttttcttg gcttgttgtg ttatgaattt gtggcttttt ctaatattaa atgaatgtaa  120
gatctcatta taatgaataa acaaatgttt ctataatcca ttgtgaatgt tttgttggat  180
ctcttctgca gcatataact actgtatgtg ctatggtatg gactatggaa tatgattaaa  240
gataagatgg gctcatagag taaaacgagg cgagggacct ataaacctcc cttcatcatg  300
ctatttcatg atctatttta taaaataaag atgtagaaaa aagtaagcgt aataaccgca  360
aaacaaatga tttaaaacat ggcacataat gaggagatta agttcggttt acgtttattt  420
tagtactaat tgtaacgtga gactacgtat cgggaatcgc ctaattaaag cattaatgcg  480
aacctg                                                             486

SEQ ID NO: 78          moltype = DNA  length = 414
FEATURE                Location/Qualifiers
source                 1..414
                       mol_type = genomic DNA
                       organism = Solanum tuberosum
SEQUENCE: 78
tttaaactga ttttaatgtt tagcaaatgt cttatcagtt ttctcttttt gtcgaacggt  60
aatttagagt tttttttgct atatggattt tcgtttttga tgtatgtgac aaccctcggg  120
attgttgatt tatttcaaaa ctaagagttt ttgtcttatt gttctcgtct attttggata  180
tcaatcttag ttttatatct tttctagttc tctacgtgtt aaatgttcaa cacactagca  240
atttggcctg ccagcgtatg gattatggaa ctatcaagtg tgtgggatcg ataaatatgc  300
ttctcaggaa tttgagattt tacagtcttt atgctcattc ccttgagtat aatatagtaa  360
```

```
aaaaatagta aatttaagca ataatgttag gtgctatgtg tctgtcgaga ctat       414

SEQ ID NO: 79          moltype = DNA  length = 220
FEATURE                Location/Qualifiers
source                 1..220
                       mol_type = genomic DNA
                       organism = Arabidopsis thaliana
SEQUENCE: 79
agaaaagatg attgattatt acttttgtaa ggctgtaagt tcgtcgcact catttccttt  60
tacctctttt tctgaattgg gattctctct ttttgtgctt tgtgtgtttt gttattgaat  120
ttctttccca aacctaagat ttgttccaga gtgtaatcac atttgcctat gcttctttgt  180
tttgtctatg aaaatatttc aatgtcaaaa gcctatacaa                        220

SEQ ID NO: 80          moltype = DNA  length = 175
FEATURE                Location/Qualifiers
source                 1..175
                       mol_type = genomic DNA
                       organism = Cauliflower mosaic virus
SEQUENCE: 80
tttctccata ataatgtgtg agtagttccc agataaggga attagggttc ctatagggtt  60
tcgctcatgt gttgagcata taagaaaccc ttagtatgta tttgtatttg taaaatactt  120
ctatcaataa aatttctaat tcctaaaacc aaaatccagt actaaaatcc agatc       175

SEQ ID NO: 81          moltype = DNA  length = 27
FEATURE                Location/Qualifiers
source                 1..27
                       mol_type = other DNA
                       organism = synthetic construct
SEQUENCE: 81
acacgctgga attctagtat actaaac                                      27

SEQ ID NO: 82          moltype = DNA  length = 543
FEATURE                Location/Qualifiers
source                 1..543
                       mol_type = genomic DNA
                       organism = Nicotiana tabacum
SEQUENCE: 82
ttatggcttt atcaaatata ggttttgaag attcagagag ccaagaaaag ctagaaccca  60
agaactagga agttagagta attcacaata ccataacgtg atataaaact ttttattgta  120
actcaaatcg gtaatatttt ttgctttagt cttaatcgat aaattatttt tttatattga  180
ttagttatag gaggctcaca aagttgggaa taattaaaat atcatatttt gtatttgaac  240
aatttatgaa atagtaattg gtaaaaaatc actttaaatt tttatcctat atccagaagg  300
attatggtgt ctggcatagt tgtttggaag atttgaatca gggtaaaagt atgttgtaat  360
ttttattttg ttataggcat tttttgtgct tgattgtttt gttgtcatta tattttatta  420
tttggaagtg tatatatatg tttgattaaa atatagataa tcaattttat aagaaatttg  480
caacaattac acaaggataa agtctacaat atgcgagtaa aatttgattg aacttaggat  540
gtc                                                                543

SEQ ID NO: 83          moltype = DNA  length = 66
FEATURE                Location/Qualifiers
source                 1..66
                       mol_type = other DNA
                       organism = synthetic construct
SEQUENCE: 83
ggcagcggcg ccacaaactt ctctctgcta aagcaagcag gtgatgttga agaaaacccc  60
gggcct                                                             66

SEQ ID NO: 84          moltype = AA  length = 22
FEATURE                Location/Qualifiers
source                 1..22
                       mol_type = protein
                       organism = synthetic construct
SEQUENCE: 84
GSGATNFSLL KQAGDVEENP GP                                           22

SEQ ID NO: 85          moltype = DNA  length = 1554
FEATURE                Location/Qualifiers
source                 1..1554
                       mol_type = other DNA
                       organism = synthetic construct
SEQUENCE: 85
atgtcgtcgt gtgttgcagc tacgatttca atatggatgg ttgtggtgtg catagtggga  60
gtgggatgga gagttgtgaa ctgggtttgg ttgaggccga agaagcttga gaagcggctg  120
agagagcaag gcctcgccgg aaactcttac cggcttctgt tcggagactt gaaggagagg  180
gcggcgatgg cggagcaggc caactccaag cccatcaact tctcccatga tatcggacca  240
cgtgtcttcc cctccatgta caaaaccatc cagaattacg gtaagaattc gtacatgtgg  300
cttggcccat atccaagagt gcacatcatg gaccctcagc aacttaaaac tgtttttact  360
ctagtctatg atatccaaaa gccaaatttg aaccccttg tcaagtttct tttggatgga  420
atagtaactc atgaaggaga aaaatgggct aaacacagaa agataatcaa ccctgcattt  480
```

```
catttggaaa agttgaagga tatgatacca gcattctttc atagttgtaa tgagatagtt  540
aacgaatggg aaagattaat ctcgaaagag ggttcgtgtg agttggatgt tatgccatat  600
ctgcaaaatt tggcagctga tgccatttct cgaactgcat ttgggagtag ctatgaagaa  660
gggaaaatga tcttccaact tctaaaagaa ctaactgatt tggtggttaa agttgcattt  720
ggagtttata ttcccggatg gaggtttcta ccaactaagt caaacaataa aatgaaagaa  780
ataaatagaa aaataaaaag tttgcttttg ggtattataa acaaaaggca aaaggctatg  840
gaagaaggtg aagctggaca aagtgattta ttaggcattc tcatggaatc caattcaaac  900
gaaattcaag gagaaggaaa caataaagaa gatggaatga gcatagaaga tgttattgaa  960
gaatgcaagg ttttctatat tggtggccaa gaaaccacag ccagattact gatttggacc  1020
atgattttgt tgagttcaca cacggaatgg caagagcgag caagaactga ggtattaaaa  1080
gtatttggta ataagaagcc agattttgat ggtttgaatc gtctaaaaat tgtaactatg  1140
attttgaacg aggttctcag gttataccca ccagcaagta tgcttactcg tattattcaa  1200
aaggaaacaa gacttggaaa attgactcta ccagctggtg tgatattgat catgccaatt  1260
attcttatcc atcgtgatca tgacctatgg ggtgaagatg caaacgaatt taaaccagaa  1320
agattttctg agggagtctc taaagcagca aaagttcaac ccgctttctt cccatttgga  1380
tggggtcctc gaatatgcat ggggcagaac tttgcgatga ttgaagcaaa aacggcatta  1440
tcattaattc tacaacgctt ctcatttgag ctttcttcgt cgtatgttca tgctcctacc  1500
gtcgttttca ctactcaacc tcaacatgga gctcatatcg tcctgcgcaa actg        1554

SEQ ID NO: 86          moltype = AA  length = 518
FEATURE                Location/Qualifiers
source                 1..518
                       mol_type = protein
                       organism = Siraitia grosvenorii
SEQUENCE: 86
MSSCVAATIS IWMVVVCIVG VGWRVVNWVW LRPKKLEKRL REQGLAGNSY RLLFGDLKER  60
AAMAEQANSK PINFSHDIGP RVFPSMYKTI QNYGKNSYMW LGPYPRVHIM DPQQLKTVFT  120
LVYDIQKPNL NPLVKFLLDG IVTHEGEKWA KHRKIINPAF HLEKLKDMIP AFFHSCNEIV  180
NEWERLISKE GSCELDVMPY LQNLAADAIS RTAFGSSYEE GKMIFQLLKE LTDLVVKVAF  240
GVYIPGWRFL PTKSNNKMKE INRKIKSLLL GIINKRQKAM EEGEAGQSDL LGILMESNSN  300
EIQGEGNNKE DGMSIEDVIE ECKVFYIGGQ ETTARLLIWT MILLSSHTEW QERARTEVLK  360
VFGNKKPDFD GLNRLKIVTM ILNEVLRLYP PASMLTRIIQ KETRLGKLTL PAGVILIMPI  420
ILIHRDHDLW GEDANEFKPE RFSEGVSKAA KVQPAFFPFG WGPRICMGQN FAMIEAKTAL  480
SLILQRFSFE LSSSYVHAPT VVFTTQPQHG AHIVLRKL                        518

SEQ ID NO: 87          moltype = DNA  length = 1584
FEATURE                Location/Qualifiers
source                 1..1584
                       mol_type = other DNA
                       organism = synthetic construct
SEQUENCE: 87
atggtggatc agtgcgcgtt gggatggatc ttggcctccg cgctgggcct cgtaattgcg  60
ctttgtttct tcgtggctcc gaggaggaat cacagaggag tggattcgaa ggagagggac  120
gagtgcgtcc aaagcgctgc aaccacgaag ggagaatgca gattcaacga tcgcgacgtt  180
gacgttatcg tcgttggcgc cggtgttgcc ggttccgctc ttgctcacac tcttggcaag  240
gatggtcgtc gagttcatgt aattgaaaga gacttgacag agcctgacag aatcgttggt  300
gaattattac aacctggggg ttacctcaaa ttgattgaat taggacttca agactgcgtc  360
gaggagattg atgctcaaag ggtgtatggc tacgcccttt tcaaggatgg aaagaacact  420
cgactctctt acccattgga aaattttcac tctgatgtat ctggaaggag ctttcacaac  480
gggcgcttca tacagagaat gagggagaag gctgcttccc ttcccaatgt cagattggag  540
caagggacag ttacttcgct gcttgaagaa aagggaacga tcaaaggtgt gcagtataag  600
tctaaaaatg gtgaagagaa aacagcatat gcacctctga ccattgtttg tgatggctgc  660
ttctcaaact tgcgccgctc tctctgcaac cctatggttg atgttccctc ttattttgtg  720
ggattagttc ttgagaattg tgagcttcct tttgcaaatc acgggcacgt tatcctcgga  780
gatccttctc ccattttatt ctaccagatt agcaggaccg agatccgttg tttggttgat  840
gttcctggtc agaaggttcc ttctatagca aatggtgaaa tggagaaata tttgaagact  900
gtagtagctc ctcaggttcc cccgcaaatc tacgattcct ttatcgctgc tatcgacaag  960
ggtaatataa ggacaatgcc aaacagaagc atgcctgctg ctccccaccc aacgcccggt  1020
gccttactga tgggtgatgc tttcaacatg cgccaccctc ttaccggtgg aggaatgacc  1080
gtagcattgt ctgatatagt tgtattgcgg aacctcctca agcctctgaa ggacttgagt  1140
gatgcatcta ccctctgcaa gtatcttgaa tccttttaca ctttgcgaaa gccagtggct  1200
tcgaccatca acacattggc aggggcatta tacaaggtct tttgtgcatc accagatcaa  1260
gctaggaagg aaatgcgaca agcctgcttc gattacttga gccttggagg aatattctca  1320
aatggacctg tctccttgct ttcagggttg aatcctcgcc ccttaagttt ggttctccat  1380
ttctttgccg tcgcgatata cggagttggt cgcttattac ttccatttcc ttcagtgaaa  1440
ggcatctgga ttggagctag attgatctat agcgcatcag gtatcatatt cccaattata  1500
cgggcggaag gagttagaca gatgttcttc cctgcaactg ttcctgctta ttatagaagt  1560
ccaccagtgt ttaaacccat agta                                        1584

SEQ ID NO: 88          moltype = DNA  length = 1419
FEATURE                Location/Qualifiers
source                 1..1419
                       mol_type = other DNA
                       organism = synthetic construct
SEQUENCE: 88
atgtggactg tcgtgctcgg tttggcgacg ctgtttgtcg cctactacat ccattggatt  60
aacaaatgga gagattccaa gttcaacgga gttctgccgc cgggcaccat gggtttgccg  120
ctcatcggag agacgattca actgagccga cccagtgact ccctcgacgt tcaccctttc  180
atccagaaaa aagttgaaag atacgggccg atcttcaaaa cctgtctggc cggaaggccg  240
```

gtggtggtgt cggcggacgc agagttcaac aactacataa tgcttcagga aggaagagca 300
gtggaaatgt ggtatttgga tacgctctcc aaatttttcg gcctcgacac cgagtggctc 360
aaagctctgg gcctcatcca caagtacatc agaagcatta ctctcaatca cttcggcgcc 420
gaggccctgc gggagagatt tcttcctttt attgaagcat cctccatgga agcccttcac 480
tcctggtcta ctcaacctag cgtcgaagtc aaaaatgcct ccgctctcat ggtttttagg 540
acctcggtga ataagatgtt cggtgaggat gcgaagaagc tatcgggaaa tatccctggg 600
aagttcacga agctgctagg aggatttctc agtttaccac tgaatttcc cggcaccacc 660
taccacaaat gcttgaagga tatgaaggaa atccagaaga agctaagaga ggttgtagac 720
gatagattgg ctaatgtggg ccctgatgtg gaagatttct tggggcaagc ccttaaagat 780
aaggaatcag agaagttcat ttcagaggag ttcatcatcc aactgttgtt ttctatcagt 840
tttgccagct ttgagtccat ctccaccact cttactttga ttctcaagct ccttgatgaa 900
cacccagaag tagtgaaaga gttggaagct gaacacgagg cgattcgaaa agctagagca 960
gatccagatg gaccaattac ttgggaagaa tacaaatcca tgacttttac attacaagtc 1020
atcaatgaaa ccctaaggtt ggggagtgtc acaccagcct tgttgaggaa aacagttaaa 1080
gaccttcaag taaaaggata cataatcccg gaaggatgga caataatgct tgtcaccgct 1140
tcacgtcaca gagatccaaa agtctataag gaccctcata tcttcaatcc atggcgttgg 1200
aaggacttgg actcaattac catccaaaag aacttcatgc cttttggggg aggcttaagg 1260
cattgtgctg gtgctgagta ctctaaagtc tacttgtgca ccttcttgca catcctctgt 1320
accaaatacc gatggaccaa acttggggga ggaacgattg caagagcgca tatattgagt 1380
tttgaagatg ggttacacgt gaagttcaca cccaaggaa 1419

SEQ ID NO: 89 moltype = DNA length = 2277
FEATURE Location/Qualifiers
source 1..2277
mol_type = other DNA
organism = synthetic construct
SEQUENCE: 89
atgtggaggt taaaggtcgg agcagaaagc gttggggaga atgatgagaa atggttgaag 60
agcataagca atcacttggg acgccaggtg tgggagttct gtccggatgc cggcacccaa 120
caacagctct tgcaagtcca caaagctcgt aaagcgttcc acgatgaccg tttccaccga 180
aagcaatctt ccgatctctt tatcactatt cagtatggaa aggaagtaga aaatggtgga 240
aagacagcgg gagtgaaatt gaaagaaggg gaagaggtga ggaaagaggc agtagagagt 300
agcttagaga gggcattaag tttctactca agcatccaga caagcgatgg gaactgggct 360
tcggatcttg gggggcccat gtttttactt ccgggtctgg tgattgccct ctacgttaca 420
ggcgtcttga actctgtttt atccaagcac caccggcaag agatgtgcag atatgtttac 480
aatcaccaga atgaagatgg ggggtgggga ctccacatcg agggcccaag caccatgttt 540
ggttccgcac tgaattatgt tgcactcagg ctgcttggag aagacgccaa cgccggggca 600
atgccaaaag cacgtgcttg gatcttggac cacggtggcg ccaccggaat cacttcctgg 660
ggcaaattgt ggctttctgt acttggagtc tacgaatgga gtggcaataa tcctcttcca 720
cccgaatttt ggttatttcc ttacttccta ccatttcatc caggaagaat gtggtgccat 780
tgtcgaatgg tttatctacc aatgtcatac ttatatggaa agagatttgt tgggccaatc 840
acacccatag ttctgtctct cagaaaagaa ctctacgcag ttccatatca tgaaatagac 900
tggaataaat ctcgcaatac ctgtgcaaag gaggatctgt actatccaca tcccaagatg 960
caagatattc tgtggggatc tctccaccac gtgtatgagc ccttgtttac tcgttggcct 1020
gccaaacgcc tgagagaaaa ggctttgcag actgcaatgc aacatattca ctatgaagat 1080
gagaataccc gatatatatg ccttggccct gtcaacaagg tactcaatct gctttgttgt 1140
tgggttgaag atccctactc cgacgccttc aaacttcatc ttcaacgagt ccatgactat 1200
ctctgggttg ctgaagatgg catgaaaatg cagggttata atgggagcca gttgtgggac 1260
actgctttct ccatccaagc aatcgtatcc accaaacttg tagacaacta tggcccaacc 1320
ttaagaaagg cacacgactt cgttaaaagt tctcagattc agcaggactg tcctggggat 1380
cctaatgttt ggtatcgtca cattcataaa ggtgcatggc cattttcaac tcgcgatcat 1440
ggatggctca tctctgactg tacagcagag ggattaaagg ctgctttgat gttatccaaa 1500
cttccatccg aaacagttgg ggaatcatta gaacggaatc gcctttgcga tgctgtaaac 1560
gttctccttt ctttgcaaaa cgataatggt ggctttgcat catatgagtt gacaagatca 1620
tacccttggt tggagttgat caaccccgca gaaacgtttg gagatattgt cattgattat 1680
ccgtatgtgg agtgcacctc agccacaatg gaagcactga cgttgtttaa gaaattacat 1740
cccggccata ggaccaaaga aattgatact gctattgtca gggcggccaa cttccttgaa 1800
aatatgcaaa ggacggatgg ctcttggtat ggatgttggg ggtttgcttt cacgtatgcg 1860
gggtggtttg gcataaaggg attggtggca gctggaagga catataataa ttgccttgcc 1920
attcgcaagg cttgcgattt tttactatct aaagagctgc ccggcggtgg atggggagag 1980
agttaccttt catgtcagaa taaggtatac acaaatcttg aaggaaacag accgcacctg 2040
gttaacacgg cctgggtttt aatggccctc atagaagctg gccaggctga gagagatcca 2100
acaccattgc atcgtgcagc aaggttgtta atcaattccc agttggagaa tggtgatttc 2160
ccccaacagg agatcatggg agtctttaat aaaaattgca tgatcacata tgctgcatac 2220
cgaaacattt ttcccatttg ggctcttgga gagtattgcc atcgggtttt gactgaa 2277

SEQ ID NO: 90 moltype = DNA length = 948
FEATURE Location/Qualifiers
source 1..948
mol_type = other DNA
organism = synthetic construct
SEQUENCE: 90
atggaccaga ttgagcatat caccatcaac accaatggca tcaaaatgca cattgcctct 60
gtagggacgg gcccagtagt tcttcttctg catggcttcc cggaactctg gtattcatgg 120
cgccaccagc ttctgtatct ttcttccgta ggatatcgag ctattgcgcc ggacctccgc 180
ggctatggcg acacggactc gccggcgtct cctacctcct acaccgctct ccacatcgtc 240
ggcgatttgg ttggggctct ggacgagctt gggatcgaga aggtgtttct ggtcggacat 300
gactgggggg cgatcatcgc ctggtacttt tgcttgttca ggcccgatag aatcaaggcg 360
ctggtgaatc tgagcgtcca gttcataccc agaaacccag cgattccttt cattgagggt 420

```
ttcagaactg cgttcggtga tgacttctat atgtgcaggt ttcaggttcc aggagaggca  480
gaagaagatt ttgcctccat cgacacagct cagctgttca agacatcatt atgtaataga  540
agttctgcac ctccatgctt gcctaaagaa attggatttc gtgcgatccc acctccagag  600
aaccttcctt cttggctgac agaagaagat atcaactatt atgctgccaa atttaagcag  660
acaggcttca ccggagcgtt gaactactat cgagcttttg acctaacttg ggaactcacg  720
gcgccttgga caggagcaca gattcaggtt ccggtgaagt tcatcgtcgg ggattcggat  780
ctaacttacc attttccggg agccaaggaa tatatccata atggcggatt caaaaaggac  840
gtgccgttgc tggaggaagt agttgtagta aaagatgctt gtcacttcat caaccaagaa  900
aggccacaag aaatcaatgc tcacatccat gacttcatca ataaattc              948

SEQ ID NO: 91          moltype = DNA  length = 1422
FEATURE                Location/Qualifiers
source                 1..1422
                       mol_type = other DNA
                       organism = synthetic construct
SEQUENCE: 91
atggtgcaac ctcgggtact gctgtttcct ttcccggcac tgggccacgt gaagcccttc  60
ttatcactgg cggagctgct ttccgacgcc ggcatagacg tcgtcttcct cagcaccgag  120
tataaccacc gtcggatctc caacactgaa gccctagcct cccgcttccc gacgcttcat  180
ttcgaaacta taccggatgg cctgccgcct aatgagtcgc gcgctcttgc cgacggccca  240
ctgtatttct ccatgcgtga gggaactaaa ccgagattcc ggcaactgat tcaatctctt  300
aacgacggtc gttggcccat cacctgtatt atcactgaca tcatgttatc ttctccgatt  360
gaagtagcgg aagaatttgg gattccagta attgccttct gcccatgcag tgctcgctac  420
ttatcgattc actttttat accgaagctc gttgaggaag gtcaaattcc atacgcagat  480
gacgatccga ttggagagat ccagggggtg cccttgttcg aaggtctttt gcgacggaat  540
catttgcctg gttcttggtc tgataaatcc gcagatatat ctttctcgca tggcttgatt  600
aatcagaccc ttgcagctgg tcgagcctcg gctcttatac tcaacacctt cgacgaactc  660
gaagctccat ttctgaccca tctctcttcc attttcaaca aaatctacac cattggaccc  720
ctccatgctc tgtccaaatc aaggctcggc gactcctcct cctccgcttc tgccctctcc  780
ggattctgga aagaggatag agcctgcatg tcctggctcg actgtcagcc gccgaggtct  840
gtggttttcg tcagtttcgg gagtacgatg aagatgaaag ccgatgaatt gagagagttc  900
tggtatgggt tggtgagcag cgggaaaccg ttcctctgcg tgttgagatc cgacgttgtt  960
tccggcggag aagcggcgga attgatcgaa cagatggcgg aggaggaggg agctggaggg  1020
aagctgggaa tggtagtgga gtgggcagcg caagagaagg tcctgagcca ccctgccgtc  1080
ggtgggtttt tgacgcactg cgggtggaac tcaacggtgg aaagcattgc cgcgggagtt  1140
ccgatgatgt gctggccgat tctcggcgac caacccagca acgccacttg gatcgacaga  1200
gtgtggaaaa ttggggttga aaggaacaat cgtgaatggg acaggttgac ggtggagaag  1260
atggtgagag cattgatgga aggccaaaag agagtggaga ttcagagatc aatggagaag  1320
ctgtcaaagt tggcaaatga gaaggttgtc aggggtgggt tgtcttttga taacttggaa  1380
gttctcgttg aagacatcaa aaaattgaaa ccatataaat tt                    1422

SEQ ID NO: 92          moltype = DNA  length = 1356
FEATURE                Location/Qualifiers
source                 1..1356
                       mol_type = other DNA
                       organism = synthetic construct
SEQUENCE: 92
atggatgctg cccaacaagg tgacaccaca accattttga tgcttccatg gctcggctat  60
ggccatcttt cagcttttct cgagctggcc aaaagcctct caaggaggaa cttccatatc  120
tacttctgtt caacctctgt taatcttgac gccattaaac caaagcttcc ttcttctttc  180
tctgattcca ttcaatttgt ggagctccat ctcccttctt ctcctgagtt ccctcctcat  240
cttcacacaa ccaacggcct tcccccctacc ctcatgcccg ctctccacca agccttctcc  300
atggctgccc agcactttga gtccatttta caaacacttg ccccgcacct tctcatttat  360
gactctcttc aaccttgggc tcctcgggta gcttcatccc tcaaaattcc ggccatcaac  420
ttcaatacca cgggagtttt cgtcatttct caagggcttc accctattca ctacccacat  480
tctaaattcc cattctcaga gttcgttctt cacaatcatt ggaaagccat gtactccact  540
gccgatggag cttctaccga aagaacccgc aaacgtggag aagcgtttct gtattgcttg  600
catgcttctt gtagtgtaat tctaatcaat agtttcagag agctcgaggg gaaatatatg  660
gattatctct ctgttctctt gaacaagaaa gttgttccgg ttggtccttt ggtttacgaa  720
ccgaatcaag acggggaaga tgaaggttat tcaagcatca aaaattggct tgacaaaaag  780
gaaccgtcct ccaccgtctt cgtgtcattt ggaagcgaat acttcccgtc aaaggaagaa  840
atggaagaga tagcccatgg gttagaggcg agcgaggtta atttcatctg ggtcgttagg  900
tttcctcaag gagacaacac cagcggcatt gaagatgcct tgccgaaggg ttttctggag  960
agggcgggag agagagggat ggtggtgaag ggttgggctc ctcaggcgaa gatactgaag  1020
cattggagca caggggggatt cgtgagccac tgtggatgga actcggtgat ggagagcatg  1080
atgtttggcg ttcccataat aggggttccg atgcatgtgg accagccctt taacgccgga  1140
ctcgtggaag aagctggcgt cggcgtggag gccaagcgag atccagacgg caaaattcaa  1200
agagacgaag ttgcaaagtt gatcaaagaa gtggtggttg agaaaaccag agaagatgtg  1260
cggaagaaag caagagaaat gagtgagatt ttgaggagca agggagagga gaagtttgat  1320
gagatggtcg ctgaaatttc tctcttgctt aaaata                           1356

SEQ ID NO: 93          moltype = DNA  length = 1029
FEATURE                Location/Qualifiers
source                 1..1029
                       mol_type = other DNA
                       organism = synthetic construct
SEQUENCE: 93
atggcggatc tcaagtcaac cttcctcaag gtctactcgg ttctgaagga tgagcttctt  60
caggaccctg cgtttgagtt tacggatgct tctcgccaat ggatcgaacg gatgctggac  120
```

```
tacaatgtgc ctggaggcaa gcttaaccga gggctctccg tcatcgatag ctacaaatta  180
ttgaaagaag ggaaggaatt gactgaagat gaaatctttc ttgctagtgt tcttggttgg  240
tgtattgaat ggctccaggc gtattttctt gttctcgatg atattatgga taactctgtc  300
acacgacgtg gtcaaccttg ctggtttaga gtacccaagg ttgggatgat tgcagtaaac  360
gatggagttc tacttcgaaa tcatattcct agaatgctaa aaatcactt caaagggaag  420
ccgtattacg ttgatctgct tgatttgttt aacgaggttg agtttcaaac agcatcagga  480
caaatgattg atttgataac cactatcgat ggagaaaaag atctttccaa atatgcattg  540
tcacttcatc ggcgcattgt acagtacaag actgcctatt attcatttta ccttccagtt  600
gcttgtgcac tagttatgtc aggtgaagat cttgagaaac atacagtggt taaagacatt  660
cttgttcaga tgggtgtcta ttttcaagtt caggatgatt atctagattg ttttggcgat  720
cctgaaacca taggaaaggt gggaacggac attgaagatt tcaaatgctc ttggttggtt  780
gtgaaagctc tggaactttg caacgaggat cagaagaagt tattacacga ggcttatggg  840
aaaccagacc cagaaaatgt tgccaaagta aaggccatct acaaggatct cgatcttcag  900
ggtgtatttg cggagtatga gagccagagc tacgctaaac tgaatgcctc cattgaagct  960
catcccaaca aatcaattca agcagttctt aagtctttct tgggtaaaat atacaggcgc  1020
cagaagtga                                                       1029

SEQ ID NO: 94          moltype = AA  length = 342
FEATURE                Location/Qualifiers
source                 1..342
                       mol_type = protein
                       organism = Citrullus lanatus
SEQUENCE: 94
MADLKSTFLK VYSVLKDELL QDPAFEFTDA SRQWIERMLD YNVPGGKLNR GLSVIDSYKL  60
LKEGKELTED EIFLASVLGW CIEWLQAYFL VLDDIMDNSV TRRGQPCWFR VPKVGMIAVN  120
DGVLLRNHIP RMLKNHFKGK PYYVDLLDLF NEVEFQTASG QMIDLITTID GEKDLSKYAL  180
SLHRRIVQYK TAYYSFYLPV ACALVMSGED LEKHTVVKDI LVQMGVYFQV QDDYLDCFGD  240
PETIGKVGTD IEDFKCSWLV VKALELCNED QKKLLHEAYG KPDPENVAKV KAIYKDLDLQ  300
GVFAEYESQS YAKLNASIEA HPNKSIQAVL KSFLGKIYRR QK                    342

SEQ ID NO: 95          moltype = DNA  length = 1425
FEATURE                Location/Qualifiers
source                 1..1425
                       mol_type = other DNA
                       organism = synthetic construct
SEQUENCE: 95
atgtggacca tcctgctggg cctggccacc ctggccatcg cctactacat ccactgggtg  60
aacaagtgga aggactccaa gttcaacggc gtgctgccgc cgggcaccat gggcctgccg  120
ctgatcggcg aaaccctgca gttcctgagg ccgtccgact ccctggacgt gcacccgttc  180
ttccagagga aggtgaagag gtacggcccg atcttcaaga cctgcctggc cggcaggccg  240
gtggtggtgt ccaccgacgc cgagttcaac cactacatca tgctgcagga gggcagggcc  300
gtggagatgt ggtacctgga caccctgtcc aagttcttcg gcctggacac cgagtggacc  360
aaggccctgg gcctgatcca caagtacatc aggtccatca ccctgaacca cttcggcgcc  420
gagtccctga gggagaggtt cctgccgagg atcgaggagt ccgccaggga aaccctgcac  480
tactggtcca cccagacctc cgtggaggtg aaggagtccg ccgccgccat ggtgttcagg  540
acctccatcg tgaagatgtt ctccgaggac tcctccaagc tgctgaccga gggcctgacc  600
aagaagttca ccggcctgct gggcggcttc ctgaccctgc cgctgaacct gccgggcacc  660
acctaccaca agtgcatcaa ggacatgaag cagatccaga agaagctgaa ggacatcctg  720
gaggagaggc tggccaaggg cgtgaagatc gacgaggact tcctgggcca ggccatcaag  780
gacaaggagt cccagcagtt catctccgag gagttcatca tccagctgct gttctccatc  840
tccttcgcct ccttcgagtc catctccacc accctgaccc tgatcctgaa cttcctggcc  900
gaccacccgg acgtggtgaa ggagctggag gccgagcacg aggccatcag gaaggccagg  960
gccgacccgg acggcccgat cacctgggag gagtacaagt ccatgaactt caccctgaac  1020
gtgatctacg aaaccctgag gctgggctcc gtgatcccgg ccctgccgag gaagaccacc  1080
aaggagatcc agatcaaggg ctacaccatc ccggagggct ggaccgtgat gctggtgacc  1140
gcctccaggc acagggaccc ggaggtgtac aaggacccgg acaccttcaa cccgtggagg  1200
tggaaggagc tggactccat caccatccag aagaacttca tgccgttcgg cggcggcctg  1260
aggcactgcg ccggcgccga gtactccaag gtgtacctgt gcaccttcct gcacatcctg  1320
ttcaccaagt acaggtggag gaagctgaag ggcggcaaga tcgccagggc ccacatcctg  1380
aggttcgagg acggcctgta cgtgaacttc accccgaagg agtga                 1425

SEQ ID NO: 96          moltype = AA  length = 474
FEATURE                Location/Qualifiers
source                 1..474
                       mol_type = protein
                       organism = Siraitia grosvenorii
SEQUENCE: 96
MWTILLGLAT LAIAYYIHWV NKWKDSKFNG VLPPGTMGLP LIGETLQFLR PSDSLDVHPF  60
FQRKVKRYGP IFKTCLAGRP VVVSTDAEFN HYIMLQEGRA VEMWYLDTLS KFFGLDTEWT  120
KALGLIHKYI RSITLNHFGA ESLRERFLPR IEESARETLH YWSTQTSVEV KESAAAMVFR  180
TSIVKMFSED SSKLLTEGLT KKFTGLLGGF LTLPLNLPGT TYHKCIKDMK QIQKKLKDIL  240
EERLAKGVKI DEDFLGQAIK DKESQQFISE EFIIQLLFSI SFASFESIST TLTLILNFLA  300
DHPDVVKELE AEHEAIRKAR ADPDGPITWE EYKSMNFTLN VIYETLRLGS VIPALPRKTT  360
KEIQIKGYTI PEGWTVMLVT ASRHRDPEVY KDPDTFNPWR WKELDSITIQ KNFMPFGGGL  420
RHCAGAEYSK VYLCTFLHIL FTKYRWRKLK GGKIARAHIL RFEDGLYVNF TPKE        474

SEQ ID NO: 97          moltype = DNA  length = 1167
FEATURE                Location/Qualifiers
source                 1..1167
```

```
                        mol_type = other DNA
                        organism = synthetic construct
SEQUENCE: 97
atggggagtt tgggggcaat tttgaaacac ccagatgatt tttacccgct tttgaaactg  60
aaaatggccg ctagacatgc ggagaagcag atcccacctg agcctcattg ggattttgc  120
tataccatgc tgcataaagt ctcaagaagt tttgcactcg ttattcagca gcttaagccc  180
gagcttcgca atgctgtatg catattttat cttgttctgc gagccctcga tactgttgag  240
gatgatacag gcatacaaac agacatcaaa gtgcccattc tgaaagcttt tcactgtcac  300
atatataacc gtgattggca tttttcatgt ggcacaaagg actataaagt tcttatggat  360
gagtttcatc atgtttcaac tgcgtttcta gaacttggga aagggtacca ggaagcaatt  420
gaggatatca caaaacggat gggtgcaggc atggctaaat tcatttgcca agaggttgag  480
acagttggtg attatgatga atattgccac tatgtagctg gacttgtcgg actaggttta  540
tctaagctgt tccacgctgc gaagtcagag gatttggcac ctgattctct ttcaaattct  600
atgggattgt ttcttcagaa aacaaacatt atccgagatt acttggagga cattaatgag  660
ataccaaagt ctagaatgtt ttggcctcgt gagatttggg gcaaatatgc tgataaatta  720
gaggatttta aatatgagga gaattcagtc aaggccgtgc aatgcctcaa tgatttggtc  780
actaatgctt tgaaccatgt ggaggattgt ctgaaataca tgtctaactt aagagatctt  840
tccatttttc gattttgtgc aatccctcag attatggcga ttggaactct agcattgtgc  900
tacaataatg tcgaagtctt cagaggggtg gtcaaaatgc gtcggggtct tactgctaag  960
gtcattgatc gaacaaaaac gatggctgac gtctatggag ctttctttga tttctctgtt  1020
atgctgaagg ctaaggtcaa cagcagtgat cctaatgctt ctaaaaccct gagcaggatc  1080
gaggcaatac agcaaacatg caagcagtcg gggctcttga acaagaggaa attgtatgta  1140
gtaagaagtg agccaatgta caattga                                     1167

SEQ ID NO: 98           moltype = AA  length = 388
FEATURE                 Location/Qualifiers
source                  1..388
                        mol_type = protein
                        organism = Citrullus lanatus
SEQUENCE: 98
MGSLGAILKH PDDFYPLLKL KMAARHAEKQ IPPEPHWGFC YTMLHKVSRS FALVIQQLKP  60
ELRNAVCIFY LVLRALDTVE DDTGIQTDIK VPILKAFHCH IYNRDWHFSC GTKDYKVLMD  120
EFHHVSTAFL ELGKGYQEAI EDITKRMGAG MAKFICQEVE TVGDYDEYCH YVAGLVGLGL  180
SKLFHAAKSE DLAPDSLSNS MGLFLQKTNI IRDYLEDINE IPKSRMFWPR EIWGKYADKL  240
EDFKYEENSV KAVQCLNDLV TNALNHVEDC LKYMSNLRDL SIFRFCAIPQ IMAIGTLALC  300
YNNVEVFRGV VKMRRGLTAK VIDRTKTMAD VYGAFFDFSV MLKAKVNSSD PNASKTLSRI  360
EAIQQTCKQS GLLNKRKLYV VRSEPMYN                                    388

SEQ ID NO: 99           moltype = DNA  length = 1425
FEATURE                 Location/Qualifiers
source                  1..1425
                        mol_type = other DNA
                        organism = synthetic construct
SEQUENCE: 99
atgtggaccg tggtgctggg cctggccacc ctgttcgtgg cctactacat ccactggatc  60
aacaagtgga gggactccaa gttcaacggc gtgctgccgc cgggcaccat gggcctgccg  120
ctgatcggcg aaaccctgca gttcctgagg ccgtccgact ccctggacgt gcacccgttc  180
ttccagaaga aggtggagag gtacggcccg atcttcaaga cctgcctggc cggcaggccg  240
gtggtggtgt ccgccgacgc cgagttcaac aactacatca tgctgcagga gggcagggcc  300
gtggagatgt ggtacctgga caccctgtcc aagttcttcg gcctggacac cgagtggacc  360
aaggccctgg gcctgatcca caagtacatc aggtccatca ccctgaacca cttcggcgcc  420
gaggccctga gggagaggtt cctgccgttc atcgaggcct cctccatgga ggccctgcac  480
tcctggtcca cccagccgtc cgtggaggtg aagaacgcct ccgccctgat ggtgttcagg  540
acctccgtga acaagatgtt cggcgaggac gccaagaagc tgctgtccgg caacatcccg  600
ggcaagttca ccaagctgct gggcggcttc ctgtccctgc cgctgaactt cccgggcacc  660
acctaccaca agtgcctgaa ggacatgaag gagatccaga agaagctgag ggaggtggtg  720
gacgacaggc tggccaacgt gggcccggac gtggaggact tcctgggcca ggccctgaag  780
gacaaggagt ccgagaagtt catctccgag gagttcatca tccagctgct gttctccatc  840
tccttcgcct ccttcgagtc catctccacc accctgaccc tgatcctgaa gctgctggac  900
gagcacccgg aggtggtgaa ggagctggag gccgagcacg aggccatcag gaaggccagg  960
gccgacccgg acggcccgat cacctgggag gagtacaagt ccatgacctt caccctgcaa  1020
gtgatctacg aaaccctgag gctgggctcc gtgatcccgg ccctgccgag gaagaccgtg  1080
aaggacctgc aagtgaaggg ctacatcatc ccggagggct ggaccatcat gctggtgacc  1140
gcctccaggc acagggaccc gaaggtgtac aaggacccgc acatcttcaa cccgtggagg  1200
tggaaggacc tggactccat caccatccag aagaacttca tgccgttcgg cggcggcctg  1260
aggcactgcg ccggcgccga gtactccaag gtgtacctgt gcaccttcct gcacatcctg  1320
tgcaccaagt acaggtggac caagctgggc ggcggcacca tcgccagggc ccacatcctg  1380
tccttcgagg acggcctgca cgtgaagttc accccgaagg agtga                 1425

SEQ ID NO: 100          moltype = AA  length = 474
FEATURE                 Location/Qualifiers
source                  1..474
                        mol_type = protein
                        organism = Siraitia grosvenorii
SEQUENCE: 100
MWTVVLGLAT LFVAYYIHWI NKWRDSKFNG VLPPGTMGLP LIGETLQFLR PSDSLDVHPF  60
FQKKVERYGP IFKTCLAGRP VVVSADAEFN NYIMLQEGRA VEMWYLDTLS KFFGLDTEWT  120
KALGLIHKYI RSITLNHFGA EALRERFLPF IEASSMEALH SWSTQPSVEV KNASALMVFR  180
TSVNKMFGED AKKLLSGNIP GKFTKLLGGF LSLPLNFPGT TYHKCLKDMK EIQKKLREVV  240
```

```
DDRLANVGPD VEDFLGQALK DKESEKFISE EFIIQLLFSI SFASFESIST TLTLILKLLD  300
EHPEVVKELE AEHEAIRKAR ADPDGPITWE EYKSMTFTLQ VIYETLRLGS VIPALPRKTV  360
KDLQVKGYII PEGWTIMLVT ASRHRDPKVY KDPHIFNPWR WKDLDSITIQ KNFMPFGGGL  420
RHCAGAEYSK VYLCTFLHIL CTKYRWTKLG GGTIARAHIL SFEDGLHVKF TPKE        474

SEQ ID NO: 101          moltype = DNA  length = 1422
FEATURE                 Location/Qualifiers
source                  1..1422
                        mol_type = other DNA
                        organism = synthetic construct
SEQUENCE: 101
atgtggaccg tggtgctggg cctggccacc ctgttcgtgg cctactacat ccactggatc  60
aacaagtgga gggactccaa gttcaacggc gtgctgccgc cgggcaccat gggcctgccg  120
ctgatcggcg aaaccctgca gttcctgagg ccgtccgact ccctggacgt gcacccgttc  180
ttccagaaga aggtggagag gtacggcccg atcttcaaga cctgcctggc cggcaggccg  240
gtggtggtgt ccgccgacgc cgagttcaac aactacatca tgctgcagga gggcagggcc  300
gtggagatgt ggtacctgga caccctgtcc aagttcttcg gcctggacac cgagtggacc  360
aaggccctgg gcctgatcca caagtacatc aggtccatca ccctgaacca cttcggcgcc  420
gaggccctga gggagaggtt cctgccgttc atcgaggcct cctccatgga ggccctgcac  480
tcctggtcca cccagccgtc cgtggaggtg aagaacgcct ccgccctgat ggtgttcagg  540
acctccgtga acaagatgtt cggcgaggac gccaagaagc tgtccggcaa catcccgggc  600
aagttcacca agctgctggg cggcttcctg tccctgccgc tgaacttccc gggcaccacc  660
taccacaagt gcctgaagga catgaaggag atccagaaga agctgaggga ggtggtggac  720
gacaggctgg ccaacgtggg cccggacgtg gaggacttcc tgggccaggc cctgaaggac  780
aaggagtccg agaagttcat ctccgaggag ttcatcatcc agctgctgtt ctccatctcc  840
ttcgcctcct tcgagtccat ctccaccacc ctgaccctga tcctgaagct gctggacgag  900
cacccggagg tggtgaagga gctggaggcc gagcacgagg ccatcaggaa ggccagggcc  960
gacccggacg gcccgatcac ctgggaggag tacaagtcca tgaccttcac cctgcaagtg  1020
atctacgaaa ccctgaggct gggctccgtg atcccggccc tgccgaggaa gaccgtgaag  1080
gacctgcaag tgaagggcta catcatcccg gagggctgga ccatcatgct ggtgaccgcc  1140
tccaggcaca gggacccgaa ggtgtacaag gacccgcaca tcttcaaccc gtggaggtgg  1200
aaggacctgg actccatcac catccagaag aacttcatgc cgttcggcgg cggcctgagg  1260
cactgcgccg gcgccgagta ctccaaggtg tacctgtgca ccttcctgca catcctgtgc  1320
accaagtaca ggtggaccaa gctgggcggc ggcaccatcg ccagggccca catcctgtcc  1380
ttcgaggacg gcctgcacgt gaagttcacc ccgaaggagt ga                     1422

SEQ ID NO: 102          moltype = AA  length = 473
FEATURE                 Location/Qualifiers
source                  1..473
                        mol_type = protein
                        organism = Siraitia grosvenorii
SEQUENCE: 102
MWTVVLGLAT LFVAYYIHWI NKWRDSKFNG VLPPGTMGLP LIGETLQFLR PSDSLDVHPF  60
FQKKVERYGP IFKTCLAGRP VVVSADAEFN NYIMLQEGRA VEMWYLDTLS KFFGLDTEWT  120
KALGLIHKYI RSITLNHFGA EALRERFLPF IEASSMEALH SWSTQPSVEV KNASALMVFR  180
TSVNKMFGED AKKLSGNIPG KFTKLLGGFL SLPLNFPGTT YHKCLKDMKE IQKKLREVVD  240
DRLANVGPDV EDFLGQALKD KESEKFISEE FIIQLLFSIS FASFESISTT LTLILKLLDE  300
HPEVVKELEA EHEAIRKARA DPDGPITWEE YKSMTFTLQV IYETLRLGSV IPALPRKTVK  360
DLQVKGYIIP EGWTIMLVTA SRHRDPKVYK DPHIFNPWRW KDLDSITIQK NFMPFGGGLR  420
HCAGAEYSKV YLCTFLHILC TKYRWTKLGG GTIARAHILS FEDGLHVKFT PKE        473

SEQ ID NO: 103          moltype = DNA  length = 2127
FEATURE                 Location/Qualifiers
source                  1..2127
                        mol_type = other DNA
                        organism = synthetic construct
SEQUENCE: 103
atgcagtccg agtccaggtc catgaaggtg tccccgctgg agctgatgtc cgccatcatc  60
aggaaggcca tggacccgtc cagggagtcc tccgagtccg tgagggaggt ggccaccctg  120
atcctggaga acagggagtt cgtgatgatc ctgaccaccc tgctggccgt gctgatcggc  180
tgcgtggtgg tgctggtgtg gaagaggtcc tccggccaga aggccaagcc gttcgagccg  240
ccgaagcagc tgatcgtgaa ggagccggag ccggaggtgg acgacggcaa gaagaaggtg  300
accgtgttct tcggcaccca gaccggcacc gccgagggct tcgccaaggc cctggccgag  360
gaggccaagg ccaggtacga gaaggccacc ttcagggtgg tggacctgga cgactacgcc  420
gccgacgacg acgagtacga ggagaagctg aagaaggaaa ccctggccat cttcttcctg  480
gccacctacg gcgacggcga gccgaccgac aacgccgcca ggttctacaa gtggttctcc  540
gagggcaagg agaagggcga ctggatctcc aacctgcagt acgccgtgtt cggcctgggc  600
aacaggcagt acgagcactt caacaagatc gccaaggtgg tggacgagca gctggccgag  660
cagggcggca agaggctggt gccggtgggc ctgggcgacg acgaccagtg catcgaggac  720
gacttctccg cctggaggga ggccctgtgg ccggagctgg acaagctgct gagggacgac  780
gacgactcca ccaccgtggc caccccgtac accgccgccg tgctggagta cagggtggtg  840
ttctacgacg ccgccgacgt gtccgtggag gacaagaggt gggccttcgc caacggccac  900
gccgtgtacg acgcccagca cccgtgcagg gccaacgtgg ccatgaggaa ggagctgcac  960
accccggcct ccgacaggtc ctgcatccac ctggagttcg acatctccgg caccggcctg  1020
acctacgaaa ccggcgacca cgtgggcgtg ttctgcgaga acctggacga aaccgtggag  1080
gacgccatca ggctgatcgg cctgtccccg gaaacctact tctccatcca caccgacaag  1140
gacgacggca ccccgctggg cggctcctcc ctgccgccgc cgttcgcccc gtgcaccctg  1200
aggaccgccc tgacccagta cgccgacctg ctgtcctccc cgaagaagtc cgccctggtg  1260
gccctggccg cccacgcctc cgacccggcc gaggccgaca ggctgaggca cctgtcctcc  1320
```

```
ccggccggca aggacgagta cgcccagtgg atcatcgcct cccagaggtc cctgctggag  1380
gtgatggccg agttcccgtc cgccaagccg ccgctgggcg tgttcttcgc cgccgtggcc  1440
ccgaggctgc agccgaggta ctactccatc tcctcctccc cgaggatggc cccgtccagg  1500
atccacgtga cctgcgccct ggtgtacgac aagaccccga ccggcaggat ccacaagggc  1560
gtgtgctcca cctggatgaa gaacgccgtg ccgctggagg agtcccaggc ctgctcctgg  1620
gccccgatct acgtgaggca gtccaacttc aagctgccga ccgactccaa gctgccgatc  1680
atcatgatcg gcccgggcac cggcctggcc ccgttcaggg gcttcctgca ggagaggctg  1740
gccctgaagg aggccggcgt ggagctgggc cactccatcc tgttcttcgg ctgcaggaac  1800
aggaagatgg actacatcta cgaggacgag ctgtccaact tcgccgaaac cggcgccctg  1860
tccgagctga tcgtggcctt ctccagggag ggcccgacca aggagtacgt gcagcacaag  1920
atggtggaca aggcctccga catctggaac atcctgtccc agggcggcta catctacgtg  1980
tgcggcgacg ccaagggcat ggccagggac gtgcacagga ccctgcacaa catcgtgcag  2040
gagcagggct ccctggactc ctccaaggcc gagtccatgg tgaagaacct gcagatgtcc  2100
ggcaggtacc tgagggacgt gtggtga                                      2127
```

```
SEQ ID NO: 104         moltype = AA  length = 708
FEATURE                Location/Qualifiers
source                 1..708
                       mol_type = protein
                       organism = Siraitia grosvenorii
SEQUENCE: 104
MQSESRSMKV SPLELMSAII RKAMDPSRES SESVREVATL ILENREFVMI LTTLLAVLIG  60
CVVVLVWKRS SGQKAKPFEP PKQLIVKEPE PEVDDGKKKV TVFFGTQTGT AEGFAKALAE  120
EAKARYEKAT FRVVDLDDYA ADDDEYEEKL KKETLAIFFL ATYGDGEPTD NAARFYKWFS  180
EGKEKGDWIS NLQYAVFGLG NRQYEHFNKI AKVVDEQLAE QGGKRLVPVG LGDDDQCIED  240
DFSAWREALW PELDKLLRDD DDSTTVATPY TAAVLEYRVV FYDAADVSVE DKRWAFANGH  300
AVYDAQHPCR ANVAMRKELH TPASDRSCIH LEFDISGTGL TYETGDHVGV FCENLDETVE  360
DAIRLIGLSP ETYFSIHTDK DDGTPLGGSS LPPPFAPCTL RTALTQYADL LSSPKKSALV  420
ALAAHASDPA EADRLRHLSS PAGKDEYAQW IIASQRSLLE VMAEFPSAKP PLGVFFAAVA  480
PRLQPRYYSI SSSPRMAPSR IHVTCALVYD KTPTGRIHKG VCSTWMKNAV PLEESQACSW  540
APIYVRQSNF KLPTDSKLPI IMIGPGTGLA PFRGFLQERL ALKEAGVELG HSILFFGCRN  600
RKMDYIYEDE LSNFAETGAL SELIVAFSRE GPTKEYVQHK MVDKASDIWN ILSQGGYIYV  660
CGDAKGMARD VHRTLHNIVQ EQGSLDSSKA ESMVKNLQMS GRYLRDVW                708
```

```
SEQ ID NO: 105         moltype = DNA  length = 1374
FEATURE                Location/Qualifiers
source                 1..1374
                       mol_type = other DNA
                       organism = synthetic construct
SEQUENCE: 105
atgggcggca gggagggcaa ggtgcacgtg ctggtggtgc tgttcccgga cggccagggc  60
cacatcaacc cgatcctgca gttctccaag aggctggcct tcaagggcct ggccgtgacc  120
ctgctgaacg tgttcaggtc ccaggagtcc cacaccctga acctgcaccc gtccatcaac  180
gtggagcaca ggccgaggct gccgtaccag ggcaccgagc cggagtccct ggagtcccac  240
atgcacaggc tgcagacctc catctgcttc cacatgacca agctgatctc ccaccaccag  300
tcctccggct ccccgatcgc ctgcgtggtg tacgactccg tgaccccgtg ggtgctggac  360
gtggccaagg gcttcggcgt gccgggcgcc ccgttcttca ccgagtcctc cgccgtgaac  420
gccatcttct accacgtgca caggggctgg ctgaagatcc cgatcgacga ctcctccgtg  480
tccctgccgg gcctgccgct gctgcagatc tccgacctgc cgtccatgat cccgaacccg  540
cagcagtacc cgatcttcct gaggctgatg atcgaccagt tctccaacaa gccggactgg  600
atgttcatca acaccttcaa ctccctggag ccggaggtgc tgcagtggat ccagacccac  660
accccgctga agaccgtggg cccgaccgtg ccgtccatca tcaccgacaa gaggctgaag  720
gacgaccagc actacggcat cgacctgttc aagtccaccg gcgacgagat caagaccatc  780
gagtggctgg actccaagga ctccggctcc gtgatctacg tgtccttcgg ctccgtgtcc  840
gacctgggcg aggagcagat ggaggagctg gcctggggcc tgaagtccac caacaagtcc  900
ttcctgtggg tggtgaggga aaccggcacc tccaagctgc cgtccaacct gctggaggag  960
atgaaggaaa ccggcatggt ggtgaactgg tgctcccagc tgcaagtgct ggcccacaag  1020
tccgtgggct gcttcatcac ccactgcggc tggaactccg tgctggaggc cctgtccctg  1080
ggcatcccga tggtggccat gccgcagtgg accgaccaga tgaccaacgc caagttcgtg  1140
gaggacgtgt ggaaggtggg cgtgagggtg tcctccaagg agaacgccat cgccggcagg  1200
gaggagatcg agctgtgcat caggcaagtg atggagggcg agaggtccgc cgagatgagg  1260
gagaacgcct ccaggtggat gaagctggcc aaggaggccg tggacgaggg cggctcctcc  1320
gacaagaaca tcgacgagtt cgtggcccag ctgaccaaca ggaacccgaa ctga        1374
```

```
SEQ ID NO: 106         moltype = AA  length = 457
FEATURE                Location/Qualifiers
source                 1..457
                       mol_type = protein
                       organism = Siraitia grosvenorii
SEQUENCE: 106
MGGREGKVHV LVVLFPDGQG HINPILQFSK RLAFKGLAVT LLNVFRSQES HTLNLHPSIN  60
VEHRPRLPYQ GTEPESLESH MHRLQTSICF HMTKLISHHQ SSGSPIACVV YDSVTPWVLD  120
VAKGFGVPGA PFFTESSAVN AIFYHVHRGW LKIPIDDSSV SLPGLPLLQI SDLPSMIPNP  180
QQYPIFLRLM IDQFSNKPDW MFINTFNSLE PEVLQWIQTH TPLKTVGPTV PSIITDKRLK  240
DDQHYGIDLF KSTGDEIKTI EWLDSKDSGS VIYVSFGSVS DLGEEQMEEL AWGLKSTNKS  300
FLWVVRETGT SKLPSNLLEE MKETGMVVNW CSQLQVLAHK SVGCFITHCG WNSVLEALSL  360
GIPMVAMPQW TDQMTNAKFV EDVWKVGVRV SSKENAIAGR EEIELCIRQV MEGERSAEMR  420
ENASRWMKLA KEAVDEGGSS DKNIDEFVAQ LTNRNPN                            457
```

-continued

```
SEQ ID NO: 107          moltype = DNA  length = 1383
FEATURE                 Location/Qualifiers
source                  1..1383
                        mol_type = other DNA
                        organism = synthetic construct
SEQUENCE: 107
atggacgaaa ccaccgtgaa cggcggcagg agggcctccg acgtggtggt gttcgccttc  60
ccgaggcacg gccacatgtc cccgatgctg cagttctcca agaggctggt gtccaagggc  120
ctgagggtga ccttcctgat caccacctcc gccaccgagt ccctgaggct gaacctgccg  180
ccgtcctcct ccctggacct gcaagtgatc tccgacgtgc cggagtccaa cgacatcgcc  240
accctggagg gctacctgag gtccttcaag gccaccgtgt ccaagaccct ggccgacttc  300
atcgacggca tcggcaaccc gccgaagttc atcgtgtacg actccgtgat gccgtgggtg  360
caggaggtgg ccaggggcag gggcctggac gccgccccgt tcttcaccca gtcctccgcc  420
gtgaaccaca tcctgaacca cgtgtacggc ggctccctgt ccatcccggc cccggagaac  480
accgccgtgt ccctgccgtc catgccggtg ctgcaggccg aggacctgcc ggccttcccg  540
gacgacccgg aggtggtgat gaacttcatg acctcccagt tctccaactt ccaggacgcc  600
aagtggatct tcttcaacac cttcgaccag ctggagtgca agaagcagtc ccaggtggtg  660
aactggatgg ccgacaggtg gccgatcaag accgtgggcc cgaccatccc gtccgcctac  720
ctggacgacg gcaggctgga ggacgacagg gccttcggcc tgaacctgct gaagccggag  780
gacggcaaga acaccaggca gtggcagtgg ctggactcca aggacaccgc ctccgtgctg  840
tacatctcct tcggctccct ggccatcctg caggaggagc aagtgaagga gctggcctac  900
ttcctgaagg acaccaacct gtccttcctg tgggtgctga gggactccga gctgcagaag  960
ctgccgcaca acttcgtgca ggaaacctcc cacaggggcc tggtggtgaa ctggtgctcc  1020
cagctgcaag tgctgtccca cagggccgtg tcctgcttcg tgacccactg cggctggaac  1080
tccaccctgg aggccctgtc cctgggcgtg ccgatggtgg ccatcccgca gtgggtggac  1140
cagaccacca acgccaagtt cgtggccgac gtgtggaggg tgggcgtgag ggtgaagaag  1200
aaggacgaga ggatcgtgac caaggaggag ctggaggcct ccatcaggca agtggtgcag  1260
ggcgagggca ggaacgagtt caagcacaac gccatcaagt ggaagaagct ggccaaggag  1320
gccgtggacg agggcggctc ctccgacaag aacatcgagg agttcgtgaa gaccatcgcc  1380
tga                                                                1383

SEQ ID NO: 108          moltype = AA  length = 460
FEATURE                 Location/Qualifiers
source                  1..460
                        mol_type = protein
                        organism = Siraitia grosvenorii
SEQUENCE: 108
MDETTVNGGR RASDVVVFAF PRHGHMSPML QFSKRLVSKG LRVTFLITTS ATESLRLNLP  60
PSSSLDLQVI SDVPESNDIA TLEGYLRSFK ATVSKTLADF IDGIGNPPKF IVYDSVMPWV  120
QEVARGRGLD AAPFFTQSSA VNHILNHVYG GSLSIPAPEN TAVSLPSMPV LQAEDLPAFP  180
DDPEVVMNFM TSQFSNFQDA KWIFFNTFDQ LECKKQSQVV NWMADRWPIK TVGPTIPSAY  240
LDDGRLEDDR AFGLNLLKPE DGKNTRQWQW LDSKDTASVL YISFGSLAIL QEEQVKELAY  300
FLKDTNLSFL WVLRDSELQK LPHNFVQETS HRGLVVNWCS QLQVLSHRAV SCFVTHCGWN  360
STLEALSLGV PMVAIPQWVD QTTNAKFVAD VWRVGVRVKK KDERIVTKEE LEASIRQVVQ  420
GEGRNEFKHN AIKWKKLAKE AVDEGGSSDK NIEEFVKTIA                        460

SEQ ID NO: 109          moltype = DNA  length = 1425
FEATURE                 Location/Qualifiers
source                  1..1425
                        mol_type = other DNA
                        organism = synthetic construct
SEQUENCE: 109
atgtggacca tcttcctggg cttcgtgacc ctgaccatcg tgtactacat ctactggacc  60
aacaagtgga aggactccaa gttcaaccgc gtgctgccgc cgggcaccat gggcctcccg  120
ctgatcggcg aaaccctgca gttcctgagg ccgtcctact ccctggacct gcacccgttc  180
ttccagacca aggtgaagag gtacggcccg atcttcaaga cctgcctggc cggcaggccg  240
gtggtggtgt ccaccgacgc cgagttcaac cactacatca tgctgcagga gggcaaggcc  300
gtggagatgt ggtacctgga cgccttctcc aagttcttcg gcctggacac cgagtggacc  360
aaggccctgg gcctgatcca caagtacatc aggtccatca ccctgaacca ctacggcgtg  420
gagtccctga gggagaggtt cctgccgagg atcgaggagt ccgtgaggga aaccctgcac  480
tactgggcca cccagccgtc cgtggaggtg aaggactccg ccgccgccat ggtgctgaag  540
acctccgtga tcaagctgtt ctccgaggac tccaacaagc tgctgtccgg cggcctgctg  600
aagaagttca ccaagctgct gggcggcttc ctgaccctgc cgctgaacct gccgggcacc  660
acctaccaca ggtgcatcaa ggacatgaag gagatccaga agaagctgaa ggagatcctg  720
gaggagaggc tggccagggg caacggctcc gacgaggact tcctgggcca ggtgatcaag  780
gacaaggagt cccagaagtt catctccgag gagttcatca tccagctgct gttctccatg  840
tccttcgcca ccttcgagtc catctccgcc tccctgaccc tgatcctgat cctgctggcc  900
gaccacccgg aggtggccaa ggagctggag gtggagcacg aggccatcag gaaggcgcgc  960
gtggacccgg acggcctgat cacctgggag gagtacaagt ccatgacctt cacccacaac  1020
gtgatctacg aaaccctgcg cctgggctcc gtgatcccgt ccctgccccg gaagaccacc  1080
aaggagatcc agatcaaggg ctacaccatc ccggagggct ggaccatcat gctggtgatc  1140
gcctcccggc accgaaaccc gaaggtgtac aaggacccgg acaccttcaa cccgtggcgg  1200
tggaaggagc tggactccat caccatccag aagaacttca tgccgttcgg cggcggcctg  1260
cgccactgcg ccggcgccga gtacaccaag gtgtacctgt gcaccttcct gcacatcctg  1320
ttcaccaagt accgctggac caagctgaag ggcggcaaga tcgcccgcgc cctgatcctc  1380
aagttcgtgg acggcctgca cgtcaacttc accccgaagg agtga                  1425

SEQ ID NO: 110          moltype = AA  length = 474
FEATURE                 Location/Qualifiers
```

```
source                  1..474
                        mol_type = protein
                        organism = Citrullus lanatus
SEQUENCE: 110
MWTIFLGFVT LTIVYYIYWT NKWKDSKFNR VLPPGTMGLP LIGETLQFLR PSYSLDLHPF  60
FQTKVKRYGP IFKTCLAGRP VVVSTDAEFN HYIMLQEGKA VEMWYLDAFS KFFGLDTEWT  120
KALGLIHKYI RSITLNHYGV ESLRERFLPR IEESVRETLH YWATQPSVEV KDSAAAMVLK  180
TSVIKLFSED SNKLLSGGLL KKFTKLLGGF LTLPLNLPGT TYHRCIKDMK EIQKKLKEIL  240
EERLARGNGS DEDFLGQVIK DKESQKFISE EFIIQLLFSM SFATFESISA SLTLILILLA  300
DHPEVAKELE VEHEAIRKAR VDPDGLITWE EYKSMTFTHN VIYETLRLGS VIPSLPRKTT  360
KEIQIKGYTI PEGWTIMLVI ASRHRNPKVY KDPDTFNPWR WKELDSITIQ KNFMPFGGGL  420
RHCAGAEYTK VYLCTFLHIL FTKYRWTKLK GGKIARALIL KFVDGLHVNF TPKE        474

SEQ ID NO: 111          moltype = DNA  length = 1422
FEATURE                 Location/Qualifiers
source                  1..1422
                        mol_type = other DNA
                        organism = synthetic construct
SEQUENCE: 111
atgtggacca tcctgctggg cctggccacc ctggccatcg cctactacat ccactgggtg  60
aacaagtgga aggactccaa gttcaacggc gtgctgccgc cgggcaccat gggcctgccg  120
ctgatcggcg aaaccctgca gttcctgagg ccgtccgact ccctggacgt gcacccgttc  180
ttccagagga aggtgaagag gtacggcccg atcttcaaga cctgcctggc cggcaggccg  240
gtggtggtgt ccaccgacgc cgagttcaac cactacatca tgctgcagga gggcagggcc  300
gtggagatgt ggtacctgga caccctgtcc aagttcttcg gcctggacac cgagtggacc  360
aaggccctgg gcctgatcca caagtacatc aggtccatca ccctgaacca cttcggcgcc  420
gagtccctga gggagaggtt cctgccgagg atcgaggagt ccgccaggga aaccctgcac  480
tactggtcca cccagacctc cgtggaggtg aaggagtccg ccgccgccat ggtgttcagg  540
acctccatcg tgaagatgtt ctccgaggac tcctccaagc tgaccgaggg cctgaccaag  600
aagttcaccg gcctgctggg cggcttcctg accctgccgc tgaacctgcc gggcaccacc  660
taccacaagt gcatcaagga catgaagcag atccagaaga agctgaagga catcctggag  720
gagaggctgg ccaagggcgt gaagatcgac gaggacttcc tgggccaggc catcaaggac  780
aaggagtccc agcagttcat ctccgaggag ttcatcatcc agctgctgtt ctccatctcc  840
ttcgcctcct tcgagtccat ctccaccacc ctgaccctga tcctgaactt cctggccgac  900
cacccggacg tggtgaagga gctggaggcc gagcacgagg ccatcaggaa ggccagggcc  960
gacccggacg gcccgatcac ctgggaggag tacaagtcca tgaacttcac cctgaacgtg  1020
atctacgaaa ccctgaggct gggctccgtg atcccggccc tgccgaggaa gaccaccaag  1080
gagatccaga tcaagggcta caccatcccg gagggctgga ccgtgatgct ggtgaccgcc  1140
tccaggcaca gggacccgga ggtgtacaag gacccggaca ccttcaaccc gtggaggtgg  1200
aaggagctgg actccatcac catccagaag aacttcatgc cgttcggcgg cggcctgagg  1260
cactgcgccg gcgccgagta ctccaaggtg tacctgtgca ccttcctgca catcctgttc  1320
accaagtaca ggtggaggaa gctgaagggc ggcaagatcg ccagggccca catcctgagg  1380
ttcgaggacg gcctgtacgt gaacttcacc ccgaaggagt ga                    1422

SEQ ID NO: 112          moltype = AA  length = 473
FEATURE                 Location/Qualifiers
source                  1..473
                        mol_type = protein
                        organism = Siraitia grosvenorii
SEQUENCE: 112
MWTILLGLAT LAIAYYIHWV NKWKDSKFNG VLPPGTMGLP LIGETLQFLR PSDSLDVHPF  60
FQRKVKRYGP IFKTCLAGRP VVVSTDAEFN HYIMLQEGRA VEMWYLDTLS KFFGLDTEWT  120
KALGLIHKYI RSITLNHFGA ESLRERFLPR IEESARETLH YWSTQTSVEV KESAAAMVFR  180
TSIVKMFSED SSKLTEGLTK KFTGLLGGFL TLPLNLPGTT YHKCIKDMKQ IQKKLKDILE  240
ERLAKGVKID EDFLGQAIKD KESQQFISEE FIIQLLFSIS FASFESISTT LTLILNFLAD  300
HPDVVKELEA EHEAIRKARA DPDGPITWEE YKSMNFTLNV IYETLRLGSV IPALPRKTTK  360
EIQIKGYTIP EGWTVMLVTA SRHRDPEVYK DPDTFNPWRW KELDSITIQK NFMPFGGGLR  420
HCAGAEYSKV YLCTFLHILF TKYRWRKLKG GKIARAHILR FEDGLYVNFT PKE         473

SEQ ID NO: 113          moltype = DNA  length = 1401
FEATURE                 Location/Qualifiers
source                  1..1401
                        mol_type = other DNA
                        organism = synthetic construct
SEQUENCE: 113
atggctgatg atcagctcca tatttttttc tttccattga tggcgcacgg ccacataatt  60
cctactttgg atatggcgaa gttgttcgtt tcacatggtg caaaggcaac tattatcacc  120
actcctctga acttacccat cttcgttcaa tccagtgaaa aaatcaaaca tttggggctg  180
gaaatttatg tcaaagctat cagattccca gcagtggaag ctggtttgcc tgaaggatgt  240
gaaagaatgg atcaattgac ttctgatgat ttggtaccca aattcttcaa ggccaccacc  300
atgcttcaac aacaactaga gctattactc catgaatgtc aacccaacgc tctcgttgct  360
gacatgttct tcccctgggc tacagaatct gctgccaaat ttgatatccc aagattggta  420
tttcatggga tgggcttctt tgcgctttgt gctttggaga accttaggca ttacaagcct  480
cagaagaatg tgtgttcgga tacagaacct ttcgttgtcc cgaatcttcc ccataaggta  540
aagctcacaa ggatgaaatt agctccgtat gatcgagaag aaacagaaat gactaagttt  600
attgaacaag tgaagggatc cgagttcaca agttttgggg ttattgtcaa tagcttctat  660
gagcttgaac cagattatgc tgattactac agaaaggttt tgggtaaaag atcatggcac  720
gttggaccct tttgctctg caacagaaaa aacgaagaaa aaatccacaa aagcgatgat  780
aaacatcatg agtgcttgca atggctggac acgaagaaac aaaattcagt aatctatgtt  840
```

```
tgtttcggga gcatgtctaa ctttactgat tcccaaatcg aagaaattgc attaggcctc  900
gaagcttcag agcaagaatt catatgggta attaggaaag gcaagattcc agaaggattc  960
gaagagcgaa caaaagaaaa aggattcatc ataagaggat gggcacccca aacgctgatt  1020
cttgatcacg aggctatagg agccttttta actcactgtg gatggaattc gacacttgaa  1080
ggcgtatcag caggggttcc aatggtgact tggcctatat ttgcagagca attcttgaat  1140
gagcaattga taactaaagt actacaaata ggagtggcag ttggggcaga ggaatggagc  1200
atagtggtgg ataatgtgaa aagtgaagca attacaaagg cagtgaagtg tgtaatggct  1260
ggggaagaat caatggaaat gaggaggaga gcagaagaag ttaagaaaat ggcgaacaag  1320
gctgttgaag aaggtggatc atcttacagt gatttgaatg cactgtttca agaactaaga  1380
accattaatt tgcacaacta a                                            1401

SEQ ID NO: 114         moltype = AA  length = 466
FEATURE                Location/Qualifiers
source                 1..466
                       mol_type = protein
                       organism = Solanum lycopersicum
SEQUENCE: 114
MADDQLHIFF FPLMAHGHII PTLDMAKLFV SHGAKATIIT TPLNLPIFVQ SSEKIKHLGL  60
EIYVKAIRFP AVEAGLPEGC ERMDQLTSDD LVPKFFKATT MLQQQLELLL HECQPNALVA  120
DMFFPWATES AAKFDIPRLV FHGMGFFALC ALENLRHYKP QKNVCSDTEP FVVPNLPHKV  180
KLTRMKLAPY DREETEMTKF IEQVKGSEFT SFGVIVNSFY ELEPDYADYY RKVLGKRSWH  240
VGPFLLCNRK NEEKIHKSDD KHHECLQWLD TKKQNSVIYV CFGSMSNFTD SQIEEIALGL  300
EASEQEFIWV IRKGKIPEGF EERTKEKGFI IRGWAPQTLI LDHEAIGAFL THCGWNSTLE  360
GVSAGVPMVT WPIFAEQFLN EQLITKVLQI GVAVGAEEWS IVVDNVKSEA ITKAVKCVMA  420
GEESMEMRRR AEEVKKMANK AVEEGGSSYS DLNALFQELR TINLHN                 466

SEQ ID NO: 115         moltype = DNA  length = 1440
FEATURE                Location/Qualifiers
source                 1..1440
                       mol_type = other DNA
                       organism = synthetic construct
SEQUENCE: 115
atggagaatg aaaaagataa acttcatgtt gtgatgtttc catggctagc catgggacat  60
atcatacctt tttttcatct atcaaagtgt ttagcacgaa ggggccatag agtcaccttc  120
atttcaactc caagaaacat tgaaagagtc gtcaataaag ttccctctga tcttgctcat  180
ctgttgcata ttgtgtggtt tcaattgcct aaagttgaaa acttgccgga tgatgcagag  240
tcatcgatgg atattcctta ccaaaaagct cagttcttga agatagcttt cgattcgctc  300
gaaatcccac tgaccaatta tcttgagagt tcatcaaatc ccaaaccaga ttggattgtc  360
tatgactatg cttctcactg gctacctcaa attgcaggta aattaggcgt ttctcgcgcc  420
ttttttagtc tgtttactgc tgcaaccatg tcattttatg gacctccttg tgctttgtta  480
aatgatgaaa ggtcaatagc tgaggactat acagttgttc caaaatggat tcctttcgaa  540
acgaaagttg tgtataggct gcatgagatt aagaagaatt tcgaagcacc agctgatgaa  600
tcaggtacat ctgatggagc cagatttggt gcttcaattg atgcaagtga tgtcatattg  660
tttcgaaatt gtgttgagtt tgaatccgaa tggttcagct tggtttctga gctttatcag  720
aaacctatta tatccattgg tgtgctacct ccatctgttg tagttgatca agaacaagat  780
gacagcaatg atgcgtcgtg gtcaggaatc aagagttggc tagataagca caatcaagat  840
tctgttgttt atgttgcact tggaactgaa gcaacactga atcaacaaga gctgaatgag  900
ctagctttgg ggttagaaaa atgcggatta ccattcgttt gggtattaag agatcagcca  960
aaacataatc aacaagattc gtgtattcag ctgcctgatg gatacgaaga cagagtcaaa  1020
aacagaggtg taatatacaa aggatgggta ccacagacga agatactgag tcattcgtca  1080
gtaggtggat tcttgactca ttgtggatgg aattcggtca tagaagcgct atgttttggg  1140
cgggttttgg ttatgttccc ggtgttgaat gatcaaggat tgaatacaag gttgttgcaa  1200
gagaaaggag ttggtgtaga gataccaaga aatgaaaaag atggattttt cactagtgat  1260
tcagtggctg aagctgtgaa gtttggtgta gtgagtgaag agggtgagtt gttgagagct  1320
aatgcaagac aaatgagttg tttgtttgga gataggaaga gaaatgaaca acttattgat  1380
gattgtgttg gttatttcat ggaaaatagg ataagcaaat ctaatagctc catcggttga  1440

SEQ ID NO: 116         moltype = AA  length = 479
FEATURE                Location/Qualifiers
source                 1..479
                       mol_type = protein
                       organism = Solanum lycopersicum
SEQUENCE: 116
MENEKDKLHV VMFPWLAMGH IIPFFHLSKC LARRGHRVTF ISTPRNIERV VNKVPSDLAH  60
LLHIVWFQLP KVENLPDDAE SSMDIPYQKA QFLKIAFDSL EIPLTNYLES SSNPKPDWIV  120
YDYASHWLPQ IAGKLGVSRA FFSLFTAATM SFYGPPCALL NDERSIAEDY TVVPKWIPFE  180
TKVVYRLHEI KKNFEAPADE SGTSDGARFG ASIDASDVIL FRNCVEFESE WFSLVSELYQ  240
KPIISIGVLP PSVVVDQEQD DSNDASWSGI KSWLDKHNQD SVVYVALGTE ATLNQQELNE  300
LALGLEKCGL PFVWVLRDQP KHNQQDSCIQ LPDGYEDRVK NRGVIYKGWV PQTKILSHSS  360
VGGFLTHCGW NSVIEALCFG RVLVMFPVLN DQGLNTRLLQ EKGVGVEIPR NEKDGFFTSD  420
SVAEAVKFGV VSEEGELLRA NARQMSCLFG DRKRNEQLID DCVGYFMENR ISKSNSSIG   479

SEQ ID NO: 117         moltype = DNA  length = 1413
FEATURE                Location/Qualifiers
source                 1..1413
                       mol_type = other DNA
                       organism = synthetic construct
SEQUENCE: 117
atggtgcaac cccatgtcct attggtgaca tttcctgcac aaggtcatat caatccatct  60
```

```
cttcaatttg ccaagaggct aatcgaaatg ggcattgagg tgacattcac cactagtgtt  120
ttcgcccacc gtcgtatggc gaaaatcgcg gcttccacgg cacccaaggg cttaaacttg  180
gcggcattct ctgatggatt tgatgatggt ttcaagtcta acgtggatga ttctaaacgt  240
tacatgtcag agataagaag tcgtgggtcc caaacattga gggatgtcat tttgaagagt  300
tcagacgaag gacgtcctgt cacgtccctc gtctacactc ttctgctacc ttgggcagct  360
gaggtagcgc gtgaactcca tatcccatcc gcgttactat ggattcaacc agcaactgtg  420
ctagacatat actactatta cttcaatggc tatgaggatg aaatgaagtg tagtagctca  480
aatgatccaa attggagtat ccaattgcca aggcttccat tactaaaaag ccaagatctt  540
ccatcttttt tagtttcatc tagctcaaaa gatgataagt atagttttgc tctaccaaca  600
ttcaaagagc aactagacac attagatggt gaagaaaatc caaaggtact tgtgaataca  660
tttgatgcat tagagctaga gccactcaaa gctattgaaa aatacaattt aattggaatt  720
ggaccattga ttccttcatc attcttgggt ggaaaagatt cattggaatc ttcatttggt  780
ggtgatcttt ttcaaaagtc aaatgatgac tacatggaat ggttaaacac aaagcctaaa  840
tcatcaattg tttatatctc atttgggagt ctattgaatt tatcaagaaa ccaaaaggag  900
gagattgcaa aagggttgat agagatccaa aggccattct tatgggtaat aagagatcaa  960
gaagaagaaa aagaagaaga gaaattaagt tgcatgatgg aattagagaa gcaagggaaa  1020
atagtaccat ggtgttcaca acttgaagtc ctgacacatc catctttagg atgttttgtc  1080
tcgcactgtg gatggaattc gactctagaa agcctatcgt caggtgtacc tgtggtggca  1140
tttcctcatt ggacagatca aggactaat gcaaagttga ttgaagatgt ttggaagaca  1200
ggtgtcagga tgagagtgaa tgaagatggt gtggttgaga gtgatgaaat aaaaaggtgc  1260
atagaaattg taatggatgg tggagaaaaa ggagaagaaa tgagaaaaaa tgcacaaaaa  1320
tggaaagaat tggcaagagc agctgtgaaa gaaggtggat cttcagaagt gaatctaaaa  1380
gcttttgttc tacaagttag caaaagttgt tga                               1413

SEQ ID NO: 118          moltype = AA  length = 470
FEATURE                 Location/Qualifiers
source                  1..470
                        mol_type = protein
                        organism = Solanum lycopersicum
SEQUENCE: 118
MVQPHVLLVT FPAQGHINPS LQFAKRLIEM GIEVTFTTSV FAHRRMAKIA ASTAPKGLNL  60
AAFSDGFDDG FKSNVDDSKR YMSEIRSRGS QTLRDVILKS SDEGRPVTSL VYTLLLPWAA  120
EVARELHIPS ALLWIQPATV LDIYYYYFNG YEDEMKCSSS NDPNWSIQLP RLPLLKSQDL  180
PSFLVSSSSK DDKYSFALPT FKEQLDTLDG EENPKVLVNT FDALELEPLK AIEKYNLIGI  240
GPLIPSSFLG GKDSLESSFG GDLFQKSNDD YMEWLNTKPK SSIVYISFGS LLNLSRNQKE  300
EIAKGLIEIQ RPFLWVIRDQ EEEKEEEKLS CMMELEKQGK IVPWCSQLEV LTHPSLGCFV  360
SHCGWNSTLE SLSSGVPVVA FPHWTDQGTN AKLIEDVWKT GVRMRVNEDG VVESDEIKRC  420
IEIVMDGGEK GEEMRKNAQK WKELARAAVK EGGSSEVNLK AFVLQVSKSC             470

SEQ ID NO: 119          moltype = DNA  length = 1428
FEATURE                 Location/Qualifiers
source                  1..1428
                        mol_type = other DNA
                        organism = synthetic construct
SEQUENCE: 119
atgaaaatag aaagaaaaca gagtgtagta ctggtgccac acccatacca ggggcattta  60
acaccaatgc tacagcttgg tagtatcctt cattcacaag gcttttctgt tatagttgca  120
catactcaat acaatactcc taattattcc aatcatccac aattcgtctt ccattctatg  180
gatgacggat tacagggaat cgacatgtca ttcccgagtt tagaaaacat atatgatatg  240
aacgaaaact gcaaggcgcc tctcagaaac taccttgtta gtatgatgga agaggaaggt  300
gatcagcttg cttgtatcgt ttatgacaac gtcatgttct ttgtcgatga tgtagcgact  360
cagttgaagc ttcccagcat tgtcctgcgc actttcagcg ctgcgtattt gcactctatg  420
atcaccattt tacagcaacc tgaaatatat ttaccttttg aagattctca gctgctggat  480
ccgttaccgg agcttcatcc cttgagattt aaggatgtac cgtttcctat catcaataat  540
acagttccag aaccgatact agacttctgt agagcaatga gtgatatagg atcatctgtc  600
gcgactatat ggaacacgat gcaagacttg gagagttcaa tgttgttacg ccttcaagaa  660
cattacaagg tgcccttttt tccaataggc ccggtacaca aaatggcatc tttggtgtca  720
tcgactagca tactagaaga agacaatagc tgcatcgagt ggctcgatag acaagcccct  780
aactctgttc tctatgtcag cttgggtagc ctagtgagga ttgatcacaa agagttgatt  840
gagactgctt ggggattagc taatagcgat caaccgttct tgtgggttat tcgacctggc  900
tctgtctctg gctttcaatg tgctgaggca ctgcctgatg gttttgagaa aatggtagga  960
gaaagaggac gaatagtgaa atgggcacca caaaaacagg tgcttgcaca tcccgcggta  1020
gcagggtttt tcactcattg tggttggaat tctacgcttg aaagtatatg tgaagaagtc  1080
cctatggtgt gcaggccatt tctagcagac caactggtga acgcaaggta tctgagccaa  1140
atatacaagg ttgggttcga attggaggtt atcgagagaa cggtcataga gaaaacaata  1200
agaaaactca tgttaagtga agaaggcaaa gatgtgaaga aaagagtagc agacatgaaa  1260
caaaagatag ttgctggaat gcagattgat tgcacttcac ataagaatct gaatgatttg  1320
gtagacttca tttctgcctt gccatcacga ctcgctccgc caacgcctgt ctttggggca  1380
atcatgagct caaaccacat agcaagcaag tgtatcatag agtcttga               1428

SEQ ID NO: 120          moltype = AA  length = 475
FEATURE                 Location/Qualifiers
source                  1..475
                        mol_type = protein
                        organism = Solanum lycopersicum
SEQUENCE: 120
MKIERKQSVV LVPHPYQGHL TPMLQLGSIL HSQGFSVIVA HTQYNTPNYS NHPQFVFHSM  60
DDGLQGIDMS FPSLENIYDM NENCKAPLRN YLVSMMEEEG DQLACIVYDN VMFFVDDVAT  120
QLKLPSIVLR TFSAAYLHSM ITILQQPEIY LPFEDSQLLD PLPELHPLRF KDVPFPIINN  180
```

```
TVPEPILDFC RAMSDIGSSV ATIWNTMQDL ESSMLLRLQE HYKVPFFPIG PVHKMASLVS  240
STSILEEDNS CIEWLDRQAP NSVLYVSLGS LVRIDHKELI ETAWGLANSD QPFLWVIRPG  300
SVSGFQCAEA LPDGFEKMVG ERGRIVKWAP QKQVLAHPAV AGFFTHCGWN STLESICEEV  360
PMVCRPFLAD QLVNARYLSQ IYKVGFELEV IERTVIEKTI RKLMLSEEGK DVKKRVADMK  420
QKIVAGMQID CTSHKNLNDL VDFISALPSR LAPPTPVFGA IMSSNHIASK CIIES       475

SEQ ID NO: 121          moltype = DNA  length = 1476
FEATURE                 Location/Qualifiers
source                  1..1476
                        mol_type = other DNA
                        organism = synthetic construct
SEQUENCE: 121
atgggtgttc ttactataga gccacatttt gtgttgtttc ctttcatggc acaaggccat  60
acaatcccta tgattgatat tgcgcgatta ctatcacaac gcggagttat tatcacaatc  120
gttacaacac atttgaacgc gaatagattc aagaaagtca ttgatcgcgc tatagaatca  180
ggactgaaaa ttcaggtggt tcatctctac tttccaagct tagaggctgg actgcctgaa  240
ggatgtgaaa atttcgacat gcttccatcg atggatttgg ggctgaaatt cttcgatgct  300
acggaaagac ttcagcccca agtggaagaa atgttgcgag aaatgaaacc ttcaccaagt  360
tgtataatat ctgatatgtg tttcccatgg acaactaatg ttgcacaaaa gttcaacatt  420
cctagaattg ttttccatgg aatgggttgc ttttctttgt tatgtttaca taatttgaaa  480
gattgggaag ggttagaaaa gatcgagtct gatacagagt attttcgagt gcctggattg  540
ttcgacaaga ttgaactaac caaaaatcag cttggaaatg ctgccaggcc gagaaatgaa  600
gagtggcgag taatgagtga aaaaatgaag aaagcggagg aggaagctta tggaatggtg  660
gtgaatacct ttgaggattt ggaaaaagaa tacatcgagg gtttaatgaa tgcgaaaaac  720
aagaaaattt ggaccattgg ccctgtttca ctctgtaaca aagaaaaaca ggacaaagct  780
gaaagaggga acgaggctgc aattgatgaa cacaagtgtc taaactggct tgattcgtgg  840
gaacaaaact ctgtactctt tgtatgtctc gggagcctat cgcgcctttc cacgtctcag  900
atggttgagc tagggcttgg gttagaatca tcgagacgac cctttatttg ggttgttaga  960
cacatgtcag atgagttcaa gaattggcta gttgaagaag attttgagga aagagttaaa  1020
gggcaaggac tattaatccg cggttgggcg ccacaagtac tactcttgtc acatccttca  1080
ataggtgcgt tcttgactca ctgtggatgg aattcgagcc tggaaggtat aaccgctggc  1140
gtggccatga tcacttggcc aatgtttgct gagcagtttt gtaatgagag gttaatagtg  1200
gatgtactca agacaggagt gaggtcaggc atagagaggc aagtgatgtt tggagaagaa  1260
gaaaaattgg gaacacaagt aagcaaagat gacattaaga aggtgattga acaagtgatg  1320
gatgaagaaa tggaaggtga aatgagaaga aaaagagcaa aagaattagg agaaaaggca  1380
aagagggcta tggaggaaga gggttcatct catttcaact tgacacaatt gattcaagat  1440
gtgacagagc aagcaaaaat tttaaaacct atgtag                            1476

SEQ ID NO: 122          moltype = AA  length = 491
FEATURE                 Location/Qualifiers
source                  1..491
                        mol_type = protein
                        organism = Solanum lycopersicum
SEQUENCE: 122
MGVLTIEPHF VLFPFMAQGH TIPMIDIARL LSQRGVIITI VTTHLNANRF KKVIDRAIES  60
GLKIQVVHLY FPSLEAGLPE GCENFDMLPS MDLGLKFFDA TERLQPQVEE MLREMKPSPS  120
CIISDMCFPW TTNVAQKFNI PRIVFHGMGC FSLLCLHNLK DWEGLEKIES DTEYFRVPGL  180
FDKIELTKNQ LGNAARPRNE EWRVMSEKMK KAEEEAYGMV VNTFEDLEKE YIEGLMNAKN  240
KKIWTIGPVS LCNKEKQDKA ERGNEAAIDE HKCLNWLDSW EQNSVLFVCL GSLSRLSTSQ  300
MVELGLGLES SRRPFIWVVR HMSDEFKNWL VEEDFEERVK GQGLLIRGWA PQVLLLSHPS  360
IGAFLTHCGW NSSLEGITAG VAMITWPMFA EQFCNERLIV DVLKTGVRSG IERQVMFGEE  420
EKLGTQVSKD DIKKVIEQVM DEEMEGEMRR KRAKELGEKA KRAMEEEGSS HFNLTQLIQD  480
VTEQAKILKP M                                                        491

SEQ ID NO: 123          moltype = DNA  length = 1359
FEATURE                 Location/Qualifiers
source                  1..1359
                        mol_type = other DNA
                        organism = synthetic construct
SEQUENCE: 123
atggatgctg cccaacaagg tgacaccaca accattttga tgcttccatg gctcggctat  60
ggccatcttt cagcttttct cgagctggcc aaaagcctct caaggaggaa cttccatatc  120
tacttctgtt caacctctgt taatcttgac gccattaaac caaagcttcc ttcttctttc  180
tctgattcca ttcaatttgt ggagctccat ctcccttctt ctcctgagtt ccctcctcat  240
cttcacacaa ccaacggcct tccccctacc ctcatgcccg ctctccacca agccttctcc  300
atggctgccc agcactttga gtccatttta caaacacttg ccccgcacct tctcatttat  360
gactctcttc aaccttgggc tcctcgggta gcttcatccc tcaaaattcc ggccatcaac  420
ttcaatacca cgggagtttt cgtcatttct caagggcttc accctattca ctacccacat  480
tctaaattcc cattctcaga gttcgttctt cacaatcatt ggaaagccat gtactccact  540
gccgatggag cttctaccga aagaacccgc aaacgtggag aagcgtttct gtattgcttg  600
catgcttctt gtagtgtaat tctaatcaat agtttcagag agctcgaggg gaaatatatg  660
gattatctct ctgttctctt gaacaagaaa gttgttccgg ttggtccttt ggtttacgaa  720
ccgaatcaag acggggaaga tgaaggttat tcaagcatca aaaattggct tgacaaaaag  780
gaaccgtcct ccaccgtctt cgtgtcattt ggaagcgaat acttcccgtc aaaggaagaa  840
atggaagaga tagcccatgg gttagaggcg agcgaggtta atttcatctg ggtcgttagg  900
tttcctcaag gagacaacac cagcggcatt gaagatgcct tgccgaaggg ttttctggag  960
agggcgggag agagagggat ggtggtgaag ggttgggctc ctcaggcgaa gatactgaag  1020
cattggagca caggggggatt cgtgagccac tgtggatgga actcggtgat ggagagcatg  1080
atgtttggcg ttcccataat aggggttccg atgcatgtgg accagccctt taacgccgga  1140
```

```
ctcgtggaag aagctggcgt cggcgtggag gccaagcgag atccagacgg caaaattcaa  1200
agagacgaag ttgcaaagtt gatcaaagaa gtggtggttg agaaaaccag agaagatgtg  1260
cggaagaaag caagagaaat gagtgagatt ttgaggagca agggagagga gaagtttgat  1320
gagatggtcg ctgaaatttc tctcttgctt aaaatataa                        1359

SEQ ID NO: 124          moltype = AA  length = 452
FEATURE                 Location/Qualifiers
source                  1..452
                        mol_type = protein
                        organism = Siraitia grosvenorii
SEQUENCE: 124
MDAAQQGDTT TILMLPWLGY GHLSAFLELA KSLSRRNFHI YFCSTSVNLD AIKPKLPSSF  60
SDSIQFVELH LPSSPEFPPH LHTTNGLPPT LMPALHQAFS MAAQHFESIL QTLAPHLLIY  120
DSLQPWAPRV ASSLKIPAIN FNTTGVFVIS QGLHPIHYPH SKFPFSEFVL HNHWKAMYST  180
ADGASTERTR KRGEAFLYCL HASCSVILIN SFRELEGKYM DYLSVLLNKK VVPVGPLVYE  240
PNQDGEDEGY SSIKNWLDKK EPSSTVFVSF GSEYFPSKEE MEEIAHGLEA SEVNFIWVVR  300
FPQGDNTSGI EDALPKGFLE RAGERGMVVK GWAPQAKILK HWSTGGFVSH CGWNSVMESM  360
MFGVPIIGVP MHVDQPFNAG LVEEAGVGVE AKRDPDGKIQ RDEVAKLIKE VVVEKTREDV  420
RKKAREMSEI LRSKGEEKFD EMVAEISLLL KI                               452

SEQ ID NO: 125          moltype = DNA  length = 906
FEATURE                 Location/Qualifiers
source                  1..906
                        mol_type = other DNA
                        organism = synthetic construct
SEQUENCE: 125
atggcgattt ctctcaatct tcttcaactt caaccaaatc cagcgcggcc caagttcttc  60
aaatggaacc ccgtccgacc ggcggttcat ttcagagctc cggcgaggtt gaccgtcgtc  120
atgtcacaga tcactccgtc gtactgggcg gccataaatg aagatattga ggatcatctc  180
cggcgggtca ttccggcaaa ggacccgccg gcggtgtacg agccgttggg ccattttgtc  240
ttctcggccc cacgaaattc cgctcctgca ctgtgtattg ccgcctgcga gctcgtcggc  300
ggcggccgag atcaggccat tgtggcggct actgcactgc aactcatcca cgctgcaacc  360
tatactcggg aataccctcc actgacggca cgtgaaatct cacgcgccgc cgtcgttgac  420
cgcgtttatg gccccaacat ccagctgttg acaggggacg gaatagcacc gatggtgttc  480
gagattctag cgggatcttg cgattggagc gagagcgggt cggagcggat tcgacgcgtg  540
atggtggaaa tggcacgtgc gatgggtacg gaagggtgga ttgggggcca atttcgggga  600
ttggaggaga cggcaacggc ggaggaagtg agcgagaaga cggaaggtgg gctacacgcg  660
tgtgggggcg cgtgtggggt gatattggga ggtggaaatg aagaggaaat agagaagatg  720
aggaaatatg ggaaattggt ggggatggtg aaaggaatgt caaaaaatgt gtttggaggg  780
aaagaaaatg agagaaagaa agagaaaatt gaggagttga agtatttggc tttcaaggaa  840
ttgaaagatt tcaaaggaga aaatgttcat gagatctatg gattccttga ttttgaggga  900
ctttag                                                            906

SEQ ID NO: 126          moltype = AA  length = 301
FEATURE                 Location/Qualifiers
source                  1..301
                        mol_type = protein
                        organism = Citrullus lanatus
SEQUENCE: 126
MAISLNLLQL QPNPARPKFF KWNPVRPAVH FRAPARLTVV MSQITPSYWA AINEDIEDHL  60
RRVIPAKDPP AVYEPLGHFV FSAPRNSAPA LCIAACELVG GGRDQAIVAA TALQLIHAAT  120
YTREYPPLTA REISRAAVVD RVYGPNIQLL TGDGIAPMVF EILAGSCDWS ESGSERIRRV  180
MVEMARAMGT EGWIGGQFRG LEETATAEEV SEKTEGGLHA CGGACGVILG GGNEEEIEKM  240
RKYGKLVGMV KGMSKNVFGG KENERKKEKI EELKYLAFKE LKDFKGENVH EIYGFLDFEG  300
L                                                                 301

SEQ ID NO: 127          moltype = DNA  length = 1461
FEATURE                 Location/Qualifiers
source                  1..1461
                        mol_type = other DNA
                        organism = synthetic construct
SEQUENCE: 127
atgggcgaca acggcgacgg cggcgagaag aaggagctga aggagaacgt gaagaagggc  60
aaggagctgg gcaggcaggc catcggcgag ggctacatca acccgagcct gcagctggcc  120
aggaggctga tcagcctggg cgtgaacgtg accttcgcca ccaccgtgct ggccggcagg  180
aggatgaaga acaagaccca ccagaccgcc accaccccgg gcctgagctt cgccaccttc  240
agcgacggct tcgacgacga aaccctgaag ccgaacggcg acctgaccca ctacttcagc  300
gagctgagga ggtgcggcag cgagagcctg acccacctga tcaccagcgc cgccaacgag  360
ggcaggccga tcaccttcgt gatctacagc ctgctgctga gctgggccgc cgacatcgcc  420
agcacctacg acatcccgag cgccctgttc ttcgcccagc cggccaccgt gctggccctg  480
tacttctact acttccacgg ctacggcgac accatctgca gcaagctgca ggacccgagc  540
agctacatcg agctgccggg cctgccgctg ctgaccagcc aggacatgcc gagcttcttc  600
agcccgagcg gcccgcacgc cttcatcctg ccgccgatga gggagcaggc cgagttcctg  660
ggcaggcaga gccagccgaa ggtgctggtg aacaccttcg acgccctgga ggccgacgcc  720
ctgagggcca tcgacaagct gaagatgctg gccatcggcc cgctgatccc gagcgccctg  780
ctgggcggca acgacagcag cgacgccagc ttctgcggcg acctgttcca ggtgagcagc  840
gaggactaca tcgagtggct gaacagcaag ccggacagca gcgtggtgta catcagcgtg  900
ggcagcatct gcgtgctgag cgacgagcag gaggacgagc tggtgcacgc cctgctgaac  960
agcggccaca ccttcctgtg ggtgaagagg agcaaggaga acaacgaggg cgtgaagcag  1020
```

```
gaaaccgacg aggagaagct gaagaagctg gaggagcagg gcaagatggt gagctggtgc  1080
aggcaagtgg aggtgctgaa gcacccggcc ctgggctgct tcctgaccca ctgcggctgg  1140
aacagcacca tcgagagcct ggtgagcggc ctgccggtgg tggccttccc gcagcagatc  1200
gaccaggcca ccaacgccaa gctgatcgag gacgtgtgga agaccggcgt gagggtgaag  1260
gccaacaccg agggcatcgt ggagagggag gagatcagga ggtgcctgga cctggtgatg  1320
ggcagcaggg acggccagaa ggaggagatc gagaggaacg ccaagaagtg gaaggagctg  1380
gccaggcagg ccatcggcga gggcggcagc agcgacagca acctgaagac cttcctgtgg  1440
gagatcgacc tggagatcta a                                          1461

SEQ ID NO: 128         moltype = AA  length = 486
FEATURE                Location/Qualifiers
source                 1..486
                       mol_type = protein
                       organism = Siraitia grosvenorii
SEQUENCE: 128
MGDNGDGGEK KELKENVKKG KELGRQAIGE GYINPSLQLA RRLISLGVNV TFATTVLAGR  60
RMKNKTHQTA TTPGLSFATF SDGFDDETLK PNGDLTHYFS ELRRCGSESL THLITSAANE  120
GRPITFVIYS LLLSWAADIA STYDIPSALF FAQPATVLAL YFYYFHGYGD TICSKLQDPS  180
SYIELPGLPL LTSQDMPSFF SPSGPHAFIL PPMREQAEFL GRQSQPKVLV NTFDALEADA  240
LRAIDKLKML AIGPLIPSAL LGGNDSSDAS FCGDLFQVSS EDYIEWLNSK PDSSVVYISV  300
GSICVLSDEQ EDELVHALLN SGHTFLWVKR SKENNEGVKQ ETDEEKLKKL EEQGKMVSWC  360
RQVEVLKHPA LGCFLTHCGW NSTIESLVSG LPVVAFPQQI DQATNAKLIE DVWKTGVRVK  420
ANTEGIVERE EIRRCLDLVM GSRDGQKEEI ERNAKKWKEL ARQAIGEGGS SDSNLKTFLW  480
EIDLEI                                                           486

SEQ ID NO: 129         moltype = DNA  length = 1362
FEATURE                Location/Qualifiers
source                 1..1362
                       mol_type = other DNA
                       organism = synthetic construct
SEQUENCE: 129
atggagaagg gcgacaccca catcctggtg ttcccgttcc cgagccaggg ccacatcaac  60
ccgctgctgc agctgagcaa gaggctgatc gccaagggca tcaaggtgag cctggtgacc  120
accctgcacg tgagcaacca cctccagctg cagggcgcct acagcaacag cgtgaagatc  180
gaggtgatca gcgacggcag cgaggacagg ctggaaaccg acaccatgag gcagaccctg  240
gacaggttca ggcagaagat gaccaagaac ctggaggact tcctgcagaa ggccatggtg  300
agcagcaacc cgccgaagtt catcctgtac gacagcacca tgccgtgggt gctggaggtg  360
gccaaggagt tcggcctgga cagggccccg ttctacaccc agagctgcgc cctgaacagc  420
atcaactacc acgtgctgca cggccagctg aagctgccgc cggaaacccc gaccatcagc  480
ctgccgagca tgccgctgct gaggccgagc gacctgccgg cctacgactt cgacccggcc  540
agcaccgaca ccatcatcga cctgctgacc agccagtaca gcaacatcca ggacgccaac  600
ctgctgttct gcaacacctt cgacaagctg gagggcgaga tcatccagtg gatggaaacc  660
ctgggcaggc cggtgaagac cgtgggcccg accgtgccga gcgcctacct ggacaagagg  720
gtggagaacg acaagcacta cggcctgagc ctgttcaagc cgaacgagga cgtgtgcctg  780
aagtggctgg acagcaagcc gagcggcagc gtgctgtacg tgagctacgg cagcctggtg  840
gagatgggcg aggagcagct gaaggagctg gccctgggca tcaaggaaac cggcaagttc  900
ttcctgtggg tggtgaggga caccgaggcc gagaagctgc cgccgaactt cgtggagagc  960
gtggccgaga agggcctggt ggtgagctgg tgcagccagc tggaggtgct ggcccacccg  1020
agcgtgggct gcttcttcac ccactgcggc tggaacagca ccctggaggc cctgtgcctg  1080
ggcgtgccgg tggtggcctt cccgcagtgg gccgaccagg tgaccaacgc caagttcctg  1140
gaggacgtgt ggaaggtggg caagagggtg aagaggaacg agcagaggct ggccagcaag  1200
gaggaggtga ggagctgcat ctgggaggtg atggagggcg agagggccag cgagttcaag  1260
agcaacagca tggagtggaa gaagtgggcc aaggaggccg tggacgaggg cggcagcagc  1320
gacaagaaca tcgaggagtt cgtggccatg ctgaagcaga cc                   1362

SEQ ID NO: 130         moltype = AA  length = 454
FEATURE                Location/Qualifiers
source                 1..454
                       mol_type = protein
                       organism = Siraitia grosvenorii
SEQUENCE: 130
MEKGDTHILV FPFPSQGHIN PLLQLSKRLI AKGIKVSLVT TLHVSNHLQL QGAYSNSVKI  60
EVISDGSEDR LETDTMRQTL DRFRQKMTKN LEDFLQKAMV SSNPPKFILY DSTMPWVLEV  120
AKEFGLDRAP FYTQSCALNS INYHVLHGQL KLPPETPTIS LPSMPLLRPS DLPAYDFDPA  180
STDTIIDLLT SQYSNIQDAN LLFCNTFDKL EGEIIQWMET LGRPVKTVGP TVPSAYLDKR  240
VENDKHYGLS LFKPNEDVCL KWLDSKPSGS VLYVSYGSLV EMGEEQLKEL ALGIKETGKF  300
FLWVVRDTEA EKLPPNFVES VAEKGLVVSW CSQLEVLAHP SVGCFFTHCG WNSTLEALCL  360
GVPVVAFPQW ADQVTNAKFL EDVWKVGKRV KRNEQRLASK EEVRSCIWEV MEGERASEFK  420
SNSMEWKKWA KEAVDEGGSS DKNIEEFVAM LKQT                             454

SEQ ID NO: 131         moltype = DNA  length = 1365
FEATURE                Location/Qualifiers
source                 1..1365
                       mol_type = other DNA
                       organism = synthetic construct
SEQUENCE: 131
atggagaagg gcgacaccca catcctggtg ttcccgttcc cggcccaggg ccacatcaac  60
ccgctgctgc agctgagcaa gcacctgatc gccaagggca tcaaggtgag cctggtgacc  120
accctgcacg tgagcaacag gatgcagctg cagggcgcct acagcaacag cgtgaagatc  180
```

```
gaggtgatca gcgacggcag cgaggacagg ctggaaaccg acaccctgag gcagtacctg  240
gacaggttca ggcagaagat gaccaagaac ctggaggact tcctgcagaa ggccatggtg  300
agcagcaacc cgccgaagtt catcatctac gacagcacca tgccgtgggt gctggaggtg  360
gccaaggagt tcggcctgga cagggccccg ttctacaccc agagctgcgc cctgaacagc  420
atcaactacc acgtgctgca cggccagctg aagctgccgc cggaaacccc gaccatcagc  480
ctgccgagca tgccgctgct gaggccgagc gacctgccgg cctacgactt cgacccggcc  540
agcaccgaca ccatcatcga cctgctgacc agccagtaca gcaacatcca ggacgccaac  600
ctgctgttct gcaacacctt cgacaagctg gagggcgaga tcatccagtg gatggaaacc  660
ctgggcaggc cggtgaagac cgtgggcccg accgtgccga gcgcctacct ggacaagagg  720
gtggagaacg acaagcacta cggcctgagc ctgttcaagc cgaacgagga cgtgtgcctg  780
aagtggctgg acagcaagcc gagcggcagc gtgctgtacg tgagctacgg cagcctggtg  840
gagatgggcg aggagcagct gaaggagctg gccctgggca tcaaggaaac cggcaagttc  900
ttcctgtggg tggtgaggga caccgaggcc gagaagctgc cgccgaactt cgtggagagc  960
gtggccgaga agggcctggt ggtgagctgg tgcagccagc tggaggtgct ggcccacccg  1020
agcgtgggct gcttcttcac ccactgcggc tggaacagca ccctggaggc cctgtgcctg  1080
ggcgtgccgg tggtggcctt cccgcagtgg gccgaccagg tgaccaacgc caagttcctg  1140
gaggacgtgt ggaaggtggg caagagggtg aagaggaacg agcagaggct ggccagcaag  1200
gaggaggtga ggagctgcat ctgggaggtg atggagggcg agagggccag cgagttcaag  1260
agcaacagca tggagtggaa gaagtgggcc aaggaggccg tggacgaggg cggcagcagc  1320
gacaagaaca tcgaggagtt cgtggccatg ctgaagcaga cctaa                  1365

SEQ ID NO: 132          moltype = AA  length = 454
FEATURE                 Location/Qualifiers
source                  1..454
                        mol_type = protein
                        organism = Siraitia grosvenorii
SEQUENCE: 132
MEKGDTHILV FPFPAQGHIN PLLQLSKHLI AKGIKVSLVT TLHVSNRMQL QGAYSNSVKI  60
EVISDGSEDR LETDTLRQYL DRFRQKMTKN LEDFLQKAMV SSNPPKFIIY DSTMPWVLEV  120
AKEFGLDRAP FYTQSCALNS INYHVLHGQL KLPPETPTIS LPSMPLLRPS DLPAYDFDPA  180
STDTIIDLLT SQYSNIQDAN LLFCNTFDKL EGEIIQWMET LGRPVKTVGP TVPSAYLDKR  240
VENDKHYGLS LFKPNEDVCL KWLDSKPSGS VLYVSYGSLV EMGEEQLKEL ALGIKETGKF  300
FLWVVRDTEA EKLPPNFVES VAEKGLVVSW CSQLEVLAHP SVGCFFTHCG WNSTLEALCL  360
GVPVVAFPQW ADQVTNAKFL EDVWKVGKRV KRNEQRLASK EEVRSCIWEV MEGERASEFK  420
SNSMEWKKWA KEAVDEGGSS DKNIEEFVAM LKQT                              454

SEQ ID NO: 133          moltype = DNA  length = 1452
FEATURE                 Location/Qualifiers
source                  1..1452
                        mol_type = other DNA
                        organism = synthetic construct
SEQUENCE: 133
atggaccaga tggcaaaaat tgatgagaag aaaccccacg ttgtgtttat accattcccg  60
gcgcaaagtc atatcaagtg tatgctcaaa ctggcccgca ttttgcatca aaagggatta  120
tatattacat ttatcaatac cgatacgaac cacgaacgac ttgtcgcttc cgggggcact  180
caatggttag aaaatgctcc tggtttctgg tttaaaacag tacctgacgg tttcggttct  240
gcaaaagatg atggagttaa gccaactgac gccttgagag aactaatgga ttacctaaaa  300
actaactttt tcgatctctt tttggactta gtattaaagt tagaggtccc cgctacctgc  360
ataatttgtg atggctgcat gacattcgcg aatacgatca gagctgctga aaaattgaat  420
ataccagtta ctttttttg gacaatggca gcctgtggtt ttatggcatt ttatcaggcc  480
aaagtgctga aggaaaaaga gattgttcct ctgaaagacg aaacttactt gaccaacgga  540
tatttagata tggaaattga ttggatccca ggtatgaaac gtattaggct tagagatcta  600
cccgagttca ttctggccac taagcaaaat tatttcgcat ttgaattttt atttgaaaca  660
gctcaattgg cggacaaagt atcgcatatg ataatccata ccttcgaaga attggaagct  720
agcttagtgt cagaaatcaa gtctatattt ccgaacgttt acactattgg acctttgcag  780
ctattgctga ataagataac cctcaaagag actaataatg actcatatag tctatggaag  840
gaagagccag aatgtgttga gtggcttaac tctaaggagc caaactccgt cgtgtacgtt  900
aacttcggtt ccttggctgt gatgtcttta caagatctcg tcgaatttgg gtggggcttg  960
gttaattcaa atcactattt cttatggatc attagagcca atctgattga tggtaagcca  1020
gctgttatgc ctcaagaact caaagaagcc atgaacgaga aagggtttgt aggttcgtgg  1080
tgttcgcagg aagaggtcct taatcatcct gtggtaggcg gtttcttgac gcattgcggt  1140
tggggaagta tcatagagag cctttcagca ggcgtgccta tgttaggatg gccgagcatt  1200
ggggaccaga gggcaaactg ccggcaaatg tgtaaagaat gggaagtggg catggagata  1260
ggtaaaaatg ttaagagaga tgaagttgaa aaactggttc gtatgttgat ggaaggtttg  1320
gaaggagagc gaatgagaaa aaaggcttta gagtggaaaa agtccgctac attagcaacg  1380
tgttgtaacg ggtcttcatc actggacgtc gaaaaattgg ccaatgaaat taagaaatta  1440
tcgcgtaatt aa                                                      1452

SEQ ID NO: 134          moltype = AA  length = 483
FEATURE                 Location/Qualifiers
source                  1..483
                        mol_type = protein
                        organism = Stevia rebaudiana
SEQUENCE: 134
MDQMAKIDEK KPHVVFIPFP AQSHIKCMLK LARILHQKGL YITFINTDTN HERLVASGGT  60
QWLENAPGFW FKTVPDGFGS AKDDGVKPTD ALRELMDYLK TNFFDLFLDL VLKLEVPATC  120
IICDGCMTFA NTIRAAEKLN IPVILFWTMA ACGFMAFYQA KVLKEKEIVP LKDETYLTNG  180
YLDMEIDWIP GMKRIRLRDL PEFILATKQN YFAFEFLFET AQLADKVSHM IIHTFEELEA  240
SLVSEIKSIF PNVYTIGPLQ LLLNKITLKE TNNDSYSLWK EEPECVEWLN SKEPNSVVYV  300
```

```
NFGSLAVMSL QDLVEFGWGL VNSNHYFLWI IRANLIDGKP AVMPQELKEA MNEKGFVGSW  360
CSQEEVLNHP VVGGFLTHCG WGSIIESLSA GVPMLGWPSI GDQRANCRQM CKEWEVGMEI  420
GKNVKRDEVE KLVRMLMEGL EGERMRKKAL EWKKSATLAT CCNGSSSLDV EKLANEIKKL  480
SRN                                                                483

SEQ ID NO: 135          moltype = DNA  length = 1488
FEATURE                 Location/Qualifiers
source                  1..1488
                        mol_type = other DNA
                        organism = synthetic construct
SEQUENCE: 135
atggtatcag aaactactaa atcttctcca ttgcattttg tattgttccc atttatggcc  60
caaggtcata tgatcccaat ggttgacatc gctagattat tggctcaaag aggtgtcatc  120
atcacaatag tcacaactcc acataacgct gctagattta agaatgtgtt gaacagagca  180
attgaatcag gtttgccaat caatttggta caagtgaaat tcccatatct tgaagcaggt  240
ttgcaagagg gtcaagaaaa catcgattct ttagatacaa tggaaagaat gatcccattt  300
tttaaagctg taaacttctt ggaagaacca gtacagaaat tgattgagga aatgaatcca  360
agaccatcat gcttgatttc cgatttctgt cttccatata cttccaagat tgccaaaaag  420
tttaatatcc caaaaatctt attccatggt atgggttgtt tttgccttct gtgtatgcat  480
gtcttgagaa aaaatagaga aatactagat aatttgaaat ctgataagga attattcact  540
gttccagatt ttccagatag agttgaattt acaagaacac aagtaccagt tgaaacttac  600
gtgccagctg gtgattggaa agatatattt gacggtatgg tggaagctaa cgaaacttcc  660
tatggagtta ttgtaaattc ttttcaagaa ttggaacctg cttatgccaa agattataag  720
gaagtcagaa gtggtaaggc ctggactatt ggtccagtat ctttatgcaa taaagttggt  780
gcagataagg cagaaagagg taacaaatct gacatagacc aagatgaatg tttaaaatgg  840
ttggattcca agaaacatgg tagtgtgttg tatgtctgcc ttggttcaat ctgcaacttg  900
ccattgtcac aattaaagga attgggtcta ggtttggaag aatcacaaag accattcatt  960
tgggtaatta gaggttggga aaaatataaa gaattggtgg aatggttttc agagtctgga  1020
tttgaagaca gaatacaaga cagaggatta ttaatcaaag gttggtcccc tcaaatgtta  1080
atattgtctc atcctagtgt cggtggtttt ttgacccatt gtggttggaa ctctacatta  1140
gaaggtataa ctgctggttt gccacttcta acttggccat tgtttgctga tcagttctgc  1200
aacgaaaaat tggttgttga agtcctaaaa gccggtgtta gatctggtgt ggaacaacca  1260
atgaagtggg gtgaagaaga aaagattggt gtgttggtgg ataaggaagg tgttaagaag  1320
gccgttgagg aattgatggg tgaatccgat gacgccaagg agcgccgccg cagagcaaaa  1380
gaattaggtg atagtgccca taaagctgtt gaagaaggtg gatcttctca ttctaacata  1440
tctttttgt tacaagacat tatggagtta gctgaaccaa acaactaa                1488

SEQ ID NO: 136          moltype = AA  length = 495
FEATURE                 Location/Qualifiers
source                  1..495
                        mol_type = protein
                        organism = Stevia rebaudiana
SEQUENCE: 136
MVSETTKSSP LHFVLFPFMA QGHMIPMVDI ARLLAQRGVI ITIVTTPHNA ARFKNVLNRA  60
IESGLPINLV QVKFPYLEAG LQEGQENIDS LDTMERMIPF FKAVNFLEEP VQKLIEEMNP  120
RPSCLISDFC LPYTSKIAKK FNIPKILFHG MGCFCLLCMH VLRKNREILD NLKSDKELFT  180
VPDFPDRVEF TRTQVPVETY VPAGDWKDIF DGMVEANETS YGVIVNSFQE LEPAYAKDYK  240
EVRSGKAWTI GPVSLCNKVG ADKAERGNKS DIDQDECLKW LDSKKHGSVL YVCLGSICNL  300
PLSQLKELGL GLEESQRPFI WVIRGWEKYK ELVEWFSESG FEDRIQDRGL LIKGWSPQML  360
ILSHPSVGGF LTHCGWNSTL EGITAGLPLL TWPLFADQFC NEKLVVEVLK AGVRSGVEQP  420
MKWGEEEKIG VLVDKEGVKK AVEELMGESD DAKERRRRAK ELGDSAHKAV EEGGSSHSNI  480
SFLLQDIMEL AEPNN                                                   495

SEQ ID NO: 137          moltype = DNA  length = 1488
FEATURE                 Location/Qualifiers
source                  1..1488
                        mol_type = other DNA
                        organism = synthetic construct
SEQUENCE: 137
atggccttcg agaaaaacaa cgaaccattt ccactacatt ttgtcttgtt ccctttcatg  60
gctcagggtc atatgatacc aatggttgat atcgctagat tgctggctca gagaggtgtt  120
cttataacaa tcgttacaac ccccacataac gctgctagat tcaaaaatgt cttgaataga  180
gcaattgaat ctggtttgcc aattaacttg gtccaagtca agttcccata ccaagaagcc  240
ggtctgcaag agggacaaga gaacatggat ttgttgacta ctatggaaca aattacttca  300
tttttaagg ctgtgaacct gttaaaggaa ccagtccaaa atttaataga agaaatgtct  360
ccaagaccat catgccttat atctgatatg tgtttgtctt acacttctga gatcgctaag  420
aagttcaaaa tcccaaagat attgttccat ggtatgggtt gtttctgctt attatgcgtg  480
aatgttttga gaaaaaacag agaaatatta gacaacttga agtctgataa ggaatatttc  540
atcgtaccat atttcccaga tagagtggaa tttactagac cacaagttcc agtcgagact  600
tacgtcccag ctggttggaa agaaatcttg gaagacatgg ttgaagcaga taagacatca  660
tacggtgtaa ttgtaaactc tttccaagaa ttggaaccag cttacgctaa agacttcaaa  720
gaagctagat caggaaaggc atggactatc ggtccagtgt ccttatgtaa taaggttggt  780
gttgacaagg ctgaaagagg taataaatca gacattgatc aagatgaatg tttggagtgg  840
ttggattcaa aagagccagg ttcagtatta tatgtgtgtt tgggttctat ctgtaacctt  900
cctttatctc aattgttgga gctaggtctt ggtttagagg aatctcaaag accatttatt  960
tgggtcatta gaggttggga aaaatacaaa gagctggtcg aatggttttc tgagagtggt  1020
tttgaagaca gaatccaaga tagaggttta ttaattaagg gttggtcccc tcaaatgtta  1080
attctttctc atccatctgt aggtggtttc ttaactcatt gcggttggaa tagtacttta  1140
gagggtatca ctgctggttt acctatgtta acctggccat tatttgctga tcaattttgt  1200
```

```
aatgagaaat tagttgtaca aatactaaaa gtaggtgtat ctgctgaagt aaaagaggtg  1260
atgaaatggg gtgaagaaga aaaaattggt gtgctagttg ataaagaggg cgtcaagaag  1320
gccgtcgagg agttgatggg tgaatccgat gatgccaagg aacgccgccg cagagctaaa  1380
gaattgggtg agtctgctca taaggctgta gaagaaggtg gttcttctca ttcaaatatt  1440
acattcctgt tgcaagatat aatgcaattg gcacaatcta ataactaa              1488

SEQ ID NO: 138         moltype = AA  length = 495
FEATURE                Location/Qualifiers
source                 1..495
                       mol_type = protein
                       organism = Stevia rebaudiana
SEQUENCE: 138
MAFEKNNEPF PLHFVLFPFM AQGHMIPMVD IARLLAQRGV LITIVTTPHN AARFKNVLNR  60
AIESGLPINL VQVKFPYQEA GLQEGQENMD LLTTMEQITS FFKAVNLLKE PVQNLIEEMS  120
PRPSCLISDM CLSYTSEIAK KFKIPKILFH GMGCFCLLCV NVLRKNREIL DNLKSDKEYF  180
IVPYFPDRVE FTRPQVPVET YVPAGWKEIL EDMVEADKTS YGVIVNSFQE LEPAYAKDFK  240
EARSGKAWTI GPVSLCNKVG VDKAERGNKS DIDQDECLEW LDSKEPGSVL YVCLGSICNL  300
PLSQLLELGL GLEESQRPFI WVIRGWEKYK ELVEWFSESG FEDRIQDRGL LIKGWSPQML  360
ILSHPSVGGF LTHCGWNSTL EGITAGLPML TWPLFADQFC NEKLVVQILK VGVSAEVKEV  420
MKWGEEEKIG VLVDKEGVKK AVEELMGESD DAKERRRRAK ELGESAHKAV EEGGSSHSNI  480
TFLLQDIMQL AQSNN                                                  495

SEQ ID NO: 139         moltype = DNA  length = 1344
FEATURE                Location/Qualifiers
source                 1..1344
                       mol_type = other DNA
                       organism = synthetic construct
SEQUENCE: 139
atggaggagc acgggggccg ccggcggccc ctggtcgtgc tcacgtcgtg cccctttcat  60
ggacatatga ttccaacatt acaattagct acaacattac atgcaaaagg atttactatt  120
gctattgcac actctaagct caatccgcct aacccgtcca atcatcctag cgattttatt  180
tttcttccac tctcagatga cattcccgct atcgataatt ccggttcttt cacagatttt  240
atacgaaaac ttaataacaa ctgtaagcca tcattcaagg aacacctaac ccggctcata  300
tcggagggca acaaatccat agtcgtggtt tacgacaacg tccttcattt tgccggtata  360
gtagctgttg acctaaattt agctgccgta atgttcagga gtagttcagc ggcttatttt  420
ccagcatttt tagcccgtca acaattgagt caaaggggac gattcctaga agaggacttt  480
aaaatggatg agatggtccc taatcattac ccaatgcgtt acaaggatct ccctttctct  540
aagtctccaa ttgaagattg gcggcaatta tactcaaatt tttcccaaca ggcacatcca  600
tccgctgtca tctggaatac tataaaattc cttgaacacg aatctctgac ccaagttcac  660
aactactatc aggttcctgt ctttgctgtt ggcccactgc ataagatgac tcctacgtcc  720
tatatcgggt cacatgagga agataatggt tgcattacct ggctagacaa acaacctcct  780
aaatctgttg tatacattag ctttggaagt ttagcaacaa tggaagccaa aatattgact  840
gagatggcgt tcggtctggc caaatcaaat cagaggttcc tttgggcagt gcgtcctgga  900
ctgatttctg gttctgggtg ggttgaattt ttaccagaag gttttgtaga agaaactcgt  960
ggtcgaggtt tgatcgtaaa atgggcacct caaaaagaag tgctagctca ttttgcagta  1020
ggtggtttct ggtcacactg tggttggaac agttgcttgg aatctatcag ttctggcgta  1080
gttatgatgt gtcaaccctt tatagcagat caaggagtca acgctcgata tgtgagttac  1140
gtatggaaga taggcctcga attggagcgt gttgaaagag gtgagataga aaggatgata  1200
aagagagtaa tggtagacga cgaaggcgaa gaaatgagag tgagagtaaa cgacatgaaa  1260
aagatggtta aagaagctct tgagattggt ggttcgtcac aggaatcctt tgaagggtta  1320
gtagaatttc ttttatcttg ctaa                                        1344

SEQ ID NO: 140         moltype = AA  length = 447
FEATURE                Location/Qualifiers
source                 1..447
                       mol_type = protein
                       organism = Stevia rebaudiana
SEQUENCE: 140
MEEHGGRRRP LVVLTSCPFH GHMIPTLQLA TTLHAKGFTI AIAHSKLNPP NPSNHPSDFI  60
FLPLSDDIPA IDNSGSFTDF IRKLNNNCKP SFKEHLTRLI SEGNKSIVVV YDNVLHFAGI  120
VAVDLNLAAV MFRSSSAAYF PAFLARQQLS QRGRFLEEDF KMDEMVPNHY PMRYKDLPFS  180
KSPIEDWRQL YSNFSQQAHP SAVIWNTIKF LEHESLTQVH NYYQVPVFAV GPLHKMTPTS  240
YIGSHEEDNG CITWLDKQPP KSVVYISFGS LATMEAKILT EMAFGLAKSN QRFLWAVRPG  300
LISGSGWVEF LPEGFVEETR GRGLIVKWAP QKEVLAHFAV GGFWSHCGWN SCLESISSGV  360
VMMCQPFIAD QGVNARYVSY VWKIGLELER VERGEIERMI KRVMVDDEGE EMRVRVNDMK  420
KMVKEALEIG GSSQESFEGL VEFLLSC                                     447

SEQ ID NO: 141         moltype = DNA  length = 1425
FEATURE                Location/Qualifiers
source                 1..1425
                       mol_type = other DNA
                       organism = synthetic construct
SEQUENCE: 141
atggtacagc cgagagtttt actgttccct tttcccgcgt tggggcatgt gaaaccattt  60
ctatccctcg ctgagctttt atcggacgcc ggaatcgatg tcgtttttct aagtacagaa  120
tataatcacc ggcgtatttc aaacacggaa gcacttgcta gccgcttccc aactttacat  180
ttcgaaacca tacctgatgg tttgccacct aatgaatcta gagcattggc cgacggcccc  240
ctgtactttt ctatgaggga gggtactaag ccaagattcc gacaactcat tcaatcacta  300
aacgatggta ggtggcccat aacatgcatt atcacggata ttatgttgtc tagtcctata  360
```

-continued

```
gaggttgctg aagaatttgg cattccagta atcgcattct gtccgtgtag cgctagatat  420
ctgtcaattc attttttat tcctaaattg gtcgaggaag gacaaatacc atacgcggat  480
gacgatccta tcggtgaaat ccagggagtg ccgttatttg aagggttgct tcgtaggaat  540
cacttaccag gttcctggtc cgacaagtct gctgatattt cgttctctca cggtttaatc  600
aaccaaactt tagccgcagg aagagctagc gccttaatac ttaatacctt cgacgagctc  660
gaagctcctt ttttgacaca tttaagttcg atatttaaca aaatttatac gattggccca  720
ctgcatgcat tgtcaaaaag tcgcctaggt gattccagtt cttcagcttc ggcgctttcc  780
ggtttttgga aggaagacag agcctgcatg agctggttag attgtcaacc cccccgatcg  840
gttgttttcg tgtcgttcgg cagcactatg aaaatgaagg cagatgaatt aagagagttt  900
tggtacggtc tagtctcttc ggggaaacca tttttatgcg ttttacgttc agatgtagtc  960
tctggtgggg aagcagctga attgattgaa cagatggcag aagaagaggg tgctggcgga  1020
aagctgggca tggttgtgga gtgggctgcg caagaaaaag tattgtcaca tcctgccgtt  1080
ggcggatttc ttacacattg tggttggaat agcaccgtcg aaagcatcgc agctggtgtt  1140
ccgatgatgt gttggccaat actcggagat caaccgtcta atgcaacttg gatagacaga  1200
gtgtggaaga tcggcgtaga gaggaacaat agagaatggg atcgactaac ggtagaaaag  1260
atggttcggg ccttgatgga aggtcagaaa cgtgtcgaga ttcaacggtc catggaaaaa  1320
ttgtccaaac tggctaatga aaaagtcgtt agaggggggtt taagtttcga taacttagag  1380
gtgctcgttg aggacattaa gaaactgaag ccttataaat tttaa                  1425

SEQ ID NO: 142          moltype = AA  length = 474
FEATURE                 Location/Qualifiers
source                  1..474
                        mol_type = protein
                        organism = Stevia rebaudiana
SEQUENCE: 142
MVQPRVLLFP FPALGHVKPF LSLAELLSDA GIDVVFLSTE YNHRRISNTE ALASRFPTLH  60
FETIPDGLPP NESRALADGP LYFSMREGTK PRFRQLIQSL NDGRWPITCI ITDIMLSSPI  120
EVAEEFGIPV IAFCPCSARY LSIHFFIPKL VEEGQIPYAD DDPIGEIQGV PLFEGLLRRN  180
HLPGSWSDKS ADISFSHGLI NQTLAAGRAS ALILNTFDEL EAPFLTHLSS IFNKIYTIGP  240
LHALSKSRLG DSSSSASALS GFWKEDRACM SWLDCQPPRS VVFVSFGSTM KMKADELREF  300
WYGLVSSGKP FLCVLRSDVV SGGEAAELIE QMAEEEGAGG KLGMVVEWAA QEKVLSHPAV  360
GGFLTHCGWN STVESIAAGV PMMCWPILGD QPSNATWIDR VWKIGVERNN REWDRLTVEK  420
MVRALMEGQK RVEIQRSMEK LSKLANEKVV RGGLSFDNLE VLVEDIKKLK PYKF         474

SEQ ID NO: 143          moltype = DNA  length = 1029
FEATURE                 Location/Qualifiers
source                  1..1029
                        mol_type = other DNA
                        organism = synthetic construct
SEQUENCE: 143
atgagtgagt tcaggtccaa attcttggag gtttactctg tgttgaaatc cgagctcctc  60
aacgaccctg ctttcgagtt cactgacgat tcgcgccaat gggtcgagcg gatgttggat  120
tacaatgtac caggaggaaa gttgaacaga ggactctctg tcattgatag ctataagtta  180
ctaaaacaag ggaaaagct aagtgatgat gaagtgtttc tggcatctgc acttggttgg  240
tgcattgaat ggcttcaagc atattttctt gttcttgatg atatcatgga taattctgtt  300
acacgccgtg gacaaccttg ctggttcagg gtaccaaagg ttggtatggt tgcggtaaat  360
gatggcatta tgttacggaa ccatatcccg agaattctaa aaaatcattt cagagaaaag  420
ccttattacg tggatctttt ggacttgttt aatgaggtgg aatttcaaac agcctcagga  480
cagatgatag atttaattac gacactagaa ggagagaaaa atctatcaaa gtactcatta  540
cctcttcatc atcgcattgt tcggtacaaa actgcatatt actcgttcta tcttccggtt  600
gcatgtgcat tacttatggc aggcgaaaat ttggataatc ataatgatgt caagaatatt  660
cttattgata tggggaccta tttccaagtg caggatgatt atctggattg tttcggtcat  720
cccgatgtga tagggaagat tgggacagat attgaagatt tcaagtgctc ttggttggtt  780
gtgaaagcac ttgaacttag tgatgagaaa cagaagactt tactacatga gaattatgga  840
aaagcagata aagattgtgt tgccaaagtg aaagagttgt ataaagccct caatctagag  900
ggcgtgtttg ctgaatacga gagcaaaagt tacgagaagc ttataaaatc catagacatt  960
catccaagta atgcagtaca ggcagtgttg aaatctttcc ttgcaaagat atacaagagg  1020
cagaaatag                                                          1029

SEQ ID NO: 144          moltype = AA  length = 342
FEATURE                 Location/Qualifiers
source                  1..342
                        mol_type = protein
                        organism = Siraitia grosvenorii
SEQUENCE: 144
MSEFRSKFLE VYSVLKSELL NDPAFEFTDD SRQWVERMLD YNVPGGKLNR GLSVIDSYKL  60
LKQGEKLSDD EVFLASALGW CIEWLQAYFL VLDDIMDNSV TRRGQPCWFR VPKVGMVAVN  120
DGIMLRNHIP RILKNHFREK PYYVDLLDLF NEVEFQTASG QMIDLITTLE GEKNLSKYSL  180
PLHHRIVRYK TAYYSFYLPV ACALLMAGEN LDNHNDVKNI LIDMGTYFQV QDDYLDCFGH  240
PDVIGKIGTD IEDFKCSWLV VKALELSDEK QKTLLHENYG KADKDCVAKV KELYKALNLE  300
GVFAEYESKS YEKLIKSIDI HPSNAVQAVL KSFLAKIYKR QK                     342

SEQ ID NO: 145          moltype = DNA  length = 1254
FEATURE                 Location/Qualifiers
source                  1..1254
                        mol_type = other DNA
                        organism = synthetic construct
SEQUENCE: 145
atgggcagct tgggggcgat tctgagacac ccagatgact tttacccgct tctgaaactg  60
```

```
aagatggccg cgaggcatgc ggagaagcag atcccgccgg agcctcattg gggattctgc  120
tacaccatgc tgcacaaggt atcccggagt tttgctctcg ttattcagca gcttgcaccc  180
gagcttcgga atgctatatg catattttat cttgttctgc gagccctcga caccgttgag  240
gatgatacaa gtatacaaac agatatcaaa gtgcccattc tgaaagcttt tcactgccac  300
atatataacc gtgattggca tttttcatgt ggcacaaagg attataaagt tcttatggac  360
cagtttcatc atgtttcaac tgcgtttcta gaacttggga aagggtatca ggaggcaatt  420
gaggatatca cgaaacggat gggtgcagga atggctaaat tcatttgcaa agaggtagag  480
acagttgatg attacgatga atattgccac tacgtagctg gacttgttgg actaggtttg  540
tctaagctgt tccatgcttc ggatttagag gatttggcac ctgattcgct ttcaaattct  600
atgggattgt ttcttcagaa aacaaacatt attcgagatt acttggagga catcaacgag  660
ataccaaagt ctcggatgtt ttggccccgt gagatttggg gcaaatatgc caataagcta  720
gaggatttta aatatgagga gaattcggtc aaggccgtgc aatgcctcaa cgatttggtc  780
actaatgctt tgaatcatgt ggaggattgt ctgaaataca tgtcaaactt aagagatctt  840
tccatatttc gattttgtgc aattcctcag attatggcga ttggaactct agcattatgc  900
tacaacaacg ttgaagtctt caggggggtg gtcaaaatgc ggcggggtct tactgctaag  960
gtcattgatc gtacacaaac gatggctgac gtctatggag ctttcttcga tttttctgtt  1020
atgctgaagg ctaaggtcaa cagcagtgat cctaatgcta ctaaaaccct gagcaggatc  1080
gaagcaatac agaaaacatg cgagcagtcg ggactcttga acaaaaggaa attatatgca  1140
gttaaaagtg agccaatgtt caacccgact ctgattgtca tacttttcag cctattgtgc  1200
atcattctcg catatctctc tgccaaacgg ttaccggcta accaacctgt atga        1254

SEQ ID NO: 146         moltype = AA  length = 417
FEATURE                Location/Qualifiers
source                 1..417
                       mol_type = protein
                       organism = Siraitia grosvenorii
SEQUENCE: 146
MGSLGAILRH PDDFYPLLKL KMAARHAEKQ IPPEPHWGFC YTMLHKVSRS FALVIQQLAP  60
ELRNAICIFY LVLRALDTVE DDTSIQTDIK VPILKAFHCH IYNRDWHFSC GTKDYKVLMD  120
QFHHVSTAFL ELGKGYQEAI EDITKRMGAG MAKFICKEVE TVDDYDEYCH YVAGLVGLGL  180
SKLFHASDLE DLAPDSLSNS MGLFLQKTNI IRDYLEDINE IPKSRMFWPR EIWGKYANKL  240
EDFKYEENSV KAVQCLNDLV TNALNHVEDC LKYMSNLRDL SIFRFCAIPQ IMAIGTLALC  300
YNNVEVFRGV VKMRRGLTAK VIDRTQTMAD VYGAFFDFSV MLKAKVNSSD PNATKTLSRI  360
EAIQKTCEQS GLLNKRKLYA VKSEPMFNPT LIVILFSLLC IILAYLSAKR LPANQPV     417

SEQ ID NO: 147         moltype = DNA  length = 1386
FEATURE                Location/Qualifiers
source                 1..1386
                       mol_type = other DNA
                       organism = synthetic construct
SEQUENCE: 147
atggcgaaga acgtagggat attggctatg gacatctatt tccctcccac ctgtgttcaa  60
caggaagctt tggaagctca tgatggagca agcaaaggga aatacaccat tggacttggt  120
caagattgtt tagctttttg cactgagctt gaagatgtta tctcaatgag tttcaatgcg  180
gtgacatctc ttcttgaaaa gtacaagatt gaccccaagc aaattgggcg tcttgaagta  240
ggcagtgaga ctgtcattga caagagcaag tccatcaaaa ccttcttgat gcaactcttt  300
gagaaatgtg gaaacactga tgtagaaggt gttgactcga ccaatgcttg ttatggtgga  360
actgcggctt tgctaaactg tgtcaattgg gttgagagta actcctggga tggacgctat  420
ggccttgtca tttgtactga cagtgcggtt tatgcagaag ggcccgcaag gcccactgga  480
ggagcagctg ccattgctat gttgatagga ccagatgctc ctattgtttt tgagagcaaa  540
ttgagaggaa gccacatggc taatgtctat gacttttaca agccaaatct tgctagcgag  600
tacccggttg ttgatggtaa gctttcacag acatgctacc ttatggcact tgactcttgc  660
tataaacatt tatgcaacaa gtttgagaaa cttgagggca aagagttctc catcaatgat  720
gctgattact ttgtcttcca ttctccatac aacaaacttg tgcagaaaag ctttgctcgt  780
ctcttgtaca acgacttctt gagaaacgca agctccattg atgaggctgc caaagaaaag  840
ttcactcctt attcctcctt gtccctcgat gagagttacc aaagccgtga tcttgaaaag  900
gtgtcacaac aactagcaaa aacgtattat gatgctaaag tgcaaccaac gactttagta  960
ccaaaacaag tcggtaacat gtacactgct tctctctacg cagcatttgc ttccctcgtc  1020
cacaacaaac acagcgattt ggcgggaaag cgggtggtta tgttctcata tggagctggt  1080
tcaaccgcaa caatgttctc attgcgtctc tgcgagaacc agtctccttt cagcttatca  1140
aacatcgctt ctgtaatgga tgttggcggt aaattgaagg ctagacatga gtatgcacct  1200
gagaagtttg tggagacaat gaagctaatg gaacataggt acggagcaaa ggagtttgtg  1260
acgagcaagg aaggcatctt agaccttttg gctccgggga cttattatct gaaagaggtt  1320
gattcattgt accggagatt ctatggcaag aaaggagacg atggatccat aaccaatgga  1380
cactga                                                             1386

SEQ ID NO: 148         moltype = AA  length = 461
FEATURE                Location/Qualifiers
source                 1..461
                       mol_type = protein
                       organism = Brassica juncea
SEQUENCE: 148
MAKNVGILAM DIYFPPTCVQ QEALEAHDGA SKGKYTIGLG QDCLAFCTEL EDVISMSFNA  60
VTSLLEKYKI DPKQIGRLEV GSETVIDKSK SIKTFLMQLF EKCGNTDVEG VDSTNACYGG  120
TAALLNCVNW VESNSWDGRY GLVICTDSAV YAEGPARPTG GAAIAMLIG PDAPIVFESK  180
LRGSHMANVY DFYKPNLASE YPVVDGKLSQ TCYLMALDSC YKHLCNKFEK LEGKEFSIND  240
ADYFVFHSPY NKLVQKSFAR LLYNDFLRNA SSIDEAAKEK FTPYSSLSLD ESYQSRDLEK  300
VSQQLAKTYY DAKVQPTTLV PKQVGNMYTA SLYAAFASLV HNKHSDLAGK RVVMFSYGAG  360
STATMFSLRL CENQSPFSLS NIASVMDVGG KLKARHEYAP EKFVETMKLM EHRYGAKEFV  420
```

```
TSKEGILDLL APGTYYLKEV DSLYRRFYGK KGDDGSITNG H                461

SEQ ID NO: 149          moltype = DNA  length = 900
FEATURE                 Location/Qualifiers
source                  1..900
                        mol_type = other DNA
                        organism = synthetic construct
SEQUENCE: 149
atgacggcca gcgctgagca ccagacgttc accaccgcca tcgtgcccgc agccggcctg  60
ggcacacgct tcctccccac gaccaaatcg gtccccaaag agctgctgcc ggtcgtggac  120
accccggcga tcgagctggt cgccgacgaa gccaggcaag ctggtgccga gcgtctggtc  180
atcgtcacct ccccggcgaa acagtccatc gccgcctact tccggcccgc accggaattg  240
gaacggtcac tggaggagaa aggcaagacc ggccaactgg ccaagatccg ccgggccccg  300
gaactgctcg aggtcgaagt cgccatccag gaacaggcac tcggcctcgg ccacgcggtg  360
gcgtgcgccg agccgaacct cgggccggag gacgacgtgg tggccgtact gctgccggac  420
gacctcgtgc tgccccacgg gatcctggag cggatggcca aggtacgcgc cgagcacggc  480
ggcagcgtcc tgtgtgcttt cgacatcccg aaggaggaaa tctccgccta cggagtcttc  540
gacgtcagcg acaccgacga cgccgacgtc aagcgggtcc acggcatggt ggagaagccg  600
cctgccgagc aagcccccctc gacgttcgcc gcggccggcc gttacctgct cgaccgggcg  660
atcttcgacg cgctgcgccg gatcgagccg ggcgccgggg gcgagctcca gctcaccgac  720
gcggtggcgc tgttgatcca ggaagggcat ccggtgcacg tggtggtgca ccgcggtgac  780
cgtcacgact tgggcaaccc cggcggcttc ctgcgtgccg cggtcgactt cgccctgcag  840
gatccggact atgggccgga actgcgcgcc tggttgacgg acagaatcgc acgaccatga  900

SEQ ID NO: 150          moltype = AA  length = 299
FEATURE                 Location/Qualifiers
source                  1..299
                        mol_type = protein
                        organism = Thermocrispum agreste
SEQUENCE: 150
MTASAEHQTF TTAIVPAAGL GTRFLPTTKS VPKELLPVVD TPAIELVADE ARQAGAERLV  60
IVTSPAKQSI AAYFRPAPEL ERSLEEKGKT GQLAKIRRAP ELLEVEVAIQ EQALGLGHAV  120
ACAEPNLGPE DDVVAVLLPD DLVLPHGILE RMAKVRAEHG GSVLCAFDIP KEEISAYGVF  180
DVSDTDDADV KRVHGMVEKP PAEQAPSTFA AAGRYLLDRA IFDALRRIEP GAGGELQLTD  240
AVALLIQEGH PVHVVVHRGD RHDLGNPGGF LRAAVDFALQ DPDYGPELRA WLTDRIARP   299

SEQ ID NO: 151          moltype = DNA  length = 942
FEATURE                 Location/Qualifiers
source                  1..942
                        mol_type = other DNA
                        organism = synthetic construct
SEQUENCE: 151
atgtccacag aaacccattg gatttctcca tctctaatgg cgatttctct caatcttctt  60
caacttcaac caaatccagc gcggcccaag ttcttcaaat ggaaccccgt ccgaccggcg  120
gttcatttca gagctccggc gaggttgacc gtcgtcatgt cacagatcac tccgtcgtac  180
tgggcggcca taaatgaaga tattgaggat catctccggc gggtcattcc ggcaaaggac  240
ccgccggcgg tgtacgagcc gttgggccat tttgtcttct cggccccacg aaattccgct  300
cctgcactgt gtattgccgc ctgcgagctc gtcggcggcg gccgtgacca ggccattgtg  360
gcggctactg cactgcaact catccacgct gcaacctata ctcgggaata ccctccactg  420
acggcacgtg aaatctcacg cgccgccgtc gttgaccgcg tttatggccc caacatccag  480
ctgttgacag gggacggaat agcaccgatg gtgttcgaga ttctagcggg atcttgcgat  540
tggagcgaga gcgggtcgga gcggattcga cgcgtgatgg tggaaatggc acgtgcgatg  600
ggtacggaag ggtggattgg ggggcaattt cggggattgg aggagacggc aacggcggag  660
gaagtgagcg agaagacgga aggtgggcta cacgcgtgtg gggcgcgtg tggggtgata  720
ttgggaggtg gaaatgaaga ggaaatagag aagatgagga aatatgggaa attggtgggg  780
atggtgaaag gaatgtcaaa aaatgtgttt ggagggaaag aaaatgagag aaagaaagag  840
aaaattgagg agttgaagta tttggctttc aaggaattga aagatttcaa aggagaaaat  900
gttcatgaga tctatggatt ccttgatttt gagggacttt ag                942

SEQ ID NO: 152          moltype = AA  length = 313
FEATURE                 Location/Qualifiers
source                  1..313
                        mol_type = protein
                        organism = Citrullus lanatus
SEQUENCE: 152
MSTETHWISP SLMAISLNLL QLQPNPARPK FFKWNPVRPA VHFRAPARLT VVMSQITPSY  60
WAAINEDIED HLRRVIPAKD PPAVYEPLGH FVFSAPRNSA PALCIAACEL VGGGRDQAIV  120
AATALQLIHA ATYTREYPPL TAREISRAAV VDRVYGPNIQ LLTGDGIAPM VFEILAGSCD  180
WSESGSERIR RVMVEMARAM GTEGWIGGQF RGLEETATAE EVSEKTEGGL HACGGACGVI  240
LGGGNEEEIE KMRKYGKLVG MVKGMSKNVF GGKENERKKE KIEELKYLAF KELKDFKGEN  300
VHEIYGFLDF EGL                                               313

SEQ ID NO: 153          moltype = DNA  length = 942
FEATURE                 Location/Qualifiers
source                  1..942
                        mol_type = other DNA
                        organism = synthetic construct
SEQUENCE: 153
atggccatta atctctccca tatcaactcc aaaacatgtt tccctctcaa aacaagatct  60
```

```
gatctcagcc gttcttcttc cgcgcgttgc atgccaactg ccgccgctgc cgccttcccc  120
actatcgcca ccgccgccca aagtcagccg tactgggccg ccatcgaggc cgacatagag  180
agatacctga agaaatccat cacaataagg ccgccggaga cagttttcgg gcccatgcac  240
cacctcacct tcgccgcccc agccaccgcc gcctccaccc tatgcttggc ggcgtgcgag  300
ctcgtcggcg gcgaccgaag ccaagccatg gcagccgcgg cggcgatcca tctcgtgcac  360
gcggcagcct acgtccacga gcacctccct ctaaccgacg ggtcgaggcc cgtatccaag  420
cccgcaatcc agcacaagta cggcccgaac gtcgagctcc tcaccggaga cgggattgtc  480
ccgttcgggt ttgagttgct ggccgggtca gtggacccgg cccgaacaga cgacccggat  540
aggattctga gagttataat agagatcagt cgggccggcg ggccggaggg aatgataagc  600
gggctgcata gggaagaaga aattgttgat ggaaatacga gtttagactt cattgaatat  660
gtgtgcaaga aaaaatacgg cgagatgcat gcttgcggcg cggcttgtgg agccatattg  720
ggcggcgcag ccgaggagga gattcagaag ctgaggaatt tcgggcttta tcaaggaact  780
ctcagaggaa tgatggaaat gaaaaattct catcaattaa ttgatgagaa tataattgga  840
aaattgaaag aattggctct cgaggagttg ggaggcttcc acgggaagaa cgctgagctg  900
atgtcgagcc ttgtagccga gccgagcctt tacgcggctt ag                    942
```

```
SEQ ID NO: 154         moltype = AA  length = 313
FEATURE                Location/Qualifiers
source                 1..313
                       mol_type = protein
                       note = Peppermint (Mentha x piperita)
                       organism = Mentha X piperita
SEQUENCE: 154
MAINLSHINS KTCFPLKTRS DLSRSSSARC MPTAAAAAFP TIATAAQSQP YWAAIEADIE  60
RYLKKSITIR PPETVFGPMH HLTFAAPATA ASTLCLAACE LVGGDRSQAM AAAAAIHLVH  120
AAAYVHEHLP LTDGSRPVSK PAIQHKYGPN VELLTGDGIV PFGFELLAGS VDPARTDDPD  180
RILRVIIEIS RAGGPEGMIS GLHREEEIVD GNTSLDFIEY VCKKKYGEMH ACGAACGAIL  240
GGAAEEEIQK LRNFGLYQGT LRGMMEMKNS HQLIDENIIG KLKELALEEL GGFHGKNAEL  300
MSSLVAEPSL YAA                                                    313
```

```
SEQ ID NO: 155         moltype = DNA  length = 897
FEATURE                Location/Qualifiers
source                 1..897
                       mol_type = other DNA
                       organism = synthetic construct
SEQUENCE: 155
atggctgcca tcctaaacca tttcacaagc aatccaatac gccctctcct ccccctaaac  60
aagctaaaac ccctctcatc ttctacaaag accattcaag tgaccactac agacagtaac  120
cccaccaact ggtccaccat aaacgcagac gtggacgccc gcctcaagca ggccctccca  180
atccgcgacc ccatcgacgt ccatcaacct atgcacgatc tcgtcttctc cgcgcccaag  240
accttggttc cagctctctg caccgcagca tgcgagctcg tgggaggggga gcataaagac  300
ggtgtggacg tcgcctcggc cctaaacctc atgctggctg cttcctacac ccatcaatac  360
ctccccaacc ttttacagag gccaaatccc ccctccttcc ctcacaacat tgagcttcta  420
acaggggatg gcatctaccc tcttgggttc gagctgctag ccagccctga tggtgtgggg  480
ggtgatgctg agcgcgctct gagggtaatt ttggaggtcg cacgtgccat gggtgggcag  540
gggttggtag aggcacagta catgaaggtg aagagggcca agggggaatt ggacgttgac  600
tgcgcgttga tgcgcatgtg cgagagagga gaaggcagtg tttactcatg tgcagcggca  660
tgtggggcta ttgtaggtgg ggcctgcgaa gaggatgtgg aaaagttaag gaggtatggg  720
ttttacgtgg gtatgatcca tgggctgttg gatggtgttg gcagagaagg cgatgtggaa  780
gaagaagtta aaaggcttag gttcttggct ctcaaggaat tggaagggtt tgatgcagag  840
aaggttcgtg ccatttccag cctagttgat gctgatacca ctcgctgtgt acagtag     897
```

```
SEQ ID NO: 156         moltype = AA  length = 298
FEATURE                Location/Qualifiers
source                 1..298
                       mol_type = protein
                       organism = Litsea cubeba
SEQUENCE: 156
MAAILNHFTS NPIRPLLPLN KLKPLSSSTK TIQVTTTDSN PTNWSTINAD VDARLKQALP  60
IRDPIDVHQP MHDLVFSAPK TLVPALCTAA CELVGGEHKD GVDVASALNL MLAASYTHQY  120
LPNLLQRPNP PSFPHNIELL TGDGIYPLGF ELLASPDGVG GDAERALRVI LEVARAMGGQ  180
GLVEAQYMKV KRAKGELDVD CALMRMCERG EGSVYSCAAA CGAIVGGACE EDVEKLRRYG  240
FYVGMIHGLL DGVGREGDVE EEVKRLRFLA LKELEGFDAE KVRAISSLVD ADTTRCVQ    298
```

```
SEQ ID NO: 157         moltype = DNA  length = 1272
FEATURE                Location/Qualifiers
source                 1..1272
                       mol_type = other DNA
                       organism = synthetic construct
SEQUENCE: 157
atgaagttta ttttattgtc cacaattttg agtggtcttc tctcgtttgc tgctgctgct  60
ccaatcattt taaagaaacg tgattgggat tacacaaaag ataaaattca tggtgtgaat  120
attggaggtt ggcttgttct agagccatac attacacctt cgctatttga gacgtttggt  180
gacgatgcac cagtggatga atatcactac actcaacagc taggcaagga agaggcttct  240
aagagattac aagagcactg ggctaactgg attacagaga aggacttcga atatattgcc  300
aatctgggtc ttaacatggt taggattcca attggatact gggcttttga attgcaggac  360
aatgatccat acgtccaggg acagcaagcg tatttggaca aggctcttgg ctgggcagaa  420
aaaaatggct tgaaagtttg gatcgatttg catggtgttc caggctctca aaatggattt  480
gataattctg gtttgcgtga tcaaatcaac tggcaaactg gttccggaaa tgtcgatttc  540
```

```
acattaaacg tgttgaaaga aatgattgag aaatattccg attccgatta cagcgacaca  600
attattggaa ttgagttgtt gaacgagcct ttaggatcct ccttgaacat ggatgaactt  660
aaggtcttct acagtagtgg ctatgaactt gttagagatc aggatgcttc cattccagtc  720
attattcaag atgctttcca gtccgattac tactgggatg actttttaaa tactgagcaa  780
gacacaaaca tttacggcgt tgttgttgat catcatcact accaggtctt ttctactggt  840
gaacttcaga gagacatgga tacacgcatt caaaccgcat gtaactgggg taagcaggaa  900
ggtggggagt accactggaa tgtctgcgga gagttctcag cagcccttac ggattgtgcc  960
aagtggctca atggtttagg aaggggtgcc agatatgact cttcatatgg aggtggtgct  1020
tatgttggaa gttgtgatga tttgtacacg tacgatgaag actactggaa caatagtgat  1080
gtcatcaagc aatacaggca gtatgtggag gcccaaatgg atgcatttga gaatggaaag  1140
atgggaggat gggttttctg gtgttggaag acagaatccg ctgttgagtg ggacttccag  1200
aggttggctg gccttaacgt cattcctcag cctttggatg acaggttata tcctaaccag  1260
tgtagcttct aa                                                      1272

SEQ ID NO: 158          moltype = AA  length = 423
FEATURE                 Location/Qualifiers
source                  1..423
                        mol_type = protein
                        organism = Dekkera bruxellensis
SEQUENCE: 158
MKFILLSTIL SGLLSFAAAA PIILKKRDWD YTKDKIHGVN IGGWLVLEPY ITPSLFETFG  60
DDAPVDEYHY TQQLGKEEAS KRLQEHWANW ITEKDFEYIA NLGLNMVRIP IGYWAFELQD  120
NDPYVQGQQA YLDKALGWAE KNGLKVWIDL HGVPGSQNGF DNSGLRDQIN WQTGSGNVDF  180
TLNVLKEMIE KYSDSDYSDT IIGIELLNEP LGSSLNMDEL KVFYSSGYEL VRDQDASIPV  240
IIQDAFQSDY YWDDFLNTEQ DTNIYGVVVD HHHYQVFSTG ELQRDMDTRI QTACNWGKQE  300
GGEYHWNVCG EFSAALTDCA KWLNGLGRGA RYDSSYGGGA YVGSCDDLYT YDEDYWNNSD  360
VIKQYRQYVE AQMDAFENGK MGGWVFWCWK TESAVEWDFQ RLAGLNVIPQ PLDDRLYPNQ  420
CSF                                                                423

SEQ ID NO: 159          moltype = DNA  length = 1524
FEATURE                 Location/Qualifiers
source                  1..1524
                        mol_type = other DNA
                        organism = synthetic construct
SEQUENCE: 159
atggctgtgg ttgcttcagc tccagggaaa gttttaatgg ccggaggtta ccttgtcttg  60
gagaaaccga atgcagggct cgtacttagt actaatgctc gtttttatgc aattgtaaaa  120
cccgtttacg aggaaatcaa gcctgacagc tgggcatggt catggacaga tgttaagttg  180
acatctcccc agctcctgag agagagcatc tacaaattgt cattgaaaaa ccaatctctt  240
cagagtatct ctccaagtca atcagggaac ccttttgtag aaagagcagt ggaatattgt  300
gtagcagctg catgtgcaaa atttgttgac aaggacaata aggatgcatt acacaaactg  360
ctcttgcaag gtcttgatat cactattcta ggttgcaatg agttctactc ttatcggagt  420
cagattgagg ctcgtggact tccactaaca tcagaatcat tggcttcctt gcctcctttt  480
tcatcaatta cattcaatga tgaggaatca tatgggaaaa cttgcaagcc tgaagttgca  540
aaaactggat tgggctcatc tgcagcaatg acagctgctg tagttgctgc tttacttaac  600
tacctagggg ttgtaaatct ttccttattg acaggtgacc aagaagagag aggcagtgcg  660
gatcttgatt tggtgcatat aatagctcaa agtgcccact gcattgcaca gggaaaagtt  720
ggcagtggct ttgatgtcag ttctgcagtt tatggcagtc aacgctatgt tcggttttca  780
ccagaagtgc tgtcttctgc tcaggctgcc aagaatggag tacccataga agaggtcatt  840
ggcgatatct taaatcagaa gtgggaccat gagaggacta agttctcttt gcctccatta  900
atgactcttg tacttgggga gccaggagtg ggagggtcat ccacgccttc aatggtaggt  960
gctgtcaaaa agtggcaaaa atctgaccct caagggtccc tagacacgtg gacaaagttg  1020
tcagaaggga actcagaact tgaaactcaa ctcaacacgt tgagtaaact tgcagctgaa  1080
cactgggatg cttataaata tatcataaac agttgttcca agctcacctt ggagaagtgg  1140
attcaccaag ccacagaacc aagccaccaa gccatcatca aagcattatt aggagcaaga  1200
aatgctatgc ttcagatcag gcatcatatg cgcttaatgg gtgaagctgc tggtgttccg  1260
attgagccag attcacaaac caagctttta gatactacca tgaatatgga aggagtcctg  1320
ttagccggtg ttccaggggc aggcgggttt gacgctgttt ttgctgtgac cttgggagac  1380
tcaaccagca atgtgattaa atcatggagt tcactggata ttttggctct ccttgttaga  1440
gaagatcccc gtggtgttgc tttggaaagt tgtgatcccc gaaccaaggc aattacatca  1500
gctgtttcat cagttcatat ttag                                         1524

SEQ ID NO: 160          moltype = AA  length = 507
FEATURE                 Location/Qualifiers
source                  1..507
                        mol_type = protein
                        organism = Citrullus lanatus
SEQUENCE: 160
MAVVASAPGK VLMAGGYLVL EKPNAGLVLS TNARFYAIVK PVYEEIKPDS WAWSWTDVKL  60
TSPQLLRESI YKLSLKNQSL QSISPSQSGN PFVERAVEYC VAAACAKFVD KDNKDALHKL  120
LLQGLDITIL GCNEFYSYRS QIEARGLPLT SESLASLPPF SSITFNDEES YGKTCKPEVA  180
KTGLGSSAAM TAAVVAALLN YLGVVNLSLL TGDQEERGSA DLDLVHIIAQ SAHCIAQGKV  240
GSGFDVSSAV YGSQRYVRFS PEVLSSAQAA KNGVPIEEVI GDILNQKWDH ERTKFSLPPL  300
MTLVLGEPGV GGSSTPSMVG AVKKWQKSDP QGSLDTWTKL SEGNSELETQ LNTLSKLAAE  360
HWDAYKYIIN SCSKLTLEKW IHQATEPSHQ AIIKALLGAR NAMLQIRHHM RLMGEAAGVP  420
IEPDSQTKLL DTTMNMEGVL LAGVPGAGGF DAVFAVTLGD STSNVIKSWS SLDILALLVR  480
EDPRGVALES CDPRTKAITS AVSSVHI                                      507

SEQ ID NO: 161          moltype = DNA  length = 1497
```

```
FEATURE                Location/Qualifiers
source                 1..1497
                       mol_type = other DNA
                       organism = synthetic construct
SEQUENCE: 161
atggccctag ttgcctcagc tcctgggaaa gtattattga caggaggata cctaattttg  60
gagaggccaa atgctggttt ggtactcagt acaaatgctc ggttttatgc aattgtgaaa  120
ccacttcacg agcaaactga gccagaaagt ggggatgggg aatgggtaga tgtgaagttg  180
acctcaccac aactttctcg agaaagtctg tataaattat cgcccgagaa cctcatgatt  240
cagtgcatct ccttgagtga gtcaaggaac cctttcatag aacatgctgt gcagtattcc  300
ctagctgctg cacatggaat atttgtcaag aacaagaaag attcactgca caggttgcta  360
ctacaaggtc ttgatatcac aatcttagga tgcaatgatt tctactctta tcggaatcag  420
attgaagcac atggacttcc tttgacacca gaatcactgg tttcttttcc accatttgca  480
tcaattacct tcaatgctga gccatcaaat agtgaaaatt gcaagcctga agttgcaaag  540
acaggattgg gatcatctgc tgcaatgaca actgctgttg ttgctgccct acttaattat  600
cttggagttg taaatctttc ctcatcaaga ggtcaagaga aagaaaatga tatgaaggat  660
cttgatatgg tgcatgcaat agcccaaact gctcattgca ttgcacaggg aaaagttgga  720
agtggatttg atgtcagctc tgccgtctat ggcagccaac ggtatgttcg tttctcacct  780
cacgtgctgg ccactgctca ggcagctgtt aaaggaccgc tagaagaggt cattgtcgat  840
atcttaaaag gaaagtggga ccatgagagg actgagtttt ccttgcctcc attaatgaat  900
cttttattag gggaaccagg agctggagga tcatccacac catctatggt aggtgctgtt  960
aaaaagtggc aaaagtctga ccctcagaaa tctcaagaaa catggaataa gttgtcgaaa  1020
gcaaatattg atttcgagaa gcaattaaat ttactgagaa aacttgcagc agaacaatgg  1080
gatgtgtata aatgcatcat aagtaaatgc agcacacttg gatcaaagaa gtggatagaa  1140
caagccactg aaccaagcca acaagcaatt gttaaagcat tgttaggagc aagagatgcc  1200
atgctcgaaa tacgaaattg tatgaagcaa atgggcgaag ctgcaggcgt tccaattgaa  1260
ccaaagccac aaactgaact tttagatgca accatggaat tggaaggagt tttgttggct  1320
ggagttccag gggcaggcgg gtttgatgct gtatttgcta ttacattggg tgattctagc  1380
agccatgtga ttaagtcatg gacttcactc aatgttcttg ccctcttagt tagagaagat  1440
cccgatggag ttgctcttga aagtgatgat cctagaggta agagctgtac tgtttaa     1497

SEQ ID NO: 162         moltype = AA  length = 498
FEATURE                Location/Qualifiers
source                 1..498
                       mol_type = protein
                       organism = Citrullus lanatus
SEQUENCE: 162
MALVASAPGK VLLTGGYLIL ERPNAGLVLS TNARFYAIVK PLHEQTEPES GDGEWVDVKL  60
TSPQLSRESL YKLSPENLMI QCISLSESRN PFIEHAVQYS LAAAHGIFVK NKKDSLHRLL  120
LQGLDITILG CNDFYSYRNQ IEAHGLPLTP ESLVSFPPFA SITFNAEPSN SENCKPEVAK  180
TGLGSSAAMT TAVVAALLNY LGVVNLSSSR GQEKENDMKD LDMVHAIAQT AHCIAQGKVG  240
SGFDVSSAVY GSQRYVRFSP HVLATAQAAV KGPLEEVIVD ILKGKWDHER TEFSLPPLMN  300
LLLGEPGAGG SSTPSMVGAV KKWQKSDPQK SQETWNKLSK ANIDFEKQLN LLRKLAAEQW  360
DVYKCIISKC STLGSKKWIE QATEPSQQAI VKALLGARDA MLEIRNCMKQ MGEAAGVPIE  420
PKPQTELLDA TMELEGVLLA GVPGAGGFDA VFAITLGDSS SHVIKSWTSL NVLALLVRED  480
PDGVALESDD PRGKSCTV                                                498

SEQ ID NO: 163         moltype = DNA  length = 975
FEATURE                Location/Qualifiers
source                 1..975
                       mol_type = other DNA
                       organism = synthetic construct
SEQUENCE: 163
atggatctaa ccaagccact ccgctgcatc gtaaaattgg ggggtgcggc cattacttgc  60
aaaaatgaat tggaaaccat acacgaagaa aatttggcga cggtttcgtc acatctgagg  120
aaaactatgg ttagtggctc ttcttctgaa aatacctttg gaatggattg gagcaggcag  180
cctggaaaat ccgacattgc atgtaatgtt gatgatttaa gagaacatga agttggcctt  240
gcgagtccct ttatagttgt tcatggagct ggttcttttg ggcattttca ggcaagtaaa  300
tcaggggttc ataaaggagg acttgataga tccttagtca aggctggatt tgttgccaca  360
cgtatatccg ttacttcact caatctccaa attgttagag cactcgcgag agagggtatt  420
ccatccgttg gaatgtctcc attttcatgt ggatggtcca cttgtgaaag aaatatggat  480
gcagttgatt tacgtggtgt ttctaaagct attaactccg gatttgttcc tgttctgcat  540
ggagatgctg tttttgacaa ttccctgggg tgcaccatat taagtggaga tgtaataata  600
cgacatcttg cagagcaact aaagcctgat tatgttgtat tccttacaga tgttttaggt  660
gtatatgatc gtcctccaac agaacctaat gcagtccttt taagagagat tgctgtgggt  720
gaagatggtc gttggtctgt tatacaacct atactgcaca acggtaacac agaagttgag  780
ataagtgtag ccgctcatga tacaactggg ggaatggtga ctaagatatc agaagcagca  840
atgattgcaa agcttggcat tgaagtctac attgtaaagg cagcaacagt ccactccttg  900
agagctctaa gtggggaaat ccgaggcaaa attccagatg actggcttgg aacggtcatt  960
agattttcag gataa                                                    975

SEQ ID NO: 164         moltype = AA  length = 324
FEATURE                Location/Qualifiers
source                 1..324
                       mol_type = protein
                       organism = Citrullus lanatus
SEQUENCE: 164
MDLTKPLRCI VKLGGAAITC KNELETIHEE NLATVSSHLR KTMVSGSSSE NTFGMDWSRQ  60
PGKSDIACNV DDLREHEVGL ASPFIVVHGA GSFGHFQASK SGVHKGGLDR SLVKAGFVAT  120
```

```
RISVTSLNLQ IVRALAREGI PSVGMSPFSC GWSTCERNMD AVDLRGVSKA INSGFVPVLH  180
GDAVFDNSLG CTILSGDVII RHLAEQLKPD YVVFLTDVLG VYDRPPTEPN AVLLREIAVG  240
EDGRWSVIQP ILHNGNTEVE ISVAAHDTTG GMVTKISEAA MIAKLGIEVY IVKAATVHSL  300
RALSGEIRGK IPDDWLGTVI RFSG                                        324

SEQ ID NO: 165         moltype = DNA  length = 1275
FEATURE                Location/Qualifiers
source                 1..1275
                       mol_type = other DNA
                       organism = synthetic construct
SEQUENCE: 165
atggcgattt ctagagaatt ggcgggtgaa aaatgggtgt tgttgaccac tgcacaaacg  60
ccgacgaaca ttgcggtgat taagtattgg gggaagaggg acgaggcctt aattttacct  120
gtcaatgata gcatcagtgt tacgcttgat ccgagtcatc tctgcaccat caccaccgtc  180
gctgttagtc ccgactttga gaaggatcgg atgtggctca atcgcaagga gatatccctt  240
tctggagcca ggtaccaaac ttgtttgagg gaaatacgca gtcgagctaa tgatgttgag  300
gataaagaaa aggggattaa gatagcaaaa aaagactggg agaagttgca tgtatatatt  360
gattcataca ataatttccc aactgctgct ggcttggctt cctctgctgc cggttttgct  420
tgtcttgtct ttgctttggc aaatttaatg aacgtcaagg aagatcatag ccagctatct  480
gctattgcaa ggcaaggttc gggaagtgca tgccgtagtc tatacggtgg atttgtgaag  540
tggagcatgg gaaaagaaaa ggatggaagt gatagtcttg caattcaact tgcggatgag  600
aagcactggg acgatcttgt aattattatt gctgtggtaa gttcgcgaca gaaggaaaca  660
agtagtacat caggaatgcg ggaaaccgta gaaacaagtt tgcttttaca acatagagct  720
aaggaaattg taccaaagcg tgtgttagct atggaagaag ctattaaaaa tcgggatttt  780
gcatcctttg cacaactgac atgcaacgat agcaaccaat ttcatgcagt ctgtctcgat  840
acgtctcccc cgatatttta catgaatgat acgtcccaca ggataattag tcttgttgag  900
aaatggaacc gttctgaagg agaacctcag gtggcatata ctttcgatgc agggccgaat  960
tcggttctga ttgcacgaaa cagaaaaatt gctgtttctt tgcttcagag gttgcttttc  1020
caattccctc caaacccaga aacggaatta aaaagttatg ttcttggcga caagtcaatt  1080
cttcaagatg ctgggattaa tagtgttgag gatattgaat ccctgccaca acctccagaa  1140
tttagcagtt cattccagaa ataccaggga gatgtcagtt acttcatctg taccagaccc  1200
ggaaaagggc cagtcattct ccccgagagt gaagctctac tcgacccgaa aactgggctg  1260
ccaaagaacc tctag                                                  1275

SEQ ID NO: 166         moltype = AA  length = 424
FEATURE                Location/Qualifiers
source                 1..424
                       mol_type = protein
                       organism = Citrullus lanatus
SEQUENCE: 166
MAISRELAGE KWVLLTTAQT PTNIAVIKYW GKRDEALILP VNDSISVTLD PSHLCTITTV  60
AVSPDFEKDR MWLNRKEISL SGARYQTCLR EIRSRANDVE DKEKGIKIAK KDWEKLHVYI  120
DSYNNFPTAA GLASSAAGFA CLVFALANLM NVKEDHSQLS AIARQGSGSA CRSLYGGFVK  180
WSMGKEKDGS DSLAIQLADE KHWDDLVIII AVVSSRQKET SSTSGMRETV ETSLLLQHRA  240
KEIVPKRVLA MEEAIKNRDF ASFAQLTCND SNQFHAVCLD TSPPIFYMND TSHRIISLVE  300
KWNRSEGEPQ VAYTFDAGPN SVLIARNRKI AVSLLQRLLF QFPPNPETEL KSYVLGDKSI  360
LQDAGINSVE DIESLPQPPE FSSSFQKYQG DVSYFICTRP GKGPVILPES EALLDPKTGL  420
PKNL                                                              424

SEQ ID NO: 167         moltype = DNA  length = 1029
FEATURE                Location/Qualifiers
source                 1..1029
                       mol_type = other DNA
                       organism = synthetic construct
SEQUENCE: 167
atggcggatc tcaagtcaac cttcctcaag gtctactcgg ttctgaaaga agagcttctc  60
caggaccctg ccttcgagtt tactgacgct tctcgccaat ggatcgaacg gatgctggac  120
tacaatgtgc ctggaggaaa gcttaaccga gggctctccg taattgatag ctacagattg  180
ttgaaagaag ggaaggaatt gacggaagat gaaatctttc ttgccagtgt tcttggatgg  240
tgtattgaat ggctccaggc atattttctt gttcttgatg atattatgga taactccgtc  300
acacgacgcg gtcaaccctg ttggtttaga gtgcccaagg ttgggatgat tgcagtaaat  360
gatggagttc tacttcgaaa tcatattcct agaattctca agaatcactt caaggggaag  420
ccatattacg tggatctgct tgatttgttt aacgaggtcg agtttcaaac agcatcagga  480
caaatgatag atttgataac cactattgaa ggagaaaaag atctttccaa atacgcgttg  540
tcaattcatc ggcgaattgt acagtacaag actgcctatt attcatttta ccttccagtc  600
gcatgtgcac tagttatatc aggtgaagat cttgacaaac atactgtggt taaggacatt  660
cttgtccaga tgggtgtcta tttccaagtt caggatgact atctagattg ttttggcgat  720
cctgaaacca tcggaaaggt gggaacagac attgaagatt tcaaatgttc ttggttggtt  780
gtgaaggctt tggaactttg caacgaggaa cagaataaat tattacatga ggcttatggg  840
aaaccagacc cagaaaatgt tgccaaagta aaggccctct acaaggagct tgatcttcag  900
ggtgtatttg cgaaatatga gagccagagc tacgctaaac tgaatgcctc cattgaagct  960
catcccagca aatcaattca agcagttctc aagtctttct tgggaaaaat atacaagcgc  1020
cagaagtga                                                         1029

SEQ ID NO: 168         moltype = AA  length = 342
FEATURE                Location/Qualifiers
source                 1..342
                       mol_type = protein
                       organism = Siraitia grosvenorii
```

```
SEQUENCE: 168
MADLKSTFLK VYSVLKEELL QDPAFEFTDA SRQWIERMLD YNVPGGKLNR GLSVIDSYRL  60
LKEGKELTED EIFLASVLGW CIEWLQAYFL VLDDIMDNSV TRRGQPCWFR VPKVGMIAVN  120
DGVLLRNHIP RILKNHFKGK PYYVDLLDLF NEVEFQTASG QMIDLITTIE GEKDLSKYAL  180
SIHRRIVQYK TAYYSFYLPV ACALVISGED LDKHTVVKDI LVQMGVYFQV QDDYLDCFGD  240
PETIGKVGTD IEDFKCSWLV VKALELCNEE QNKLLHEAYG KPDPENVAKV KALYKELDLQ  300
GVFAKYESQS YAKLNASIEA HPSKSIQAVL KSFLGKIYKR QK                    342

SEQ ID NO: 169         moltype = DNA  length = 1254
FEATURE                Location/Qualifiers
source                 1..1254
                       mol_type = other DNA
                       organism = synthetic construct
SEQUENCE: 169
atgggcagct tgggggcgat tctgagacac ccagatgact tttacccgct tctgaaactg  60
aagatggccg cgaggcatgc ggagaagcag atcccgccgg agccccattg gggattctgc  120
tacaccatgc tgcacaaggt atcccggagt tttgctctcg ttattcagca gcttgcaccc  180
gagcttcgga atgctatatg catattttat cttgttctgc gagccctcga caccgttgag  240
gatgatacaa gtatacaaac agatatcaaa gtgcccattc tgaaagcttt tcactgccac  300
atatataacc gtgattggca tttttcatgt ggcacaaagg attataaagt tcttatggac  360
cagtttcatc atgtttcaac tgcgtttcta gaacttggga aagggtatca ggaggcaatt  420
gaggatatca cgaaacggat gggggcagga atggctaaat tcatttgcaa agaggtagag  480
acagttgatg attacgatga atattgccac tacgtagctg gacttgttgg actaggtttg  540
tctaagctgt tccatgcttc ggatttagag gatttggcac ctgattctct ttcaaattct  600
atgggattgt ttcttcagaa aacaaacatt attcgagatt acttggagga catcaacgag  660
ataccaaagt ctcggatgtt ttggccccgt gagatttggg gcaaatatgc cgataaacta  720
gaggatttta aatatgagga gaattcggtc aaggccgtgc aatgcctcaa cgatttggtc  780
actaatgctt tgaatcatgt ggaggattgt ctgaaataca tgtcaaactt aagagatctt  840
tccatatttc gattttgtgc aattcctcag attatggcga ttggaactct agcattatgc  900
tacaacaacg ttgaagtttt caggggggtg gtcaaaatgc ggcggggtct tactgctaag  960
gtcattgatc gtacacaaac gatggctgac gtctatggag ctttcttcga tttttctgtt  1020
atgctgaagg ctaaggtcaa cagcagtgat cctaatgcta ctaaaaccct gagcaggatc  1080
gaagcaatac agaaaacatg cgagcagtcg ggactcttga acaaaaggaa attatatgca  1140
gttaaaagtg agccaatgtt caacccgact ctgattgtca tacttttcag cctattgtgc  1200
atcattctcg catatctctc tgccaaacgg ttaccggcta accaacctgt atga        1254

SEQ ID NO: 170         moltype = AA  length = 417
FEATURE                Location/Qualifiers
source                 1..417
                       mol_type = protein
                       organism = Siraitia grosvenorii
SEQUENCE: 170
MGSLGAILRH PDDFYPLLKL KMAARHAEKQ IPPEPHWGFC YTMLHKVSRS FALVIQQLAP  60
ELRNAICIFY LVLRALDTVE DDTSIQTDIK VPILKAFHCH IYNRDWHFSC GTKDYKVLMD  120
QFHHVSTAFL ELGKGYQEAI EDITKRMGAG MAKFICKEVE TVDDYDEYCH YVAGLVGLGL  180
SKLFHASDLE DLAPDSLSNS MGLFLQKTNI IRDYLEDINE IPKSRMFWPR EIWGKYADKL  240
EDFKYEENSV KAVQCLNDLV TNALNHVEDC LKYMSNLRDL SIFRFCAIPQ IMAIGTLALC  300
YNNVEVFRGV VKMRRGLTAK VIDRTQTMAD VYGAFFDFSV MLKAKVNSSD PNATKTLSRI  360
EAIQKTCEQS GLLNKRKLYA VKSEPMFNPT LIVILFSLLC IILAYLSAKR LPANQPV     417

SEQ ID NO: 171         moltype = DNA  length = 1503
FEATURE                Location/Qualifiers
source                 1..1503
                       mol_type = other DNA
                       organism = synthetic construct
SEQUENCE: 171
atggccgtag ttgcttcagc tcctgggaaa gtcctattga cgggaggata cctgattttg  60
gagaggccaa atgctggttt ggtactcagt acaaatgctc ggttttatgc aattgtgaaa  120
ccacttcacg agcataccga gccagaaagt gggggtggga aatgggtaga tgtgaaattg  180
acctcaccac agctctgccg tgaaagtcta tataagttgt caccagagaa ctttacgatt  240
cagtgtatct cctcgattga gttgaggaac cctttcgtgg aacatgcagt tcaatattct  300
gtagccgccg cacatggaat atttgacaag aacaagaaag attcactgca cagattgctt  360
ctgcaaggcc tcgatatcac aattttaggt tgcaatgatt tctactctta tcggaatcag  420
attgaagcac gtggacttcc tttgacacca gaatcactga tttcttttcc accatttgca  480
tcaattacct tcaatgctga agaatcaaat agtgaaaatt gcaagcctga agttgcgaag  540
actggattgg gatcttctgc tgcaatgaca actgctgttg ttgctgccct acttaattat  600
cttggagttg taaatctttc ctcaccaaga ggtcaagaca aagaaaatga tattaaggat  660
cttgatatgg tgcatgtaat agcccaaact gctcattgca ttgcacaggg gaaagttgga  720
agtggatttg atgtctgttc tgcagtctat ggcagccaac gttatgttcg tttttcacct  780
gaagtgcttg ctactgctca ggtagcagtt aaaggaccac tagaagaggt cattgtcaat  840
atcctaaaag gaaagtggga ccatgagagg actgagtttt ccttgcctcc attaatgaat  900
ctcttattag gggaaccagg agcaggagga tcatcgacac catctatggt aggtgctgtt  960
aaaaagtggc aaaagtctga ccctcagaaa tctcaagaaa catggaataa gttgtcggaa  1020
gcaaatttgg gcctcgaaaa acaactaaac ttactaagaa aacttgcagc agaacactgg  1080
gatgtatata aatgcatcat aagcggatgc agcatacttg gatcaaagaa gtggatggaa  1140
caagccactg aacaaagcca acaagccatc gtcaaagcat tgttaggagc aagagacgcc  1200
atgctcgaga tacggaatca tatgcggcaa atgggcgaag ctgccggtgt tccaattgag  1260
ccaaagtcac aaactcagct tctggatgca accatggaat tggaaggagt cctgttggct  1320
ggagttccag ggccggtggg gtttgatgct gtattcgcta ttaccttggg tgattctagc  1380
```

```
aggcatgtga ttgagtcatg gacttcactc aatgttcttg ccctcttagt tagagaagat  1440
cccaatggag ttgctctaga aagtggtgat cctagaagta agaatattgc accttctgtt  1500
taa                                                                1503

SEQ ID NO: 172          moltype = AA  length = 500
FEATURE                 Location/Qualifiers
source                  1..500
                        mol_type = protein
                        organism = Siraitia grosvenorii
SEQUENCE: 172
MAVVASAPGK VLLTGGYLIL ERPNAGLVLS TNARFYAIVK PLHEHTEPES GGGKWVDVKL  60
TSPQLCRESL YKLSPENFTI QCISSIELRN PFVEHAVQYS VAAAHGIFDK NKKDSLHRLL  120
LQGLDITILG CNDFYSYRNQ IEARGLPLTP ESLISFPPFA SITFNAEESN SENCKPEVAK  180
TGLGSSAAMT TAVVAALLNY LGVVNLSSPR GQDKENDIKD LDMVHVIAQT AHCIAQGKVG  240
SGFDVCSAVY GSQRYVRFSP EVLATAQVAV KGPLEEVIVN ILKGKWDHER TEFSLPPLMN  300
LLLGEPGAGG SSTPSMVGAV KKWQKSDPQK SQETWNKLSE ANLGLEKQLN LLRKLAAEHW  360
DVYKCIISGC SILGSKKWME QATEQSQQAI VKALLGARDA MLEIRNHMRQ MGEAAGVPIE  420
PKSQTQLLDA TMELEGVLLA GVPGAGGFDA VFAITLGDSS RHVIESWTSL NVLALLVRED  480
PNGVALESGD PRSKNIAPSV                                              500

SEQ ID NO: 173          moltype = DNA  length = 1275
FEATURE                 Location/Qualifiers
source                  1..1275
                        mol_type = other DNA
                        organism = synthetic construct
SEQUENCE: 173
atggccccgg agaagatgcc ggaggaggac gaggagatcg tcgccggggt ggtcgcgggc  60
aagatcccct cctacgtcct ggaaacccgg ctgggcgact gccggcgggc ggcggggatc  120
cgccgcgagg cgctccggcg gatcaccggg cgggagatcg acggcctgcc cctggacggg  180
ttcgactacg acagcatcct ggggcagtgc tgcgagatgc cggtgggcta cgtccagctg  240
ccggtgggcg tggccggccc gctcgtgctg gacggccgcc gcatctacgt gccgatggcc  300
acgaccgagg ggtgcctgat cgcgagcacg aaccgcggct gcaaggcgat cgcggagagc  360
gggggcgcgt ccagcgtcgt ctaccgggac ggcatgaccc gggcgccggt cgccaggttc  420
ccctccgccc ggcgcgccgc cgagctgaag ggcttcctgg agaaccccgc caactacgac  480
accctgtccg tggtcttcaa ccggtcctcc cgcttcgcga ggctgcaggg cgtgaagtgc  540
gcgatggcgg gcggaacct gtacatgcgc ttcacgtgct ccaccggcga cgcgatgggc  600
atgaacatgg tgagcaaggg ggtgcagaac gtgctcgact acctccagga ggacttcccg  660
gacatggacg tcgtgtccat ctccggcaac ttctgctccg acaagaagtc cgcggccgtg  720
aactggatcg aggggcgcgg gaagagcgtc gtctgcgagg cggtgatccg ggaggaggtg  780
gtgcacaagg tgctgaagac caacgtgcag tccctggtgg agctgaacgt gatcaagaac  840
ctggcgggca gcgccgtggc gggggcgctg ggcgggttca acgcccacgc ctccaacatc  900
gtgacggcga tcttcatcgc gacgggccag gacccggcgc agaacgtgga gtcctcccag  960
tgcatcacca tgctcgaggc ggtcaacgac gggagggacc tgcacatcag cgtgacgatg  1020
ccgagcatcg aggtggggac cgtcggcggc gggacccagc tcgcctccca gtccgcgtgc  1080
ctcgacctgc tcggggtgaa gggggccaac cgcgaatccc cgggatctaa cgcacgcctt  1140
ctggccaccg tggtcgccgg cgcggtgctg gcgggggagc tctccctgat cagcgcccag  1200
gccgcgggcc acctggtcca gtcccacatg aagtacaaca ggtcctccaa ggacatgtcc  1260
aagatcgcct gctga                                                   1275

SEQ ID NO: 174          moltype = AA  length = 424
FEATURE                 Location/Qualifiers
source                  1..424
                        mol_type = protein
                        organism = Avena strigosa
SEQUENCE: 174
MAPEKMPEED EEIVAGVVAG KIPSYVLETR LGDCRRAAGI RREALRRITG REIDGLPLDG  60
FDYDSILGQC CEMPVGYVQL PVGVAGPLVL DGRRIYVPMA TTEGCLIAST NRGCKAIAES  120
GGASSVVYRD GMTRAPVARF PSARRAAELK GFLENPANYD TLSVVFNRSS RFARLQGVKC  180
AMAGRNLYMR FTCSTGDAMG MNMVSKGVQN VLDYLQEDFP DMDVVSISGN FCSDKKSAAV  240
NWIEGRGKSV VCEAVIREEV VHKVLKTNVQ SLVELNVIKN LAGSAVAGAL GGFNAHASNI  300
VTAIFIATGQ DPAQNVESSQ CITMLEAVND GRDLHISVTM PSIEVGTVGG GTQLASQSAC  360
LDLLGVKGAN RESPGSNARL LATVVAGAVL AGELSLISAQ AAGHLVQSHM KYNRSSKDMS  420
KIAC                                                               424

SEQ ID NO: 175          moltype = DNA  length = 1572
FEATURE                 Location/Qualifiers
source                  1..1572
                        mol_type = other DNA
                        organism = synthetic construct
SEQUENCE: 175
atggaggaca ggaacgccat ggacatgagc aggatcaagt acaggccgca gccgctgagg  60
ccggccagca tggtgcagcc gagggtgctg ctgttcccgt tcccggccct gggccacgtg  120
aagccgttcc tgagcctggc cgagctgctg agcgacgccg gcatcgacgt ggtgttcctg  180
agcaccgagt acaaccacag gaggatcagc aacaccgagg ccctggccag caggttcccg  240
accctgcact tcgaaaccat cccggacggc ctgccgccga acgagagcag ggccctggcc  300
gacggcccgc tgtacttcag catgagggag ggcaccaagc cgaggttcag gcagctgatc  360
cagagcctga acgacggtag gtggccgatc acctgtatca tcaccgacat catgctgagc  420
agcccgatcg aggtggccga ggagttcggc atcccggtga tcgccttctg cccgtgcagc  480
gccaggtacc tgagcatcca cttcttcatc ccgaagctgg tggaggaggg ccagatcccg  540
```

```
tacgccgacg acgacccgat cggcgagatc cagggcgtgc cgctgttcga gggcctgctg  600
aggaggaacc atctgccggg cagctggagc gacaagagcg ccgacatcag cttcagccac  660
ggcctgatca accagaccct ggccgccggc agggccagcg ccctgatcct gaacaccttc  720
gacgagctgg aggccccgtt cctgacccac ctgagcagca tcttcaacaa gatctacacc  780
atcggcccgc tgcacgccct gagcaagagc aggctgggcg acagcagcag cagcgccagc  840
gccctgagcg gcttctggaa ggaggacagg gcctgcatga gctggctgga ctgccagccg  900
ccgaggagcg tggtgttcgt gagcttcggc agcaccatga agatgaaggc cgacgagctg  960
agggagttct ggtacggcct ggtgagcagc ggcaagccgt tcctgtgcgt gctgaggagc  1020
gacgtggtga gcggcggcga ggccgccgag ctgatcgagc agatggccga ggaggagggc  1080
gccggcggca agctgggcat ggtggtggag tgggccgccc aggagaaggt gctgagccac  1140
ccggccgtgg gcggcttcct gacccactgc ggctggaaca gcaccgtgga gagcatcgcc  1200
gccggcgtgc cgatgatgtg ctggccgatc ctgggcgacc agccgagcaa cgccacctgg  1260
atcgacaggg tgtggaagat cggcgtggag aggaacaaca gggagtggga caggctgacc  1320
gtggagaaga tggtgagggc cctgatggag ggccagaaga gggtggagat ccagaggagc  1380
atggagaagc tgagcaagct ggccaacgag aaggtggtga ggggcatcaa cctgcacccg  1440
accatcagcc tgaagaagga caccccgacc accagcgagc acccgaggca cgagttcgag  1500
aacatgaggg gcatgaacta cgagatgctg gtgggcaacg ccatcaagag cccgaccctg  1560
accaagaagt aa                                                      1572

SEQ ID NO: 176         moltype = AA  length = 523
FEATURE                Location/Qualifiers
source                 1..523
                       mol_type = protein
                       organism = Siraitia grosvenorii
SEQUENCE: 176
MEDRNAMDMS RIKYRPQPLR PASMVQPRVL LFPFPALGHV KPFLSLAELL SDAGIDVVFL  60
STEYNHRRIS NTEALASRFP TLHFETIPDG LPPNESRALA DGPLYFSMRE GTKPRFRQLI  120
QSLNDGRWPI TCIITDIMLS SPIEVAEEFG IPVIAFCPCS ARYLSIHFFI PKLVEEGQIP  180
YADDDPIGEI QGVPLFEGLL RRNHLPGSWS DKSADISFSH GLINQTLAAG RASALILNTF  240
DELEAPFLTH LSSIFNKIYT IGPLHALSKS RLGDSSSSAS ALSGFWKEDR ACMSWLDCQP  300
PRSVVFVSFG STMKMKADEL REFWYGLVSS GKPFLCVLRS DVVSGGEAAE LIEQMAEEEG  360
AGGKLGMVVE WAAQEKVLSH PAVGGFLTHC GWNSTVESIA AGVPMMCWPI LGDQPSNATW  420
IDRVWKIGVE RNNREWDRLT VEKMVRALME GQKRVEIQRS MEKLSKLANE KVVRGINLHP  480
TISLKKDTPT TSEHPRHEFE NMRGMNYEML VGNAIKSPTL TKK                    523

SEQ ID NO: 177         moltype = DNA  length = 1458
FEATURE                Location/Qualifiers
source                 1..1458
                       mol_type = other DNA
                       organism = synthetic construct
SEQUENCE: 177
atggccgagc aggcccacga cctgctgcac gtgctgctgt tcccgttccc ggccgagggc  60
cacatcaagc cgttcctgtg cctggccgag ctgctgtgca acgccggctt ccacgtgacc  120
ttcctgaaca ccgactacaa ccacaggagg ctgcacaacc tgcacctact ggccgccagg  180
ttcccgagcc tgcacttcga gagcatcagc gacggcctgc cgccggacca gccgagggac  240
atcctggacc cgaagttctt catcagcatc tgccaggtga ccaagccgct gttcagggag  300
ctgctgctga gctacaagag gatcagcagc gtgcagaccg gcaggccgcc gatcacatgc  360
gtgatcaccg acgtgatctt caggttcccg atcgacgtgg ccgaggagct ggacatcccg  420
gtgttcagct tctgcacctt cagcgccagg ttcatgttcc tgtacttctg gatcccgaag  480
ctgatcgagg acggccagct gccgtacccg aacggcaaca tcaaccagaa gctgtacggc  540
gtggccccgg aggccgaggg cctgctgagg tgcaaggacc tgccgggcca ctgggccttc  600
gccgacgagc tgaaggacga ccagctgaac ttcgtggacc agaccaccgc cagcagcagg  660
agcagcggcc tgatcctgaa caccttcgac gacctggagg ccccgttcct gggcaggctg  720
agcaccatct tcaagaagat ctacgccgtg ggcccgatcc acagcctgct gaacagccac  780
cactgcggcc tgtggaagga ggaccacagc tgcctggcct ggctggacag cagggccgcc  840
aagagcgtgg tgttcgtgag cttcggcagc ctggtgaaga tcaccagcag gcagctgatg  900
gagttctggc acggcctgct gaacagcggc aagagcttcc tgttcgtgct gaggagcgac  960
gtggtggagg gcgacgacga gaagcaagtg gtgaaggaga tctacgaaac caaggccgag  1020
ggcaagtggc tggtggtggg ctgggccccg caggagaagg tgctggccca cgaggccgtg  1080
ggcggcttcc tgacccacag cggctggaac agcatcctgg agagcatcgc cgccggcgtg  1140
ccgatgatca gctgcccgaa gatcggcgac cagagcagca actgcacctg gatcagcaag  1200
gtgtggaaga tcggcctgga gatggaggac aggtacgaca gggtgagcgt ggaaaccatg  1260
gtgaggagca tcatggagca ggagggcgag aagatgcaga agaccatcgc cgagctggcc  1320
aagcaggcca agtacaaggt gagcaaggac ggcaccagct accagaacct ggagtgcctg  1380
atccaggaca tcaagaagct gaaccagatc gagggcttca tcaacaaccc gaacttcagc  1440
gacctgctga gggtgtaa                                                1458

SEQ ID NO: 178         moltype = AA  length = 485
FEATURE                Location/Qualifiers
source                 1..485
                       mol_type = protein
                       organism = Siraitia grosvenorii
SEQUENCE: 178
MAEQAHDLLH VLLFPFPAEG HIKPFLCLAE LLCNAGFHVT FLNTDYNHRR LHNLHLLAAR  60
FPSLHFESIS DGLPPDQPRD ILDPKFFISI CQVTKPLFRE LLLSYKRISS VQTGRPPITC  120
VITDVIFRFP IDVAEELDIP VFSFCTFSAR FMFLYFWIPK LIEDGQLPYP NGNINQKLYG  180
VAPEAEGLLR CKDLPGHWAF ADELKDDQLN FVDQTTASSR SSGLILNTFD DLEAPFLGRL  240
STIFKKIYAV GPIHSLLNSH HCGLWKEDHS CLAWLDSRAA KSVVFVSFGS LVKITSRQLM  300
EFWHGLLNSG KSFLFVLRSD VVEGDDEKQV VKEIYETKAE GKWLVVGWAP QEKVLAHEAV  360
```

```
GGFLTHSGWN SILESIAAGV PMISCPKIGD QSSNCTWISK VWKIGLEMED RYDRVSVETM  420
VRSIMEQEGE KMQKTIAELA KQAKYKVSKD GTSYQNLECL IQDIKKLNQI EGFINNPNFS  480
DLLRV                                                              485

SEQ ID NO: 179         moltype = DNA  length = 1380
FEATURE                Location/Qualifiers
source                 1..1380
                       mol_type = other DNA
                       organism = synthetic construct
SEQUENCE: 179
atggatgccc agcaaggtca caccaccacc attttgatgc ttccatgggt cggctacggc  60
catctcttgc ctttcctcga gctggccaaa agcctctcca ggaggaaatt attccacatc  120
tacttctgtt caacgtctgt tagcctcgac gccattaaac caaagcttcc tccttctatc  180
tcttctgatg attccatcca acttgtggaa cttcgtctcc cttcttctcc tgagttacct  240
cctcatcttc acacaaccaa cggccttccc tctcacctca tgcccgctct ccaccaagcc  300
ttcgtcatgg ctgcccaaca ctttcaggtc attttacaaa cacttgcccc gcatctcctc  360
atttatgaca ttctccaacc ttgggctcct caagtggctt catccctcaa cattccagcc  420
atcaacttca gtactaccgg agcttcaatg ctttctcgaa cgcttcaccc cactcactac  480
ccaagttcta aattcccaat ctcagagttt gttcttcaca atcactggag agccatgtac  540
accaccgccg atggggctct tacagaagaa ggccacaaaa ttgaagaaaa acttacgaat  600
tgcttgcata cttcttgcgg ggtagttttg gtcaatagtt tcagagagct tgagacgaaa  660
tatatcgatt atctctctgt tctcttgaac aagaaagttg ttccggtcgg tcctttggtt  720
tacgaaccga atcaagaagg ggaagatgaa ggttattcaa gcatcaaaaa ttggcttgac  780
gaaaaggaac cgtcctcaac cgtcttcgtt tcatttggaa ccgaatactt cccgtcaaag  840
gaagaaacgg aagagatagc gtacgggtta gagctgagcg aggttaattt catctgggtc  900
cttagatttc ctcaaggaga cagaaccagc accattgaag acgccttgcc gaaggggttt  960
ctggagagag cgggagagag ggcgatggtg gtgaagggtt gggctcctca ggcgaagata  1020
ctgaaacatt ggagcacagg ggggcttgtg agtcactgtg gatggaactc gatgatggag  1080
ggcatgatgt ttggcgtacc cataatagcg gttccgatgc atctggacca gccctttaac  1140
gccggactcg tggaagaagc tggcgtcggc gtggaagcca agcgagattc ggacggcaaa  1200
attcaaagag aagaagttgc aaagtcgatc aaagaagtgg tgattgagaa aaccagggaa  1260
gacgtgagga agaaagcaag agaaatgggt gagattttga ggagtaaagg agatgagaaa  1320
attgatgtgt tggtggctga aatttctctt ttgcgcaaaa aggctccatg ttcaatttaa  1380

SEQ ID NO: 180         moltype = AA  length = 459
FEATURE                Location/Qualifiers
source                 1..459
                       mol_type = protein
                       organism = Siraitia grosvenorii
SEQUENCE: 180
MDAQQGHTTT ILMLPWVGYG HLLPFLELAK SLSRRKLFHI YFCSTSVSLD AIKPKLPPSI  60
SSDDSIQLVE LRLPSSPELP PHLHTTNGLP SHLMPALHQA FVMAAQHFQV ILQTLAPHLL  120
IYDILQPWAP QVASSLNIPA INFSTTGASM LSRTLHPTHY PSSKFPISEF VLHNHWRAMY  180
TTADGALTEE GHKIEEKLTN CLHTSCGVVL VNSFRELETK YIDYLSVLLN KKVVPVGPLV  240
YEPNQEGEDE GYSSIKNWLD EKEPSSTVFV SFGTEYFPSK EETEEIAYGL ELSEVNFIWV  300
LRFPQGDRTS TIEDALPKGF LERAGERAMV VKGWAPQAKI LKHWSTGGLV SHCGWNSMME  360
GMMFGVPIIA VPMHLDQPFN AGLVEEAGVG VEAKRDSDGK IQREEVAKSI KEVVIEKTRE  420
DVRKKAREMG EILRSKGDEK IDVLVAEISL LRKKAPCSI                        459

SEQ ID NO: 181         moltype = DNA  length = 1422
FEATURE                Location/Qualifiers
source                 1..1422
                       mol_type = other DNA
                       organism = synthetic construct
SEQUENCE: 181
atggatgctc aacaaggaca tactactact attcttatgc ttccttgggt tggatatgga  60
catcttcttc cttttcttga acttgctaag tctctttcta gaagaaagct tttttcatatt  120
tatttttgtt ctacttctgt ttctcttgat gctattaagc ctaagcttcc tccttctatt  180
tcttctgatg attctattca acttgttgaa cttagacttc cttcttctcc tgaacttcct  240
cctcatcttc atactactaa tggacttcct tctcatctta tgcctgctct tcatcaagct  300
tttgttatgg ctgctcaaca ttttcaagtt attcttcaaa ctcttgctcc tcatcttctt  360
atttatgata ttcttcaacc ttgggctcct caagttgctt cttctcttaa tattcctgct  420
attaattttt ctactactgg agcttctatg ctttctagaa ctcttcatcc tactcattat  480
ccttcttcta agtttcctat ttctgaattt gttcttcata atcattggag agctatgtat  540
actactgctg atggagctct tactgaagaa ggacataaga ttgaagaaac tcttgctaat  600
tgtcttcata cttcttgtgg agttgttctt gttaattctt ttagagaact tgaaactaag  660
tatattgatt atctttctgt tcttcttaat aagaaggttg ttcctgttgg acctcttgtt  720
tatgaaccta atcaagaagg agaagatgaa ggatattctt ctattaagaa ttggcttgat  780
aagaaggaac cttcttctac tgtttttgtt tcttttggaa ctgaatattt tccttctaag  840
gaagaaatgg aagaaattgc ttatggactt gaactttctg aagttaattt tatttgggtt  900
cttagatttc ctcaaggaga ttctacttct actattgaag atgctcttcc taagggattt  960
cttgaaagag ctggagaaag agctatggtt gttaagggat gggctcctca agctaagatt  1020
cttaagcatt ggtctactgg aggacttgtt tctcattgtg gatggaattc tatgatggaa  1080
ggaatgatgt ttggagttcc tattattgct gttcctatgc atcttgatca accttttaat  1140
gctggacttg ttgaagaagc tggagttgga gttgaagcta agagagattc tgatggaaag  1200
attcaaagag aagaagttgc taagtctatt aaggaagttg ttattgaaaa gactagagaa  1260
gatgttagaa agaaggctag agaaatggat actaagcatg gacctactta tttttctaga  1320
tctaaggttt cttcttttgg aagactttat aagattaata gacctactac tcttactgtt  1380
ggaagatttt ggtctaagca aattaagatg aagagagaat aa                    1422
```

```
SEQ ID NO: 182          moltype = AA  length = 473
FEATURE                 Location/Qualifiers
source                  1..473
                        mol_type = protein
                        organism = Siraitia grosvenorii
SEQUENCE: 182
MDAQQGHTTT ILMLPWVGYG HLLPFLELAK SLSRRKLFHI YFCSTSVSLD AIKPKLPPSI  60
SSDDSIQLVE LRLPSSPELP PHLHTTNGLP SHLMPALHQA FVMAAQHFQV ILQTLAPHLL  120
IYDILQPWAP QVASSLNIPA INFSTTGASM LSRTLHPTHY PSSKFPISEF VLHNHWRAMY  180
TTADGALTEE GHKIEETLAN CLHTSCGVVL VNSFRELETK YIDYLSVLLN KKVVPVGPLV  240
YEPNQEGEDE GYSSIKNWLD KKEPSSTVFV SFGTEYFPSK EEMEEIAYGL ELSEVNFIWV  300
LRFPQGDSTS TIEDALPKGF LERAGERAMV VKGWAPQAKI LKHWSTGGLV SHCGWNSMME  360
GMMFGVPIIA VPMHLDQPFN AGLVEEAGVG VEAKRDSDGK IQREEVAKSI KEVVIEKTRE  420
DVRKKAREMD TKHGPTYFSR SKVSSFGRLY KINRPTTLTV GRFWSKQIKM KRE         473

SEQ ID NO: 183          moltype = DNA  length = 1422
FEATURE                 Location/Qualifiers
source                  1..1422
                        mol_type = other DNA
                        organism = synthetic construct
SEQUENCE: 183
atgactattt ttttttctgt tgaaattctt gttcttggaa ttgctgaatt tgctgctatt  60
gctatggatg ctgcccaaca aggtgacacc acaaccattt tgatgcttcc atggctcggc  120
tatggccatc tttcagcttt tctcgagctg gccaaaagcc tctcaaggag gaacttccat  180
atctacttct gttcaacctc tgttaatctt gacgccatta aaccaaagct tccttcttct  240
ttctctgatt ccattcaatt tgtggagctc catctccctt cttctcctga gttccctcct  300
catcttcaca caaccaacgg ccttcccct accctcatgc ccgctctcca ccaagccttc  360
tccatggctg cccagcactt tgagtccatt ttacaaacac ttgccccgca ccttctcatt  420
tatgactctc ttcaaccttg ggctcctcgg gtagcttcat ccctcaaaat tccggccatc  480
aacttcaata ccacgggagt tttcgtcatt tctcaagggc ttcaccctat tcactaccca  540
cattctaaat tcccattctc agagttcgtt cttcacaatc attggaaagc catgtactcc  600
actgccgatg gagcttctac cgaaagaacc cgcaaacgtg gagaagcgtt tctgtattgc  660
ttgcatgctt cttgtagtgt aattctaatc aatagtttca gagagctcga ggggaaatat  720
atggattatc tctctgttct cttgaacaag aaagttgttc cggttggtcc tttggtttac  780
gaaccgaatc aagacgggga agatgaaggt tattcaagca tcaaaaattg gcttgacaaa  840
aaggaaccgt cctccaccgt cttcgtgtca tttggaagcg aatacttccc gtcaaaggaa  900
gaaatggaag agatagccca tgggttagag gcgagcgagg ttaatttcat ctgggtcgtt  960
aggtttcctc aaggagacaa caccagcggc attgaagatg ccttgccgaa gggttttctg  1020
gagagggcgg gagagagagg gatggtggtg aagggttggg ctcctcaggc gaagatactg  1080
aagcattgga gcacaggggg attcgtgagc cactgtggat ggaactcggt gatggagagc  1140
atgatgtttg gcgttcccat aataggggtt ccgatgcatg tggaccagcc ctttaacgcc  1200
ggactcgtgg aagaagctgg cgtcggcgtg gaggccaagc gagatccaga cggcaaaatt  1260
caaagagacg aagttgcaaa gttgatcaaa gaagtggtgg ttgagaaaac cagagaagat  1320
gtgcggaaga aagcaagaga aatgagtgag attttgagga gcaagggaga ggagaagttt  1380
gatgagatgg tcgctgaaat ttctctcttg cttaaaatat aa                    1422

SEQ ID NO: 184          moltype = AA  length = 473
FEATURE                 Location/Qualifiers
source                  1..473
                        mol_type = protein
                        organism = Siraitia grosvenorii
SEQUENCE: 184
MTIFFSVEIL VLGIAEFAAI AMDAAQQGDT TTILMLPWLG YGHLSAFLEL AKSLSRRNFH  60
IYFCSTSVNL DAIKPKLPSS FSDSIQFVEL HLPSSPEFPP HLHTTNGLPP TLMPALHQAF  120
SMAAQHFESI LQTLAPHLLI YDSLQPWAPR VASSLKIPAI NFNTTGVFVI SQGLHPIHYP  180
HSKFPFSEFV LHNHWKAMYS TADGASTERT RKRGEAFLYC LHASCSVILI NSFRELEGKY  240
MDYLSVLLNK KVVPVGPLVY EPNQDGEDEG YSSIKNWLDK KEPSSTVFVS FGSEYFPSKE  300
EMEEIAHGLE ASEVNFIWVV RFPQGDNTSG IEDALPKGFL ERAGERGMVV KGWAPQAKIL  360
KHWSTGGFVS HCGWNSVMES MMFGVPIIGV PMHVDQPFNA GLVEEAGVGV EAKRDPDGKI  420
QRDEVAKLIK EVVVEKTRED VRKKAREMSE ILRSKGEEKF DEMVAEISLL LKI         473

SEQ ID NO: 185          moltype = DNA  length = 1599
FEATURE                 Location/Qualifiers
source                  1..1599
                        mol_type = other DNA
                        organism = synthetic construct
SEQUENCE: 185
atgttaatgc atgcattgac tcctacagct ccatttttct ccataaagcc aaataccgaa  60
cctccatcag ccactactcg tcagccacca atggattctc caccacaaaa acctcacttc  120
ttgttgtttc cattcatggc tcaaggtcac atgatcccta tgattgactt agctaagttg  180
ttagcccaaa gaggggctat tatcaccgtc gttaccactc cacataacgc tgccagatat  240
cactctgttt tggctagagc tattgattcc ggtttgcata ttcacgtctt gcaattacaa  300
ttcccatgta acgagggtgg tttgccagaa ggttgcgaaa actttgactt gttgccatct  360
ttaggttcag cctctacttt ctttagagca accttcttat tgtacgaacc ttctgaaaag  420
gttttcgaag aattgatccc aagacctaca tgtatcatat ccgacatgtg tttaccatgg  480
acagtccgtt tggctcagaa ataccacgtt ccaagattgg ttttttattc cttgtcatgt  540
tttttcttgt tgtgcatgag atctttgaag aataaccaag ctttaatttc ttctaagtcc  600
gattctgagt tggtcacttt ttccgatttg ccagatccag tcgaattttt aaaatcacaa  660
```

```
ttgcctaagt ctaatgacga agaaatggct aagttcggtt acgagatcgg tgaagctgat  720
agacaatccc atggtgttat tgttaacgtt ttcgaagaga tggaaccaaa atacttagca  780
gaatatagaa aggaaagaga atctcctgaa aaggtctggt gtgttggtcc agtctccttg  840
tgtaatgaca acaagttaga caaagcccaa cgtggtaaca aggcttcaat tgatgaaaga  900
gaatgtatcg agtggttgga cggtcaacaa ccatcttctg ttgtttacgt ctctttaggt  960
tctttgtgta acttagttac cgcccaattg attgagttgg gtttgggttt agaagcttct  1020
aacaagccat tcatttgggt tatcagaaaa ggtaatatta ccgaagaatt acagaaatgg  1080
ttggtcgaat atgacttcga ggaaaagact aagggtcgtg gtttggttat attgggttgg  1140
gctccacaag tcttgatttt atcccatcca gcaatcggtt gctttttaac acactgtggg  1200
tggaactcct ccatcgaagg tatctcagcc ggtatgccaa tgattacctg gccattgttc  1260
gctgatcaag ttttcaatga aaagttgatc gttgaaatct tgagaatagg tgtttctgtc  1320
ggtatggaaa ccgctatgca ttggggtgaa gaagaagaaa agggtgtcgt cgttaagaga  1380
gaaaaagtca gagaggcaat agaaagagca atggatggtg acgaaagaga agaacgtcgt  1440
gagagatgca aggagttggc cgaaatggct aagagagctg ttgaagaagg tggttcatct  1500
cacagaaact tgactttgtt gactgaagat attttggtca atggtggtgg tcaggaaaga  1560
atggatgacg ccgatgactt cccaactatc gtcaactaa                         1599
```

```
SEQ ID NO: 186          moltype = AA  length = 532
FEATURE                 Location/Qualifiers
source                  1..532
                        mol_type = protein
                        organism = Siraitia grosvenorii
SEQUENCE: 186
MLMHALTPTA PFFSIKPNTE PPSATTRQPP MDSPPQKPHF LLFPFMAQGH MIPMIDLAKL  60
LAQRGAIITV VTTPHNAARY HSVLARAIDS GLHIHVLQLQ FPCNEGGLPE GCENFDLLPS  120
LGSASTFFRA TFLLYEPSEK VFEELIPRPT CIISDMCLPW TVRLAQKYHV PRLVFYSLSC  180
FFLLCMRSLK NNQALISSKS DSELVTFSDL PDPVEFLKSQ LPKSNDEEMA KFGYEIGEAD  240
RQSHGVIVNV FEEMEPKYLA EYRKERESPE KVWCVGPVSL CNDNKLDKAQ RGNKASIDER  300
ECIEWLDGQQ PSSVVYVSLG SLCNLVTAQL IELGLGLEAS NKPFIWVIRK GNITEELQKW  360
LVEYDFEEKT KGRGLVILGW APQVLILSHP AIGCFLTHCG WNSSIEGISA GMPMITWPLF  420
ADQVFNEKLI VEILRIGVSV GMETAMHWGE EEKGVVVKR EKVREAIERA MDGDEREERR  480
ERCKELAEMA KRAVEEGGSS HRNLTLLTED ILVNGGGQER MDDADDFPTI VN          532
```

```
SEQ ID NO: 187          moltype = DNA  length = 1377
FEATURE                 Location/Qualifiers
source                  1..1377
                        mol_type = other DNA
                        organism = synthetic construct
SEQUENCE: 187
atggaaaata aaactgaaac aactgttaga agaagaagaa gaatcatctt gttcccagtc  60
ccattccaag gtcatattaa cccaatcttg caactggcta atgtgctgta ctccaaaggt  120
ttttctatca ctatttttca tactaatttt aataaaccta aaacttctaa ttacccacat  180
ttcacattta gatttatttt ggacaatgac ccacaagacg agagaatctc caacctgcca  240
acccatggtc cattggccgg catgcgcatc ccaatcatca acgaacatgg tgccgatgaa  300
ttgcgcagag aacttgaatt gttgatgtta gcatctgaag aagacgagga agtttcctgt  360
ctgattactg acgctttgtg gtattttgct caatctgttg ctgattcttt gaatttgaga  420
agattggttt tgatgacatc ttctttgttt aattttcatg ctcatgttag tctaccacag  480
tttgatgagc ttggttactt agatccagat gataagacta gactagaaga acaagcttct  540
ggtttcccaa tgctaaaggt aaaggatatc aaatccgctt attccaattg gcaaatccta  600
aaggaaatat tgggtaaaat gatcaagcag acaagagctt cttctggtgt tatctggaac  660
tcttttaaag agctagagga gtctgaattg gaaacagtca ttagagaaat cccagctcca  720
tcttttctaa ttccattgcc aaaacatttg accgcatcat cttcttctct gctagaccat  780
gatagaactg ttttccaatg gttggatcaa caaccaccat cttccgtctt gtatgtttct  840
tttggctcca cttcagaggt ggacgagaaa gattttctgg aaattgctag aggtttagta  900
gatagtaaac agagtttttt atgggtagta agaccaggtt ttgttaaagg ttctacatgg  960
gttgagccac tacctgatgg ttttttgggt gaaagaggta gaatagttaa atgggtacca  1020
caacaagaag tcttggcaca tggtgccatt ggtgctttct ggacacattc tggatggaac  1080
tctacacttg aatctgtttg tgaaggtgtt ccaatgattt tctccgattt tggtttggat  1140
caaccattga atgctagata catgtcagac gtcctgaagg ttggtgttta cctggaaaac  1200
ggttgggaac gcggtgaaat cgccaacgcc attcgcagag tcatggtgga cgaggaaggt  1260
gaatacatta gacaaaatgc cagagtactt aagcaaaaag cagatgtctc tttgatgaaa  1320
ggtggttctt cttatgagtc tttggaatca ttagtgtctt atatctctag tctctaa     1377
```

```
SEQ ID NO: 188          moltype = AA  length = 458
FEATURE                 Location/Qualifiers
source                  1..458
                        mol_type = protein
                        organism = Siraitia grosvenorii
SEQUENCE: 188
MENKTETTVR RRRRIILFPV PFQGHINPIL QLANVLYSKG FSITIFHTNF NKPKTSNYPH  60
FTFRFILDND PQDERISNLP THGPLAGMRI PIINEHGADE LRRELELLML ASEEDEEVSC  120
LITDALWYFA QSVADSLNLR RLVLMTSSLF NFHAHVSLPQ FDELGYLDPD DKTRLEEQAS  180
GFPMLKVKDI KSAYSNWQIL KEILGKMIKQ TRASSGVIWN SFKELEESEL ETVIREIPAP  240
SFLIPLPKHL TASSSSLLDH DRTVFQWLDQ QPPSSVLYVS FGSTSEVDEK DFLEIARGLV  300
DSKQSFLWVV RPGFVKGSTW VEPLPDGFLG ERGRIVKWVP QQEVLAHGAI GAFWTHSGWN  360
STLESVCEGV PMIFSDFGLD QPLNARYMSD VLKVGVYLEN GWERGEIANA IRRVMVDEEG  420
EYIRQNARVL KQKADVSLMK GGSSYESLES LVSYISSL                          458
```

```
SEQ ID NO: 189          moltype = DNA  length = 1401
```

```
FEATURE                 Location/Qualifiers
source                  1..1401
                        mol_type = other DNA
                        organism = synthetic construct
SEQUENCE: 189
atgctgctcc agtccaaccc gatggagaac gagacggaga cgacggtgag ccgccggcgc  60
agaatattat tatttcctgt accatttcaa ggtcatataa atccaatgtt acaacttgca  120
aatgtccttt atagcaaagg attctccatc actattttcc ataccaattt caacagtcca  180
aagacctcaa attaccccca ctttactttt cgatttatcc tagacaatga cccccaagat  240
aaaagaattt ccaatctccc cacacacggc ccagcagctt caatcaggat tccatttttc  300
aatgagtaca gagccgatga attaagacgt gagctagaat tactcatgtt ggcttccgaa  360
gaagatggag aggtaagttg cctgattgca gatcagatat ggtattttac tcaatctgtc  420
gcggatagcc tcaatcttag aagattagtc ttggttacat cctcattgtt caacttccac  480
gcacatgtaa gcctaccgca attcgatgag ttaggatatt tggaccctga tgataaaact  540
cggctagaag agcaagcttc aggatttcct atgctaaaag taaaagatat aaaatgtagc  600
ttttctatgt ggaagaagta caaggaatat ttcgagaaca ttactaagca gacgaaagcg  660
tcatccggcg tgatttggaa tagctttaaa gaattggaag agtctgagct tgaaaccgta  720
attcgggaaa taccagcccc ttcttttctt attcctctac caaaacactt aacggcatct  780
tcgtcgtctt tattagatca cgatcgtaca gtgttcccgt ggctggatca acaacctagc  840
aggtcggtct tatacgtatc atttggaagt ggtactgagg tgttagatga aaaagacttt  900
ttagaaatag ctagaggttt ggttgactca aagcaatctt ttttgtgggt cgtcagaccc  960
ggcttcgtta aaggttcaac gtgggtcgaa cctctaccag atggtttctt gggtgaaaga  1020
ggtagaattg ttaagtgggt accacaacaa gaagtcctag ctcatggagc tataggtgca  1080
ttttggactc actcaggctg gaactcaaca ttggaatctg tgtgcgaggg agtaccaatg  1140
atcttctctg atttcggttt agatcagcct ctgaacgcaa ggtacatgtc ggatgtacta  1200
aaggtagggg tctatttgga aaatggatgg gagagaggag agattgctaa tgctatcaga  1260
cgcgtaatgg ttgatgagga aggtgaatat atcagacaaa atgccagagt gttaaagcaa  1320
aaagccgatg ttagtttaat gaagggaggt agttcttacg agtcgttgga gagtcttgtc  1380
tcatacatat cttccttgta a                                            1401

SEQ ID NO: 190          moltype = AA  length = 466
FEATURE                 Location/Qualifiers
source                  1..466
                        mol_type = protein
                        organism = Siraitia grosvenorii
SEQUENCE: 190
MLLQSNPMEN ETETTVSRRR RILLFPVPFQ GHINPMLQLA NVLYSKGFSI TIFHTNFNSP  60
KTSNYPHFTF RFILDNDPQD KRISNLPTHG PAASIRIPFF NEYRADELRR ELELLMLASE  120
EDGEVSCLIA DQIWYFTQSV ADSLNLRRLV LVTSSLFNFH AHVSLPQFDE LGYLDPDDKT  180
RLEEQASGFP MLKVKDIKCS FSMWKKYKEY FENITKQTKA SSGVIWNSFK ELEESELETV  240
IREIPAPSFL IPLPKHLTAS SSSLLDHDRT VFPWLDQQPS RSVLYVSFGS GTEVLDEKDF  300
LEIARGLVDS KQSFLWVVRP GFVKGSTWVE PLPDGFLGER GRIVKWVPQQ EVLAHGAIGA  360
FWTHSGWNST LESVCEGVPM IFSDFGLDQP LNARYMSDVL KVGVYLENGW ERGEIANAIR  420
RVMVDEEGEY IRQNARVLKQ KADVSLMKGG SSYESLESLV SYISSL                 466

SEQ ID NO: 191          moltype = DNA  length = 1524
FEATURE                 Location/Qualifiers
source                  1..1524
                        mol_type = other DNA
                        organism = synthetic construct
SEQUENCE: 191
atggccgtcg ttgcttcggc tccagggaaa gttttaatga cgggaggtta ccttgtcttg  60
gagaggccga atgcagggct cgtacttagt actaatgctc ggttttatgc aattgtaaaa  120
ccactttacg aggaaatcaa gcctgacagc tgggcatggt catggacaga tgttaaattg  180
acatctcctc aactcctgag agagagcatc tacaaattgt cattgaaaaa ccaatctctt  240
cagagtgtct ctccaagtca atcaagaaac ccttttgtag aaaaagcagt agaatattgt  300
gtagcagctg catgtgcaaa atttgttgac aaggacaatg aggatgcatt gcacaaactg  360
ctcttgcatg gtcttgatat cactatttta ggttgcaatg agttctactc ctatcgaagt  420
cagattgagg ctcgtggact cccattaaca tcagaatctt tggcttccct gcctcctttt  480
tcatcaatta ccttcaatga tgaggaatca tatgggaaaa attgcaagcc tgaagttgca  540
aaaactggat tgggctcatc tgctgcaatg acagctgctg tagttgctgc tttacttaac  600
taccttgggg ttgtaaatgt ttccttattg acaggtgacc aagaacagaa aggcagtgcg  660
gatcttgatt tggtgcatat gatagctcaa agtgcccact gcattgcaca aggaaaagtt  720
ggcagtggct ttgatgtcag ttctgcagtt tatggcagtc agcgctacat tcggttttca  780
ccagaagtgc tatcttctgc tcaggctgcc acggaaggaa tacccataca agaggttatt  840
gtcggtatct taaaccagaa gtgggaccat gagaggacta agttctcttt gcctccatta  900
atgactcttt tacttggaga gccaggagtg ggagggtcgt ccacaccttc aatggtaggt  960
gctgtcagaa aatggcaaaa atctgaccct caaaattccc tggacacgtg gaggaagttg  1020
tcagaagcaa actcggaact tgaaactcag ctcaatatgt tgcgtaaact tgcagcagaa  1080
cactgggatg cttataaatg tatcataaac agttgttgca agttgacctc cgagaagtgg  1140
attcatcaag ccactgaacc aagccagcaa gccatcatca aagcattatt aggagcaaga  1200
tatgctatgc ttgagatcag gcatcatatg cacctgatgg gtgaagctgc tggtgttcca  1260
attgagccgg attcacaaac caagctttta gatgctacca tgaatatgga aggagtcctg  1320
ttagccggag ttccgggcgc aggcgggttt gatgctgttt ttgctgttac cttgggagat  1380
tcaaccagca acgtgattaa atcatggagt tcactcgata ttttggctct ccttgttaga  1440
gaagatcctc gtggtattgc tttggaaagt ggcgatcctc gaaccaaggc aattacatca  1500
gctgtttcat cagttcatat ttag                                         1524

SEQ ID NO: 192          moltype = AA  length = 507
```

```
FEATURE                 Location/Qualifiers
source                  1..507
                        mol_type = protein
                        organism = Siraitia grosvenorii
SEQUENCE: 192
MAVVASAPGK VLMTGGYLVL ERPNAGLVLS TNARFYAIVK PLYEEIKPDS WAWSWTDVKL  60
TSPQLLRESI YKLSLKNQSL QSVSPSQSRN PFVEKAVEYC VAAACAKFVD KDNEDALHKL  120
LLHGLDITIL GCNEFYSYRS QIEARGLPLT SESLASLPPF SSITFNDEES YGKNCKPEVA  180
KTGLGSSAAM TAAVVAALLN YLGVVNVSLL TGDQEQKGSA DLDLVHMIAQ SAHCIAQGKV  240
GSGFDVSSAV YGSQRYIRFS PEVLSSAQAA TEGIPIQEVI VGILNQKWDH ERTKFSLPPL  300
MTLLLGEPGV GGSSTPSMVG AVRKWQKSDP QNSLDTWRKL SEANSELETQ LNMLRKLAAE  360
HWDAYKCIIN SCCKLTSEKW IHQATEPSQQ AIIKALLGAR YAMLEIRHHM HLMGEAAGVP  420
IEPDSQTKLL DATMNMEGVL LAGVPGAGGF DAVFAVTLGD STSNVIKSWS SLDILALLVR  480
EDPRGIALES GDPRTKAITS AVSSVHI                                     507

SEQ ID NO: 193          moltype = DNA  length = 1026
FEATURE                 Location/Qualifiers
source                  1..1026
                        mol_type = other DNA
                        organism = synthetic construct
SEQUENCE: 193
atggaagagg gaaatcgaac gcacccattc tccaacaaca gtatcaaagc tgcggaactg  60
gctagaccag tccgctgcat tgtgaaattg ggaggtgcag ctattacttg caaaaatgaa  120
ttggagacga tcaatgaaga aaatttgtcg acagtttcgt ctcatatgag gaagatgatg  180
gttagtggct cgtcttctgc aaggaccatt ggaatggatt ggagcaagca acctggaaaa  240
tccgacattg catgtactat agatgattcc ggagaacaag aagttggcct tgcgagcccc  300
tttatagttg ttcatggagc tggttctttt gggcacttcc aggcaagtaa atcaggggtt  360
cataaaggag gactcgatag atccttggtc aaggctggat ttgttgccac acgtatatct  420
gttacttcgc tcaatctcca aattgttaga gcactagcga gagagggtat tccttcggtt  480
ggaatgtctc cattttcatg tggatggtcc acttgtgaaa gaaatatagc cgcagttgat  540
ttacgtggag tttctaaagc tattaacttc ggatttattc ctgttctgca tggagatgcc  600
gttttggatg attccctggg gtgcaccata ttaagcggag atgtaataat acgacatctt  660
gcagagcaac taaagcctga ttatgttgtt ttcctcacag atgtcttagg tgtatatgat  720
cgtcctccta cagaacctaa tgcagtcctt ttgagagaga ttgttgtggg tgaagatggt  780
cgttggtctg ttatacgacc tatactagag aacataaata cagaagttga gattagcgta  840
gctgcccatg atacaactgg gggaatggtt actaagatat cagaggcggc aatgattgca  900
aagcttggta ttgaagtcta catcgtaaag gcagcaactg tccactcctt gagagcccta  960
agtggggaaa tccgaggcaa aattcctgat gactggcttg ggacggtcat ccggttttca  1020
agataa                                                            1026

SEQ ID NO: 194          moltype = AA  length = 341
FEATURE                 Location/Qualifiers
source                  1..341
                        mol_type = protein
                        organism = Siraitia grosvenorii
SEQUENCE: 194
MEEGNRTHPF SNNSIKAAEL ARPVRCIVKL GGAAITCKNE LETINEENLS TVSSHMRKMM  60
VSGSSSARTI GMDWSKQPGK SDIACTIDDS GEQEVGLASP FIVVHGAGSF GHFQASKSGV  120
HKGGLDRSLV KAGFVATRIS VTSLNLQIVR ALAREGIPSV GMSPFSCGWS TCERNIAAVD  180
LRGVSKAINF GFIPVLHGDA VLDDSLGCTI LSGDVIIRHL AEQLKPDYVV FLTDVLGVYD  240
RPPTEPNAVL LREIVVGEDG RWSVIRPILE NINTEVEISV AAHDTTGGMV TKISEAAMIA  300
KLGIEVYIVK AATVHSLRAL SGEIRGKIPD DWLGTVIRFS R                      341

SEQ ID NO: 195          moltype = DNA  length = 1257
FEATURE                 Location/Qualifiers
source                  1..1257
                        mol_type = other DNA
                        organism = synthetic construct
SEQUENCE: 195
atggcgggtg aaaaatgggt gctgatggcg actgcgcaga cgccgacgaa catcgcggtg  60
attaagtatt ggggcaagag ggacgaggaa ttaatcttgc ctgtcaatga tagcatcagt  120
gttacccttg atccgagcca cctctgcacc atcaccaccg tcgccgttag tcctgccttc  180
gagcaggatc ggatgtggct caatcgcaag gagatatccc tttctggagc caggtaccaa  240
aattgtttga gggaaatacg cagccgagct aatgatgttg aggataaaga aaagggtatt  300
aagatagcaa aaaaagattg ggagaaattg catgtatata ttgattctta caataatttc  360
ccaactgccg ctggcttggc ttcctctgct gccggtttcg cttgtcttgt ctttgctctg  420
gcaaatttaa tgaatgtcaa ggaagatcag agcaagttat ctgctattgc aaggcaaggt  480
tcaggaagtg cttgccgtag tttatatggt ggatttgtga agtggagcat gggaaaagaa  540
aaggatggaa gtgatagtct tgcaattcaa cttgctgacg agaagcactg ggatgatctt  600
gtaattatca ttgctgtggt aagttcacga caaaaggaaa caagtagcac ttcaggaatg  660
cgggaaactg tagaaacaag tttgctttta caacatagag caaaggaagt tgtaccaaag  720
cgcgtgttag ctatggaaga agctatcaaa aatcgcgatt ttgtatcctt tgcacaactg  780
acatgctccg acagcaacca atttcatgca gtctgtcttg atacgtctcc cccaatattt  840
tatatgaatg atacatccca caggataatc agtcttgttg agaagtggaa ccgttctgaa  900
ggagaacctc aggtggcata tacttttgat gcggggccaa attcggttct aattgcacgt  960
aatagaaaaa ctgctgtatc tttgcttcag aggttgcttt tctacttccc tcccaatcca  1020
gaaacggatt taaacagtta tgttcttggt gacaagtcaa ttcttcaaga tgctgggatt  1080
aagggtgttg aggatattga gtccctgcta caacctccag aaattaacag tccattccag  1140
aaattccagg gggatgtcag ttatttcatc tgtaccaggc cggggaaagg gccggttgtg  1200
```

```
ctccccgaca gtcaagctct actcgaccca aaaactgggc tgccaaagaa tctttag     1257

SEQ ID NO: 196         moltype = AA  length = 418
FEATURE                Location/Qualifiers
source                 1..418
                       mol_type = protein
                       organism = Siraitia grosvenorii
SEQUENCE: 196
MAGEKWVLMA TAQTPTNIAV IKYWGKRDEE LILPVNDSIS VTLDPSHLCT ITTVAVSPAF  60
EQDRMWLNRK EISLSGARYQ NCLREIRSRA NDVEDKEKGI KIAKKDWEKL HVYIDSYNNF  120
PTAAGLASSA AGFACLVFAL ANLMNVKEDQ SKLSAIARQG SGSACRSLYG GFVKWSMGKE  180
KDGSDSLAIQ LADEKHWDDL VIIIAVVSSR QKETSSTSGM RETVETSLLL QHRAKEVVPK  240
RVLAMEEAIK NRDFVSFAQL TCSDSNQFHA VCLDTSPPIF YMNDTSHRII SLVEKWNRSE  300
GEPQVAYTFD AGPNSVLIAR NRKTAVSLLQ RLLFYFPPNP ETDLNSYVLG DKSILQDAGI  360
KGVEDIESLL QPPEINSPFQ KFQGDVSYFI CTRPGKGPVV LPDSQALLDP KTGLPKNL    418

SEQ ID NO: 197         moltype = DNA  length = 3018
FEATURE                Location/Qualifiers
source                 1..3018
                       mol_type = other DNA
                       organism = synthetic construct
SEQUENCE: 197
atgaagctgc tgagcgtggc cgccgtggcc ctgctggccg cccaggccgc cggcgccagc  60
atcaagcaca ggctgaacgg cttcaccatc ctggagcacc cggacccggc caagagggac  120
ctgctgcagg acatcgtgac ctgggacgac aagagcctgt tcatcaacgg cgagaggatc  180
atgctgttca gcggcgaggt gcacccgttc aggctgccgg tgccgagcct gtggctggac  240
atcttccaca agatcagggc cctgggcttc aactgcgtga gcttctacat cgactgggcc  300
ctgctggagg gcaagccggg cgactacagg gccgagggca tcttcgccct ggagccgttc  360
ttcgacgccg ccaaggaggc cggcatctac ctgatcgcca ggccgggcag ctacatcaac  420
gccgccgtga gcggcggcgg cttcccgggc tggctgcaga gggtgaacgg caccctgagg  480
agcagcgacg agccgttcct gaaggccacc gacaactaca tcgccaacgc cgccgccgcc  540
gtggccaagg cccagatcac caacggcggc ccggtgatcc tgtaccagcc ggagaacgag  600
tacagcggcg gcagatgcgg cgagaagtac ccggacgccg actacatgca gtacgtgatg  660
gaccaggcca ggaaggccga catcgtggtg ccgttcatca gcaacgacgc cagcccgagc  720
ggccacaacg ccccgggcag cggcaccagc gccgtggaca tctacggcca cgacagctac  780
ccgctgggct tcgactgcgc caacccgagc gtgtggccgg agggcaagct gccggacaac  840
ttcaggaccc tgcacctgga gcagagcccg agcacccegt acagcctgct ggagttccag  900
gccggcgcct tcgacccgtg gggcggcccg ggcttcgaga agtgctacgc cctggtgaac  960
cacgagttca gcagggtgtt ctacaggaac gacctgagct tcggcgtgag caccttcaac  1020
ctgtacatga ccttcggcgg caccaactgg ggcaacctgg gccacccggg cggctacacc  1080
agctacgact acggcagccc gatcaccgaa accaggaacg tgaccaggga gaagtacagc  1140
gacatcaagc tgctggccaa cttcgtgaag gccagcccga gctacctgac cgccaccccg  1200
aggaacctga ccaccggcgt gtacaccgac accagcgacc tggccgtgac cccgctgatc  1260
ggcgacagcc cgggcagctt cttcgtggtg aggcacaccg actacagcag ccaggagagc  1320
accagctaca agctgaagct gccgaccagc gccggcaacc tgaccatccc gcagctggag  1380
ggcaccctga gcctgaacgg cagggacagc aagatccacg tggtggacta caacgtgagc  1440
ggcaccaaca tcatctacag caccgccgag gtgttcacct ggaagaagtt cgacggcaac  1500
aaggtgctgg tgctgtacgg cggcccgaag gagcaccacg agctggccat cgccagcaag  1560
agcaacgtga ccatcatcga gggcagcgac agcggcatcg tgagcaccag gaagggcagc  1620
agcgtgatca tcggctggga cgtgagcagc accaggagga tcgtgcaagt gggcgacctg  1680
agggtgttcc tgctggacag gaacagcgcc tacaactact gggtgccgga gctgccgacc  1740
gagggcacca gccccgggctt cagcaccagc aagaccaccg ccagcagcat catcgtgaag  1800
gccggctacc tgctgagggg cgcccacctg gacggcgccg acctgcacct gaccgccgac  1860
ttcaacgcca ccaccccgat cgaggtgatc ggcgccccga ccggcgccaa gaacctgttc  1920
gtgaacggcg agaaggccag ccacaccgtg gacaagaacg gcatctggag cagcgaggtg  1980
aagtacgccg ccccggagat caagctgccg ggcctgaagg acctggactg gaagtacctg  2040
gacaccctgc cggagatcaa gagcagctac gacgacagcg cctgggtgag cgccgacctg  2100
ccgaagacca agaacaccca caggccgctg gacaccccga ccagcctgta cagcagcgac  2160
tacggcttcc acaccggcta cctgatctac aggggccact tcgtggccaa cggcaaggag  2220
agcgagttct tcatcaggac ccagggcggc agcgccttcg gcagcagcgt gtggctgaac  2280
gaaacctacc tgggcagctg gaccggcgcc gactacgcca tggacggcaa cagcacctac  2340
aagctgagcc agctggagag cggcaagaac tacgtgatca ccgtggtgat cgacaacctg  2400
ggcctggacg agaactggac cgtgggcgag gaaaccatga agaaccccgag gggcatcctg  2460
agctacaagc tgagcggcca ggacgccagc gccatcacct ggaagctgac cggcaacctg  2520
ggcggcgagg actaccagga caaggtgagg ggcccgctga acgagggcgg cctgtacgcc  2580
gagaggcagg gcttccacca gccgcagccg ccgagcgaga gctgggagag cggcagcccg  2640
ctggagggcc tgagcaagcc gggcatcggc ttctacaccg cccagttcga cctggacctg  2700
ccgaagggct gggacgtgcc gctgtacttc aacttcggca acaacaccca ggccgccagg  2760
gcccagctgt acgtgaacgg ctaccagtac ggcaagttca ccggcaacgt gggcccgcag  2820
accagcttcc cggtgccgga gggcatcctg aactacaggg gcaccaacta cgtggccctg  2880
agcctgtggg ccctggagag cgacggcgcc aagctgggca gcttcgagct gagctacacc  2940
accccggtgc tgaccggcta cggcaacgtg gagagcccgg agcagccgaa gtacgagcag  3000
aggaagggcg cctactaa                                                3018

SEQ ID NO: 198         moltype = AA  length = 1005
FEATURE                Location/Qualifiers
source                 1..1005
                       mol_type = protein
                       organism = Aspergillus oryzae
```

```
SEQUENCE: 198
MKLLSVAAVA LLAAQAAGAS IKHRLNGFTI LEHPDPAKRD LLQDIVTWDD KSLFINGERI  60
MLFSGEVHPF RLPVPSLWLD IFHKIRALGF NCVSFYIDWA LLEGKPGDYR AEGIFALEPF  120
FDAAKEAGIY LIARPGSYIN AAVSGGGFPG WLQRVNGTLR SSDEPFLKAT DNYIANAAAA  180
VAKAQITNGG PVILYQPENE YSGGRCGEKY PDADYMQYVM DQARKADIVV PFISNDASPS  240
GHNAPGSGTS AVDIYGHDSY PLGFDCANPS VWPEGKLPDN FRTLHLEQSP STPYSLLEFQ  300
AGAFDPWGGP GFEKCYALVN HEFSRVFYRN DLSFGVSTFN LYMTFGGTNW GNLGHPGGYT  360
SYDYGSPITE TRNVTREKYS DIKLLANFVK ASPSYLTATP RNLTTGVYTD TSDLAVTPLI  420
GDSPGSFFVV RHTDYSSQES TSYKLKLPTS AGNLTIPQLE GTLSLNGRDS KIHVVDYNVS  480
GTNIIYSTAE VFTWKKFDGN KVLVLYGGPK EHHELAIASK SNVTIIEGSD SGIVSTRKGS  540
SVIIGWDVSS TRRIVQVGDL RVFLLDRNSA YNYWVPELPT EGTSPGFSTS KTTASSIIVK  600
AGYLLRGAHL DGADLHLTAD FNATTPIEVI GAPTGAKNLF VNGEKASHTV DKNGIWSSEV  660
KYAAPEIKLP GLKDLDWKYL DTLPEIKSSY DDSAWVSADL PKTKNTHRPL DTPTSLYSSD  720
YGFHTGYLIY RGHFVANGKE SEFFIRTQGG SAFGSSVWLN ETYLGSWTGA DYAMDGNSTY  780
KLSQLESGKN YVITVVIDNL GLDENWTVGE ETMKNPRGIL SYKLSGQDAS AITWKLTGNL  840
GGEDYQDKVR GPLNEGGLYA ERQGFHQPQP PSESWESGSP LEGLSKPGIG FYTAQFDLDL  900
PKGWDVPLYF NFGNNTQAAR AQLYVNGYQY GKFTGNVGPQ TSFPVPEGIL NYRGTNYVAL  960
SLWALESDGA KLGSFELSYT TPVLTGYGNV ESPEQPKYEQ RKGAY                 1005

SEQ ID NO: 199         moltype = DNA  length = 2289
FEATURE                Location/Qualifiers
source                 1..2289
                       mol_type = other DNA
                       organism = synthetic construct
SEQUENCE: 199
atgtggaggt taaaggtggg agcagagagc gttggcgaga atgatgagaa atgggtaaag  60
agcataagca atcacttggg acggcaagtg tgggagttct gtccagatgc cggaactcca  120
caacagctat tgcaaatcga gaaagctaag aaagccttcc aagataaccg tttccatcga  180
aagcaaactt ccgatctcct tgtctccatt cagtgcgaaa agggaacaac aaatggtgca  240
agggtaccgg gaaccaagtt gaaagagggg gaagaggtga ggaaagaggc agtaaagagt  300
acattagaaa gggcattaag tttctactct agcatccaga caagcgatgg gaactgggct  360
tcggatcttg gggggcccat gtttttactt ccgggtctgg tgattgctct ctgcgttaca  420
ggcgccctga attctgtttt atccaagcac cacaggcaag agatgtgcag atatctttac  480
aaccaccaga atgaagatgg ggggtgggct ctccacatcg agagcccaag caccatgttt  540
ggttccgcac tgaattatgt tgcactgagg ttgcttgggg aagacgcgga tggcggagag  600
ggcagggcaa tgaccaaagc acgtgcttgg atcttgggcc acggtggcgc caccgcaatc  660
acttcctggg gcaaattgtg gctttctgta cttggagtct acgaatggag tggcaacaat  720
cctcttccac ccgaattttg gttacttcct tacttcctac catttcatcc aggaagaatg  780
tggtgccatt gtcgaatggt ttatctacca atgtcatact tatatgggaa gaggtttgtt  840
gggcccatca caccgtagt tttgtctctt agaaaagagc tctacacagt tccatatcat  900
gaaatagact ggaacaaatc tcgcaataca tgtgcaaagg aggatctgta ctatccacat  960
tccaagatgc aagatattct gtggggatct atccaccata tgtatgagcc cttgttcaca  1020
cattggcctg ccaaacgcct gagggaaaag gctttgaaaa ctgcaatgca acatattcac  1080
tatgaagatg agaacactcg atatatatgc ctcgggcctg tcaacaaggt actcaatatg  1140
ctttgttgtt gggttgaaga tccctactca gaggccttca aacttcatct tcaacgagtc  1200
catgactatc tctgggttgc tgaggatggc atgaaaatgc agggttataa tggaagccag  1260
ttgtgggaca ctgctttctc cgtccaagca atcatatcca ccaagcttgt agacaactat  1320
ggcccaactt taagaaaggc acacgactac gttaaaaatt ctcagatcca acaggactgt  1380
cctggggaac ctaatgtttg gttccgtcac attcataaag gtgcatggcc attttcaact  1440
cgagatcatg gatggctcat ctctgactgt acagcagagg gattaaaggc ttctttaatg  1500
ttatccaaac ttccatccga aacggttggg gagccattag aaaggaatcg cctttgtgat  1560
gctgtaaacg ttctcctttc tttgcaaaac gacaatggtg gctttgcatc atatgagttg  1620
acgagatcat atccttggtt ggagttgatc aaccctgcgg aaacgtttgg agatattgtc  1680
attgattatc cgtatgtgga gtgcacctca gccacaatgg aagcactggc gttgtttaag  1740
aaattacatc ccggccatag gaccaaagaa attgatactg ctattgccag ggcagccgac  1800
ttcctcgaaa atatgcaaag gacggatggt tcttggtacg gatgttgggg ggtttgcttc  1860
acttatgcgg gttggtttgg cataaaggga ttagtggctg caggaagggc atatagtaat  1920
tgcctcgcca ttcgcaaggc ttgcgatttt ctactgtcta aagagctgcc cggcggtgga  1980
tggggggaga gttacctttc atgtcagaat aaggtctaca caaatcttga aggaaacaga  2040
ccacacctgg ttaacacggc ttgggtttta atggccctca tcgaagctgg ccagggtgag  2100
agagatccag caccattgca tcgtgcagca aggttgttaa tcaattcaca gttggagaat  2160
ggcgatttcc cacaagagga gatcatggga gtcttcaata aaaattgcat gatcacatat  2220
gctgcatacc ggaacatttt tcccatttgg gctcttggag agtattgcca tagggttttg  2280
accgaataa                                                          2289

SEQ ID NO: 200         moltype = AA  length = 762
FEATURE                Location/Qualifiers
source                 1..762
                       mol_type = protein
                       organism = Momordica charantia
SEQUENCE: 200
MWRLKVGAES VGENDEKWVK SISNHLGRQV WEFCPDAGTP QQLLQIEKAK KAFQDNRFHR  60
KQTSDLLVSI QCEKGTTNGA RVPGTKLKEG EEVRKEAVKS TLERALSFYS SIQTSDGNWA  120
SDLGGPMFLL PGLVIALCVT GALNSVLSKH HRQEMCRYLY NHQNEDGGWA LHIESPSTMF  180
GSALNYVALR LLGEDADGGE GRAMTKARAW ILGHGGATAI TSWGKLWLSV LGVYEWSGNN  240
PLPPEFWLLP YFLPFHPGRM WCHCRMVYLP MSYLYGKRFV GPITPVVLSL RKELYTVPYH  300
EIDWNKSRNT CAKEDLYYPH SKMQDILWGS IHHMYEPLFT HWPAKRLREK ALKTAMQHIH  360
YEDENTRYIC LGPVNKVLNM LCCWVEDPYS EAFKLHLQRV HDYLWVAEDG MKMQGYNGSQ  420
LWDTAFSVQA IISTKLVDNY GPTLRKAHDY VKNSQIQQDC PGEPNVWFRH IHKGAWPFST  480
```

```
RDHGWLISDC TAEGLKASLM LSKLPSETVG EPLERNRLCD AVNVLLSLQN DNGGFASYEL  540
TRSYPWLELI NPAETFGDIV IDYPYVECTS ATMEALALFK KLHPGHRTKE IDTAIARAAD  600
FLENMQRTDG SWYGCWGVCF TYAGWFGIKG LVAAGRAYSN CLAIRKACDF LLSKELPGGG  660
WGESYLSCQN KVYTNLEGNR PHLVNTAWVL MALIEAGQGE RDPAPLHRAA RLLINSQLEN  720
GDFPQEEIMG VFNKNCMITY AAYRNIFPIW ALGEYCHRVL TE                    762

SEQ ID NO: 201          moltype = DNA  length = 2295
FEATURE                 Location/Qualifiers
source                  1..2295
                        mol_type = other DNA
                        organism = synthetic construct
SEQUENCE: 201
atgtggaggc tgaaggtggg agcagagagc gttggggagg aggatgagaa atgggtgaag  60
agcgtaagca atcacttggg ccgccaagtt tgggagttct gtgccgacgc cgccgccgac  120
actcctcacc agttactaca aattcagaat gctaagaacc acttccatca caatcgtttc  180
caccggaagc agtcttccga tctctttctg gctattcaat atgaaaagga aatagcaaag  240
ggcgcaaaag gtggagcggt gaaagtgaaa gaaggggagg aggtggggaa agaggcggtg  300
aagagtacgt tagaaagggc actcggtttc tactcggccg tgcagacaag agatgggaat  360
tgggcctcgg atcttggagg gcccttgttt ttacttccgg gcctcgtgat tgcccttcat  420
gtcacaggcg tcttgaattc agttttgtcc aagcaccacc gcgtagagat gtgcagatat  480
ctttacaatc accagaatga agatggaggg tggggtctac atattgaggg cacaagcacc  540
atgtttggtt cggcactgaa ttacgttgca ctaaggctgc ttggagaaga cgccgatggc  600
ggagacggtg gcgcaatgac aaaagcacgt gcttggatct tggagcgcgg cggcgccact  660
gcgatcactt cgtggggaaa attgtggctg tccgtacttg gagtgtacga atggagtggc  720
aacaaccctc ttccgcctga gttttggctt ctcccttaca gcctaccatt tcatccagga  780
agaatgtggt gccattgtcg aatggtttat cttccaatgt cttacttata tgggaagaga  840
tttgttgggc caatcactcc caaagttctt tctctaaggc aagagctcta cacaattcct  900
tatcatgaaa tagactggaa taaatcccgc aatacatgtg caaaggagga tctgtactat  960
ccacatccca agatgcaaga cattctatgg ggatccatct accatgtata tgagccattg  1020
ttcactcgtt ggcctgggaa acgcctgagg gaaaaggctt tacaagctgc aatgaaacat  1080
attcactatg aagatgaaaa tagtcgatat atatgtcttg gcccagtcaa caaggtactc  1140
aacatgcttt gttgttgggt tgaagatccc tactcagacg ccttcaaact tcaccttcaa  1200
cgcgtccatg actatctctg ggttgctgaa gatggcatga gaatgcaggg ctacaatggc  1260
agccagttgt gggacactgc tttctccatc caagccatcg tagccaccaa acttgtagac  1320
agctatgccc caactttaag aaaagcacat gactttgtta aggattctca gatccaggag  1380
gactgtcctg gggatcctaa tgtttggttc cgtcatattc ataaaggtgc ttggccactt  1440
tcgacacgag atcatggatg gctcatctcc gactgtacag ctgagggatt gaaggcttct  1500
ttgatgttat ccaaacttcc atccacaatg gttggggagc cattagaaaa gaatcgcctt  1560
tgtgatgctg ttaatgttct cctttctttg caaaatgata atggtggatt tgcatcatac  1620
gagttgacga gatcataccc ttggttggag ttgatcaacc cagctgaaac attcggagac  1680
attgtcattg actatccgta tgtggagtgc accgcagcaa caatggaagc actgacgtta  1740
tttaagaagc tacatccagg ccataggacc aaagagattg acacagctat tggcaaggca  1800
gccaacttcc ttgagaaaat gcagagggcg gatggctctt ggtacgggtg ttggggggtt  1860
tgttttacgt atgcgggttg gtttggcata aagggattgg tggctgcagg aagaacatat  1920
aatagctgcc ttgccattcg caaggcttgt gagtttctgc tatctaaaga gctgcccggc  1980
ggtggatggg gggagagtta cctttcatgt cagaataagg tgtacaccaa tcttgagggg  2040
aacaagccac acttggttaa cactgcctgg gttttaatgg ctctcattga agctggccag  2100
ggtgagagag atccagcacc attgcaccgt gcagcaaggt tgctaatgaa ttcccaattg  2160
gagaatggcg atttcgtgca acaggagatc atgggagtgt tcaataagaa ctgcatgatc  2220
acatatgctg cataccgaaa catcttcccc atttgggcgc ttggagagta ttgccatcgg  2280
gttcttactg aatga                                                  2295

SEQ ID NO: 202          moltype = AA  length = 764
FEATURE                 Location/Qualifiers
source                  1..764
                        mol_type = protein
                        organism = Cucurbita pepo
SEQUENCE: 202
MWRLKVGAES VGEEDEKWVK SVSNHLGRQV WEFCADAAAD TPHQLLQIQN AKNHFHHNRF  60
HRKQSSDLFL AIQYEKEIAK GAKGGAVKVK EGEEVGKEAV KSTLERALGF YSAVQTRDGN  120
WASDLGGPLF LLPGLVIALH VTGVLNSVLS KHHRVEMCRY LYNHQNEDGG WGLHIEGTST  180
MFGSALNYVA LRLLGEDADG GDGGAMTKAR AWILERGGAT AITSWGKLWL SVLGVYEWSG  240
NNPLPPEFWL LPYSLPFHPG RMWCHCRMVY LPMSYLYGKR FVGPITPKVL SLRQELYTIP  300
YHEIDWNKSR NTCAKEDLYY PHPKMQDILW GSIYHVYEPL FTRWPGKRLR EKALQAAMKH  360
IHYEDENSRY ICLGPVNKVL NMLCCWVEDP YSDAFKLHLQ RVHDYLWVAE DGMRMQGYNG  420
SQLWDTAFSI QAIVATKLVD SYAPTLRKAH DFVKDSQIQE DCPGDPNVWF RHIHKGAWPL  480
STRDHGWLIS DCTAEGLKAS LMLSKLPSTM VGEPLEKNRL CDAVNVLLSL QNDNGGFASY  540
ELTRSYPWLE LINPAETFGD IVIDYPYVEC TAATMEALTL FKKLHPGHRT KEIDTAIGKA  600
ANFLEKMQRA DGSWYGCWGV CFTYAGWFGI KGLVAAGRTY NSCLAIRKAC EFLLSKELPG  660
GGWGESYLSC QNKVYTNLEG NKPHLVNTAW VLMALIEAGQ GERDPAPLHR AARLLMNSQL  720
ENGDFVQQEI MGVFNKNCMI TYAAYRNIFP IWALGEYCHR VLTE                  764

SEQ ID NO: 203          moltype = DNA  length = 2289
FEATURE                 Location/Qualifiers
source                  1..2289
                        mol_type = other DNA
                        organism = synthetic construct
SEQUENCE: 203
atgtggaagt taaaagtggg agcagagagc gctggcgaga agaatgagaa atggttgaag  60
```

```
agcataagca atcacttggg ccgccaagtg tgggagttct gtcccgacgc cgccgctcca  120
caccaccaat tgcagctcca caacgctaag aaacacttcc atcataaccg tttttcccgc  180
aagcaatctt ccgatctcct tctcgccatt cagtgcgaaa aggaaatagc aaatggtgca  240
aaagttgcag caatcaaact gaaagaagga gaaggggtga ggaaagaggc agtaaagatt  300
acattagaaa gggcattagg tttctactca gccatccaga cacctgatgg caactgggct  360
tcggatcttg gtgggcccat gtttctcatt ccgggtctag taattgctct gtacgtcaca  420
ggcgccttga attctatttt atccaagcac caccgccagg agatgtgcag atatctttac  480
aatcaccaga atgaagatgg gggatggggc ctccacatcg agggcccaag caccatgttt  540
ggttcaggac tgaattatgt tgcactcaga ctgctcggag aagatgctga cggcggagag  600
ggcggcgcga tgacaaaagc acgtgcctgg atcttggccc gcggtggcgc cactgcaatc  660
ccttcctggg gcaagttgtg gctctctgta cttggagtct atgaatggag tggcaataat  720
cctcttcccc ctgaatttgg gttacttcct tactccctac catttcatcc cggaagaatg  780
tggtgccact gtcgaatggt ttatctgcca atgtcatact tatatggaaa gagatttgtt  840
gggccaatca cccccatagt tctatctctc agaaaagagc tcttcactat tccatatcat  900
gaaatagact ggaacaaatc tcgcaataca tgtgcaaagg aggatctgtt ctatccacat  960
ccgaagatgc aagatattct gtggggatcc ctccaccatt tgtatgagcc attgttcagt  1020
cgttggcctg gcaaacgcat cagggaaaag gctttgcaaa ctgcaatgca acatattcac  1080
tatgaagatg agaatactcg atatatatgt cttggccctg tcaacaaggt tctcaatatg  1140
ctttgttgtt gggttgaaga tccctactcc gacgccttca agcttcatct tcaacgagtc  1200
catgactatc tctggattgc tgaagatggc atgagaatgc agggctacaa tgggagccaa  1260
ttgtgggaca ctgctttctc catccaagca atcctatcca ccaaactcgt agacagctat  1320
ggcccaacct taagaaaagc acacgacttc gttaaaaatt ctcagatcca gcaggactgt  1380
cctggggatc ccaatgtttg gttccgtcac attcataaag gtgcatggcc attttcgact  1440
cgagatcatg gctggcttat ctctgactgt accgcagagg gattaaaggc ttctttgatg  1500
ttatccaaac ttccatctga aatagttggg gagccattag agaagaatcg cctttgtgat  1560
gctgtaaatg ttctcctttc tttgcaaaat gataatggtg ggtttgcatc gtacgagttg  1620
acaagatcat acccttggtt ggagttaatc aacccttcag aaatgtttgg agacatcgtc  1680
attgattatt cgtatgtaga gtgcaccgca gccacaatgg aagcactggc gttgtttaag  1740
aagttacatc cgggccatag gaccaaagaa atcgatacca ctttagccaa ggcagccaac  1800
ttccttgaaa acattcaaag gccggatggc tcttggtatg gatgttgggg ggtttgcttc  1860
acttatgccg gctggtttgg cataaaggga ttggtagctg caggaaggac atataatagt  1920
tgcctagcca ttcgcaaggc ttgtgatttt ctactctcta aagagctgcc cggcggtgga  1980
tggggggaga gttacctttc atgtcagaat agggtctaca ccaatctcaa aggaaaccga  2040
ccacacttgg ttaacacagc ctgggtttta ttggccctca tcgaagctgg ccaggctgag  2100
agagatccag caccactgca cagagcagcc aggttgttaa tcaattccca gttggagaat  2160
ggtgatttcc cccaagagga gatcatggga gtgttcaata aaaattgcat gatcacatat  2220
gctgcataca gaaacttttt tcccatttgg gctcttggag aatattccca tcgggtattg  2280
actgaataa                                                         2289
```

```
SEQ ID NO: 204          moltype = AA  length = 762
FEATURE                 Location/Qualifiers
source                  1..762
                        mol_type = protein
                        organism = Trichosanthes cucumerina
SEQUENCE: 204
MWKLKVGAES AGEKNEKWLK SISNHLGRQV WEFCPDAAAP HHQLQLHNAK KHFHHNRFSR  60
KQSSDLLLAI QCEKEIANGA KVAAIKLKEG EGVRKEAVKI TLERALGFYS AIQTPDGNWA  120
SDLGGPMFLI PGLVIALYVT GALNSILSKH HRQEMCRYLY NHQNEDGGWG LHIEGPSTMF  180
GSGLNYVALR LLGEDADGGE GGAMTKARAW ILARGGATAI PSWGKLWLSV LGVYEWSGNN  240
PLPPEFWLLP YSLPFHPGRM WCHCRMVYLP MSYLYGKRFV GPITPIVLSL RKELFTIPYH  300
EIDWNKSRNT CAKEDLFYPH PKMQDILWGS LHHLYEPLFS RWPGKRIREK ALQTAMQHIH  360
YEDENTRYIC LGPVNKVLNM LCCWVEDPYS DAFKLHLQRV HDYLWIAEDG MRMQGYNGSQ  420
LWDTAFSIQA ILSTKLVDSY GPTLRKAHDF VKNSQIQQDC PGDPNVWFRH IHKGAWPFST  480
RDHGWLISDC TAEGLKASLM LSKLPSEIVG EPLEKNRLCD AVNVLLSLQN DNGGFASYEL  540
TRSYPWLELI NPSEMFGDIV IDYSYVECTA ATMEALALFK KLHPGHRTKE IDTTLAKAAN  600
FLENIQRPDG SWYGCWGVCF TYAGWFGIKG LVAAGRTYNS CLAIRKACDF LLSKELPGGG  660
WGESYLSCQN RVYTNLKGNR PHLVNTAWVL LALIEAGQAE RDPAPLHRAA RLLINSQLEN  720
GDFPQEEIMG VFNKNCMITY AAYRNFFPIW ALGEYSHRVL TE                    762
```

```
SEQ ID NO: 205          moltype = DNA  length = 2295
FEATURE                 Location/Qualifiers
source                  1..2295
                        mol_type = other DNA
                        organism = synthetic construct
SEQUENCE: 205
atgtggaggt taaaagttgg ggcggagagc gttggggaga aagaagagaa atggttgaag  60
agtataagca atcacttggg acgccaagtg tgggagtttt gtgccgacca acccactgct  120
tctccaaatc acttacaaca aatcgataat gcgaagaagc actttcgtaa taatcgcttc  180
caccggaagc aatcttccga tctctttctt gctattcaga atgaaaagga gatagcaaat  240
ggtacaaaag gtggaggaat caaagtgaaa gaagaggaag atgtaaggaa agagacagtg  300
aagaatacag tagaaagggc attaagtttc tattcagcca ttcagacaaa cgatgggaat  360
tgggcttcgg atcttggagg gcccatgttt ttactcccgg gtcttgtgat tgctctctat  420
gtcactggcg tcttgaattc ggttctatcc aagcaccatc gacaagaaat gtgtagatat  480
ctttataatc accagaatga agatggtgga tggggcctcc acatcgaagg tacgagcacg  540
atgtttggtt cggcactgaa ttatgttgca ctgaggttgc ttggagaaga cgctgatggc  600
ggagagggcg gtgcaatgac aaaagcacgt ggttggatct tggaccgcgg cggtgccacc  660
gcaatcactt cttggggaaa attgtggctc tctgtacttg gagtctatga atggagtggc  720
aataatcctc ttccacctga gttttggtta ctcccttatt gcctaccctt tcatccagga  780
agaatgtggt gccattgtcg aatggtttat ctaccaatgt catacttata tggaaagaga  840
```

```
tttgttgggc caatcacacc catagttcta tctctaagaa aagagctcta cacaattcca  900
tatcatgaaa tagattggaa taaatctcgc aatacatgtg caaaggagga tctgtactat  960
ccacatccga agatgcaaga tattctgtgg ggatcaatat accatttgta tgagccttta  1020
tttactcgtt ggcctggaaa acggctgagg gaaaaggctt tgcaaatggc aatgaaacat  1080
attcactatg aagatgaaaa cagtagatat atatgtcttg gacctgtcaa taaagtactt  1140
aatatgcttt gttgttgggt tgaagatcct tattcagatg ccttcaaatt tcatcttcaa  1200
cgagtccccg actatctttg gattgctgaa gatggcatga gaatgcaggg ttacaatggg  1260
agccagttgt gggacactgc tttctctgtt caagcaatca tatccaccaa acttatagac  1320
agctttggca caaccttaaa aaaagcacat gattttgtca aagattctca gatccagcag  1380
gactttcctg ggatcctaa tgtttggttc cgtcacattc ataaaggtgc ttggccattt  1440
tcaactcgtg atcatggatg gctcatctct gactgtacag ctgaggggtt aaaggcttct  1500
ttgatgttat ccaaacttcc atccaaaata gttggggagc cattagaaaa gagtcgcctt  1560
tgcgatgctg taaatgttct cctttcttta caaaatgaaa atggtggatt tgcatcatat  1620
gagttgacaa gatcatacc ttggttggag ttgatcaacc ctgcagaaac attcggagat  1680
atcgttatcg attatcccta tgtggagtgc acctcagcta caatggaagc attgacactg  1740
tttaagaagt tacatccagg ccataggacc aaagagattg atactgcagt tgccaaggca  1800
gctaacttcc tagaaaatat gcaaaggacg gatggctctt ggtacgggtg ttgggggtt  1860
tgcttcacgt atgcagggtg gtttggcata aagggtttgg ttgctgcagg aaggacatat  1920
agtacttgtg ttgccattcg caaggcttgt gattttttgc tatctaaaga attacctggc  1980
ggtggatggg gagagagtta cctttcatgt cagaataagg tctataccaa tcttgaaggc  2040
aacaggccgc atttggttaa cactgcttgg gttttgatgg ctctcattga agctggccag  2100
gctgagagag atccagcacc attgcaccgt gcagcaaggt tgttaatcaa ttcccaattg  2160
gagaatggtg atttccccca agaggaaatc atgggagtgt ttaataaaaa ttgcatgatc  2220
acatatgctg catatcgaaa tatctttccc atttgggctc ttggagagta tttccatcgg  2280
gttcttactg aatga                                                   2295

SEQ ID NO: 206         moltype = AA  length = 764
FEATURE                Location/Qualifiers
source                 1..764
                       mol_type = protein
                       organism = Citrullus colocynthis
SEQUENCE: 206
MWRLKVGAES VGEKEEKWLK SISNHLGRQV WEFCADQPTA SPNHLQQIDN AKKHFRNNRF  60
HRKQSSDLFL AIQNEKEIAN GTKGGGIKVK EEEDVRKETV KNTVERALSF YSAIQTNDGN  120
WASDLGGPMF LLPGLVIALY VTGVLNSVLS KHHRQEMCRY LYNHQNEDGG WGLHIEGTST  180
MFGSALNYVA LRLLGEDADG GEGGAMTKAR GWILDRGGAT AITSWGKLWL SVLGVYEWSG  240
NNPLPPEFWL LPYCLPFHPG RMWCHCRMVY LPMSYLYGKR FVGPITPIVL SLRKELYTIP  300
YHEIDWNKSR NTCAKEDLYY PHPKMQDILW GSIYHLYEPL FTRWPGKRLR EKALQMAMKH  360
IHYEDENSRY ICLGPVNKVL NMLCCWVEDP YSDAFKFHLQ RVPDYLWIAE DGMRMQGYNG  420
SQLWDTAFSV QAIISTKLID SFGTTLKKAH DFVKDSQIQQ DFPGDPNVWF RHIHKGAWPF  480
STRDHGWLIS DCTAEGLKAS LMLSKLPSKI VGEPLEKSRL CDAVNVLLSL QNENGGFASY  540
ELTRSYPWLE LINPAETFGD IVIDYPYVEC TSATMEALTL FKKLHPGHRT KEIDTAVAKA  600
ANFLENMQRT DGSWYGCWGV CFTYAGWFGI KGLVAAGRTY STCVAIRKAC DFLLSKELPG  660
GGWGESYLSC QNKVYTNLEG NRPHLVNTAW VLMALIEAGQ AERDPAPLHR AARLLINSQL  720
ENGDFPQEEI MGVFNKNCMI TYAAYRNIFP IWALGEYFHR VLTE                  764

SEQ ID NO: 207         moltype = DNA  length = 1365
FEATURE                Location/Qualifiers
source                 1..1365
                       mol_type = other DNA
                       organism = synthetic construct
SEQUENCE: 207
atggggagtt taggagcaat tttgaaacac ccagatgaat tttacccact tttgaagttg  60
aagatggctg ttaaagaagc tgagaaacag atcccatctg aatctcattg ggggttttgt  120
tactctatgc ttcataaagt ttccagaagt tttgctcttg ttattcagca acttggcact  180
gagcttcgca atgctgtatg tgtcttttac ttggtccttc gagccctcga cactgtagag  240
gatgatacaa gcatagctac agatgtcaaa ttgcctatcc tgaaagcttt ttatcagcac  300
atatatgatc gcgaatggca cttttcttgt ggcacaaaac actacaaagt tctcatggat  360
gagtttcatc aagtctcaac tgcttttttg gagcttgaaa gaggttacca gctcgcaatt  420
gaggatatta ccaaaaggat gggtgcggga atggcaaaat tcatctgtca ggaggtagaa  480
acagttagcg actatgacga atactgccac tatgtagcag gactcgtggg tttagggttg  540
tctaagcttt tccataatgc aggtttggag gatcttgcat cggatgatct ttccaattcg  600
atgggtttat ttcttcaggt atttcctttt gcttggaaca tgaatttgca aacttctgtg  660
ctctgtgaga ctgtgatact atacctaata agatgttaca tagtgtaatc agtaatgtgc  720
ctattttttg tgtagaaaac caacattatc cgtgattacc tcgaagatat aaatgagatt  780
ccaaaatgtc gcatgttttg gcctcgggag atatggagta aatatgtcaa caagcttgag  840
gacctgaaat atgaggagaa ctctgtgaag gcagttcaat gtttaaatga catggtaaca  900
aatgctttat tgcatgtgga agattgccta aagtacatgt cggctctgcg ggatcatgct  960
atattccggt tctgtgctat tccacaaatc atggccattg gaactttagc tttatgctac  1020
aacaacgttg aagtcttcag aggtgtggtt aaaatgagac gtggtcttac cgcaagagtt  1080
attgataaga cagactcgat gcctgatgtt tatggtgcct tctacgattt tgcctgcatg  1140
ataaaaccaa aggtcgacaa gaatgatcca aacgccatga aaacactaag tagaatcgat  1200
gctatcgaga agatttgtag ggactccggc actctgaaca aaaggaaact gcacatcaca  1260
agcaccaagt cggcatacac tccaatcatg gtgatggtgt tattcattgt attggcaatc  1320
ttcttcaatc gtttatcaga atccaacaga atgattaata actaa                  1365

SEQ ID NO: 208         moltype = AA  length = 415
FEATURE                Location/Qualifiers
source                 1..415
```

```
                        mol_type = protein
                        organism = synthetic construct
SEQUENCE: 208
MGSLGAILKH PDEFYPLLKL KMAVKEAEKQ IPSESHWGFC YSMLHKVSRS FALVIQQLGT  60
ELRNAVCVFY LVLRALDTVE DDTSIATDVK LPILKAFYQH IYDREWHFSC GTKHYKVLMD  120
EFHQVSTAFL ELERGYQLAI EDITKRMGAG MAKFICQEVE TVSDYDEYCH YVAGLVGLGL  180
SKLFHNAGLE DLASDDLSNS MGLFLQKTNI IRDYLEDINE IPKCRMFWPR EIWSKYVNKL  240
EDLKYEENSV KAVQCLNDMV TNALLHVEDC LKYMSALRDH AIFRFCAIPQ IMAIGTLALC  300
YNNVEVFRGV VKMRRGLTAR VIDKTDSMPD VYGAFYDFAC MIKPKVDKND PNAMKTLSRI  360
DAIEKICRDS GTLNKRKLHI TSTKSAYTPI MVMVLFIVLA IFFNRLSESN RMINN       415

SEQ ID NO: 209          moltype = DNA  length = 1245
FEATURE                 Location/Qualifiers
source                  1..1245
                        mol_type = other DNA
                        organism = synthetic construct
SEQUENCE: 209
atggggagtt tgagggcgat tttgaagcac cctgatgatt tgtacccgtt ggtgaaactg  60
aaactggcgg cgaggcacgc agagaagcag atcccgcggg agccacactg ggatttttgc  120
tacgctatgc tacacaaggt ttctaggagt tttgctctcg tcattcaaca gctcgacacc  180
gatcttcgtg atgccatatg cattttctac ttggttcttc gagcgcttga cactgttgag  240
gacgatacaa gcatagctac ggacatcaaa gtacctatcc tgatggcttt tcatcgtcac  300
atatatgatc gtgaatggca tttttcatgt ggtgtaaagc actacaaagt tctcatggat  360
gagttccatc acgtttccac tgcttttctg gagcttggaa gaagttatca ggaggcaatt  420
gaggatatta ccatgaggat gggagcagga atggcaaaat ttatatgcaa ggaggtagaa  480
acaattgatg attatgatga atattgccac tatgtggctg gacttgttgg gttagggttg  540
tcgaagctgt tctatgcatc tggaaaagaa gatttggctt ctgatactct ctccaactca  600
atggggttat ttcttcagaa aacaaacatt atcagagact acctggagga tattaatgag  660
ataccaaagt cacgtatgtt ctggcctcgt cagatatgga gtaaatatgt caacaaactt  720
gaggatttaa aatatgagga aaactctgtc aaggcagtac agtgcctcaa tgacatggtt  780
acaaatgctt tgatacatgt agaagattgc ctgaagtaca tgtctgcatt gcgagatcca  840
gctatctttc ggttttgtgc tattccacag atcatggcaa ttggaacact agctttgtgc  900
tacaacaata ttcaagtctt caggggtgtt gtgaaaatga gacgtggtct tacagctaaa  960
gttattgacc gaaccaaaac aatgtcagat gtctatgggg atttttatga tttctctcgc  1020
atgctgaagt ctaaggtgga caacagtgat cctaacgcta ataaaacaaa ggagaagcta  1080
gaaacaatct tgaaaatttg cagagactct ggatctctaa acaataggaa atcttacatc  1140
attaggagcg agcctagata caattcaact acgatcgttg tcatcttcat catacttgct  1200
atgcttcttg cctacctctc tgcgactaga ccaaataata tatga                 1245

SEQ ID NO: 210          moltype = AA  length = 414
FEATURE                 Location/Qualifiers
source                  1..414
                        mol_type = protein
                        organism = Olea europaea
SEQUENCE: 210
MGSLRAILKH PDDLYPLVKL KLAARHAEKQ IPREPHWGFC YAMLHKVSRS FALVIQQLDT  60
DLRDAICIFY LVLRALDTVE DDTSIATDIK VPILMAFHRH IYDREWHFSC GVKHYKVLMD  120
EFHHVSTAFL ELGRSYQEAI EDITMRMGAG MAKFICKEVE TIDDYDEYCH YVAGLVGLGL  180
SKLFYASGKE DLASDTLSNS MGLFLQKTNI IRDYLEDINE IPKSRMFWPR QIWSKYVNKL  240
EDLKYEENSV KAVQCLNDMV TNALIHVEDC LKYMSALRDP AIFRFCAIPQ IMAIGTLALC  300
YNNIQVFRGV VKMRRGLTAK VIDRTKTMSD VYGDFYDFSR MLKSKVDNSD PNANKTKEKL  360
ETILKICRDS GSLNNRKSYI IRSEPRYNST TIVVIFIILA MLLAYLSATR PNNI        414

SEQ ID NO: 211          moltype = DNA  length = 1386
FEATURE                 Location/Qualifiers
source                  1..1386
                        mol_type = other DNA
                        organism = synthetic construct
SEQUENCE: 211
atgggaaagt taggggagct actctcacat ccaaatgaga tcatgccact gctgcgcatg  60
tatcgcgcag ctaagcgcgc caccaagctt ccaaaggacc cggacctggc tttctgctac  120
gggatgctga acgacgtgtc tcgaagcttc gccatcgtca ttcagcagct gcccaacccg  180
ctgcgcgact ccatctgcgt gttctacctg gtgctgcgcg ggctggacac cgtggaggat  240
gacatggcac tggacgtgga cttcaagctg cccgagctgc gtcgtttcca tgagcgcata  300
tacgacaggg gcttcacgat ggagtgcggc tacaaccact acaagcggct gatggcgcag  360
ttcggggtgg tggtgaacgt gttcctggcg ctgccgccgc cgcaccaggc cgtcatcgcc  420
gacatcacgc ggcgcatggg ctacggcatg gcggagttca tcgagaagga ggtggtgacg  480
gtggccgact acgacaagta ctgccactac gtggcgggcc tggtgggcat cggcctcagc  540
cagctgttcg ccgccagcgg cctggaggcc aactccatcg gcaccgagga ggacctggcc  600
aaccacatgg ggctgttcct gcagaagacc aacatcatcc gcgactacct ggaggacatt  660
ctggaggagc cggcgccgcg catgttctgg ccccgtgaca tctggggcaa gtacgcgccc  720
gcgctggccg acttcaagga gccggccaac agggggggcgg cggtgcggtg cctcaacgac  780
atgatcacgg acgcgctgcg gcaccttccg tactgcctgg cctacatgga gcagctgcgg  840
cacgtgatgg tgttccgctt ctgcgccatc ccgcagatca tggcggctgg caccctggca  900
gcatgctaca acaacggccg cgtgttcgag ggcgtggtga agatgcggcg cggcgagacg  960
gcccgcatct ttgagacgtg caacgacctg ggcgacctgt acacctggtt cctgcagttc  1020
ctggcggcca tggaggccaa ggtgtcaaac gaggtagacc caacggaccc ctcgctgccc  1080
ctcacgcggc aacgcatcgc ggaggcacgc aaggcctgcg ccgccaagct cacagagtgg  1140
aagcgcacgc acccgccgcc cagcgagagc ggcgccgcgc tgacccgcga cttcctggcg  1200
```

-continued

```
ctctctatca ccggcgccta cttctactac gtgtggcagc tgggcgggcc gggctcggaa  1260
gcgctgccgg agctgctgcg cccctacgcc tgggtattgg agcagcaggc ggggctgcag  1320
aaggccgtga gcctggcgct gctggtgctg gtgttcctgc tggtggcggt actgcggcgt  1380
gcgtga                                                             1386

SEQ ID NO: 212         moltype = AA  length = 461
FEATURE                Location/Qualifiers
source                 1..461
                       mol_type = protein
                       organism = Chlamydomonas reinhardtii
SEQUENCE: 212
MGKLGELLSH PNEIMPLLRM YRAAKRATKL PKDPDLAFCY GMLNDVSRSF AIVIQQLPNP  60
LRDSICVFYL VLRGLDTVED DMALDVDFKL PELRRFHERI YDRGFTMECG YNHYKRLMAQ  120
FGVVVNVFLA LPPPHQAVIA DITRRMGYGM AEFIEKEVVT VADYDKYCHY VAGLVGIGLS  180
QLFAASGLEA NSIGTEEDLA NHMGLFLQKT NIIRDYLEDI LEEPAPRMFW PRDIWGKYAP  240
ALADFKEPAN RGAAVRCLND MITDALRHLP YCLAYMEQLR HVMVFRFCAI PQIMAAGTLA  300
ACYNNGRVFE GVVKMRRGET ARIFETCNDL GDLYTWFLQF LAAMEAKVSN EVDPTDPSLP  360
LTRQRIAEAR KACAAKLTEW KRTHPPPSES GAALTRDFLA LSITGAYFYY VWQLGGPGSE  420
ALPELLRPYA WVLEQQAGLQ KAVSLALLVL VFLLVAVLRR A                      461

SEQ ID NO: 213         moltype = DNA  length = 1575
FEATURE                Location/Qualifiers
source                 1..1575
                       mol_type = other DNA
                       organism = synthetic construct
SEQUENCE: 213
atggagttcc tatccgcggc tcttctcggc cttctattgg cctccatcct tcctctcttt  60
ttcttcttct ctttcagaga cggaatcaaa cacgacggcg acaacaacac caccgccgta  120
atcgattcaa agattccgtc gggaaatgac gtccgtcgcg ccgaatcctc cgatgatttt  180
gacgttatca tcgtcggcgc tggagttgcc ggcgccgccc ttgcttatac tctcgccaag  240
gatggacgaa aagtgcatgt aattgaaaga gacttgtcgg agccggagag aatcgtcgga  300
gaattgcttc aacccggcgg ctatttgaag ctcatcgagt tagggcttga agacagtctg  360
aaggggatcg atgctcagca agtgtttggt tatgcgctct tcaaagacgg aaaccacacc  420
agattggctt atcctttgga caaatttgat tccaatattt ctgggagaag cttccacaat  480
ggccgattca ttcagaggtt gaggcaaaag gctgctgctc tttccaatgt aaaactggaa  540
caagggactg taacttccat agttgaagaa gatgggactg taaaaggtgt gcaatataaa  600
accaagaatg gacaagagtt gacatcttat gctcccctca ccattgtttg tgatggcggc  660
ttttcgaatt tgcgtcgcaa cctctgcaaa cctcagattg atattccctc atgctttgtt  720
ggtttggtcc tggagaactg taagctgccc cttgaaaatc atggacatgt tgtgcttgct  780
gacccatcgc ctatcttgtt ataccggatt agcagcacgg agatacgctg cttagtcgat  840
atccccggcc aaaaagtgcc ttctgtggct aacggcgaca tggcacacta cttgaaaacc  900
gctgtggctc ctcagctacc gcccgagttg cagaccgcct tcatagcttc agttgataag  960
gggaacataa aaagcacaac aaacagaagc atgccagcag ccccacatcc cacaccagga  1020
gcacttctct tgggtgatgc attcaacatg cgacatcctt taaccggtgg aggtatgacc  1080
gttgctctcg ccgatatcgt cgtgctacga gatcttcttc gaccccttte aaatttgaac  1140
gatgccgatg ccttgtgcaa ctatctcgaa tccttctaca cattgcgaaa gccagtggca  1200
tctacaataa acacattggc cggtgcctta taccaggtct ttgtgcatcc gcccgacccg  1260
gccaggaagg aaatgcgcga agcttgtttc gattatttga gtctaggagg tgtattttcc  1320
tctggaccag tgtctcttct ctctggtctg aacccgcgcc cattaagcct gttctgtcac  1380
ttctttgccg tggccatata cggtgtcact cggttgctaa tcccattccc ttcgcctaag  1440
cgtatatgga tcggagttcg attgattacg ggagcagcag gcataatttt tcccataatc  1500
aaggctgaag gagtgagaca aatgttcttt cctgcaacaa tgcctgcata ctacagagcc  1560
cctcctatgc agtga                                                  1575

SEQ ID NO: 214         moltype = AA  length = 524
FEATURE                Location/Qualifiers
source                 1..524
                       mol_type = protein
                       organism = Cucurbita pepo
SEQUENCE: 214
MEFLSAALLG LLLASILPLF FFFSFRDGIK HDGDNNTTAV IDSKIPSGND VRRAESSDDF  60
DVIIVGAGVA GAALAYTLAK DGRKVHVIER DLSEPERIVG ELLQPGGYLK LIELGLEDSL  120
KGIDAQQVFG YALFKDGNHT RLAYPLDKFD SNISGRSFHN GRFIQRLRQK AAALSNVKLE  180
QGTVTSIVEE DGTVKGVQYK TKNGQELTSY APLTIVCDGG FSNLRRNLCK PQIDIPSCFV  240
GLVLENCKLP LENHGHVVLA DPSPILLYRI SSTEIRCLVD IPGQKVPSVA NGDMAHYLKT  300
AVAPQLPPEL QTAFIASVDK GNIKSTTNRS MPAAPHPTPG ALLLGDAFNM RHPLTGGGMT  360
VALADIVVLR DLLRPLSNLN DADALCNYLE SFYTLRKPVA STINTLAGAL YQVFCASPDP  420
ARKEMREACF DYLSLGGVFS SGPVSLLSGL NPRPLSLFCH FFAVAIYGVT RLLIPFPSPK  480
RIWIGVRLIT GAAGIIFPII KAEGVRQMFF PATMPAYYRA PPMQ                  524

SEQ ID NO: 215         moltype = DNA  length = 1599
FEATURE                Location/Qualifiers
source                 1..1599
                       mol_type = other DNA
                       organism = synthetic construct
SEQUENCE: 215
atggagtttc aatctgcggc tctctgcggc cttctcttgg cttccatttc cgctctcatt  60
ttcttcttcg ctcacctcag attcaataat ggaatatcca acaaaaccaa cactgacaac  120
atgatcaaga agaagaagat cttcatcgcc ggttcccgtg ccgccgtcaa cccgccgtcg  180
```

```
gaaaatgtcc aatccaacga acccgatgtc gtcatcgtcg gcgccggagt cgctggcgcc  240
gccctcgctt atactctcgc caaggatgga cgaaaagttc atgtaatcga aagagactta  300
gcggagccag agagaatcgt gggggaattg cttcaacccg gcggctatct gaagctgatc  360
gaattagggc ttgaagacag tgtgaatggg atcgatgcgc agcaagtgtt tggatatgcg  420
ctgtacaagg atgggaagca caccaaattg gcttatcctt tgcaaaactt tgattcccat  480
gtttctggga gaagcttcca caatggccgt ttcattcagc ggttgaggca aatggctgct  540
tctctttcca atgtaagact ggaacagggg actgtaacat ccatagttga agaagatggg  600
actgtgaaag gtgtgcagta caagaccaag aatggccaag agttgacagc ttatgctccc  660
ctcaccattg tttgcgatgg cggattttcg aatttgcgcc gcaacctctg caaacctcag  720
attgatattc cctcctgctt tgttggattg gtcctggaga actgcaagct gccctttgaa  780
aatcatggac atgtcgtgct agcagatccg tcacctatct tgttgtaccc tatcagcagc  840
acagagatac gctgcttggt cgatatcccg ggccagaaag ttccttctgt agctaatggt  900
gaaatggcac actacttgaa gaccgttgtg gctcctcagg taccacccga gttgcacgcc  960
tccttcattg ctgcgatcga gaagggaaac attaaaagca caacaaacag aaccatgcca  1020
gcagcaccac gtcccacacc aggagcactt ctcttggggg atgcattcaa catgcgacat  1080
cctttaacgg gcggaggaat gacggtcgct ctggctgata tcgttgtgct acgtgacctt  1140
cttcgacctc ttgcaaattt gaaagatgcc gatgcattgt gcaactattt tgaatccttc  1200
tacactttgc gcaagccagt ggcatctaca ataaacacat tggctggtgc cttatacaag  1260
gtgttctgtg cctcacctga tccagccagg aaggaaatgc gagaagcttg tttcgactat  1320
ttgagtctag gaggcctgtt ttcatccggt ccagtggctc ttctctccgg tcttaaccca  1380
cgcccgttaa gcctgttctg tcacttcttc gctgtcgcta tatacggtgt cagccgcttg  1440
ctaatcccat tcccttcgcc cactcgcata tggatcggag ttcggttgat tacgggagca  1500
gcaggcatca tttttcccat aataaaggct gaaggagtga gacaaatgtt cttccctgca  1560
acagtgcctg catattatag agcccctcct atgaactga                        1599

SEQ ID NO: 216         moltype = AA  length = 532
FEATURE                Location/Qualifiers
source                 1..532
                       mol_type = protein
                       organism = Momordica charantia
SEQUENCE: 216
MEFQSAALCG LLLASISALI FFFAHLRFNN GISNKTNTDN MIKKKKIFIA GSRAAVNPPS  60
ENVQSNEPDV VIVGAGVAGA ALAYTLAKDG RKVHVIERDL AEPERIVGEL LQPGGYLKLI  120
ELGLEDSVNG IDAQQVFGYA LYKDGKHTKL AYPLQNFDSH VSGRSFHNGR FIQRLRQMAA  180
SLSNVRLEQG TVTSIVEEDG TVKGVQYKTK NGQELTAYAP LTIVCDGGFS NLRRNLCKPQ  240
IDIPSCFVGL VLENCKLPFE NHGHVVLADP SPILLYPISS TEIRCLVDIP GQKVPSVANG  300
EMAHYLKTVV APQVPPELHA SFIAAIEKGN IKSTTNRTMP AAPRPTPGAL LLGDAFNMRH  360
PLTGGGMTVA LADIVVLRDL LRPLANLKDA DALCNYFESF YTLRKPVAST INTLAGALYK  420
VFCASPDPAR KEMREACFDY LSLGGLFSSG PVALLSGLNP RPLSLFCHFF AVAIYGVSRL  480
LIPFPSPTRI WIGVRLITGA AGIIFPIIKA EGVRQMFFPA TVPAYYRAPP MN          532

SEQ ID NO: 217         moltype = DNA  length = 1611
FEATURE                Location/Qualifiers
source                 1..1611
                       mol_type = other DNA
                       organism = synthetic construct
SEQUENCE: 217
atgaattcat cttcttctag tactactgat acgttgcatt cttttatgga agctctgctc  60
attgatcaat attttcttgg atggatcttt gctttccttt ttgggttcct gctcttgctt  120
aatttcaaaa ggaagagaga gaaaaataat tccacggagt ttggaacaga tgatagcaac  180
ggttactaca caccggaaaa tattgccgga agtacggacg tcatcatcgt cggcgccggg  240
gttgctggct ctgctcttgc ttatacgctt gccaaagatg gccggagagt tcatgtaatt  300
gagagggact taactgagca agaccgaatt gtaggtgaac ttctacaacc aggaggctac  360
ttgaaattga ttgaattggg gttagaggat tgtgtgaatg aaatcgatgc gcaacgagtt  420
tttggatatg ccctatacat ggatggtaaa aacaccaggc tttcttaccc cttggagaaa  480
tttcattcgg atgtagccgg aagaagcttt cataacgggc gttttgttca acgaatgagg  540
gagaaagctg catcacttcc aaatgtaaga atggaacagg ggactgttac atctctggtt  600
gagaaaaagg caagtgtaaa aggggtgcaa tacaaaacca aggatggcca agaattgtct  660
gcatttgctc ctcttacaat tgtttgtgat ggttgttttt cgaatctgcg tcgctccctc  720
tgcaatccca aggtggaggt gccttcgtgt tttgttggtt tgattttgga aaatattgat  780
cttccacatg taaaccatgg ccatgtcatt ctagcagatc cttctccgat cttgttttat  840
aaaattagta gtaccgagat tcgctgtttg gttgatgtgc ctggacaaaa ggtgccttgt  900
atttctaatg gggaattggc taattatctc aagacagtag tagctcctca ggttccaaaa  960
cagctatata actctttcat agcagcagtt gacaaaggaa acattagaac catgccaaac  1020
agaagcatgc cagccgatcc tcatccaact ccgggtgcac ttctattagg ggatgctttc  1080
aatatgcgcc atcctttaac cggcggggga atgacagtgg ctctgtccga tattgtcttg  1140
attcgggatc ttcttagacc tttacgcgat ctccatgact catcaaccct ctgcaaatat  1200
ctcgaatcct tttacaccct tcgtaagccc gtggcatcta ctataaatac attggcaggc  1260
gccctttata aagttttttg tgcatcacct gataaagcaa ggcaagaaat gcgcaatgcg  1320
tgttttgatt atctgagcct cggaggaatt tgttcccaag ggccaattgc tttactttct  1380
ggcctaaacc cgcgtccaat tagcctattt ctccacttct ttgccgtggc tatctatggc  1440
gttggccgct tgttgattcc ttttccttca ccaaaacgaa tgtggctcgg cgctagattg  1500
attttgggtg catctggaat tattttccct attataaagt cagaaggact tcgacaaatg  1560
ttcttccctg caacggttcc tgcttactac agagctcccc ccattcacta a          1611

SEQ ID NO: 218         moltype = AA  length = 536
FEATURE                Location/Qualifiers
source                 1..536
                       mol_type = protein
```

```
                        organism = Panax ginseng
SEQUENCE: 218
MNSSSSSTTD TLHSFMEALL IDQYFLGWIF AFLFGFLLLL NFKRKREKNN STEFGTDDSN  60
GYYTPENIAG STDVIIVGAG VAGSALAYTL AKDGRRVHVI ERDLTEQDRI VGELLQPGGY  120
LKLIELGLED CVNEIDAQRV FGYALYMDGK NTRLSYPLEK FHSDVAGRSF HNGRFVQRMR  180
EKAASLPNVR MEQGTVTSLV EKKASVKGVQ YKTKDGQELS AFAPLTIVCD GCFSNLRRSL  240
CNPKVEVPSC FVGLILENID LPHVNHGHVI LADPSPILFY KISSTEIRCL VDVPGQKVPC  300
ISNGELANYL KTVVAPQVPK QLYNSFIAAV DKGNIRTMPN RSMPADPHPT PGALLLGDAF  360
NMRHPLTGGG MTVALSDIVL IRDLLRPLRD LHDSSTLCKY LESFYTLRKP VASTINTLAG  420
ALYKVFCASP DKARQEMRNA CFDYLSLGGI CSQGPIALLS GLNPRPISLF LHFFAVAIYG  480
VGRLLIPFPS PKRMWLGARL ILGASGIIFP IIKSEGLRQM FFPATVPAYY RAPPIH      536

SEQ ID NO: 219          moltype = DNA  length = 1254
FEATURE                 Location/Qualifiers
source                  1..1254
                        mol_type = other DNA
                        organism = synthetic construct
SEQUENCE: 219
atgctggttc gatccgtggt ggatggatca atgccatcgt actctctaga aacccgcctc  60
aaagactgcc gtagagcggc gatgatcagg cgtgaggcgg tggagatgat aactgggagg  120
tcccttgaag ggctaccatt agaggggttt gattacgagt cgattttgaa caagtgctgt  180
gagatgacag ttgggtatgt tcagattcct gtaggagttg tgggtccatt gttgttggat  240
gggattgagt atattgtacc aatggctact actgaggggt gtttggtagc gagtacaaat  300
cgcgggtgta agactatata tgcttctggg ggtgttacta gttttgttct taaggatcca  360
atgactagag ctcctgttgt taggtttcct tctgctaaac gagcttctga attgaagttt  420
ttcttgaag atccacttaa ttttgacacc atggctgtta ttttcaatga gtcgagcagg  480
ttcgcgaggc tgcaaagcgt aaaatgtgga atggcaggga agaatttgta cctacgattc  540
agttgtagca caggggatgc gatgggcatg aacatggcgt ccaaagctgt tgagcaagtc  600
ctcagtttcc tccaggatga gtttcctgac atggatgcta ttggcgtttc tgggaacttc  660
tgttcagaca aaaaagctgc tgcagtgaac tggatagagg ggcgtggaaa gtcggttgtt  720
tgtgaagcag taatcaagga agaagtggtg acaagggtgt taagaagcag tgcctcggcc  780
ctagttgagc ttaatattct aaaaaatctc gctggttctg ccatagctgg agctcttggt  840
ggttttaatg cctatgccag caatatagtg tccgcaatat ttatagccac aggacaagat  900
ccagctcaaa atgttgaaag ctctcagtgc atcaccatga ttgaagctgt gaatgatggc  960
aaggatcttc atgtctctgt ctcaatgcca tccattgagg tgggtacagt tggagggggg  1020
actacacttg catcgcaagc agcatgtctg aacctgctag gagtgaaggg tgcaagtgaa  1080
ggctcagcag gagcaaactc aaggcttctg gctaccatag ttgctggatc agtccttgca  1140
ggggaactct cattaatgtc cgccatagca gaaggtgagc tggtgagtag tcacatgaaa  1200
tacaacaggt caagcaagga tatggctaaa tctatgctca catcttgctc ttaa        1254

SEQ ID NO: 220          moltype = AA  length = 417
FEATURE                 Location/Qualifiers
source                  1..417
                        mol_type = protein
                        organism = Achyranthes bidentata
SEQUENCE: 220
MLVRSVVDGS MPSYSLETRL KDCRRAAMIR REAVEMITGR SLEGLPLEGF DYESILNKCC  60
EMTVGYVQIP VGVVGPLLLD GIEYIVPMAT TEGCLVASTN RGCKTIYASG GVTSFVLKDP  120
MTRAPVVRFP SAKRASELKF FLEDPLNFDT MAVIFNESSR FARLQSVKCG MAGKNLYLRF  180
SCSTGDAMGM NMASKAVEQV LSFLQDEFPD MDAIGVSGNF CSDKKAAAVN WIEGRGKSVV  240
CEAVIKEEVV TRVLRSSASA LVELNILKNL AGSAIAGALG GFNAYASNIV SAIFIATGQD  300
PAQNVESSQC ITMIEAVNDG KDLHVSVSMP SIEVGTVGGG TTLASQAACL NLLGVKGASE  360
GSAGANSRLL ATIVAGSVLA GELSLMSAIA EGELVSSHMK YNRSSKDMAK SMLTSCS      417

SEQ ID NO: 221          moltype = DNA  length = 1275
FEATURE                 Location/Qualifiers
source                  1..1275
                        mol_type = other DNA
                        organism = synthetic construct
SEQUENCE: 221
atgattgcac ccttagtctc ggaggaagac gaaatgatcg tcaactccgt cgtggatggg  60
aagataccct cctattctct ggagtcgaag ctcggggact gcaaacgagc ggctgcgatt  120
cgacgcgagg ctttgcagag gatgacaagg aggtcgctgg aaggcttgcc agtagaaggg  180
ttcgattacg agtcgatttt aggacaatgc tgtgaaatgc cagtgggata cgtgcagatt  240
ccggtgggga ttgcggggcc gttgttgctg aacgggcggg agtactctgt tccaatggcg  300
accacggagg gttgtttggt ggcgagcact aatagagggt gtaaggcgat ttacttgtca  360
ggtggggcca ccagcgtctt gttgaaggat ggcatgacaa gagcgcctgt tgtaagattc  420
gcgtcggcga ctagagccgc ggagttgaag ttcttcttgg aggatcctga caattttgat  480
accttggccg tagtttttaa caagtccagt agatttgcga ggctccaagg cattaaatgc  540
tcaattgctg gtaagaatct ttatataaga ttcagctgca gcactggcga tgcaatgggg  600
atgaacatgg tttctaaagg ggttcaaaac gttcttgaat ttcttcaaag tgatttttct  660
gatatggatg tcattggaat ctcaggaaat ttttgttcgg ataagaagcc tgctgctgta  720
aattggattg aaggacgtgg caaatcagtt gtttgtgagg caattatcaa ggaagaggtg  780
gtgaagaagg tgttgaaaac caatgtggcc tccctagtgg agcttaacat gctcaagaat  840
cttgctggtt ctgctgttgc tggtgctttg ggtggattta atgcccatgc aggcaacatc  900
gtatctgcaa tctttattgc cactggccag gatccagcac agaatgttga gagttctcat  960
tgcattacca tgatggaagc tgtcaatgat ggaaaggatc tccatatctc tgtgaccatg  1020
ccctccattg aggtgggtac agtcggaggt ggaactcaac ttgcatctca gtctgcttgt  1080
ctcaatttgc ttggggtgaa gggtgcaaac aaagagtcgc caggatcaaa ctcaaggctc  1140
```

```
cttgctgcca tcgtagctgg ttcagttttg gctggtgagc tctccttgat gtctgccatt  1200
gcagctgggc agcttgtcaa gagtcacatg aagtacaaca gatccagcaa agatatgtct  1260
aaagctgcat cttag                                                   1275

SEQ ID NO: 222         moltype = AA  length = 424
FEATURE                Location/Qualifiers
source                 1..424
                       mol_type = protein
                       organism = Hevea brasiliensis
SEQUENCE: 222
MIAPLVSEED EMIVNSVVDG KIPSYSLESK LGDCKRAAAI RREALQRMTR RSLEGLPVEG  60
FDYESILGQC CEMPVGYVQI PVGIAGPLLL NGREYSVPMA TTEGCLVAST NRGCKAIYLS  120
GGATSVLLKD GMTRAPVVRF ASATRAAELK FFLEDPDNFD TLAVVFNKSS RFARLQGIKC  180
SIAGKNLYIR FSCSTGDAMG MNMVSKGVQN VLEFLQSDFS DMDVIGISGN FCSDKKPAAV  240
NWIEGRGKSV VCEAIIKEEV VKKVLKTNVA SLVELNMLKN LAGSAVAGAL GGFNAHAGNI  300
VSAIFIATGQ DPAQNVESSH CITMMEAVND GKDLHISVTM PSIEVGTVGG GTQLASQSAC  360
LNLLGVKGAN KESPGSNSRL LAAIVAGSVL AGELSLMSAI AAGQLVKSHM KYNRSSKDMS  420
KAAS                                                               424

SEQ ID NO: 223         moltype = DNA  length = 1263
FEATURE                Location/Qualifiers
source                 1..1263
                       mol_type = other DNA
                       organism = synthetic construct
SEQUENCE: 223
atgtcatcgg aggaggacga agaaatcgtg aaatccgtgg tttcggggaa aacgccgtcg  60
tattcgctgg aatcaaaact cggggactgt tatagagcgg cgtcgattcg acgcgaggcg  120
gtgcagagga ctacggggag gtcactgctg ggttgccgt tggatggttt cgattatgaa  180
tccatattag ggcagtgctg tgagatgccg atagggtatg tgcaaattcc ggtggggatt  240
gcgggtccat tgctgctcaa tggatgcgag tatgtggtgc cgatggccac aacggagggg  300
tgtttggttg cgagtactaa cagaggctgc aaggccattt atgcgtgcgg tggtgccacg  360
gggattttgc taaaagatgg gatgaccaga gcgcctgtgg ttaggttttc tacggcaaaa  420
agggcctcgg atttgaagtt ctttttggaa gatcctctta attttgatac actggccgtc  480
gtttttaata aatcaagcag atttgctagg ctgcaaagca ttcaatgctc aatggcaggg  540
aaaaatcttt acatcagatt ttgctgcagc actggggatg cgatgggaat gaacatggtg  600
tccaagggtg ttcagaatgt cttggagttt cttcaaagtg atttccctga catggatgtg  660
attggtatct ctggaaattt ttgttctgat aagaaaccag ctgcagtcaa ttggattgaa  720
gggcgaggta aatctgttgt ttgtgaggca attataactg atgatgtggt gaagaaggta  780
ttgaaaacca cagtgcctgc ccttgtagag cttaacatgc ttaagaatct tgctggttct  840
gctgttgctg gtgctcttgg tggctttaat gcccatgctg ccaatatcgt ctctgcagtt  900
ttcatagcca ctgggcagga cccagcacaa aatattgaaa gttctcactg cataactatg  960
atggaggcca ttaacaatgg aaaagatctt cacatttctg tcacaatgcc atcgattgag  1020
gttggtactg tcggaggtgg aacacaactg gcgtctcaat ctgcttgctt gaaccttctt  1080
ggtgtgaagg gcgcaaacaa agaatcccat ggatcaaact ccaggctctt ggccaccata  1140
gtagctggct cagttttggc tggagagctc tccttgatgt ctgccattgc agctgggcag  1200
cttgtcagga gccacatgaa atataacagg tcaagccggg atatgtccaa aattggatct  1260
taa                                                                1263

SEQ ID NO: 224         moltype = AA  length = 420
FEATURE                Location/Qualifiers
source                 1..420
                       mol_type = protein
                       organism = Panax ginseng
SEQUENCE: 224
MSSEEDEEIV KSVVSGKTPS YSLESKLGDC YRAASIRREA VQRTTGRSLL GLPLDGFDYE  60
SILGQCCEMP IGYVQIPVGI AGPLLLNGCE YVVPMATTEG CLVASTNRGC KAIYACGGAT  120
GILLKDGMTR APVVRFSTAK RASDLKFFLE DPLNFDTLAV VFNKSSRFAR LQSIQCSMAG  180
KNLYIRFCCS TGDAMGMNMV SKGVQNVLEF LQSDFPDMDV IGISGNFCSD KKPAAVNWIE  240
GRGKSVVCEA IITDDVVKKV LKTTVPALVE LNMLKNLAGS AVAGALGGFN AHAANIVSAV  300
FIATGQDPAQ NIESSHCITM MEAINNGKDL HISVTMPSIE VGTVGGGTQL ASQSACLNLL  360
GVKGANKESH GSNSRLLATI VAGSVLAGEL SLMSAIAAGQ LVRSHMKYNR SSRDMSKIGS  420

SEQ ID NO: 225         moltype = DNA  length = 1872
FEATURE                Location/Qualifiers
source                 1..1872
                       mol_type = other DNA
                       organism = synthetic construct
SEQUENCE: 225
atgactgatt accggctaca accaacgatg aatctttgga ccaccgacga caacgcttct  60
atgatggaag ctttcatgag ctcttccgat atctcaactt tatggcctcc ggcgtcgacg  120
acaaccacga cggcgacgac tgaaacaact ccgacgccgg cgatggagat tccggcacag  180
gcgggattta atcaagagac tcttcagcaa cgtttacaag ctttgattga aggaacacac  240
gaaggttgga cctacgctat attctggcaa ccgtcgtatg atttctccgg cgcctccgtg  300
ctcggatggg gaaacggtta ttacaaaggt gaagaagata aagcaaaccc gagacggaga  360
tcgagttcgc cgccgttttc tactccggcg gatcaggagt acaggaaaaa agtgttgaga  420
gagcttaact cgttgatctc cggtggtgtt gctccgtcgg atgacgctgt tgatgaggag  480
gtgacggata cggaatggtt tttcttggtt tcgatgacgc agagcttcgc ttgcggtgcg  540
ggattagctg gtaaagcgtt tgcaacgggt aacgcggttt gggtttccgg gtcagatcaa  600
ttatccgggt cgggttgtga acgggctaag caaggaggag tgtttgggat gcatactatt  660
```

```
gcgtgtattc cttcggcgaa cggagttgtg gaagtcgggt caacggagcc gatccgacag  720
agttcggacc ttattaacaa ggttcgaatt cttttcaatt tcgacggcgg agctggagat  780
ttatcgggtc ttaattggaa tcttgacccg gatcaaggtg agaacgaccc gtctatgtgg  840
attaatgacc cgattggaac acctggatct aacgaaccgg gtaacggagc tccaagttct  900
agctcccagc ttttttcaaa gtctattcag tttgagaacg gtagctcaag cacaataacc  960
gaaaacccga atctggatcc gactccgagt ccggttcatt ctcagaccca gaatccgaaa  1020
ttcaataaca ctttctcccg agaacttaat ttttcgacgt caagttctac tttagtgaaa  1080
ccaagatccg gcgagatatt aaacttcggc gatgaaggta aacgaagctc cggaaacccg  1140
gatccaagtt cttattcggg tcaaacacaa ttcgaaaaca aaagaaagag gtcgatggtt  1200
ttgaacgaag ataaagttct atcattcgga gataaaaccg ccggagaatc agatcactcc  1260
gatctagaag cttccgtcgt gaaagaagta gcagtagaga aacgtccaaa gaaacgagga  1320
agaaagccag caaacggtag agaagagcca ctaaaccacg tcgaagcaga gagacaaaga  1380
cgcgagaaac taaaccaaag attctacgcg ttacgagcgg ttgtaccaaa cgtttcaaaa  1440
atggataaag cttcgttact cggtgacgca atcgcttaca tcaacgagct taaatccaaa  1500
gtagtcaaaa cagagtcaga gaaactccaa atcaagaacc agctcgagga agtgaaactc  1560
gagctcgccg gaagaaaagc gagtgctagt ggaggagata tgtcgtcttc gtgttcttcg  1620
attaaaccgg tggggatgga gattgaagtg aagataattg gttgggacgc aatgattaga  1680
gttgaatcta gtaagaggaa tcatccggcg gcgaggttga tgtcggcgtt gatggatttg  1740
gagttggaag tgaatcacgc gagtatgtcg gtggttaacg atttgatgat tcaacaagcg  1800
acggtgaaga tgggttttag gatctatacg caagaacagc tcagagcaag tttgatttca  1860
aaaatcggtt aa                                                      1872
```

```
SEQ ID NO: 226          moltype = AA  length = 623
FEATURE                 Location/Qualifiers
source                  1..623
                        mol_type = protein
                        organism = Arabidopsis thaliana
SEQUENCE: 226
MTDYRLQPTM NLWTTDDNAS MMEAFMSSSD ISTLWPPAST TTTTATTETT PTPAMEIPAQ  60
AGFNQETLQQ RLQALIEGTH EGWTYAIFWQ PSYDFSGASV LGWGNGYYKG EEDKANPRRR  120
SSSPPFSTPA DQEYRKKVLR ELNSLISGGV APSDDAVDEE VTDTEWFFLV SMTQSFACGA  180
GLAGKAFATG NAVWVSGSDQ LSGSGCERAK QGGVFGMHTI ACIPSANGVV EVGSTEPIRQ  240
SSDLINKVRI LFNFDGGAGD LSGLNWNLDP DQGENDPSMW INDPIGTPGS NEPGNGAPSS  300
SSQLFSKSIQ FENGSSSTIT ENPNLDPTPS PVHSQTQNPK FNNTFSRELN FSTSSSTLVK  360
PRSGEILNFG DEGKRSSGNP DPSSYSGQTQ FENKRKRSMV LNEDKVLSFG DKTAGESDHS  420
DLEASVVKEV AVEKRPKKRG RKPANGREEP LNHVEAERQR REKLNQRFYA LRAVVPNVSK  480
MDKASLLGDA IAYINELKSK VVKTESEKLQ IKNQLEEVKL ELAGRKASAS GGDMSSSCSS  540
IKPVGMEIEV KIIGWDAMIR VESSKRNHPA ARLMSALMDL ELEVNHASMS VVNDLMIQQA  600
TVKMGFRIYT QEQLRASLIS KIG                                          623
```

```
SEQ ID NO: 227          moltype = DNA  length = 768
FEATURE                 Location/Qualifiers
source                  1..768
                        mol_type = other DNA
                        organism = synthetic construct
SEQUENCE: 227
atggacttgg attgtataca atctccattc ccttttgatc aagtagatga gttatttcca  60
ctcccttctc tttcccctat acacctttct gttgctgatc accctccatt gatcgcttcc  120
atcaacaaca ccaacagaaa tatctccgaa aagccaaaaa aaggtcgtcg gcggaagtcc  180
cctaacactt cggccgatat tgaggacgag aacccgaacc caaacgaaca taaaaagaag  240
aagattatcc acagagatgt tgaacgccaa agaaggcaag aaatgtccac tctttacgcc  300
gctcttcgct cacttctccc ggtggaatat ctcaagggaa agcgatcgat atgtgatcac  360
atgcatgaga cagtgaaata catacaacac atgcaaacca agattcaaat gctgagaaac  420
aagagagatg agcttaaaaa gaatattgaa gatggtgagg attccgggaa cattaccaca  480
atcgaaacat taaactcctc aaaaagggat agtgtgctag tgatgccaag atcatgtgga  540
ggagttcaaa ttcttctaga cacagctaca caccataggc ttccactttc caatcttatc  600
aaatttctaa ttactcaaaa tcttcaaatc attagttgtc attctactag gaagaacgac  660
aggttcctcc acactattga aactgaagct gctgtcgatg ttgaaacaat tgatatgtcg  720
gaactacaga ataaattgac taacttggaa tattttccat tagattaa               768
```

```
SEQ ID NO: 228          moltype = AA  length = 255
FEATURE                 Location/Qualifiers
source                  1..255
                        mol_type = protein
                        organism = Cucumis sativus
SEQUENCE: 228
MDLDCIQSPF PFDQVDELFP LPSLSPIHLS VADHPPLIAS INNTNRNISE KPKKGRRRKS  60
PNTSADIEDE NPNPNEHKKK KIIHRDVERQ RRQEMSTLYA ALRSLLPVEY LKGKRSICDH  120
MHETVKYIQH MQTKIQMLRN KRDELKKNIE DGEDSGNITT IETLNSSKRD SVLVMPRSCG  180
GVQILLDTAT HHRLPLSNLI KFLITQNLQI ISCHSTRKND RFLHTIETEA AVDVETIDMS  240
ELQNKLTNLE YFPLD                                                   255
```

```
SEQ ID NO: 229          moltype = DNA  length = 735
FEATURE                 Location/Qualifiers
source                  1..735
                        mol_type = other DNA
                        organism = synthetic construct
SEQUENCE: 229
atggaatttc cattcccatt tgatcaagca gatgagttat ttccacttcc tgctctttcc  60
```

```
cctatagacc tttctgttcc tcagtcttca ttgatacctt ccaagaacaa gactaacaaa  120
aatatctctg aaaagcccaa aggcagccgt cagcgaaagt ctccgaacgc ttctgatgat  180
atcgatgacg agaacccgag cgaacacaaa aagaagaaga ttatccacag agatgttgaa  240
cggcaaagaa ggcaagaaat gtctactctt tatgccactc ttcgctcact tctcccggtg  300
gaatatctca aggggaagcg atctatatgt gatcacatgc atgaaacagt gaaatacata  360
gaacatatgc aaagcaagat tcagaagcta acaaagaaga gagatgagct gaaaaaggac  420
attgaggatg attccaacat tagtacaatc gaaacgttaa actcctcgaa aagggacagt  480
gttgtagtga agccaagaca tggaggattt caaattcttt tagacacagc cactcaacat  540
aggctcccac tttcgaacct tatcaaattt ctaattactg atcagaggct acaaatcgtc  600
agttgccact ccactaagat aaacgacagg ttccttcaca ccattgaatc tgaagctctc  660
gttaatattg gaaccatcga tgtgtcggaa ctccaacata aattgaccaa cttggaatat  720
tttccattag attaa                                                   735

SEQ ID NO: 230         moltype = AA  length = 244
FEATURE                Location/Qualifiers
source                 1..244
                       mol_type = protein
                       organism = Benincasa hispida
SEQUENCE: 230
MEFPFPFDQA DELFPLPALS PIDLSVPQSS LIPSKNKTNK NISEKPKGSR QRKSPNASDD  60
IDDENPSEHK KKKIIHRDVE RQRRQEMSTL YATLRSLLPV EYLKGKRSIC DHMHETVKYI  120
EHMQSKIQKL TKKRDELKKD IEDDSNISTI ETLNSSKRDS VVVKPRHGGF QILLDTATQH  180
RLPLSNLIKF LITDQRLQIV SCHSTKINDR FLHTIESEAL VNIGTIDVSE LQHKLTNLEY  240
FPLD                                                               244

SEQ ID NO: 231         moltype = DNA  length = 756
FEATURE                Location/Qualifiers
source                 1..756
                       mol_type = other DNA
                       organism = synthetic construct
SEQUENCE: 231
atggaaatgt tcaatgctga gtcccctttt tcttttgacg tgggagaaga tctggtccct  60
ctgccctctc ttccatcctc ctcagtcatc tctccgccct tggacaacta cggtaaccgt  120
gtttctcaaa agccaaaaaa tggccgccgg aaaaagccac tgccaaacac ttgcaatgat  180
gatggcggcg atgagaacca tgacgaacaa aagaagaaga agataataca tagagatgtg  240
gagcgccaaa gaagacaaga aatgtcttct ctttacacca cacttcgctc gcttctccct  300
cttgaatacc ttaagggaaa acgatcaata tcagaccaca tgcaagagac agttagttac  360
attcaacata tgcaaagaag gatccaacaa ctgaaagata aaagaggtac gctaagagaa  420
ctcgccagcc aaactacggt cgccatagcc ggtacgacag aaacgcttaa ttcctcagaa  480
agggcctcag cagtggtgag ggcaaaagat ggaataggaa ttcaagttgt tttagacact  540
gccacaaaac aaaggctccc tctttccatc tttgttcaag ctttagtttc tgaaggcctt  600
gaaatcctca actgcatttc aaacagactg aatgagaggt tcattcacac cattgaatgc  660
caacctcttc taaatgatga tggctgttat ccaaccattg atgtctctgt gcttcagcat  720
aagttagcca atttggaata ttatcctta gattag                              756

SEQ ID NO: 232         moltype = AA  length = 251
FEATURE                Location/Qualifiers
source                 1..251
                       mol_type = protein
                       organism = Cucumis sativus
SEQUENCE: 232
MEMFNAESPF SFDVGEDLVP LPSLPSSSVI SPPLDNYGNR VSQKPKNGRR KKPLPNTCND  60
DGGDENHDEQ KKKKIIHRDV ERQRRQEMSS LYTTLRSLLP LEYLKGKRSI SDHMQETVSY  120
IQHMQRRIQQ LKDKRGTLRE LASQTTVAIA GTTETLNSSE RASAVVRAKD GIGIQVVLDT  180
ATKQRLPLSI FVQALVSEGL EILNCISNRL NERFIHTIEC QPLLNDDGCY PTIDVSVLQH  240
KLANLEYYPL D                                                       251

SEQ ID NO: 233         moltype = DNA  length = 747
FEATURE                Location/Qualifiers
source                 1..747
                       mol_type = other DNA
                       organism = synthetic construct
SEQUENCE: 233
atggacttca atgttgagtc tccagtttca tttgatttag gagatgacct acttcctctg  60
ccatctcttc catcgtcctc cgcaatctct atgccagtgg acaaccgtcg taatggtgtc  120
tcccaaaatc aaaaaaatgg ccgccggaaa aagccattgc ccaacacttg caatgacaat  180
ggcaatgaga gccccaacga agaaagaaaa aagaagataa tacatagaga tgtggagcgg  240
caaagaagac aagaaatgtc ttccctttat accactcttc gctcacttct ccctcttgaa  300
tacctcaagg gaaaaaggtc aatatccgac cacatacatg agacagttaa ctacattcaa  360
catatgcaag aaagaattca acaactgtct gataaaagag atgagctaag aaaactctcc  420
aatggaacta cggccaccgt cgatacggca aaaacactta attcctcaga aagggactct  480
gtggtggtga ggccaaaaga tggaatagga attcaagttg taatagacac tgccacaaaa  540
cataggttcc ctctttccaa ctttcttcaa gctttagctg cggaaggact tgaaatcctc  600
agctgcattt ccaacagact gaatgagagg ttcattcata ccattgaatg ccaacctatt  660
cttaataatg acggcgtcta tccaaacatc gatgtgtttg agcttcacca taagttaacg  720
aatttggaat attttccttt agattag                                      747

SEQ ID NO: 234         moltype = AA  length = 248
FEATURE                Location/Qualifiers
```

```
source                  1..248
                        mol_type = protein
                        organism = Benincasa hispida
SEQUENCE: 234
MDFNVESPVS FDLGDDLLPL PSLPSSSAIS MPVDNRRNGV SQNQKNGRRK KPLPNTCNDN  60
GNESPNEERK KKIIHRDVER QRRQEMSSLY TTLRSLLPLE YLKGKRSISD HIHETVNYIQ  120
HMQERIQQLS DKRDELRKLS NGTTATVDTA KTLNSSERDS VVVRPKDGIG IQVVIDTATK  180
HRFPLSNFLQ ALAAEGLEIL SCISNRLNER FIHTIECQPI LNNDGVYPNI DVFELHHKLT  240
NLEYFPLD                                                         248

SEQ ID NO: 235          moltype = DNA  length = 2418
FEATURE                 Location/Qualifiers
source                  1..2418
                        mol_type = other DNA
                        organism = synthetic construct
SEQUENCE: 235
atggctgaac gtgctcttac tcgtgtccat agcattcgtg aacgtgtaga tgagactctc  60
aaggctcatc gcaatgaaat tgttgcgtta ctcacaagga tcgaaggtaa gggaaaagga  120
attctccaac accaccagat tgttgctgag tttgaagcaa ttcctgaaga caccaggaaa  180
acattggcag gcggtgcttt tgctgaagtt ctcagatcca cacaggaagc aattgttgtg  240
cctccatgga ttgctcttgc tctgcgcccg aggcctggtg tctgggagta cattagactg  300
aatgtccaag cacttgttgt tgaggagttg cgtgttgctg agtatcttca tttcaaggag  360
gagcttgttg atggaggctg caacggcaac ttcgtgcttg aattggactt cgaaccattc  420
aatgcatctt tccctcgccc aactctttca aagtatattg gtaatggtgt tgagttcctc  480
aatcgccacc tttcggctaa gttgttccat gacaaggaaa gcctgcatcc cctgcttgca  540
tttctcaaag tgcactgtca caaggggaag aatatgatgc tgaatgacag aattcgtaac  600
ctagactctc tgcaatatgt tctgagaaag gctgaggagt ttctgtctac tctgaaacct  660
gatactccat attctcaatt tgaacacaag ttccaggaga ttggcttgga gagaggatgg  720
ggtgatactg ctgagcgtgt tcttgagatg attcgacttc ttttggatct tcttgaggca  780
ccagatccct gcactctcga aacattccta ggcagaattc ctatggtctt caatgttgtg  840
attatgtccc ctcatggata ctttgcccaa gacaatgttt tggggtatcc tgatactgga  900
ggccaggttg tttacatttt ggatcaagtc cgtgccttgg agaatgaaat gcttcagcgt  960
atcaagaagc aaggacttga tattatcccc cgaattctca ttattactcg actactccct  1020
gatgcagtag gaaccacttg tggtcaacgt ttggagagag tgtatggatc tgagcattgt  1080
gatattcttc gagttccctt cagagatgga aagggtatgg tccgcaaatg gatctctcgc  1140
tttgaagtgt ggccatacct agaaactttc accgaggacg ttgctgctga aattgctaag  1200
gagttgcagg gcaagcctga tcttatcatt ggaaattaca gtgatggaaa catcgttgcc  1260
tccttgttag cacacaaatt aggtgttaca gagtgcacca ttgcgcatgc tctagaaaaa  1320
acaaagtatc cagactcaga tatatactgg aagaagtttg atgaaaagta ccacttctca  1380
tgccagttta cagctgatct ttttgcaatg aaccatacag atttcattat caccagcaca  1440
ttccaagaga ttgctggaag caaggatact gttggacagt atgaaagcca cactgctttc  1500
actctccctg gcctctatag agttgttcat ggtattgatg tctttgatcc caaattcaac  1560
attgtatccc ctggcgctga tgagagcata tacttcccct acactgacga gaaacgtagg  1620
ttgacttctt tccatccaga aattgacgag cttctttaca gccctgttga gaatgaagag  1680
cacttatgtg tgctaaaaga ccgaaacaaa ccaattctat ttaccatggc aaggctggac  1740
agagttaaga atttatctgg tcttgtagag tggtatggaa agaacaccaa gctacgtgaa  1800
ttagttaatc ttgttgtagt tggtggagat agaagaaagg agtctaaaga tctagaagag  1860
caagctgaga tgaagaaaat gtacagtcat atagagaaat acaacttgaa tggccagttc  1920
agatggattt cttcccagat gaaccgtgtg aggaatggag agctttaccg ttacatttgt  1980
gataccaagg gagctttcgt gcagcctgct ttgtatgagg cttttggatt gacagttgtt  2040
gaggccatga cttgtggttt gccaactttt gctacctgca atggtggtcc tgctgagatc  2100
attgtgaatg gaaaatccgg attccacatc gatccttatc atggtgagaa ggctgctgag  2160
ctccttgttg acttctttga gaagtgcaag gtcgatcccg ctcactggga caaaatctcc  2220
cacggaggtc tgcaacgaat ccaagagaag tatacctggc aaatttactc tcaaaggctc  2280
ctgacgctca caggagttta tggattctgg aagcacgttt cgaaccttga tcgtcttgag  2340
agccgtcggt atatggaaat gttctatgca ctcaaatacc gtaaattggc tgagtctgtt  2400
cctctgacta aggagtaa                                              2418

SEQ ID NO: 236          moltype = AA  length = 805
FEATURE                 Location/Qualifiers
source                  1..805
                        mol_type = protein
                        organism = Populus alba
SEQUENCE: 236
MAERALTRVH SIRERVDETL KAHRNEIVAL LTRIEGKGKG ILQHHQIVAE FEAIPEDTRK  60
TLAGGAFAEV LRSTQEAIVV PPWIALALRP RPGVWEYIRL NVQALVVEEL RVAEYLHFKE  120
ELVDGGCNGN FVLELDFEPF NASFPRPTLS KYIGNGVEFL NRHLSAKLFH DKESLHPLLA  180
FLKVHCHKGK NMMLNDRIRN LDSLQYVLRK AEEFLSTLKP DTPYSQFEHK FQEIGLERGW  240
GDTAERVLEM IRLLLDLLEA PDPCTLETFL GRIPMVFNVV IMSPHGYFAQ DNVLGYPDTG  300
GQVVYILDQV RALENEMLQR IKKQGLDIIP RILIITRLLP DAVGTTCGQR LERVYGSEHC  360
DILRVPFRDG KGMVRKWISR FEVWPYLETF TEDVAAEIAK ELQGKPDLII GNYSDGNIVA  420
SLLAHKLGVT ECTIAHALEK TKYPDSDIYW KKFDEKYHFS CQFTADLFAM NHTDFIITST  480
FQEIAGSKDT VGQYESHTAF TLPGLYRVVH GIDVFDPKFN IVSPGADESI YFPYTDEKRR  540
LTSFHPEIDE LLYSPVENEE HLCVLKDRNK PILFTMARLD RVKNLSGLVE WYGKNTKLRE  600
LVNLVVVGGD RRKESKDLEE QAEMKKMYSH IEKYNLNGQF RWISSQMNRV RNGELYRYIC  660
DTKGAFVQPA LYEAFGLTVV EAMTCGLPTF ATCNGGPAEI IVNGKSGFHI DPYHGEKAAE  720
LLVDFFEKCK VDPAHWDKIS HGGLQRIQEK YTWQIYSQRL LTLTGVYGFW KHVSNLDRLE  780
SRRYMEMFYA LKYRKLAESV PLTKE                                      805
```

```
SEQ ID NO: 237         moltype = DNA  length = 1443
FEATURE                Location/Qualifiers
source                 1..1443
                       mol_type = other DNA
                       organism = synthetic construct
SEQUENCE: 237
atggctgcag caccagcagt tgcttcaccc gcagtcgaaa ccgaccggat ctttaagctt  60
aaagccgagg tcgcgaagct gaaccagatc agtgttaatg agaaggaagg atttgtccga  120
ctagtttctc gctacctaag cggcgaagaa gagagaattg aatgggaaaa aatcaagacc  180
ccgactgacg aggtcgtagt tccctacgat actttggctg atctgggaga agatccatcg  240
gaagccaagg aactcctgga caagcttgtt gtgctaaagc ttaatggcgg tttgggaaca  300
accatgggct gtactggtcc caagtctgtc attgaagtac gaaatggcct aacatttctg  360
gacttgattg tgaagcaaat agagtctctg aacaacaaat acgattgcag agtaccattg  420
gtgttgatga attcattcaa cacacatgac gatacaatta agattgtaga aaagtacact  480
ggctcaaata tcgacatcca catctttaac cagagtcagt atccacgcat ggtggcagaa  540
gatttgatgc catggccaac taaaggtcgt acagataaag gaggatggta cccacctggc  600
cacggagatg ttttccctgc tcttttgaac agtggaaagc ttggtgaact actctcacag  660
ggaaaggagt atgtgtttgt agctaactca gacaacttgg gagcgatagt tgatctcaaa  720
attttgaatc atcttgtcaa aaataaaaac gaatactgca tggaggtcac tcccaaaaca  780
ctcgcagatg taaaaggtgg tactcttatt tcttatgaag gcagggttca gcttctggag  840
attgcacagg ttcccgagga gcatgttggt gagttcaagt caattgagaa gttcaaaatc  900
ttcaatacca ataatttgtg ggtgaacttg aaggccatta agaggcttgt ggagtctgat  960
gctcttaaaa tggagataat tccaaatcca aaggaggtgg atggggtaaa ggtgcttcag  1020
cttgaaacgg ctgccggtgc tgctataagg ttttttgatc gtgcaattgg tgtcaatgtt  1080
ccaagatcac gttttctccc agtgaaggcg gcttcagatc tactacttgt gcagtcggat  1140
ctttacactg tggaggaagg tttcgtcatc cgaaatcctg ctagagtcaa ccctgcaaat  1200
ccctccattg agctgggtcc tgaattcaag aaggttggca actttctaaa gcgtttcaag  1260
tccataccta gtatcattga tcttgatagt ctaaaggtgt caggcgatgt gtggtttggc  1320
agtggaatca tcctaaaggg aaaggttact attgaagcaa agcagggggt taaacttgag  1380
atacctgatg aatctgtgat tgaaaacaag gtagtgagca gtcctgatga tattgtgaac  1440
tag                                                                1443

SEQ ID NO: 238         moltype = AA  length = 480
FEATURE                Location/Qualifiers
source                 1..480
                       mol_type = protein
                       organism = Larix gmelinii
SEQUENCE: 238
MAAAPAVASP AVETDRIFKL KAEVAKLNQI SVNEKEGFVR LVSRYLSGEE ERIEWEKIKT  60
PTDEVVVPYD TLADLGEDPS EAKELLDKLV VLKLNGGLGT TMGCTGPKSV IEVRNGLTFL  120
DLIVKQIESL NNKYDCRVPL VLMNSFNTHD DTIKIVEKYT GSNIDIHIFN QSQYPRMVAE  180
DLMPWPTKGR TDKGGWYPPG HGDVFPALLN SGKLGELLSQ GKEYVFVANS DNLGAIVDLK  240
ILNHLVKNKN EYCMEVTPKT LADVKGGTLI SYEGRVQLLE IAQVPEEHVG EFKSIEKFKI  300
FNTNNLWVNL KAIKRLVESD ALKMEIIPNP KEVDGVKVLQ LETAAGAAIR FFDRAIGVNV  360
PRSRFLPVKA ASDLLLVQSD LYTVEEGFVI RNPARVNPAN PSIELGPEFK KVGNFLKRFK  420
SIPSIIDLDS LKVSGDVWFG SGIILKGKVT IEAKQGVKLE IPDESVIENK VVSSPDDIVN  480

SEQ ID NO: 239         moltype = DNA  length = 1971
FEATURE                Location/Qualifiers
source                 1..1971
                       mol_type = other DNA
                       organism = synthetic construct
SEQUENCE: 239
atgatcgtta atttctcttt cttcctcctt ctcttcgtct ccgtcttcgt ttcctctgct  60
gattctaaag cgaccatttc aatttcccct aatgctctca atcgatctgg cgattccgtt  120
gtgatacaat ggtccggtgt cgattctccg tcagatctcg attggttagg actctactcg  180
ccgccggagt ctcctaatga tcactttatt ggttacaaat tcctcaatga atcgtccact  240
tggaaagatg gtttcggttc gatttctctt cctttaacca atctccgatc aaattacaca  300
ttccggatct tccgttggag cgaatccgag attgatccga aacataagga tcatgatcag  360
aatcctttac caggaactaa acatcttcta gctgaatcgg agcagctgac tttcggatcc  420
ggtgttggta tgccggagca gatccatttg tcgttcacaa atatggttaa cacgatgcgt  480
gttatgtttg tagctggaga tggtgaagaa cgttttgtta gatacggtga atcgaaggat  540
ttgttaggta attccgcggc ggcgcgtggg atgaggtacg agagagagca catgtgtgat  600
tcgccggcga attccactat tggttggaga gatcctggtt ggatttttga taccgtcatg  660
aagaatttga atgatggcgt tagatactat tatcaggttg ggagtgattc taagggatgg  720
agtgagatcc atagctacat tgctcgagat gtgactgcag aagaaaccgt agctttcatg  780
tttggagata tgggttgtgc tacaccatac acgacattta tccgcacaca agatgagagc  840
atatctacag tgaagtggat cctccgtgac attgaagctc ttggtgataa gccagctatg  900
atttcacaca ttggagatat aagttatgct cgtggttact cgtgggtatg ggatgagttc  960
tttgctcagg ttgagcctat tgcctcgaca gttccttacc atgtttgcat tggtaaccat  1020
gagtatgatt tctctactca gccgtggaaa cctgattggg cagcttctat ttatggaaac  1080
gatggtggtg gcgaatgtgg tgtgccgtat agcttgaagt ttaacatgcc tgggaattct  1140
tcagagtcta caggaatgaa agctcctccg acaaggaatt tatattattc ttatgatatg  1200
ggaacggtcc atttcgttta tatctccaca gagacgaatt ttcttaaagg aggtagtcaa  1260
tatgaattca taaagcgaga tctagagtct gtagacagga agaaaacacc gtttgttgtt  1320
gtgcaaggac atagaccaat gtacactacg agcaacgagg ttagagacac tatgattcga  1380
caaaagatgg ttgagcatct agaacctttg tttgtgaaaa acaatgtcac acttgctcta  1440
tggggacatg ttcatagata cgaaaggttt tgtcccataa gcaacaacac ttgcggcaca  1500
cagtggcaag gaaatccggt tcatcttgtg atcggtatgg ctggtcaaga ttggcaaccg  1560
```

```
atttggcagc ctagaccaaa ccatccagat cttcctatat tccctcagcc tgaacaatca  1620
atgtatcgta caggtgagtt tggttacact cgtttagttg caaacaaaga aaagctcact  1680
gtttcttttg tgggtaatca cgatggcgaa gttcatgata ctgttgagat gttagcatct  1740
ggggtagtaa tcagtgggag caaagagagt actaaaatcc caaatctgaa aaccgttcct  1800
gcttctgcta cacttatggg aaaatcagaa tctaatgctt tgtggtatgc caaaggagca  1860
ggcttgatgg ttgtgggtgt gcttttaggg ttcattatcg ggtttttac ccggggaaag   1920
aaatcttcgt ctggaaaccg ttggatccca gtcaagaacg aggagacata a            1971

SEQ ID NO: 240          moltype = AA  length = 656
FEATURE                 Location/Qualifiers
source                  1..656
                        mol_type = protein
                        organism = Arabidopsis thaliana
SEQUENCE: 240
MIVNFSFFLL LFVSVFVSSA DSKATISISP NALNRSGDSV VIQWSGVDSP SDLDWLGLYS  60
PPESPNDHFI GYKFLNESST WKDGFGSISL PLTNLRSNYT FRIFRWSESE IDPKHKDHDQ  120
NPLPGTKHLL AESEQLTFGS GVGMPEQIHL SFTNMVNTMR VMFVAGDGEE RFVRYGESKD  180
LLGNSAAARG MRYEREHMCD SPANSTIGWR DPGWIFDTVM KNLNDGVRYY YQVGSDSKGW  240
SEIHSYIARD VTAEETVAFM FGDMGCATPY TTFIRTQDES ISTVKWILRD IEALGDKPAM  300
ISHIGDISYA RGYSWVWDEF FAQVEPIAST VPYHVCIGNH EYDFSTQPWK PDWAASIYGN  360
DGGGECGVPY SLKFNMPGNS SESTGMKAPP TRNLYYSYDM GTVHFVYIST ETNFLKGGSQ  420
YEFIKRDLES VDRKKTPFVV VQGHRPMYTT SNEVRDTMIR QKMVEHLEPL FVKNNVTLAL  480
WGHVHRYERF CPISNNTCGT QWQGNPVHLV IGMAGQDWQP IWQPRPNHPD LPIFPQPEQS  540
MYRTGEFGYT RLVANKEKLT VSFVGNHDGE VHDTVEMLAS GVVISGSKES TKIPNLKTVP  600
ASATLMGKSE SNALWYAKGA GLMVVGVLLG FIIGFFTRGK KSSSGNRWIP VKNEET      656

SEQ ID NO: 241          moltype = DNA  length = 477
FEATURE                 Location/Qualifiers
source                  1..477
                        mol_type = other DNA
                        organism = synthetic construct
SEQUENCE: 241
atggatttca ggctaatggg tttggattca ccactcttca acaccctcca ccacataatg  60
gacctcacag atgacacaac agagaagaat ctaaacgcac caacacgaac ctacgttcgc  120
gacgcaaaag caatggctgc aacaccagca gacgtgaaag agtatccaaa ttcatacgtg  180
ttcgtggtgg acatgccagg gttgaaatca ggtgacatca aggttcaggt tgaagatgag  240
aatgtgcttc tgataagcgg tgaaaggaag agagaagaag agaaagaagg tggtaaatat  300
ttgaagatgg aaagaagggt tggtaagttt atgaggaaat ttgtgttacc tgagaatgct  360
gatgttgaag gtggtgtttc tgctgtttgt caagatggtg ttcttactgt tactgttaat  420
aagttgcctc ctcctgaacc taagaagcct aagactattg aggttaaggt tgcttga     477

SEQ ID NO: 242          moltype = AA  length = 158
FEATURE                 Location/Qualifiers
source                  1..158
                        mol_type = protein
                        organism = Medicago sativa
SEQUENCE: 242
MDFRLMGLDS PLFNTLHHIM DLTDDTTEKN LNAPTRTYVR DAKAMAATPA DVKEYPNSYV  60
FVVDMPGLKS GDIKVQVEDE NVLLISGERK REEEKEGGKY LKMERRVGKF MRKFVLPENA  120
DVEGGVSAVC QDGVLTVTVN KLPPPEPKKP KTIEVKVA                          158

SEQ ID NO: 243          moltype = DNA  length = 594
FEATURE                 Location/Qualifiers
source                  1..594
                        mol_type = other DNA
                        organism = synthetic construct
SEQUENCE: 243
atgagaggta ggaaatacag gaatagcgtt cgaccaaacc gagtgaccgg ttcaggtttc  60
tggaaagcca ctggtattga taaaccggtt tactccaatc ttgactgtgt tggcctcaag  120
aaatctctgg tttactatct tggttcagcc ggtaaaggca ccaaaaccga ttggatgatg  180
catgaattcc gcctcccctc caccacgaaa accgactctc cagctcaaca agcagaggta  240
tggacacttt gcagaatctt caaacgagtc acatctcaaa gaaacccaac catcttacca  300
ccaaaccgaa aaccggttat cactttaacc gacacttgtt ctaagaccag cagcttagat  360
tccgaccaca cgagccaccg tacagtagat tccatgtccc acgagccgcc gcttccacag  420
ccacagaatc cttattggaa ccaacatata gttggtttta atcaaccgac atatactggt  480
aatgataata acctcctgat gagtttctgg aacggcaacg gtggagattt cataggagac  540
tcagcaagtt gggatgaact tagatctgtt atagatggca acactaaacc ctag         594

SEQ ID NO: 244          moltype = AA  length = 197
FEATURE                 Location/Qualifiers
source                  1..197
                        mol_type = protein
                        organism = Arabidopsis thaliana
SEQUENCE: 244
MRGRKYRNSV RPNRVTGSGF WKATGIDKPV YSNLDCVGLK KSLVYYLGSA GKGTKTDWMM  60
HEFRLPSTTK TDSPAQQAEV WTLCRIFKRV TSQRNPTILP PNRKPVITLT DTCSKTSSLD  120
SDHTSHRTVD SMSHEPPLPQ PQNPYWNQHI VGFNQPTYTG NDNNLLMSFW NGNGGDFIGD  180
SASWDELRSV IDGNTKP                                                 197
```

```
SEQ ID NO: 245          moltype = DNA  length = 891
FEATURE                Location/Qualifiers
source                 1..891
                       mol_type = other DNA
                       organism = synthetic construct
SEQUENCE: 245
atggcccacg gcctcaccca tttcaacacc aaatcgggtt tattcccatc tatcaccaaa  60
tcaaaaacaa cccgtccatc aacccgaccc gtgattctcg ccatgacccg gacccaaact  120
taccgggcca ccattgaatc cgacattgaa tcttatctca agaaggccat cccaatccgg  180
gcacctgaat ccgtattcga gcccatgcac cacctcacgt ttgccgcccc aagaaccagc  240
gcatcggctt tatgcgtggc agcgtgcgag ctcgttggcg gcgaccgaag cgatgccatg  300
gcggcggcgg cggcggtgca tctcatgcac gtggcggcgt acacacacga gaaccttcct  360
cttaccgacg ggcccatgtc caaatcggaa atccaacaca agttcgatcc gaatatcgaa  420
cttttgacag gagacggaat cataccattc gggctggagt tgatggcgag atcaatggat  480
ccgacccgga acaacccgga taggatccta agagcgataa tcgaactcac ccgggtcatg  540
ggctcagagg gaattgtaga agggcaatac catgaacttg gtctaaatca attaaacgat  600
ttagaactca tcgagtatgt ttgcaagaaa aaagaaggga cactacatgc atgtggggcc  660
gcttgtggag caattttagg tggatgtgat gaagataaaa tagaaaagtt gagaagattc  720
ggactttatg tgggtacggt tcaagggttg ttgggtaaaa atagatccgg atttgaagga  780
agaattaagg aattgaagga attggctgtt aaggaactgg agagctttgg tggtgagaaa  840
attgagctga ttaggggcgt ttttgagcta gagcatagtc ttgctggtgt t           891

SEQ ID NO: 246          moltype = AA  length = 297
FEATURE                Location/Qualifiers
source                 1..297
                       mol_type = protein
                       organism = Antirrhinum majus
SEQUENCE: 246
MAHGLTHFNT KSGLFPSITK SKTTRPSTRP VILAMTRTQT YRATIESDIE SYLKKAIPIR  60
APESVFEPMH HLTFAAPRTS ASALCVAACE LVGGDRSDAM AAAAAVHLMH VAAYTHENLP  120
LTDGPMSKSE IQHKFDPNIE LLTGDGIIPF GLELMARSMD PTRNNPDRIL RAIIELTRVM  180
GSEGIVEGQY HELGLNQLND LELIEYVCKK KEGTLHACGA ACGAILGGCD EDKIEKLRRF  240
GLYVGTVQGL LGKNRSGFEG RIKELKELAV KELESFGGEK IELIRGVFEL EHSLAGV     297

SEQ ID NO: 247          moltype = DNA  length = 1029
FEATURE                Location/Qualifiers
source                 1..1029
                       mol_type = other DNA
                       organism = synthetic construct
SEQUENCE: 247
atgagcgatc tgaagacgag atttctggag gtgtactctg ttctgaaatc cgagctactc  60
aacgaccctg ctttcgagtt caccgatgat tctcgccaat gggtcgagcg gatgctggac  120
tataatgtgc ctggaggaaa gctgaatcga gggctgtctg ttattgacag ctacaagttg  180
ctgaaagaag gaaaagaact aagtgatgat gaaatttttc tttcaagtgc acttggttgg  240
tgcattgaat ggcttcaagc ttattttctt gtgctcgatg atattatgga tagctctcat  300
acgcgcagag gtcaaccctg ttggttcaga ttacctaagg ttggtatgat tgccgtaaat  360
gatggcatat tacttcgcaa ccatatccca aggattctca agaagcattt ccgacaaaag  420
ccttactatg tggatctgtt ggatctattt aatgaggtag aattccagac agctagtgga  480
cagatgatag atttgatcac caccettgta ggagagaaag acttatcgaa atactcattg  540
cctattcatc gccggattgt gcagtacaaa actgcttact actcatttta ccttccagtg  600
gcctgtgcac ttcttatgtc aggcgaagat ctggagaaac atactaatgt aaaggacata  660
cttattgaaa tgggaaccta ttttcaagtg caggatgatt atctggattg ctttggtgca  720
ccagaggtga ttgggaagat tggcacagat attgaagatt tcaagtgctc ctggttggta  780
gtaaaagcac tggaactttc taacgaggaa cagaagaagt ttttacatga gaactatgga  840
aaggatgatc cggcctctgt agcaaaagtg aaagagcttt ataacactct caagcttcag  900
gatgtatttg ccgagtatga gagcaagagc tatgacaagt tgatcaaatt cattgaagct  960
catccgagcc aagccgtaca agcagtgtta aaatcattct tgggaaagat atataagcgg  1020
caaaagtaa                                                         1029

SEQ ID NO: 248          moltype = AA  length = 342
FEATURE                Location/Qualifiers
source                 1..342
                       mol_type = protein
                       organism = Panax ginseng
SEQUENCE: 248
MSDLKTRFLE VYSVLKSELL NDPAFEFTDD SRQWVERMLD YNVPGGKLNR GLSVIDSYKL  60
LKEGKELSDD EIFLSSALGW CIEWLQAYFL VLDDIMDSSH TRRGQPCWFR LPKVGMIAVN  120
DGILLRNHIP RILKKHFRQK PYYVDLLDLF NEVEFQTASG QMIDLITTLV GEKDLSKYSL  180
PIHRRIVQYK TAYYSFYLPV ACALLMSGED LEKHTNVKDI LIEMGTYFQV QDDYLDCFGA  240
PEVIGKIGTD IEDFKCSWLV VKALELSNEE QKKFLHENYG KDDPASVAKV KELYNTLKLQ  300
DVFAEYESKS YDKLIKFIEA HPSQAVQAVL KSFLGKIYKR QK                    342

SEQ ID NO: 249          moltype = DNA  length = 1248
FEATURE                Location/Qualifiers
source                 1..1248
                       mol_type = other DNA
                       organism = synthetic construct
SEQUENCE: 249
atgggaagtt tgggggcaat tctgaagcat ccggaagatt tctatccgtt gttgaagctt  60
```

```
aaatttgcgg ctaggcatgc ggaaaagcag atccctccgg agccacactg ggccttctgt  120
tactctatgc ttcataaagt ttctcgaagt ttcggcctcg tcattcaaca gctcggccct  180
cagctccgcg atgctgtatg catttttat ttggttcttc gagcacttga cactgttgag   240
gatgacacaa gtatacctac agaggttaaa gtacctatct tgatggcttt tcatcgccac  300
atatatgata aggactggca cttttcatgt ggtacgaagg aatacaaagt tctcatggac  360
gagtttcatc atgtttctaa tgcttttctt gagcttggaa gcggttacca ggaggcaata  420
gaagatatta ccatgagaat gggtgcagga atggcaaaat ttatatgcaa ggaggtggag  480
acaataaatg attatgatga atattgtcac tatgtagcag gacttgttgg attagggttg  540
tcaaagctct tccatgcctc tggggcagaa gatttggcta cagattctct gtccaattca  600
atgggtttat ttctccagaa gacaaacata attcgagatt acttggagga cataaatgag  660
ataccaaagt cacgcatgtt ttggcctcgc cagatttgga gtaaatatgt cgataaactt  720
gaggacttga aatatgagga aaactcagcc aaggcagtgc agtgcctaaa tgacatggtc  780
acagatgctt tggttcatgc tgaagattgc ctaaagtaca tgtctgactt gcgaggtcct  840
gctatcttcc ggttctgtgc aataccacag attatggcaa ttggaacact agctttatgc  900
tttaacaaca ctcaagtctt cagaggggta gtgaaaatga gacgtggtct tactgctaaa  960
gttattgacc aaacaaaaac aatgtcagat gtatatggtg ctttcttcga tttttcttgt  1020
ttgctgaagt ccaaggttga caacaatgat cccaatgcta caaaaacttt gagcaggcta  1080
gaagcaattc agaaaacatg caaggagtct ggaaccctgt ccaaaaggaa atcatacata  1140
atcgagagcg agtcaggaca caattcagcc ctgattgcta ttatcttcat tatactagct  1200
atcctttatg catatctatc ttcaaaccta ctactgaaca aacagtga             1248

SEQ ID NO: 250          moltype = AA  length = 415
FEATURE                 Location/Qualifiers
source                  1..415
                        mol_type = protein
                        organism = Panax ginseng
SEQUENCE: 250
MGSLGAILKH PEDFYPLLKL KFAARHAEKQ IPPEPHWAFC YSMLHKVSRS FGLVIQQLGP  60
QLRDAVCIFY LVLRALDTVE DDTSIPTEVK VPILMAFHRH IYDKDWHFSC GTKEYKVLMD  120
EFHHVSNAFL ELGSGYQEAI EDITMRMGAG MAKFICKEVE TINDYDEYCH YVAGLVGLGL  180
SKLFHASGAE DLATDSLSNS MGLFLQKTNI IRDYLEDINE IPKSRMFWPR QIWSKYVDKL  240
EDLKYEENSA KAVQCLNDMV TDALVHAEDC LKYMSDLRGP AIFRFCAIPQ IMAIGTLALC  300
FNNTQVFRGV VKMRRGLTAK VIDQTKTMSD VYGAFFDFSC LLKSKVDNND PNATKTLSRL  360
EAIQKTCKES GTLSKRKSYI IESESGHNSA LIAIIFIILA ILYAYLSSNL LLNKQ       415

SEQ ID NO: 251          moltype = DNA  length = 1425
FEATURE                 Location/Qualifiers
source                  1..1425
                        mol_type = other DNA
                        organism = synthetic construct
SEQUENCE: 251
atggcgtctc atccagaaaa tgttggtatt ttggctatgg atatctactt tccgagcaca  60
tgtgttcagc aggatgccct ggaaaccttt gatggagtaa gtaaagggaa atacacaatt  120
ggccttggac aagactgcat ggcattttgc atggacttgg aagatgtgat ttccatgagc  180
ttgactgtag tatcctcact cttggacaag tatggaatcg atccaaaaag aattggtcgc  240
ttggaagttg gcagtgaaac tgttattgac aagagcaagt ccataaagac ctggttgatg  300
cagatttttg aggaatgtgg caatagtgag attgaaggtg tggactcaac aaatgcatgc  360
tatggaggaa ctgcagctct gcttaactgt gttaactggg ttgaaagcag gtcttgggat  420
gggcgatatg gactcgttgt ttctacagac agtgcagtct atgctgaagg tccagcccga  480
cctacagggg gagcagctgc tgttgctatg ctgatagggc ccaatgcacc tatagtgttt  540
gaaagcaaat acaggggaac acacatgtct catgcgtatg acttttataa gcccaattta  600
gccagcgagt acccagttgt ggatgggaag ctttcacaaa cttgctatct catgggactg  660
gactcatgct acaaacggtt ttgtaatcgg tttgaggagg gagaaggaag acaatttct   720
ctttcagatg cagattatgt agcatttcac tctccataca ataagcttgt gcaaaagagc  780
tttgctcgac tgttgttcaa tgatttctca agacatgcca gttctgttgg gaaggatgcg  840
caagaaaagc tagagccgta tgcaggcttg tctgatgaag atagctacag tagccgtgaa  900
ctagaaaagg tttctcagca ggttgctagg ccattgtatg atgtaaaagt tcaaccatca  960
accttattgc caaagcaagt aggcaacatg tacacagcat ctctttatgc agcgtttgcc  1020
tctattatac ataacaagca tgataccctg gaggggcaga gggtgttgat gttttcttat  1080
gggagtggtt tggcttccac aatgttttct ttgaaaattc gggagggtca gcatcctttc  1140
accttaacaa atattgcaga tgttatggat gtctcgagca agcttgattc tcgacatgtg  1200
ttgtcccctg aagattttat ggtcaacatg aagctgatgg agactctata tggagcaaaa  1260
gatttcattt catgctctga tcacaacttg ctgcgatctg gaacatttta tttgactcaa  1320
gtagattcaa tgtaccgacg tttctatgcc cagaaggttg caagtccaga tgacactcat  1380
gagaaggtca aacttgcaaa tggtatcatc catgatcaat tgtaa                1425

SEQ ID NO: 252          moltype = AA  length = 474
FEATURE                 Location/Qualifiers
source                  1..474
                        mol_type = protein
                        organism = Ginkgo biloba
SEQUENCE: 252
MASHPENVGI LAMDIYFPST CVQQDALETF DGVSKGKYTI GLGQDCMAFC MDLEDVISMS  60
LTVVSSLLDK YGIDPKRIGR LEVGSETVID KSKSIKTWLM QIFEECGNSE IEGVDSTNAC  120
YGGTAALLNC VNWVESRSWD GRYGLVVSTD SAVYAEGPAR PTGGAAAVAM LIGPNAPIVF  180
ESKYRGTHMS HAYDFYKPNL ASEYPVVDGK LSQTCYLMGL DSCYKRFCNR FEEGEGRQFS  240
LSDADYVAFH SPYNKLVQKS FARLLFNDFS RHASSVGKDA QEKLEPYAGL SDEDSYSSRE  300
LEKVSQQVAR PLYDVKVQPS TLLPKQVGNM YTASLYAAFA SIIHNKHDTL EGQRVLMFSY  360
GSGLASTMFS LKIREGQHPF TLTNIADVMD VSSKLDSRHV LSPEDFMVNM KLMETLYGAK  420
```

DFISCSDHNL LRSGTFYLTQ VDSMYRRFYA QKVASPDDTH EKVKLANGII HDQL 474

SEQ ID NO: 253 moltype = DNA length = 1488
FEATURE Location/Qualifiers
source 1..1488
mol_type = other DNA
organism = synthetic construct
SEQUENCE: 253
atggattctc acacccatgg aacacctcat tttcttctct tccctttcat ggcacaaggc 60
catatgatcc ccatgatcga cctagccaag tttctagctc gccgtggagc cattgtcacc 120
atcgtcacca ctcctctcaa ctctgctcgc ttccactctg ttctcactcg cgccattgat 180
tccggccatc aaatccatgt ccgtgaactc caattcccta gccaccaaga aaccggcctc 240
ccagaaggct gcgagaatgt cgacttgcta ccttcacttg cttccatatc ccaattctac 300
agagctatca gtctccttca ccaaccatcg gaaaagttgt tcgaacaact cacccctcgt 360
cccaattgca tcatctccga catgtgcatc ccttggactt tcgatatttc tcagaaattc 420
cacgtcccca gactcgtttt ctacagttta agctgtttct tcctgctctg catgcggagt 480
ttaaccacta actatgaatt tctgaactcc aaccctgatt ccgaattcct gactttacca 540
ggcctccctt ctcaagttga gtttcgcagg tcccagatct ttacatccac cgatgattac 600
ttaatccaat atagtttcag aatgtgggag gttgatcggc aatcgtatgg cgtaattgta 660
aatgtgtttg aagaaatgga gccagagcat gtaacagagt atataaaagg aagagaatcc 720
cctgaaaaag tatggtgcgt tggtcctctt tcactttcca acgacaacga gcttgacaaa 780
gccgaaagag gaaacaaagc gataatcgac ggccatgaat gcatcaaatg gatggacgaa 840
cagaagccgt cgtcggtggt ttacgtgtca ttaggaagtc tctgcaatct gtgtacagag 900
caaatcaaag agctgggatt gggattggtg gcatcgaaca aaccattcat ttgggtgata 960
agaaaagcaa atctgaccga agctctagtc aaatggatgg atgaatatga attcgaggag 1020
aaaacaaaag ggcgtgggtt agtgatacgt ggatgggctc cacaagttct gatactctcg 1080
cactctgcaa ttgggtgctt cttgacacat tgtggatgga attcaagcgt tgaagggata 1140
tccgcagggg tgccgatgat cacatggcca ttgtttgcag atcaactgta caaccacaag 1200
ttcatcgtgg agatactgaa agtgggtgtg agtgttggag agggaacagt tggagatttg 1260
ggaggtgtgc aaaaggtagt ggtgaagagg gagaaagtga aggaagccat tgaaatggtg 1320
atggatggag atggaagtga agaaaggaga aagagatgta aagagtacgg tgagaaggcg 1380
aagaaggcgg cagaagaagg aggttcatct catcggaatc tgaatcggct agttgaagat 1440
attactgctc atgcctttgc ctgtggtaat ggaaatggaa gctgctga 1488

SEQ ID NO: 254 moltype = AA length = 495
FEATURE Location/Qualifiers
source 1..495
mol_type = protein
organism = Cucumis sativus
SEQUENCE: 254
MDSHTHGTPH FLLFPFMAQG HMIPMIDLAK FLARRGAIVT IVTTPLNSAR FHSVLTRAID 60
SGHQIHVREL QFPSHQETGL PEGCENVDLL PSLASISQFY RAISLLHQPS EKLFEQLTPR 120
PNCIISDMCI PWTFDISQKF HVPRLVFYSL SCFFLLCMRS LTTNYEFLNS NPDSEFLTLP 180
GLPSQVEFRR SQIFTSTDDY LIQYSFRMWE VDRQSYGVIV NVFEEMEPEH VTEYIKGRES 240
PEKVWCVGPL SLSNDNELDK AERGNKAIID GHECIKWMDE QKPSSVVYVS LGSLCNLCTE 300
QIKELGLGLV ASNKPFIWVI RKANLTEALV KWMDEYEFEE KTKGRGLVIR GWAPQVLILS 360
HSAIGCFLTH CGWNSSVEGI SAGVPMITWP LFADQLYNHK FIVEILKVGV SVGEGTVGDL 420
GGVQKVVVKR EKVKEAIEMV MDGDGSEERR KRCKEYGEKA KKAAEEGGSS HRNLNRLVED 480
ITAHAFACGN GNGSC 495

SEQ ID NO: 255 moltype = DNA length = 1428
FEATURE Location/Qualifiers
source 1..1428
mol_type = other DNA
organism = synthetic construct
SEQUENCE: 255
atgaagatag agcggaagca gagtgtcgta ctggttcccc atccctacca ggggcacctc 60
acgccaatgc ttcagctcgg cagcattctc cactcgcaag gcttctccgt catcgtcgcg 120
cacacccagt acaatacgcc caactactcc aatcacccgc agttcgtctt ccattccatg 180
gacgatggcc tccagggcat cgacatgagc tttccgtccc tcgagaacat ctacgacatg 240
aacgagaact gcaaggcccc cctccgcaac tatctggttt ccatgatgga ggaggaaggg 300
gaccagctgg cgtgcatcgt ctacgacaac gtcatgttct tcgtcgacga cgttgcgacg 360
cagttgaagc ttccgtcgat cgtgctgcgg accttctcgg ccgcctacct gcactctatg 420
atcaccatcc tgcagcagcc ggagatctac ctgcccttcg aggactcgca actgctggac 480
ccgctgcccg agctccaccc cctccgcttc aaggacgtgc ccttccccat catcaacaac 540
accgtgccgg agccgatcct cgacttctgc cgcgcgatgt ccgacatcgg gtcctccgtc 600
gcgaccatct ggaacaccat gcaggacctc gagagctcca tgctcctgcg cctgcaggag 660
cactacaagg tgcccttctt cccgatcggc ccggtgcaca agatggcctc gctcgtgtcc 720
tcaacgtcga tcctcgagga ggacaacagc tgcatcgagt ggctcgaccg tcaggccccg 780
aactccgtcc tgtacgtcag cctggggagc ttggtccgga ttgaccacaa ggagctcatc 840
gagacagcat gggggctggc caactcggac cagccgttcc tctgggtcat ccggccgggc 900
tcggtcagtg gcttccagtg cgcggaagca ctgcccgacg gcttcgagaa gatggtcggc 960
gagcggggac gaatcgtgaa gtgggcgccc cagaagcagg tcctggccca tcccgcggtc 1020
gcggggttct tcacgcattg cgggtggaac tccacgctcg agtccatctg cgaagaggtc 1080
ccgatggtgt gccgcccctt cctggcggac cagctggtga acgcgcggta cctgagccag 1140
atctacaaag tgggcttcga gctggaggtc atcgagcgca cggtgatcga gaagaccatt 1200
cgcaagctga tgctgtccga ggaggggaag gacgtcaaga agcgggtcgc ggacatgaag 1260
cagaagatcg tggccggcat gcagatcgac tgcacgtcgc acaagaacct gaacgacctc 1320
gtggacttta tctcggcgct gccgtcgcgg ctcgccccgc ccacccccgt cttcggagcc 1380

```
atcatgtcct cgaaccacat agcaagcaag tgtatcatag agtcttga              1428

SEQ ID NO: 256         moltype = AA  length = 475
FEATURE                Location/Qualifiers
source                 1..475
                       mol_type = protein
                       organism = Solanum lycopersicum
SEQUENCE: 256
MKIERKQSVV LVPHPYQGHL TPMLQLGSIL HSQGFSVIVA HTQYNTPNYS NHPQFVFHSM  60
DDGLQGIDMS FPSLENIYDM NENCKAPLRN YLVSMMEEEG DQLACIVYDN VMFFVDDVAT  120
QLKLPSIVLR TFSAAYLHSM ITILQQPEIY LPFEDSQLLD PLPELHPLRF KDVPFPIINN  180
TVPEPILDFC RAMSDIGSSV ATIWNTMQDL ESSMLLRLQE HYKVPFFPIG PVHKMASLVS  240
STSILEEDNS CIEWLDRQAP NSVLYVSLGS LVRIDHKELI ETAWGLANSD QPFLWVIRPG  300
SVSGFQCAEA LPDGFEKMVG ERGRIVKWAP QKQVLAHPAV AGFFTHCGWN STLESICEEV  360
PMVCRPFLAD QLVNARYLSQ IYKVGFELEV IERTVIEKTI RKLMLSEEGK DVKKRVADMK  420
QKIVAGMQID CTSHKNLNDL VDFISALPSR LAPPTPVFGA IMSSNHIASK CIIES       475

SEQ ID NO: 257         moltype = DNA  length = 1488
FEATURE                Location/Qualifiers
source                 1..1488
                       mol_type = other DNA
                       organism = synthetic construct
SEQUENCE: 257
atggactccc acacacatgg cacgcctcac ttcctgttgt tccccttcat ggcccagggc  60
cacatgatcc ccatgatcga cctggccaag ttcctggccc gccgcggggc catcgtcacg  120
atcgtcacca cccccctcaa cagcgcgcgg ttccacagcg tcctcacccg cgcgattgac  180
tccggccacc aaatccatgt ccgagagctc cagttcccga gccaccagga gacgggcctc  240
cccgaggggt gcgagaacgt cgacctcctg ccgagcctcg caagcatctc ccagttctac  300
cgggcgatct cgctactcca ccagccttcg gagaagctgt tcgagcagct cacgccccgg  360
cccaactgca tcatctcgga catgtgcatc ccgtggacct tcgacatcag ccagaagttc  420
cacgtccccc gcctcgtgtt ctactcgctg tcgtgcttct tcctgctgtg catgcggtcg  480
ctcaccacca actacgagtt cctgaactcc aacccggaca gcgagttcct gacgctgccc  540
ggcctgccct cccaggtcga gttccggagg agccagatct tcacgtcgac cgacgactac  600
ctgatccagt acagtttccg gatgtgggag gtcgaccggc agagctacgg ggtgatcgtc  660
aacgtgttcg aggagatgga gcccgagcac gtgacggagt acatcaaggg ccgggagtcg  720
ccggagaagg tgtggtgcgt ggggcccctt tcgcttagca acgacaatga gcttgacaag  780
gccgagcggg ggaacaaggc gatcatcgac gggcacgagt gcatcaagtg gatggacgag  840
cagaagccga gcagcgtcgt ctacgtgagc ctcggcagcc tctgcaacct ctgcacggag  900
cagatcaagg agctggggct aggcctcgtg gcgtcgaaca agccgttcat ctgggtgatc  960
cggaaggcca acctgaccga ggccctcgtc aagtggatgg atgagtacga gttcgaggag  1020
aagacgaagg ggcgcgggct ggtcatccgc gggtgggccc cgcaggtcct aatcctctcg  1080
cactctgcga tcgggtgctt cctgacgcac tgcggctgga acagctcggt cgaggggatc  1140
tccgccggcg ttccgatgat cacgtggccg ctgttcgccg accagctcta caaccacaag  1200
ttcatcgtgg agatcctgaa ggtcggggtg tcggtggggg aggggaccgt gggggacctc  1260
gggggggtgc agaaggttgt cgtcaagcgc gagaaggtga aggaggccat cgagatggtg  1320
atggacggcg acggcagcga ggagcggcgg aagcgctgca aggagtacgg cgagaaggcc  1380
aagaaggcgg cagaggaggg cggctcgtcg caccggaacc tgaaccgcct cgtggaggac  1440
atcacggccc acgccttcgc gtgcggtaac gggaatggga gttgctga              1488

SEQ ID NO: 258         moltype = AA  length = 495
FEATURE                Location/Qualifiers
source                 1..495
                       mol_type = protein
                       organism = Cucumis sativus
SEQUENCE: 258
MDSHTHGTPH FLLFPFMAQG HMIPMIDLAK FLARRGAIVT IVTTPLNSAR FHSVLTRAID  60
SGHQIHVREL QFPSHQETGL PEGCENVDLL PSLASISQFY RAISLLHQPS EKLFEQLTPR  120
PNCIISDMCI PWTFDISQKF HVPRLVFYSL SCFFLLCMRS LTTNYEFLNS NPDSEFLTLP  180
GLPSQVEFRR SQIFTSTDDY LIQYSFRMWE VDRQSYGVIV NVFEEMEPEH VTEYIKGRES  240
PEKVWCVGPL SLSNDNELDK AERGNKAIID GHECIKWMDE QKPSSVVYVS LGSLCNLCTE  300
QIKELGLGLV ASNKPFIWVI RKANLTEALV KWMDEYEFEE KTKGRGLVIR GWAPQVLILS  360
HSAIGCFLTH CGWNSSVEGI SAGVPMITWP LFADQLYNHK FIVEILKVGV SVGEGTVGDL  420
GGVQKVVVKR EKVKEAIEMV MDGDGSEERR KRCKEYGEKA KKAAEEGGSS HRNLNRLVED  480
ITAHAFACGN GNGSC                                                  495

SEQ ID NO: 259         moltype = DNA  length = 1327
FEATURE                Location/Qualifiers
source                 1..1327
                       mol_type = genomic DNA
                       organism = Arabidopsis thaliana
SEQUENCE: 259
cgcttggcgc gccgtcaacg gatcaggata tccttgttta agatgttgaa ctctatggag  60
gtttgtatga actgatgatc taggaccgga taagttccct tcttcatagc gaacttattc  120
aaagaatgtt ttgtgtatca ttcttgttac attgttatta atgaaaaaat attattggtc  180
attggactga acacgagtgt taaatatgga ccaggcccca aataagatcc attgatatat  240
gaattaaata acaagaataa atcgagtcac caaaccactt gcctttttta acgagacttg  300
ttcaccaact tgatacaaaa gtcattatcc tatgcaaatc aataatcata caaaaatatc  360
caataacact aaaaaattaa aagaaatgga taatttcaca atatgttata cgataaagaa  420
gttacttttc caagaaattc actgatttta taagcccact tgcattagat aaatggcaaa  480
```

```
aaaaaacaaa aaggaaaaga aataaagcac gaagaattct agaaaatacg aaatacgctt  540
caatgcagtg ggacccacgg ttcaattatt gccaattttc agctccaccg tatatttaaa  600
aaataaaacg ataatgctaa aaaaatataa atcgtaacga tcgttaaatc tcaacggctg  660
gatcttatga cgaccgttag aaattgtggt tgtcgacgag tcagtaataa acggcgtcaa  720
agtggttgca gccggcacac acgagtcgtg tttatcaact caaagcacaa atacttttcc  780
tcaacctaaa aataaggcaa ttagccaaaa acaactttgc gtgtaaacaa cgctcaatac  840
acgtgtcatt ttattattag ctattgcttc accgccttag ctttctcgtg acctagtcgt  900
cctcgtcttt tcttcttctt cttctataaa acaataccca aagagctctt cttcttcaca  960
attcagattt caatttctca aaatcttaaa aactttctct caattctctc taccgtgatc  1020
aaggtaaatt tctgtgttcc ttattctctc aaaatcttcg attttgtttt cgttcgatcc  1080
caatttcgta tatgttcttt ggtttagatt ctgttaatct tagatcgaag acgatttttct  1140
gggtttgatc gttagatatc atcttaattc tcgattaggg tttcataaat atcatccgat  1200
ttgttcaaat aatttgagtt ttgtcgaata attactcttc gatttgtgat ttctatctag  1260
atctggtgtt agtttctagt ttgtgcgatc gaatttgtcg attaatctga gtttttctga  1320
ttaacag                                                            1327

SEQ ID NO: 260         moltype = DNA  length = 242
FEATURE                Location/Qualifiers
source                 1..242
                       mol_type = genomic DNA
                       organism = Peanut chlorotic streak virus
SEQUENCE: 260
tgagccaatc aaagaggagt gatgtagacc taaagcaata atggagccat gacgtaaggg  60
cttacgccat tacgaaataa ttaaaggctg atgtgacctg tcggtctatc agaaccttta  120
ctttttatat ttggcgtgta tttttaaatt tccacggcaa tgacgatgtg acctgtggat  180
ccgctttgcc tataaataag ttttagtttg tattgatcga cacgatcgag aagacacggc  240
ca                                                                 242

SEQ ID NO: 261         moltype = DNA  length = 1504
FEATURE                Location/Qualifiers
source                 1..1504
                       mol_type = genomic DNA
                       organism = Citrullus lanatus
SEQUENCE: 261
ggagtactcc ttaccctaaa tacttcttta atctcaaaat ttcattaaat acgtacttta  60
aatttttcgg gttaatcaat ttaaaataac tatgaagcga tattttaaat ttaatagtta  120
taaaaaatag aaaatttaa ttaattataa tctttatctt tttaaataaa acttatttcc  180
caaattttta atatttctct caacataatg tttcatgaat agtaatcaca agtcaaatta  240
aacctattat gatagtgaaa ttagaagtaa aacggttaaa agtgaattta atttagtgat  300
aattgaccta tattatttat tttggagatg gagattccat ttcaatttcg ataattgtca  360
tagaaaaaat agtgaaatta gaaaatttct taacatatat tagcagaata aattaaaaaa  420
aaaaaagtgt tggagcataa tttatttatt gaaacaaaaa ctgatggagc attcattcat  480
ttttttaaag catcgtccaa gtcaatttaa acattaccca acattgaaat tataaaattt  540
ctgtctaaaa aaagtcttga cggtatatgt ataataaata aatattaaaa tatctgttag  600
aaagaataaa ttgaaaatga ttaaataagt ttttaacgca aatataaagt tgaaatttaa  660
gatttagaga ataaaattat acaactgtgt taagtttatt attattatta tttttttaat  720
ttttatatta gtttacttta aatattttgg ccaacttata tgcaattcaa ttaatctcaa  780
gtgaaaattc gtctaatcct acaacaattt taatataaag attgattatt gctgtcaaaa  840
ttcattctct cttattggag actttttcaa atataagaaa attaactaaa atatttataa  900
atatagcaaa atttcaacat ctctttgaaa tagatcgtaa tagactacta tctatgttat  960
catacacatc agtagtctat cgcaatttat aaaaaataaa ttgtgatttt ttattattat  1020
tagtaaatat tttaaaaaaa tttgtttttt aaactaattt tcattatttt ccttattgtt  1080
attattatta ttaatactaa ccaggatgga gcattagtaa cttaggaagg gaaaaggttg  1140
atttactcgt caaacgccaa tcacaatgat tacggattcc caacccatga gaatccacag  1200
agatcaccgc actccaaaaa ccactttttc tttctttctt tattttcttt tcaaaaccgc  1260
ttttatttat tattattact accattattt taaattctta taatttaaaa ttatgttaaa  1320
tggcttcttc tctaaatttc tcttaccact tggccaccca ctgccactcc cacgccactc  1380
cctctgttta tatataaaca tcttcatttc ctctccattt catcactcaa aaaccaccat  1440
tctctgattc cccaaaaacc acttttctgt cttccaaaac cctcattgaa tcactcctca  1500
ttca                                                               1504

SEQ ID NO: 262         moltype = DNA  length = 1216
FEATURE                Location/Qualifiers
source                 1..1216
                       mol_type = genomic DNA
                       organism = Arabidopsis thaliana
SEQUENCE: 262
caactatttt tatgtatgca agagtcagca tatgtataat tgattcagaa tcgttttgac  60
gagttcggat gtagtagtag ccattattta atgtacatac taatcgtgaa tagtgatatg  120
atgaaacatt gtatcttatt gtataaatat ccataaacac atcatgaaag acactttctt  180
tcacggtctg aattaattat gatacaattc taatagaaaa cgaattaaat tacgttgaat  240
tgtatgaaat ctaattgaac aagccaacca cgacgacgac taacgttgcc tggattgact  300
cggtttaagt taaccactaa aaaaacggag ctgtcatgta acacgcggat cgagcaggtc  360
acagtcatga agccatcaaa gcaaaagaac taatccaagg gctgagatga ttaattagtt  420
taaaaattag ttaacacgag ggaaaaggct gtctgacagc caggtcacgt tatctttacc  480
tgtggtcgaa atgattcgtg tctgtcgatt ttaattattt ttttgaaagg ccgaaaataa  540
agttgtaaga gataaacccg cctatataaa ttcatatatt ttcctctccg ctttgaattg  600
tctcgttgtc ctcctcactt tcatcagccg ttttgaatct ccggcgactt gacagagaag  660
aacaaggaag aagactaaga gagaaagtaa gagataatcc aggagattca ttctccgttt  720
```

```
tgaatcttcc tcaatctcat cttcttccgc tctttctttc caaggtaata ggaactttct  780
ggatctactt tatttgctgg atctcgatct tgttttctca atttccttga gatctggaat  840
tcgtttaatt tggatctgtg aacctccact aaatcttttg gttttactag aatcgatcta  900
agttgaccga tcagttagct cgattatagc taccagaatt tggcttgacc ttgatggaga  960
gatccatgtt catgttacct gggaaatgat ttgtatatgt gaattgaaat ctgaactgtt  1020
gaagttagat tgaatctgaa cactgtcaat gttagattga atctgaacac tgtttaagtt  1080
agatgaagtt tgtgtataga ttcttcgaaa ctttaggatt tgtagtgtcg tacgttgaac  1140
agaaagctat ttctgattca atcagggttt atttgactgt attgaactct ttttgtgtgt  1200
ttgcagctca taaaaa                                                  1216

SEQ ID NO: 263         moltype = DNA  length = 1425
FEATURE                Location/Qualifiers
source                 1..1425
                       mol_type = other DNA
                       organism = synthetic construct
SEQUENCE: 263
tgagactttt caacaaaggg taatatcggg aaacctcctc ggattccatt gcccagctat  60
ctgtcacttc atcaaaagga cagtagaaaa ggaaggtggc acctacaaat gccatcattg  120
cgataaagga aaggctatcg ttcaagatgc ctctgccgac agtggtccca aagatggacc  180
cccacccacg aggagcatcg tggaaaaaga agacgttcca accacgtctt caaagcaagt  240
ggattgatgt gaagatctga ttaaacatgg aagtttctct cttgagggag gttgctcgtg  300
gaatgggaca catatggttg ttataataaa ccattccatt gtcatgagat tttgaggtta  360
atatatactt tacttgttca ttattttatt tggtgtttga ataaatgata taaatggctc  420
ttgataatct gcattcattg agatatcaaa tatttactct agagaagagt gtcatataga  480
ttgatggtcc acaatcaatg aaatttttgg gagacgaaca tgtataacca tttgcttgaa  540
taaccttaat taaaaggtgt gattaaatga tgtttgtaac atgtagtact aaacattcat  600
aaaacacaac caacccaaga ggtattgagt attcacggct aaacaggggc ataatggtaa  660
tttaaagaat gatattattt tatgttaaac cctaacattg gtttcggatt caacgctata  720
aataaaacca ctctcgttgc tgattccatt tatcgttctt attgacccta gccgctacac  780
acttttctgc gatatctctg aggtaagcgt taacgtaccc ttagatcgtt ctttttcttt  840
ttcgtctgct gatcgttgct catattattt cgatgattgt tggattcgat gctctttgtt  900
gattgatcgt tctgaaaatt ctgatctgtt gtttagattt tatcgattgt taatatcaac  960
gtttcactgc ttctaaacga taatttattc atgaaactat tttcccattc tgatcgatct  1020
tgttttgaga ttttaatttg ttcgattgat tgttggttgg tggatctata tacgagtgaa  1080
cttgttgatt tgcgtattta agatgtatgt cgatttgaat tgtgattggg taattctgga  1140
gtagcataac aaatccagtg ttccctttttt ctaagggtaa ttctcggatt gtttgcttta  1200
tatctcttga aattgccgat ttgattgaat ttagcgcgct tagctcagat gatagagcac  1260
cacaattttt gtggtgagaa atcggtttga ctccgatagc ggctttttac tatgattgtt  1320
ttgtgttaaa gatgatttttc ataatggtta tatatgtcta ctgtttttta ttgattcaat  1380
atttgattgt tcttttttttt gcagatttgt tgacagtctc taaca                 1425

SEQ ID NO: 264         moltype = DNA  length = 385
FEATURE                Location/Qualifiers
source                 1..385
                       mol_type = genomic DNA
                       note = Figwort mosaic virus hybrid P
                       organism = Figwort mosaic virus
SEQUENCE: 264
cagctggctt gtggggacca gacaaaaaag gaatggtgca gaattgttag gcgcacctac  60
caaaagcatc tttgccttta ttgcaaagat aaagcagatt cctctagtac aagtggggaa  120
caaaataacg tggaaaagag ctgtcctgac agcccactca ctaatgcgta tgacgaacgc  180
agtgacgacc acaaaagccc gactcgaaca tcttgaaggt gtacaaaacg ttttagcaga  240
ttgcctcacg agagatttta atgcttaaaa cgtaagcgct gacgtatgat ttcaaaaaac  300
gcagctataa aagaagccct ccagcttcaa agtttcatc aacacaaatt ctaaaaacaa  360
aatttttag agaggggggag tgaca                                         385

SEQ ID NO: 265         moltype = DNA  length = 230
FEATURE                Location/Qualifiers
source                 1..230
                       mol_type = genomic DNA
                       organism = Arabidopsis thaliana
SEQUENCE: 265
ggatgatggt gaagaaattg tcgacctttc tcttgtctgt ttgtcttttg ttaaagaagc  60
tatgcttcgt tttaataatc ttattgtcca ttttgttgtg ttatgacatt ttggctgctc  120
attatgttat gtgggaagtt agtgttcaaa tgttttgtgt cggtattgtt cttctcatcg  180
ctgttttgtt gggatcgtag aaatgtgacc ttcggacagt aaaactcttg             230

SEQ ID NO: 266         moltype = DNA  length = 220
FEATURE                Location/Qualifiers
source                 1..220
                       mol_type = genomic DNA
                       organism = Arabidopsis thaliana
SEQUENCE: 266
gaatcacaag ttcttgtcat gttttgattt gtatctcata ataaagcaaa atgttcattt  60
ttgaatgagc tttactctct ccatctcttg tttgttgtca tcccatttat ttcctctcag  120
atgctttcgt agtgagttcc aaagacaact aaatgactca gttttattgt tcgatggttc  180
actaatcagc acagaatgga acaattgttt ttatctgctt                        220

SEQ ID NO: 267         moltype = DNA  length = 309
```

```
FEATURE                Location/Qualifiers
source                 1..309
                       mol_type = genomic DNA
                       organism = Cucumis sativus
SEQUENCE: 267
agttgaagaa tttgatgaag aatgctttgt ttgggttgat ttggttaata aaggacttca  60
aatgtatttt gtgtaacttt tgagtgtcga aacagttcga tcgtttactt tttgtattat  120
attatcgtgg gaatgaatac aataaaataa aatttcatgg tataccacac tgctacattg  180
aaaatctaat catttatcaa ttataagata cacatgttac ttcaattcga gagcccatga  240
agtctgggtg taagcgatct tgaagaaaaa ccccgaagcc aattatgttt tcttttatat  300
attatattc                                                          309

SEQ ID NO: 268         moltype = DNA  length = 299
FEATURE                Location/Qualifiers
source                 1..299
                       mol_type = genomic DNA
                       organism = Cucumis sativus
SEQUENCE: 268
aaatgaagat gaaggtttg caataaaagt gttctctttt ttttgttttg gtaattacct  60
attaatgtag agaagttgaa gaaggatgtt aactagtggg gttttgtctt ctgtttgata  120
tataataaac gtaagctttg catataattc aatggatatc tttttctgtt ttcttcttct  180
ctctctctat ctcaaagcca tactttggtg aagaaatggg tttttgtaa taaaatgaag  240
ccattctcaa gcaacgaata tgccacgcgc gccttattag cgggcgcggg cgtggacac   299

SEQ ID NO: 269         moltype = DNA  length = 858
FEATURE                Location/Qualifiers
source                 1..858
                       mol_type = genomic DNA
                       organism = Citrullus lanatus
SEQUENCE: 269
gaccaaattt atttatggtt gaaatcttaa aggcctattt gattggtaat ttagattctg  60
ttatgttttg aaattcactg ggttaagcaa aatatacgct tgacagacaa tttaaattat  120
atttactgta tagttagatt ttgaatttga tttataaata aagtttttta tgttataaac  180
tcaaactttt tttccttgag aaaatattgt aaatttaatt cactatttaa aaaattaagg  240
attttttca aatatagcca aagcaatcaa aatatttata aatatagcaa aattttatta  300
tttatctaca atagaccacg ataaatcgtg atagatggtg tattttacta ttaatccata  360
tatttttaag cagttttcac atttaagatg atttctgatt ttattatgtt tttcctcaaa  420
aagtaattaa tgatataaat tgatttcctt tttatcttcc tttacgagtc ccatgactta  480
tctctttgga ctcctctcca acggcggatt acaatgatct actcctacac acattgttgt  540
cacttttctg ccaatcatag gcatccacgt aactcgagat cacataaacc ttagcgcagt  600
ggatcgaaat tagcctctat aaataaagca aacgccattg atggattcac cggagctagg  660
gtttctcccc aattctctgc ctataaaaaa aacttctcct ccaattcggc tcgtattctc  720
tcaatcaaca aattcaaaaa aacccatcga tttcttttgt tttgattgga tttgctaaac  780
ccgtcgattt cctttgtttc gatttgattt gctttaccca gaaacaaaga agaacaaaaa  840
agcaacaatc aatcggcc                                                858

SEQ ID NO: 270         moltype = DNA  length = 1229
FEATURE                Location/Qualifiers
source                 1..1229
                       mol_type = genomic DNA
                       note = Cucumis melo L.
                       organism = Cucumis melo
SEQUENCE: 270
gatcttactt taccataatg gtgaaaagga tagtgaccca catggttttt acttcgttat  60
agagacaaga tgaaaacaaa tctaaaattt aatattatag atggatagat gatggacaac  120
aaaaagagaa aagaagatac tggtcattgg tccaaaacag ccacccgaat caatatatga  180
ccgaaaaaca aaagctacag aatcatatct gtgcaacggt gccacagtgc tataggatag  240
cacaaccaca ctgtcacata aaaaagagga ttttgcactc gttttagatg gagtttcgta  300
attttcgggt ctttcaagct taaatatata cttcattaaa gcttcgaatt ttgtaatgtt  360
caattctacc tctttgatgt tcgataccta taaaataatt aaataaacgt atagacgtag  420
gaacaattaa gcggagttag atagtgcatt tatgattcta cctgtgagtg caatggtaaa  480
atggacatta taaaagagta ggggcaaaga gggaagtgaa aaattctccc cacttagcca  540
tgtttaatat agtagggata ggaatatgta ataagtagtg ttttttctat ttaattttct  600
gtatacttct tccatctcct ttaattatta aaaggtttc ctctctttac tctttctctc  660
taaattacta ttctgaagta tattttcttt tataaaaaga gtaataaact ttatttccat  720
taaaagaaca aacaacaaga aatgataatc aaatacacat tcatattttt aaaaaaaaag  780
ttaaacaaga tatagaaata gttatcaaat atatttatgt tgtcattcct tgtatacaat  840
ggcattcctt tagctttgtt tatgtatttc ctgagcttct cttagtgtac tatatccttt  900
aatattaatg catctttcga tcttgctaag atatgataaa aatagacgac acgtgtcaca  960
acctaattga gatatttcga tgtactttct atccgtctta gcttgtaatt aattattgtt  1020
aaaaaagaat actcaattaa ctagaaacaa gaaataagaa acgaaaacat tacaaaacgg  1080
agttgaagcg tgcaaatttg tggaaatgat tgttatcatg aaccagaaaa cattaaataa  1140
ctcttcctat aaaaggccct tattcttcac tttctcaaat cacgtcctaa agatatcaaa  1200
gatttcaact gatagcaaaa agcactact                                     1229

SEQ ID NO: 271         moltype = DNA  length = 2001
FEATURE                Location/Qualifiers
source                 1..2001
                       mol_type = genomic DNA
```

```
                        organism = Siraitia grosvenorii
SEQUENCE: 271
attagtattt tcaaaagtca tcaaacttac taaaagaaaa ttttatattt ttacattcct  60
ctgtacttaa ttgcatttat tcaataaact ttgacaataa ttataatttg atttgatatt  120
atcatatgaa tttactacga aaatagtttt gcatgcatgt taatcatgaa atgcacaatg  180
attttcgtat ataaaattct tttgctgaat ggtattattt gtcgccataa ccattatttt  240
atactaaata ataaattgat aaaattccta gacacgaacg ctttgttgac ttggatagaa  300
cgtaaacacg tgaatcatga gtattgcgaa gtaatggtca gaaaggtttc ttttgatttt  360
tttttttaat tccatgtaag tttaatttaa tatgtctatc taattttatt aaattaaact  420
aaaaaataag tggtagaaat taatatcttc tattagttga gttttttttt ttttttttt  480
taaattatgg ctatttatta gctctattgt gactggaaaa atctattttg tatttagact  540
agattatatg cttttttttt gtttgttaat ttggagattt tagtagtaag tttggacaat  600
tttacctaat taatcttgtg gctatgttag atactagcat ttctggtggc aagagacaat  660
ttatccctct aatacttgac cttaattgtg gtcatatgac caacatgaac atagctaatg  720
gttaaggtat tactacttct tctaagaagt cgtaggttcg aatcctcacc ccacatttgt  780
gatatgatat ctcaaaataa aaattgtggt tatatgtatt ttctttttct gaaacaagcc  840
ttctcgttaa aaagataata aattataatt cgctacaaat agttgaggta tatgttttga  900
aattaataat taattaaaaa aatagtaagt catgcattat tattattatt ttggtttaaa  960
tattatgtta gtccttgtac tttgaacttt tgtttatttt agtccttgta ctttcaaaat  1020
gttcattttt ggtccctgta ctttgagctt ttattcattt tgatcattgt actttcaaaa  1080
tgttcatttt tggactctgt actatcattt tttgtccact ttagtcccta tactttcaag  1140
aaatttacca ttttggtctt ttgattttcc tttttatctc atttttttaa tcacattttc  1200
agcacaataa tacactcagt aaatttcttg aaatattatc atatttttgt attaaaaggt  1260
tttcgttgag tatagaattt gtattagaat ttatcaaata tgaaccaaaa tgattatttt  1320
ttaaaagtac agggactaaa atggatgttt taaaagtata aggactaaaa tggataaaaa  1380
ctgaaagtat agggactaaa aatgaacatt ttgaaagtat atggaccaaa atgaataaaa  1440
actcaaagta tagagactaa aataatattt aaacctatta tttattattt tgaaaatata  1500
gcattaatta caatagtagg agtgggaatt tgaagcttgg atctataggt tgaaccattt  1560
ttacagtaca ggtatagaat aattttgaag agagataatt tgagaaaaat agacaccatt  1620
ggcttgatag aaacatttta ttatatatat ttatgagaat atgaagagat acataaaaat  1680
gcattacttt acttggtagc aggcgcagat atataagtgt cgttggtgtg tggaaagctg  1740
aaagcagagg cgtccaagtg ttaatgtaga ttggttttat gtggaagaaa aagttgggcg  1800
ttgggatgag ttgaagttgc caaacgtccc agagagtctg agctgtgaag agagaggtga  1860
ggcagtatgg gtatatagtt agcgttaata taatttagcc agcttgtgtc ccatttaatg  1920
aatatataat ttgtgtattt gtatgcattg gtggtataca aagtagttaa gaggtagaag  1980
aagcagaaat tatattaaag g                                            2001

SEQ ID NO: 272          moltype = DNA  length = 1275
FEATURE                 Location/Qualifiers
source                  1..1275
                        mol_type = other DNA
                        organism = synthetic construct
SEQUENCE: 272
atgaacacga ccccgctgcc ggaggaggac gaggaggtgg tgaagatggt ggtggacggg  60
tccgtgccgt cctactcgct cgagtccaag ctcggcgacc cgaagcgcgc ggcgtccatc  120
cggcgggagg cgctgcagcg catgacgggg cggagcatcc acgggctgcc gttcgagggc  180
ttcgactacg agagcatcct gggccagtgc tgcgagatgc cggtggggta cgtccagatc  240
ccggtgggca tcgcggggcc gctgctgctc gacgggttcg agtacaccgt gccgatggcc  300
accacggagg gctgcctggt ggcctccacc aacaggggct gcaaggccat ctacgcctcc  360
ggcggggcga cctcaatgct cctcaaagac ggcatgacga gggccccggt ggtcaggttc  420
ggcagcgcga agagggcgag cgagctgaag ttcttcctgg aggacccgaa caacttcgac  480
accctggccg tggtgttcaa ccgctccagc cgcttcgccc gcctgcagag catcaggtgc  540
agcatcgcgg gcaagaacct gtacgtccgc ttctgctgct ccaccggcga cgccatgggc  600
atgaacatgg tgtccaaggg cgtgcagaac gtgctggagt tcctgcagca cgacttctcc  660
gacatggagg tgatcggcat ctccggcaac ttctgcgccg acaagaagcc ggccgccgtg  720
aactggatcg agggcagggg caagtccgtg gtgtgcgagg ccattatcaa ggacgaggtg  780
gtgcgcaagg tgctcaagac cagcgtggcg agcctggtgg agctgaacat gctgaagaac  840
ctgaccggct ccgccatggc cggggccctc ggcggcttca acgcgcacag cagcaacatc  900
gtgtccgcca tcttcctggc caccggccag gacccggccc agaacgtgga gtcctcccac  960
tgcatcacga tgatggagcc ggtcaacaac ggcaaggacc tccacatctc cgtgaccatg  1020
ccgtccatcg aggtcgggac cgtgggggc ggcacccagc tggcgtccca gagcgcgtgc  1080
ctgaacctgc tgggggtcaa gggcgcgtcc aaggagagcc cgggggccaa cagcaggctg  1140
ctggcgacca tcgtggccgg ctccgtgctg gccggcgagc tctccctgat gtccgccatc  1200
gcggcgggcc agctggtgag gtcccacatg aagtacaacc gctcctccag ggatgtgtcc  1260
aaggtggaga gctaa                                                   1275

SEQ ID NO: 273          moltype = AA  length = 424
FEATURE                 Location/Qualifiers
source                  1..424
                        mol_type = protein
                        organism = Citrullus lanatus
SEQUENCE: 273
MNTTPLPEED EEVVKMVVDG SVPSYSLESK LGDPKRAASI RREALQRMTG RSIHGLPFEG  60
FDYESILGQC CEMPVGYVQI PVGIAGPLLL DGFEYTVPMA TTEGCLVAST NRGCKAIYAS  120
GGATSMLLKD GMTRAPVVRF GSAKRASELK FFLEDPNNFD TLAVVFNRSS RFARLQSIRC  180
SIAGKNLYVR FCCSTGDAMG MNMVSKGVQN VLEFLQHDFS DMEVIGISGN FCADKKPAAV  240
NWIEGRGKSV VCEAIIKDEV VRKVLKTSVA SLVELNMLKN LTGSAMAGAL GGFNAHSSNI  300
VSAIFLATGQ DPAQNVESSH CITMMEPVNN GKDLHISVTM PSIEVGTVGG GTQLASQSAC  360
LNLLGVKGAS KESPGANSRL LATIVAGSVL AGELSLMSAI AAGQLVRSHM KYNRSSRDVS  420
```

```
KVES                                                                   424

SEQ ID NO: 274          moltype = DNA  length = 1272
FEATURE                 Location/Qualifiers
source                  1..1272
                        mol_type = other DNA
                        organism = synthetic construct
SEQUENCE: 274
atgaacacga ccccgctgcc ggaggaggac gaggaggtgg tgaagatggt ggtggacggg  60
tccgtgccgt cctactcgct cgagtccaag ctcggcgacc cgaagcgcgc ggcgtccatc  120
cggcgggagg cgctgcagcg catgacgggg cggagcatcc acgggctgcc gttcgagggc  180
ttcgactacg agagcatcct gggccagtgc tgcgagatgc cggtggggta cgtccagatc  240
ccggtgggca tcgcggggcc gctgctgctc gacgggttcg agtacaccgt gccgatggcc  300
accacggagg gctgcctggt ggcctccacc aacaggggct gcaaggccat ctacgcctcc  360
ggcggggcga cctcaatgct cctcaaagac ggcatgacga gggccccggt ggtcaggttc  420
ggcagcgcga agagggcgag cgagctgaag ttcttcctgg aggacccgaa caacttcgac  480
accctggccg tggtgttcaa ccgctccagc cgcttcgccc gcctgcagag catcaggtgc  540
agcatcgcgg gcaagaacct gtacgtccgc ttctgctgct ccaccggcga cgccatgggc  600
atgaacatgg tgtccaaggg cgtgcagaac gtgctggagt tcctgcagca cgacttctcc  660
gacatggagg tgatcggcat ctccggcaac ttctgcgccg acaagaagcc ggccgccgtg  720
aactggatcg agggcagggg caagtccgtg gtgtgcgagg ccattatcaa ggacgaggtg  780
gtgcgcaagg tgctcaagac cagcgtggcg agcctggtgg agctgaacat gctgaagaac  840
ctgaccggct ccgccatggc cggggccctc ggcggcttca acgcgcacag cagcaacatc  900
gtgtccgcca tcttcctggc caccggccag gacccggccc agaacgtgga gtcctcccac  960
tgcatcacga tgatggagcc ggtcaacaac ggcaaggacc tccacatctc cgtgaccatg  1020
ccgtccatcg aggtcgggac cgtgggggc ggcacccagc tggcgtccca gagcgcgtgc  1080
ctgaacctgc tgggggtcaa gggcgcgtcc aaggagagcc cgggggccaa cagcaggctg  1140
ctggcgacca tcgtggccgg ctccgtgctg gccggcgagc tctccctgat gtccgccatc  1200
gcggcgggcc agctggtgag gtcccacatg aagtacaacc gctcctccag ggatgtgtcc  1260
aaggtggaga gc                                                      1272

SEQ ID NO: 275          moltype = AA  length = 424
FEATURE                 Location/Qualifiers
source                  1..424
                        mol_type = protein
                        organism = Citrullus lanatus
SEQUENCE: 275
MNTTPLPEED EEVVKMVVDG SVPSYSLESK LGDPKRAASI RREALQRMTG RSIHGLPFEG  60
FDYESILGQC CEMPVGYVQI PVGIAGPLLL DGFEYTVPMA TTEGCLVAST NRGCKAIYAS  120
GGATSMLLKD GMTRAPVVRF GSAKRASELK FFLEDPNNFD TLAVVFNRSS RFARLQSIRC  180
SIAGKNLYVR FCCSTGDAMG MNMVSKGVQN VLEFLQHDFS DMEVIGISGN FCADKKPAAV  240
NWIEGRGKSV VCEAIIKDEV VRKVLKTSVA SLVELNMLKN LTGSAMAGAL GGFNAHSSNI  300
VSAIFLATGQ DPAQNVESSH CITMMEPVNN GKDLHISVTM PSIEVGTVGG GTQLASQSAC  360
LNLLGVKGAS KESPGANSRL LATIVAGSVL AGELSLMSAI AAGQLVRSHM KYNRSSRDVS  420
KVES                                                               424

SEQ ID NO: 276          moltype = DNA  length = 1275
FEATURE                 Location/Qualifiers
source                  1..1275
                        mol_type = other DNA
                        organism = synthetic construct
SEQUENCE: 276
atgaacacga cccctttgcc ggaggaggat gaagaagttg tgaaaatggt ggttgatggc  60
agcgtgccat cgtactcgct cgagtcaaag ctcggcgacc caaaacgggc agcctcaatc  120
cggcgggagg cattgcagcg gatgacaggt cggagcatcc acgggctgcc ttttgaaggc  180
tttgactatg aatctatact tggcaatgc tgcgaaatgc ccgtcggtta tgtccagatt  240
ccggttggca tcgctggacc tctgttgctc gatgggtttg aatatacggt gcccatggca  300
actacggagg gttgccttgt ggcttctact aatcgcggtt gcaaagctat ctacgcctca  360
ggaggggcga cctcaatgct cctcaaagac ggtatgacga gggcacctgt tgtcagattc  420
ggtagcgcga agagagcgtc agagttgaaa ttctttcttg aagacccgaa taatttcgac  480
accttggctg tcgtgttcaa tcggtcttcg agatttgcga gattgcaatc gatcaggtgc  540
agcatcgcgg gcaaaaatct ctatgttaga ttctgttgct caacaggaga tgcaatgggt  600
atgaacatgg tttccaaagg ggtccaaaac gtgcttgaat ttctgcaaca cgattttagc  660
gatatggaag ttataggcat ttcaggcaat ttctgcgccg ataagaagcc cgctgccgtt  720
aattggatcg agggtcgcgg aaaatctgtt gtctgtgagg caattatcaa ggatgaggtt  780
gtgcgcaaag ttctcaagac tagcgtcgca agcttggtcg aattgaacat gctgaagaac  840
ctgactggct ccgcgatggc aggggccttg ggtggtttca acgctcacag cagcaacata  900
gtttctgcca tatttttggc gaccggacag gacccggcac aaaatgttga gtcttctcac  960
tgcatcacga tgatggaacc agtcaacaat ggaaaagacc tccatatttc tgtcacgatg  1020
ccttcaatcg aagtcgggac agttggtgga ggaacacaat tggcttcaca gagcgcgtgc  1080
cttaatttgc tgggtgtcaa gggtgcctcc aaggaatcgc ctggggcgaa ttctaggctt  1140
ttggcgacca tcgttgcagg aagcgttttg gcgggggagc tctcgctgat gtccgccatc  1200
gcggcgggtc agttggtgag atcgcacatg aaatataaca gaagctccag agatgtgtca  1260
aaagttgaaa gctaa                                                   1275

SEQ ID NO: 277          moltype = AA  length = 424
FEATURE                 Location/Qualifiers
source                  1..424
                        mol_type = protein
```

```
                         organism = Citrullus lanatus
SEQUENCE: 277
MNTTPLPEED EEVVKMVVDG SVPSYSLESK LGDPKRAASI RREALQRMTG RSIHGLPFEG  60
FDYESILGQC CEMPVGYVQI PVGIAGPLLL DGFEYTVPMA TTEGCLVAST NRGCKAIYAS  120
GGATSMLLKD GMTRAPVVRF GSAKRASELK FFLEDPNNFD TLAVVFNRSS RFARLQSIRC  180
SIAGKNLYVR FCCSTGDAMG MNMVSKGVQN VLEFLQHDFS DMEVIGISGN FCADKKPAAV  240
NWIEGRGKSV VCEAIIKDEV VRKVLKTSVA SLVELNMLKN LTGSAMAGAL GGFNAHSSNI  300
VSAIFLATGQ DPAQNVESSH CITMMEPVNN GKDLHISVTM PSIEVGTVGG GTQLASQSAC  360
LNLLGVKGAS KESPGANSRL LATIVAGSVL AGELSLMSAI AAGQLVRSHM KYNRSSRDVS  420
KVES                                                              424

SEQ ID NO: 278           moltype = DNA  length = 1557
FEATURE                  Location/Qualifiers
source                   1..1557
                         mol_type = other DNA
                         organism = synthetic construct
SEQUENCE: 278
atgtcctcat cagttgcagc tactatcagc atatggatgg tggtggtgtg catcgttggt  60
gttggctggc gggtggtgaa ttgggtttgg ttgaggccaa aaaaattgga gaagcggctc  120
cgcgaacagg gcttggcggg caactcgtat aggttgcttt tcggtgactt gaaggagaga  180
gccgctatgg cggagcaagc gaactctaag cccataaatt tttcccacga catcggtcct  240
agagtcttcc cgtcaatgta caagacgatt cagaactatg gaaagaattc ttatatgtgg  300
ctgggtccct atcctcgcgt ccacatcatg gacccccagc aattgaaaac ggtttttacg  360
ctcgtgtacg acatccagaa acccaacctg aatccactca ttaaattctt gctcgacggg  420
attgtcacac acgagggtga gaagtgggca aaacatagga agataataaa tcccgctttt  480
catatggcta agcttaaaga catgataccc gcttttttc agtcgtgtaa cgaaatagtc  540
tccgagtggg agcggatgat cccgaaagaa ggtagctttg aacttgatgt tatgccctac  600
atgcagaacc tcgccgcaga cgcaatttcc cgcactgctt tcggttcctc ctacaaggaa  660
ggacagatga tctttcagct gctgaaagag ctgactgact tggtggttaa agccgcgttt  720
ggaatctata ttcccggctg gcggtttctt cccacgaagt cgaacaacaa aatgaaagaa  780
ataaacagga agataaaaac cttgttgttg ggcataatag ataaacggca gaaagcgatg  840
aaggagggcg aggtcgttca gaacgacctg ctgggtattc tcgtggaatc gaatcttaat  900
gaaatcagag gccacgaaaa taataaggat gcaggaatgt caattgagga tgtgattgaa  960
gagtgtaagg tttttatat cgggggtcaa gaaactaccg ctggcctcct tatctggact  1020
atgattctgc tttccttcca tacagagtgg caagaaagag ctcggacaga agtgctcgaa  1080
gtcgtgggca acaagaagcc tgactttgat ggattgaata gattgaaaat agttactatg  1140
atcctctacg aagtgttgag actctatccg cctgcgtcaa tgctgacccg gatagtccag  1200
aaggaaaccc gcataggaaa gttgacattg ccagctgggg ttactctgat aatcccaacg  1260
gtcctcattc atagagatca cgaattgtgg ggcgaagacg ctaacgagtt caagccggag  1320
cggttttctg agggagtgtc caaagccgcc aaggtccagc cggctttttt tcccttcggg  1380
tgggggccgc gcttgtgcct cggacagaat tttgcaatga tcgaagctaa aatggctttt  1440
agcctcattc ttcagcggtt tagctttcac ctctcatcat cttacgcgca tgccccaact  1500
gttgtgatga ctacgcagcc gcagcacggc gcccacatag tcctgcgcaa actctaa     1557

SEQ ID NO: 279           moltype = AA  length = 518
FEATURE                  Location/Qualifiers
source                   1..518
                         mol_type = protein
                         organism = Siraitia grosvenorii
SEQUENCE: 279
MSSSVAATIS IWMVVVCIVG VGWRVVNWVW LRPKKLEKRL REQGLAGNSY RLLFGDLKER  60
AAMAEQANSK PINFSHDIGP RVFPSMYKTI QNYGKNSYMW LGPYPRVHIM DPQQLKTVFT  120
LVYDIQKPNL NPLIKFLLDG IVTHEGEKWA KHRKIINPAF HMAKLKDMIP AFFQSCNEIV  180
SEWERMIPKE GSFELDVMPY MQNLAADAIS RTAFGSSYKE GQMIFQLLKE LTDLVVKAAF  240
GIYIPGWRFL PTKSNNKMKE INRKIKTLLL GIIDKRQKAM KEGEVVQNDL LGILVESNLN  300
EIRGHENNKD AGMSIEDVIE ECKVFYIGGQ ETTAGLLIWT MILLSFHTEW QERARTEVLE  360
VVGNKKPDFD GLNRLKIVTM ILYEVLRLYP PASMLTRIVQ KETRIGKLTL PAGVTLIIPT  420
VLIHRDHELW GEDANEFKPE RFSEGVSKAA KVQPAFFPFG WGPRLCLGQN FAMIEAKMAF  480
SLILQRFSFH LSSSYAHAPT VVMTTQPQHG AHIVLRKL                          518

SEQ ID NO: 280           moltype = DNA  length = 1425
FEATURE                  Location/Qualifiers
source                   1..1425
                         mol_type = other DNA
                         organism = synthetic construct
SEQUENCE: 280
atggtgcaac ctcgggtact gctgtttcct ttcccggcac tgggccacgt gaagcccttc  60
ttatcactgg cggagctgct ttccgacgcc ggcatagacg tcgtcttcct cagcaccgag  120
tataaccacc gtcggatctc caacactgaa gccctagcct cccgcttccc gacgcttcat  180
ttcgaaacta taccggatgg cctgccgcct aatgagtcgc gcgctcttgc cgacggccca  240
ctgtatttct ccatgcgtga gggaactaaa ccgagattcc ggcaactgat tcaatctctt  300
aacgacggtc gttggcccat cacctgtatt atcactgaca tcatgttatc ttctccgatt  360
gaagtagcgg aagaatttgg gattccagta attgccttct gcccatgcag tgctcgctac  420
ttatcgattc actttttat accgaagctc gttgaggaag gtcaaattcc atacgcagat  480
gacgatccga ttggagagat ccagggggtg cccttgttcg aaggtctttt gcgacggaat  540
catttgcctg gttcttggtc tgataaatcc gcagatatat ctttctcgca tggcttgatt  600
aatcagaccc ttgcagctgg tcgagcctcg gctcttatac tcaacacctt cgacgaactc  660
gaagctccat ttctgaccca tctcttcttcc attttcaaca aaatctacac cattggaccc  720
ctccatgctc tgtccaaatc aaggctcggc gactcctcct cctccgcttc tgccctctcc  780
```

```
ggattctgga aagaggatag agcctgcatg tcctggctcg actgtcagcc gccgaggtct  840
gtggttttcg tcagtttcgg gagtacgatg aagatgaaag ccgatgaatt gagagagttc  900
tggtatgggt tggtgagcag cgggaaaccg ttcctctgcg tgttgagatc cgacgttgtt  960
tccggcggag aagcggcgga attgatcgaa cagatggcgg aggaggaggg agctggaggg  1020
aagctgggaa tggtagtgga gtgggcagcg caagagaagg tcctgagcca ccctgccgtc  1080
ggtgggtttt tgacgcactg cgggtggaac tcaacggtgg aaagcattgc cgcgggagtt  1140
ccgatgatgt gctggccgat tctcggcgac caacccagca acgccacttg gatcgacaga  1200
gtgtggaaaa ttggggttga aaggaacaat cgtgaatggg acaggttgac ggtggagaag  1260
atggtgagag cattgatgga aggccaaaag agagtggaga ttcagagatc aatggagaag  1320
ctgtcaaagt tggcaaatga gaaggttgtc aggggtgggt tgtcttttga taacttggaa  1380
gttctcgttg aagacatcaa aaaattgaaa ccatataaat tttaa                 1425

SEQ ID NO: 281         moltype = AA  length = 474
FEATURE                Location/Qualifiers
source                 1..474
                       mol_type = protein
                       organism = Siraitia grosvenorii
SEQUENCE: 281
MVQPRVLLFP FPALGHVKPF LSLAELLSDA GIDVVFLSTE YNHRRISNTE ALASRFPTLH  60
FETIPDGLPP NESRALADGP LYFSMREGTK PRFRQLIQSL NDGRWPITCI ITDIMLSSPI  120
EVAEEFGIPV IAFCPCSARY LSIHFFIPKL VEEGQIPYAD DDPIGEIQGV PLFEGLLRRN  180
HLPGSWSDKS ADISFSHGLI NQTLAAGRAS ALILNTFDEL EAPFLTHLSS IFNKIYTIGP  240
LHALSKSRLG DSSSSASALS GFWKEDRACM SWLDCQPPRS VVFVSFGSTM KMKADELREF  300
WYGLVSSGKP FLCVLRSDVV SGGEAAELIE QMAEEEGAGG KLGMVVEWAA QEKVLSHPAV  360
GGFLTHCGWN STVESIAAGV PMMCWPILGD QPSNATWIDR VWKIGVERNN REWDRLTVEK  420
MVRALMEGQK RVEIQRSMEK LSKLANEKVV RGGLSFDNLE VLVEDIKKLK PYKF        474

SEQ ID NO: 282         moltype = DNA  length = 1362
FEATURE                Location/Qualifiers
source                 1..1362
                       mol_type = other DNA
                       organism = synthetic construct
SEQUENCE: 282
atggacgcgc agcggggcca cacgacgacg atcctgatgt tcccctggct cggctacggg  60
cacctcagcg ccttcctcga gctggcgaag agcctgtccc ggcgcaactt ccacatctac  120
ttctgctcga ccagcgtcaa cctggacgcg atcaagccca agctgccctc cagcagctcc  180
tccgacagca tccagctggt ggagctgtgc ctgccctcca gccccgacca gctcccccg   240
cacctccaca ccaccaacgc gctcccgccc cacctcatgc ccaccctcca ccaggccttc  300
agcatggcgg cgcagcactt cgcggccatc ctgcacaccc tcgcgcccca cctcctgatc  360
tacgactcgt tccagccgtg ggcaccccag ctggcctcct cgctcaacat cccggccatc  420
aacttcaaca cgaccggggc gtccgtcctg acccggatgc tgcacgcgac ccactacccg  480
agcagcaagt tccccatcag cgagttcgtg ctccacgact actggaaggc catgtacagc  540
gcggccgggg gcgcggtgac gaagaaggac cacaagatcg gcgagacgct ggcgaactgc  600
ctccacgcca gctgctcggt catcctgatc aactccttcc gcgagctgga ggagaagtac  660
atggactacc tgtccgtgct cctgaacaag aaggtggtgc cggtggggcc gctggtgtac  720
gagccgaacc aggatggaga ggacgagggg tactccagca taaagaactg gctcgacaag  780
aaggagccga gctccacggt gttcgtgtcc ttcggcagcg agtacttccc gagcaaggag  840
gagatggagg agatcgccca cgggctcgag gcctctgaag ttcatttcat ctgggttgtg  900
cggttcccgc agggggacaa cacctccgcg atcgaggacg ccctgccgaa gggcttcctc  960
gagagggtgg gcgagagggg catggtggtg aagggctggg ccccgcaggc gaagatcctg  1020
aagcactggt ccaccggggg cttcgtgtcc cactgcggct ggaacagcgt gatggagagc  1080
atgatgttcg gggtgccgat catcggcgtg ccgatgcacc tggaccagcc gttcaacgcc  1140
ggcctggccg aggaggccgg cgtgggggtg gaggcgaagc gcgaccccga cgggaagatc  1200
cagcgcgacg aggtcgccaa gctgatcaag gaggtggtgg tggagaagac ccgggaggac  1260
gtgaggaaga aggcgcgcga gatgtccgag atcctccgca gcaaggggga ggagaagatg  1320
gacgagatgg tggccgcgat ctccctcttc ctcaagatct ga                    1362

SEQ ID NO: 283         moltype = AA  length = 453
FEATURE                Location/Qualifiers
source                 1..453
                       mol_type = protein
                       organism = Siraitia grosvenorii
SEQUENCE: 283
MDAQRGHTTT ILMFPWLGYG HLSAFLELAK SLSRRNFHIY FCSTSVNLDA IKPKLPSSSS  60
SDSIQLVELC LPSSPDQLPP HLHTTNALPP HLMPTLHQAF SMAAQHFAAI LHTLAPHLLI  120
YDSFQPWAPQ LASSLNIPAI NFNTTGASVL TRMLHATHYP SSKFPISEFV LHDYWKAMYS  180
AAGGAVTKKD HKIGETLANC LHASCSVILI NSFRELEEKY MDYLSVLLNK KVVPVGPLVY  240
EPNQDGEDEG YSSIKNWLDK KEPSSTVFVS FGSEYFPSKE EMEEIAHGLE ASEVHFIWVV  300
RFPQGDNTSA IEDALPKGFL ERVGERGMVV KGWAPQAKIL KHWSTGGFVS HCGWNSVMES  360
MMFGVPIIGV PMHLDQPFNA GLAEEAGVGV EAKRDPDGKI QRDEVAKLIK EVVVEKTRED  420
VRKKAREMSE ILRSKGEEKM DEMVAAISLF LKI                                453

SEQ ID NO: 284         moltype = DNA  length = 2280
FEATURE                Location/Qualifiers
source                 1..2280
                       mol_type = other DNA
                       organism = synthetic construct
SEQUENCE: 284
atgtggcgcc ttaaggttgg ggccgagtct gtcggcgaga acgatgaaaa gtggctcaaa  60
```

```
tcaatcagca atcatcttgg caggcaggtc tgggaatttt gtcccgatgc cggaactcaa  120
caacagttgt tgcaagtcca caaagcgaga aaggcgttcc atgacgatag atttcatcgg  180
aaacagtcgt cggatctttt cattactata caatacggga aggaagttga gaacggtggg  240
aagacggctg gcgtgaaact taaagagggc gaagaggtga gaaaggaagc cgttgagagc  300
tccttggagc gggccttgtc gttttattca agcatccaga cgtctgacgg taattgggca  360
tcggacctcg gggccccat gttcctcctg cccgggctgg tcatcgcgct ctacgttacc  420
ggtgttttga attcggtcct gtcaaaacat cacaggcagg agatgtgtcg gtatgtctat  480
aatcatcaga atgaggatgg cggttggggc ctgcacatag aagggccgtc tactatgttc  540
ggttcagcat tgaactacgt ggctctgcgg cttctcggtg aggacgccaa tgcgggtgca  600
atgccaaaag cgcgcgcttg gattctggac cacggcgggg ccaccggaat tacttcttgg  660
ggaaagctct ggctctcagt tcttggcgtg tacgagtggt ctggcaacaa cccactcccc  720
ccagaatttt ggctctttcc gtatttcctt cccttccatc cgggcagaat gtggtgtcat  780
tgtcggatgg tgtatttgcc gatgtcctat ttgtacggga aaaggttcgt tgggccgata  840
acgccgatcg ttcttagcct tagaaaagag ctctatgcgg tcccttatca cgagatcgac  900
tggaacaaat ctcggaacac atgtgcaaaa gaggacttgt actacccca ccccaagatg  960
caggacatct tgtggggatc attgcaccat gtttacgagc cctgtttac tcggtggcca  1020
gcgaaaaggc ttagggaaaa ggcgctgcag acggctatgc aacatattca ctatgaagat  1080
gaaaacactc gctatatttg cctgggccca gttaataaag tgctgaatct gctttgttgt  1140
tgggtcgaag atccatactc tgatgctttt aaactgcatc ttcaacgcgt gcatgattac  1200
ctttgggtgg cagaggatgg catgaaaatg cagggatata acggttccca actttgggat  1260
accgctttca gcattcaagc aatagtctca acgaagttgg tcgataacta cggtcccact  1320
ttgcggaagg cgcacgattt cgtcaaatca tcgcaaatac aacaggactg ccctggcgat  1380
cccaacgtgt ggtacaggca tatccacaaa ggagcatggc cattttctac gagggaccat  1440
gggtggctga tatcggattg taccgccgaa ggactcaagg cagccctat gctcagcaag  1500
ttgccgtccg agacagtggg tgagtcgctt gaacgcaatc ggctgtgcga cgctgttaac  1560
gtcttgctgt ctttgcagaa cgacaacggc gggttcgcat cgtatgagct tactagatcg  1620
tatccgtggc ttgaactcat taatcccgcc gaaacattcg gagatatcgt gattgactat  1680
ccctatgtgg aatgcacttc tgcaacaatg gaagcgctta cacttttcaa aaaacttcac  1740
cctgggcaca ggactaagga aatcgacaca gcgatagtgc gcgccgcgaa cttcctggag  1800
aatatgcaga gaactgacgg ctcttggtat ggctgctggg gcgtttgctt cacatatgca  1860
ggctggtttg gaattaaagg cctcgttgcc gccgggcgca cgtacaataa ctgtcttgct  1920
atcaggaaag cttgtgattt tctgctttcc aaggagcttc cgggcggtgg gtggggcgag  1980
tcgtatttga gctgccaaaa taaagtctat acaaacctcg agggtaaccg gcctcacctt  2040
gtcaacacag cttgggtttt gatggcgttg atagaggctg gtcaagctga gcgggacccc  2100
acaccacttc atagggccgc aaggcttttg ataaattcac agctcgaaaa tggcgatttc  2160
ccgcaacagg aaatcatggg agtttttaac aaaaactgca tgataaccta cgccgcttat  2220
aggaatatat tcccgatctg ggccctgggt gaatactgcc atcgggtgtt gaccgagtaa  2280
```

```
SEQ ID NO: 285         moltype = AA  length = 759
FEATURE                Location/Qualifiers
source                 1..759
                       mol_type = protein
                       organism = Siraitia grosvenorii
SEQUENCE: 285
MWRLKVGAES VGENDEKWLK SISNHLGRQV WEFCPDAGTQ QQLLQVHKAR KAFHDDRFHR  60
KQSSDLFITI QYGKEVENGG KTAGVKLKEG EEVRKEAVES SLERALSFYS SIQTSDGNWA  120
SDLGGPMFLL PGLVIALYVT GVLNSVLSKH HRQEMCRYVY NHQNEDGGWG LHIEGPSTMF  180
GSALNYVALR LLGEDANAGA MPKARAWILD HGGATGITSW GKLWLSVLGV YEWSGNNPLP  240
PEFWLFPYFL PFHPGRMWCH CRMVYLPMSY LYGKRFVGPI TPIVLSLRKE LYAVPYHEID  300
WNKSRNTCAK EDLYYPHPKM QDILWGSLHH VYEPLFTRWP AKRLREKALQ TAMQHIHYED  360
ENTRYICLGP VNKVLNLLCC WVEDPYSDAF KLHLQRVHDY LWVAEDGMKM QGYNGSQLWD  420
TAFSIQAIVS TKLVDNYGPT LRKAHDFVKS SQIQQDCPGD PNVWYRHIHK GAWPFSTRDH  480
GWLISDCTAE GLKAALMLSK LPSETVGESL ERNRLCDAVN VLLSLQNDNG GFASYELTRS  540
YPWLELINPA ETFGDIVIDY PYVECTSATM EALTLFKKLH PGHRTKEIDT AIVRAANFLE  600
NMQRTDGSWY GCWGVCFTYA GWFGIKGLVA AGRTYNNCLA IRKACDFLLS KELPGGGWGE  660
SYLSCQNKVY TNLEGNRPHL VNTAWVLMAL IEAGQAERDP TPLHRAARLL INSQLENGDF  720
PQQEIMGVFN KNCMITYAAY RNIFPIWALG EYCHRVLTE                        759
```

```
SEQ ID NO: 286         moltype = DNA  length = 1425
FEATURE                Location/Qualifiers
source                 1..1425
                       mol_type = other DNA
                       organism = synthetic construct
SEQUENCE: 286
atggtgcagc cccgggtgct gctgttccct ttccccgcgc tgggccacgt gaagcccttc  60
ctgtcgctgg cggagctcct gtccgacgcc ggcatcgacg tggtcttcct ctcgacggag  120
tataaccacc gccgcatctc caacaccgag gccctggcct cccgcttccc caccctgcac  180
ttcgaaacga taccggacgg cctgccccc aacgagtcgc gcgccctcgc ggacggcccc  240
ctgtacttca gcatgaggga gggcaccaag ccgcgcttcc ggcagctgat ccagagcctt  300
aacgacggcc gttggcccat cacctgtatc atcacggaca tcatgctcag ttcgcccatc  360
gaggtggcgg aggagttcgg gatcccggtg atcgcgttct gcccgtgctc cgctcgctac  420
ctctcgatcc acttcttcat cccgaagctg gtggaggagg ggcagatccc gtacgcggac  480
gacgacccca ttggggagat ccagggggtg cccctcttcg aggggcttct ccgacggaac  540
cacctcccgg gatcttggtc cgacaagtcc gcggacattt ccttctcgca cggcctcatc  600
aaccagacgc tcgcggccgg gcgggcctcg gccctgatcc tcaacacctt cgacgagctc  660
gaggcccctt tcctcaccca cctgagctcc atcttcaaca agatctacac catcggcccc  720
ctccacgccc tgtccaagag ccggctcggg gactcctcct cgtcggccag cgcgctctcg  780
gggttctgga aggaggaccg cgcgtgcatg tcctggctcg actgccagcc gccgcgctcg  840
gtcgtgttcg tctccttcgg gtcgaccatg aagatgaagg cggacgagct tcgggagttc  900
```

```
tggtacgggc tggtgagcag cgggaagccg ttcctctgcg tgttgcggtc cgacgtcgtc  960
agcggcggcg aggcggcgga gctcatcgag cagatggcgg aggaggaggg ggctgggggc  1020
aagctgggca tggtcgtcga gtgggcggcg caggagaagg tcctctccca ccctgccgtg  1080
gggggcttcc tgacgcactg cggctggaac tcgacggtgg agagcatcgc cgccggcgtc  1140
cccatgatgt gctggccgat cctcggggac cagccctcca acgccacttg gatcgaccgg  1200
gtctggaaga tcggggtcga gcgaaacaac cgggagtggg accggttgac ggtggagaag  1260
atggtccgcg cattgatgga gggccagaag cgggtggaga tccagcggtc gatggagaag  1320
ctgtcgaagc tggcgaacga gaaggtcgtc cggggggggc tgtctttcga caacctcgag  1380
gtcctcgtgg aggacatcaa gaagctgaag ccgtacaagt tctag                  1425

SEQ ID NO: 287          moltype = AA  length = 474
FEATURE                 Location/Qualifiers
source                  1..474
                        mol_type = protein
                        organism = Siraitia grosvenorii
SEQUENCE: 287
MVQPRVLLFP FPALGHVKPF LSLAELLSDA GIDVVFLSTE YNHRRISNTE ALASRFPTLH  60
FETIPDGLPP NESRALADGP LYFSMREGTK PRFRQLIQSL NDGRWPITCI ITDIMLSSPI  120
EVAEEFGIPV IAFCPCSARY LSIHFFIPKL VEEGQIPYAD DDPIGEIQGV PLFEGLLRRN  180
HLPGSWSDKS ADISFSHGLI NQTLAAGRAS ALILNTFDEL EAPFLTHLSS IFNKIYTIGP  240
LHALSKSRLG DSSSSASALS GFWKEDRACM SWLDCQPPRS VVFVSFGSTM KMKADELREF  300
WYGLVSSGKP FLCVLRSDVV SGGEAAELIE QMAEEEGAGG KLGMVVEWAA QEKVLSHPAV  360
GGFLTHCGWN STVESIAAGV PMMCWPILGD QPSNATWIDR VWKIGVERNN REWDRLTVEK  420
MVRALMEGQK RVEIQRSMEK LSKLANEKVV RGGLSFDNLE VLVEDIKKLK PYKF        474

SEQ ID NO: 288          moltype = DNA  length = 1422
FEATURE                 Location/Qualifiers
source                  1..1422
                        mol_type = other DNA
                        organism = synthetic construct
SEQUENCE: 288
atgtggaccg tcgtgttggg cctcgcgacc ctgttcgtcg cgtactatat ccactggatt  60
aacaagtggc gcgacagcaa gttcaacggc gtcctccccc ccggcactat ggggcttccg  120
ctcataggcg aaacaatcca gctctcccgg ccgtccgaca gcctggacgt gcacccgttc  180
atccagaaga aggtggagcg gtacgggccg atcttcaaga cctgcctggc cgggcgcccg  240
gtggtcgtct cggcggacgc ggagttcaac aactacatca tgctccagga gggccgcgcc  300
gtcgagatgt ggtatcttga caccctgtcc aaatttttcg gcctggacac cgagtggctg  360
aaggcgctgg gcctgatcca caagtacatc cgctccatca ccctgaacca cttcggcgcc  420
gaggcgctcc gcgagcgctt cctgccgttc atcgaggcgt cctccatgga ggcgctgcac  480
tcttggtcta ctcagccgtc ggtcgaggtg aagaacgcgt ccgcgctgat ggtgttccgc  540
accagcgtga acaagatgtt cggcgaggac gcgaagaagc tgtccgggaa catcccgggc  600
aagttcacga agctcctcgg gggcttcctc tcgctcccgc tcaacttccc ggggaccacc  660
taccacaagt gcctcaagga catgaaggag atccagaaga agctgcgcga ggtggtcgac  720
gaccgcctgg cgaacgtggg gccggacgtg gaggacttcc tcggccaggc gctgaaggac  780
aaggagagcg agaagttcat ctccgaggag ttcatcatcc agcttctttt cagcatcagc  840
ttcgcgagct tcgagtccat cagcaccacg ctcacgctga tcctcaagct gctggacgag  900
cacccggagg tcgtgaagga gctggaggcg gagcacgagg cgatccgcaa ggcccgcgcc  960
gacccagacg gcccgatcac ctgggaggag tacaagtcca tgaccttcac cctccaggtg  1020
atcaacgaga cgctgcgcct ggggtccgtg accccggccc tgctgaggaa gaccgtcaag  1080
gacctccagg tgaagggcta catcatcccc gagggctgga ccatcatgct ggtgacggcc  1140
tcccgccacc gcgacccgaa ggtgtacaag gacccgcaca tcttcaaccc gtggaggtgg  1200
aaggacctgg actccatcac catccagaag aacttcatgc cgttcggcgg cggcctgcgc  1260
cactgcgcgg gggccgagta ctccaaagtg tacctgtgca ccttcctgca catcctgtgc  1320
accaagtacc gctggaccaa gctgggcggg gggacgatcg cccgcgccca catcctgtcc  1380
ttcgaggacg gcctgcacgt gaagttcacc ccaaaggagt ga                     1422

SEQ ID NO: 289          moltype = AA  length = 473
FEATURE                 Location/Qualifiers
source                  1..473
                        mol_type = protein
                        organism = Siraitia grosvenorii
SEQUENCE: 289
MWTVVLGLAT LFVAYYIHWI NKWRDSKFNG VLPPGTMGLP LIGETIQLSR PSDSLDVHPF  60
IQKKVERYGP IFKTCLAGRP VVVSADAEFN NYIMLQEGRA VEMWYLDTLS KFFGLDTEWL  120
KALGLIHKYI RSITLNHFGA EALRERFLPF IEASSMEALH SWSTQPSVEV KNASALMVFR  180
TSVNKMFGED AKKLSGNIPG KFTKLLGGFL SLPLNFPGTT YHKCLKDMKE IQKKLREVVD  240
DRLANVGPDV EDFLGQALKD KESEKFISEE FIIQLLFSIS FASFESISTT LTLILKLLDE  300
HPEVVKELEA EHEAIRKARA DPDGPITWEE YKSMTFTLQV INETLRLGSV TPALLRKTVK  360
DLQVKGYIIP EGWTIMLVTA SRHRDPKVYK DPHIFNPWRW KDLDSITIQK NFMPFGGGLR  420
HCAGAEYSKV YLCTFLHILC TKYRWTKLGG GTIARAHILS FEDGLHVKFT PKE         473

SEQ ID NO: 290          moltype = DNA  length = 1587
FEATURE                 Location/Qualifiers
source                  1..1587
                        mol_type = other DNA
                        organism = synthetic construct
SEQUENCE: 290
atggtggacc agtgcgcctt gggctggatc ttggcctccg cgctgggcct cgtgatcgcc  60
ctgtgcttct tcgtcgcccc ccggcggaac caccgggggg tcgactcgaa ggagagggac  120
```

```
gagtgcgtcc agagcgcggc caccacgaag ggggagtgcc ggttcaacga ccgcgacgtc  180
gacgtgatcg tcgttggcgc cggcgtcgcg ggcagcgccc tcgcccacac tctggggaag  240
gacgggcggc gcgtgcacgt cattgagcgc gacctgacgg agcccgaccg gatcgtgggg  300
gagctcctcc agcccggggg gtacctcaag ctcatcgagc tgggtctgca ggactgcgtc  360
gaggagatcg acgcgcagag ggtgtacggc tacgcgctgt tcaaggacgg gaagaacacc  420
cggctctctt acccgttgga gaatttccac tccgacgtgt cggggcggag cttccacaac  480
ggccgcttca tccagcgcat gagggagaag gccgcgtccc tgcccaacgt gcggttggag  540
cagggcacgg ttacctccct gctggaggag aagggcacga tcaagggcgt gcagtacaag  600
tccaagaacg gtgaggagaa gacggcctac gcccccctga ccatcgtctg cgacggctgc  660
ttctcgaacc tgcgccgctc cctgtgcaac cctatggtgg acgtgcccag ctacttcgtg  720
ggcctcgtcc tggagaactg cgagctaccc ttcgcgaacc acgggcacgt tatcctcggg  780
gatccctcgc ccatcctctt ctaccagatc agccgtaccg agatccgttg cctcgtggac  840
gtccccgggc agaaggtccc ctccatcgcg aacggggaga tggagaagta ccttaagacg  900
gtggtcgcgc cccaggtgcc cccgcagatc tacgactcct tcatcgcggc gatcgacaag  960
gggaacatcc ggacgatgcc gaaccgctcc atgcccgctg cgccccaccc cacgcccggc  1020
gccttgctca tgggcgacgc gttcaacatg cgccaccccc tgaccggggg cggcatgacc  1080
gtggccctca gtgacatcgt cgtactccgc aacctgctca agccgctgaa ggacctgtcg  1140
gacgcctcta ccctctgcaa gtacctcgag agcttctaca cattgcggaa gccagtggct  1200
tcgaccatca acacgctagc gggggcgctg tacaaggtct tctgcgccag ccccgaccag  1260
gcgcgaaagg agatgcggca ggcctgcttc gactacctca gcctgggcgg catcttctca  1320
aacggccccg tctccctgct tagcggcttg aacccgcgcc ccctgtctct ggttctccac  1380
ttcttcgcgg tcgcgatcta cggcgtcggc cgcctgctgc tgccgttccc ctcggtgaag  1440
ggcatctgga tcggcgccag gttgatctac agcgcctcgg gcatcatctt ccccatcatc  1500
cgggccgagg gcgtccggca gatgttcttc cccgccacgg tcccggccta ctaccgctcc  1560
ccccccgtgt tcaagcccat cgtctga                                     1587

SEQ ID NO: 291          moltype = AA  length = 528
FEATURE                 Location/Qualifiers
source                  1..528
                        mol_type = protein
                        organism = Siraitia grosvenorii
SEQUENCE: 291
MVDQCALGWI LASALGLVIA LCFFVAPRRN HRGVDSKERD ECVQSAATTK GECRFNDRDV  60
DVIVVGAGVA GSALAHTLGK DGRRVHVIER DLTEPDRIVG ELLQPGGYLK LIELGLQDCV  120
EEIDAQRVYG YALFKDGKNT RLSYPLENFH SDVSGRSFHN GRFIQRMREK AASLPNVRLE  180
QGTVTSLLEE KGTIKGVQYK SKNGEEKTAY APLTIVCDGC FSNLRRSLCN PMVDVPSYFV  240
GLVLENCELP FANHGHVILG DPSPILFYQI SRTEIRCLVD VPGQKVPSIA NGEMEKYLKT  300
VVAPQVPPQI YDSFIAAIDK GNIRTMPNRS MPAAPHPTPG ALLMGDAFNM RHPLTGGGMT  360
VALSDIVVLR NLLKPLKDLS DASTLCKYLE SFYTLRKPVA STINTLAGAL YKVFCASPDQ  420
ARKEMRQACF DYLSLGGIFS NGPVSLLSGL NPRPLSLVLH FFAVAIYGVG RLLLPFPSVK  480
GIWIGARLIY SASGIIFPII RAEGVRQMFF PATVPAYYRS PPVFKPIV              528

SEQ ID NO: 292          moltype = DNA  length = 951
FEATURE                 Location/Qualifiers
source                  1..951
                        mol_type = other DNA
                        organism = synthetic construct
SEQUENCE: 292
atggaccaga tcgagcacat caccatcaac accaacggca tcaagatgca catcgcctcc  60
gtgggcacgg gcccggtggt gctgctgctg cacggcttcc cggagctgtg gtactcctgg  120
cgccaccagc tgctctacct gtcctccgtg ggctacaggg ccatcgcccc ggacctgagg  180
ggctacggcg acaccgactc cccggcctcc ccgaccagct acaccgccct gcacatcgtc  240
ggggacctgg tgggcgccct ggacgagctc ggcatcgaga aggtgtttct cgtgggccac  300
gactggggcg cgatcatcgc ctggtacttc tgcctgttcc gcccggaccg catcaaggcc  360
ctggtgaacc tgtccgtgca gttcatcccg aggaacccgg ccatcccgtt catcgagggc  420
ttcaggaccg ccttcggcga cgacttctac atgtgcaggt tccaggtgcc gggcgaggcc  480
gaggaggact tcgcctccat cgacaccgcc cagctgttca agacctccct gtgcaaccgc  540
tcctccgccc cgccgtgcct gccgaaggag atcgggttca gggccatccc gccgccggag  600
aatctgccgt cctggctgac ggaggaagac atcaactatt atgccgccaa gttcaagcag  660
accggcttca ccggcgccct gaactactac agggccttcg acctgacctg ggagctgacc  720
gccccgtgga ccggcgcgca gatccaggtg ccggtgaagt tcatcgtcgg cgactccgac  780
ctgacgtacc acttcccggg cgccaaggag tacatccaca acggcgggtt caagaaggac  840
gtgccgctgc tggaggaggt cgtggtggtg aaggacgcct gccacttcat caatcaggag  900
cgcccgcagg agatcaacgc ccacatccac gacttcatca acaagttctg a          951

SEQ ID NO: 293          moltype = AA  length = 316
FEATURE                 Location/Qualifiers
source                  1..316
                        mol_type = protein
                        organism = Siraitia grosvenorii
SEQUENCE: 293
MDQIEHITIN TNGIKMHIAS VGTGPVVLLL HGFPELWYSW RHQLLYLSSV GYRAIAPDLR  60
GYGDTDSPAS PTSYTALHIV GDLVGALDEL GIEKVFLVGH DWGAIIAWYF CLFRPDRIKA  120
LVNLSVQFIP RNPAIPFIEG FRTAFGDDFY MCRFQVPGEA EEDFASIDTA QLFKTSLCNR  180
SSAPPCLPKE IGFRAIPPPE NLPSWLTEED INYYAAKFKQ TGFTGALNYY RAFDLTWELT  240
APWTGAQIQV PVKFIVGDSD LTYHFPGAKE YIHNGGFKKD VPLLEEVVVV KDACHFINQE  300
RPQEINAHIH DFINKF                                                 316

SEQ ID NO: 294          moltype = DNA  length = 1422
```

```
FEATURE                Location/Qualifiers
source                 1..1422
                       mol_type = other DNA
                       organism = synthetic construct
SEQUENCE: 294
atggtgcagc cccgggtgct gctgttccct ttccccgcgc tgggccacgt gaagcccttc  60
ctgtcgctgg cggagctcct gtccgacgcc ggcatcgacg tggtcttcct ctcgacggag  120
tataaccacc gccgcatctc caacaccgag gccctggcct cccgcttccc caccctgcac  180
ttcgaaacga taccggacgg cctgcccccc aacgagtcgc gcgccctcgc ggacggcccc  240
ctgtacttca gcatgaggga gggcaccaag ccgcgcttcc ggcagctgat ccagagcctt  300
aacgacggcc gttggcccat cacctgtatc atcacggaca tcatgctcag ttcgcccatc  360
gaggtggcgg aggagttcgg gatcccggtg atcgcgttct gcccgtgctc cgctcgctac  420
ctctcgatcc acttcttcat cccgaagctg gtggaggagg ggcagatccc gtacgcggac  480
gacgacccca ttggggagat ccagggggtg cccctcttcg aggggcttct ccgacggaac  540
cacctcccgg gatcttggtc cgacaagtcc gcggacattt ccttctcgca cggcctcatc  600
aaccagacgc tcgcggccgg gcgggcctcg gccctgatcc tcaacacctt cgacgagctc  660
gaggcccctt tcctcaccca cctgagctcc atcttcaaca agatctacac catcggcccc  720
ctccacgccc tgtccaagag ccggctcggg gactcctcct cgtcggccag cgcgctctcg  780
gggttctgga aggaggaccg cgcgtgcatg tcctggctcg actgccagcc gccgcgctcg  840
gtcgtgttcg tctccttcgg gtcgaccatg aagatgaagg cggacgagct tcgggagttc  900
tggtacgggc tggtgagcag cgggaagccg ttcctctgcg tgttgcggtc cgacgtcgtc  960
agcggcggcg aggcggcgga gctcatcgag cagatggcgg aggaggaggg ggctgggggc  1020
aagctgggca tggtcgtcga gtgggcggcg caggagaagg tcctctccca ccctgccgtg  1080
gggggcttcc tgacgcactg cggctggaac tcgacggtgg agagcatcgc cgccggcgtc  1140
cccatgatgt gctggccgat cctcggggac cagccctcca acgccacttg gatcgaccgg  1200
gtctggaaga tcggggtcga gcgaaacaac cgggagtggg accggttgac ggtggagaag  1260
atggtccgcg cattgatgga gggccagaag cgggtggaga tccagcggtc gatggagaag  1320
ctgtcgaagc tggcgaacga gaaggtcgtc cggggggggc tgtctttcga caacctcgag  1380
gtcctcgtgg aggacatcaa gaagctgaag ccgtacaagt tc                    1422

SEQ ID NO: 295         moltype = AA  length = 474
FEATURE                Location/Qualifiers
source                 1..474
                       mol_type = protein
                       organism = Siraitia grosvenorii
SEQUENCE: 295
MVQPRVLLFP FPALGHVKPF LSLAELLSDA GIDVVFLSTE YNHRRISNTE ALASRFPTLH  60
FETIPDGLPP NESRALADGP LYFSMREGTK PRFRQLIQSL NDGRWPITCI ITDIMLSSPI  120
EVAEEFGIPV IAFCPCSARY LSIHFFIPKL VEEGQIPYAD DDPIGEIQGV PLFEGLLRRN  180
HLPGSWSDKS ADISFSHGLI NQTLAAGRAS ALILNTFDEL EAPFLTHLSS IFNKIYTIGP  240
LHALSKSRLG DSSSSASALS GFWKEDRACM SWLDCQPPRS VVFVSFGSTM KMKADELREF  300
WYGLVSSGKP FLCVLRSDVV SGGEAAELIE QMAEEEGAGG KLGMVVEWAA QEKVLSHPAV  360
GGFLTHCGWN STVESIAAGV PMMCWPILGD QPSNATWIDR VWKIGVERNN REWDRLTVEK  420
MVRALMEGQK RVEIQRSMEK LSKLANEKVV RGGLSFDNLE VLVEDIKKLK PYKF        474

SEQ ID NO: 296         moltype = DNA  length = 1557
FEATURE                Location/Qualifiers
source                 1..1557
                       mol_type = other DNA
                       organism = synthetic construct
SEQUENCE: 296
atgtccagct cagtcgcggc taccataagc atatggatgg tcgttgtctg tatagtgggt  60
gtcgggtggc gggtggtcaa ctgggtttgg cttcgcccca aaaaacttga gaagcggctc  120
cgggaacaag gtctggctgg aaattcgtat cggctccttt tcggggacct taaagaaaga  180
gccgcgatgg ctgaacaggc aaattcaaag ccaattaact tttcgcatga tatagggcca  240
cgggtttttc cgtcgatgta taaaactatt cagaactatg gtaagaactc ttacatgtgg  300
ttgggacctt atccgagggt tcatatcatg gatcctcagc agctgaagac tgtgtttacg  360
cttgtgtacg acatacagaa gcccaatctt aatcccttga ttaaattttt gttggatgga  420
attgttacgc atgaagggga aaagtgggct aaacaccgca aaatcattaa ccccgcattc  480
catatggcaa agttgaaaga tatgattcca gctttttttcc aatcctgtaa tgaaattgtc  540
agcgaatggg agaggatgat cccgaaggag gggagcttcg aattggatgt gatgccctat  600
atgcagaatc tggccgctga cgctattagc cggactgcct tcggaagcag ctataaggaa  660
ggtcaaatga tttttcagtt gctcaaagag ttgaccgatc ttgtggtgaa agcagccttc  720
ggcatttata tccccggatg gagattcctc cccacgaaaa gcaacaataa aatgaaggag  780
ataaaccgga agattaaaac tcttttgctt ggtattatag ataagaggca gaaggcaatg  840
aaagaaggcg aggtcgtcca gaatgacctt cttgggattt tggtcgagtc gaaccttaac  900
gagataagag ggcatgagaa taataaagac gcggggatgt ccatcgaaga tgtgatagaa  960
gagtgtaagg tgttctacat aggtggccag gagacaactg caggcctgtt gatatggacc  1020
atgatattgc tcagcttcca tacggaatgg caggaacgcg ctagaaccga agttctcgaa  1080
gtcgttggga acaaaaaacc tgatttcgac ggattgaatc ggctgaagat agttacaatg  1140
attctctatg aggtgctccg gttgtatcct cccgcctcta tgttgacccg cattgtccaa  1200
aaggaaacga gaatagggaa gcttactctt ccggctggag tcacactgat aatcccaacg  1260
gtgttgatac accgcgatca cgaattgtgg ggcgaggacg cgaatgaatt caagcccgaa  1320
cgcttcagcg agggagttag caaggccgct aaggtgcagc ctgcgttctt cccgttcgga  1380
tgggggccca gactttgtct cgggcaaaac ttcgcaatga ttgaggccaa aatggcgttt  1440
tctctgattc tgcaaagatt ctctttccac ctctcatcat catatgcaca cgcgcctacc  1500
gtcgttatga caactcagcc tcagcatggc gctcatatag ttctcagaaa gctctaa     1557

SEQ ID NO: 297         moltype = AA  length = 518
```

```
FEATURE                Location/Qualifiers
source                 1..518
                       mol_type = protein
                       organism = Siraitia grosvenorii
SEQUENCE: 297
MSSSVAATIS IWMVVVCIVG VGWRVVNWVW LRPKKLEKRL REQGLAGNSY RLLFGDLKER  60
AAMAEQANSK PINFSHDIGP RVFPSMYKTI QNYGKNSYMW LGPYPRVHIM DPQQLKTVFT  120
LVYDIQKPNL NPLIKFLLDG IVTHEGEKWA KHRKIINPAF HMAKLKDMIP AFFQSCNEIV  180
SEWERMIPKE GSFELDVMPY MQNLAADAIS RTAFGSSYKE GQMIFQLLKE LTDLVVKAAF  240
GIYIPGWRFL PTKSNNKMKE INRKIKTLLL GIIDKRQKAM KEGEVVQNDL LGILVESNLN  300
EIRGHENNKD AGMSIEDVIE ECKVFYIGGQ ETTAGLLIWT MILLSFHTEW QERARTEVLE  360
VVGNKKPDFD GLNRLKIVTM ILYEVLRLYP PASMLTRIVQ KETRIGKLTL PAGVTLIIPT  420
VLIHRDHELW GEDANEFKPE RFSEGVSKAA KVQPAFFPFG WGPRLCLGQN FAMIEAKMAF  480
SLILQRFSFH LSSSYAHAPT VVMTTQPQHG AHIVLRKL                          518

SEQ ID NO: 298         moltype = DNA  length = 1359
FEATURE                Location/Qualifiers
source                 1..1359
                       mol_type = other DNA
                       organism = synthetic construct
SEQUENCE: 298
atggacgcgc agcggggcca cacgacgacg atcctgatgt tcccctggct cggctacggg  60
cacctcagcg ccttcctcga gctggcgaag agcctgtccc ggcgcaactt ccacatctac  120
ttctgctcga ccagcgtcaa cctggacgcg atcaagccca agctgccctc cagcagctcc  180
tccgacagca tccagctggt ggagctgtgc ctgccctcca gccccgacca gctccccccg  240
cacctccaca ccaccaacgc gctcccgccc cacctcatgc ccaccctcca ccaggccttc  300
agcatggcgg cgcagcactt cgcggccatc ctgcacaccc tcgcgcccca cctcctgatc  360
tacgactcgt tccagccgtg ggcaccccag ctggcctcct cgctcaacat cccggccatc  420
aacttcaaca cgaccggggc gtccgtcctg acccggatgc tgcacgcgac ccactacccg  480
agcagcaagt tccccatcag cgagttcgtg ctccacgact actggaaggc catgtacagc  540
gcggccgggg gcgcggtgac gaagaaggac cacaagatcg gcgagacgct ggcgaactgc  600
ctccacgcca gctgctcggt catcctgatc aactccttcc gcgagctgga ggagaagtac  660
atggactacc tgtccgtgct cctgaacaag aaggtggtgc cggtggggcc gctggtgtac  720
gagccgaacc aggatggaga ggacgagggg tactccagca taaagaactg gctcgacaag  780
aaggagccga gctccacggt gttcgtgtcc ttcggcagcg agtacttccc gagcaaggag  840
gagatggagg agatcgccca cgggctcgag gcctctgaag ttcatttcat ctgggttgtg  900
cggttcccgc agggggacaa cacctccgcg atcgaggacg ccctgccgaa gggcttcctc  960
gagagggtgg gcgagagggg catggtggtg aagggctggg ccccgcaggc gaagatcctg  1020
aagcactggt ccaccggggg cttcgtgtcc cactgcggct ggaacagcgt gatggagagc  1080
atgatgttcg gggtgccgat catcggcgtg ccgatgcacc tggaccagcc gttcaacgcc  1140
ggcctggccg aggaggccgg cgtgggggtg gaggcgaagc gcgaccccga cgggaagatc  1200
cagcgcgacg aggtcgccaa gctgatcaag gaggtggtgg tggagaagac ccgggaggac  1260
gtgaggaaga aggcgcgcga gatgtccgag atcctccgca gcaaggggga ggagaagatg  1320
gacgagatgg tggccgcgat ctccctcttc ctcaagatc                         1359

SEQ ID NO: 299         moltype = AA  length = 453
FEATURE                Location/Qualifiers
source                 1..453
                       mol_type = protein
                       organism = Siraitia grosvenorii
SEQUENCE: 299
MDAQRGHTTT ILMFPWLGYG HLSAFLELAK SLSRRNFHIY FCSTSVNLDA IKPKLPSSSS  60
SDSIQLVELC LPSSPDQLPP HLHTTNALPP HLMPTLHQAF SMAAQHFAAI LHTLAPHLLI  120
YDSFQPWAPQ LASSLNIPAI NFNTTGASVL TRMLHATHYP SSKFPISEFV LHDYWKAMYS  180
AAGGAVTKKD HKIGETLANC LHASCSVILI NSFRELEEKY MDYLSVLLNK KVVPVGPLVY  240
EPNQDGEDEG YSSIKNWLDK KEPSSTVFVS FGSEYFPSKE EMEEIAHGLE ASEVHFIWVV  300
RFPQGDNTSA IEDALPKGFL ERVGERGMVV KGWAPQAKIL KHWSTGGFVS HCGWNSVMES  360
MMFGVPIIGV PMHLDQPFNA GLAEEAGVGV EAKRDPDGKI QRDEVAKLIK EVVVEKTRED  420
VRKKAREMSE ILRSKGEEKM DEMVAAISLF LKI                               453

SEQ ID NO: 300         moltype = DNA  length = 1425
FEATURE                Location/Qualifiers
source                 1..1425
                       mol_type = other DNA
                       organism = synthetic construct
SEQUENCE: 300
atggtccaac cccgggtcct gctctttccg tttccggctc ttggccatgt taaaccattc  60
ctttcccttg ccgagctcct gtcggacgca ggaatagatg tcgtcttttt gtcaacggag  120
tataatcatc ggaggatctc aaatacagag gcacttgcaa gccggtttcc cactcttcac  180
ttcgaaacca ttccagatgg gctgccgcca aatgagagca gggctttggc cgacggccct  240
ctttacttct cgatgaggga ggggacaaaa ccgaggtttc gccagcttat acagagcctg  300
aatgatggtc ggtggcccat tacttgtata attacggata taatgctttc cagccccatc  360
gaagttgcgg aggagtttgg gataccggtg atagcatttt gtccttgctc ggctcgctac  420
ttgtctatac acttctttat cccgaagctc gtcgaagaag gccagatacc atacgcggat  480
gacgacccca ttggagaaat acaaggagtg cctcttttttg aggggctcct gcgcagaaat  540
catctgcctg gttcttggag cgataaatcc gctgacatct cattcagcca tgggctgata  600
aatcagacgc ttgcggccgg tcgggcatcg gcactgattc ttaacacctt tgatgaactt  660
gaggccccat ttcttactca cctctcgtcg atttttaaca agatttacac aatcgggcca  720
cttcatgctc tttccaaatc acggcttgga gattcgagca gcagcgcatc cgctctgtcg  780
```

```
ggattctgga aagaggacag agcgtgcatg tcttggcttg attgccaacc accccggtcg  840
gttgtttttg tttcctttgg gtcgacaatg aagatgaagg cggatgagtt gcgggagttt  900
tggtacgggc ttgtctcttc cggaaagccc ttcctctgtg tgctgagatc agatgttgtc  960
tcgggcggtg aggcagccga gctcatagag caaatggcgg aagaggaggg ggccgggggt  1020
aaactcggta tggtggtcga gtgggcggct caggagaaag tgttgtcaca tcctgctgtc  1080
gggggattcc tgacacattg cggatggaat tctactgtcg agtcaattgc ggcgggcgtg  1140
cctatgatgt gctggcccat actgggcgac cagccctcta atgcgacttg gatagaccgg  1200
gtctggaaaa ttggcgttga acggaacaac cgcgaatggg accgcctgac agttgagaag  1260
atggttagag cactcatgga agggcaaaag agagtcgaaa ttcaacgctc tatggaaaaa  1320
ttgagcaaac ttgcaaatga aaaggtcgtg agaggtgggc tgtcgtttga taatctggag  1380
gttctggttg aggacataaa aaagcttaag ccctacaaat tttga                  1425
```

```
SEQ ID NO: 301         moltype = AA  length = 474
FEATURE                Location/Qualifiers
source                 1..474
                       mol_type = protein
                       organism = Siraitia grosvenorii
SEQUENCE: 301
MVQPRVLLFP FPALGHVKPF LSLAELLSDA GIDVVFLSTE YNHRRISNTE ALASRFPTLH  60
FETIPDGLPP NESRALADGP LYFSMREGTK PRFRQLIQSL NDGRWPITCI ITDIMLSSPI  120
EVAEEFGIPV IAFCPCSARY LSIHFFIPKL VEEGQIPYAD DDPIGEIQGV PLFEGLLRRN  180
HLPGSWSDKS ADISFSHGLI NQTLAAGRAS ALILNTFDEL EAPFLTHLSS IFNKIYTIGP  240
LHALSKSRLG DSSSSASALS GFWKEDRACM SWLDCQPPRS VVFVSFGSTM KMKADELREF  300
WYGLVSSGKP FLCVLRSDVV SGGEAAELIE QMAEEEGAGG KLGMVVEWAA QEKVLSHPAV  360
GGFLTHCGWN STVESIAAGV PMMCWPILGD QPSNATWIDR VWKIGVERNN REWDRLTVEK  420
MVRALMEGQK RVEIQRSMEK LSKLANEKVV RGGLSFDNLE VLVEDIKKLK PYKF        474
```

```
SEQ ID NO: 302         moltype = DNA  length = 1425
FEATURE                Location/Qualifiers
source                 1..1425
                       mol_type = other DNA
                       organism = synthetic construct
SEQUENCE: 302
atggtgcaac ctcgggtact gctgtttcct ttcccggcac tgggccacgt gaagcccttc  60
ttatcactgg cggagctgct ttccgacgcc ggcatagacg tcgtcttcct cagcaccgag  120
tataaccacc gtcggatctc caacactgaa gccctagcct cccgcttccc gacgcttcat  180
ttcgaaacta taccggatgg cctgccgcct aatgagtcgc gcgctcttgc cgacggccca  240
ctgtatttct ccatgcgtga gggaactaaa ccgagattcc ggcaactgat tcaatctctt  300
aacgacggtc gttggcccat cacctgtatt atcactgaca tcatgttatc ttctccgatt  360
gaagtagcgg aagaatttgg gattccagta attgccttct gcccatgcag tgctcgctac  420
ttatcgattc actttttttat accgaagctc gttgaggaag gtcaaattcc atacgcagat  480
gacgatccga ttggagagat ccaggggggtg cccttgttcg aaggtctttt gcgacggaat  540
catttgcctg gttcttggtc tgataaatcc gcagatatat ctttctcgca tggcttgatt  600
aatcagaccc ttgcagctgg tcgagcctcg gctcttatac tcaacacctt cgacgaactc  660
gaagctccat ttctgaccca tctctcttcc attttcaaca aaatctacac cattggaccc  720
ctccatgctc tgtccaaatc aaggctcggc gactcctcct cctccgcttc tgccctctcc  780
ggattctgga aagaggatag agcctgcatg tcctggctcg actgtcagcc gccgaggtct  840
gtggttttcg tcagtttcgg gagtacgatg aagatgaaag ccgatgaatt gagagagttc  900
tggtatgggt tggtgagcag cgggaaaccg ttcctctgcg tgttgagatc cgacgttgtt  960
tccggcggag aagcggcgga attgatcgaa cagatggcgg aggaggaggg agctggaggg  1020
aagctgggaa tggtagtgga gtgggcagcg caagagaagg tcctgagcca ccctgccgtc  1080
ggtgggtttt tgacgcactg cgggtggaac tcaacggtgg aaagcattgc cgcgggagtt  1140
ccgatgatgt gctggccgat tctcggcgac caacccagca acgccacttg gatcgacaga  1200
gtgtggaaaa ttggggttga aaggaacaat cgtgaatggg acaggttgac ggtggagaag  1260
atggtgagag cattgatgga aggccaaaag agagtggaga ttcagagatc aatggagaag  1320
ctgtcaaagt tggcaaatga gaaggttgtc aggggtgggt tgtcttttga taacttggaa  1380
gttctcgttg aagacatcaa aaaattgaaa ccatataaat tttaa                  1425
```

```
SEQ ID NO: 303         moltype = AA  length = 474
FEATURE                Location/Qualifiers
source                 1..474
                       mol_type = protein
                       organism = Siraitia grosvenorii
SEQUENCE: 303
MVQPRVLLFP FPALGHVKPF LSLAELLSDA GIDVVFLSTE YNHRRISNTE ALASRFPTLH  60
FETIPDGLPP NESRALADGP LYFSMREGTK PRFRQLIQSL NDGRWPITCI ITDIMLSSPI  120
EVAEEFGIPV IAFCPCSARY LSIHFFIPKL VEEGQIPYAD DDPIGEIQGV PLFEGLLRRN  180
HLPGSWSDKS ADISFSHGLI NQTLAAGRAS ALILNTFDEL EAPFLTHLSS IFNKIYTIGP  240
LHALSKSRLG DSSSSASALS GFWKEDRACM SWLDCQPPRS VVFVSFGSTM KMKADELREF  300
WYGLVSSGKP FLCVLRSDVV SGGEAAELIE QMAEEEGAGG KLGMVVEWAA QEKVLSHPAV  360
GGFLTHCGWN STVESIAAGV PMMCWPILGD QPSNATWIDR VWKIGVERNN REWDRLTVEK  420
MVRALMEGQK RVEIQRSMEK LSKLANEKVV RGGLSFDNLE VLVEDIKKLK PYKF        474
```

```
SEQ ID NO: 304         moltype = DNA  length = 1362
FEATURE                Location/Qualifiers
source                 1..1362
                       mol_type = other DNA
                       organism = synthetic construct
SEQUENCE: 304
```

-continued

```
atggacgcgc agcggggcca cacgacgacg atcctgatgt tcccctggct cggctacggg  60
cacctcagcg ccttcctcga gctggcgaag agcctgtccc ggcgcaactt ccacatctac  120
ttctgctcga ccagcgtcaa cctggacgcg atcaagccca agctgccctc cagcagctcc  180
tccgacagca tccagctggt ggagctgtgc ctgccctcca gccccgacca gctccccccg  240
cacctccaca ccaccaacgc gctcccgccc cacctcatgc ccaccctcca ccaggccttc  300
agcatggcgg cgcagcactt cgcggccatc ctgcacaccc tcgcgcccca cctcctgatc  360
tacgactcgt tccagccgtg ggcaccccag ctggcctcct cgctcaacat cccggccatc  420
aacttcaaca cgaccggggc gtccgtcctg acccggatgc tgcacgcgac ccactacccg  480
agcagcaagt tccccatcag cgagttcgtg ctccacgact actggaaggc catgtacagc  540
gcggccgggg gcgcggtgac gaagaaggac cacaagatcg gcgagacgct ggcgaactgc  600
ctccacgcca gctgctcggt catcctgatc aactccttcc gcgagctgga ggagaagtac  660
atggactacc tgtccgtgct cctgaacaag aaggtggtgc cggtggggcc gctggtgtac  720
gagccgaacc aggatggaga ggacgagggg tactccagca taaagaactg gctcgacaag  780
aaggagccga gctccacggt gttcgtgtcc ttcggcagcg agtacttccc gagcaaggag  840
gagatggagg agatcgccca cgggctcgag gcctctgaag ttcatttcat ctgggttgtg  900
cggttcccgc agggggacaa cacctccgcg atcgaggacg ccctgccgaa gggcttcctc  960
gagagggtgg gcgagagggg catggtggtg aagggctggg ccccgcaggc gaagatcctg  1020
aagcactggt ccaccggggg cttcgtgtcc cactgcggct ggaacagcgt gatggagagc  1080
atgatgttcg gggtgccgat catcggcgtg ccgatgcacc tggaccagcc gttcaacgcc  1140
ggcctggccg aggaggccgg cgtgggggtg gaggcgaagc gcgaccccga cgggaagatc  1200
cagcgcgacg aggtcgccaa gctgatcaag gaggtggtgg tggagaagac ccgggaggac  1260
gtgaggaaga aggcgcgcga gatgtccgag atcctccgca gcaaggggga ggagaagatg  1320
gacgagatgg tggccgcgat ctccctcttc ctcaagatct ga                    1362

SEQ ID NO: 305          moltype = AA  length = 453
FEATURE                 Location/Qualifiers
source                  1..453
                        mol_type = protein
                        organism = Siraitia grosvenorii
SEQUENCE: 305
MDAQRGHTTT ILMFPWLGYG HLSAFLELAK SLSRRNFHIY FCSTSVNLDA IKPKLPSSSS  60
SDSIQLVELC LPSSPDQLPP HLHTTNALPP HLMPTLHQAF SMAAQHFAAI LHTLAPHLLI  120
YDSFQPWAPQ LASSLNIPAI NFNTTGASVL TRMLHATHYP SSKFPISEFV LHDYWKAMYS  180
AAGGAVTKKD HKIGETLANC LHASCSVILI NSFRELEEKY MDYLSVLLNK KVVPVGPLVY  240
EPNQDGEDEG YSSIKNWLDK KEPSSTVFVS FGSEYFPSKE EMEEIAHGLE ASEVHFIWVV  300
RFPQGDNTSA IEDALPKGFL ERVGERGMVV KGWAPQAKIL KHWSTGGFVS HCGWNSVMES  360
MMFGVPIIGV PMHLDQPFNA GLAEEAGVGV EAKRDPDGKI QRDEVAKLIK EVVVEKTRED  420
VRKKAREMSE ILRSKGEEKM DEMVAAISLF LKI                               453
```